(12) United States Patent
Koch et al.

(10) Patent No.: US 12,006,526 B2
(45) Date of Patent: Jun. 11, 2024

(54) MICROORGANISMS AND METHODS FOR THE PRODUCTION OF OXYGENATED COMPOUNDS FROM HEXOSES

(71) Applicant: Braskem S.A., Sao Paulo (BR)

(72) Inventors: Daniel Johannes Koch, Campinas (BR); Lucas Pedersen Parizzi, Campinas (BR); Felipe Galzerani, Campinas (BR)

(73) Assignee: BRASKEM S.A., Sao Paulo (BR)

( * ) Notice: Subject to any disclaimer, the term of this patent is extended or adjusted under 35 U.S.C. 154(b) by 417 days.

(21) Appl. No.: 16/796,417

(22) Filed: Feb. 20, 2020

(65) Prior Publication Data

US 2020/0283806 A1 Sep. 10, 2020

Related U.S. Application Data

(60) Provisional application No. 62/808,247, filed on Feb. 20, 2019.

(51) Int. Cl.
| | |
|---|---|
| *C12N 1/20* | (2006.01) |
| *C12N 15/52* | (2006.01) |
| *C12P 5/02* | (2006.01) |
| *C12P 7/18* | (2006.01) |
| *C12P 7/28* | (2006.01) |
| *C12P 17/02* | (2006.01) |
| *C12R 1/19* | (2006.01) |

(52) U.S. Cl.
CPC ............... *C12P 7/18* (2013.01); *C12N 1/20* (2013.01); *C12N 15/52* (2013.01); *C12P 5/026* (2013.01); *C12P 7/28* (2013.01); *C12P 17/02* (2013.01); *C12N 1/205* (2021.05); *C12R 2001/19* (2021.05); *C12Y 101/01043* (2013.01); *C12Y 101/01301* (2013.01); *C12Y 102/01009* (2013.01); *C12Y 203/01008* (2013.01); *C12Y 207/01011* (2013.01); *C12Y 207/02003* (2013.01); *C12Y 301/01031* (2013.01); *C12Y 401/02022* (2013.01); *C12Y 501/03001* (2013.01); *C12Y 503/01006* (2013.01); *C12Y 504/02* (2013.01)

(58) Field of Classification Search
CPC .. C12N 1/16; C12N 1/205; C12Y 202/01001; C12Y 202/01002
See application file for complete search history.

(56) References Cited

U.S. PATENT DOCUMENTS

| | | | |
|---|---|---|---|
| 7,226,761 B2 | 6/2007 | Miasnikov et al. | |
| 2003/0068791 A1 | 4/2003 | Miasnikov et al. | |
| 2006/0110805 A1 | 5/2006 | Fotheringham et al. | |
| 2009/0155867 A1* | 6/2009 | Soucaille ............... | C12P 7/42 435/146 |
| 2012/0315682 A1* | 12/2012 | Dischert ............... | C12P 7/42 435/146 |

FOREIGN PATENT DOCUMENTS

| | | |
|---|---|---|
| EP | 2411502 A1 | 2/2012 |
| WO | WO-2013066568 A1 | 5/2013 |
| WO | WO-2014187357 A1 | 11/2014 |
| WO | 2017156166 A1 | 9/2017 |

OTHER PUBLICATIONS

Lane et al. (2018) Value-added biotransformation of cellulosic sugars by engineered *Saccharomyces cerevisiae*, Biosou. Technoil, vol. 260, pp. 380-394.*
Meng (2016) High-yield anaerobic succinate production by strategically regulating multiple metabolic pathways based on stoichiometric maximum in *Escherichia coli*, Microb. Cell Fact, vol. 15, No. 141, pp. 1-13.*
NCBI reference (2020) tktA *Scherichia coli*, https://www.ncbi.nlm.nih.gov/protein/CAD6004304.1, pp. 1-2.*
NCBI reference (2016) tktA [*Escherichia coli* O25b:H4], https://www.ncbi.nlm.nih.gov/protein/ANK03247.1, pp. 1-2.*
NCBI (2017) ribulose-5-phosphate 3-epimerase [*Escherichia coli*], https://www.ncbi.nlm.nih.gov/protein/SMH60947.1, pp. 1-2.*
NCBI (2020) phosphate acetyltransferase [*Escherichia coli*], https://www.ncbi.nlm.nih.gov/protein/WP_045228131.1, pp. 1-2.*
Han, M-J., et al. 2006 Microbiology and Molecular Biology Reviews 70(2): 362-439. (Year: 2006).*
Posthuma, C.C., et al. 2002 Applied and Environmental Microbiology 68(2): 831-837. (Year: 2002).*
Salusjärvi, L, et al. 2019 Applied Microbiology and Biotechnology 103: 2525-2535. (Year: 2019).*
Nicolas, C., et al. 2007 FEBS Letters 581: 3771-3776. (Year: 2007).*

(Continued)

*Primary Examiner* — Marsha Tsay
(74) *Attorney, Agent, or Firm* — MORGAN, LEWIS & BOCKIUS LLP

(57) ABSTRACT

The present application relates to recombinant microorganisms useful in the biosynthesis of monoethylene glycol (MEG), or optionally MEG and one or more co-product, from one or more hexose feedstock. The present application also relates to recombinant microorganisms useful in the biosynthesis of glycolic acid (GA), or optionally GA and one or more co-product, from one or more hexose feedstock. The present application relates to recombinant microorganisms useful in the biosynthesis of xylitol, or optionally xylitol and one or more co-product, from one or more hexose feedstock. Also provided are methods of producing MEG (or GA or xylitol), or optionally MEG (or GA or xylitol) and one or more co-product, from one or more hexose feedstock using the recombinant microorganisms, as well as compositions comprising the recombinant microorganisms and/or the products MEG (or GA or xylitol), or optionally MEG (or GA or xylitol) and one or more co-product.

17 Claims, 18 Drawing Sheets
Specification includes a Sequence Listing.

(56) References Cited

OTHER PUBLICATIONS

Keasling, J.D. 2010 Science 330(6009): 1355-1358. (Year: 2010).*
Bailey, J.E. 1991 Science 252(5013): 1668-1675. (Year: 1991).*
Yadav, V.G., et al. 2012 Metabolic Engineering 14: 233-241. (Year: 2012).*
Walther, T., et al. 2012 FEBS Letters 586: 4114-4118. (Year: 2012).*
Jang, Y-S., et al. 2012 Biotechnology and Bioengineering 109(10): 2437-2459. (Year: 2012).*
International Search Report and Written Opinion for Application No. PCT/BR2020/050052, dated Apr. 30, 2020, 13 pages.
Soo Rin Kim et al., Rational and Evolutionary Engineering Approaches Uncover a Small Set of Genetic Changes Efficient for Rapid Xylose Fermentation in *Saccharomyces cerevisiae*, PLoS One, Feb. 2013, vol. 8, Issue 2, : e57048. pp. 1-13 (13 pages). doi:10.1371/journal.pone.0057048.
Paul H. Opgenorth et al., A synthetic biochemistry module for production of bio-based chemicals from glucose, Nature Chemical Biology, Jun. 2016, vol. 12, pp. 393-395 (3 pages).

* cited by examiner

SEQUENCE LISTING

```
<160> NUMBER OF SEQ ID NOS: 258

<210> SEQ ID NO 1
<211> LENGTH: 873
<212> TYPE: DNA
<213> ORGANISM: Pseudomonas cichorii

<400> SEQUENCE: 1
gtgaacaaag ttggcatgtt ctacacctac tggtcgactg agtggatggt cgactttccg      60
gcgactgcga agcgcattgc cgggctcggc ttcgacttaa tggaaatctc gctcggcgag     120
tttcacaatc tttccgacgc gaagaagcgt gagctaaaag ccgtggctga tgatctgggg     180
ctcacggtga tgtgctgtat cggactgaag tctgagtacg actttgcctc gccggacaag     240
agcgttcgtg atgccggcac ggaatatgtg aagcgcttgc tcgacgactg tcacctcctc     300
ggcgcgccgg tctttgctgg ccttacgttc tgcgcgtggc cccaatctcc gccgctggac     360
atgaaggata agcgcccta cgtcgaccgt gcaatcgaaa gcgttcgtcg tgttatcaag     420
gtagctgaag actacggcat tatttatgca ctggaagtgg tgaaccgatt cgagcagtgg     480
ctttgcaatg acgccaagga agcaattgcg tttgccgacg cggttgacag tccggcgtgc     540
aaggtccagc tcgacacatt ccacatgaat atcgaagaga cttccttccg cgatgcaatc     600
cttgcctgca agggcaagat gggccatttc catttgggcg aagcgaaccg tctgccgccg     660
ggcgagggtc gcctgccgtg ggatgaaata ttcggggcgc tgaaggaaat cggatatgac     720
ggcaccatcg ttatggaacc gttcatgcgc aagggcggct cggtcagccg cgcggtgggc     780
gtatggcggg atatgtcgaa cggtgcgacg gacgaagaga tggacgagcg cgctcgccgc     840
tcgttgcagt ttgttcgtga caagctggcc tga                                 873

<210> SEQ ID NO 2
<211> LENGTH: 873
<212> TYPE: DNA
<213> ORGANISM: Artificial Sequence
<220> FEATURE:
<223> OTHER INFORMATION: Codon Optimized Pseudomonas cichorii Sequence

<400> SEQUENCE: 2
atgaacaaag tgggtatgtt ctatacgtac tggtccacgg aatggatggt tgactttccg      60
gcaaccgcga aacgtattgc gggcctgggc ttcgacctga tggaaatttc tctgggcgaa     120
tttcacaacc tgtccgatgc gaaaaagcgt gaactgaaag ccgttgccga cgatctgggt     180
ctgactgtga tgtgctgtat cggcctgaaa tctgaatacg atttcgcgag cccggataaa     240
agcgttcgcg acgccggtac tgaatatgtc aaacgtctgc tggatgactg tcacctgctg     300
ggcgcaccag tgttcgcggg tctgaccttc tgtgcgtggc cgcagtcccc accgctggac     360
atgaaggata aacgtccgta cgtggaccgt gccatcgaaa gcgtgcgccg cgtaatcaaa     420
gtcgctgaag attatggcat tatttacgct ctggaagttg ttaaccgttt cgaacagtgg     480
```

```
ctgtgcaacg acgcgaaaga ggccattgcc ttcgctgacg cggtggattc tccggcttgc    540
aaagttcagc tggacacttt ccatatgaac atcgaggaaa cctccttccg tgacgcgatc    600
ctggcttgca agggtaaaat gggccatttc catctgggcg aagcaaaccg cctgccgccg    660
ggcgaaggtc gtctgccgtg ggacgaaatt tttggcgctc tgaaggaaat cggctacgat    720
ggcacgattg ttatggagcc gttcatgcgc aaaggtggct ccgtttcccg tgcagttggt    780
gtttggcgtg atatgtctaa cggtgccacc gatgaagaaa tggacgaacg tgcacgtcgc    840
tccctgcaat tcgttcgcga taaactggcg taa                                 873
```

\<210\> SEQ ID NO 3
\<211\> LENGTH: 290
\<212\> TYPE: PRT
\<213\> ORGANISM: Pseudomonas cichorii

\<400\> SEQUENCE: 3

```
Met Asn Lys Val Gly Met Phe Tyr Thr Tyr Trp Ser Thr Glu Trp Met
1               5                   10                  15

Val Asp Phe Pro Ala Thr Ala Lys Arg Ile Ala Gly Leu Gly Phe Asp
            20                  25                  30

Leu Met Glu Ile Ser Leu Gly Glu Phe His Asn Leu Ser Asp Ala Lys
        35                  40                  45

Lys Arg Glu Leu Lys Ala Val Ala Asp Asp Leu Gly Leu Thr Val Met
    50                  55                  60

Cys Cys Ile Gly Leu Lys Ser Glu Tyr Asp Phe Ala Ser Pro Asp Lys
65                  70                  75                  80

Ser Val Arg Asp Ala Gly Thr Glu Tyr Val Lys Arg Leu Leu Asp Asp
                85                  90                  95

Cys His Leu Leu Gly Ala Pro Val Phe Ala Gly Leu Thr Phe Cys Ala
            100                 105                 110

Trp Pro Gln Ser Pro Pro Leu Asp Met Lys Asp Lys Arg Pro Tyr Val
        115                 120                 125

Asp Arg Ala Ile Glu Ser Val Arg Arg Val Ile Lys Val Ala Glu Asp
    130                 135                 140

Tyr Gly Ile Ile Tyr Ala Leu Glu Val Val Asn Arg Phe Glu Gln Trp
145                 150                 155                 160

Leu Cys Asn Asp Ala Lys Glu Ala Ile Ala Phe Ala Asp Ala Val Asp
                165                 170                 175

Ser Pro Ala Cys Lys Val Gln Leu Asp Thr Phe His Met Asn Ile Glu
            180                 185                 190

Glu Thr Ser Phe Arg Asp Ala Ile Leu Ala Cys Lys Gly Lys Met Gly
        195                 200                 205

His Phe His Leu Gly Glu Ala Asn Arg Leu Pro Pro Gly Glu Gly Arg
    210                 215                 220

Leu Pro Trp Asp Glu Ile Phe Gly Ala Leu Lys Glu Ile Gly Tyr Asp
225                 230                 235                 240

Gly Thr Ile Val Met Glu Pro Phe Met Arg Lys Gly Gly Ser Val Ser
                245                 250                 255

Arg Ala Val Gly Val Trp Arg Asp Met Ser Asn Gly Ala Thr Asp Glu
            260                 265                 270

Glu Met Asp Glu Arg Ala Arg Arg Ser Leu Gln Phe Val Arg Asp Lys
        275                 280                 285

Leu Ala
    290
```

<210> SEQ ID NO 4
<211> LENGTH: 888
<212> TYPE: DNA
<213> ORGANISM: Rhodobacter sphaeroides

<400> SEQUENCE: 4

```
gtgaaaaatc ctgtcggcat catctcgatg cagttcatcc ggcccttcac ctcggagtcg      60
ctgcatttcc tgaagaagtc ccgggccctg ggcttcgatt tcatcgagct tctcgtgccc     120
gagcccgaag acgggctcga cgcggccgag gtgcggcgca tctgcgaggg cgaggggctg     180
ggcctcgttc tggccgcgcg cgtgaacctc cagcgctcga tcgcgagcga ggaggccgcg     240
gcgcgggccg gcgggcgcga ctatctgaaa tactgcatcg aggccgccga ggcgctcggc     300
gcgaccatcg tcggcggccc gctctatggc gagccgctgg tcttcgccgg ccgcccgccc     360
ttcccctgga cggccgagca gatcgccacc cgcgccgccc gcaccgtcga ggggctggcc     420
gaagtggccc cgctcgccgc gagcgcgggc aaggtcttcg gctcgagcc gctgaaccgc     480
ttcgagaccg acatcgtgaa cacgaccgca caggccatcg aggtggtgga tgcggtgggc     540
tcgcccggtc tcggcgtcat gctcgacacg ttccacatga acatggagga acgctcgatc     600
cccgatgcga tccgcgccac aggcgcgcgc ctcgtccatt ttcaggccaa cgagaaccac     660
cgcggcttcc ccggcaccgg caccatggac tggacggcca tcgcgcgggc gctggggcag     720
gcgggctacg cgggtccggt ctcgctcgag cctttccggc gcgacgacga gcgcgtggcg     780
ctgcccatcg cccactggcg cgccccgcac gaggacgagg acgagaagct gcgcgcgggg     840
ctgggtctca tccgctccgc gatcaccctg gcggaggtga cccactga                  888
```

<210> SEQ ID NO 5
<211> LENGTH: 295
<212> TYPE: PRT
<213> ORGANISM: Rhodobacter sphaeroides

<400> SEQUENCE: 5

```
Met Lys Asn Pro Val Gly Ile Ile Ser Met Gln Phe Ile Arg Pro Phe
1               5                   10                  15

Thr Ser Glu Ser Leu His Phe Leu Lys Lys Ser Arg Ala Leu Gly Phe
            20                  25                  30

Asp Phe Ile Glu Leu Leu Val Pro Glu Pro Glu Asp Gly Leu Asp Ala
        35                  40                  45

Ala Glu Val Arg Arg Ile Cys Glu Gly Glu Gly Leu Gly Leu Val Leu
    50                  55                  60

Ala Ala Arg Val Asn Leu Gln Arg Ser Ile Ala Ser Glu Glu Ala Ala
65                  70                  75                  80

Ala Arg Ala Gly Gly Arg Asp Tyr Leu Lys Tyr Cys Ile Glu Ala Ala
                85                  90                  95

Glu Ala Leu Gly Ala Thr Ile Val Gly Gly Pro Leu Tyr Gly Glu Pro
            100                 105                 110

Leu Val Phe Ala Gly Arg Pro Pro Phe Pro Trp Thr Ala Glu Gln Ile
        115                 120                 125

Ala Thr Arg Ala Ala Arg Thr Val Glu Gly Leu Ala Glu Val Ala Pro
    130                 135                 140

Leu Ala Ala Ser Ala Gly Lys Val Phe Gly Leu Glu Pro Leu Asn Arg
145                 150                 155                 160

Phe Glu Thr Asp Ile Val Asn Thr Thr Ala Gln Ala Ile Glu Val Val
                165                 170                 175
```

Asp Ala Val Gly Ser Pro Gly Leu Gly Val Met Leu Asp Thr Phe His
        180                 185                 190

Met Asn Met Glu Glu Arg Ser Ile Pro Asp Ala Ile Arg Ala Thr Gly
            195                 200                 205

Ala Arg Leu Val His Phe Gln Ala Asn Glu Asn His Arg Gly Phe Pro
    210                 215                 220

Gly Thr Gly Thr Met Asp Trp Thr Ala Ile Ala Arg Ala Leu Gly Gln
225                 230                 235                 240

Ala Gly Tyr Ala Gly Pro Val Ser Leu Glu Pro Phe Arg Arg Asp Asp
                245                 250                 255

Glu Arg Val Ala Leu Pro Ile Ala His Trp Arg Ala Pro His Glu Asp
            260                 265                 270

Glu Asp Glu Lys Leu Arg Ala Gly Leu Gly Leu Ile Arg Ser Ala Ile
        275                 280                 285

Thr Leu Ala Glu Val Thr His
        290                 295

<210> SEQ ID NO 6
<211> LENGTH: 1422
<212> TYPE: DNA
<213> ORGANISM: Escherichia coli

<400> SEQUENCE: 6

| | | | | |
|---|---|---|---|---|
| atgatgaaac | aagaagttat | cctggtactc | gactgtggcg | cgaccaatgt | caggg ccatc | 60 |
| gcggttaatc | ggcagggcaa | aattgttgcc | cgcgcctcaa | cgcctaatgc | cagcgatatc | 120 |
| gcgatggaaa | caacacctg | gcaccagtgg | tctttagacg | ccattttgca | acgctttgct | 180 |
| gattgctgtc | ggcaaatcaa | tagtgaactg | actgaatgcc | acatccgcgg | tatcgccgtc | 240 |
| accacctttg | gtgtggatgg | cgctctggta | gataagcaag | gcaatctgct | ctatccgatt | 300 |
| attagctgga | aatgtccgcg | aacagcagcg | gttatggaca | atattgaacg | gttaatctcc | 360 |
| gcacagcggt | tgcaggctat | ttctggcgtc | ggagccttta | gtttcaatac | gttatataag | 420 |
| ttggtgtggt | tgaaagaaaa | tcatccacaa | ctgctggaac | gcgcgcacgc | ctggctcttt | 480 |
| atttcgtcgc | tgattaacca | ccgtttaacc | ggcgaattca | ctactgatat | cacgatggcc | 540 |
| ggaaccagcc | agatgctgga | tatccagcaa | cgcgatttca | gtccgcaaat | tttacaagcc | 600 |
| accggtattc | cacgccgact | cttccctcgt | ctggtggaag | cgggtgaaca | gattggtacg | 660 |
| ctacagaaca | gcgccgcagc | aatgctcggc | ttacccgttg | gcataccggt | gatttccgca | 720 |
| ggtcacgata | cccagttcgc | ccttttggc | gctggtgctg | aacaaaatga | acccgtgctc | 780 |
| tcttccggta | catgggaaat | tttaatggtt | cgcagcgccc | aggttgatac | ttcgctgtta | 840 |
| agtcagtacg | ccggttccac | ctgcgaactg | gatagccagg | cagggttgta | taacccaggt | 900 |
| atgcaatggc | tggcatccgg | cgtgctggaa | tgggtgagaa | aactgttctg | gacggctgaa | 960 |
| acaccctggc | aaatgttgat | tgaagaagct | cgtctgatcg | cgcctggcgc | ggatggcgta | 1020 |
| aaaatgcagt | gtgatttatt | gtcgtgtcag | aacgctggct | ggcaaggagt | gacgcttaat | 1080 |
| accacgcggg | ggcatttcta | tcgcgcggcg | ctggaagggt | taactgcgca | attacagcgc | 1140 |
| aatctacaga | tgctggaaaa | aatcgggcac | tttaaggcct | ctgaattatt | gttagtcggt | 1200 |
| ggaggaagtc | gcaacacatt | gtggaatcag | attaaagcca | atatgcttga | tattccggta | 1260 |
| aaagttctcg | acgacgccga | aacgaccgtc | gcaggagctg | cgctgttcgg | ttggtatggc | 1320 |
| gtaggggaat | taacagccc | ggaagaagcc | cgcgcacaga | ttcattatca | gtaccgttat | 1380 |
| ttctacccgc | aaactgaacc | tgaatttata | gaggaagtgt | ga | | 1422 |

<210> SEQ ID NO 7
<211> LENGTH: 1422
<212> TYPE: DNA
<213> ORGANISM: Artificial Sequence
<220> FEATURE:
<223> OTHER INFORMATION: Codon Optimized E. coli Sequence

<400> SEQUENCE: 7

```
atgatgaaac aagaagttat cctggtactc gactgtggcg cgaccaatgt cagggccatc      60
gcggttaatc ggcagggcaa aattgttgcc cgcgcctcaa cgcctaatgc cagcgatatc     120
gcgatggaaa acaacacctg gcaccagtgg tctttagacg ccattttgca acgctttgct     180
gattgctgtc ggcaaatcaa tagtgaactg actgaatgcc acatccgcgg tatcgccgtc     240
accacctttg gtgtggatgg cgctctggta gataagcaag gcaatctgct ctatccgatt     300
attagctgga atgtccgcg aacagcagcg gttatggaca atattgaacg gttaatctcc     360
gcacagcggt tgcaggctat ttctggcgtc ggagccttta gtttcaatac gttatataag     420
ttggtgtggt tgaaagaaaa tcatccacaa ctgctggaac gcgcgcacgc ctggctcttt     480
atttcgtcgc tgattaacca ccgtttaacc ggcgaattca ctactgatat cacgatggcc     540
ggaaccagcc agatgctgga tatccagcaa cgcgatttca gtccgcaaat tttacaagcc     600
accggtattc cacgccgact cttccctcgt ctggtggaag cgggtgaaca gattggtacg     660
ctacagaaca gcgccgcagc aatgctcggc ttacccgttg cataccggt gatttccgca     720
ggtcacgata cccagttcgc cctttttggc gctggtgctg aacaaaatga acccgtgctc     780
tcttccggta catgggaaat tttaatggtt cgcagcgccc aggttgatac ttcgctgtta     840
agtcagtacg ccggttccac ctgcgaactg gatagccagg cagggttgta taacccaggt     900
atgcaatggc tggcatccgg cgtgctggaa tgggtgagaa aactgttctg gacggctgaa     960
acacctggc aaatgttgat tgaagaagct cgtctgatcg cgcctggcgc ggatggcgta    1020
aaaatgcagt gtgatttatt gtcgtgtcag aacgctggct ggcaaggagt gacgcttaat    1080
accacgcggg gcatttcta tcgcgcggcg ctggaagggt taactgcgca attacagcgc    1140
aatctacaga tgctggaaaa atcgggcac tttaaggcct ctgaattatt gttagtcggt    1200
ggaggaagtc gcaacacatt gtggaatcag attaaagcca atatgcttga tattccggta    1260
aaagttctcg acgacgccga aacgaccgtc gcaggagctg cgctgttcgg ttggtatggc    1320
gtaggggaat taacagcccc ggaagaagcc cgcgcacaga ttcattatca gtaccgttat    1380
ttctacccgc aaactgaacc tgaatttata gaggaagtgt ga                       1422
```

<210> SEQ ID NO 8
<211> LENGTH: 473
<212> TYPE: PRT
<213> ORGANISM: Escherichia coli

<400> SEQUENCE: 8

```
Met Met Lys Gln Glu Val Ile Leu Val Leu Asp Cys Gly Ala Thr Asn
1               5                   10                  15

Val Arg Ala Ile Ala Val Asn Arg Gln Gly Lys Ile Val Ala Arg Ala
            20                  25                  30

Ser Thr Pro Asn Ala Ser Asp Ile Ala Met Glu Asn Asn Thr Trp His
        35                  40                  45

Gln Trp Ser Leu Asp Ala Ile Leu Gln Arg Phe Ala Asp Cys Cys Arg
    50                  55                  60
```

```
Gln Ile Asn Ser Glu Leu Thr Glu Cys His Ile Arg Gly Ile Ala Val
 65                  70                  75                  80

Thr Thr Phe Gly Val Asp Gly Ala Leu Val Asp Lys Gln Gly Asn Leu
                 85                  90                  95

Leu Tyr Pro Ile Ile Ser Trp Lys Cys Pro Arg Thr Ala Ala Val Met
            100                 105                 110

Asp Asn Ile Glu Arg Leu Ile Ser Ala Gln Arg Leu Gln Ala Ile Ser
        115                 120                 125

Gly Val Gly Ala Phe Ser Phe Asn Thr Leu Tyr Lys Leu Val Trp Leu
130                 135                 140

Lys Glu Asn His Pro Gln Leu Leu Glu Arg Ala His Ala Trp Leu Phe
145                 150                 155                 160

Ile Ser Ser Leu Ile Asn His Arg Leu Thr Gly Glu Phe Thr Thr Asp
            165                 170                 175

Ile Thr Met Ala Gly Thr Ser Gln Met Leu Asp Ile Gln Gln Arg Asp
        180                 185                 190

Phe Ser Pro Gln Ile Leu Gln Ala Thr Gly Ile Pro Arg Arg Leu Phe
    195                 200                 205

Pro Arg Leu Val Glu Ala Gly Glu Gln Ile Gly Thr Leu Gln Asn Ser
210                 215                 220

Ala Ala Ala Met Leu Gly Leu Pro Val Gly Ile Pro Val Ile Ser Ala
225                 230                 235                 240

Gly His Asp Thr Gln Phe Ala Leu Phe Gly Ala Gly Ala Glu Gln Asn
                245                 250                 255

Glu Pro Val Leu Ser Ser Gly Thr Trp Glu Ile Leu Met Val Arg Ser
            260                 265                 270

Ala Gln Val Asp Thr Ser Leu Leu Ser Gln Tyr Ala Gly Ser Thr Cys
        275                 280                 285

Glu Leu Asp Ser Gln Ala Gly Leu Tyr Asn Pro Gly Met Gln Trp Leu
    290                 295                 300

Ala Ser Gly Val Leu Glu Trp Val Arg Lys Leu Phe Trp Thr Ala Glu
305                 310                 315                 320

Thr Pro Trp Gln Met Leu Ile Glu Glu Ala Arg Leu Ile Ala Pro Gly
                325                 330                 335

Ala Asp Gly Val Lys Met Gln Cys Asp Leu Leu Ser Cys Gln Asn Ala
            340                 345                 350

Gly Trp Gln Gly Val Thr Leu Asn Thr Thr Arg Gly His Phe Tyr Arg
        355                 360                 365

Ala Ala Leu Glu Gly Leu Thr Ala Gln Leu Gln Arg Asn Leu Gln Met
    370                 375                 380

Leu Glu Lys Ile Gly His Phe Lys Ala Ser Glu Leu Leu Leu Val Gly
385                 390                 395                 400

Gly Gly Ser Arg Asn Thr Leu Trp Asn Gln Ile Lys Ala Asn Met Leu
                405                 410                 415

Asp Ile Pro Val Lys Val Leu Asp Ala Glu Thr Thr Val Ala Gly
            420                 425                 430

Ala Ala Leu Phe Gly Trp Tyr Gly Val Gly Glu Phe Asn Ser Pro Glu
        435                 440                 445

Glu Ala Arg Ala Gln Ile His Tyr Gln Tyr Arg Tyr Phe Tyr Pro Gln
    450                 455                 460

Thr Glu Pro Glu Phe Ile Glu Glu Val
465                 470
```

<210> SEQ ID NO 9
<211> LENGTH: 648
<212> TYPE: DNA
<213> ORGANISM: Escherichia coli

<400> SEQUENCE: 9

| | | | | | |
|---|---|---|---|---|---|
| atggaacgaa | ataaacttgc | tcgtcagatt | attgacactt | gcctggaaat | gacccgcctg | 60 |
| ggactgaacc | aggggacagc | ggggaacgtc | agtgtacgtt | atcaggatgg | gatgctgatt | 120 |
| acgcctacag | gcattccata | tgaaaaactg | acggagtcgc | atattgtctt | tattgatggc | 180 |
| aacggtaaac | atgaggaagg | aaagctcccc | tcaagcgaat | ggcgtttcca | tatggcagcc | 240 |
| tatcaaagca | gaccggatgc | caacgcggtt | gttcacaatc | atgccgttca | ttgcacggca | 300 |
| gtttccattc | ttaaccgatc | gatccccgct | attcactaca | tgattgcggc | ggctggcggt | 360 |
| aattctattc | cttgcgcgcc | ttatgcgacc | tttggaacac | gcgaactttc | tgaacatgtt | 420 |
| gcgctggctc | tcaaaaatcg | taaggcaact | ttgttacaac | atcatgggct | tatcgcttgt | 480 |
| gaggtgaatc | tggaaaaagc | gttatggctg | gcgcatgaag | ttgaagtgct | ggcgcaactt | 540 |
| tacctgacga | ccctggcgat | tacggacccg | gtgccagtgc | tgagcgatga | agagattgcc | 600 |
| gtagtgctgg | agaaattcaa | aacctatggg | ttacgaattg | aagagtaa | | 648 |

<210> SEQ ID NO 10
<211> LENGTH: 648
<212> TYPE: DNA
<213> ORGANISM: Escherichia coli

<400> SEQUENCE: 10

| | | | | | |
|---|---|---|---|---|---|
| atggaacgaa | ataaacttgc | tcgtcagatt | attgacactt | gcctggaaat | gacccgcctg | 60 |
| ggactgaacc | aggggacagc | ggggaacgtc | agtgtacgtt | atcaggatgg | gatgctgatt | 120 |
| acgcctacag | gcattccata | tgaaaaactg | acggagtcgc | atattgtctt | tattgatggc | 180 |
| aacggtaaac | atgaggaagg | aaagctcccc | tcaagcgaat | ggcgtttcca | tatggcagcc | 240 |
| tatcaaagca | gaccggatgc | caacgcggtt | gttcacaatc | atgccgttca | ttgcacggca | 300 |
| gtttccattc | ttaaccgatc | gatccccgct | attcactaca | tgattgcggc | ggctggcggt | 360 |
| aattctattc | cttgcgcgcc | ttatgcgacc | tttggaacac | gcgaactttc | tgaacatgtt | 420 |
| gcgctggctc | tcaaaaatcg | taaggcaact | ttgttacaac | atcatgggct | tatcgcttgt | 480 |
| gaggtgaatc | tggaaaaagc | gttatggctg | gcgcatgaag | ttgaagtgct | ggcgcaactt | 540 |
| tacctgacga | ccctggcgat | tacggacccg | gtgccagtgc | tgagcgatga | agagattgcc | 600 |
| gtagtgctgg | agaaattcaa | aacctatggg | ttacgaattg | aagagtaa | | 648 |

<210> SEQ ID NO 11
<211> LENGTH: 215
<212> TYPE: PRT
<213> ORGANISM: Escherichia coli

<400> SEQUENCE: 11

Met Glu Arg Asn Lys Leu Ala Arg Gln Ile Ile Asp Thr Cys Leu Glu
1               5                   10                  15

Met Thr Arg Leu Gly Leu Asn Gln Gly Thr Ala Gly Asn Val Ser Val
            20                  25                  30

Arg Tyr Gln Asp Gly Met Leu Ile Thr Pro Thr Gly Ile Pro Tyr Glu
        35                  40                  45

Lys Leu Thr Glu Ser His Ile Val Phe Ile Asp Gly Asn Gly Lys His
    50                  55                  60

Glu Glu Gly Lys Leu Pro Ser Ser Glu Trp Arg Phe His Met Ala Ala
 65                  70                  75                  80

Tyr Gln Ser Arg Pro Asp Ala Asn Ala Val Val His Asn His Ala Val
                 85                  90                  95

His Cys Thr Ala Val Ser Ile Leu Asn Arg Ser Ile Pro Ala Ile His
            100                 105                 110

Tyr Met Ile Ala Ala Ala Gly Gly Asn Ser Ile Pro Cys Ala Pro Tyr
        115                 120                 125

Ala Thr Phe Gly Thr Arg Glu Leu Ser Glu His Val Ala Leu Ala Leu
    130                 135                 140

Lys Asn Arg Lys Ala Thr Leu Leu Gln His His Gly Leu Ile Ala Cys
145                 150                 155                 160

Glu Val Asn Leu Glu Lys Ala Leu Trp Leu Ala His Glu Val Glu Val
                165                 170                 175

Leu Ala Gln Leu Tyr Leu Thr Thr Leu Ala Ile Thr Asp Pro Val Pro
            180                 185                 190

Val Leu Ser Asp Glu Glu Ile Ala Val Val Leu Glu Lys Phe Lys Thr
        195                 200                 205

Tyr Gly Leu Arg Ile Glu Glu
    210                 215

<210> SEQ ID NO 12
<211> LENGTH: 1104
<212> TYPE: DNA
<213> ORGANISM: Escherichia coli

<400> SEQUENCE: 12
atggaccgca ttattcaatc accgggtaaa tacatccagg gcgctgatgt gattaatcgt      60
ctgggcgaat acctgaagcc gctggcagaa cgctggttag tggtgggtga caaatttgtt     120
ttaggttttg ctcaatccac tgtcgagaaa agctttaaag atgctggact ggtagtagaa     180
attgcgccgt ttggcggtga atgttcgcaa aatgagatcg accgtctgcg tggcatcgcg     240
gagactgcgc agtgtggcgc aattctcggt atcggtggcg aaaaaccct cgatactgcc      300 aaagcactgg cacatttcat gggtgttccg gtagcgatcg caccgactat cgcctctacc     360
gatgcaccgt gcagcgcatt gtctgttatc tacaccgatg agggtgagtt tgaccgctat     420
ctgctgttgc aaataacccc gaatatggtc attgtcgaca ccaaaatcgt cgctggcgca     480
cctgcacgtc tgttagcggc gggtatcggc gatgcgctgg caacctggtt tgaagcgcgt     540
gcctgctctc gtagcggcgc gaccaccatg gcgggcggca agtgcaccca ggctgcgctg     600
gcactggctg aactgtgcta acacccctg ctggaagaag gcgaaaaagc gatgcttgct     660
gccgaacagc atgtagtgac tccggcgctg gagcgcgtga ttgaagcgaa cacctatttg     720
agcggtgttg gttttgaaag tggtggtctg gctgcggcgc acgcagtgca taacggcctg     780
accgctatcc cggacgcgca tcactattat cacggtgaaa aagtggcatt cggtacgctg     840
acgcagctgg ttctggaaaa tgcgccggtg gaggaaatcg aaaccgtagc tgcccttagc     900
catgcggtag gtttgccaat aactctcgct caactggata ttaagaagaa tgtcccggcg     960
aaaatgcgaa ttgtgcaga gcggcatgt gcagaaggtg aaaccattca caacatgcct      1020
ggcggcgcga cgccagatca ggtttacgcc gctctgctgg tagccgacca gtacggtcag    1080
cgtttcctgc aagagtggga ataa                                           1104

<210> SEQ ID NO 13
<211> LENGTH: 367

<212> TYPE: PRT
<213> ORGANISM: Escherichia coli

<400> SEQUENCE: 13

Met Asp Arg Ile Ile Gln Ser Pro Gly Lys Tyr Ile Gln Gly Ala Asp
1               5                   10                  15

Val Ile Asn Arg Leu Gly Glu Tyr Leu Lys Pro Leu Ala Glu Arg Trp
            20                  25                  30

Leu Val Val Gly Asp Lys Phe Val Leu Gly Phe Ala Gln Ser Thr Val
        35                  40                  45

Glu Lys Ser Phe Lys Asp Ala Gly Leu Val Val Glu Ile Ala Pro Phe
    50                  55                  60

Gly Gly Glu Cys Ser Gln Asn Glu Ile Asp Arg Leu Arg Gly Ile Ala
65                  70                  75                  80

Glu Thr Ala Gln Cys Gly Ala Ile Leu Gly Ile Gly Gly Gly Lys Thr
                85                  90                  95

Leu Asp Thr Ala Lys Ala Leu Ala His Phe Met Gly Val Pro Val Ala
            100                 105                 110

Ile Ala Pro Thr Ile Ala Ser Thr Asp Ala Pro Cys Ser Ala Leu Ser
        115                 120                 125

Val Ile Tyr Thr Asp Glu Gly Glu Phe Asp Arg Tyr Leu Leu Leu Pro
    130                 135                 140

Asn Asn Pro Asn Met Val Ile Val Asp Thr Lys Ile Val Ala Gly Ala
145                 150                 155                 160

Pro Ala Arg Leu Leu Ala Ala Gly Ile Gly Asp Ala Leu Ala Thr Trp
                165                 170                 175

Phe Glu Ala Arg Ala Cys Ser Arg Ser Gly Ala Thr Thr Met Ala Gly
            180                 185                 190

Gly Lys Cys Thr Gln Ala Ala Leu Ala Leu Ala Glu Leu Cys Tyr Asn
        195                 200                 205

Thr Leu Leu Glu Glu Gly Glu Lys Ala Met Leu Ala Ala Glu Gln His
    210                 215                 220

Val Val Thr Pro Ala Leu Glu Arg Val Ile Glu Ala Asn Thr Tyr Leu
225                 230                 235                 240

Ser Gly Val Gly Phe Glu Ser Gly Gly Leu Ala Ala Ala His Ala Val
                245                 250                 255

His Asn Gly Leu Thr Ala Ile Pro Asp Ala His His Tyr His Tyr His Gly
            260                 265                 270

Glu Lys Val Ala Phe Gly Thr Leu Thr Gln Leu Val Leu Glu Asn Ala
        275                 280                 285

Pro Val Glu Glu Ile Glu Thr Val Ala Ala Leu Ser His Ala Val Gly
    290                 295                 300

Leu Pro Ile Thr Leu Ala Gln Leu Asp Ile Lys Glu Asp Val Pro Ala
305                 310                 315                 320

Lys Met Arg Ile Val Ala Glu Ala Ala Cys Ala Glu Gly Glu Thr Ile
                325                 330                 335

His Asn Met Pro Gly Gly Ala Thr Pro Asp Gln Val Tyr Ala Ala Leu
            340                 345                 350

Leu Val Ala Asp Gln Tyr Gly Gln Arg Phe Leu Gln Glu Trp Glu
        355                 360                 365

<210> SEQ ID NO 14
<211> LENGTH: 1029
<212> TYPE: DNA
<213> ORGANISM: Saccharomyces cerevisiae

<400> SEQUENCE: 14

```
atgtcagttt tcgtttcagg tgctaacggg ttcattgccc aacacattgt cgatctcctg      60
ttgaaggaag actataaggt catcggttct gccagaagtc aagaaaaggc cgagaattta     120
acggaggcct ttggtaacaa cccaaaattc tccatggaag ttgtcccaga catatctaag     180
ctggacgcat tgaccatgt tttccaaaag cacggcaagg atatcaagat agttctacat      240
acggcctctc cattctgctt tgatatcact gacagtgaac gcgatttatt aattcctgct     300
gtgaacggtg ttaagggaat tctccactca attaaaaaat acgccgctga ttctgtagaa     360
cgtgtagttc tcacctcttc ttatgcagct gtgttcgata tggcaaaaga aaacgataag     420
tctttaacat ttaacgaaga atcctggaac ccagctacct gggagagttg ccaaagtgac     480
ccagttaacg cctactgtgg ttctaagaag tttgctgaaa aagcagcttg ggaatttcta     540
gaggagaata gagactctgt aaaattcgaa ttaactgccg ttaacccagt ttacgttttt     600
ggtccgcaaa tgtttgacaa agatgtgaaa aaacacttga acacatcttg cgaactcgtc     660
aacagcttga tgcatttatc accagaggac aagataccgg aactatttgg tggatacatt     720
gatgttcgtg atgttgcaaa ggctcattta gttgccttcc aaaagaggga acaattggt      780
caaagactaa tcgtatcgga ggccagattt actatgcagg atgttctcga tatccttaac     840
gaagacttcc ctgttctaaa aggcaatatt ccagtgggga aaccaggttc tggtgctacc     900
cataacaccc ttggtgctac tcttgataat aaaaagagta agaaattgtt aggtttcaag     960
ttcaggaact tgaaagagac cattgacgac actgcctccc aaattttaaa atttgagggc    1020
agaatataa                                                            1029
```

<210> SEQ ID NO 15
<211> LENGTH: 342
<212> TYPE: PRT
<213> ORGANISM: Saccharomyces cerevisiae

<400> SEQUENCE: 15

```
Met Ser Val Phe Val Ser Gly Ala Asn Gly Phe Ile Ala Gln His Ile
1               5                   10                  15

Val Asp Leu Leu Leu Lys Glu Asp Tyr Lys Val Ile Gly Ser Ala Arg
            20                  25                  30

Ser Gln Glu Lys Ala Glu Asn Leu Thr Glu Ala Phe Gly Asn Asn Pro
        35                  40                  45

Lys Phe Ser Met Glu Val Val Pro Asp Ile Ser Lys Leu Asp Ala Phe
    50                  55                  60

Asp His Val Phe Gln Lys His Gly Lys Asp Ile Lys Ile Val Leu His
65                  70                  75                  80

Thr Ala Ser Pro Phe Cys Phe Asp Ile Thr Asp Ser Glu Arg Asp Leu
                85                  90                  95

Leu Ile Pro Ala Val Asn Gly Val Lys Gly Ile Leu His Ser Ile Lys
            100                 105                 110

Lys Tyr Ala Ala Asp Ser Val Glu Arg Val Val Leu Thr Ser Ser Tyr
        115                 120                 125

Ala Ala Val Phe Asp Met Ala Lys Glu Asn Asp Lys Ser Leu Thr Phe
    130                 135                 140

Asn Glu Glu Ser Trp Asn Pro Ala Thr Trp Glu Ser Cys Gln Ser Asp
145                 150                 155                 160

Pro Val Asn Ala Tyr Cys Gly Ser Lys Lys Phe Ala Glu Lys Ala Ala
                165                 170                 175
```

```
Trp Glu Phe Leu Glu Glu Asn Arg Asp Ser Val Lys Phe Glu Leu Thr
            180                 185                 190
Ala Val Asn Pro Val Tyr Val Phe Gly Pro Gln Met Phe Asp Lys Asp
        195                 200                 205
Val Lys Lys His Leu Asn Thr Ser Cys Glu Leu Val Asn Ser Leu Met
210                 215                 220
His Leu Ser Pro Glu Asp Lys Ile Pro Glu Leu Phe Gly Gly Tyr Ile
225                 230                 235                 240
Asp Val Arg Asp Val Ala Lys Ala His Leu Val Ala Phe Gln Lys Arg
                245                 250                 255
Glu Thr Ile Gly Gln Arg Leu Ile Val Ser Glu Ala Arg Phe Thr Met
            260                 265                 270
Gln Asp Val Leu Asp Ile Leu Asn Glu Asp Phe Pro Val Leu Lys Gly
        275                 280                 285
Asn Ile Pro Val Gly Lys Pro Gly Ser Gly Ala Thr His Asn Thr Leu
290                 295                 300
Gly Ala Thr Leu Asp Asn Lys Lys Ser Lys Lys Leu Leu Gly Phe Lys
305                 310                 315                 320
Phe Arg Asn Leu Lys Glu Thr Ile Asp Asp Thr Ala Ser Gln Ile Leu
                325                 330                 335
Lys Phe Glu Gly Arg Ile
            340

<210> SEQ ID NO 16
<211> LENGTH: 984
<212> TYPE: DNA
<213> ORGANISM: Saccharomyces cerevisiae

<400> SEQUENCE: 16
atgtcttcac tggttactct taataacggt ctgaaaatgc ccctagtcgg cttagggtgc      60
tggaaaattg acaaaaaagt ctgtgcgaat caaatttatg aagctatcaa attaggctac     120
cgtttattcg atggtgcttg cgactacggc aacgaaaagg aagttggtga aggtatcagg     180
aaagccatct ccgaaggtct tgtttctaga aaggatatat ttgttgtttc aaagttatgg     240
aacaattttc accatcctga tcatgtaaaa ttagctttaa agaagacctt aagcgatatg     300
ggacttgatt atttagacct gtattatatt cacttcccaa tcgccttcaa atatgttcca     360
tttgaagaga atacccctcc aggattctat acgggcgcag atgacgagaa gaaaggtcac     420
atcaccgaag cacatgtacc aatcatagat acgtaccggg ctctggaaga atgtgttgat     480
gaaggcttga ttaagtctat tggtgtttcc aactttcagg gaagcttgat tcaagattta     540
ttacgtggtt gtagaatcaa gcccgtggct ttgcaaattg aacaccatcc ttatttgact     600
caagaacacc tagttgagtt tgtaaaatta cacgatatcc aagtagttgc ttactcctcc     660
ttcggtcctc aatcattcat tgagatggac ttacagttgg caaaaaccac gccaactctg     720
ttcgagaatg atgtaatcaa gaaggtctca caaaaccatc caggcagtac cacttcccaa     780
gtattgctta gatgggcaac tcagagaggc attgccgtca ttccaaaatc ttccaagaag     840
gaaaggttac ttggcaacct agaaatcgaa aaaaagttca ctttaacgga gcaagaattg     900
aaggatattt ctgcactaaa tgccaacatc agatttaatg atccatggac ctggttggat     960
ggtaaattcc ccacttttgc ctga                                           984

<210> SEQ ID NO 17
<211> LENGTH: 327
```

<212> TYPE: PRT
<213> ORGANISM: Saccharomyces cerevisiae

<400> SEQUENCE: 17

Met Ser Ser Leu Val Thr Leu Asn Asn Gly Leu Lys Met Pro Leu Val
1               5                   10                  15

Gly Leu Gly Cys Trp Lys Ile Asp Lys Val Cys Ala Asn Gln Ile
            20                  25                  30

Tyr Glu Ala Ile Lys Leu Gly Tyr Arg Leu Phe Asp Gly Ala Cys Asp
        35                  40                  45

Tyr Gly Asn Glu Lys Glu Val Gly Glu Gly Ile Arg Lys Ala Ile Ser
    50                  55                  60

Glu Gly Leu Val Ser Arg Lys Asp Ile Phe Val Val Ser Lys Leu Trp
65                  70                  75                  80

Asn Asn Phe His His Pro Asp His Val Lys Leu Ala Leu Lys Lys Thr
                85                  90                  95

Leu Ser Asp Met Gly Leu Asp Tyr Leu Asp Leu Tyr Tyr Ile His Phe
            100                 105                 110

Pro Ile Ala Phe Lys Tyr Val Pro Phe Glu Glu Lys Tyr Pro Pro Gly
        115                 120                 125

Phe Tyr Thr Gly Ala Asp Asp Glu Lys Lys Gly His Ile Thr Glu Ala
130                 135                 140

His Val Pro Ile Ile Asp Thr Tyr Arg Ala Leu Glu Glu Cys Val Asp
145                 150                 155                 160

Glu Gly Leu Ile Lys Ser Ile Gly Val Ser Asn Phe Gln Gly Ser Leu
            165                 170                 175

Ile Gln Asp Leu Leu Arg Gly Cys Arg Ile Lys Pro Val Ala Leu Gln
        180                 185                 190

Ile Glu His His Pro Tyr Leu Thr Gln Glu His Leu Val Glu Phe Cys
    195                 200                 205

Lys Leu His Asp Ile Gln Val Val Ala Tyr Ser Ser Phe Gly Pro Gln
210                 215                 220

Ser Phe Ile Glu Met Asp Leu Gln Leu Ala Lys Thr Thr Pro Thr Leu
225                 230                 235                 240

Phe Glu Asn Asp Val Ile Lys Lys Val Ser Gln Asn His Pro Gly Ser
            245                 250                 255

Thr Thr Ser Gln Val Leu Leu Arg Trp Ala Thr Gln Arg Gly Ile Ala
        260                 265                 270

Val Ile Pro Lys Ser Ser Lys Lys Glu Arg Leu Leu Gly Asn Leu Glu
    275                 280                 285

Ile Glu Lys Lys Phe Thr Leu Thr Glu Gln Glu Leu Lys Asp Ile Ser
290                 295                 300

Ala Leu Asn Ala Asn Ile Arg Phe Asn Asp Pro Trp Thr Trp Leu Asp
305                 310                 315                 320

Gly Lys Phe Pro Thr Phe Ala
                325

<210> SEQ ID NO 18
<211> LENGTH: 1164
<212> TYPE: DNA
<213> ORGANISM: Escherichia coli

<400> SEQUENCE: 18
atgaacaact taatctgca cacccccaacc cgcattctgt tggtaaagg cgcaatcgct      60 ggtttacgcg aacaaattcc tcacgatgct cgcgtattga ttacctacgg cggcggcagc    120

```
gtgaaaaaaa ccggcgttct cgatcaagtt ctggatgccc tgaaaggcat ggacgtgctg        180
gaatttggcg gtattgagcc aaacccggct tatgaaacgc tgatgaacgc cgtgaaactg        240
gttcgcgaac agaaagtgac tttcctgctg gcggttggcg gcggttctgt actggacggc        300
accaaattta tcgccgcagc ggctaactat ccggaaaata tcgatccgtg gcacattctg        360
caaacgggcg gtaaagagat taaaagcgcc atcccgatgg gctgtgtgct gacgctgcca        420
gcaaccggtt cagaatccaa cgcagaagcg gtgatctccc gtaaaaccac aggcgacaag        480
caggcgttcc attctgccca tgttcagccg gtatttgccg tgctcgatcc ggtttatacc        540
tacaccctgc cgccgcgtca ggtggctaac ggcgtagtgg acgcctttgt acacaccgtg        600
gaacagtatg ttaccaaacc ggttgatgcc aaaattcagg accgtttcgc agaaggcatt        660
ttgctgacgc taatcgaaga tggtccgaaa gccctgaaag agccagaaaa ctacgatgtg        720
cgcgccaacg tcatgtgggc ggcgactcag gcgctgaacg gtttgattgg cgctggcgta        780
ccgcaggact gggcaacgca tatgctgggc acgaactga ctgcgatgca cggtctggat        840
cacgcgcaaa cactggctat cgtcctgcct gcactgtgga tgaaaaacg cgataccaag        900 cgcgctaagc tgctgcaata tgctgaacgc gtctggaaca tcactgaagg ttccgatgat        960
gagcgtattg acgccgcgat tgccgcaacc cgcaatttct ttgagcaatt aggcgtgccg       1020
acccacctct ccgactacgg tctggacggc agctccatcc cggctttgct gaaaaaactg       1080
gaagagcacg gcatgaccca actgggcgaa aatcatgaca ttacgttgga tgtcagccgc       1140
cgtatatacg aagccgcccg ctaa                                              1164
```

<210> SEQ ID NO 19
<211> LENGTH: 1167
<212> TYPE: DNA
<213> ORGANISM: Artificial Sequence
<220> FEATURE:
<223> OTHER INFORMATION: Codon Optimized E. coli Sequence

<400> SEQUENCE: 19

```
atgaacaatt ttaatttgca tactccaact agaatattat ttggaaaagg tgcaattgca         60
ggtttaaggg aacaaatacc acatgatgca agggtattaa tcacatacgg tggtggttct        120
gtcaagaaaa ctggtgtatt ggatcaagta ttggatgctt taagggtat ggatgtcttg        180 gaatttggag gaatcgaacc aaaccctgct tacgagactt aatgaatgc tgtcaaattg        240 gtcagagaac aaaaggtaac attcttattg gctgttggag gtggatcagt attagatggt        300
acaaagttca ttgctgctgc agcaaattat ccagaaaaca ttgatccatg gcatatattg        360
caaactggtg gtaaggaaat aaagtcagct atcccaatgg gatgtgtttt gacattgcct        420
gcaacaggat cagaatcaaa cgctgaagca gtcatctcaa gaaagactac aggtgacaaa        480
caggcattcc attctgccca tgtccaacct gtatttgctg ttttagaccc tgtatacact        540
tacacattac caccaaggca agtcgcaaat ggagttgtcg atgcctttgt tcacactgta        600
gaacagtacg tcaccaaacc agtcgatgca agatccagg acaggtttgc agaaggtatt        660
ttattgacat taatcgaaga tggaccaaaa gcattgaaag agccagagaa ctatgacgtt        720
agggcaaatg ttatgtgggc tgctacccag gcattgaacg gtttaattgg tgcaggagtt        780
ccacaagatt gggctacaca catgttgggt cacgagttga ccgccatgca cggtttggac        840
catgcacaga ctttagccat tgttttgcct gccttatgga acgagaaaag agatactaag        900
agggctaagt tattacaata cgctgaaagg gtttggaata tcaccgaggg atctgatgat        960
```

-continued

```
gaaaggattg atgccgctat tgcagccact agaaacttct ttgaacaatt aggtgttcca    1020
actcacttgt ctgactatgg tttagatgga tcatctattc cagctttgtt gaagaaattg    1080
gaagagcacg gtatgaccca gttgggtgag aatcatgata taaccttaga tgtatctagg    1140
agaatctacg aggctgctag ataatga                                        1167
```

<210> SEQ ID NO 20
<211> LENGTH: 387
<212> TYPE: PRT
<213> ORGANISM: Escherichia coli

<400> SEQUENCE: 20

```
Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Glu Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Thr Arg Asn Phe Phe Glu Gln
                325                 330                 335
```

```
Leu Gly Val Pro Thr His Leu Ser Asp Tyr Gly Leu Asp Gly Ser Ser
        340                 345                 350

Ile Pro Ala Leu Leu Lys Lys Leu Glu Glu His Gly Met Thr Gln Leu
    355                 360                 365

Gly Glu Asn His Asp Ile Thr Leu Asp Val Ser Arg Arg Ile Tyr Glu
    370                 375                 380

Ala Ala Arg
385
```

<210> SEQ ID NO 21
<211> LENGTH: 1164
<212> TYPE: DNA
<213> ORGANISM: Escherichia coli

<400> SEQUENCE: 21

```
atgaacaact ttaatctgca caccccaacc cgcattctgt ttggtaaagg cgcaatcgct      60
ggtttacgcg aacaaattcc tcacgatgct cgcgtattga ttacctacgg cggcggcagc     120
gtgaaaaaaa ccggcgttct cgatcaagtt ctggatgccc tgaaaggcat ggacgtgctg     180
gaatttggcg gtattgagcc aaacccggct tatgaaacgc tgatgaacgc cgtgaaactg     240
gttcgcgaac agaaagtgac tttcctgctg gcggttggcg gcggttctgt actggacggc     300
accaaattta cgccgcagc ggctaactat ccggaaaata tcgatccgtg gcacattctg     360
caaacgggcg taaagagat aaaagcgcc atcccgatgg ctgtgtgct gacgctgcca     420
gcaaccggtt cagaatccaa cgcaggcgcg gtgatctccc gtaaaaccac aggcgacaag     480
caggcgttcc attctgccca tgttcagccg gtatttgccg tgctcgatcc ggtttatacc     540
tacacccctgc cgccgcgtca ggtggctaac ggcgtagtgg acgcctttgt acacaccgtg     600
gaacagtatg ttaccaaacc ggttgatgcc aaaattcagg accgtttcgc agaaggcatt     660
ttgctgacgc taatcgaaga tggtccgaaa gccctgaaag agccagaaaa ctacgatgtg     720
cgcgccaacg tcatgtgggc ggcgactcag cgcctgaacg gtttgattgg cgctggcgta     780
ccgcaggact gggcaacgca tatgctgggc acgaactga ctgcgatgca cggtctggat     840
cacgcgcaaa cactggctat cgtcctgcct gcactgtgga tgaaaaacg cgataccaag     900
cgcgctaagc tgctgcaata tgctgaacgc gtctggaaca tcactgaagg ttccgatgat     960
gagcgtattg acgccgcgat tgccgcaacc cgcaatttct ttgagcaatt aggcgtgccg    1020
acccacctct ccgactacgg tctggacggc agctccatcc cggctttgct gaaaaaactg    1080
gaagagcacg gcatgaccca actgggcgaa aatcatgaca ttacgttgga tgtcagccgc    1140
cgtatatacg aagccgcccg ctaa                                          1164
```

<210> SEQ ID NO 22
<211> LENGTH: 1164
<212> TYPE: DNA
<213> ORGANISM: Artificial Sequence
<220> FEATURE:
<223> OTHER INFORMATION: Codon Optimized E. coli Sequence

<400> SEQUENCE: 22

```
atgaacaact ttaatctgca caccccaacc cgcattctgt ttggtaaagg cgcaatcgct      60
ggtttacgcg aacaaattcc tcacgatgct cgcgtattga ttacctacgg cggcggcagc     120
gtgaaaaaaa ccggcgttct cgatcaagtt ctggatgccc tgaaaggcat ggacgtgctg     180
gaatttggcg gtattgagcc aaacccggct tatgaaacgc tgatgaacgc cgtgaaactg     240
gttcgcgaac agaaagtgac tttcctgctg gcggttggcg gcggttctgt actggacggc     300
```

-continued

```
accaaattta tcgccgcagc ggctaactat ccggaaaata tcgatccgtg gcacattctg    360
caaacgggcg gtaaagagat taaaagcgcc atcccgatgg gctgtgtgct gacgctgcca    420
gcaaccggtt cagaatccaa cgcaggcgcg gtgatctccc gtaaaaccac aggcgacaag    480
caggcgttcc attctgccca tgttcagccg gtatttgccg tgctcgatcc ggtttatacc    540
tacaccctgc cgccgcgtca ggtggctaac ggcgtagtgg acgcctttgt acacaccgtg    600
gaacagtatg ttaccaaacc ggttgatgcc aaaattcagg accgtttcgc agaaggcatt    660
ttgctgacgc taatcgaaga tggtccgaaa gccctgaaag agccagaaaa ctacgatgtg    720
cgcgccaacg tcatgtgggc ggcgactcag gcgctgaacg gtttgattgg cgctggcgta    780
ccgcaggact gggcaacgca tatgctgggc cacgaactga ctgcgatgca cggtctggat    840
cacgcgcaaa cactggctat cgtcctgcct gcactgtgga atgaaaaacg cgataccaag    900
cgcgctaagc tgctgcaata tgctgaacgc gtctggaaca tcactgaagg ttccgatgat    960
gagcgtattg acgccgcgat tgccgcaacc cgcaatttct ttgagcaatt aggcgtgccg   1020
acccacctct ccgactacgg tctggacggc agctccatcc cggctttgct gaaaaaactg   1080
gaagagcacg gcatgaccca actgggcgaa aatcatgaca ttacgttgga tgtcagccgc   1140
cgtatatacg aagccgcccg ctaa                                          1164
```

<210> SEQ ID NO 23
<211> LENGTH: 387
<212> TYPE: PRT
<213> ORGANISM: Escherichia coli

<400> SEQUENCE: 23

```
Met Asn Asn Phe Asn Leu His Thr Pro Thr Arg Ile Leu Phe Gly Lys
 1               5                  10                  15

Gly Ala Ile Ala Gly Leu Arg Glu Gln Ile Pro His Asp Ala Arg Val
                20                  25                  30

Leu Ile Thr Tyr Gly Gly Gly Ser Val Lys Lys Thr Gly Val Leu Asp
            35                  40                  45

Gln Val Leu Asp Ala Leu Lys Gly Met Asp Val Leu Glu Phe Gly Gly
        50                  55                  60

Ile Glu Pro Asn Pro Ala Tyr Glu Thr Leu Met Asn Ala Val Lys Leu
 65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
```

```
                 210                 215                 220
Ile Glu Asp Gly Pro Lys Ala Leu Lys Glu Pro Glu Asn Tyr Asp Val
225                 230                 235                 240

Arg Ala Asn Val Met Trp Ala Thr Gln Ala Leu Asn Gly Leu Ile
                245                 250                 255

Gly Ala Gly Val Pro Gln Asp Trp Ala Thr His Met Leu Gly His Glu
                260                 265                 270

Leu Thr Ala Met His Gly Leu Asp His Ala Gln Thr Leu Ala Ile Val
            275                 280                 285

Leu Pro Ala Leu Trp Asn Glu Lys Arg Asp Thr Lys Arg Ala Lys Leu
290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
                340                 345                 350

Ile Pro Ala Leu Leu Lys Lys Leu Glu Glu His Gly Met Thr Gln Leu
            355                 360                 365

Gly Glu Asn His Asp Ile Thr Leu Asp Val Ser Arg Arg Ile Tyr Glu
370                 375                 380

Ala Ala Arg
385

<210> SEQ ID NO 24
<211> LENGTH: 981
<212> TYPE: DNA
<213> ORGANISM: Escherichia coli

<400> SEQUENCE: 24
atgaaaaaga tacctttagg cacaacggat attacgcttt cgcgaatggg gttggggaca    60
tgggccattg gcggcggtcc tgcatggaat ggcgatctcg atcggcaaat atgtattgat   120
acgattcttg aagcccatcg ttgtggcatt aatctgattg atactgcgcc aggatataac   180
tttggcaata gtgaagttat cgtcggtcag gcgttaaaaa aactgccccg tgaacaggtt   240
gtagtagaaa ccaaatgcgg cattgtctgg gaacgaaaag gaagtttatt caacaaagtt   300
ggcgatcggc agttgtataa aaaccttttcc ccggaatcta tccgcgaaga ggtagcagcg   360
agcttgcaac gtctgggtat tgattacatc gatatctaca tgacgcactg gcagtcggtg   420
ccgccatttt ttacgccgat cgctgaaact gtcgcagtgc ttaatgagtt aaagtctgaa   480
gggaaaattc gcgctatagg cgctgctaac gtcgatgctg accatatccg cgagtatctg   540
caatatggtg aactggatat tattcaggcg aaatacagta cctcgaccg ggcaatggaa    600 aacgaactgc tgccactatg tcgtgataat ggcattgtgg ttcaggttta ttccccgcta   660
gagcagggat tgttgaccgg caccatcact cgtgattacg ttccgggcgg cgctcgggca   720
aataaagtct ggttccagcg tgaaaacatg ctgaaagtga ttgatatgct tgaacagtgg   780
cagccacttt gtgctcgtta tcagtgcaca attcccactc tggcactggc gtggatatta   840
aaacagagtg atttaatctc cattcttagt ggggctactg caccggaaca ggtacgcgaa   900
aatgtcgcgg cactgaatat caacttatcg gatgcagacg caacattgat gagggaaatg   960
gcagaggccc tggagcgtta a                                             981

<210> SEQ ID NO 25
```

```
<211> LENGTH: 326
<212> TYPE: PRT
<213> ORGANISM: Escherichia coli

<400> SEQUENCE: 25

Met Lys Lys Ile Pro Leu Gly Thr Thr Asp Ile Thr Leu Ser Arg Met
1               5                   10                  15

Gly Leu Gly Thr Trp Ala Ile Gly Gly Pro Ala Trp Asn Gly Asp
            20                  25                  30

Leu Asp Arg Gln Ile Cys Ile Asp Thr Ile Leu Glu Ala His Arg Cys
        35                  40                  45

Gly Ile Asn Leu Ile Asp Thr Ala Pro Gly Tyr Asn Phe Gly Asn Ser
    50                  55                  60

Glu Val Ile Val Gly Gln Ala Leu Lys Lys Leu Pro Arg Glu Gln Val
65                  70                  75                  80

Val Val Glu Thr Lys Cys Gly Ile Val Trp Glu Arg Lys Gly Ser Leu
                85                  90                  95

Phe Asn Lys Val Gly Asp Arg Gln Leu Tyr Lys Asn Leu Ser Pro Glu
            100                 105                 110

Ser Ile Arg Glu Glu Val Ala Ala Ser Leu Gln Arg Leu Gly Ile Asp
        115                 120                 125

Tyr Ile Asp Ile Tyr Met Thr His Trp Gln Ser Val Pro Pro Phe Phe
    130                 135                 140

Thr Pro Ile Ala Glu Thr Val Ala Val Leu Asn Glu Leu Lys Ser Glu
145                 150                 155                 160

Gly Lys Ile Arg Ala Ile Gly Ala Ala Asn Val Asp Ala Asp His Ile
                165                 170                 175

Arg Glu Tyr Leu Gln Tyr Gly Glu Leu Asp Ile Ile Gln Ala Lys Tyr
            180                 185                 190

Ser Ile Leu Asp Arg Ala Met Glu Asn Glu Leu Leu Pro Leu Cys Arg
        195                 200                 205

Asp Asn Gly Ile Val Val Gln Val Tyr Ser Pro Leu Glu Gln Gly Leu
    210                 215                 220

Leu Thr Gly Thr Ile Thr Arg Asp Tyr Val Pro Gly Gly Ala Arg Ala
225                 230                 235                 240

Asn Lys Val Trp Phe Gln Arg Glu Asn Met Leu Lys Val Ile Asp Met
                245                 250                 255

Leu Glu Gln Trp Gln Pro Leu Cys Ala Arg Tyr Gln Cys Thr Ile Pro
            260                 265                 270

Thr Leu Ala Leu Ala Trp Ile Leu Lys Gln Ser Asp Leu Ile Ser Ile
        275                 280                 285

Leu Ser Gly Ala Thr Ala Pro Glu Gln Val Arg Glu Asn Val Ala Ala
    290                 295                 300

Leu Asn Ile Asn Leu Ser Asp Ala Asp Ala Thr Leu Met Arg Glu Met
305                 310                 315                 320

Ala Glu Ala Leu Glu Arg
                325

<210> SEQ ID NO 26
<211> LENGTH: 1149
<212> TYPE: DNA
<213> ORGANISM: Escherichia coli

<400> SEQUENCE: 26
atggctaaca gaatgattct gaacgaaacg gcatggtttg gtcggggtgc tgttggggct      60
```

```
ttaaccgatg aggtgaaacg ccgtggttat cagaaggcgc tgatcgtcac cgataaaacg      120
ctggtgcaat gcggcgtggt ggcgaaagtg accgataaga tggatgctgc agggctggca      180
tgggcgattt acgacggcgt agtgcccaac ccaacaatta ctgtcgtcaa agaagggctc      240
ggtgtattcc agaatagcgg cgcggattac ctgatcgcta ttggtggtgg ttctccacag      300
gatacttgta aagcgattgg cattatcagc aacaacccgg agtttgccga tgtgcgtagc      360
ctggaagggc tttccccgac caataaaccc agtgtaccga ttctggcaat tcctaccaca      420
gcaggtactg cggcagaagt gaccattaac tacgtgatca ctgacgaaga gaaacggcgc      480
aagtttgttt gcgttgatcc gcatgatatc ccgcaggtgg cgtttattga cgctgacatg      540
atggatggta tgcctccagc gctgaaagct gcgacgggtg tcgatgcgct cactcatgct      600
attgaggggt atattacccg tggcgcgtgg gcgctaaccg atgcactgca cattaaagcg      660
attgaaatca ttgctggggc gctgcgagga tcggttgctg gtgataagga tgccggagaa      720
gaaatggcgc tcgggcagta tgttgcgggt atgggcttct cgaatgttgg gttagggttg      780
gtgcatggta tggcgcatcc actgggcgcg ttttataaca ctccacacgg tgttgcgaac      840
gccatcctgt taccgcatgt catgcgttat aacgctgact ttaccggtga agtaccgcc     900 gatatcgcgc gcgttatggg cgtgaaagtg gaaggtatga gcctggaaga ggcgcgtaat      960
gccgctgttg aagcggtgtt tgctctcaac cgtgatgtcg gtattccgcc acatttgcgt     1020
gatgttggtg tacgcaagga agacattccg gcactggcgc aggcggcact ggatgatgtt     1080
tgtaccggtg caacccgcg tgaagcaacg cttgaggata ttgtagagct ttaccatacc     1140
gcctggtaa                                                             1149

<210> SEQ ID NO 27
<211> LENGTH: 1149
<212> TYPE: DNA
<213> ORGANISM: Artificial Sequence
<220> FEATURE:
<223> OTHER INFORMATION: Codon Optimized E. coli Sequence

<400> SEQUENCE: 27
atggctaaca gaatgattct gaacgaaacg catggtttg gtcggggtgc tgttggggct        60
ttaaccgatg aggtgaaacg ccgtggttat cagaaggcgc tgatcgtcac cgataaaacg      120
ctggtgcaat gcggcgtggt ggcgaaagtg accgataaga tggatgctgc agggctggca      180
tgggcgattt acgacggcgt agtgcccaac ccaacaatta ctgtcgtcaa agaagggctc      240
ggtgtattcc agaatagcgg cgcggattac ctgatcgcta ttggtggtgg ttctccacag      300
gatacttgta aagcgattgg cattatcagc aacaacccgg agtttgccga tgtgcgtagc      360
ctggaagggc tttccccgac caataaaccc agtgtaccga ttctggcaat tcctaccaca      420
gcaggtactg cggcagaagt gaccattaac tacgtgatca ctgacgaaga gaaacggcgc      480
aagtttgttt gcgttgatcc gcatgatatc ccgcaggtgg cgtttattga cgctgacatg      540
atggatggta tgcctccagc gctgaaagct gcgacgggtg tcgatgcgct cactcatgct      600
attgaggggt atattacccg tggcgcgtgg gcgctaaccg atgcactgca cattaaagcg      660
attgaaatca ttgctggggc gctgcgagga tcggttgctg gtgataagga tgccggagaa      720
gaaatggcgc tcgggcagta tgttgcgggt atgggcttct cgaatgttgg gttagggttg      780
gtgcatggta tggcgcatcc actgggcgcg ttttataaca ctccacacgg tgttgcgaac      840
gccatcctgt taccgcatgt catgcgttat aacgctgact ttaccggtga agtaccgcc     900 gatatcgcgc gcgttatggg cgtgaaagtg gaaggtatga gcctggaaga ggcgcgtaat      960
```

```
gccgctgttg aagcggtgtt tgctctcaac cgtgatgtcg gtattccgcc acatttgcgt    1020
gatgttggtg tacgcaagga agacattccg gcactggcgc aggcggcact ggatgatgtt    1080
tgtaccggtg caacccgcg tgaagcaacg cttgaggata ttgtagagct ttaccatacc     1140
gcctggtaa                                                            1149
```

<210> SEQ ID NO 28
<211> LENGTH: 382
<212> TYPE: PRT
<213> ORGANISM: Escherichia coli

<400> SEQUENCE: 28

```
Met Ala Asn Arg Met Ile Leu Asn Glu Thr Ala Trp Phe Gly Arg Gly
1               5                   10                  15

Ala Val Gly Ala Leu Thr Asp Glu Val Lys Arg Gly Tyr Gln Lys
            20                  25                  30

Ala Leu Ile Val Thr Asp Lys Thr Leu Val Gln Cys Gly Val Val Ala
        35                  40                  45

Lys Val Thr Asp Lys Met Asp Ala Ala Gly Leu Ala Trp Ala Ile Tyr
    50                  55                  60

Asp Gly Val Val Pro Asn Pro Thr Ile Thr Val Lys Glu Gly Leu
65                  70                  75                  80

Gly Val Phe Gln Asn Ser Gly Ala Asp Tyr Leu Ile Ala Ile Gly Gly
                85                  90                  95

Gly Ser Pro Gln Asp Thr Cys Lys Ala Ile Gly Ile Ile Ser Asn Asn
            100                 105                 110

Pro Glu Phe Ala Asp Val Arg Ser Leu Glu Gly Leu Ser Pro Thr Asn
        115                 120                 125

Lys Pro Ser Val Pro Ile Leu Ala Ile Pro Thr Thr Ala Gly Thr Ala
    130                 135                 140

Ala Glu Val Thr Ile Asn Tyr Val Ile Thr Asp Glu Glu Lys Arg Arg
145                 150                 155                 160

Lys Phe Val Cys Val Asp Pro His Asp Ile Pro Gln Val Ala Phe Ile
                165                 170                 175

Asp Ala Asp Met Met Asp Gly Met Pro Pro Ala Leu Lys Ala Ala Thr
            180                 185                 190

Gly Val Asp Ala Leu Thr His Ala Ile Glu Gly Tyr Ile Thr Arg Gly
        195                 200                 205

Ala Trp Ala Leu Thr Asp Ala Leu His Ile Lys Ala Ile Glu Ile Ile
    210                 215                 220

Ala Gly Ala Leu Arg Gly Ser Val Ala Gly Asp Lys Asp Ala Gly Glu
225                 230                 235                 240

Glu Met Ala Leu Gly Gln Tyr Val Ala Gly Met Gly Phe Ser Asn Val
                245                 250                 255

Gly Leu Gly Leu Val His Gly Met Ala His Pro Leu Gly Ala Phe Tyr
            260                 265                 270

Asn Thr Pro His Gly Val Ala Asn Ala Ile Leu Leu Pro His Val Met
        275                 280                 285

Arg Tyr Asn Ala Asp Phe Thr Gly Glu Lys Tyr Arg Asp Ile Ala Arg
    290                 295                 300

Val Met Gly Val Lys Val Glu Gly Met Ser Leu Glu Glu Ala Arg Asn
305                 310                 315                 320

Ala Ala Val Glu Ala Val Phe Ala Leu Asn Arg Asp Val Gly Ile Pro
                325                 330                 335
```

```
Pro His Leu Arg Asp Val Gly Val Arg Lys Glu Asp Ile Pro Ala Leu
            340                 345                 350
Ala Gln Ala Ala Leu Asp Asp Val Cys Thr Gly Gly Asn Pro Arg Glu
            355                 360                 365
Ala Thr Leu Glu Asp Ile Val Glu Leu Tyr His Thr Ala Trp
            370                 375                 380

<210> SEQ ID NO 29
<211> LENGTH: 804
<212> TYPE: DNA
<213> ORGANISM: Escherichia coli

<400> SEQUENCE: 29
atggctatcc ctgcatttgg tttaggtact ttccgtctga agacgacgt tgttatttca      60 tctgtgataa cggcgcttga acttggttat cgcgcaattg ataccgcaca aatctatgat    120
aacgaagccg cagtaggtca ggcgattgca gaaagtggcg tgccacgtca tgaactctac    180
atcaccacta aaatctggat tgaaaatctc agcaaagaca aattgatccc aagtctgaaa    240
gagagcctgc aaaaattgcg taccgattat gttgatctga cgctaatcca ctggccgtca    300
ccaaacgatg aagtctctgt tgaagagttt atgcaggcgc tgctggaagc caaaaaacaa    360
gggctgacgc gtgagatcgg tatttccaac ttcacgatcc cgttgatgga aaaagcgatt    420
gctgctgttg gtgctgaaaa catcgctact aaccagattg aactctctcc ttatctgcaa    480
aaccgtaaag tggttgcctg ggctaaacag cacggcatcc atattacttc ctatatgacg    540
ctggcgtatg gtaaggccct gaaagatgag gttattgctc gtatcgcagc taaacacaat    600
gcgactccgg cacaagtgat tctggcgtgg gctatggggg aaggttactc agtaattcct    660
tcttctacta aacgtaaaaa cctggaaagt aatcttaagg cacaaaattt acagcttgat    720
gccgaagata aaaagcgat cgccgcactg gattgcaacg accgcctggt tagcccggaa    780
ggtctggctc ctgaatggga ttaa                                             804

<210> SEQ ID NO 30
<211> LENGTH: 267
<212> TYPE: PRT
<213> ORGANISM: Escherichia coli

<400> SEQUENCE: 30

Met Ala Ile Pro Ala Phe Gly Leu Gly Thr Phe Arg Leu Lys Asp Asp
1               5                   10                  15
Val Val Ile Ser Ser Val Ile Thr Ala Leu Glu Leu Gly Tyr Arg Ala
            20                  25                  30
Ile Asp Thr Ala Gln Ile Tyr Asp Asn Glu Ala Ala Val Gly Gln Ala
            35                  40                  45
Ile Ala Glu Ser Gly Val Pro Arg His Glu Leu Tyr Ile Thr Thr Lys
        50                  55                  60
Ile Trp Ile Glu Asn Leu Ser Lys Asp Lys Leu Ile Pro Ser Leu Lys
65                  70                  75                  80
Glu Ser Leu Gln Lys Leu Arg Thr Asp Tyr Val Asp Leu Thr Leu Ile
                85                  90                  95
His Trp Pro Ser Pro Asn Asp Glu Val Ser Val Glu Glu Phe Met Gln
            100                 105                 110
Ala Leu Leu Glu Ala Lys Lys Gln Gly Leu Thr Arg Glu Ile Gly Ile
            115                 120                 125
Ser Asn Phe Thr Ile Pro Leu Met Glu Lys Ala Ile Ala Ala Val Gly
```

Ala Glu Asn Ile Ala Thr Asn Gln Ile Glu Leu Ser Pro Tyr Leu Gln
            130                 135                 140

Asn Arg Lys Val Val Ala Trp Ala Lys Gln His Gly Ile His Ile Thr
145                 150                 155                 160

Ser Tyr Met Thr Leu Ala Tyr Gly Lys Ala Leu Lys Asp Glu Val Ile
                165                 170                 175

Ala Arg Ile Ala Ala Lys His Asn Ala Thr Pro Ala Gln Val Ile Leu
            180                 185                 190

Ala Trp Ala Met Gly Glu Gly Tyr Ser Val Ile Pro Ser Ser Thr Lys
        195                 200                 205

Arg Lys Asn Leu Glu Ser Asn Leu Lys Ala Gln Asn Leu Gln Leu Asp
    210                 215                 220

Ala Glu Asp Lys Lys Ala Ile Ala Ala Leu Asp Cys Asn Asp Arg Leu
225                 230                 235                 240

Val Ser Pro Glu Gly Leu Ala Pro Glu Trp Asp
                245                 250                 255

260                 265

<210> SEQ ID NO 31
<211> LENGTH: 828
<212> TYPE: DNA
<213> ORGANISM: Escherichia coli

<400> SEQUENCE: 31
atggctaatc caaccgttat taagctacag gatggcaatg tcatgcccca gctgggactg      60
ggcgtctggc aagcaagtaa tgaggaagta atcaccgcca ttcaaaaagc gttagaagtg     120
ggttatcgct cgattgatac cgccgcggcc tacaagaacg aagaaggtgt cggcaaagcc     180
ctgaaaaatg cctcagtcaa cagagaagaa ctgttcatca ccactaagct gtggaacgac     240
gaccacaagc gccccgcga agccctgctc gacagcctga aaaaactcca gcttgattat     300
atcgacctct acttaatgca ctggcccgtt cccgctatcg accattatgt cgaagcatgg     360
aaaggcatga tcgaattgca aaagaggga ttaatcaaaa gcatcggcgt gtgcaacttc     420
cagatccatc acctgcaacg cctgattgat gaaactggcg tgacgcctgt gataaaccag     480
atcgaacttc atccgctgat gcaacaacgc cagctacacg cctggaacgc gacacacaaa     540
atccagaccg aatcctggag cccattagcc aaggagggga aaggcgtttt cgatcagaaa     600
gtcattcgcg atctggcaga taaatacggc aaaaccccgg cgcagattgt tatccgctgg     660
catctggata cggcctggt ggtgatcccg aaatcggtca caccttcacg tattgccgaa     720
aactttgatg tctgggattt ccgtctcgac aaagacgaac tcggcgaaat tgcaaaactc     780
gatcagggca agcgtctcgg tcccgatcct gaccagttcg cggctaa             828

<210> SEQ ID NO 32
<211> LENGTH: 275
<212> TYPE: PRT
<213> ORGANISM: Escherichia coli

<400> SEQUENCE: 32

Met Ala Asn Pro Thr Val Ile Lys Leu Gln Asp Gly Asn Val Met Pro
1               5                   10                  15

Gln Leu Gly Leu Gly Val Trp Gln Ala Ser Asn Glu Glu Val Ile Thr
            20                  25                  30

Ala Ile Gln Lys Ala Leu Glu Val Gly Tyr Arg Ser Ile Asp Thr Ala
        35                  40                  45

```
Ala Ala Tyr Lys Asn Glu Glu Gly Val Gly Lys Ala Leu Lys Asn Ala
        50                  55                  60
Ser Val Asn Arg Glu Glu Leu Phe Ile Thr Thr Lys Leu Trp Asn Asp
 65                  70                  75                  80
Asp His Lys Arg Pro Arg Glu Ala Leu Leu Asp Ser Leu Lys Lys Leu
                 85                  90                  95
Gln Leu Asp Tyr Ile Asp Leu Tyr Leu Met His Trp Pro Val Pro Ala
                100                 105                 110
Ile Asp His Tyr Val Glu Ala Trp Lys Gly Met Ile Glu Leu Gln Lys
            115                 120                 125
Glu Gly Leu Ile Lys Ser Ile Gly Val Cys Asn Phe Gln Ile His His
130                 135                 140
Leu Gln Arg Leu Ile Asp Glu Thr Gly Val Thr Pro Val Ile Asn Gln
145                 150                 155                 160
Ile Glu Leu His Pro Leu Met Gln Gln Arg Gln Leu His Ala Trp Asn
                165                 170                 175
Ala Thr His Lys Ile Gln Thr Glu Ser Trp Ser Pro Leu Ala Gln Gly
            180                 185                 190
Gly Lys Gly Val Phe Asp Gln Lys Val Ile Arg Asp Leu Ala Asp Lys
        195                 200                 205
Tyr Gly Lys Thr Pro Ala Gln Ile Val Ile Arg Trp His Leu Asp Ser
    210                 215                 220
Gly Leu Val Val Ile Pro Lys Ser Val Thr Pro Ser Arg Ile Ala Glu
225                 230                 235                 240
Asn Phe Asp Val Trp Asp Phe Arg Leu Asp Lys Asp Glu Leu Gly Glu
                245                 250                 255
Ile Ala Lys Leu Asp Gln Gly Lys Arg Leu Gly Pro Asp Pro Asp Gln
            260                 265                 270
Phe Gly Gly
        275

<210> SEQ ID NO 33
<211> LENGTH: 1179
<212> TYPE: DNA
<213> ORGANISM: Clostridium acetobutylicum

<400> SEQUENCE: 33
atgaaagaag ttgtaatagc tagtgcagta agaacagcga ttggatctta tggaaagtct    60
cttaaggatg taccagcagt agatttagga gctacagcta taaggaagc agttaaaaaa   120 gcaggaataa aaccagagga tgttaatgaa gtcattttag gaatgttct tcaagcaggt   180 ttaggacaga atccagcaag acaggcatct tttaaagcag gattaccagt tgaaattcca   240
gctatgacta ttaataaggt ttgtggttca ggacttagaa cagttagctt agcagcacaa   300
attataaaag caggagatgc tgacgtaata atagcaggtg gtatggaaaa tatgtctaga   360
gctccttact tagcgaataa cgctagatgg ggatatagaa tgggaaacgc taaatttgtt   420
gatgaaatga tcactgacgg attgtgggat gcatttaatg attaccacat gggaataaca   480
gcagaaaaca tagctgagag atggaacatt tcaagagaag aacaagatga gtttgctctt   540
gcatcacaaa aaaagctga agaagctata aaatcaggtc aatttaaaga tgaaatagtt   600
cctgtagtaa ttaaaggcag aaagggagaa actgtagttg atacagatga gcaccctaga   660
tttggatcaa ctagaagg acttgcaaaa ttaaaacctg ccttcaaaaa agatggaaca   720
gttacagctg gtaatgcatc aggattaaat gactgtgcag cagtacttgt aatcatgagt   780
```

```
gcagaaaaag ctaaagagct tggagtaaaa ccacttgcta agatagtttc ttatggttca      840
gcaggagttg acccagcaat aatgggatat ggacctttct atgcaacaaa agcagctatt      900
gaaaaagcag gttggacagt tgatgaatta gatttaatag aatcaaatga agcttttgca      960
gctcaaagtt tagcagtagc aaaagattta aaatttgata tgaataaagt aaatgtaaat     1020
ggaggagcta ttgcccttgg tcatccaatt ggagcatcag gtgcaagaat actcgttact     1080
cttgtacacg caatgcaaaa aagagatgca aaaaaaggct tagcaacttt atgtataggt     1140
ggcggacaag gaacagcaat attgctagaa aagtgctag                           1179
```

<210> SEQ ID NO 34
<211> LENGTH: 1179
<212> TYPE: DNA
<213> ORGANISM: Artificial Sequence
<220> FEATURE:
<223> OTHER INFORMATION: Codon Aoptimized Clostridium acetobutylicum
      Sequence

<400> SEQUENCE: 34

```
atgaaagaag ttgttattgc gagcgcggtt cgtaccgcga ttggcagcta tggcaagagc       60
ctgaaggatg ttccggcggt ggacctgggt gcgaccgcga tcaaagaggc ggttaagaaa      120
gcgggcatta aaccggagga tgtgaacgaa gttatcctgg taacgtgct gcaagcgggt       180 ctgggccaaa accggcgcg tcaggcgagc ttcaaggcgg gctgccggt tgaaatcccg        240 gcgatgacca ttaacaaagt tgcggtagcc ggcctgcgta ccgtgagcct ggcggcgcaa      300
atcattaagg cgggtgacgc ggatgttatc attgcgggtg gcatggagaa catgagccgt      360
gcgccgtacc tggcgaacaa cgcgcgttgg ggttatcgta tgggcaacgc gaaattcgtg      420
gacgaaatga ttaccgacgg tctgtgggat gcgtttaacg actaccacat gggcatcacc      480
gcggagaaca ttgcggaacg ttggaacatt agccgtgagg aacaagatga gttcgcgctg      540
gcgagccaga agaaagcgga ggaagcgatc aagagcggcc agtttaaaga cgaaatcgtt      600
ccggtggtta ttaagggtcg taagggtgaa accgtggtgg acaccgatga cacccgcgt       660 ttcggtagca ccattgaggg cctggcgaag ctgaaaccgg cgtttaagaa agatggcacc      720
gtgaccgcgg gtaacgcgag cggcctgaac gactgcgcgg cggtgctggt tatcatgagc      780
gcggagaagg cgaaagaact gggtgtgaag ccgctggcga aaattgttag ctacggtagc      840
gcgggtgtga cccggcgat catgggttac ggcccgtttt atgcgaccaa gcggcgatt       900 gagaaagcgg gttggaccgt ggacgaactg gatctgatcg agagcaacga agcgttcgcg      960
gcgcaaagcc tggcggtggc gaaggatctg aaatttgaca tgaacaaggt gaacgtgaac     1020
ggtggtgcga ttgcgctggg tcacccgatt ggtgcgagcg gcgcgcgtat cctggtgacc     1080
ctggttcacg cgatgcagaa acgtgacgcg aagaaaggtc tggcgaccct gtgcattggt     1140
ggtggtcaag gcaccgcgat tctgctggaa aagtgctaa                           1179
```

<210> SEQ ID NO 35
<211> LENGTH: 392
<212> TYPE: PRT
<213> ORGANISM: Clostridium acetobutylicum

<400> SEQUENCE: 35

```
Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
            20                  25                  30
```

Ala Ile Lys Glu Ala Val Lys Ala Gly Ile Lys Pro Glu Asp Val
         35                  40                  45

Asn Glu Val Ile Leu Gly Asn Val Leu Gln Ala Gly Leu Gly Gln Asn
 50                  55                  60

Pro Ala Arg Gln Ala Ser Phe Lys Ala Gly Leu Pro Val Glu Ile Pro
 65                  70                  75                  80

Ala Met Thr Ile Asn Lys Val Cys Gly Ser Gly Leu Arg Thr Val Ser
                 85                  90                  95

Leu Ala Ala Gln Ile Ile Lys Ala Gly Asp Ala Asp Val Ile Ile Ala
                100                 105                 110

Gly Gly Met Glu Asn Met Ser Arg Ala Pro Tyr Leu Ala Asn Asn Ala
            115                 120                 125

Arg Trp Gly Tyr Arg Met Gly Asn Ala Lys Phe Val Asp Glu Met Ile
130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Glu Ala Ile Lys Ser
            180                 185                 190

Gly Gln Phe Lys Asp Glu Ile Val Pro Val Ile Lys Gly Arg Lys
            195                 200                 205

Gly Glu Thr Val Val Asp Thr Asp Glu His Pro Arg Phe Gly Ser Thr
210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
            275                 280                 285

Gly Tyr Gly Pro Phe Tyr Ala Thr Lys Ala Ala Ile Glu Lys Ala Gly
290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Val His Ala Met Gln Lys Arg
            355                 360                 365

Asp Ala Lys Lys Gly Leu Ala Thr Leu Cys Ile Gly Gly Gly Gln Gly
370                 375                 380

Thr Ala Ile Leu Leu Glu Lys Cys
385                 390

<210> SEQ ID NO 36
<211> LENGTH: 1185
<212> TYPE: DNA
<213> ORGANISM: Escherichia coli

<400> SEQUENCE: 36
atgaaaaatt gtgtcatcgt cagtgcggta cgtactgcta tcggtagttt taacggttca    60

-continued

```
ctcgcttcca ccagcgccat cgacctgggg gcgacagtaa ttaaagccgc cattgaacgt    120
gcaaaaatcg attcacaaca cgttgatgaa gtgattatgg gtaacgtgtt acaagccggg    180
ctggggcaaa atccggcgcg tcaggcactg ttaaaaagcg ggctggcaga acggtgtgc    240 ggattcacgg tcaataaagt atgtggttcg ggtcttaaaa gtgtggcgct tgccgcccag    300
gccattcagg caggtcaggc gcagagcatt gtggcggggg gtatggaaaa tatgagttta    360 gcccccctact tactcgatgc aaaagcacgc tctggttatc gtcttggaga cggacaggtt    420
tatgacgtaa tcctgcgcga tggcctgatg tgcgccaccc atggttatca tatggggatt    480
accgccgaaa acgtggctaa agagtacgga attacccgtg aaatgcagga tgaactggcg    540
ctacattcac agcgtaaagc ggcagccgca attgagtccg gtgcttttac agccgaaatc    600
gtcccggtaa atgttgtcac tcgaaagaaa accttcgtct tcagtcaaga cgaattcccg    660
aaagcgaatt caacggctga agcgttaggt gcattgcgcc cggccttcga taaagcagga    720
acagtcaccg ctgggaacgc gtctggtatt aacgacggtg ctgccgctct ggtgattatg    780
gaagaatctg cggcgctggc agcaggcctt acccccctgg ctcgcattaa aagttatgcc    840
agcggtggcg tgccccccgc attgatgggt atggggccag tacctgccac gcaaaaagcg    900
ttacaactgg cggggctgca actggcggat attgatctca ttgaggctaa tgaagcattt    960
gctgcacagt tccttgccgt tgggaaaaac ctgggctttg attctgagaa agtgaatgtc   1020
aacggcgggg ccatcgcgct cgggcatcct atcggtgcca gtggtgctcg tattctggtc   1080
acactattac atgccatgca ggcacgcgat aaaacgctgg ggctggcaac actgtgcatt   1140
ggcggcggtc agggaattgc gatggtgatt gaacggttga attaa                    1185
```

<210> SEQ ID NO 37
<211> LENGTH: 394
<212> TYPE: PRT
<213> ORGANISM: Escherichia coli

<400> SEQUENCE: 37

```
Met Lys Asn Cys Val Ile Val Ser Ala Val Arg Thr Ala Ile Gly Ser
1               5                   10                  15

Phe Asn Gly Ser Leu Ala Ser Thr Ser Ala Ile Asp Leu Gly Ala Thr
            20                  25                  30

Val Ile Lys Ala Ala Ile Glu Arg Ala Lys Ile Asp Ser Gln His Val
        35                  40                  45

Asp Glu Val Ile Met Gly Asn Val Leu Gln Ala Gly Leu Gly Gln Asn
    50                  55                  60

Pro Ala Arg Gln Ala Leu Leu Lys Ser Gly Leu Ala Glu Thr Val Cys
65                  70                  75                  80

Gly Phe Thr Val Asn Lys Val Cys Gly Ser Gly Leu Lys Ser Val Ala
                85                  90                  95

Leu Ala Ala Gln Ala Ile Gln Ala Gly Gln Ala Gln Ser Ile Val Ala
            100                 105                 110

Gly Gly Met Glu Asn Met Ser Leu Ala Pro Tyr Leu Leu Asp Ala Lys
        115                 120                 125

Ala Arg Ser Gly Tyr Arg Leu Gly Asp Gly Gln Val Tyr Asp Val Ile
    130                 135                 140

Leu Arg Asp Gly Leu Met Cys Ala Thr His Gly Tyr His Met Gly Ile
145                 150                 155                 160

Thr Ala Glu Asn Val Ala Lys Glu Tyr Gly Ile Thr Arg Glu Met Gln
                165                 170                 175
```

```
Asp Glu Leu Ala Leu His Ser Gln Arg Lys Ala Ala Ala Ile Glu
            180                 185                 190

Ser Gly Ala Phe Thr Ala Glu Ile Val Pro Val Asn Val Val Thr Arg
        195                 200                 205

Lys Lys Thr Phe Val Phe Ser Gln Asp Glu Phe Pro Lys Ala Asn Ser
    210                 215                 220

Thr Ala Glu Ala Leu Gly Ala Leu Arg Pro Ala Phe Asp Lys Ala Gly
225                 230                 235                 240

Thr Val Thr Ala Gly Asn Ala Ser Gly Ile Asn Asp Gly Ala Ala Ala
                245                 250                 255

Leu Val Ile Met Glu Glu Ser Ala Ala Leu Ala Ala Gly Leu Thr Pro
            260                 265                 270

Leu Ala Arg Ile Lys Ser Tyr Ala Ser Gly Gly Val Pro Pro Ala Leu
        275                 280                 285

Met Gly Met Gly Pro Val Pro Ala Thr Gln Lys Ala Leu Gln Leu Ala
    290                 295                 300

Gly Leu Gln Leu Ala Asp Ile Asp Leu Ile Glu Ala Asn Glu Ala Phe
305                 310                 315                 320

Ala Ala Gln Phe Leu Ala Val Gly Lys Asn Leu Gly Phe Asp Ser Glu
                325                 330                 335

Lys Val Asn Val Asn Gly Gly Ala Ile Ala Leu Gly His Pro Ile Gly
            340                 345                 350

Ala Ser Gly Ala Arg Ile Leu Val Thr Leu Leu His Ala Met Gln Ala
        355                 360                 365

Arg Asp Lys Thr Leu Gly Leu Ala Thr Leu Cys Ile Gly Gly Gln
370                 375                 380

Gly Ile Ala Met Val Ile Glu Arg Leu Asn
385                 390

<210> SEQ ID NO 38
<211> LENGTH: 1197
<212> TYPE: DNA
<213> ORGANISM: Saccharomyces cerevisiae

<400> SEQUENCE: 38
atgtctcaga acgtttacat tgtatcgact gccagaaccc caattggttc attccagggt      60
tctctatcct ccaagacagc agtggaattg ggtgctgttg ctttaaaagg cgccttggct     120
aaggttccag aattggatgc atccaaggat tttgacgaaa ttattttggg taacgttctt     180
tctgccaatt gggccaagc tccggccaga caagttgctt ggctgccgg tttgagtaat      240 catatcgttg caagcacagt taacaaggtc tgtgcatccg ctatgaaggc aatcattttg     300
ggtgctcaat ccatcaaatg tggtaatgct gatgttgtcg tagctggtgg ttgtgaatct     360
atgactaacg caccatacta catgccagca gcccgtgcgg gtgccaaatt tggccaaact     420
gttcttgttg atggtgtcga agagatgggt tgaacgatg cgtacgatgg tctagccatg     480
ggtgtacacg cagaaaagtg tgcccgtgat tgggatatta ctagagaaca acaagacaat     540
tttgccatcg aatcctacca aaaatctcaa aaatctcaaa aggaaggtaa attcgacaat     600
gaaattgtac tgttaccat aagggattt agaggtaagc ctgatactca agtcacgaag      660
gacgaggaac ctgctagatt acacgttgaa aaattgagat ctgcaaggac tgttttccaa     720
aaagaaaacg gtactgttac tgccgctaac gcttctccaa tcaacgatgg tgctgcagcc     780
gtcatcttgg tttccgaaaa agttttgaag gaaaagaatt tgaagccttt ggctattatc     840
aaaggttggg gtgaggccgc tcatcaacca gctgatttta catgggctcc atctcttgca     900
```

```
gttccaaagg ctttgaaaca tgctggcatc gaagacatca attctgttga ttactttgaa      960
ttcaatgaag ccttttcggt tgtcggtttg gtgaacacta agattttgaa gctagaccca     1020
tctaaggtta atgtatatgg tggtgctgtt gctctaggtc acccattggg ttgttctggt     1080
gctagagtgg ttgttacact gctatccatc ttacagcaag aaggaggtaa gatcggtgtt     1140
gccgccattt gtaatggtgg tggtggtgct tcctctattg tcattgaaaa gatatga       1197
```

<210> SEQ ID NO 39
<211> LENGTH: 1197
<212> TYPE: DNA
<213> ORGANISM: Artificial Sequence
<220> FEATURE:
<223> OTHER INFORMATION: Codon Optimized Sacharomyces cerevisiae Sequence

<400> SEQUENCE: 39

```
atgtctcaga acgtttacat tgtatcgact gccagaaccc caattggttc attccagggt       60
tctctatcct ccaagacagc agtggaattg ggtgctgttg ctttaaaagg cgccttggct      120
aaggttccag aattggatgc atccaaggat tttgacgaaa ttatttttgg taacgttctt      180
tctgccaatt tgggccaagc tccggccaga caagttgctt ggctgccgg tttgagtaat       240 catatcgttg caagcacagt taacaaggtc tgtgcatccg ctatgaaggc aatcattttg      300
ggtgctcaat ccatcaaatg tggtaatgct gatgttgtcg tagctggtgg ttgtgaatct      360
atgactaacg caccatacta catgccagca gcccgtgcgg gtgccaaatt tggccaaact      420
gttcttgttg atggtgtcga aagagatggg ttgaacgatg cgtacgatgg tctagccatg      480
ggtgtacacg cagaaaagtg tgcccgtgat tgggatatta ctagagaaca acaagacaat      540
tttgccatcg aatcctacca aaatctcaa aaatctcaaa aggaaggtaa attcgacaat       600
gaaattgtac ctgttaccat taagggattt agaggtaagc ctgatactca agtcacgaag      660
gacgaggaac ctgctagatt acacgttgaa aaattgagat ctgcaaggac tgttttccaa      720
aaagaaaacg gtactgttac tgccgctaac gcttctccaa tcaacgatgg tgctgcagcc      780
gtcatcttgg tttccgaaaa agttttgaag gaaaagaatt tgaagccttt ggctattatc      840
aaaggttggg gtgaggccgc tcatcaacca gctgatttta catgggctcc atctcttgca      900
gttccaaagg ctttgaaaca tgctggcatc gaagacatca attctgttga ttactttgaa      960
ttcaatgaag ccttttcggt tgtcggtttg gtgaacacta agattttgaa gctagaccca     1020
tctaaggtta atgtatatgg tggtgctgtt gctctaggtc acccattggg ttgttctggt     1080
gctagagtgg ttgttacact gctatccatc ttacagcaag aaggaggtaa gatcggtgtt     1140
gccgccattt gtaatggtgg tggtggtgct tcctctattg tcattgaaaa gatatga       1197
```

<210> SEQ ID NO 40
<211> LENGTH: 398
<212> TYPE: PRT
<213> ORGANISM: Saccharomyces cerevisiae

<400> SEQUENCE: 40

```
Met Ser Gln Asn Val Tyr Ile Val Ser Thr Ala Arg Thr Pro Ile Gly
1               5                   10                  15

Ser Phe Gln Gly Ser Leu Ser Ser Lys Thr Ala Val Glu Leu Gly Ala
            20                  25                  30

Val Ala Leu Lys Gly Ala Leu Ala Lys Val Pro Glu Leu Asp Ala Ser
        35                  40                  45
```

-continued

```
Lys Asp Phe Asp Glu Ile Ile Phe Gly Asn Val Leu Ser Ala Asn Leu
 50                  55                  60
Gly Gln Ala Pro Ala Arg Gln Val Ala Leu Ala Ala Gly Leu Ser Asn
 65                  70                  75                  80
His Ile Val Ala Ser Thr Val Asn Lys Val Cys Ala Ser Ala Met Lys
                 85                  90                  95
Ala Ile Ile Leu Gly Ala Gln Ser Ile Lys Cys Gly Asn Ala Asp Val
                100                 105                 110
Val Val Ala Gly Gly Cys Glu Ser Met Thr Asn Ala Pro Tyr Tyr Met
                115                 120                 125
Pro Ala Ala Arg Ala Gly Ala Lys Phe Gly Gln Thr Val Leu Val Asp
130                 135                 140
Gly Val Glu Arg Asp Gly Leu Asn Asp Ala Tyr Asp Gly Leu Ala Met
145                 150                 155                 160
Gly Val His Ala Glu Lys Cys Ala Arg Asp Trp Ile Thr Arg Glu
                165                 170                 175
Gln Gln Asp Asn Phe Ala Ile Glu Ser Tyr Gln Lys Ser Gln Lys Ser
                180                 185                 190
Gln Lys Glu Gly Lys Phe Asp Asn Glu Ile Val Pro Val Thr Ile Lys
                195                 200                 205
Gly Phe Arg Gly Lys Pro Asp Thr Gln Val Thr Lys Asp Glu Glu Pro
                210                 215                 220
Ala Arg Leu His Val Glu Lys Leu Arg Ser Ala Arg Thr Val Phe Gln
225                 230                 235                 240
Lys Glu Asn Gly Thr Val Thr Ala Ala Asn Ala Ser Pro Ile Asn Asp
                245                 250                 255
Gly Ala Ala Ala Val Ile Leu Val Ser Glu Lys Val Leu Lys Glu Lys
                260                 265                 270
Asn Leu Lys Pro Leu Ala Ile Ile Lys Gly Trp Gly Glu Ala Ala His
                275                 280                 285
Gln Pro Ala Asp Phe Thr Trp Ala Pro Ser Leu Ala Val Pro Lys Ala
                290                 295                 300
Leu Lys His Ala Gly Ile Glu Asp Ile Asn Ser Val Asp Tyr Phe Glu
305                 310                 315                 320
Phe Asn Glu Ala Phe Ser Val Val Gly Leu Val Asn Thr Lys Ile Leu
                325                 330                 335
Lys Leu Asp Pro Ser Lys Val Asn Val Tyr Gly Gly Ala Val Ala Leu
                340                 345                 350
Gly His Pro Leu Gly Cys Ser Gly Ala Arg Val Val Thr Leu Leu
                355                 360                 365
Ser Ile Leu Gln Gln Glu Gly Gly Lys Ile Gly Val Ala Ala Ile Cys
370                 375                 380
Asn Gly Gly Gly Gly Ala Ser Ser Ile Val Ile Glu Lys Ile
385                 390                 395

<210> SEQ ID NO 41
<211> LENGTH: 651
<212> TYPE: DNA
<213> ORGANISM: Escherichia coli

<400> SEQUENCE: 41
atggatgcga aacaacgtat tgcgcgccgt gtggcgcaag agcttcgtga tggtgacatc      60
gttaacttag ggatcggttt acccacaatg gtcgccaatt atttaccgga ggtattcat     120 atcactctgc aatcggaaaa cggcttcctc ggtttaggcc cggtcacgac agcgcatcca    180
```

```
gatctggtga acgctggcgg gcaaccgtgc ggtgttttac ccggtgcagc catgtttgat    240
agcgccatgt catttgcgct aatccgtggc ggtcatattg atgcctgcgt gctcggcggt    300
ttgcaagtag acgaagaagc aaacctcgcg aactgggtag tgcctgggaa atggtgccc    360 ggtatgggtg gcgcgatgga tctggtgacc gggtcgcgca aagtgatcat cgccatggaa    420
cattgcgcca agatggttc agcaaaaatt ttgcgccgct gcaccatgcc actcactgcg    480
caacatgcgg tgcatatgct ggttactgaa ctggctgtct ttcgttttat tgacggcaaa    540
atgtggctca ccgaaattgc cgacgggtgt gatttagcca ccgtgcgtgc caaaacagaa    600
gctcggtttg aagtcgccgc cgatctgaat acgcaacggg gtgatttatg a            651
```

<210> SEQ ID NO 42
<211> LENGTH: 651
<212> TYPE: DNA
<213> ORGANISM: Artificial Sequence
<220> FEATURE:
<223> OTHER INFORMATION: Codon Optimized E. coli Sequence

<400> SEQUENCE: 42

```
atggatgcga acaacgtat tgcgcgccgt gtggcgcaag agcttcgtga tggtgacatc     60
gttaacttag ggatcggttt acccacaatg gtcgccaatt atttaccgga gggtattcat    120
atcactctgc aatcggaaaa cggcttcctc ggtttaggcc cggtcacgac agcgcatcca    180
gatctggtga acgctggcgg gcaaccgtgc ggtgttttac ccggtgcagc catgtttgat    240
agcgccatgt catttgcgct aatccgtggc ggtcatattg atgcctgcgt gctcggcggt    300
ttgcaagtag acgaagaagc aaacctcgcg aactgggtag tgcctgggaa atggtgccc    360 ggtatgggtg gcgcgatgga tctggtgacc gggtcgcgca aagtgatcat cgccatggaa    420
cattgcgcca agatggttc agcaaaaatt ttgcgccgct gcaccatgcc actcactgcg    480
caacatgcgg tgcatatgct ggttactgaa ctggctgtct ttcgttttat tgacggcaaa    540
atgtggctca ccgaaattgc cgacgggtgt gatttagcca ccgtgcgtgc caaaacagaa    600
gctcggtttg aagtcgccgc cgatctgaat acgcaacggg gtgatttatg a            651
```

<210> SEQ ID NO 43
<211> LENGTH: 216
<212> TYPE: PRT
<213> ORGANISM: Escherichia coli

<400> SEQUENCE: 43

Met Asp Ala Lys Gln Arg Ile Ala Arg Arg Val Ala Gln Glu Leu Arg
1               5                   10                  15

Asp Gly Asp Ile Val Asn Leu Gly Ile Gly Leu Pro Thr Met Val Ala
            20                  25                  30

Asn Tyr Leu Pro Glu Gly Ile His Ile Thr Leu Gln Ser Glu Asn Gly
        35                  40                  45

Phe Leu Gly Leu Gly Pro Val Thr Thr Ala His Pro Asp Leu Val Asn
    50                  55                  60

Ala Gly Gly Gln Pro Cys Gly Val Leu Pro Gly Ala Ala Met Phe Asp
65                  70                  75                  80

Ser Ala Met Ser Phe Ala Leu Ile Arg Gly Gly His Ile Asp Ala Cys
                85                  90                  95

Val Leu Gly Gly Leu Gln Val Asp Glu Glu Ala Asn Leu Ala Asn Trp
            100                 105                 110

Val Val Pro Gly Lys Met Val Pro Gly Met Gly Gly Ala Met Asp Leu

```
            115                 120                 125
Val Thr Gly Ser Arg Lys Val Ile Ile Ala Met Glu His Cys Ala Lys
    130                 135                 140

Asp Gly Ser Ala Lys Ile Leu Arg Arg Cys Thr Met Pro Leu Thr Ala
145                 150                 155                 160

Gln His Ala Val His Met Leu Val Thr Glu Leu Ala Val Phe Arg Phe
                165                 170                 175

Ile Asp Gly Lys Met Trp Leu Thr Glu Ile Ala Asp Gly Cys Asp Leu
            180                 185                 190

Ala Thr Val Arg Ala Lys Thr Glu Ala Arg Phe Glu Val Ala Ala Asp
            195                 200                 205

Leu Asn Thr Gln Arg Gly Asp Leu
210                 215

<210> SEQ ID NO 44
<211> LENGTH: 663
<212> TYPE: DNA
<213> ORGANISM: Escherichia coli

<400> SEQUENCE: 44
atgaaaacaa aattgatgac attacaagac gccaccggct tctttcgtga cggcatgacc    60
atcatggtgg gcggatttat ggggattggc actccatccc gcctggttga agcattactg   120
gaatctggtg ttcgcgacct gacattgata gccaatgata ccgcgtttgt tgataccggc   180
atcggtccgc tcatcgtcaa tggtcgagtc cgcaaagtga ttgcttcaca tatcggcacc   240
aacccggaaa caggtcggcg catgatatct ggtgagatgg acgtcgttct ggtgccgcaa   300
ggtacgctaa tcgagcaaat tcgctgtggt ggagctggac ttggtggttt tctcaccca   360 acgggtgtcg gcaccgtcgt agaggaaggc aaacagacac tgacactcga cggtaaaacc   420
tggctgctcg aacgcccact gcgcgccgac ctggcgctaa ttcgcgctca tcgttgcgac   480
acacttggca acctgaccta tcaacttagc gcccgcaact ttaacccct gatagccctt   540 gcggctgata tcacgctggt agagccagat gaactggtcg aaaccggcga gctgcaacct   600
gaccatattg tcaccctgg tgccgttatc gaccacatca tcgtttcaca ggagagcaaa   660
taa                                                                663

<210> SEQ ID NO 45
<211> LENGTH: 663
<212> TYPE: DNA
<213> ORGANISM: Artificial Sequence
<220> FEATURE:
<223> OTHER INFORMATION: Codon Optimized E. coli Sequence

<400> SEQUENCE: 45
atgaaaacaa aattgatgac attacaagac gccaccggct tctttcgtga cggcatgacc    60
atcatggtgg gcggatttat ggggattggc actccatccc gcctggttga agcattactg   120
gaatctggtg ttcgcgacct gacattgata gccaatgata ccgcgtttgt tgataccggc   180
atcggtccgc tcatcgtcaa tggtcgagtc cgcaaagtga ttgcttcaca tatcggcacc   240
aacccggaaa caggtcggcg catgatatct ggtgagatgg acgtcgttct ggtgccgcaa   300
ggtacgctaa tcgagcaaat tcgctgtggt ggagctggac ttggtggttt tctcaccca   360 acgggtgtcg gcaccgtcgt agaggaaggc aaacagacac tgacactcga cggtaaaacc   420
tggctgctcg aacgcccact gcgcgccgac ctggcgctaa ttcgcgctca tcgttgcgac   480
acacttggca acctgaccta tcaacttagc gcccgcaact ttaacccct gatagccctt   540
```

```
gcggctgata tcacgctggt agagccagat gaactggtcg aaaccggcga gctgcaacct    600
gaccatattg tcacccctgg tgccgttatc gaccacatca tcgtttcaca ggagagcaaa    660
taa                                                                  663
```

<210> SEQ ID NO 46
<211> LENGTH: 220
<212> TYPE: PRT
<213> ORGANISM: Escherichia coli

<400> SEQUENCE: 46

```
Met Lys Thr Lys Leu Met Thr Leu Gln Asp Ala Thr Gly Phe Phe Arg
1               5                   10                  15

Asp Gly Met Thr Ile Met Val Gly Gly Phe Met Gly Ile Gly Thr Pro
                20                  25                  30

Ser Arg Leu Val Glu Ala Leu Leu Glu Ser Gly Val Arg Asp Leu Thr
            35                  40                  45

Leu Ile Ala Asn Asp Thr Ala Phe Val Asp Thr Gly Ile Gly Pro Leu
        50                  55                  60

Ile Val Asn Gly Arg Val Arg Lys Val Ile Ala Ser His Ile Gly Thr
65                  70                  75                  80

Asn Pro Glu Thr Gly Arg Arg Met Ile Ser Gly Glu Met Asp Val Val
                85                  90                  95

Leu Val Pro Gln Gly Thr Leu Ile Glu Gln Ile Arg Cys Gly Gly Ala
                100                 105                 110

Gly Leu Gly Gly Phe Leu Thr Pro Thr Gly Val Gly Thr Val Val Glu
            115                 120                 125

Glu Gly Lys Gln Thr Leu Thr Leu Asp Gly Lys Thr Trp Leu Leu Glu
        130                 135                 140

Arg Pro Leu Arg Ala Asp Leu Ala Leu Ile Arg Ala His Arg Cys Asp
145                 150                 155                 160

Thr Leu Gly Asn Leu Thr Tyr Gln Leu Ser Ala Arg Asn Phe Asn Pro
                165                 170                 175

Leu Ile Ala Leu Ala Ala Asp Ile Thr Leu Val Glu Pro Asp Glu Leu
                180                 185                 190

Val Glu Thr Gly Glu Leu Gln Pro Asp His Ile Val Thr Pro Gly Ala
            195                 200                 205

Val Ile Asp His Ile Ile Val Ser Gln Glu Ser Lys
        210                 215                 220
```

<210> SEQ ID NO 47
<211> LENGTH: 735
<212> TYPE: DNA
<213> ORGANISM: Clostridium acetobutylicum

<400> SEQUENCE: 47

```
atgttaaagg atgaagtaat taaacaaatt agcacgccat taacttcgcc tgcatttcct    60
agaggaccct ataaatttca taatcgtgag tattttaaca ttgtatatcg tacagatatg    120
gatgcacttc gtaaagttgt gccagagcct ttagaaattg atgagccctt agtcaggttt    180
gaaattatgg caatgcatga tacgagtgga cttggttgtt atacagaaag cggacaggct    240
attcccgtaa gctttaatgg agttaaggga gattatcttc atatgatgta tttagataat    300
gagcctgcaa ttgcagtagg aagggaatta agtgcatatc ctaaaaagct cgggtatcca    360
aagctttttg tggattcaga tactttagta ggaactttag actatggaaa acttagagtt    420
```

```
gcgacagcta caatggggta caaacataaa gccttagatg ctaatgaagc aaaggatcaa    480
atttgtcgcc ctaattatat gttgaaaata atacccaatt atgatggaag ccctagaata    540
tgtgagctta taaatgcgaa aatcacagat gttaccgtac atgaagcttg acaggacca     600 actcgactgc agttatttga tcacgctatg gcgccactta atgatttgcc agtaaaagag    660
attgtttcta gctctcacat tcttgcagat ataatattgc ctagagctga agttatatat    720
gattatctta agtaa                                                      735
```

<210> SEQ ID NO 48
<211> LENGTH: 735
<212> TYPE: DNA
<213> ORGANISM: Artificial Sequence
<220> FEATURE:
<223> OTHER INFORMATION: Codon Optimized Clostridium acetobutylicum
      Sequence

<400> SEQUENCE: 48

```
atgctgaagg acgaggttat taagcagatt agcacccccgc tgaccagccc ggcgttcccg     60
cgtggtccgt acaagttcca taatcgcgaa tacttcaaca ttgtgtatcg taccgacatg    120
gatgcgctgc gtaaggtggt tccggagccg ctggaaattg acgagccgct ggttcgtttc    180
gaaatcatgg cgatgcacga taccagcggt ctgggctgct acaccgagag cggtcaggcg    240
attccggtga gctttaacgg tgttaaaggc gactacctgc acatgatgta tctggataac    300
gaaccggcga ttgcggtggg tcgtgagctg agcgcgtacc cgaagaaact gggctatccg    360
aagctgttcg tggacagcga tacccctggtg ggcaccctgg actacggcaa actgcgtgtt    420
gcgaccgcga ccatgggcta taagcacaaa gcgctggacg cgaacgaagc gaaggatcag    480
atttgccgtc cgaactacat gctgaaaaatc attccgaact atgacggtag cccgcgtatc    540
tgcgaactga ttaacgcgaa gatcaccgat gttaccgttc atgaggcgtg gaccggcccg    600
acccgtctgc aactgtttga ccacgcgatg gcgccgctga cgatctgcc ggtgaaagag    660 atcgttagca gcagccacat cctggcggac atcatcctgc cgcgtgcgga agttatctac    720
gattacctga agtaa                                                     735
```

<210> SEQ ID NO 49
<211> LENGTH: 244
<212> TYPE: PRT
<213> ORGANISM: Clostridium acetobutylicum

<400> SEQUENCE: 49

Met Leu Lys Asp Glu Val Ile Lys Gln Ile Ser Thr Pro Leu Thr Ser
1               5                   10                  15

Pro Ala Phe Pro Arg Gly Pro Tyr Lys Phe His Asn Arg Glu Tyr Phe
            20                  25                  30

Asn Ile Val Tyr Arg Thr Asp Met Asp Ala Leu Arg Lys Val Val Pro
        35                  40                  45

Glu Pro Leu Glu Ile Asp Glu Pro Leu Val Arg Phe Glu Ile Met Ala
    50                  55                  60

Met His Asp Thr Ser Gly Leu Gly Cys Tyr Thr Glu Ser Gly Gln Ala
65                  70                  75                  80

Ile Pro Val Ser Phe Asn Gly Val Lys Gly Asp Tyr Leu His Met Met
                85                  90                  95

Tyr Leu Asp Asn Glu Pro Ala Ile Ala Val Gly Arg Glu Leu Ser Ala
            100                 105                 110

Tyr Pro Lys Lys Leu Gly Tyr Pro Lys Leu Phe Val Asp Ser Asp Thr

```
        115                 120                 125

Leu Val Gly Thr Leu Asp Tyr Gly Lys Leu Arg Val Ala Thr Ala Thr
    130                 135                 140

Met Gly Tyr Lys His Lys Ala Leu Asp Ala Asn Glu Ala Lys Asp Gln
145                 150                 155                 160

Ile Cys Arg Pro Asn Tyr Met Leu Lys Ile Ile Pro Asn Tyr Asp Gly
                165                 170                 175

Ser Pro Arg Ile Cys Glu Leu Ile Asn Ala Lys Ile Thr Asp Val Thr
            180                 185                 190

Val His Glu Ala Trp Thr Gly Pro Thr Arg Leu Gln Leu Phe Asp His
        195                 200                 205

Ala Met Ala Pro Leu Asn Asp Leu Pro Val Lys Glu Ile Val Ser Ser
    210                 215                 220

Ser His Ile Leu Ala Asp Ile Ile Leu Pro Arg Ala Glu Val Ile Tyr
225                 230                 235                 240

Asp Tyr Leu Lys
```

<210> SEQ ID NO 50
<211> LENGTH: 741
<212> TYPE: DNA
<213> ORGANISM: Clostridium beijerinckii

<400> SEQUENCE: 50

```
atgttagaaa gtgaagtatc taaacaaatt acaactccac ttgctgctcc agcgtttcct     60
agaggaccat ataggtttca caatagagaa tatctaaaca ttatttatcg aactgattta    120
gatgctcttc gaaaaatagt accagagcca cttgaattag atagagcata tgttagattt    180
gaaatgatgg ctatgcctga tacaaccgga ctaggctcat atacagaatg tggtcaagct    240
attccagtaa aatataatgg tgttaagggt gactacttgc atatgatgta tctagataat    300
gaacctgcta ttgctgttgg aagagaaagt agcgcttatc caaaaaagct tggctatcca    360
aagctatttg ttgattcaga tactttagtt gggacactta aatatggtac attaccagta    420
gctactgcaa caatgggata taagcacgag cctctagatc ttaaagaagc ctatgctcaa    480
attgcaagac ccaattttat gctaaaaatc attcaaggtt acgatggtaa gccaagaatt    540
tgtgaactaa tatgtgcaga aaatactgat ataactattc acggtgcttg gactggaagt    600
gcacgtctac aattatttag ccatgcacta gctcctcttg ctgatttacc tgtattagag    660
attgtatcag catctcatat cctcacagat ttaactcttg gaacacctaa ggttgtacat    720
gattatcttt cagtaaaata a                                              741
```

<210> SEQ ID NO 51
<211> LENGTH: 741
<212> TYPE: DNA
<213> ORGANISM: Artificial Sequence
<220> FEATURE:
<223> OTHER INFORMATION: Codon Optimized Clostridium beijerinckii
      Sequence

<400> SEQUENCE: 51

```
atgctggaga gcgaagttag caaacaaatc accaccccgc tggcggcgcc ggcgttcccg     60
cgtggcccgt accgttttca taaccgtgag tacctgaaca tcatttatcg taccgacctg    120
gatgcgctgc gtaagattgt gccggagccg ctggaactgg accgtgcgta cgttcgtttc    180
gagatgatgg cgatgccgga taccaccggt ctgggcagct acaccgaatg cggtcaggcg    240
atcccggtga agtataacgg tgttaaaggc gactacctgc acatgatgta tctggataac    300
```

```
gagccggcga ttgcggtggg tcgtgaaagc agcgcgtacc cgaagaaact gggctatccg      360
aagctgtttg tggacagcga taccctggtg ggcaccctga aatatggcac cctgccggtt      420
gcgaccgcga ccatgggcta caagcacgag ccgctggacc tgaaagaagc gtatgcgcag      480
attgcgcgtc cgaacttcat gctgaagatc attcaaggtt atgacggcaa accgcgtatc      540
tgcgagctga tttgcgcgga aaacaccgat atcaccatcc atggtgcgtg gaccggcagc      600
gcgcgtctgc aactgtttag ccatgcgctg gcgccgctgg cggatctgcc ggtgctggaa      660
atcgttagcg cgagccacat tctgaccgat ctgaccctgg gcaccccgaa ggttgtgcat      720
gactatctga gcgtgaagta a                                                741
```

```
<210> SEQ ID NO 52
<211> LENGTH: 246
<212> TYPE: PRT
<213> ORGANISM: Clostridium beijerinckii

<400> SEQUENCE: 52
```

Met Leu Glu Ser Glu Val Ser Lys Gln Ile Thr Thr Pro Leu Ala Ala
1               5                   10                  15

Pro Ala Phe Pro Arg Gly Pro Tyr Arg Phe His Asn Arg Glu Tyr Leu
            20                  25                  30

Asn Ile Ile Tyr Arg Thr Asp Leu Asp Ala Leu Arg Lys Ile Val Pro
        35                  40                  45

Glu Pro Leu Glu Leu Asp Arg Ala Tyr Val Arg Phe Glu Met Met Ala
    50                  55                  60

Met Pro Asp Thr Thr Gly Leu Gly Ser Tyr Thr Glu Cys Gly Gln Ala
65                  70                  75                  80

Ile Pro Val Lys Tyr Asn Gly Val Lys Gly Asp Tyr Leu His Met Met
                85                  90                  95

Tyr Leu Asp Asn Glu Pro Ala Ile Ala Val Gly Arg Glu Ser Ser Ala
            100                 105                 110

Tyr Pro Lys Lys Leu Gly Tyr Pro Lys Leu Phe Val Asp Ser Asp Thr
        115                 120                 125

Leu Val Gly Thr Leu Lys Tyr Gly Thr Leu Pro Val Ala Thr Ala Thr
    130                 135                 140

Met Gly Tyr Lys His Glu Pro Leu Asp Leu Lys Glu Ala Tyr Ala Gln
145                 150                 155                 160

Ile Ala Arg Pro Asn Phe Met Leu Lys Ile Ile Gln Gly Tyr Asp Gly
                165                 170                 175

Lys Pro Arg Ile Cys Glu Leu Ile Cys Ala Glu Asn Thr Asp Ile Thr
            180                 185                 190

Ile His Gly Ala Trp Thr Gly Ser Ala Arg Leu Gln Leu Phe Ser His
        195                 200                 205

Ala Leu Ala Pro Leu Ala Asp Leu Pro Val Leu Glu Ile Val Ser Ala
    210                 215                 220

Ser His Ile Leu Thr Asp Leu Thr Leu Gly Thr Pro Lys Val Val His
225                 230                 235                 240

Asp Tyr Leu Ser Val Lys
                245

```
<210> SEQ ID NO 53
<211> LENGTH: 770
<212> TYPE: DNA
<213> ORGANISM: Homo sapiens
```

<400> SEQUENCE: 53

```
atggaagaga agcagatcct gtgcgtgggg ctagtggtgc tggacgtcat cagcctggtg      60
gacaagtacc ctaaggagga ctcggagata aggtgtttgt cccagagatg gcagcgcgga     120
ggcaacgcgt ccaactcctg caccgttctc tccctgctcg gagcccctg tgccttcatg      180
ggctcaatgg ctcctggcca tgttgctgat tttgtcctgg atgacctccg ccgctattct     240
gtggacctac gctacacagt ctttcagacc acaggctccg tccccatcgc acgtgtcatc     300
atcaacgagg ccagtggtag ccgcaccatc ctatactatg acaggagcct gccagatgtg     360
tctgctacag actttgagaa ggttgatctg acccagttca gtggatcca cattgagggc      420
cggaacgcat cggagcaggt gaagatgctg cagcggatag acgcacacaa caccaggcag     480
cctccagagc agaagatccg ggtgtccgtg gaggtggaga gccacgaga ggagctcttc      540
cagctgtttg gctacggaga cgtggtgttt gtcagcaaag atgtggccaa gcacttgggg     600
ttccagtcag cagaggaagc cttgaggggc ttgtatggtc gtgtgaggaa agggctgtg      660
cttgtctgtg cctgggctga ggaggcgcc gacgccctgg gccctgatgg caaattgctc      720
cactcggatg ctttcccgcc accccgcgtg gtggatacac tgggagctgg                770
```

<210> SEQ ID NO 54
<211> LENGTH: 897
<212> TYPE: DNA
<213> ORGANISM: Artificial Sequence
<220> FEATURE:
<223> OTHER INFORMATION: Codon Optimized Homo sapiens Sequence

<400> SEQUENCE: 54

```
atggaggaaa agcaaattct gtgcgttggt ctggtggttc tggacgtgat tagcctggtt      60
gataagtacc cgaaagagga tagcgaaatc cgttgcctga ccagcgttg gcaacgtggt     120
ggcaacgcga gcaatagctg caccgttctg agcctgctgg gtgcgccgtg cgcgttcatg     180
ggtagcatgg cgccgggtca tgttgcggac ttcctggtgg cggattttcg tcgtcgtggt     240
gtggacgtta gccaggttgc gtggcaaagc aagggcgata ccccgagctc ctgctgcatc     300
attaacaaca gcaacggtaa ccgtaccatt gtgctgcacg acaccagcct gccggatgtt     360
agcgcgaccg acttcgagaa ggtggatctg acccagttta atggattca cattgagggc      420
cgtaacgcga gcgaacaggt taaaatgctg caacgtattg atgcgcacaa cacccgtcag     480
ccgccggaac aaaagattcg tgtgagcgtt gaggtggaaa accgcgtga ggaactgttc      540
caactgtttg gttacggcga cgtggttttc gttagcaagg atgtggcgaa cacctgggt     600
tttcaaagcg cggaggaagc gctgcgtggt ctgtatggcc gtgtgcgtaa aggcgcggtt     660
ctggtgtgcg cgtgggcgga ggaaggcgcg gatgcgctgg gtccggatgg caaactgctg     720
cacagcgatg cgttcccgcc gccgcgtgtg gttgacaccc tgggtgcggg cgataccttc     780
aacgcgagcg ttatctttag cctgagccag ggccgtagcg tgcaagaggc gctgcgtttc     840
ggctgccaag ttgcgggtaa aaatgcggt ctgcaaggct tgacggtat cgtgtaa         897
```

<210> SEQ ID NO 55
<211> LENGTH: 298
<212> TYPE: PRT
<213> ORGANISM: Homo sapiens

<400> SEQUENCE: 55

Met Glu Glu Lys Gln Ile Leu Cys Val Gly Leu Val Val Leu Asp Val
1               5                   10                  15

Ile Ser Leu Val Asp Lys Tyr Pro Lys Glu Asp Ser Glu Ile Arg Cys
            20                  25                  30

Leu Ser Gln Arg Trp Gln Arg Gly Gly Asn Ala Ser Asn Ser Cys Thr
        35                  40                  45

Val Leu Ser Leu Leu Gly Ala Pro Cys Ala Phe Met Gly Ser Met Ala
    50                  55                  60

Pro Gly His Val Ala Asp Phe Leu Val Ala Asp Phe Arg Arg Arg Gly
65                  70                  75                  80

Val Asp Val Ser Gln Val Ala Trp Gln Ser Lys Gly Asp Thr Pro Ser
                85                  90                  95

Ser Cys Cys Ile Ile Asn Asn Ser Asn Gly Asn Arg Thr Ile Val Leu
            100                 105                 110

His Asp Thr Ser Leu Pro Asp Val Ser Ala Thr Asp Phe Glu Lys Val
        115                 120                 125

Asp Leu Thr Gln Phe Lys Trp Ile His Ile Glu Gly Arg Asn Ala Ser
    130                 135                 140

Glu Gln Val Lys Met Leu Gln Arg Ile Asp Ala His Asn Thr Arg Gln
145                 150                 155                 160

Pro Pro Glu Gln Lys Ile Arg Val Ser Val Glu Val Glu Lys Pro Arg
                165                 170                 175

Glu Glu Leu Phe Gln Leu Phe Gly Tyr Gly Asp Val Val Phe Val Ser
            180                 185                 190

Lys Asp Val Ala Lys His Leu Gly Phe Gln Ser Ala Glu Glu Ala Leu
        195                 200                 205

Arg Gly Leu Tyr Gly Arg Val Arg Lys Gly Ala Val Leu Val Cys Ala
    210                 215                 220

Trp Ala Glu Glu Gly Ala Asp Ala Leu Gly Pro Asp Gly Lys Leu Leu
225                 230                 235                 240

His Ser Asp Ala Phe Pro Pro Arg Val Val Asp Thr Leu Gly Ala
                245                 250                 255

Gly Asp Thr Phe Asn Ala Ser Val Ile Phe Ser Leu Ser Gln Gly Arg
            260                 265                 270

Ser Val Gln Glu Ala Leu Arg Phe Gly Cys Gln Val Ala Gly Lys Lys
        275                 280                 285

Cys Gly Leu Gln Gly Phe Asp Gly Ile Val
    290                 295

<210> SEQ ID NO 56
<211> LENGTH: 1095
<212> TYPE: DNA
<213> ORGANISM: Homo sapiens

<400> SEQUENCE: 56
atggcccacc gatttccagc cctcacccag gagcagaaga aggagctctc agaaattgcc          60
cagagcattg ttgccaatgg aaagggatc ctggctgcag atgaatctgt aggtaccatg         120
gggaaccgcc tgcagaggat caaggtggaa acactgaag agaaccgccg gcagttccga         180
gaaatcctct tctctgtgga cagttccatc aaccagagca tcggggggtgt gatccttttc        240 cacgagaccc tctaccagaa ggacagccag ggaaagctgt tcagaaacat cctcaaggaa        300
aaggggatcg tggtgggaat caagttagac caaggaggtg ctcctcttgc aggaacaaac       360
aaagaaacca ccattcaagg gcttgatggc ctctcagagc gctgtgctca gtacaagaaa       420
gatggtgttg actttgggaa gtggcgtgct gtgctgagga ttgccgacca gtgtccatcc       480
agcctcgcta tccaggaaaa cgccaacgcc ctggctcgct acgccagcat ctgtcagcag       540

```
aatggactgg tacctattgt tgaaccagag gtaattcctg atggagacca tgacctggaa    600
cactgccagt atgttactga gaaggtcctg gctgctgtct acaaggccct gaatgaccat    660
catgtttacc tggagggcac cctgctaaag cccaacatgg tgactgctgg acatgcctgc    720
accaagaagt atactccaga acaagtagct atggccaccg taacagctct ccaccgtact    780
gttcctgcag ctgttcctgg catctgcttt ttgtctggtg gcatgagtga agaggatgcc    840
actctcaacc tcaatgctat caacctttgc cctctaccaa gccctggaa  actaagtttc    900 tcttatggac gggccctgca ggccagtgca ctggctgcct ggggtggcaa ggctgcaaac    960
aaggaggcaa cccaggaggc tttatgaag  cgggccatgg ctaactgcca ggcggccaaa   1020
ggacagtatg ttcacacggg ttcttctggg gctgcttcca cccagtcgct cttcacagcc   1080
tgctatacct actag                                                    1095

<210> SEQ ID NO 57
<211> LENGTH: 1095
<212> TYPE: DNA
<213> ORGANISM: Artificial Sequence
<220> FEATURE:
<223> OTHER INFORMATION: Codon Optimized Homo sapiens Sequence

<400> SEQUENCE: 57
atggcgcacc gttttccggc gctgacccaa gagcagaaga aggagctgag cgagattgcg     60
cagagcatcg tggcgaatgg taaaggtatt ctggcggcgg atgagagcgt tggtaccatg    120
ggcaaccgtc tgcagcgtat taaggtggag aacaccgagg aaaaccgtcg tcaattccgt    180
gaaatcctgt ttagcgttga tagcagcatc aaccagagca ttggtggcgt gatcctgttc    240
cacgaaaccc tgtaccagaa ggacagccaa ggtaaactgt ttcgtaacat tctgaaggaa    300
aaaggtattg tggttggcat caagctggat caaggtggcg cgccgctggc gggcaccaac    360
aaggaaacca ccatccaggg tctggacggc ctgagcgaac gttgcgcgca atataagaaa    420
gatggtgttg acttcggcaa gtggcgtgcg gtgctgcgta ttgcggacca gtgcccgagc    480
agcctggcga tccaagaaaa cgcgaacgcg ctggcgcgtt acgcgagcat ctgccagcaa    540
aacggtctgg tgccgattgt tgagccggaa gttatcccgg acggcgatca cgacctggag    600
cactgccagt atgtgaccga aaaggttctg gcggcggtgt acaaagcgct gaacgatcac    660
cacgtttatc tggagggtac cctgctgaaa ccgaacatgg tgaccgcggg ccatgcgtgc    720
accaagaaat acacccccga acaggtggcg atggcgaccg tgaccgcgct gcaccgtacc    780
gttccggcgg cggtgccggg tatttgcttt ctgagcggtg gcatgagcga agaggacgcg    840
accctgaacc tgaacgcgat caacctgtgc ccgctgccga gccgtggaa  actgagcttc    900 agctacggcc gtgcgctgca ggcgagcgcg ctggcgcgt  ggggtggcaa ggcggcgaac    960
aaagaggcga cccaagaagc gtttatgaag cgtgcgatgg cgaactgcca ggcggcgaaa   1020
ggtcaatatg tgcataccgg cagcagcggt gcggcgagca cccagagcct gtttaccgcg   1080
tgctatacct attaa                                                    1095

<210> SEQ ID NO 58
<211> LENGTH: 364
<212> TYPE: PRT
<213> ORGANISM: Homo sapiens

<400> SEQUENCE: 58

Met Ala His Arg Phe Pro Ala Leu Thr Gln Glu Gln Lys Lys Glu Leu
1               5                   10                  15
```

```
Ser Glu Ile Ala Gln Ser Ile Val Ala Asn Gly Lys Gly Ile Leu Ala
            20                  25                  30

Ala Asp Glu Ser Val Gly Thr Met Gly Asn Arg Leu Gln Arg Ile Lys
        35                  40                  45

Val Glu Asn Thr Glu Glu Asn Arg Arg Gln Phe Arg Glu Ile Leu Phe
 50                  55                  60

Ser Val Asp Ser Ser Ile Asn Gln Ser Ile Gly Gly Val Ile Leu Phe
 65                  70                  75                  80

His Glu Thr Leu Tyr Gln Lys Asp Ser Gln Gly Lys Leu Phe Arg Asn
                85                  90                  95

Ile Leu Lys Glu Lys Gly Ile Val Val Gly Ile Lys Leu Asp Gln Gly
            100                 105                 110

Gly Ala Pro Leu Ala Gly Thr Asn Lys Glu Thr Thr Ile Gln Gly Leu
        115                 120                 125

Asp Gly Leu Ser Glu Arg Cys Ala Gln Tyr Lys Lys Asp Gly Val Asp
130                 135                 140

Phe Gly Lys Trp Arg Ala Val Leu Arg Ile Ala Asp Gln Cys Pro Ser
145                 150                 155                 160

Ser Leu Ala Ile Gln Glu Asn Ala Asn Ala Leu Ala Arg Tyr Ala Ser
                165                 170                 175

Ile Cys Gln Gln Asn Gly Leu Val Pro Ile Val Glu Pro Glu Val Ile
            180                 185                 190

Pro Asp Gly Asp His Asp Leu Glu His Cys Gln Tyr Val Thr Glu Lys
        195                 200                 205

Val Leu Ala Ala Val Tyr Lys Ala Leu Asn Asp His His Val Tyr Leu
210                 215                 220

Glu Gly Thr Leu Leu Lys Pro Asn Met Val Thr Ala Gly His Ala Cys
225                 230                 235                 240

Thr Lys Lys Tyr Thr Pro Glu Gln Val Ala Met Ala Thr Val Thr Ala
                245                 250                 255

Leu His Arg Thr Val Pro Ala Ala Val Pro Gly Ile Cys Phe Leu Ser
            260                 265                 270

Gly Gly Met Ser Glu Glu Asp Ala Thr Leu Asn Leu Asn Ala Ile Asn
        275                 280                 285

Leu Cys Pro Leu Pro Lys Pro Trp Lys Leu Ser Phe Ser Tyr Gly Arg
290                 295                 300

Ala Leu Gln Ala Ser Ala Leu Ala Ala Trp Gly Gly Lys Ala Ala Asn
305                 310                 315                 320

Lys Glu Ala Thr Gln Glu Ala Phe Met Lys Arg Ala Met Ala Asn Cys
                325                 330                 335

Gln Ala Ala Lys Gly Gln Tyr Val His Thr Gly Ser Ser Gly Ala Ala
            340                 345                 350

Ser Thr Gln Ser Leu Phe Thr Ala Cys Tyr Thr Tyr
        355                 360

<210> SEQ ID NO 59
<211> LENGTH: 747
<212> TYPE: DNA
<213> ORGANISM: Caulobacter crescentus

<400> SEQUENCE: 59
atgtcctcag ccatctatcc cagcctgaag ggcaagcgcg tcgtcatcac cggcggcggc    60
tcgggcatcg gggccggcct caccgccggc ttcgcccgtc agggcgcgga ggtgatcttc   120
```

```
ctcgacatcg ccgacgagga ctccagggct cttgaggccg agctggccgg ctcgccgatc        180
ccgccggtct acaagcgctg cgacctgatg aacctcgagg cgatcaaggc ggtcttcgcc        240
gagatcggcg acgtcgacgt gctggtcaac aacgccggca tgacgaccg ccacaagctg         300 gccgacgtga ccgcgcccta ttgggacgag cggatcaacg tcaacctgcg ccacatgctg        360
ttctgcaccc aggccgtcgc gccgggcatg aagaagcgtg gcggcgggc ggtgatcaac         420 ttcggttcga tcagctggca cctggggctt gaggacctcg tcctctacga aaccgccaag        480
gccggcatcg aaggcatgac ccgcgcgctg gcccgggagc tgggtcccga cgacatccgc       540
gtcacctgcg tggtgccggg caacgtcaag accaagcgcc aggagaagtg gtacacgccc        600
gaaggcgagg cccagatcgt ggcggcccaa tgcctgaagg gccgcatcgt cccggagaac        660
gtcgccgcgc tggtgctgtt cctggcctcg gatgacgcgt cgctctgcac cggccacgaa        720
tactggatcg acgccggctg gcgttga                                           747

<210> SEQ ID NO 60
<211> LENGTH: 747
<212> TYPE: DNA
<213> ORGANISM: Artificial Sequence
<220> FEATURE:
<223> OTHER INFORMATION: Codon Optimized Caulobacter crescentus Sequence

<400> SEQUENCE: 60
atgagcagcg cgatctaccc gagcctgaaa ggtaaacgtg tggtgattac cggcggcggc         60
agcggcattg gtgcgggcct gaccgcgggc ttcgcgcgtc agggtgcgga agtgatcttt        120
ctggacattg cggacgaaga tagccgtgcg ctggaggcgg aactggcggg cagcccgatc        180
ccgccggtgt acaagcgttg cgatctgatg aacctggagg cgatcaaagc ggttttcgcg        240
gaaattggcg acgtggatgt tctggtgaac aacgcgggta acgacgaccg tcacaagctg        300
gcggatgtga ccggtgcgta ttgggatgag cgtattaacg ttaacctgcg tcacatgctg        360
ttctgcaccc aggcggtggc gccgggtatg aagaaacgtg gtggcggtgc ggttatcaac        420
tttggcagca ttagctggca cctgggtctg gaggacctgg tgctgtacga aaccgcgaaa        480
gcgggcatcg agggtatgac ccgtgcgctg gcgcgtgaac tgggtccgga cgatattcgt        540
gtgacctgcg tggttccggg taacgttaag accaaacgtc aagagaagtg gtataccccg        600
gagggtgaag cgcagattgt tgcggcgcaa tgcctgaaag gtcgtattgt tccggaaaac        660
gtggcggcgc tggttctgtt tctggcgagc gatgatgcga gcctgtgcac cggccatgag        720
tattggattg atgcgggctg gcgttaa                                           747

<210> SEQ ID NO 61
<211> LENGTH: 248
<212> TYPE: PRT
<213> ORGANISM: Caulobacter crescentus

<400> SEQUENCE: 61
```

Met Ser Ser Ala Ile Tyr Pro Ser Leu Lys Gly Lys Arg Val Val Ile
1               5                   10                  15

Thr Gly Gly Gly Ser Gly Ile Gly Ala Gly Leu Thr Ala Gly Phe Ala
                20                  25                  30

Arg Gln Gly Ala Glu Val Ile Phe Leu Asp Ile Ala Asp Glu Asp Ser
            35                  40                  45

Arg Ala Leu Glu Ala Glu Leu Ala Gly Ser Pro Ile Pro Pro Val Tyr
        50                  55                  60

Lys Arg Cys Asp Leu Met Asn Leu Glu Ala Ile Lys Ala Val Phe Ala

```
                65                  70                  75                  80
Glu Ile Gly Asp Val Asp Val Leu Val Asn Asn Ala Gly Asn Asp Asp
                    85                  90                  95

Arg His Lys Leu Ala Asp Val Thr Gly Ala Tyr Trp Asp Glu Arg Ile
                100                 105                 110

Asn Val Asn Leu Arg His Met Leu Phe Cys Thr Gln Ala Val Ala Pro
                115                 120                 125

Gly Met Lys Lys Arg Gly Gly Ala Val Ile Asn Phe Gly Ser Ile
            130                 135                 140

Ser Trp His Leu Gly Leu Glu Asp Leu Val Leu Tyr Glu Thr Ala Lys
145                 150                 155                 160

Ala Gly Ile Glu Gly Met Thr Arg Ala Leu Ala Arg Glu Leu Gly Pro
                    165                 170                 175

Asp Asp Ile Arg Val Thr Cys Val Val Pro Gly Asn Val Lys Thr Lys
                180                 185                 190

Arg Gln Glu Lys Trp Tyr Thr Pro Glu Gly Glu Ala Gln Ile Val Ala
                195                 200                 205

Ala Gln Cys Leu Lys Gly Arg Ile Val Pro Gly Asn Val Ala Ala Leu
                210                 215                 220

Val Leu Phe Leu Ala Ser Asp Asp Ala Ser Leu Cys Thr Gly His Glu
225                 230                 235                 240

Tyr Trp Ile Asp Ala Gly Trp Arg
                245
```

<210> SEQ ID NO 62
<211> LENGTH: 1173
<212> TYPE: DNA
<213> ORGANISM: Haloferax volcanii

<400> SEQUENCE: 62

```
atgagcccccg cccccaccga catcgtcgag gagttcacgc gccgcgactg gcagggagac      60
gacgtgacgg gcaccgtgcg ggtcgccatg atcggcctcg gctggtggac ccgcgacgag    120
gcgattcccg cggtcgaggc gtccgagttc tgcgagacga cggtcgtcgt cagcagttcg    180
aaggagaaag ccgagggcgc gacggcgttg accgagtcga taacccacgg cctcacctac    240
gacgagttcc acgaggggggt cgccgccgac gcctacgacg cggtgtacgt cgtcacgccg    300
aacggtctgc atctcccgta cgtcgagacc gccgccgagt ggggaaggc ggtcctctgc     360
gagaaaccgc tggaagcgtc ggtcgagcgg gccgaaaagc tcgtcgccgc ctgcgaccgc    420
gccgacgtgc cctgatggt cgcctatcgg atgcagaccg agccggccgt ccggcgcgcc    480
cgcgaactcg tcgaggccgg cgtcatcggc gagccggtgt cgtccacgg ccacatgtcc     540
cagcgcctgc tcgacgaggt cgtccccgac cccgaccagt ggcggctcga ccccgaactc    600
tccggcggcg cgaccgtcat ggacatcggg ctctacccgc tgaacaccgc ccggttcgtc    660
ctcgacgccg accccgtccg cgtcagggcg accgccgcg tcgacgacga ggcgttcgag     720
gccgtcggcg acgagcacgt cagtttcggc gtcgacttcg acgacggcac gctcgcggtc    780
tgcaccgcca gccagtcggc ttaccagttg agccacctcc gggtgaccgg caccgagggc    840
gaactcgaaa tcgagcccgc gttctacaac cgccaaaagc gggattccg actgtcgtgg      900
gggaccagt ccgccgacta cgacttcgag caggtaaaacc agatgacgga ggagttcgac    960
tacttcgcgt cccggctcct gtcggattcc gaccccgcgc ccgacggcga ccacgcgctc   1020
gtggacatgc gcgcgatgga cgcgatttac gccgcggcgg agcgcgggac cgatgtcgcc   1080
```

```
gtcgacgccg ccgactccga ttccgccgac tccgattccg ccgacgctgc cgccgccaac    1140
cacgacgccg accccgattc cgacgggacg tag                                 1173
```

<210> SEQ ID NO 63
<211> LENGTH: 390
<212> TYPE: PRT
<213> ORGANISM: Haloferax volcanii

<400> SEQUENCE: 63

```
Met Ser Pro Ala Pro Thr Asp Ile Val Glu Glu Phe Thr Arg Arg Asp
1               5                   10                  15

Trp Gln Gly Asp Asp Val Thr Gly Thr Val Arg Val Ala Met Ile Gly
            20                  25                  30

Leu Gly Trp Trp Thr Arg Asp Glu Ala Ile Pro Ala Val Glu Ala Ser
        35                  40                  45

Glu Phe Cys Glu Thr Thr Val Val Ser Ser Lys Glu Lys Ala
    50                  55                  60

Glu Gly Ala Thr Ala Leu Thr Glu Ser Ile Thr His Gly Leu Thr Tyr
65                  70                  75                  80

Asp Glu Phe His Glu Gly Val Ala Ala Asp Ala Tyr Asp Ala Val Tyr
                85                  90                  95

Val Val Thr Pro Asn Gly Leu His Leu Pro Tyr Val Glu Thr Ala Ala
            100                 105                 110

Glu Leu Gly Lys Ala Val Leu Cys Glu Lys Pro Leu Glu Ala Ser Val
        115                 120                 125

Glu Arg Ala Glu Lys Leu Val Ala Ala Cys Asp Arg Ala Asp Val Pro
130                 135                 140

Leu Met Val Ala Tyr Arg Met Gln Thr Glu Pro Ala Val Arg Arg Ala
145                 150                 155                 160

Arg Glu Leu Val Glu Ala Gly Val Ile Gly Glu Pro Val Phe Val His
                165                 170                 175

Gly His Met Ser Gln Arg Leu Leu Asp Glu Val Val Pro Asp Pro Asp
            180                 185                 190

Gln Trp Arg Leu Asp Pro Glu Leu Ser Gly Gly Ala Thr Val Met Asp
        195                 200                 205

Ile Gly Leu Tyr Pro Leu Asn Thr Ala Arg Phe Val Leu Asp Ala Asp
    210                 215                 220

Pro Val Arg Val Arg Ala Thr Ala Arg Val Asp Asp Glu Ala Phe Glu
225                 230                 235                 240

Ala Val Gly Asp Glu His Val Ser Phe Gly Val Asp Phe Asp Asp Gly
                245                 250                 255

Thr Leu Ala Val Cys Thr Ala Ser Gln Ser Ala Tyr Gln Leu Ser His
            260                 265                 270

Leu Arg Val Thr Gly Thr Glu Gly Glu Leu Glu Ile Glu Pro Ala Phe
        275                 280                 285

Tyr Asn Arg Gln Lys Arg Gly Phe Arg Leu Ser Trp Gly Asp Gln Ser
    290                 295                 300

Ala Asp Tyr Asp Phe Glu Gln Val Asn Gln Met Thr Glu Glu Phe Asp
305                 310                 315                 320

Tyr Phe Ala Ser Arg Leu Leu Ser Asp Ser Pro Ala Pro Asp Gly
                325                 330                 335

Asp His Ala Leu Val Asp Met Arg Ala Met Asp Ala Ile Tyr Ala Ala
            340                 345                 350

Ala Glu Arg Gly Thr Asp Val Ala Val Asp Ala Ala Asp Ser Asp Ser
```

```
                355                 360                 365
Ala Asp Ser Asp Ser Ala Asp Ala Ala Ala Asn His Asp Ala Asp
        370                 375                 380

Pro Asp Ser Asp Gly Thr
385                 390

<210> SEQ ID NO 64
<211> LENGTH: 1176
<212> TYPE: DNA
<213> ORGANISM: Unknown
<220> FEATURE:
<223> OTHER INFORMATION: Trichoderma reesei Sequence

<400> SEQUENCE: 64
atggcgtctg gaaacccttg cacoctgaaa tggggcatca tggccaccgg cggaatcgca      60
gagaccttct gcaaggatct cctgtgcaac cccgcgattc gaggcgccga tgatgtgcgc     120
cacgagattg tggccgtggc ctcttccagc agcagcaaga gagcagagga gttcctccag     180
agaatcgacg gtgcctttga cgccaagacg tacggatcat cccggaact tgtggcagac      240 cccaacgtcg acatcgtcta tgtggcaact ccccacagcc accacttcca gaacaccatg     300
ctggcgctgg aagccggcaa gaacgtcttg tgcgaaaagg cttcaccgt gacggccgcg       360 caggcccgaa agctggttga cggccaag gccaagaagc tcttcctgat ggaagctgtg        420
tggacacggt actttccgct gagtatcaag attcgagagc tcattgccgc cggcgagatt     480
ggcactgtct ttcgaacaat cgccgacttg tccatcaacg caaactcaga gcagggtcaa     540
gccctgaaat cgcagactc acatcgaatg gtcaacccgg acctcgcagg cggtgccacc      600
ttggatctcg gagtctatcc cttgacctgg gtgttccaga ccctgtatca tttgcaaccg     660
gaggaagaca aggaggctcc caccgtggtt gcttccagca acaagtacac cactggcgca     720
gacgagaata ccgccatcat ctgcagcttc cctcgccaca acagcattgg aattgcttcg     780
acgacgatga gggcggacac cgaccccgag aaggacacca ttccggcggt ccgaattcaa     840
ggatccaagg gagaaatcca gtcttcttc ccgacctacc gaccgctcaa gtacaaggtg      900
gtgaagacga acggcgaggc gcagacggtt gactgcccca tccccggaga ccccgcgcgc    960
aagggctcgg gccacggaat gttctgggag gcggacgagt gtgctcgatg ccttcgcgat   1020
ggcaagttgg agagtgccac gttgccatgg aaggagagca ttgtcattat ggaaacgatg   1080
gaggaggcgc tgaggcaggg tggcgtcacg tatccggagc tgattaccac ggatgtctat   1140
gatcccaaga gccctctcaa cacggggaat cagtag                              1176

<210> SEQ ID NO 65
<211> LENGTH: 391
<212> TYPE: PRT
<213> ORGANISM: Unknown
<220> FEATURE:
<223> OTHER INFORMATION: Trichoderma reesei Sequence

<400> SEQUENCE: 65

Met Ala Ser Gly Asn Pro Tyr Thr Leu Lys Trp Gly Ile Met Ala Thr
1               5                   10                  15

Gly Gly Ile Ala Glu Thr Phe Cys Lys Asp Leu Leu Cys Asn Pro Ala
                20                  25                  30

Ile Arg Gly Ala Asp Asp Val Arg His Glu Ile Val Ala Val Ala Ser
            35                  40                  45

Ser Ser Ser Ser Lys Arg Ala Glu Glu Phe Leu Gln Arg Ile Asp Gly
        50                  55                  60
```

```
Ala Phe Asp Ala Lys Thr Tyr Gly Ser Tyr Pro Glu Leu Val Ala Asp
 65                  70                  75                  80

Pro Asn Val Asp Ile Val Tyr Val Ala Thr Pro His Ser His His Phe
                 85                  90                  95

Gln Asn Thr Met Leu Ala Leu Glu Ala Gly Lys Asn Val Leu Cys Glu
            100                 105                 110

Lys Ala Phe Thr Val Thr Ala Ala Gln Ala Arg Lys Leu Val Glu Thr
            115                 120                 125

Ala Lys Ala Lys Lys Leu Phe Leu Met Glu Ala Val Trp Thr Arg Tyr
130                 135                 140

Phe Pro Leu Ser Ile Lys Ile Arg Glu Leu Ile Ala Ala Gly Glu Ile
145                 150                 155                 160

Gly Thr Val Phe Arg Thr Ile Ala Asp Leu Ser Ile Asn Ala Asn Ser
                165                 170                 175

Glu Gln Gly Gln Ala Leu Lys Phe Ala Asp Ser His Arg Met Val Asn
            180                 185                 190

Pro Asp Leu Ala Gly Gly Ala Thr Leu Asp Leu Gly Val Tyr Pro Leu
            195                 200                 205

Thr Trp Val Phe Gln Thr Leu Tyr His Leu Gln Pro Glu Glu Asp Lys
210                 215                 220

Glu Ala Pro Thr Val Val Ala Ser Ser Asn Lys Tyr Thr Thr Gly Ala
225                 230                 235                 240

Asp Glu Asn Thr Ala Ile Ile Cys Ser Phe Pro Arg His Asn Ser Ile
                245                 250                 255

Gly Ile Ala Ser Thr Thr Met Arg Ala Asp Thr Asp Pro Glu Lys Asp
            260                 265                 270

Thr Ile Pro Ala Val Arg Ile Gln Gly Ser Lys Gly Glu Ile Gln Val
            275                 280                 285

Phe Phe Pro Thr Tyr Arg Pro Leu Lys Tyr Lys Val Val Lys Thr Asn
290                 295                 300

Gly Glu Ala Gln Thr Val Asp Cys Pro Ile Pro Gly Asp Pro Ala Arg
305                 310                 315                 320

Lys Gly Ser Gly His Gly Met Phe Trp Glu Ala Asp Glu Cys Ala Arg
                325                 330                 335

Cys Leu Arg Asp Gly Lys Leu Glu Ser Ala Thr Leu Pro Trp Lys Glu
            340                 345                 350

Ser Ile Val Ile Met Glu Thr Met Glu Glu Ala Leu Arg Gln Gly Gly
            355                 360                 365

Val Thr Tyr Pro Glu Leu Ile Thr Thr Asp Val Tyr Asp Pro Lys Ser
370                 375                 380

Pro Leu Asn Thr Gly Asn Gln
385                 390

<210> SEQ ID NO 66
<211> LENGTH: 870
<212> TYPE: DNA
<213> ORGANISM: Caulobacter crescentus

<400> SEQUENCE: 66
atgaccgctc aagtcacttg cgtatgggat ctgaaggcca cgttgggcga aggcccgatc     60
tggcatggcg acaccctgtg gttcgtcgac atcaagcagc gtaaaatcca caactaccac    120
cccgccaccg gcgagcgctt cagcttcgac gcgccggatc aggtgacctt cctcgcgccg    180
atcgtcggcg cgaccggctt tgtcgtcggt ctgaagaccg ggattcaccg cttccacccg    240
```

-continued

```
gccacgggct tcagcctgct gctcgaggtc gaggacgcgg cgctgaacaa ccgccccaac    300
gacgccacgg tcgacgcgca aggccgtctg tggttcggca ccatgcacga cggggaagag    360
aacaatagcg gctcgctcta tcggatggac ctcaccggcg tcgcccggat ggaccgcgac    420
atctgcatca ccaacggccc gtgcgtctcg cccgacggca agaccttcta ccacaccgac    480
accctggaaa agacgatcta cgccttcgac ctggccgagg acggcctgct gtcgaacaag    540
cgcgtcttcg tgcagttcgc cctgggcgac gatgtctatc cggacggttc ggtcgtcgat    600
tccgaaggct atctgtggac cgccctgtgg ggcggtttcg gcgcggtccg cttctcgccg    660
caaggcgacg ccgtgacgcg catcgaactg cccgcccccca acgtcaccaa gccctgcttc    720
ggcgggcctg acctgaagac cctctatttc accaccgccc gcaagggcct gagcgacgag    780
accctggccc agtacccgct ggccggcggt gtgttcgccg ttccggtcga tgtggccggc    840
caacccccagc atgaggtccg ccttgtctaa                                     870
```

<210> SEQ ID NO 67
<211> LENGTH: 289
<212> TYPE: PRT
<213> ORGANISM: Caulobacter crescentus

<400> SEQUENCE: 67

```
Met Thr Ala Gln Val Thr Cys Val Trp Asp Leu Lys Ala Thr Leu Gly
1               5                   10                  15

Glu Gly Pro Ile Trp His Gly Asp Thr Leu Trp Phe Val Asp Ile Lys
            20                  25                  30

Gln Arg Lys Ile His Asn Tyr His Pro Ala Thr Gly Glu Arg Phe Ser
        35                  40                  45

Phe Asp Ala Pro Asp Gln Val Thr Phe Leu Ala Pro Ile Val Gly Ala
    50                  55                  60

Thr Gly Phe Val Val Gly Leu Lys Thr Gly Ile His Arg Phe His Pro
65                  70                  75                  80

Ala Thr Gly Phe Ser Leu Leu Glu Val Glu Asp Ala Ala Leu Asn
                85                  90                  95

Asn Arg Pro Asn Asp Ala Thr Val Asp Ala Gln Gly Arg Leu Trp Phe
            100                 105                 110

Gly Thr Met His Asp Gly Glu Glu Asn Asn Ser Gly Ser Leu Tyr Arg
        115                 120                 125

Met Asp Leu Thr Gly Val Ala Arg Met Asp Arg Asp Ile Cys Ile Thr
    130                 135                 140

Asn Gly Pro Cys Val Ser Pro Asp Gly Lys Thr Phe Tyr His Thr Asp
145                 150                 155                 160

Thr Leu Glu Lys Thr Ile Tyr Ala Phe Asp Leu Ala Glu Asp Gly Leu
                165                 170                 175

Leu Ser Asn Lys Arg Val Phe Val Gln Phe Ala Leu Gly Asp Asp Val
            180                 185                 190

Tyr Pro Asp Gly Ser Val Val Asp Ser Glu Gly Tyr Leu Trp Thr Ala
        195                 200                 205

Leu Trp Gly Gly Phe Gly Ala Val Arg Phe Ser Pro Gln Gly Asp Ala
    210                 215                 220

Val Thr Arg Ile Glu Leu Pro Ala Pro Asn Val Thr Lys Pro Cys Phe
225                 230                 235                 240

Gly Gly Pro Asp Leu Lys Thr Leu Tyr Phe Thr Thr Ala Arg Lys Gly
                245                 250                 255
```

Leu Ser Asp Glu Thr Leu Ala Gln Tyr Pro Leu Ala Gly Gly Val Phe
            260                 265                 270

Ala Val Pro Val Asp Val Ala Gly Gln Pro Gln His Glu Val Arg Leu
        275                 280                 285

Val

<210> SEQ ID NO 68
<211> LENGTH: 1776
<212> TYPE: DNA
<213> ORGANISM: Caulobacter crescentus

<400> SEQUENCE: 68

| | |
|---|---:|
| ttgtctaacc gcacgccccg ccggttccgg tcccgcgatt ggttcgataa ccccgaccat | 60 |
| atcgacatga ccgcgctcta tctggagcgc ttcatgaact acgggatcac gccgaggag | 120 |
| ctgcgcagcg gcaagccgat catcggcatc gcccagaccg cagcgacat ctcgccctgc | 180 |
| aaccgcatcc acctggacct ggtccagcgg gtgcgggacg ggatccgcga cgccggggc | 240 |
| atccccatgg agttcccggt ccatccgatc ttcgagaact gccgtcgccc gacggcggcg | 300 |
| ctggaccgga acctctcgta cctgggtctc gtcgagaccc tgcacggcta tccgatcgac | 360 |
| gccgtggttc tgaccaccgg ctgcgacaag accaccccgg ccgggatcat ggccgccacc | 420 |
| acggtcaata tcccggccat cgtgctgtcg ggcggcccga tgctggacgg ctggcacgag | 480 |
| aacgagctcg tgggctcggg caccgtgatc tggcgctcgc ccgcaagct ggcggccggc | 540 |
| gagatcaccg aggaagagtt catcgaccgc gccgccagct cggcgccgtc ggcgggccac | 600 |
| tgcaacacca tgggcacggc ctcgaccatg aacgccgtgg ccgaggcgct gggcctgtcg | 660 |
| ctgaccggct gcgcggccat ccccgccccc taccgcgagc gcggccagat ggcctacaag | 720 |
| accgccagc gcatcgtcga tctggcctat gacgacgtca aaccgctcga catcctgacc | 780 |
| aagcaagcct tcgagaacgc catcgccctg gtggcggcgg ccggcggctc gaccaacgcc | 840 |
| cagccgcaca tcgtggccat ggcccgtcac gccggcgtcg agatcaccgc cgacgactgg | 900 |
| cgcgcggcct atgacatccc gctgatcgtc aacatgcagc cggccggcaa gtatctgggc | 960 |
| gagcgcttcc accgagccgg cggcgcgccg cggtgctgt gggagctgtt gcagcaaggc | 1020 |
| cgcctgcacg gcgacgtgct gaccgtcacc ggcaagacga tgagcgagaa cctgcaaggc | 1080 |
| cgcgaaacca gcgaccgcga ggtgatcttc ccgtaccacg agccgctggc cgagaaggcc | 1140 |
| gggttcctgg ttctcaaggg caacctcttc gacttcgcga tcatgaagtc cagcgtgatc | 1200 |
| ggcgaggagt tccgcaagcg ctacctgtcg cagcccggcc aggaaggcgt gttcgaagcc | 1260 |
| cgcgccatcg tgttcgacgg ctcggacgac tatcacaagc ggatcaacga tccggccctg | 1320 |
| gagatcgacg agcgctgcat cctggtgatc cgcggcgcgg gtccgatcgg ctggcccggc | 1380 |
| tcggccgagg tcgtcaacat gcagccgccg gatcaccttc tgaagaaggg gatcatgagc | 1440 |
| ctgcccaccc tgggcgatgg ccgtcagtcg ggcaccgccg acagcccctc gatcctgaac | 1500 |
| gcctcgcccg aaagcgcgat cggcggcggc ctgtcgtggc tgcgcaccgg cgacaccatc | 1560 |
| cgcatcgacc tcaacaccgg ccgctgcgac gccctggtcg acgaggcgac gatcgccgcg | 1620 |
| cgcaagcagg acggcatccc ggcggttccc gccaccatga cgccctggca ggaaatctac | 1680 |
| cgcgcccacg ccagtcagct cgacaccggc ggcgtgctgg agttcgcggt caagtaccag | 1740 |
| gacctggcgg ccaagctgcc ccgccacaac cactga | 1776 |

<210> SEQ ID NO 69
<211> LENGTH: 591

<212> TYPE: PRT
<213> ORGANISM: Caulobacter crescentus

<400> SEQUENCE: 69

Met Ser Asn Arg Thr Pro Arg Phe Arg Ser Arg Asp Trp Phe Asp
1               5                   10                  15

Asn Pro Asp His Ile Asp Met Thr Ala Leu Tyr Leu Glu Arg Phe Met
                20                  25                  30

Asn Tyr Gly Ile Thr Pro Glu Glu Leu Arg Ser Gly Lys Pro Ile Ile
            35                  40                  45

Gly Ile Ala Gln Thr Gly Ser Asp Ile Ser Pro Cys Asn Arg Ile His
50                  55                  60

Leu Asp Leu Val Gln Arg Val Arg Asp Gly Ile Arg Asp Ala Gly Gly
65                  70                  75                  80

Ile Pro Met Glu Phe Pro Val His Pro Ile Phe Glu Asn Cys Arg Arg
                85                  90                  95

Pro Thr Ala Ala Leu Asp Arg Asn Leu Ser Tyr Leu Gly Leu Val Glu
            100                 105                 110

Thr Leu His Gly Tyr Pro Ile Asp Ala Val Val Leu Thr Thr Gly Cys
            115                 120                 125

Asp Lys Thr Thr Pro Ala Gly Ile Met Ala Ala Thr Thr Val Asn Ile
130                 135                 140

Pro Ala Ile Val Leu Ser Gly Gly Pro Met Leu Asp Gly Trp His Glu
145                 150                 155                 160

Asn Glu Leu Val Gly Ser Gly Thr Val Ile Trp Arg Ser Arg Arg Lys
                165                 170                 175

Leu Ala Ala Gly Glu Ile Thr Glu Glu Phe Ile Asp Arg Ala Ala
            180                 185                 190

Ser Ser Ala Pro Ser Ala Gly His Cys Asn Thr Met Gly Thr Ala Ser
            195                 200                 205

Thr Met Asn Ala Val Ala Glu Ala Leu Gly Leu Ser Leu Thr Gly Cys
210                 215                 220

Ala Ala Ile Pro Ala Pro Tyr Arg Glu Arg Gly Gln Met Ala Tyr Lys
225                 230                 235                 240

Thr Gly Gln Arg Ile Val Asp Leu Ala Tyr Asp Asp Val Lys Pro Leu
                245                 250                 255

Asp Ile Leu Thr Lys Gln Ala Phe Glu Asn Ala Ile Ala Leu Val Ala
            260                 265                 270

Ala Ala Gly Gly Ser Thr Asn Ala Gln Pro His Ile Val Ala Met Ala
            275                 280                 285

Arg His Ala Gly Val Glu Ile Thr Ala Asp Asp Trp Arg Ala Ala Tyr
290                 295                 300

Asp Ile Pro Leu Ile Val Asn Met Gln Pro Ala Gly Lys Tyr Leu Gly
305                 310                 315                 320

Glu Arg Phe His Arg Ala Gly Gly Ala Pro Ala Val Leu Trp Glu Leu
                325                 330                 335

Leu Gln Gln Gly Arg Leu His Gly Asp Val Leu Thr Val Thr Gly Lys
            340                 345                 350

Thr Met Ser Glu Asn Leu Gln Gly Arg Glu Thr Ser Asp Arg Glu Val
            355                 360                 365

Ile Phe Pro Tyr His Glu Pro Leu Ala Glu Lys Ala Gly Phe Leu Val
370                 375                 380

Leu Lys Gly Asn Leu Phe Asp Phe Ala Ile Met Lys Ser Ser Val Ile
385                 390                 395                 400

```
Gly Glu Glu Phe Arg Lys Arg Tyr Leu Ser Gln Pro Gly Gln Glu Gly
                405                 410                 415

Val Phe Glu Ala Arg Ala Ile Val Phe Asp Gly Ser Asp Tyr His
            420                 425                 430

Lys Arg Ile Asn Asp Pro Ala Leu Glu Ile Asp Glu Arg Cys Ile Leu
                435                 440                 445

Val Ile Arg Gly Ala Gly Pro Ile Gly Trp Pro Gly Ser Ala Glu Val
        450                 455                 460

Val Asn Met Gln Pro Pro Asp His Leu Leu Lys Lys Gly Ile Met Ser
465                 470                 475                 480

Leu Pro Thr Leu Gly Asp Gly Arg Gln Ser Gly Thr Ala Asp Ser Pro
                485                 490                 495

Ser Ile Leu Asn Ala Ser Pro Glu Ser Ala Ile Gly Gly Leu Ser
                500                 505                 510

Trp Leu Arg Thr Gly Asp Thr Ile Arg Ile Asp Leu Asn Thr Gly Arg
                515                 520                 525

Cys Asp Ala Leu Val Asp Glu Ala Thr Ile Ala Ala Arg Lys Gln Asp
            530                 535                 540

Gly Ile Pro Ala Val Pro Ala Thr Met Thr Pro Trp Gln Glu Ile Tyr
545                 550                 555                 560

Arg Ala His Ala Ser Gln Leu Asp Thr Gly Gly Val Leu Glu Phe Ala
                565                 570                 575

Val Lys Tyr Gln Asp Leu Ala Ala Lys Leu Pro Arg His Asn His
                580                 585                 590

<210> SEQ ID NO 70
<211> LENGTH: 1968
<212> TYPE: DNA
<213> ORGANISM: Escherichia coli

<400> SEQUENCE: 70
atgtctgttc gcaatatttt tgctgacgag agccacgata tttacaccgt cagaacgcac      60
gccgatggcc cggacggcga actcccatta accgcagaga tgcttatcaa ccgcccgagc     120
ggggatctgt tcggtatgac catgaatgcc ggaatgggtt ggtctccgga cgagctggat     180
cgggacggta ttttactgct cagtacactc ggtggcttac gcggcgcaga cggtaaaccc     240
gtggcgctgg cgttgcacca ggggcattac gaactggaca tccagatgaa gcggcggcc     300 gaggttatta aagccaacca tgccctgccc tatgccgtgt acgtctccga tccttgtgac     360
gggcgtactc agggtacaac ggggatgttt gattcgctac ataccgaaa tgacgcatcg     420 atggtaatgc ccgccttat cgctctctg cccgacgcga aagcagttat tggtgtggcg     480
agttgcgata agggcttcc ggccaccatg atggcactcg ccgcgcagca acatcgca     540 accgtgctgg tccccggcgg cgcgacgctg cccgcaaagg atggagaaga caacggcaag     600
gtgcaaacca ttggcgcacg cttcgccaat ggcgaattat ctctacagga cgcacgccgt     660
gcgggctgta aagcctgtgc ctcttccggc ggcggctgtc aattttttggg cactgccggg     720 acatctcagg tggtggccga aggattggga ctggcaatcc cacattcagc cctggcccct     780
tccggtgagc ctgtgtggcg ggagatcgcc agagcttccg cgcgagctgc gctgaacctg     840
agtcaaaaag gcatcaccac ccgggaaatt ctcaccgata aagcgataga gaatgcgatg     900
acggtccatg ccgcgttcgg tggttcaaca aacctgctgt acacatccc ggcaattgct     960 caccaggcag gttgccatat cccgaccgtt gatgactgga tccgcatcaa caagcgcgtg    1020
```

```
ccccgactgg tgagcgtact gcctaatggc ccggtttatc atccaacggt caatgccttt    1080
atggcaggtg gtgtgccgga agtcatgttg catctgcgca gcctcggatt gttgcatgaa    1140
gacgttatga cggttaccgg cagcacgctg aaagaaaacc tcgactggtg ggagcactcc    1200
gaacggcgtc agcggttcaa gcaactcctg ctcgatcagg aacaaatcaa cgctgacgaa    1260
gtgatcatgt ctccgcagca agcaaaagcg cgcggattaa cctcaactat caccttcccg    1320
gtgggcaata ttgcgccaga aggttcggtg atcaaatcca ccgccattga ccctcgatg    1380 attgatgagc aaggtatcta ttaccataaa ggtgtggcga aggtttatct gtccgagaaa    1440
agtgcgattt acgatatcaa acatgacaag atcaaggcgg cgatattct ggtcattatt     1500 ggcgttggac cttcaggtac agggatggaa gaaacctacc aggttaccag tgccctgaag    1560
catctgtcat acggtaagca tgtttcgtta atcaccgatg cacgtttctc gggcgtttct    1620
actggcgcgt gcatcggcca tgtggggcca gaagcgctgg ccggaggccc catcggtaaa    1680
ttacgcaccg gggatttaat tgaaattaaa attgattgtc gcgagcttca cggcgaagtc    1740
aatttcctcg gaacccgtag cgatgaacaa ttaccttcac aggaggaggc aactgcaata    1800
ttaaatgcca gacccagcca tcaggattta cttcccgatc ctgaattgcc agatgatacc    1860
cggctatggg caatgcttca ggccgtgagt ggtgggacat ggaccggttg tatttatgat    1920
gtaaacaaaa ttggcgcggc tttgcgcgat tttatgaata aaaactga                1968
```

\<210\> SEQ ID NO 71
\<211\> LENGTH: 1968
\<212\> TYPE: DNA
\<213\> ORGANISM: Artificial Sequence
\<220\> FEATURE:
\<223\> OTHER INFORMATION: Codon Optimized E. coli Sequence

\<400\> SEQUENCE: 71

```
atgtctgttc gcaatatttt tgctgacgag agccacgata tttacaccgt cagaacgcac      60
gccgatggcc cggacggcga actcccatta accgcagaga tgcttatcaa ccgcccgagc     120
ggggatctgt tcggtatgac catgaatgcc ggaatgggtt ggtctccgga cgagctggat     180
cgggacggta ttttactgct cagtacactc ggtggcttac gcggcgcaga cggtaaaccc     240
gtggcgctgg cgttgcacca ggggcattac gaactggaca tccagatgaa agcggcggcc     300
gaggttatta agccaacca tgccctgccc tatgccgtgt acgtctccga tccttgtgac     360
gggcgtactc agggtacaac ggggatgttt gattcgctac ataccgaaa tgacgcatcg     420 atggtaatgc gccgccttat tcgctctctg cccgacgcga aagcagttat tggtgtggcg     480
agttgcgata aggggcttcc ggccaccatg atggcactcg ccgcgcagca acatcgca       540 accgtgctgg tccccggcgg cgcgacgctg cccgcaaagg atggagaaga caacggcaag     600
gtgcaaacca ttggcgcacg cttcgccaat ggcgaattat ctctacagga cgcacgccgt     660
gcgggctgta agcctgtgc ctcttccggc ggcggctgtc aatttttggg cactgccggg     720
acatctcagg tggtggccga aggattggga ctggcaatcc acattcagc cctggcccct     780 tccggtgagc ctgtgtggcg ggagatcgcc agagcttccg cgcgagctgc gctgaacctg     840
agtcaaaaag gcatcaccac ccgggaaatt ctcaccgata aagcgataga gaatgcgatg     900
acggtccatg ccgcgttcgg tggttcaaca aacctgctgt acacatcccc ggcaattgct     960
caccaggcag gttgccatat cccgaccgtt gatgactgga tccgcatcaa caagcgcgtg    1020
ccccgactgg tgagcgtact gcctaatggc ccggtttatc atccaacggt caatgccttt    1080
atggcaggtg gtgtgccgga agtcatgttg catctgcgca gcctcggatt gttgcatgaa    1140
```

-continued

```
gacgttatga cggttaccgg cagcacgctg aaagaaaacc tcgactggtg ggagcactcc   1200
gaacggcgtc agcggttcaa gcaactcctg ctcgatcagg aacaaatcaa cgctgacgaa   1260
gtgatcatgt ctccgcagca agcaaaagcg cgcggattaa cctcaactat caccttcccg   1320
gtgggcaata ttgcgccaga aggttcggtg atcaaatcca ccgccattga ccctcgatg    1380
attgatgagc aaggtatcta ttaccataaa ggtgtggcga aggtttatct gtccgagaaa   1440
agtgcgattt acgatatcaa acatgacaag atcaaggcgg cgatattct ggtcattatt    1500
ggcgttggac cttcaggtac agggatggaa gaaacctacc aggttaccag tgccctgaag   1560
catctgtcat acggtaagca tgtttcgtta atcaccgatg cacgtttctc gggcgtttct   1620
actggcgcgt gcatcggcca tgtggggcca gaagcgctgg ccggaggccc catcggtaaa   1680
ttacgcaccg gggatttaat tgaaattaaa attgattgtc gcgagcttca cggcgaagtc   1740
aatttcctcg gaacccgtag cgatgaacaa ttaccttcac aggaggaggc aactgcaata   1800
ttaaatgcca gacccagcca tcaggattta cttcccgatc ctgaattgcc agatgatacc   1860
cggctatggg caatgcttca ggccgtgagt ggtgggacat ggaccggttg tatttatgat   1920
gtaaacaaaa ttggcgcggc tttgcgcgat tttatgaata aaaactga                1968
```

<210> SEQ ID NO 72
<211> LENGTH: 655
<212> TYPE: PRT
<213> ORGANISM: Escherichia coli

<400> SEQUENCE: 72

```
Met Ser Val Arg Asn Ile Phe Ala Asp Glu Ser His Asp Ile Tyr Thr
1               5                   10                  15

Val Arg Thr His Ala Asp Gly Pro Asp Gly Glu Leu Pro Leu Thr Ala
            20                  25                  30

Glu Met Leu Ile Asn Arg Pro Ser Gly Asp Leu Phe Gly Met Thr Met
        35                  40                  45

Asn Ala Gly Met Gly Trp Ser Pro Asp Glu Leu Asp Arg Asp Gly Ile
    50                  55                  60

Leu Leu Leu Ser Thr Leu Gly Gly Leu Arg Gly Ala Asp Gly Lys Pro
65                  70                  75                  80

Val Ala Leu Ala Leu His Gln Gly His Tyr Glu Leu Asp Ile Gln Met
                85                  90                  95

Lys Ala Ala Ala Glu Val Ile Lys Ala Asn His Ala Leu Pro Tyr Ala
            100                 105                 110

Val Tyr Val Ser Asp Pro Cys Asp Gly Arg Thr Gln Gly Thr Thr Gly
        115                 120                 125

Met Phe Asp Ser Leu Pro Tyr Arg Asn Asp Ala Ser Met Val Met Arg
    130                 135                 140

Arg Leu Ile Arg Ser Leu Pro Asp Ala Lys Ala Val Ile Gly Val Ala
145                 150                 155                 160

Ser Cys Asp Lys Gly Leu Pro Ala Thr Met Met Ala Leu Ala Ala Gln
                165                 170                 175

His Asn Ile Ala Thr Val Leu Val Pro Gly Gly Ala Thr Leu Pro Ala
            180                 185                 190

Lys Asp Gly Glu Asp Asn Gly Lys Val Gln Thr Ile Gly Ala Arg Phe
        195                 200                 205

Ala Asn Gly Glu Leu Ser Leu Gln Asp Ala Arg Arg Ala Gly Cys Lys
    210                 215                 220
```

-continued

```
Ala Cys Ala Ser Ser Gly Gly Gly Cys Gln Phe Leu Gly Thr Ala Gly
225                 230                 235                 240

Thr Ser Gln Val Val Ala Glu Gly Leu Gly Leu Ala Ile Pro His Ser
            245                 250                 255

Ala Leu Ala Pro Ser Gly Glu Pro Val Trp Arg Glu Ile Ala Arg Ala
        260                 265                 270

Ser Ala Arg Ala Ala Leu Asn Leu Ser Gln Lys Gly Ile Thr Thr Arg
    275                 280                 285

Glu Ile Leu Thr Asp Lys Ala Ile Glu Asn Ala Met Thr Val His Ala
290                 295                 300

Ala Phe Gly Gly Ser Thr Asn Leu Leu Leu His Ile Pro Ala Ile Ala
305                 310                 315                 320

His Gln Ala Gly Cys His Ile Pro Thr Val Asp Asp Trp Ile Arg Ile
                325                 330                 335

Asn Lys Arg Val Pro Arg Leu Val Ser Val Leu Pro Asn Gly Pro Val
            340                 345                 350

Tyr His Pro Thr Val Asn Ala Phe Met Ala Gly Gly Val Pro Glu Val
        355                 360                 365

Met Leu His Leu Arg Ser Leu Gly Leu Leu His Glu Asp Val Met Thr
    370                 375                 380

Val Thr Gly Ser Thr Leu Lys Glu Asn Leu Asp Trp Trp Glu His Ser
385                 390                 395                 400

Glu Arg Arg Gln Arg Phe Lys Gln Leu Leu Asp Gln Glu Gln Ile
                405                 410                 415

Asn Ala Asp Glu Val Ile Met Ser Pro Gln Gln Ala Lys Ala Arg Gly
            420                 425                 430

Leu Thr Ser Thr Ile Thr Phe Pro Val Gly Asn Ile Ala Pro Glu Gly
        435                 440                 445

Ser Val Ile Lys Ser Thr Ala Ile Asp Pro Ser Met Ile Asp Glu Gln
    450                 455                 460

Gly Ile Tyr Tyr His Lys Gly Val Ala Lys Val Tyr Leu Ser Glu Lys
465                 470                 475                 480

Ser Ala Ile Tyr Asp Ile Lys His Asp Lys Ile Lys Ala Gly Asp Ile
                485                 490                 495

Leu Val Ile Ile Gly Val Gly Pro Ser Gly Thr Gly Met Glu Glu Thr
            500                 505                 510

Tyr Gln Val Thr Ser Ala Leu Lys His Leu Ser Tyr Gly Lys His Val
        515                 520                 525

Ser Leu Ile Thr Asp Ala Arg Phe Ser Gly Val Ser Thr Gly Ala Cys
    530                 535                 540

Ile Gly His Val Gly Pro Glu Ala Leu Ala Gly Gly Pro Ile Gly Lys
545                 550                 555                 560

Leu Arg Thr Gly Asp Leu Ile Glu Ile Lys Ile Asp Cys Arg Glu Leu
                565                 570                 575

His Gly Glu Val Asn Phe Leu Gly Thr Arg Ser Asp Glu Gln Leu Pro
            580                 585                 590

Ser Gln Glu Glu Ala Thr Ala Ile Leu Asn Ala Arg Pro Ser His Gln
    595                 600                 605

Asp Leu Leu Pro Asp Pro Glu Leu Pro Asp Asp Thr Arg Leu Trp Ala
        610                 615                 620

Met Leu Gln Ala Val Ser Gly Gly Thr Trp Thr Gly Cys Ile Tyr Asp
625                 630                 635                 640

Val Asn Lys Ile Gly Ala Ala Leu Arg Asp Phe Met Asn Lys Asn
```

645        650        655

<210> SEQ ID NO 73
<211> LENGTH: 1968
<212> TYPE: DNA
<213> ORGANISM: Escherichia coli

<400> SEQUENCE: 73

| | | | | | |
|---|---|---|---|---|---|
| atgaccattg | agaaaatttt | cacccogcag | gacgacgcgt | tttatgcggt | gatcacccac | 60 |
| gcggcgggc | cgcagggcgc | tctgccgctg | accccgcaga | tgctgatgga | atctcccagc | 120 |
| ggcaacctgt | tcggcatgac | gcagaacgcc | gggatgggct | gggacgccaa | caagctcacc | 180 |
| ggcaaagagg | tgctgattat | cggcactcag | ggcggcatcc | gcgccggaga | cggacgccca | 240 |
| atcgcgctgg | gctaccacac | cgggcattgg | gagatcggca | tgcagatgca | ggcggcggcg | 300 |
| aaggagatca | cccgcaatgg | cgggatcccg | ttcgcggcct | tcgtcagcga | tccgtgcgac | 360 |
| gggcgctcgc | agggcacgca | cggtatgttc | gattccctgc | cgtaccgcaa | cgacgcggcg | 420 |
| atcgtgtttc | gccgcctgat | ccgctccctg | ccgacgcggc | gggcggtgat | cggcgtagcg | 480 |
| acctgcgata | aagggctgcc | cgccaccatg | attgcgctgg | ccgcgatgca | cgacctgccg | 540 |
| actattctgg | tgccgggcgg | ggcgacgctg | ccgccgaccg | tcggggaaga | cgcgggcaag | 600 |
| gtgcagacca | tcggcgcgcg | tttcgccaac | cacgaactct | ccctgcagga | ggccgccgaa | 660 |
| ctgggctgtc | gcgcctgcgc | ctcgccgggc | ggcgggtgtc | agttcctcgg | cacggcgggc | 720 |
| acctcgcagg | tggtcgcgga | ggcgctgggt | ctggcgctgc | cgcactccgc | gctggcgccg | 780 |
| tccgggcagg | cggtgtggct | ggagatcgcc | cgccagtcgg | cgcgcgcggt | cagcgagctg | 840 |
| gatagccgcg | gcatcaccac | gcgggatatc | ctctccgata | aagccatcga | aaacgcgatg | 900 |
| gtgatccacg | cggcgttcgg | cggctccacc | aatttactgc | tgcacattcc | ggccatcgcc | 960 |
| cacgcggcgg | gctgcacgat | cccggacgtt | gagcactgga | cgcgcatcaa | ccgtaaagtg | 1020 |
| ccgcgtctgg | tgagcgtgct | gcccaacggc | ccggactatc | acccgaccgt | gcgcgccttc | 1080 |
| ctcgcgggcg | gcgtgccgga | ggtgatgctc | cacctgcgcg | acctcggcct | gctgcatctg | 1140 |
| gacgccatga | ccgtgaccgg | ccagacggtg | ggcgagaacc | ttgaatggtg | gcaggcgtcc | 1200 |
| gagcgccggg | cgcgcttccg | ccagtgcctg | cgcgagcagg | acggcgtaga | gccggatgac | 1260 |
| gtgatcctgc | cgccggagaa | ggcaaaaagcg | aaagggctga | cctcgacggt | ctgcttcccg | 1320 |
| acgggcaaca | tcgctccgga | aggttcggtg | atcaaggcca | cggcgatcga | cccgtcggtg | 1380 |
| gtgggcgaag | atggcgtata | ccaccacacc | ggccgggtgc | gggtgtttgt | ctcggaagcg | 1440 |
| caggcgatca | aggcgatcaa | gcgggaagag | attgtgcagg | gcgatatcat | ggtggtgatc | 1500 |
| ggcggcgggc | cgtccggcac | cggcatggaa | gagacctacc | agctcacctc | cgcgctaaag | 1560 |
| catatctcgt | ggggcaagac | ggtgtcgctc | atcaccgatg | cgcgcttctc | gggcgtgtcg | 1620 |
| acgggcgcct | gcttcggcca | cgtgtcgccg | gaggcgctgg | cgggcgggcc | gattggcaag | 1680 |
| ctgcgcgata | acgacatcat | cgagattgcc | gtggatcgtc | tgacgttaac | tggcagcgtg | 1740 |
| aacttcatcg | gcaccgcgga | caacccgctg | acgccggaag | agggcgcgcg | cgagctggcg | 1800 |
| cggcggcaga | cgcaccccga | cctgcacgcc | acgactttt | tgccggacga | cacccggctg | 1860 |
| tgggcggcac | tgcagtcggt | gagcggcggc | acctggaaag | gctgtattta | tgacaccgat | 1920 |
| aaaattatcg | aggtaattaa | cgccggtaaa | aaagcgctcg | gaatttaa | | 1968 |

<210> SEQ ID NO 74
<211> LENGTH: 1968

<212> TYPE: DNA
<213> ORGANISM: Artificial Sequence
<220> FEATURE:
<223> OTHER INFORMATION: Codon Optimized E. coli Sequence

<400> SEQUENCE: 74

| | |
|---|---|
| atgaccattg agaaaatttt cacccccgcag gacgacgcgt tttatgcggt gatcacccac | 60 |
| gcggcgggc cgcagggcgc tctgccgctg accccgcaga tgctgatgga atctcccagc | 120 |
| ggcaacctgt tcggcatgac gcagaacgcc gggatgggct gggacgccaa caagctcacc | 180 |
| ggcaaagagg tgctgattat cggcactcag ggcggcatcc gcgccggaga cggacgccca | 240 |
| atcgcgctgg gctaccacac cgggcattgg gagatcggca tgcagatgca ggcggcggcg | 300 |
| aaggagatca cccgcaatgg cgggatcccg ttcgcggcct tcgtcagcga tccgtgcgac | 360 |
| gggcgctcgc agggcacgca cggtatgttc gattccctgc cgtaccgcaa cgacgcggcg | 420 |
| atcgtgtttc gccgcctgat ccgctccctg ccgacgcggc gggcggtgat cggcgtagcg | 480 |
| acctgcgata aagggctgcc cgccaccatg attgcgctgg ccgcgatgca cgacctgccg | 540 |
| actattctgg tgccgggcgg ggcgacgctg ccgccgaccg tcggggaaga cgcgggcaag | 600 |
| gtgcagacca tcgcgcgcg tttcgccaac cacgaactct ccctgcagga ggccgccgaa | 660 |
| ctgggctgtc gcgcctgcgc ctcgccgggc ggcgggtgtc agttcctcgg cacggcgggc | 720 |
| acctcgcagg tggtcgcgga ggcgctgggt ctggcgctgc cgcactccgc gctggcgccg | 780 |
| tccgggcagg cggtgtggct ggagatcgcc cgccagtcgg cgcgcgcggt cagcgagctg | 840 |
| gatagccgcg gcatcaccac gcgggatatc ctctccgata aagccatcga aaacgcgatg | 900 |
| gtgatccacg cggcgttcgg cggctccacc aatttactgc tgcacattcc ggccatcgcc | 960 |
| cacgcggcgg gctgcacgat cccggacgtt gagcactgga cgcgcatcaa ccgtaaagtg | 1020 |
| ccgcgtctgg tgagcgtgct gcccaacggc ccggactatc acccgaccgt gcgcgccttc | 1080 |
| ctcgcgggcg gcgtgccgga ggtgatgctc cacctgcgcg acctcggcct gctgcatctg | 1140 |
| gacgccatga ccgtgaccgg ccagacggtg gcgagaacc ttgaatggtg gcaggcgtcc | 1200 |
| gagcgccggg cgcgcttccg ccagtgcctg cgcgagcagg acggcgtaga gccggatgac | 1260 |
| gtgatcctgc cgccggagaa ggcaaaagcg aaagggctga cctcgacggt ctgcttcccg | 1320 |
| acgggcaaca tcgctccgga aggttcggtg atcaaggcca cggcgatcga cccgtcggtg | 1380 |
| gtgggcgaag atggcgtata ccaccacacc ggccgggtgc gggtgtttgt ctcggaagcg | 1440 |
| caggcgatca aggcgatcaa gcgggaagag attgtgcagg gcgatatcat ggtggtgatc | 1500 |
| ggcggcgggc cgtccggcac cggcatggaa gagacctacc agctcacctc cgcgctaaag | 1560 |
| catatctcgt ggggcaagac ggtgtcgctc atcaccgatg cgcgcttctc gggcgtgtcg | 1620 |
| acgggcgcct gcttcggcca cgtgtcgccg gaggcgctgg cgggcgggcc gattggcaag | 1680 |
| ctgcgcgata cgacatcat cgagattgcc gtggatcgtc tgacgttaac tggcagcgtg | 1740 |
| aacttcatcg gcaccgcgga caacccgctg acgccggaag agggcgcgcg cgagctggcg | 1800 |
| cggcggcaga cgcacccgga cctgcacgcc cacgactttt tgccggacga cacccggctg | 1860 |
| tgggcggcac tgcagtcggt gagcggcggc acctggaaag gctgtattta tgacaccgat | 1920 |
| aaaattatcg aggtaattaa cgccggtaaa aaagcgctcg gaatttaa | 1968 |

<210> SEQ ID NO 75
<211> LENGTH: 655
<212> TYPE: PRT
<213> ORGANISM: Escherichia coli

```
<400> SEQUENCE: 75

Met Thr Ile Glu Lys Ile Phe Thr Pro Gln Asp Asp Ala Phe Tyr Ala
1               5                   10                  15

Val Ile Thr His Ala Ala Gly Pro Gln Gly Ala Leu Pro Leu Thr Pro
                20                  25                  30

Gln Met Leu Met Glu Ser Pro Ser Gly Asn Leu Phe Gly Met Thr Gln
            35                  40                  45

Asn Ala Gly Met Gly Trp Asp Ala Asn Lys Leu Thr Gly Lys Glu Val
        50                  55                  60

Leu Ile Ile Gly Thr Gln Gly Gly Ile Arg Ala Gly Asp Gly Arg Pro
65                  70                  75                  80

Ile Ala Leu Gly Tyr His Thr Gly His Trp Glu Ile Gly Met Gln Met
                85                  90                  95

Gln Ala Ala Ala Lys Glu Ile Thr Arg Asn Gly Gly Ile Pro Phe Ala
            100                 105                 110

Ala Phe Val Ser Asp Pro Cys Asp Gly Arg Ser Gln Gly Thr His Gly
        115                 120                 125

Met Phe Asp Ser Leu Pro Tyr Arg Asn Asp Ala Ala Ile Val Phe Arg
130                 135                 140

Arg Leu Ile Arg Ser Leu Pro Thr Arg Arg Ala Val Ile Gly Val Ala
145                 150                 155                 160

Thr Cys Asp Lys Gly Leu Pro Ala Thr Met Ile Ala Leu Ala Ala Met
                165                 170                 175

His Asp Leu Pro Thr Ile Leu Val Pro Gly Gly Ala Thr Leu Pro Pro
            180                 185                 190

Thr Val Gly Glu Asp Ala Gly Lys Val Gln Thr Ile Gly Ala Arg Phe
        195                 200                 205

Ala Asn His Glu Leu Ser Leu Gln Glu Ala Ala Glu Leu Gly Cys Arg
    210                 215                 220

Ala Cys Ala Ser Pro Gly Gly Cys Gln Phe Leu Gly Thr Ala Gly
225                 230                 235                 240

Thr Ser Gln Val Val Ala Glu Ala Leu Gly Leu Ala Leu Pro His Ser
                245                 250                 255

Ala Leu Ala Pro Ser Gly Gln Ala Val Trp Leu Glu Ile Ala Arg Gln
            260                 265                 270

Ser Ala Arg Ala Val Ser Glu Leu Asp Ser Arg Gly Ile Thr Thr Arg
        275                 280                 285

Asp Ile Leu Ser Asp Lys Ala Ile Glu Asn Ala Met Val Ile His Ala
    290                 295                 300

Ala Phe Gly Gly Ser Thr Asn Leu Leu Leu His Ile Pro Ala Ile Ala
305                 310                 315                 320

His Ala Ala Gly Cys Thr Ile Pro Asp Val Glu His Trp Thr Arg Ile
                325                 330                 335

Asn Arg Lys Val Pro Arg Leu Val Ser Val Leu Pro Asn Gly Pro Asp
            340                 345                 350

Tyr His Pro Thr Val Arg Ala Phe Leu Ala Gly Gly Val Pro Glu Val
        355                 360                 365

Met Leu His Leu Arg Asp Leu Gly Leu Leu His Leu Asp Ala Met Thr
    370                 375                 380

Val Thr Gly Gln Thr Val Gly Glu Asn Leu Glu Trp Trp Gln Ala Ser
385                 390                 395                 400

Glu Arg Arg Ala Arg Phe Arg Gln Cys Leu Arg Glu Gln Asp Gly Val
                405                 410                 415
```

Glu Pro Asp Asp Val Ile Leu Pro Pro Glu Lys Ala Lys Ala Lys Gly
                420                 425                 430

Leu Thr Ser Thr Val Cys Phe Pro Thr Gly Asn Ile Ala Pro Glu Gly
            435                 440                 445

Ser Val Ile Lys Ala Thr Ala Ile Asp Pro Ser Val Val Gly Glu Asp
    450                 455                 460

Gly Val Tyr His His Thr Gly Arg Val Arg Val Phe Val Ser Glu Ala
465                 470                 475                 480

Gln Ala Ile Lys Ala Ile Lys Arg Glu Glu Ile Val Gln Gly Asp Ile
                485                 490                 495

Met Val Val Ile Gly Gly Pro Ser Gly Thr Gly Met Glu Glu Thr
            500                 505                 510

Tyr Gln Leu Thr Ser Ala Leu Lys His Ile Ser Trp Gly Lys Thr Val
            515                 520                 525

Ser Leu Ile Thr Asp Ala Arg Phe Ser Gly Val Ser Thr Gly Ala Cys
    530                 535                 540

Phe Gly His Val Ser Pro Glu Ala Leu Ala Gly Gly Pro Ile Gly Lys
545                 550                 555                 560

Leu Arg Asp Asn Asp Ile Ile Glu Ile Ala Val Asp Arg Leu Thr Leu
                565                 570                 575

Thr Gly Ser Val Asn Phe Ile Gly Thr Ala Asp Asn Pro Leu Thr Pro
            580                 585                 590

Glu Glu Gly Ala Arg Glu Leu Ala Arg Arg Gln Thr His Pro Asp Leu
            595                 600                 605

His Ala His Asp Phe Leu Pro Asp Asp Thr Arg Leu Trp Ala Ala Leu
            610                 615                 620

Gln Ser Val Ser Gly Gly Thr Trp Lys Gly Cys Ile Tyr Asp Thr Asp
625                 630                 635                 640

Lys Ile Ile Glu Val Ile Asn Ala Gly Lys Lys Ala Leu Gly Ile
                645                 650                 655

<210> SEQ ID NO 76
<211> LENGTH: 906
<212> TYPE: DNA
<213> ORGANISM: Escherichia coli

<400> SEQUENCE: 76
atgaaaaaat tcagcggcat tattccaccg gtatccagca cgtttcatcg tgacggaacc      60
cttgataaaa aggcaatgcg cgaagttgcc gacttcctga ttaataaagg ggtcgacggg     120
ctgttttatc tgggtaccgg tggtgaattt agccaaatga atacagccca gcgcatggca     180
ctcgccgaag aagctgtaac cattgtcgac gggcgagtgc cggtattgat tggcgtcggt     240 tcccctttcca ctgacgaagc ggtcaaactg gcgcagcatg cgcaagccta cggcgctgat     300
ggtatcgtcg ccatcaaccc ctactactgg aaagtcgcac cacgaaatct tgacgactat     360
taccagcaga tcgcccgtag cgtcacccta ccggtgatcc tgtacaactt tccggatctg     420
acgggtcagg acttaacccc ggaaaccgtg acgcgtctgg ctctgcaaaa cgagaatatc     480
gttggcatca agacaccat cgacagcgtt ggtcacttgc gtacgatgat caacacagtt     540
aagtcggtac gcccgtcgtt ttcggtattc tgcggttacg atgatcattt gctgaatacg     600
atgctgctgg gcggcgacgg tgcgataacc gccagcgcta actttgctcc ggaactctcc     660
gtcggcatct accgcgcctg gcgtgaaggc gatctggcga ccgctgcgac gctgaataaa     720
aaactactac aactgcccgc tatttacgcc ctcgaaacac cgtttgtctc actgatcaaa     780

```
tacagcatgc agtgtgtcgg gctgcctgta gagacatatt gcttaccacc gattcttgaa    840
gcatctgaag aagcaaaaga taaagtccac gtgctgctta ccgcgcaggg cattttacca    900
gtctga                                                                906
```

<210> SEQ ID NO 77
<211> LENGTH: 906
<212> TYPE: DNA
<213> ORGANISM: Artificial Sequence
<220> FEATURE:
<223> OTHER INFORMATION: Codon Optimized E. coli Sequence

<400> SEQUENCE: 77

```
atgaaaaaat tcagcggcat tattccaccg gtatccagca cgtttcatcg tgacggaacc     60
cttgataaaa aggcaatgcg cgaagttgcc gacttcctga ttaataaagg ggtcgacggg    120
ctgttttatc tgggtaccgg tggtgaattt agccaaatga atacagccca gcgcatggca    180
ctcgccgaag aagctgtaac cattgtcgac gggcgagtgc cggtattgat tggcgtcggt    240
tccccttcca ctgacgaagc ggtcaaactg gcgcagcatg cgcaagccta cggcgctgat    300
ggtatcgtcg ccatcaaccc ctactactgg aaagtcgcac cacgaaatct tgacgactat    360
taccagcaga tcgcccgtag cgtcacccta ccggtgatcc tgtacaactt ccggatctg     420 acgggtcagg acttaacccc ggaaaccgtg acgcgtctgg ctctgcaaaa cgagaatatc    480
gttggcatca agacaccat cgacagcgtt ggtcacttgc gtacgatgat caacacagtt     540
aagtcggtac gcccgtcgtt ttcggtattc tgcggttacg atgatcattt gctgaatacg    600
atgctgctgg gcggcgacgg tgcgataacc gccagcgcta actttgctcc ggaactctcc    660
gtcggcatct accgcgcctg gcgtgaaggc gatctggcga ccgctgcgac gctgaataaa    720
aaactactac aactgcccgc tatttacgcc ctcgaaacac cgtttgtctc actgatcaaa    780
tacagcatgc agtgtgtcgg gctgcctgta gagacatatt gcttaccacc gattcttgaa    840
gcatctgaag aagcaaaaga taaagtccac gtgctgctta ccgcgcaggg cattttacca    900
gtctga                                                                906
```

<210> SEQ ID NO 78
<211> LENGTH: 301
<212> TYPE: PRT
<213> ORGANISM: Escherichia coli

<400> SEQUENCE: 78

```
Met Lys Lys Phe Ser Gly Ile Ile Pro Pro Val Ser Ser Thr Phe His
1               5                   10                  15

Arg Asp Gly Thr Leu Asp Lys Lys Ala Met Arg Glu Val Ala Asp Phe
                20                  25                  30

Leu Ile Asn Lys Gly Val Asp Gly Leu Phe Tyr Leu Gly Thr Gly Gly
            35                  40                  45

Glu Phe Ser Gln Met Asn Thr Ala Gln Arg Met Ala Leu Ala Glu Glu
        50                  55                  60

Ala Val Thr Ile Val Asp Gly Arg Val Pro Val Leu Ile Gly Val Gly
65                  70                  75                  80

Ser Pro Ser Thr Asp Glu Ala Val Lys Leu Ala Gln His Ala Gln Ala
                85                  90                  95

Tyr Gly Ala Asp Gly Ile Val Ala Ile Asn Pro Tyr Tyr Trp Lys Val
                100                 105                 110

Ala Pro Arg Asn Leu Asp Asp Tyr Tyr Gln Gln Ile Ala Arg Ser Val
```

```
                115                 120                 125
Thr Leu Pro Val Ile Leu Tyr Asn Phe Pro Asp Leu Thr Gly Gln Asp
    130                 135                 140
Leu Thr Pro Glu Thr Val Thr Arg Leu Ala Leu Gln Asn Glu Asn Ile
145                 150                 155                 160
Val Gly Ile Lys Asp Thr Ile Asp Ser Val Gly His Leu Arg Thr Met
                165                 170                 175
Ile Asn Thr Val Lys Ser Val Arg Pro Ser Phe Ser Val Phe Cys Gly
            180                 185                 190
Tyr Asp Asp His Leu Leu Asn Thr Met Leu Leu Gly Gly Asp Gly Ala
            195                 200                 205
Ile Thr Ala Ser Ala Asn Phe Ala Pro Glu Leu Ser Val Gly Ile Tyr
    210                 215                 220
Arg Ala Trp Arg Glu Gly Asp Leu Ala Thr Ala Ala Thr Leu Asn Lys
225                 230                 235                 240
Lys Leu Leu Gln Leu Pro Ala Ile Tyr Ala Leu Glu Thr Pro Phe Val
                245                 250                 255
Ser Leu Ile Lys Tyr Ser Met Gln Cys Val Gly Leu Pro Val Glu Thr
            260                 265                 270
Tyr Cys Leu Pro Pro Ile Leu Glu Ala Ser Glu Glu Ala Lys Asp Lys
    275                 280                 285
Val His Val Leu Leu Thr Ala Gln Gly Ile Leu Pro Val
290                 295                 300

<210> SEQ ID NO 79
<211> LENGTH: 909
<212> TYPE: DNA
<213> ORGANISM: Escherichia coli

<400> SEQUENCE: 79
atgccgcagt ccgcgttgtt cacgggaatc attccccctg tctccaccat ttttaccgcc      60
gacggccagc tcgataagcc gggcaccgcc gcgctgatcg acgatctgat caaagcaggc     120
gttgacggcc tgttcttcct gggcagcggt ggcgagttct cccagctcgg cgccgaagag     180
cgtaaagcca ttgcccgctt tgctatcgat catgtcgatc gtcgcgtgcc ggtgctgatc     240
ggcaccggcg caccaacgc ccgggaaacc atcgaactca gccagcacgc gcagcaggcg     300
ggcgcggacg catcgtggt gatcaacccc tactactgga agtgtcgga agcgaacctg     360
atccgctatt tcgagcaggt ggccgacagc gtcacgctgc cggtgatgct ctataacttc     420
ccggcgctga ccgggcagga tctgactccg gcgctggtga aaccctcgc cgactcgcgc     480
agcaatatta tcggcatcaa agacaccatc gactccgtcg cccacctgcg cagcatgatc     540
cataccgtca aggtgccca tccgcacttc accgtgctct gcggctacga cgatcatctg     600
ttcaataccc tgctgctcgg cggcgacggg gcgatatcgg cgagcggcaa ctttgccccg     660
caggtgtcgg tgaatcttct gaaagcctgg cgcgacgggg acgtggcgaa agcggccggg     720
tatcatcaga ccttgctgca aattccgcag atgtatcagc tggatacgcc gtttgtgaac     780
gtgattaaag aggcgatcgt gctctgcggt cgtcctgtct ccacgcacgt gctgccgccc     840
gcctcgccgc tggacgagcc gcgcaaggcg cagctgaaaa ccctgctgca acagctcaag     900
ctttgctga                                                            909

<210> SEQ ID NO 80
<211> LENGTH: 909
<212> TYPE: DNA
```

<213> ORGANISM: Artificial Sequence
<220> FEATURE:
<223> OTHER INFORMATION: Codon Optimized E. coli Sequence

<400> SEQUENCE: 80

```
atgccgcagt ccgcgttgtt cacgggaatc attccccctg tctccaccat ttttaccgcc      60
gacggccagc tcgataagcc gggcaccgcc gcgctgatcg acgatctgat caaagcaggc     120
gttgacggcc tgttcttcct gggcagcggt ggcgagttct cccagctcgg cgccgaagag     180
cgtaaagcca ttgcccgctt tgctatcgat catgtcgatc gtcgcgtgcc ggtgctgatc     240
ggcaccggcg gcaccaacgc ccgggaaacc atcgaactca gccagcacgc gcagcaggcg     300
ggcgcggacg gcatcgtggt gatcaacccc tactactgga aagtgtcgga agcgaacctg     360
atccgctatt tcgagcaggt ggccgacagc gtcacgctgc cggtgatgct ctataacttc     420
ccggcgctga ccgggcagga tctgactccg gcgctggtga aaaccctcgc cgactcgcgc     480
agcaatatta tcggcatcaa agacaccatc gactccgtcg cccacctgcg cagcatgatc     540
cataccgtca aggtgcccca tccgcacttc accgtgctct gcggctacga cgatcatctg     600
ttcaataccc tgctgctcgg cggcgacggg gcgatatcgg cgagcggcaa ctttgccccg     660
caggtgtcgg tgaatcttct gaaagcctgg cgcgacgggg acgtggcgaa agcggccggg     720
tatcatcaga ccttgctgca aattccgcag atgtatcagc tggatacgcc gtttgtgaac     780
gtgattaaag aggcgatcgt gctctgcggt cgtcctgtct ccacgcacgt gctgccgccc     840
gcctcgccgc tggacgagcc gcgcaaggcg cagctgaaaa ccctgctgca acagctcaag     900
ctttgctga                                                             909
```

<210> SEQ ID NO 81
<211> LENGTH: 302
<212> TYPE: PRT
<213> ORGANISM: Escherichia coli

<400> SEQUENCE: 81

```
Met Pro Gln Ser Ala Leu Phe Thr Gly Ile Ile Pro Pro Val Ser Thr
1               5                   10                  15

Ile Phe Thr Ala Asp Gly Gln Leu Asp Lys Pro Gly Thr Ala Ala Leu
            20                  25                  30

Ile Asp Asp Leu Ile Lys Ala Gly Val Asp Gly Leu Phe Phe Leu Gly
        35                  40                  45

Ser Gly Gly Glu Phe Ser Gln Leu Gly Ala Glu Glu Arg Lys Ala Ile
    50                  55                  60

Ala Arg Phe Ala Ile Asp His Val Asp Arg Arg Val Pro Val Leu Ile
65                  70                  75                  80

Gly Thr Gly Gly Thr Asn Ala Arg Glu Thr Ile Glu Leu Ser Gln His
                85                  90                  95

Ala Gln Gln Ala Gly Ala Asp Gly Ile Val Val Ile Asn Pro Tyr Tyr
            100                 105                 110

Trp Lys Val Ser Glu Ala Asn Leu Ile Arg Tyr Phe Glu Gln Val Ala
        115                 120                 125

Asp Ser Val Thr Leu Pro Val Met Leu Tyr Asn Phe Pro Ala Leu Thr
    130                 135                 140

Gly Gln Asp Leu Thr Pro Ala Leu Val Lys Thr Leu Ala Asp Ser Arg
145                 150                 155                 160

Ser Asn Ile Ile Gly Ile Lys Asp Thr Ile Asp Ser Val Ala His Leu
                165                 170                 175
```

Arg Ser Met Ile His Thr Val Lys Gly Ala His Pro His Phe Thr Val
            180                 185                 190

Leu Cys Gly Tyr Asp Asp His Leu Phe Asn Thr Leu Leu Leu Gly Gly
        195                 200                 205

Asp Gly Ala Ile Ser Ala Ser Gly Asn Phe Ala Pro Gln Val Ser Val
    210                 215                 220

Asn Leu Leu Lys Ala Trp Arg Asp Gly Asp Val Ala Lys Ala Ala Gly
225                 230                 235                 240

Tyr His Gln Thr Leu Leu Gln Ile Pro Gln Met Tyr Gln Leu Asp Thr
                245                 250                 255

Pro Phe Val Asn Val Ile Lys Glu Ala Ile Val Leu Cys Gly Arg Pro
            260                 265                 270

Val Ser Thr His Val Leu Pro Pro Ala Ser Pro Leu Asp Glu Pro Arg
        275                 280                 285

Lys Ala Gln Leu Lys Thr Leu Leu Gln Gln Leu Lys Leu Cys
    290                 295                 300

<210> SEQ ID NO 82
<211> LENGTH: 957
<212> TYPE: DNA
<213> ORGANISM: Unknown
<220> FEATURE:
<223> OTHER INFORMATION: Scheffersomyces stipitis Sequence

<400> SEQUENCE: 82
atgccttcta ttaagttgaa ctctggttac gacatgccag ccgtcggttt cggctgttgg      60
aaagtcgacg tcgacacctg ttctgaacag atctaccgtg ctatcaagac cggttacaga     120
ttgttcgacg gtgccgaaga ttacgccaac gaaaagttag ttggtgccgg tgtcaagaag     180
gccattgacg aaggtatcgt caagcgtgaa gatttgttcc ttacctccaa gttgtggaac     240
aactaccacc acccagacaa cgtcgaaaag gccttgaaca gaacccttc tgacttgcaa      300 gttgactacg ttgacttgtt cttgatccac ttcccagtca ccttcaagtt cgttccatta     360
gaagaaaagt acccaccagg attctactgt ggtaagggtg acaacttcga ctacgaagat     420
gttccaattt tagagacttg gaaggctctt gaaaagttgg tcaaggccgg taagatcaga     480
tctatcggtg tttctaactt cccaggtgct ttgctcttgg acttgttgag aggtgctacc     540
atcaagccat ctgtcttgca agttgaacac cacccatact gcaacaacc aagattgatc     600 gaattcgctc aatcccgtgg tattgctgtc accgcttact cttcgttcgg tcctcaatct     660
ttcgttgaat tgaaccaagg tagagctttg aacacttctc cattgttcga gaacgaaact     720
atcaaggcta tcgctgctaa gcacggtaag tctccagctc aagtcttgtt gagatggtca     780
tcccaaagag gcattgccat cattccaaag tccaacactg tcccaagatt gttggaaaac     840
aaggacgtca acagcttcga cttggacgaa caagatttcg ctgacattgc caagttggac     900
atcaacttga gattcaacga cccatgggac tgggacaaga ttcctatctt cgtctaa       957

<210> SEQ ID NO 83
<211> LENGTH: 957
<212> TYPE: DNA
<213> ORGANISM: Artificial Sequence
<220> FEATURE:
<223> OTHER INFORMATION: Codon Optimized Scheffersomyces stipitis
      Sequence

<400> SEQUENCE: 83
atgccatcta tcaagttaaa ttccggttac gacatgcctg ctgttggttt cggttgctgg      60

```
aaggttgatg tcgatacttg ttccgagcaa atttaccgtg ctatcaagac tggttacaga    120
ttgttcgatg gtgctgaaga ctacgccaac gaaaagttag tcggtgctgg tgttaaaaag    180
gctatcgacg aaggtattgt taaaagagaa gacttgttct tgacttctaa gttgtggaac    240
aactaccacc atcctgataa cgtcgaaaaa gctttgaacc gtaccttgtc cgatttgcaa    300
gtcgattacg ttgatttgtt cttgattcat ttcccagtta ccttcaagtt cgttccattg    360
gaagagaagt atccaccagg tttctactgt ggtaagggtg ataacttcga ttacgaagat    420
gtcccaatct tagaaacctg gaaggcttta gaaaagttgg ttaaggctgg taagatcaga    480
tccatcggtg tttctaactt cccaggtgcc ttattgttag acttattgag aggtgctacc    540
attaagcctt ccgttttgca agttgaacat catccttact gcaacaacc aagattgatc    600 gaattcgctc aatctagagg tatcgctgtt actgcctact cttccttcgg tccacaatct    660
ttcgttgagt tgaaccaagg tagagctttg aacacctctc cattgttcga aaacgaaact    720
attaaggcca ttgctgctaa gcatggtaag tctccagccc aagttttgtt gagatggtct    780
tctcaaagag gtatcgctat tatcccaaag tctaatactg tcccaagatt gttggaaaac    840
aaggacgtta actcctttga tttggatgaa caagactttg ctgacatcgc taaattggac    900
atcaacttga gattcaacga cccatgggac tgggacaaga ttccaatttt tgtttaa     957
```

<210> SEQ ID NO 84
<211> LENGTH: 318
<212> TYPE: PRT
<213> ORGANISM: Unknown
<220> FEATURE:
<223> OTHER INFORMATION: Scheffersomyces stipitis Sequence

<400> SEQUENCE: 84

```
Met Pro Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Ile Tyr
            20                  25                  30

Arg Ala Ile Lys Thr Gly Tyr Arg Leu Phe Asp Gly Ala Glu Asp Tyr
        35                  40                  45

Ala Asn Glu Lys Leu Val Gly Ala Gly Val Lys Lys Ala Ile Asp Glu
    50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Lys Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205
```

```
Ala Val Thr Ala Tyr Ser Ser Phe Gly Pro Gln Ser Phe Val Glu Leu
    210                 215                 220
Asn Gln Gly Arg Ala Leu Asn Thr Ser Pro Leu Phe Glu Asn Glu Thr
225                 230                 235                 240
Ile Lys Ala Ile Ala Ala Lys His Gly Lys Ser Pro Ala Gln Val Leu
                245                 250                 255
Leu Arg Trp Ser Ser Gln Arg Gly Ile Ala Ile Pro Lys Ser Asn
                260                 265                 270
Thr Val Pro Arg Leu Leu Glu Asn Lys Asp Val Asn Ser Phe Asp Leu
            275                 280                 285
Asp Glu Gln Asp Phe Ala Asp Ile Ala Lys Leu Asp Ile Asn Leu Arg
        290                 295                 300
Phe Asn Asp Pro Trp Asp Trp Asp Lys Ile Pro Ile Phe Val
305                 310                 315
```

<210> SEQ ID NO 85
<211> LENGTH: 984
<212> TYPE: DNA
<213> ORGANISM: Saccharomyces cerevisiae

<400> SEQUENCE: 85

```
atgtcttcac tggttactct taataacggt ctgaaaatgc ccctagtcgg cttagggtgc      60
tggaaaattg acaaaaaagt ctgtgcgaat caaatttatg aagctatcaa attaggctac     120
cgtttattcg atggtgcttg cgactacggc aacgaaaagg aagttggtga aggtatcagg     180
aaagccatct ccgaaggtct tgtttctaga aggatatat ttgttgtttc aaagttatgg      240
aacaattttc accatcctga tcatgtaaaa ttagctttaa agaagacctt aagcgatatg     300
ggacttgatt atttagacct gtattatatt cacttcccaa tcgccttcaa atatgttcca     360
tttgaagaga ataccctcc aggattctat acgggcgcag atgacgagaa gaaaggtcac     420
atcaccgaag cacatgtacc aatcatagat acgtaccggg ctctggaaga atgtgttgat     480
gaaggcttga ttaagtctat tggtgtttcc aactttcagg gaagcttgat tcaagattta     540
ttacgtggtt gtagaatcaa gcccgtggct ttgcaaattg aacaccatcc ttatttgact     600
caagaacacc tagttgagtt ttgtaaatta cacgatatcc aagtagttgc ttactcctcc     660
ttcggtcctc aatcattcat tgagatggac ttacagttgg caaaaaccac gccaactctg     720
ttcgagaatg atgtaatcaa gaaggtctca caaaaccatc caggcagtac cacttcccaa     780
gtattgctta gatgggcaac tcagagaggc attgccgtca ttccaaaaatc ttccaagaag     840
gaaaggttac ttggcaacct agaaatcgaa aaaaagttca ctttaacgga gcaagaattg     900
aaggatattt ctgcactaaa tgccaacatc agatttaatg atccatggac ctggttggat     960
ggtaaattcc ccacttttgc ctga                                            984
```

<210> SEQ ID NO 86
<211> LENGTH: 984
<212> TYPE: DNA
<213> ORGANISM: Artificial Sequence
<220> FEATURE:
<223> OTHER INFORMATION: Codon Optimized Saccharomyces cerevisiae
       Sequence

<400> SEQUENCE: 86

```
atgtcttcac tggttactct taataacggt ctgaaaatgc ccctagtcgg cttagggtgc      60
tggaaaattg acaaaaaagt ctgtgcgaat caaatttatg aagctatcaa attaggctac     120
cgtttattcg atggtgcttg cgactacggc aacgaaaagg aagttggtga aggtatcagg     180
```

```
aaagccatct ccgaaggtct tgtttctaga aaggatatat ttgttgtttc aaagttatgg    240
aacaattttc accatcctga tcatgtaaaa ttagctttaa agaagacctt aagcgatatg    300
ggacttgatt atttagacct gtattatatt cacttcccaa tcgccttcaa atatgttcca    360
tttgaagaga ataccctcc aggattctat acgggcgcag atgacgagaa gaaaggtcac    420
atcaccgaag cacatgtacc aatcatagat acgtaccggg ctctggaaga atgtgttgat    480
gaaggcttga ttaagtctat tggtgttttcc aactttcagg gaagcttgat tcaagattta    540
ttacgtggtt gtagaatcaa gcccgtggct ttgcaaattg aacaccatcc ttatttgact    600
caagaacacc tagttgagtt ttgtaaaatta cacgatatcc aagtagttgc ttactcctcc    660
ttcggtcctc aatcattcat tgagatggac ttacagttgg caaaaaccac gccaactctg    720
ttcgagaatg atgtaatcaa gaaggtctca caaaaccatc caggcagtac cacttcccaa    780
gtattgctta gatgggcaac tcagagaggc attgccgtca ttccaaaatc ttccaagaag    840
gaaaggttac ttggcaacct agaaatcgaa aaaaagttca ctttaacgga gcaagaattg    900
aaggatattt ctgcactaaa tgccaacatc agatttaatg atccatggac ctggttggat    960
ggtaaattcc ccacttttgc ctga                                            984

<210> SEQ ID NO 87
<211> LENGTH: 327
<212> TYPE: PRT
<213> ORGANISM: Saccharomyces cerevisiae

<400> SEQUENCE: 87

Met Ser Ser Leu Val Thr Leu Asn Asn Gly Leu Lys Met Pro Leu Val
1               5                   10                  15

Gly Leu Gly Cys Trp Lys Ile Asp Lys Lys Val Cys Ala Asn Gln Ile
            20                  25                  30

Tyr Glu Ala Ile Lys Leu Gly Tyr Arg Leu Phe Asp Gly Ala Cys Asp
        35                  40                  45

Tyr Gly Asn Glu Lys Glu Val Gly Glu Gly Ile Arg Lys Ala Ile Ser
    50                  55                  60

Glu Gly Leu Val Ser Arg Lys Asp Ile Phe Val Val Ser Lys Leu Trp
65                  70                  75                  80

Asn Asn Phe His His Pro Asp His Val Lys Leu Ala Leu Lys Lys Thr
                85                  90                  95

Leu Ser Asp Met Gly Leu Asp Tyr Leu Asp Leu Tyr Tyr Ile His Phe
            100                 105                 110

Pro Ile Ala Phe Lys Tyr Val Pro Phe Glu Glu Lys Tyr Pro Pro Gly
        115                 120                 125

Phe Tyr Thr Gly Ala Asp Asp Glu Lys Lys Gly His Ile Thr Glu Ala
    130                 135                 140

His Val Pro Ile Ile Asp Thr Tyr Arg Ala Leu Glu Glu Cys Val Asp
145                 150                 155                 160

Glu Gly Leu Ile Lys Ser Ile Gly Val Ser Asn Phe Gln Gly Ser Leu
                165                 170                 175

Ile Gln Asp Leu Leu Arg Gly Cys Arg Ile Lys Pro Val Ala Leu Gln
            180                 185                 190

Ile Glu His His Pro Tyr Leu Thr Gln Glu His Leu Val Glu Phe Cys
        195                 200                 205

Lys Leu His Asp Ile Gln Val Val Ala Tyr Ser Ser Phe Gly Pro Gln
    210                 215                 220
```

Ser Phe Ile Glu Met Asp Leu Gln Leu Ala Lys Thr Thr Pro Thr Leu
225                 230                 235                 240

Phe Glu Asn Asp Val Ile Lys Lys Val Ser Gln Asn His Pro Gly Ser
                245                 250                 255

Thr Thr Ser Gln Val Leu Leu Arg Trp Ala Thr Gln Arg Gly Ile Ala
            260                 265                 270

Val Ile Pro Lys Ser Ser Lys Lys Glu Arg Leu Leu Gly Asn Leu Glu
        275                 280                 285

Ile Glu Lys Lys Phe Thr Leu Thr Glu Gln Glu Leu Lys Asp Ile Ser
    290                 295                 300

Ala Leu Asn Ala Asn Ile Arg Phe Asn Asp Pro Trp Thr Trp Leu Asp
305                 310                 315                 320

Gly Lys Phe Pro Thr Phe Ala
                325

<210> SEQ ID NO 88
<211> LENGTH: 1092
<212> TYPE: DNA
<213> ORGANISM: Unknown
<220> FEATURE:
<223> OTHER INFORMATION: Scheffersomyces stipitis Sequence

<400> SEQUENCE: 88
atgactgcta acccttcctt ggtgttgaac aagatcgacg acatttcgtt cgaaacttac      60
gatgccccag aaatctctga acctaccgat gtcctcgtcc aggtcaagaa accggtatc     120 tgtggttccg acatccactt ctacgccat ggtagaatcg gtaacttcgt tttgaccaag     180
ccaatggtct tgggtcacga atccgccggt actgttgtcc aggttggtaa gggtgtcacc     240
tctcttaagg ttggtgacaa cgtcgctatc gaaccaggta ttccatccag attctccgac     300
gaatacaaga gcggtcacta caacttgtgt cctcacatgg ccttcgccgc tactcctaac     360
tccaaggaag gcgaaccaaa cccaccaggt accttatgta agtacttcaa gtcgccagaa     420
gacttcttgg tcaagttgcc agaccacgtc agcttggaac tcggtgctct tgttgagcca     480
ttgtctgttg gtgtccacgc ctctaagttg ggttccgttg ctttcggcga ctacgttgcc     540
gtctttggtg ctggtcctgt tggtcttttg gctgctgctg tcgccaagac cttcggtgct     600
aagggtgtca tcgtcgttga cattttcgac aacaagttga agatggccaa ggacattggt     660
gctgctactc acaccttcaa ctccaagacc ggtggttctg aagaattgat caaggctttc     720
ggtggtaacg tgccaaacgt cgttttggaa tgtactggtg ctgaaccttg tatcaagttg     780
ggtgttgacg ccattgcccc aggtggtcgt ttcgttcaag tcggtaacgc tgctggtcca     840
gtcagcttcc caatcaccgt tttcgccatg aaggaattga ctttgttcgg ttctttcaga     900
tacggattca acgactacaa gactgctgtt ggaatctttg acactaacta ccaaaacggt     960
agagaaaatg ctccaattga ctttgaacaa ttgatcaccc acagatacaa gttcaaggac    1020
gctattgaag cctacgactt ggtcagagcc ggtaagggtg ctgtcaagtg tctcattgac    1080
ggccctgagt aa                                                       1092

<210> SEQ ID NO 89
<211> LENGTH: 1092
<212> TYPE: DNA
<213> ORGANISM: Artificial Sequence
<220> FEATURE:
<223> OTHER INFORMATION: Codon Optimized Scheffersomyces stipitis

<400> SEQUENCE: 89

```
atgactgcta acccttcctt ggtgttgaac aagatcgacg acatttcgtt cgaaacttac      60
gatgccccag aaatctctga acctaccgat gtcctcgtcc aggtcaagaa aaccggtatc     120
tgtggttccg acatccactt ctacgcccat ggtagaatcg gtaacttcgt tttgaccaag     180
ccaatggtct tgggtcacga atccgccggt actgttgtcc aggttggtaa gggtgtcacc     240
tctcttaagg ttggtgacaa cgtcgctatc gaaccaggta ttccatccag attctccgac     300
gaatacaaga gcggtcacta caacttgtgt cctcacatgg ccttcgccgc tactcctaac     360
tccaaggaag gcgaaccaaa cccaccaggt accttatgta agtacttcaa gtcgccagaa     420
gatttcttgg tcaagttgcc agaccacgtc agcttggaac tcggtgctct tgttgagcca     480
ttgtctgttg gtgtccacgc tctaagttg ggttccgttg ctttcggcga ctacgttgcc     540
gtctttggag caggtcctgt tggtctttg gctgctgctg tcgccaagac cttcggtgct     600
aagggtgtca tcgtcgttga cattttcgac aacaagttga agatggccaa ggacattgga     660
gctgctactc acaccttcaa ctccaagacc gtggttctg aagaattgat caaggctttc     720
ggtggtaacg tgccaaacgt cgtttttggaa tgtacaggtg cagaaccttg tatcaagttg     780
ggtgttgacg ccattgcccc aggtggtcgt ttcgttcaag tcggtaacgc tgctggtcca     840
gtcagcttcc caatcaccgt tttcgccatg aaggaattga ctttgttcgg ttctttcaga     900
tacggattca cgactacaa gactgctgtt ggaatctttg acactaacta ccaaaacggt     960
agagaaaatg ctccaattga ctttgaacaa ttgatcaccc acagatacaa gttcaaggac    1020
gctattgaag cctacgactt ggtcagagcc ggtaagggtg ctgtcaagtg tctcattgac    1080
ggccctgagt aa                                                        1092
```

<210> SEQ ID NO 90
<211> LENGTH: 363
<212> TYPE: PRT
<213> ORGANISM: Unknown
<220> FEATURE:
<223> OTHER INFORMATION: Scheffersomyces stipitis Sequence

<400> SEQUENCE: 90

```
Met Thr Ala Asn Pro Ser Leu Val Leu Asn Lys Ile Asp Asp Ile Ser
1               5                   10                  15

Phe Glu Thr Tyr Asp Ala Pro Glu Ile Ser Glu Pro Thr Asp Val Leu
            20                  25                  30

Val Gln Val Lys Lys Thr Gly Ile Cys Gly Ser Asp Ile His Phe Tyr
        35                  40                  45

Ala His Gly Arg Ile Gly Asn Phe Val Leu Thr Lys Pro Met Val Leu
    50                  55                  60

Gly His Glu Ser Ala Gly Thr Val Val Gln Val Gly Lys Gly Val Thr
65                  70                  75                  80

Ser Leu Lys Val Gly Asp Asn Val Ala Ile Glu Pro Gly Ile Pro Ser
                85                  90                  95

Arg Phe Ser Asp Glu Tyr Lys Ser Gly His Tyr Asn Leu Cys Pro His
            100                 105                 110

Met Ala Phe Ala Ala Thr Pro Asn Ser Lys Glu Gly Glu Pro Asn Pro
        115                 120                 125

Pro Gly Thr Leu Cys Lys Tyr Phe Lys Ser Pro Glu Asp Phe Leu Val
    130                 135                 140

Lys Leu Pro Asp His Val Ser Leu Glu Leu Gly Ala Leu Val Glu Pro
145                 150                 155                 160

Leu Ser Val Gly Val His Ala Ser Lys Leu Gly Ser Val Ala Phe Gly
```

|  | 165 | 170 | 175 |

Asp Tyr Val Ala Val Phe Gly Ala Gly Pro Val Gly Leu Leu Ala Ala
                180                 185                 190

Ala Val Ala Lys Thr Phe Gly Ala Lys Gly Val Ile Val Val Asp Ile
            195                 200                 205

Phe Asp Asn Lys Leu Lys Met Ala Lys Asp Ile Gly Ala Ala Thr His
210                 215                 220

Thr Phe Asn Ser Lys Thr Gly Ser Glu Glu Leu Ile Lys Ala Phe
225                 230                 235                 240

Gly Gly Asn Val Pro Asn Val Val Leu Glu Cys Thr Gly Ala Glu Pro
                245                 250                 255

Cys Ile Lys Leu Gly Val Asp Ala Ile Ala Pro Gly Gly Arg Phe Val
            260                 265                 270

Gln Val Gly Asn Ala Ala Gly Pro Val Ser Phe Pro Ile Thr Val Phe
        275                 280                 285

Ala Met Lys Glu Leu Thr Leu Phe Gly Ser Phe Arg Tyr Gly Phe Asn
    290                 295                 300

Asp Tyr Lys Thr Ala Val Gly Ile Phe Asp Thr Asn Tyr Gln Asn Gly
305                 310                 315                 320

Arg Glu Asn Ala Pro Ile Asp Phe Glu Gln Leu Ile Thr His Arg Tyr
                325                 330                 335

Lys Phe Asp Ala Ile Glu Ala Tyr Asp Leu Val Arg Ala Gly Lys
            340                 345                 350

Gly Ala Val Lys Cys Leu Ile Asp Gly Pro Glu
        355                 360

<210> SEQ ID NO 91
<211> LENGTH: 1092
<212> TYPE: DNA
<213> ORGANISM: Unknown
<220> FEATURE:
<223> OTHER INFORMATION: Trichoderma reesei Sequence

<400> SEQUENCE: 91
atggcgactc aaacgatcaa caaggatgcg atcagcaacc tctccttcgt cctcaacaag      60
cccggcgacg tgacctttga ggagcggccg aagccgacca tcacggaccc caacgacgtc     120
ctcgtcgccg tcaactacac gggcatctgc ggctccgacg tgcactactg ggtgcacggc     180
gccatcgggc acttcgtcgt caaggacccg atggtgctgg ccacgagtc ggccggcacc     240 gtcgtcgagg tcggcccggc cgtcaagagc ctcaagcccg cgaccgcgt cgccctcgag     300 cccggctacc cgtgccggcg cgtgctcctt cgccgcgccg gcaaatacaa cctgtgcccg     360
gacatggtct tcgccgccac gccgccgtac acggcacccc tgacgggcct gtgggcggcg     420
cccgccgact tctgctacaa gctgccggac ggcgtgtcgc tgcaggaggg cgcgctgatc     480
gagccgctgg ccgtgccgt ccacattgtc aagcaggccc gcgtccagcc gggccagtcc     540
gtcgtcgtca tgggcgccgg cccgtcggc ctgctgtgcg ccgccgtggc caaggcgtac     600
ggcgcctcca ccattgtcag cgtcgacatc gtgcagtcca agctcgactt tgcgcgcggc     660
ttctgctcga cgcacacgta cgtctcgcag cgcatctcgg ctgaggacaa cgcaaaggcc     720
atcaaggagc tggcgggcct gccggcggc gccgacgtcg tgattgacgc cagcggcgcg     780
gagccgtcga tccagacgag cattcacgtc gtccgcatgg gcggcacgta cgtccagggc     840
ggcatgggca gagcgacat cacgttcccc atcatggcca tgtgcctcaa ggaggtgacg     900
gtccggggct cgttccgcta cggcgccggc gactacgagc tggcggtcga gctggtccgg     960

```
acggggcggg tggacgtcaa gaagctgatt acgggcaccg tcagcttcaa gcaggcggag    1020
gaggcgttcc aaaaggtcaa gtctggggag gccatcaaga ttctgattgc cgggcccaac    1080
gagaaggtgt aa                                                        1092
```

<210> SEQ ID NO 92
<211> LENGTH: 363
<212> TYPE: PRT
<213> ORGANISM: Unknown
<220> FEATURE:
<223> OTHER INFORMATION: Trichoderma reesei Sequence

<400> SEQUENCE: 92

```
Met Ala Thr Gln Thr Ile Asn Lys Asp Ala Ile Ser Asn Leu Ser Phe
1               5                   10                  15

Val Leu Asn Lys Pro Gly Asp Val Thr Phe Glu Glu Arg Pro Lys Pro
            20                  25                  30

Thr Ile Thr Asp Pro Asn Asp Val Leu Val Ala Val Asn Tyr Thr Gly
        35                  40                  45

Ile Cys Gly Ser Asp Val His Tyr Trp Val His Gly Ala Ile Gly His
    50                  55                  60

Phe Val Val Lys Asp Pro Met Val Leu Gly His Glu Ser Ala Gly Thr
65                  70                  75                  80

Val Val Glu Val Gly Pro Ala Val Lys Ser Leu Lys Pro Gly Asp Arg
                85                  90                  95

Val Ala Leu Glu Pro Gly Tyr Pro Cys Arg Arg Cys Ser Phe Cys Arg
            100                 105                 110

Ala Gly Lys Tyr Asn Leu Cys Pro Asp Met Val Phe Ala Ala Thr Pro
        115                 120                 125

Pro Tyr His Gly Thr Leu Thr Gly Leu Trp Ala Pro Ala Asp Phe
    130                 135                 140

Cys Tyr Lys Leu Pro Asp Gly Val Ser Leu Gln Glu Gly Ala Leu Ile
145                 150                 155                 160

Glu Pro Leu Ala Val Ala Val His Ile Val Lys Gln Ala Arg Val Gln
                165                 170                 175

Pro Gly Gln Ser Val Val Val Met Gly Ala Gly Pro Val Gly Leu Leu
            180                 185                 190

Cys Ala Ala Val Ala Lys Ala Tyr Gly Ala Ser Thr Ile Val Ser Val
        195                 200                 205

Asp Ile Val Gln Ser Lys Leu Asp Phe Ala Arg Gly Phe Cys Ser Thr
    210                 215                 220

His Thr Tyr Val Ser Gln Arg Ile Ser Ala Glu Asp Asn Ala Lys Ala
225                 230                 235                 240

Ile Lys Glu Leu Ala Gly Leu Pro Gly Gly Ala Asp Val Val Ile Asp
                245                 250                 255

Ala Ser Gly Ala Glu Pro Ser Ile Gln Thr Ser Ile His Val Val Arg
            260                 265                 270

Met Gly Gly Thr Tyr Val Gln Gly Gly Met Gly Lys Ser Asp Ile Thr
        275                 280                 285

Phe Pro Ile Met Ala Met Cys Leu Lys Glu Val Thr Val Arg Gly Ser
    290                 295                 300

Phe Arg Tyr Gly Ala Gly Asp Tyr Glu Leu Ala Val Glu Leu Val Arg
305                 310                 315                 320

Thr Gly Arg Val Asp Val Lys Lys Leu Ile Thr Gly Thr Val Ser Phe
                325                 330                 335
```

Lys Gln Ala Glu Glu Ala Phe Gln Lys Val Lys Ser Gly Glu Ala Ile
         340                 345                 350

Lys Ile Leu Ile Ala Gly Pro Asn Glu Lys Val
         355                 360

<210> SEQ ID NO 93
<211> LENGTH: 1314
<212> TYPE: DNA
<213> ORGANISM: Unknown
<220> FEATURE:
<223> OTHER INFORMATION: Pyromyces sp. Sequence

<400> SEQUENCE: 93

```
atggctaagg aatatttccc acaaattcaa aagattaagt tcgaaggtaa ggattctaag      60
aatccattag ccttccacta ctacgatgct gaaaaggaag tcatgggtaa gaaaatgaag     120
gattggttac gtttcgccat ggcctggtgg cacactcttt gcgccgaagg tgctgaccaa     180
ttcggtggag gtacaaagtc tttcccatgg aacgaaggta ctgatgctat tgaaattgcc     240
aagcaaaagg ttgatgctgg tttcgaaatc atgcaaaagc ttggtattcc atactactgt     300
ttccacgatg ttgatcttgt ttccgaaggt aactctattg aagaatacga atccaacctt     360
aaggctgtcg ttgcttacct caaggaaaag caaaaggaaa ccggtattaa gcttctctgg     420
agtactgcta acgtcttcgg tcacaagcgt tacatgaacg tgcctccac taacccagac      480
tttgatgttg tcgcccgtgc tattgttcaa attaagaacg ccatagacgc cggtattgaa     540
cttggtgctg aaaactacgt cttctggggt ggtcgtgaag gttacatgag tctccttaac     600
actgaccaaa agcgtgaaaa ggaacacatg gccactatgc ttaccatggc tcgtgactac     660
gctcgttcca agggattcaa gggtactttc ctcattgaac aaagccaat ggaaccaacc      720
aagcaccaat acgatgttga cactgaaacc gctattggtt tccttaaggc ccacaactta     780
gacaaggact tcaaggtcaa cattgaagtt aaccacgcta ctcttgctgg tcacactttc     840
gaacacgaac ttgcctgtgc tgttgatgct ggtatgctcg gttccattga tgctaaccgt     900
ggtgactacc aaaacggttg ggatactgat caattcccaa ttgatcaata cgaactcgtc     960
caagcttgga tggaaatcat ccgtggtggt ggtttcgtta ctggtggtac caacttcgat    1020
gccaagactc gtcgtaactc tactgacctc gaagacatca tcattgccca cgtttctggt    1080
atggatgcta tggctcgtgc tcttgaaaac gctgccaagc tcctccaaga atctccatac    1140
accaagatga agaaggaacg ttacgcttcc ttcgacagtg gtattggtaa ggactttgaa    1200
gatggtaagc tcaccctcga acaagtttac gaatacggta agaagaacgg tgaaccaaag    1260
caaacttctg gtaagcaaga actctacgaa gctattgttg ccatgtacca ataa          1314
```

<210> SEQ ID NO 94
<211> LENGTH: 1314
<212> TYPE: DNA
<213> ORGANISM: Unknown
<220> FEATURE:
<223> OTHER INFORMATION: Codon Optimized Pyromyces sp. Sequence

<400> SEQUENCE: 94

```
atggccaagg aatacttccc acaaatccaa aagattaaat tcgaaggtaa agattccaag      60
aacccattgg cttttcacta ctacgatgct gagaaggaag ttatgggtaa gaagatgaag     120
gattggttga gattcgctat ggcttggtgg cacactttgt gcgctgaagg tgctgaccaa     180
ttcggtggtg gtactaagtc tttcccatgg aacgaaggta ctgatgctat tgaaatcgct     240
```

```
aagcaaaaag tcgatgctgg ttttgagatt atgcaaaaat tgggtatccc atactactgt    300
ttccacgacg tcgacttggt ttctgaaggt aattctatcg aagaatacga atctaatttg    360
aaggctgttg tcgcttactt aaaagaaaag caaaaggaga ctggtattaa gttgttgtgg    420
tccaccgcta acgtctttgg tcataaaaga tacatgaacg gtgcttccac caacccagac    480
ttcgatgtcg tcgccagagc tatcgttcaa attaaaaacg ccatcgacgc tggtattgaa    540
ttgggtgctg aaaattacgt cttttgggg ggtcgtgaag gttacatgtc tttgttgaac    600
actgaccaaa agagagaaaa agaacacatg gccactatgt tgaccatggc cagagattac    660
gccagatcta agggtttcaa gggtaccttc ttaattgaac caaaacctat ggaaccaact    720
aagcaccaat acgacgttga cactgaaact gctatcggtt ttttgaaggc tcacaacttg    780
gataaggatt ttaaagtcaa cattgaagtt aaccatgcta ctttggctgg tcacactttt    840
gaacatgaat tggcctgtgc tgttgatgct ggtatgttgg ttctatcga tgctaataga    900 ggtgactatc aaaacggttg ggacactgat caattcccaa tcgatcaata tgaattagtt    960
caagcttgga tggaaattat cagaggtggt ggtttcgtta ctggtggtac taacttcgat   1020
gctaagacca aagaaaactc tactgatttg aagatatta tcattgccca cgtttccggt   1080
atggatgcca tggccagagc tttggaaaac gccgccaagt tattgcaaga gtccccatac   1140
accaagatga aaaaggaacg ttacgcttct ttcgactctg gtatcggtaa agacttcgaa   1200
gatggtaagt tgaccttgga acaagtttac gaatacggta gaagaacgg tgaacctaaa   1260 caaacctctg gtaaacaaga attgtatgaa gctattgttg ccatgtacca ataa         1314
```

<210> SEQ ID NO 95
<211> LENGTH: 437
<212> TYPE: PRT
<213> ORGANISM: Unknown
<220> FEATURE:
<223> OTHER INFORMATION: Pyromyces sp. Sequence

<400> SEQUENCE: 95

```
Met Ala Lys Glu Tyr Phe Pro Gln Ile Gln Lys Ile Lys Phe Glu Gly
1               5                   10                  15

Lys Asp Ser Lys Asn Pro Leu Ala Phe His Tyr Tyr Asp Ala Glu Lys
            20                  25                  30

Glu Val Met Gly Lys Lys Met Lys Asp Trp Leu Arg Phe Ala Met Ala
        35                  40                  45

Trp Trp His Thr Leu Cys Ala Glu Gly Ala Asp Gln Phe Gly Gly Gly
    50                  55                  60

Thr Lys Ser Phe Pro Trp Asn Glu Gly Thr Asp Ala Ile Glu Ile Ala
65                  70                  75                  80

Lys Gln Lys Val Asp Ala Gly Phe Glu Ile Met Gln Lys Leu Gly Ile
                85                  90                  95

Pro Tyr Tyr Cys Phe His Asp Val Asp Leu Val Ser Glu Gly Asn Ser
            100                 105                 110

Ile Glu Glu Tyr Glu Ser Asn Leu Lys Ala Val Val Ala Tyr Leu Lys
        115                 120                 125

Glu Lys Gln Lys Glu Thr Gly Ile Lys Leu Leu Trp Ser Thr Ala Asn
    130                 135                 140

Val Phe Gly His Lys Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175
```

```
Ala Gly Ile Glu Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Ala Ile Gly Phe Leu Lys
            245                 250                 255

Ala His Asn Leu Asp Lys Asp Phe Lys Val Asn Ile Glu Val Asn His
        260                 265                 270

Ala Thr Leu Ala Gly His Thr Phe Glu His Glu Leu Ala Cys Ala Val
    275                 280                 285

Asp Ala Gly Met Leu Gly Ser Ile Asp Ala Asn Arg Gly Asp Tyr Gln
290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Phe Val Thr Gly Gly
            325                 330                 335

Thr Asn Phe Asp Ala Lys Thr Arg Arg Asn Ser Thr Asp Leu Glu Asp
            340                 345                 350

Ile Ile Ile Ala His Val Ser Gly Met Asp Ala Met Ala Arg Ala Leu
            355                 360                 365

Glu Asn Ala Ala Lys Leu Leu Gln Glu Ser Pro Tyr Thr Lys Met Lys
370                 375                 380

Lys Glu Arg Tyr Ala Ser Phe Asp Ser Gly Ile Gly Lys Asp Phe Glu
385                 390                 395                 400

Asp Gly Lys Leu Thr Leu Glu Gln Val Tyr Glu Tyr Gly Lys Lys Asn
            405                 410                 415

Gly Glu Pro Lys Gln Thr Ser Gly Lys Gln Glu Leu Tyr Glu Ala Ile
            420                 425                 430

Val Ala Met Tyr Gln
            435

<210> SEQ ID NO 96
<211> LENGTH: 657
<212> TYPE: DNA
<213> ORGANISM: Clostridium acetobutylicum

<400> SEQUENCE: 96
atgaactcta aaataattag atttgaaaat ttaaggtcat tctttaaaga tgggatgaca      60
attatgattg gaggtttttt aaactgtggc actccaacca aattaattga tttttagtt     120 aatttaaata taagaattt aacgattata agtaatgata catgttatcc taatacaggt     180
attggtaagt taatatcaaa taatcaagta aaaaagctta ttgcttcata taggcagc      240 aacccagata ctgcaaaaa acttttttaat aatgaacttg aagtagagct ctctccccaa    300
ggaactctag tggaaagaat acgtgcaggc ggatctggct taggtggtgt actaactaaa    360
acaggtttag gaactttgat tgaaaaagga agaaaaaaa tatctataaa tggaacggaa    420
tatttgttag agctaccctct tacagccgat gtagcattaa ttaaaggtag tattgtagat    480
gaggccggaa acaccttcta taaggtact actaaaaact ttaatcccta tatggcaatg     540
gcagctaaaa ccgtaatagt tgaagctgaa aattagtta gctgtgaaaa actagaaag      600
```

```
gaaaaagcaa tgaccccggg agttcttata aattatatag taaaggagcc tgcataa       657
```

<210> SEQ ID NO 97
<211> LENGTH: 218
<212> TYPE: PRT
<213> ORGANISM: Clostridium acetobutylicum

<400> SEQUENCE: 97

```
Met Asn Ser Lys Ile Ile Arg Phe Glu Asn Leu Arg Ser Phe Phe Lys
1               5                   10                  15

Asp Gly Met Thr Ile Met Ile Gly Gly Phe Leu Asn Cys Gly Thr Pro
            20                  25                  30

Thr Lys Leu Ile Asp Phe Leu Val Asn Leu Asn Ile Lys Asn Leu Thr
        35                  40                  45

Ile Ile Ser Asn Asp Thr Cys Tyr Pro Asn Thr Gly Ile Gly Lys Leu
    50                  55                  60

Ile Ser Asn Asn Gln Val Lys Lys Leu Ile Ala Ser Tyr Ile Gly Ser
65                  70                  75                  80

Asn Pro Asp Thr Gly Lys Lys Leu Phe Asn Asn Glu Leu Glu Val Glu
                85                  90                  95

Leu Ser Pro Gln Gly Thr Leu Val Glu Arg Ile Arg Ala Gly Gly Ser
            100                 105                 110

Gly Leu Gly Gly Val Leu Thr Lys Thr Gly Leu Gly Thr Leu Ile Glu
        115                 120                 125

Lys Gly Lys Lys Lys Ile Ser Ile Asn Gly Thr Glu Tyr Leu Leu Glu
130                 135                 140

Leu Pro Leu Thr Ala Asp Val Ala Leu Ile Lys Gly Ser Ile Val Asp
145                 150                 155                 160

Glu Ala Gly Asn Thr Phe Tyr Lys Gly Thr Thr Lys Asn Phe Asn Pro
                165                 170                 175

Tyr Met Ala Met Ala Ala Lys Thr Val Ile Val Glu Ala Glu Asn Leu
            180                 185                 190

Val Ser Cys Glu Lys Leu Glu Lys Glu Lys Ala Met Thr Pro Gly Val
        195                 200                 205

Leu Ile Asn Tyr Ile Val Lys Glu Pro Ala
    210                 215
```

<210> SEQ ID NO 98
<211> LENGTH: 660
<212> TYPE: DNA
<213> ORGANISM: Clostridium acetobutylicum

<400> SEQUENCE: 98

```
atgattaatg ataaaaacct agcgaaagaa ataatagcca aaagagttgc aagagaatta       60
aaaaatggtc aacttgtaaa cttaggtgta ggtcttccta ccatggttgc agattatata      120
ccaaaaaatt tcaaaattac tttccaatca gaaaacggaa tagttggaat gggcgctagt      180
cctaaaataa atgaggcaga taagatgta gtaaatgcag aggagactta tacaacagta      240
cttcctgacg gcacattttt cgatagctca gtttcgtttt cactaatccg tggtggtcac      300
gtagatgtta ctgttttagg ggctctccag gtagatgaaa agggtaatat agccaattgg      360
attgttcctg gaaaaatgct ctctggtatg ggtggagcta tggatttagt aaatggagct      420
aagaaagtaa taattgcaat gagacataca aataaaggtc aacctaaaat tttaaaaaaa      480
tgtacacttc ccctcacggc aaagtctcaa gcaaatctaa ttgtaacaga acttggagta      540
attgaggtta ttaatgatgg tttacttctc actgaaatta taaaaacac aaccattgat      600
```

```
gaaataaggt ctttaactgc tgcagattta ctcatatcca atgaacttag acccatggct    660
```

<210> SEQ ID NO 99
<211> LENGTH: 221
<212> TYPE: PRT
<213> ORGANISM: Clostridium acetobutylicum

<400> SEQUENCE: 99

```
Met Ile Asn Asp Lys Asn Leu Ala Lys Glu Ile Ile Ala Lys Arg Val
1               5                   10                  15

Ala Arg Glu Leu Lys Asn Gly Gln Leu Val Asn Leu Gly Val Gly Leu
            20                  25                  30

Pro Thr Met Val Ala Asp Tyr Ile Pro Lys Asn Phe Lys Ile Thr Phe
        35                  40                  45

Gln Ser Glu Asn Gly Ile Val Gly Met Gly Ala Ser Pro Lys Ile Asn
    50                  55                  60

Glu Ala Asp Lys Asp Val Val Asn Ala Gly Gly Asp Tyr Thr Thr Val
65                  70                  75                  80

Leu Pro Asp Gly Thr Phe Phe Asp Ser Ser Val Ser Phe Ser Leu Ile
                85                  90                  95

Arg Gly Gly His Val Asp Val Thr Val Leu Gly Ala Leu Gln Val Asp
            100                 105                 110

Glu Lys Gly Asn Ile Ala Asn Trp Ile Val Pro Gly Lys Met Leu Ser
        115                 120                 125

Gly Met Gly Gly Ala Met Asp Leu Val Asn Gly Ala Lys Lys Val Ile
    130                 135                 140

Ile Ala Met Arg His Thr Asn Lys Gly Gln Pro Lys Ile Leu Lys Lys
145                 150                 155                 160

Cys Thr Leu Pro Leu Thr Ala Lys Ser Gln Ala Asn Leu Ile Val Thr
                165                 170                 175

Glu Leu Gly Val Ile Glu Val Ile Asn Asp Gly Leu Leu Leu Thr Glu
            180                 185                 190

Ile Asn Lys Asn Thr Thr Ile Asp Glu Ile Arg Ser Leu Thr Ala Ala
        195                 200                 205

Asp Leu Leu Ile Ser Asn Glu Leu Arg Pro Met Ala Val
    210                 215                 220
```

<210> SEQ ID NO 100
<211> LENGTH: 651
<212> TYPE: DNA
<213> ORGANISM: Escherichia coli

<400> SEQUENCE: 100

```
atggatgcga aacaacgtat tgcgcgccgt gtggcgcaag agcttcgtga tggtgacatc    60
gttaacttag ggatcggttt acccacaatg gtcgccaatt atttaccgga gggtattcat   120
atcactctgc aatcggaaaa cggcttcctc ggtttaggcc cggtcacgac agcgcatcca   180
gatctggtga acgctggcgg gcaaccgtgc ggtgttttac ccggtgcagc catgtttgat   240
agcgccatgt catttgcgct aatccgtggc ggtcatattg atgcctgcgt gctcggcggt   300
ttgcaagtag acgaagaagc aaacctcgcg aactgggtag tgcctgggaa atggtgccc   360 ggtatgggtg gcgcgatgga tctggtgacc gggtcgcgca agtgatcat cgccatggaa   420 cattgcgcca agatggggttc agcaaaaatt ttgcgccgct gcaccatgcc actcactgcg   480
caacatgcgg tgcatatgct ggttactgaa ctggctgtct ttcgttttat tgacggcaaa   540
```

| | | |
|---|---|---|
| atgtggctca ccgaaattgc cgacgggtgt gatttagcca ccgtgcgtgc caaaacagaa | | 600 |
| gctcggtttg aagtcgccgc cgatctgaat acgcaacggg gtgatttatg a | | 651 |

<210> SEQ ID NO 101
<211> LENGTH: 216
<212> TYPE: PRT
<213> ORGANISM: Escherichia coli

<400> SEQUENCE: 101

| Met | Asp | Ala | Lys | Gln | Arg | Ile | Ala | Arg | Arg | Val | Ala | Gln | Glu | Leu | Arg |
|---|---|---|---|---|---|---|---|---|---|---|---|---|---|---|---|
| 1 | | | | 5 | | | | | 10 | | | | | 15 | |
| Asp | Gly | Asp | Ile | Val | Asn | Leu | Gly | Ile | Gly | Leu | Pro | Thr | Met | Val | Ala |
| | | | 20 | | | | | 25 | | | | | 30 | | |
| Asn | Tyr | Leu | Pro | Glu | Gly | Ile | His | Ile | Thr | Leu | Gln | Ser | Glu | Asn | Gly |
| | | | 35 | | | | | 40 | | | | | 45 | | |
| Phe | Leu | Gly | Leu | Gly | Pro | Val | Thr | Thr | Ala | His | Pro | Asp | Leu | Val | Asn |
| | 50 | | | | | 55 | | | | | 60 | | | | |
| Ala | Gly | Gly | Gln | Pro | Cys | Gly | Val | Leu | Pro | Gly | Ala | Ala | Met | Phe | Asp |
| 65 | | | | | 70 | | | | | 75 | | | | | 80 |
| Ser | Ala | Met | Ser | Phe | Ala | Leu | Ile | Arg | Gly | Gly | His | Ile | Asp | Ala | Cys |
| | | | | 85 | | | | | 90 | | | | | 95 | |
| Val | Leu | Gly | Gly | Leu | Gln | Val | Asp | Glu | Glu | Ala | Asn | Leu | Ala | Asn | Trp |
| | | | 100 | | | | | 105 | | | | | 110 | | |
| Val | Val | Pro | Gly | Lys | Met | Val | Pro | Gly | Met | Gly | Ala | Met | Asp | Leu |
| | | | 115 | | | | | 120 | | | | | 125 | | |
| Val | Thr | Gly | Ser | Arg | Lys | Val | Ile | Ile | Ala | Met | Glu | His | Cys | Ala | Lys |
| | 130 | | | | | 135 | | | | | 140 | | | | |
| Asp | Gly | Ser | Ala | Lys | Ile | Leu | Arg | Arg | Cys | Thr | Met | Pro | Leu | Thr | Ala |
| 145 | | | | | 150 | | | | | 155 | | | | | 160 |
| Gln | His | Ala | Val | His | Met | Leu | Val | Thr | Glu | Leu | Ala | Val | Phe | Arg | Phe |
| | | | | 165 | | | | | 170 | | | | | 175 | |
| Ile | Asp | Gly | Lys | Met | Trp | Leu | Thr | Glu | Ile | Ala | Asp | Gly | Cys | Asp | Leu |
| | | | 180 | | | | | 185 | | | | | 190 | | |
| Ala | Thr | Val | Arg | Ala | Lys | Thr | Glu | Ala | Arg | Phe | Glu | Val | Ala | Ala | Asp |
| | | | 195 | | | | | 200 | | | | | 205 | | |
| Leu | Asn | Thr | Gln | Arg | Gly | Asp | Leu | | | | | | | | |
| | 210 | | | | | 215 | | | | | | | | | |

<210> SEQ ID NO 102
<211> LENGTH: 663
<212> TYPE: DNA
<213> ORGANISM: Escherichia coli

<400> SEQUENCE: 102

| | | |
|---|---|---|
| atgaaaacaa aattgatgac attacaagac gccaccggct tctttcgtga cggcatgacc | | 60 |
| atcatggtgg gcggatttat ggggattggc actccatccc gcctggttga agcattactg | | 120 |
| gaatctggtg ttcgcgacct gacattgata gccaatgata ccgcgtttgt tgataccggc | | 180 |
| atcggtccgc tcatcgtcaa tggtcgagtc cgcaaagtga ttgcttcaca tatcggcacc | | 240 |
| aacccggaaa caggtcggcg catgatatct ggtgagatgg acgtcgttct ggtgccgcaa | | 300 |
| ggtacgctaa tcgagcaaat tcgctgtggt ggagctggac ttggtggttt tctcaccccca | | 360 |
| acgggtgtcg gcaccgtcgt agaggaaggc aaacagacac tgacactcga cggtaaaacc | | 420 |
| tggctgctcg aacgcccact gcgcgccgac ctggcgctaa ttcgcgctca tcgttgcgac | | 480 |
| acacttggca acctgaccta tcaacttagc gcccgcaact ttaaccccct gatagccctt | | 540 |

-continued

```
gcggctgata tcacgctggt agagccagat gaactggtcg aaaccggcga gctgcaacct    600
gaccatattg tcacccctgg tgccgttatc gaccacatca tcgtttcaca ggagagcaaa    660
taa                                                                  663
```

<210> SEQ ID NO 103
<211> LENGTH: 220
<212> TYPE: PRT
<213> ORGANISM: Escherichia coli

<400> SEQUENCE: 103

```
Met Lys Thr Lys Leu Met Thr Leu Gln Asp Ala Thr Gly Phe Phe Arg
1               5                   10                  15

Asp Gly Met Thr Ile Met Val Gly Gly Phe Met Gly Ile Gly Thr Pro
            20                  25                  30

Ser Arg Leu Val Glu Ala Leu Leu Glu Ser Gly Val Arg Asp Leu Thr
        35                  40                  45

Leu Ile Ala Asn Asp Thr Ala Phe Val Asp Thr Gly Ile Gly Pro Leu
    50                  55                  60

Ile Val Asn Gly Arg Val Arg Lys Val Ile Ala Ser His Ile Gly Thr
65                  70                  75                  80

Asn Pro Glu Thr Gly Arg Arg Met Ile Ser Gly Glu Met Asp Val Val
                85                  90                  95

Leu Val Pro Gln Gly Thr Leu Ile Glu Gln Ile Arg Cys Gly Gly Ala
            100                 105                 110

Gly Leu Gly Gly Phe Leu Thr Pro Thr Gly Val Gly Thr Val Val Glu
        115                 120                 125

Glu Gly Lys Gln Thr Leu Thr Leu Asp Gly Lys Thr Trp Leu Leu Glu
    130                 135                 140

Arg Pro Leu Arg Ala Asp Leu Ala Leu Ile Arg Ala His Arg Cys Asp
145                 150                 155                 160

Thr Leu Gly Asn Leu Thr Tyr Gln Leu Ser Ala Arg Asn Phe Asn Pro
                165                 170                 175

Leu Ile Ala Leu Ala Ala Asp Ile Thr Leu Val Glu Pro Asp Glu Leu
            180                 185                 190

Val Glu Thr Gly Glu Leu Gln Pro Asp His Ile Val Thr Pro Gly Ala
        195                 200                 205

Val Ile Asp His Ile Ile Val Ser Gln Glu Ser Lys
    210                 215                 220
```

<210> SEQ ID NO 104
<211> LENGTH: 1563
<212> TYPE: DNA
<213> ORGANISM: Mus musculus

<400> SEQUENCE: 104

```
atgcctgggt cacttccttt gaatgcagag gcttgctggc aaaagatgt gggaatcgtt     60 gcccttgaaa tctactttcc ttctcaatat gtcgatcaag ctgagttgga aaaatacgat    120
ggtgtagatg ctggaaagta taccatcggc ctgggccagg ccaggatggg cttctgcacg    180
gatcgtgaag acatcaactc tctttgcctg actgtggttc agaaactgat ggagagacat    240 agccttttcct atgattgcat gggcggcta aagttggaa cagagacaat catcgacaaa    300
tcgaaatcag tgaagtctaa tttgatgcag ctgtttgagg agtctgggaa tacagatata    360
gaaggaatag atacaaccaa tgcatgctat ggggcacag ctgcagtctt caatgccgtg    420
```

```
aactgggtcg aatccagctc ttgggatgga cgatatgctc tggtagttgc aggagacatt    480
gctatatatg ccacaggaaa tgccagacct acaggtggag ttggagctgt ggccctgcta    540
attgggccaa acgctcctct aattttgac cgagggctcc gtgggacaca catgcagcat     600
gcctatgact tttacaagcc tgacatgctc tccgagtacc ctgtggtcga cggaaagctc    660
tccatacagt gctacctcag cgccctggac cgctgctatt ctgtctaccg caaaaagatc    720
cgtgcccagt ggcagaaaga gggaaaggat aaagatttta ccctgaatga ttttggcttc    780
atgatctttc actcaccata ttgtaaactg gtgcagaaat ctctagctcg gatgttcctg    840
aatgactttc ttaatgatca aaacagagat aaaaacagta tttacagtgg actggaagcc    900
tttggggacg ttaaattaga agatacttac tttgacagag atgtagaaaa ggcatttatg    960
aaggctagtt ctgagctatt caaccagaaa acaaaggcgt ctttgcttgt gtctaatcag   1020
aatgaaaata tgtacacatc ctctgtctat ggttccctgg cttctgtcct ggcacagtac   1080
tcacctcagc agttggcagg gaagagggtt ggagtgttct cttacggttc tggcttggct   1140
gccacgctgt actcccttaa agtcacacaa gacgccacac caggatctgc ccttgataaa   1200
ataacagcaa gttatgtgac ccttaaatca aggcttgact cgagaacttg tgtggcaccg   1260
gatgtctttg ctgaaaacat gaagctcaga gaggacacac atcacttagc caactatatt   1320
ccccagtgtt caatagactc actctttgaa ggaacgtggt atctggtcag agtggatgaa   1380
aaacacagaa ggacttacgc ccggcgcccc ttcacaaatg accacagttt ggatgaagga   1440
atggggctcg tgcatagtaa cacagcaaca gagcatattc caagccctgc taagaaagtg   1500
ccaagactcc ctgcaacctc ggccgaatct gaatcagctg tcatcagtaa cggggagcac   1560
tga                                                                 1563
```

<210> SEQ ID NO 105
<211> LENGTH: 520
<212> TYPE: PRT
<213> ORGANISM: Mus musculus

<400> SEQUENCE: 105

| Met | Pro | Gly | Ser | Leu | Pro | Leu | Asn | Ala | Glu | Ala | Cys | Trp | Pro | Lys | Asp |
|---|---|---|---|---|---|---|---|---|---|---|---|---|---|---|---|
| 1 | | | | 5 | | | | | 10 | | | | | 15 | |

| Val | Gly | Ile | Val | Ala | Leu | Glu | Ile | Tyr | Phe | Pro | Ser | Gln | Tyr | Val | Asp |
| | | | 20 | | | | | 25 | | | | | 30 | | |

| Gln | Ala | Glu | Leu | Glu | Lys | Tyr | Asp | Gly | Val | Asp | Ala | Gly | Lys | Tyr | Thr |
| | | 35 | | | | | 40 | | | | | 45 | | | |

| Ile | Gly | Leu | Gly | Gln | Ala | Arg | Met | Gly | Phe | Cys | Thr | Asp | Arg | Glu | Asp |
| | 50 | | | | | 55 | | | | | 60 | | | | |

| Ile | Asn | Ser | Leu | Cys | Leu | Thr | Val | Val | Gln | Lys | Leu | Met | Glu | Arg | His |
| 65 | | | | | 70 | | | | | 75 | | | | | 80 |

| Ser | Leu | Ser | Tyr | Asp | Cys | Ile | Gly | Arg | Leu | Glu | Val | Gly | Thr | Glu | Thr |
| | | | 85 | | | | | 90 | | | | | 95 | | |

| Ile | Ile | Asp | Lys | Ser | Lys | Ser | Val | Lys | Ser | Leu | Met | Gln | Leu | Phe |
| | | | 100 | | | | | 105 | | | | | 110 | | |

| Glu | Glu | Ser | Gly | Asn | Thr | Asp | Ile | Glu | Gly | Ile | Asp | Thr | Thr | Asn | Ala |
| | | | 115 | | | | | 120 | | | | | 125 | | |

| Cys | Tyr | Gly | Gly | Thr | Ala | Ala | Val | Phe | Asn | Ala | Val | Asn | Trp | Val | Glu |
| | | 130 | | | | | 135 | | | | | 140 | | | |

| Ser | Ser | Ser | Trp | Asp | Gly | Arg | Tyr | Ala | Leu | Val | Val | Ala | Gly | Asp | Ile |
| 145 | | | | | 150 | | | | | 155 | | | | | 160 |

| Ala | Ile | Tyr | Ala | Thr | Gly | Asn | Ala | Arg | Pro | Thr | Gly | Gly | Val | Gly | Ala |

```
                165                 170                 175
Val Ala Leu Leu Ile Gly Pro Asn Ala Pro Leu Ile Phe Asp Arg Gly
            180                 185                 190

Leu Arg Gly Thr His Met Gln His Ala Tyr Asp Phe Tyr Lys Pro Asp
        195                 200                 205

Met Leu Ser Glu Tyr Pro Val Val Asp Gly Lys Leu Ser Ile Gln Cys
    210                 215                 220

Tyr Leu Ser Ala Leu Asp Arg Cys Tyr Ser Val Tyr Arg Lys Lys Ile
225                 230                 235                 240

Arg Ala Gln Trp Gln Lys Glu Gly Lys Asp Lys Asp Phe Thr Leu Asn
                245                 250                 255

Asp Phe Gly Phe Met Ile Phe His Ser Pro Tyr Cys Lys Leu Val Gln
            260                 265                 270

Lys Ser Leu Ala Arg Met Phe Leu Asn Asp Phe Leu Asn Asp Gln Asn
        275                 280                 285

Arg Asp Lys Asn Ser Ile Tyr Ser Gly Leu Glu Ala Phe Gly Asp Val
    290                 295                 300

Lys Leu Glu Asp Thr Tyr Phe Asp Arg Asp Val Glu Lys Ala Phe Met
305                 310                 315                 320

Lys Ala Ser Ser Glu Leu Phe Asn Gln Lys Thr Lys Ala Ser Leu Leu
                325                 330                 335

Val Ser Asn Gln Asn Gly Asn Met Tyr Thr Ser Ser Val Tyr Gly Ser
            340                 345                 350

Leu Ala Ser Val Leu Ala Gln Tyr Ser Pro Gln Gln Leu Ala Gly Lys
        355                 360                 365

Arg Val Gly Val Phe Ser Tyr Gly Ser Gly Leu Ala Ala Thr Leu Tyr
    370                 375                 380

Ser Leu Lys Val Thr Gln Asp Ala Thr Pro Gly Ser Ala Leu Asp Lys
385                 390                 395                 400

Ile Thr Ala Ser Leu Cys Asp Leu Lys Ser Arg Leu Asp Ser Arg Thr
                405                 410                 415

Cys Val Ala Pro Asp Val Phe Ala Glu Asn Met Lys Leu Arg Glu Asp
            420                 425                 430

Thr His His Leu Ala Asn Tyr Ile Pro Gln Cys Ser Ile Asp Ser Leu
        435                 440                 445

Phe Glu Gly Thr Trp Tyr Leu Val Arg Val Asp Glu Lys His Arg Arg
    450                 455                 460

Thr Tyr Ala Arg Arg Pro Phe Thr Asn Asp His Ser Leu Asp Glu Gly
465                 470                 475                 480

Met Gly Leu Val His Ser Asn Thr Ala Thr Glu His Ile Pro Ser Pro
                485                 490                 495

Ala Lys Lys Val Pro Arg Leu Pro Ala Thr Ser Ala Glu Ser Glu Ser
            500                 505                 510

Ala Val Ile Ser Asn Gly Glu His
        515                 520

<210> SEQ ID NO 106
<211> LENGTH: 770
<212> TYPE: DNA
<213> ORGANISM: Saccharomyces cerevisiae

<400> SEQUENCE: 106
atgaaactct caactaaact ttgttggtgt ggtattaaag gaagacttag gccgcaaaag    60
caacaacaat tacacaatac aaacttgcaa atgactgaac taaaaaaaca aaagaccgct   120
```

-continued

```
gaacaaaaaa ccagacctca aaatgtcggt attaaaggta tccaaattta catcccaact    180
caatgtgtca accaatctga gctagagaaa tttgatggcg tttctcaagg taaatacaca    240
attggtctgg gccaaaccaa catgtctttt gtcaatgaca gagaagatat ctactcgatg    300
tccctaactg ttttgtctaa gttgatcaag agttacaaca tcgacaccaa caaaattggt    360
agattagaag tcggtactga aactctgatt gacaagtcca agtctgtcaa gtctgtcttg    420
atgcaattgt ttggtgaaaa cactgacgtc gaaggtattg acacgcttaa tgcctgttac    480
ggtggtacca acgcgttgtt caactctttg aactggattg aatctaacgc atgggatggt    540
agagacgcca ttgtagtttg cggtgatatt gccatctacg ataagggtgc cgcaagacca    600
accggtggtg ccggtactgt tgctatgtgg atcggtcctg atgctccaat tgtatttgac    660
tctgtaagag cttcttacat ggaacacgcc tacgattttt acaagccaga tttcaccagc    720
gaatatcctt acgtcgatgg tcattttca ttaacttgtt acgtcaaggc    770
```

<210> SEQ ID NO 107
<211> LENGTH: 491
<212> TYPE: PRT
<213> ORGANISM: Saccharomyces cerevisiae

<400> SEQUENCE: 107

```
Met Lys Leu Ser Thr Lys Leu Cys Trp Cys Gly Ile Lys Gly Arg Leu
1               5                   10                  15

Arg Pro Gln Lys Gln Gln Leu His Asn Thr Asn Leu Gln Met Thr
            20                  25                  30

Glu Leu Lys Lys Gln Lys Thr Ala Glu Gln Lys Thr Arg Pro Gln Asn
        35                  40                  45

Val Gly Ile Lys Gly Ile Gln Ile Tyr Ile Pro Thr Gln Cys Val Asn
    50                  55                  60

Gln Ser Glu Leu Glu Lys Phe Asp Gly Val Ser Gln Gly Lys Tyr Thr
65                  70                  75                  80

Ile Gly Leu Gly Gln Thr Asn Met Ser Phe Val Asn Asp Arg Glu Asp
                85                  90                  95

Ile Tyr Ser Met Ser Leu Thr Val Leu Ser Lys Leu Ile Lys Ser Tyr
            100                 105                 110

Asn Ile Asp Thr Asn Lys Ile Gly Arg Leu Glu Val Gly Thr Glu Thr
        115                 120                 125

Leu Ile Asp Lys Ser Lys Ser Val Lys Ser Val Leu Met Gln Leu Phe
    130                 135                 140

Gly Glu Asn Thr Asp Val Glu Gly Ile Asp Thr Leu Asn Ala Cys Tyr
145                 150                 155                 160

Gly Gly Thr Asn Ala Leu Phe Asn Ser Leu Asn Trp Ile Glu Ser Asn
                165                 170                 175

Ala Trp Asp Gly Arg Asp Ala Ile Val Val Cys Gly Asp Ile Ala Ile
            180                 185                 190

Tyr Asp Lys Gly Ala Ala Arg Pro Thr Gly Gly Ala Gly Thr Val Ala
        195                 200                 205

Met Trp Ile Gly Pro Asp Ala Pro Ile Val Phe Asp Ser Val Arg Ala
    210                 215                 220

Ser Tyr Met Glu His Ala Tyr Asp Phe Tyr Lys Pro Asp Phe Thr Ser
225                 230                 235                 240

Glu Tyr Pro Tyr Val Asp Gly His Phe Ser Leu Thr Cys Tyr Val Lys
                245                 250                 255
```

Ala Leu Asp Gln Val Tyr Lys Ser Tyr Ser Lys Ala Ile Ser Lys
            260                 265                 270

Gly Leu Val Ser Asp Pro Ala Gly Ser Asp Ala Leu Asn Val Leu Lys
        275                 280                 285

Tyr Phe Asp Tyr Asn Val Phe His Val Pro Thr Cys Lys Leu Val Thr
    290                 295                 300

Lys Ser Tyr Gly Arg Leu Leu Tyr Asn Asp Phe Arg Ala Asn Pro Gln
305                 310                 315                 320

Leu Phe Pro Glu Val Asp Ala Glu Leu Ala Thr Arg Asp Tyr Asp Glu
                325                 330                 335

Ser Leu Thr Asp Lys Asn Ile Glu Lys Thr Phe Val Asn Val Ala Lys
            340                 345                 350

Pro Phe His Lys Glu Arg Val Ala Gln Ser Leu Ile Val Pro Thr Asn
        355                 360                 365

Thr Gly Asn Met Tyr Thr Ala Ser Val Tyr Ala Ala Phe Ala Ser Leu
    370                 375                 380

Leu Asn Tyr Val Gly Ser Asp Leu Gln Gly Lys Arg Val Gly Leu
385                 390                 395                 400

Phe Ser Tyr Gly Ser Gly Leu Ala Ala Ser Leu Tyr Ser Cys Lys Ile
                405                 410                 415

Val Gly Asp Val Gln His Ile Ile Lys Glu Leu Asp Ile Thr Asn Lys
            420                 425                 430

Leu Ala Lys Arg Ile Thr Glu Thr Pro Lys Asp Tyr Glu Ala Ala Ile
        435                 440                 445

Glu Leu Arg Glu Asn Ala His Leu Lys Lys Asn Phe Lys Pro Gln Gly
    450                 455                 460

Ser Ile Glu His Leu Gln Ser Gly Val Tyr Tyr Leu Thr Asn Ile Asp
465                 470                 475                 480

Asp Lys Phe Arg Arg Ser Tyr Asp Val Lys Lys
                485                 490

<210> SEQ ID NO 108
<211> LENGTH: 1167
<212> TYPE: DNA
<213> ORGANISM: Lactobacillus crispatus

<400> SEQUENCE: 108
atgcaagtag gtattgatca aattggactt tttacgccag acaagtacgt tgatatggtc    60
gatttggcga acgcaagaaa gcaagatcca aataagtttt tagttggcat tggtcaaaga   120
gagatgagtg ttgcggatat tacgcaagat gcagtttcaa tgggaattaa tgcgacttta   180
aagtttattg acaagattga taagaataaa gtcggtctat taattttggg gactgaaagc   240
agtattgatc aatcaaagtc agcttcttta tttgtaaaaa cagccttaaa gttgaagcca   300
gaagtaagaa cttttgaagt aaaggaagct tgctttggtt taacggcagc cttaatgatg   360
gcacgtgatt tgttcgggt acatcctgaa caaaccgcaa ttgtcatcgg tagtgatatt   420
gctcgctatg gtgttaatac tgctggtgag gtaacacaag gagccggtag cgtggcaatg   480
ctcatcaaag ctgacccaag cattttagcc ctaaataatg gtcattcagc ttacagcgaa   540
gatattaacg acttctggag accaaattat tctcgcaccg ctttagttga cggcaagtat   600
tcgactcaag tttacttgga tttcttcaag aagaccttta ctgattataa gagcaaaaaa   660
ggattgaaaa caagcgactt tgatgcgatt acttaccatt tgccatttac taagatgggg   720
atgaaggcta acaatattgc tattgagggg caagatcaag caacaatgat caagttggag   780

```
cgtagttttg cggctgctaa acaattatca agccgagtag gtaatatcta caccgcttca    840
ctttatatga gtttacttag tttgctagag aatggtgaat tacccgctgg ctcattaatt    900
ggcctgtttt catatggttc aggtgcaatg gctgagtttt atagtggcaa gttggttgaa    960
ggatatgaaa acaaattga tcctacagct gatcaagcaa tgcttgatcg gcggaagaag   1020
ctgacagtta agcaatatga agacgtcttc aatacggctt tgttagatcc tgaggatggc   1080
ttagaattaa ctagcgacga tgaagtaggt acttggtatt tgctggtac taaggatcat   1140 attcgtcaat accgcgtaaa agaataa                                        1167

<210> SEQ ID NO 109
<211> LENGTH: 388
<212> TYPE: PRT
<213> ORGANISM: Lactobacillus crispatus

<400> SEQUENCE: 109
```

Met Gln Val Gly Ile Asp Gln Ile Gly Leu Phe Thr Pro Asp Lys Tyr
1               5                   10                  15

Val Asp Met Val Asp Leu Ala Asn Ala Arg Lys Gln Asp Pro Asn Lys
            20                  25                  30

Phe Leu Val Gly Ile Gly Gln Arg Glu Met Ser Val Ala Asp Ile Thr
        35                  40                  45

Gln Asp Ala Val Ser Met Gly Ile Asn Ala Thr Leu Lys Phe Ile Asp
    50                  55                  60

Lys Ile Asp Lys Asn Lys Val Gly Leu Leu Ile Phe Gly Thr Glu Ser
65                  70                  75                  80

Ser Ile Asp Gln Ser Lys Ser Ala Ser Leu Phe Val Lys Thr Ala Leu
                85                  90                  95

Lys Leu Lys Pro Glu Val Arg Thr Phe Glu Val Lys Glu Ala Cys Phe
            100                 105                 110

Gly Leu Thr Ala Ala Leu Met Met Ala Arg Asp Phe Val Arg Val His
        115                 120                 125

Pro Glu Gln Thr Ala Ile Val Ile Gly Ser Asp Ile Ala Arg Tyr Gly
    130                 135                 140

Val Asn Thr Ala Gly Glu Val Thr Gln Gly Ala Gly Ser Val Ala Met
145                 150                 155                 160

Leu Ile Lys Ala Asp Pro Ser Ile Leu Ala Leu Asn Asn Gly His Ser
                165                 170                 175

Ala Tyr Ser Glu Asp Ile Asn Asp Phe Trp Arg Pro Asn Tyr Ser Arg
            180                 185                 190

Thr Ala Leu Val Asp Gly Lys Tyr Ser Thr Gln Val Tyr Leu Asp Phe
        195                 200                 205

Phe Lys Lys Thr Phe Thr Asp Tyr Lys Lys Gln Lys Gly Leu Lys Thr
    210                 215                 220

Ser Asp Phe Asp Ala Ile Thr Tyr His Leu Pro Phe Thr Lys Met Gly
225                 230                 235                 240

Met Lys Ala Asn Asn Ile Ala Ile Glu Gly Gln Asp Gln Ala Thr Met
                245                 250                 255

Ile Lys Leu Glu Arg Ser Phe Ala Ala Lys Gln Leu Ser Ser Arg
            260                 265                 270

Val Gly Asn Ile Tyr Thr Ala Ser Leu Tyr Met Ser Leu Leu Ser Leu
        275                 280                 285

Leu Glu Asn Gly Glu Leu Pro Ala Gly Ser Leu Ile Gly Leu Phe Ser
    290                 295                 300

Tyr Gly Ser Gly Ala Met Ala Glu Phe Tyr Ser Gly Lys Leu Val Glu
305                 310                 315                 320

Gly Tyr Glu Lys Gln Ile Asp Pro Thr Ala Asp Gln Ala Met Leu Asp
                325                 330                 335

Arg Arg Lys Lys Leu Thr Val Lys Gln Tyr Glu Asp Val Phe Asn Thr
            340                 345                 350

Ala Leu Leu Asp Pro Glu Asp Gly Leu Glu Leu Thr Ser Asp Asp Glu
        355                 360                 365

Val Gly Thr Trp Tyr Phe Ala Gly Thr Lys Asp His Ile Arg Gln Tyr
    370                 375                 380

Arg Val Lys Glu
385

<210> SEQ ID NO 110
<211> LENGTH: 660
<212> TYPE: DNA
<213> ORGANISM: Unknown
<220> FEATURE:
<223> OTHER INFORMATION: Polaromonas naphthalenivorans Sequence

<400> SEQUENCE: 110
atgaccctgc atttaccttc cagagtcaag ctcgtcgatg tcggtccccg cgacggcctg      60
cagaacgaaa aatcgcccgt tcccgccgcc gtgaaaatcg aactcgtgca tcgcctgcag     120
gacgccggtc tcacggaaat cgaggtcacc agttacgttt cgcccaaatg ggtgccgcag     180
atggctgaca acgccgaagt catggccggc atccggcgca agcccggcgt gcgctattcg     240
gtgctgacgc ccaacatgca gggtctagag gcggcgatga agccagcgcc cgagttgtgg     300
cccgacgaga tcgtggtgtt cggcgcggcc agcgaagcct tcagccagcg caacatcaac     360
tgctcgattg ccgaaagcat cgagcgtttc cggccggtgg tggctgcggc ccgggccaac     420
aatatttatg ttcgcggcgc catttcctgc accgtcggct gccctacga gggcgagatt      480 gcgccggagc gcgtcgaaat ggtggcgcgc ctgatgaagg acatcggcgt gcagcacatc     540
ggcgtggccg acacgattgg cgtcggcacg ccgctgaagg tgcagcgcgc cctggaagcg     600
gcgctgaagc attacgacct cgatggcgtg tcgggccatt ccatgacac ctacggccag      660

<210> SEQ ID NO 111
<211> LENGTH: 308
<212> TYPE: PRT
<213> ORGANISM: Unknown
<220> FEATURE:
<223> OTHER INFORMATION: Polaromonas naphthalenivorans Sequence

<400> SEQUENCE: 111

Met Thr Leu His Leu Pro Ser Arg Val Lys Leu Val Asp Val Gly Pro
1               5                   10                  15

Arg Asp Gly Leu Gln Asn Glu Lys Ser Pro Val Pro Ala Ala Val Lys
            20                  25                  30

Ile Glu Leu Val His Arg Leu Gln Asp Ala Gly Leu Thr Glu Ile Glu
        35                  40                  45

Val Thr Ser Tyr Val Ser Pro Lys Trp Val Pro Gln Met Ala Asp Asn
    50                  55                  60

Ala Glu Val Met Ala Gly Ile Arg Arg Lys Pro Gly Val Arg Tyr Ser
65                  70                  75                  80

Val Leu Thr Pro Asn Met Gln Gly Leu Glu Ala Ala Met Lys Pro Ala
                85                  90                  95

Pro Glu Leu Trp Pro Asp Glu Ile Val Val Phe Gly Ala Ala Ser Glu

```
            100                 105                 110
Ala Phe Ser Gln Arg Asn Ile Asn Cys Ser Ile Ala Glu Ser Ile Glu
            115                 120                 125

Arg Phe Arg Pro Val Val Ala Ala Arg Ala Asn Asn Ile Tyr Val
130                 135                 140

Arg Gly Ala Ile Ser Cys Thr Val Gly Cys Pro Tyr Glu Gly Glu Ile
145                 150                 155                 160

Ala Pro Glu Arg Val Glu Met Val Ala Arg Leu Met Lys Asp Ile Gly
                165                 170                 175

Val Gln His Ile Gly Val Ala Asp Thr Ile Gly Val Gly Thr Pro Leu
            180                 185                 190

Lys Val Gln Arg Ala Leu Glu Ala Ala Leu Lys His Tyr Asp Leu Asp
        195                 200                 205

Gly Val Ser Gly His Phe His Asp Thr Tyr Gly Gln Ala Leu Ala Asn
    210                 215                 220

Thr Leu Ala Ser Leu Gln Met Gly Val Trp Gln Phe Asp Thr Ser Val
225                 230                 235                 240

Ala Gly Leu Gly Gly Cys Pro Tyr Ala Lys Gly Ala Thr Gly Asn Val
                245                 250                 255

Ala Thr Glu Asp Val Val Tyr Leu Leu His Gly Met Gly Ile Glu Thr
                260                 265                 270

Gly Ile Asp Leu Asp Lys Leu Ile Asp Ala Gly Lys Phe Ile Ser Asp
            275                 280                 285

Phe Leu Gly Arg Gln Pro Asn Ser Arg Ala Ala Thr Ala Leu Leu Asn
        290                 295                 300

Lys Arg Met Asn
305

<210> SEQ ID NO 112
<211> LENGTH: 770
<212> TYPE: DNA
<213> ORGANISM: Thermoplasma acidophilum

<400> SEQUENCE: 112
atgacctaca gatcaatagg atcaactgct tatccaacga tcggcgttgt tctcctgggc     60
gggatagcaa atcccgtcac gaggacgccg ctgcatacct cggcagggat agcatacagt    120
gattcctgcg atcgataag atccgagacc aggatatacg ccgatgaggc tacgcacata    180
tatttcaatg gtacggaatc gacagatgac aatagatccg tgaggcgtgt gcttgatcgt    240
tattcaagcg tcttcgagga ggcgttcggt acgaagactt tttcatattc ttcacagaac    300
ttcggcatac tgagcggcag ttccgatgct ggagcggcat cgataggcgc agctatattg    360
ggcctcaaac ccgatctgga tccgcacgat gttgaaaatg acctcagggc ggtctccgaa    420
agcgcaggca ggagcctctt cggcggctta acaataactt ggagcgatgg tttccatgca    480
tatacggaaa agattcttga tcctgaggca ttctccgggt attcgatcgt tgccttcgcg    540
tttgactatc agagaaatcc gtccgatgtc ataccagag atatagtgag aagcgatctc    600
tatccggcca ggaagaagca tgccgatgaa catgcgcaca tgatcaagga gtacgcaaag    660
acaaacgaca taagggcat atttgatctg gcccaggaag atacagagga ataccattcc    720
atacttcgtg gcgtgggcgt gaacgtgata agggagaaca tgcagaagct                770

<210> SEQ ID NO 113
<211> LENGTH: 318
<212> TYPE: PRT
```

<213> ORGANISM: Thermoplasma acidophilum

<400> SEQUENCE: 113

Met Thr Tyr Arg Ser Ile Gly Ser Thr Ala Tyr Pro Thr Ile Gly Val
1               5                   10                  15

Val Leu Leu Gly Gly Ile Ala Asn Pro Val Thr Arg Thr Pro Leu His
            20                  25                  30

Thr Ser Ala Gly Ile Ala Tyr Ser Asp Ser Cys Gly Ser Ile Arg Ser
        35                  40                  45

Glu Thr Arg Ile Tyr Ala Asp Glu Ala Thr His Ile Tyr Phe Asn Gly
50                  55                  60

Thr Glu Ser Thr Asp Asp Asn Arg Ser Val Arg Arg Val Leu Asp Arg
65                  70                  75                  80

Tyr Ser Ser Val Phe Glu Glu Ala Phe Gly Thr Lys Thr Val Ser Tyr
                85                  90                  95

Ser Ser Gln Asn Phe Gly Ile Leu Ser Gly Ser Ser Asp Ala Gly Ala
            100                 105                 110

Ala Ser Ile Gly Ala Ala Ile Leu Gly Leu Lys Pro Asp Leu Asp Pro
        115                 120                 125

His Asp Val Glu Asn Asp Leu Arg Ala Val Ser Glu Ser Ala Gly Arg
130                 135                 140

Ser Leu Phe Gly Gly Leu Thr Ile Thr Trp Ser Asp Gly Phe His Ala
145                 150                 155                 160

Tyr Thr Glu Lys Ile Leu Asp Pro Glu Ala Phe Ser Gly Tyr Ser Ile
                165                 170                 175

Val Ala Phe Ala Phe Asp Tyr Gln Arg Asn Pro Ser Asp Val Ile His
            180                 185                 190

Gln Asn Ile Val Arg Ser Asp Leu Tyr Pro Ala Arg Lys Lys His Ala
        195                 200                 205

Asp Glu His Ala His Met Ile Lys Glu Tyr Ala Lys Thr Asn Asp Ile
210                 215                 220

Lys Gly Ile Phe Asp Leu Ala Gln Glu Asp Thr Glu Glu Tyr His Ser
225                 230                 235                 240

Ile Leu Arg Gly Val Gly Val Asn Val Ile Arg Glu Asn Met Gln Lys
                245                 250                 255

Leu Ile Ser Tyr Leu Lys Leu Ile Arg Lys Asp Tyr Trp Asn Ala Tyr
            260                 265                 270

Ile Val Thr Gly Gly Ser Asn Val Tyr Val Ala Val Glu Ser Glu Asn
        275                 280                 285

Ala Asp Arg Leu Phe Ser Ile Glu Asn Thr Phe Gly Ser Lys Lys Lys
290                 295                 300

Met Leu Arg Ile Val Gly Gly Ala Trp His Arg Arg Pro Glu
305                 310                 315

<210> SEQ ID NO 114
<211> LENGTH: 957
<212> TYPE: DNA
<213> ORGANISM: Thermoplasma acidophilum

<400> SEQUENCE: 114
atgacctaca gatcaatagg atcaactgct tatccaacga tcggcgttgt tctcctgggc      60
gggatagcaa atcccgtcac gaggacgccg ctgcatacct cggcagggat agcatacagt     120
gattcctgcg gatcgataag atccgagacc aggatatacg ccgatgaggc tacgcacata     180
tatttcaatg gtacggaatc gacagatgac aatagatccg tgaggcgtgt gcttgatcgt     240

```
tattcaagcg tcttcgagga ggcgttcggt acgaagactg tttcatattc ttcacagaac      300
ttcggcatac tgagcggcag ttccgatgct ggagcggcat cgataggcgc agctatattg      360
ggcctcaaac ccgatctgga tccgcacgat gttgaaaatg acctcagggc ggtctccgaa      420
agcgcaggca ggagcctctt cggcggctta acaataactt ggagcgatgg tttccatgca      480
tatacggaaa agattcttga tcctgaggca ttctccgggt attcgatcgt tgccttcgcg      540
tttgactatc agagaaatcc gtccgatgtc ataccccaga atatagtgag aagcgatgag      600
tatccggcca ggaagaagca tgccgatgaa catgcgcaca tgatcaagga gtacgcaaag      660
acaaacgaca taagggcat atttgatctg cccaggaag atacagagga ataccattcc        720
atacttcgtg gcgtgggcgt gaacgtgata agggagaaca tgcagaagct catcagttac      780
ctgaagctga tcaggaagga ttactggaat gcctacatcg tgaccggcgg aagcaacgtc      840
tacgtggctg tagaaagcga gaatgcagat aggctgtttt cgatcgaaaa taccttcggt      900
tcaaaaaaga gatgctcag gatagttggc ggtgcctggc atagaagacc agagtga         957

<210> SEQ ID NO 115
<211> LENGTH: 318
<212> TYPE: PRT
<213> ORGANISM: Thermoplasma acidophilum

<400> SEQUENCE: 115

Met Thr Tyr Arg Ser Ile Gly Ser Thr Ala Tyr Pro Thr Ile Gly Val
1               5                   10                  15

Val Leu Leu Gly Gly Ile Ala Asn Pro Val Thr Arg Thr Pro Leu His
            20                  25                  30

Thr Ser Ala Gly Ile Ala Tyr Ser Asp Ser Cys Gly Ser Ile Arg Ser
        35                  40                  45

Glu Thr Arg Ile Tyr Ala Asp Glu Ala Thr His Ile Tyr Phe Asn Gly
    50                  55                  60

Thr Glu Ser Thr Asp Asp Asn Arg Ser Val Arg Val Leu Asp Arg
65                  70                  75                  80

Tyr Ser Ser Val Phe Glu Glu Ala Phe Gly Thr Lys Thr Val Ser Tyr
                85                  90                  95

Ser Ser Gln Asn Phe Gly Ile Leu Ser Gly Ser Ser Asp Ala Gly Ala
            100                 105                 110

Ala Ser Ile Gly Ala Ala Ile Leu Gly Leu Lys Pro Asp Leu Asp Pro
        115                 120                 125

His Asp Val Glu Asn Asp Leu Arg Ala Val Ser Glu Ser Ala Gly Arg
    130                 135                 140

Ser Leu Phe Gly Gly Leu Thr Ile Thr Trp Ser Asp Gly Phe His Ala
145                 150                 155                 160

Tyr Thr Glu Lys Ile Leu Asp Pro Glu Ala Phe Ser Gly Tyr Ser Ile
                165                 170                 175

Val Ala Phe Ala Phe Asp Tyr Gln Arg Asn Pro Ser Asp Val Ile His
            180                 185                 190

Gln Asn Ile Val Arg Ser Asp Glu Tyr Pro Ala Arg Lys Lys His Ala
        195                 200                 205

Asp Glu His Ala His Met Ile Lys Glu Tyr Ala Lys Thr Asn Asp Ile
    210                 215                 220

Lys Gly Ile Phe Asp Leu Ala Gln Glu Asp Thr Glu Glu Tyr His Ser
225                 230                 235                 240

Ile Leu Arg Gly Val Gly Val Asn Val Ile Arg Glu Asn Met Gln Lys
```

```
                245                 250                 255
Leu Ile Ser Tyr Leu Lys Leu Ile Arg Lys Asp Tyr Trp Asn Ala Tyr
            260                 265                 270

Ile Val Thr Gly Gly Ser Asn Val Tyr Val Ala Val Glu Ser Glu Asn
        275                 280                 285

Ala Asp Arg Leu Phe Ser Ile Glu Asn Thr Phe Gly Ser Lys Lys Lys
    290                 295                 300

Met Leu Arg Ile Val Gly Gly Ala Trp His Arg Arg Pro Glu
305                 310                 315
```

<210> SEQ ID NO 116
<211> LENGTH: 770
<212> TYPE: DNA
<213> ORGANISM: Unknown
<220> FEATURE:
<223> OTHER INFORMATION: Picrophilus torridus Sequence

<400> SEQUENCE: 116

```
atggaaaatt acaatgttaa gacaagggcg ttcccaacaa taggcataat actgcttggt      60
gggatctcgg ataaaagaa caggataccg ctgcatacaa cggcaggcat agcatatact      120
ggtataaaca atgatgttta cactgagaca aagctttatg tatcaaaaga tgaaaaatgc     180
tatattgatg gaaaggaaat tgatttaaat tcagatagat caccatcgaa ggttattgat     240
aaattcaagc atgaaatact tatgagagta atcttgatg atgaaaataa cctttcaatt      300
gattcaagga actttaatat attaagtggc agctcagatt ctggggccgc tgcactggga     360
gagtgcatag aatcaatttt tgaatacaat ataaatatat ttacatttga aaacgatctt     420
cagaggatat cagaaagtgt tggaagaagc ctttacggtg gtttaacagt aaactatgcc     480
aatggcaggg aatcattaac agagccatta cttgagcctg aggcatttaa taactttaca     540
ataattggtg cacattttaa cattgataga aaaccatcaa atgagattca tgaaaatatc     600
ataaaacatg aaaattacag ggaagaata aaaagtgctg agagaaaggc gaaaaaactt      660
gaggagctat caaggaatgc aaacataaag ggtatctttg aacttgcaga atccgataca     720
gtggaatacc ataaaatgct ccatgatgtt ggcgttgaca taataaatga                770
```

<210> SEQ ID NO 117
<211> LENGTH: 324
<212> TYPE: PRT
<213> ORGANISM: Unknown
<220> FEATURE:
<223> OTHER INFORMATION: Picrophilus torridus Sequence

<400> SEQUENCE: 117

```
Met Glu Asn Tyr Asn Val Lys Thr Arg Ala Phe Pro Thr Ile Gly Ile
1               5                   10                  15

Ile Leu Leu Gly Gly Ile Ser Asp Lys Lys Asn Arg Ile Pro Leu His
            20                  25                  30

Thr Thr Ala Gly Ile Ala Tyr Thr Gly Ile Asn Asn Asp Val Tyr Thr
        35                  40                  45

Glu Thr Lys Leu Tyr Val Ser Lys Asp Glu Lys Cys Tyr Ile Asp Gly
    50                  55                  60

Lys Glu Ile Asp Leu Asn Ser Asp Arg Ser Pro Ser Lys Val Ile Asp
65                  70                  75                  80

Lys Phe Lys His Glu Ile Leu Met Arg Val Asn Leu Asp Asp Glu Asn
                85                  90                  95

Asn Leu Ser Ile Asp Ser Arg Asn Phe Asn Ile Leu Ser Gly Ser Ser
```

```
                 100                 105                 110
Asp Ser Gly Ala Ala Leu Gly Glu Cys Ile Glu Ser Ile Phe Glu
            115                 120             125

Tyr Asn Ile Asn Ile Phe Thr Phe Glu Asn Asp Leu Gln Arg Ile Ser
    130                 135                 140

Glu Ser Val Gly Arg Ser Leu Tyr Gly Gly Leu Thr Val Asn Tyr Ala
145                 150                 155                 160

Asn Gly Arg Glu Ser Leu Thr Glu Pro Leu Leu Glu Pro Glu Ala Phe
                165                 170                 175

Asn Asn Phe Thr Ile Ile Gly Ala His Phe Asn Ile Asp Arg Lys Pro
            180                 185                 190

Ser Asn Glu Ile His Glu Asn Ile Ile Lys His Glu Asn Tyr Arg Glu
        195                 200                 205

Arg Ile Lys Ser Ala Glu Arg Lys Ala Lys Leu Glu Glu Leu Ser
    210                 215                 220

Arg Asn Ala Asn Ile Lys Gly Ile Phe Glu Leu Ala Glu Ser Asp Thr
225                 230                 235                 240

Val Glu Tyr His Lys Met Leu His Asp Val Gly Val Asp Ile Asn
                245                 250                 255

Asp Arg Met Glu Asn Leu Ile Glu Arg Val Lys Glu Met Lys Asn Asn
            260                 265                 270

Phe Trp Asn Ser Tyr Ile Val Thr Gly Gly Pro Asn Val Phe Val Ile
        275                 280                 285

Thr Glu Lys Lys Asp Val Asp Lys Ala Met Glu Gly Leu Asn Asp Leu
    290                 295                 300

Cys Asp Asp Ile Arg Leu Leu Lys Val Ala Gly Lys Pro Gln Val Ile
305                 310                 315                 320

Ser Lys Asn Phe

<210> SEQ ID NO 118
<211> LENGTH: 660
<212> TYPE: DNA
<213> ORGANISM: Streptococcus mitis

<400> SEQUENCE: 118
atggatagag agcctgtaac agtacgttcc tacgcaaata ttgccattat caaatactgg      60
ggaaagaaaa aagaaaaaga gatggttcct gctactagca gtatttctct gactttggaa     120
aatatgtaca cggagacgac cttgtcatct ctaccgacgg atgcgacagc tgatgcattt     180
tatatcaatg gtcagttaca aaatgaggca gagcatgtca agatgagtaa gattattgac     240
cgctaccgtc cagatggtga tggctttgtt cgtatcgata ctcaaaacag tatgcctacc     300
gcagcgggct tgtcatcaag ttctagtggt ttgtctgcct ggtcaaggc ttgtaatgct     360 tatttcaagc ttggtttgaa tcggagtcag ttggcacagg aggctaagtt tgcctcaggc     420
tcttcctctc ggagttttta tggaccactc ggtgcctggg ataaggatag cggagagatt     480
tacccggtag agacaggcct gaaactagct atgattatgt tggtgctaga agacaagaaa     540
aaaccaatct ctagccgtga tgggatgaaa ctttgtgtgg aaacttcgac gacctttgac     600
gactgggtgc gtcagtctga aaggattat caggatatgc tggtttacct caaggcaaat     660

<210> SEQ ID NO 119
<211> LENGTH: 317
<212> TYPE: PRT
<213> ORGANISM: Streptococcus mitis
```

<400> SEQUENCE: 119

| Met | Asp | Arg | Glu | Pro | Val | Thr | Val | Arg | Ser | Tyr | Ala | Asn | Ile | Ala | Ile |
|---|---|---|---|---|---|---|---|---|---|---|---|---|---|---|---|
| 1 | | | | 5 | | | | | 10 | | | | | 15 | |

| Ile | Lys | Tyr | Trp | Gly | Lys | Lys | Glu | Lys | Glu | Met | Val | Pro | Ala | Thr |
|---|---|---|---|---|---|---|---|---|---|---|---|---|---|---|
| | | | 20 | | | | | 25 | | | | | 30 | |

| Ser | Ser | Ile | Ser | Leu | Thr | Leu | Glu | Asn | Met | Tyr | Thr | Glu | Thr | Thr | Leu |
|---|---|---|---|---|---|---|---|---|---|---|---|---|---|---|---|
| | | | 35 | | | | | 40 | | | | | 45 | | |

| Ser | Ser | Leu | Pro | Thr | Asp | Ala | Thr | Ala | Asp | Ala | Phe | Tyr | Ile | Asn | Gly |
|---|---|---|---|---|---|---|---|---|---|---|---|---|---|---|---|
| | 50 | | | | | 55 | | | | | 60 | | | | |

| Gln | Leu | Gln | Asn | Glu | Ala | Glu | His | Val | Lys | Met | Ser | Lys | Ile | Ile | Asp |
|---|---|---|---|---|---|---|---|---|---|---|---|---|---|---|---|
| 65 | | | | | 70 | | | | | 75 | | | | | 80 |

| Arg | Tyr | Arg | Pro | Asp | Gly | Asp | Gly | Phe | Val | Arg | Ile | Asp | Thr | Gln | Asn |
|---|---|---|---|---|---|---|---|---|---|---|---|---|---|---|---|
| | | | | 85 | | | | | 90 | | | | | 95 | |

| Ser | Met | Pro | Thr | Ala | Ala | Gly | Leu | Ser | Ser | Ser | Ser | Gly | Leu | Ser |
|---|---|---|---|---|---|---|---|---|---|---|---|---|---|---|
| | | | 100 | | | | | 105 | | | | | 110 | |

| Ala | Leu | Val | Lys | Ala | Cys | Asn | Ala | Tyr | Phe | Lys | Leu | Gly | Leu | Asn | Arg |
|---|---|---|---|---|---|---|---|---|---|---|---|---|---|---|---|
| | | | 115 | | | | | 120 | | | | | 125 | | |

| Ser | Gln | Leu | Ala | Gln | Glu | Ala | Lys | Phe | Ala | Ser | Gly | Ser | Ser | Ser | Arg |
|---|---|---|---|---|---|---|---|---|---|---|---|---|---|---|---|
| | 130 | | | | | 135 | | | | | 140 | | | | |

| Ser | Phe | Tyr | Gly | Pro | Leu | Gly | Ala | Trp | Asp | Lys | Asp | Ser | Gly | Glu | Ile |
|---|---|---|---|---|---|---|---|---|---|---|---|---|---|---|---|
| 145 | | | | | 150 | | | | | 155 | | | | | 160 |

| Tyr | Pro | Val | Glu | Thr | Gly | Leu | Lys | Leu | Ala | Met | Ile | Met | Leu | Val | Leu |
|---|---|---|---|---|---|---|---|---|---|---|---|---|---|---|---|
| | | | | 165 | | | | | 170 | | | | | 175 | |

| Glu | Asp | Lys | Lys | Lys | Pro | Ile | Ser | Ser | Arg | Asp | Gly | Met | Lys | Leu | Cys |
|---|---|---|---|---|---|---|---|---|---|---|---|---|---|---|---|
| | | | 180 | | | | | 185 | | | | | 190 | | |

| Val | Glu | Thr | Ser | Thr | Thr | Phe | Asp | Asp | Trp | Val | Arg | Gln | Ser | Glu | Lys |
|---|---|---|---|---|---|---|---|---|---|---|---|---|---|---|---|
| | | 195 | | | | | 200 | | | | | 205 | | | |

| Asp | Tyr | Gln | Asp | Met | Leu | Val | Tyr | Leu | Lys | Ala | Asn | Asp | Phe | Ala | Lys |
|---|---|---|---|---|---|---|---|---|---|---|---|---|---|---|---|
| | 210 | | | | | 215 | | | | | 220 | | | | |

| Val | Gly | Glu | Leu | Thr | Glu | Lys | Asn | Ala | Leu | Ala | Met | His | Ala | Thr | Thr |
|---|---|---|---|---|---|---|---|---|---|---|---|---|---|---|---|
| 225 | | | | | 230 | | | | | 235 | | | | | 240 |

| Lys | Thr | Ala | Ser | Pro | Ala | Phe | Ser | Tyr | Leu | Thr | Asp | Ala | Ser | Tyr | Glu |
|---|---|---|---|---|---|---|---|---|---|---|---|---|---|---|---|
| | | | | 245 | | | | | 250 | | | | | 255 | |

| Ala | Met | Asp | Phe | Val | Arg | Gln | Leu | Arg | Glu | Gln | Gly | Glu | Ala | Cys | Tyr |
|---|---|---|---|---|---|---|---|---|---|---|---|---|---|---|---|
| | | | 260 | | | | | 265 | | | | | 270 | | |

| Phe | Thr | Met | Asp | Ala | Gly | Pro | Asn | Val | Lys | Val | Leu | Cys | Gln | Glu | Lys |
|---|---|---|---|---|---|---|---|---|---|---|---|---|---|---|---|
| | | 275 | | | | | 280 | | | | | 285 | | | |

| Asp | Leu | Glu | His | Leu | Ser | Glu | Ile | Phe | Gly | Gln | Arg | Tyr | Arg | Leu | Ile |
|---|---|---|---|---|---|---|---|---|---|---|---|---|---|---|---|
| | 290 | | | | | 295 | | | | | 300 | | | | |

| Val | Ser | Lys | Thr | Lys | Asp | Leu | Ser | Gln | Asp | Gly | Cys | Cys |
|---|---|---|---|---|---|---|---|---|---|---|---|---|
| 305 | | | | | 310 | | | | | 315 | | |

<210> SEQ ID NO 120
<211> LENGTH: 948
<212> TYPE: DNA
<213> ORGANISM: Streptococcus gordonii

<400> SEQUENCE: 120

| | |
|---|---|
| atggatcgaa agcctgtaag tgtcaaatcc tatgccaata ttgcaattgt caaatattgg | 60 |
| ggcaagaaag atgcagaaaa gatgattccg tctacaagca gtatctcact gacactggaa | 120 |
| aatatgtata ccgagacgca gctgagtcct ttgccggata cagcgactgg tgatgagttt | 180 |
| tatattgacg gtcagctgca aagcccggca gaacatgcca aaatcagtaa aattattgac | 240 |
| cgttttcgct ctccagaaga tggttttgtc cgtgttgata ccagcaataa tatgccaaca | 300 |

```
gcagcagggc tgtcttccag ctccagcggt ctatctgctc tggtcaaggc ttgcaatgct    360
tattttcaga caggctatca gacggaagaa ctggctcaac tggccaagtt tgcttcaggg    420
tcctctgctc ggtctttctt tggtccgcta gcggcctggg ataaggacag tggagccatc    480
tatccagtca agacggattt gaagctagcc atgattatgc tggttctgca cgatgagaaa    540
aagcccattt ccagccgcga cggtatggag ctctgtgcta aaacttccac aattttccca    600
gattggattg cccaatctgc cttggattat caggccatgc taggctattt gcaggacaat    660
gattttgcca aggttggtca actgacggaa gaaaatgccc ttcggatgca tgctacaaca    720
gaaaaagctt atccgccgtt ttcttatctg acagaggagt cttatcaggc tatggatgct    780
gtcagaaagc tacgggagca gggcgagcgt tgctacttta ccatggatgc ggggccaaat    840
gtcaaggtgc tctgcttgga ggaagatcta gaccatttgg ctgccatatt tgagaaggac    900
tatcgcctta ttgtctccaa aacaaaggac ttgtcagatg aaagctag              948
```

<210> SEQ ID NO 121  
<211> LENGTH: 315  
<212> TYPE: PRT  
<213> ORGANISM: Streptococcus gordonii

<400> SEQUENCE: 121

```
Met Asp Arg Lys Pro Val Ser Val Lys Ser Tyr Ala Asn Ile Ala Ile
1               5                   10                  15

Val Lys Tyr Trp Gly Lys Lys Asp Ala Glu Lys Met Ile Pro Ser Thr
            20                  25                  30

Ser Ser Ile Ser Leu Thr Leu Glu Asn Met Tyr Thr Glu Thr Gln Leu
        35                  40                  45

Ser Pro Leu Pro Asp Thr Ala Thr Gly Asp Glu Phe Tyr Ile Asp Gly
    50                  55                  60

Gln Leu Gln Ser Pro Ala Glu His Ala Lys Ile Ser Lys Ile Ile Asp
65                  70                  75                  80

Arg Phe Arg Ser Pro Glu Asp Gly Phe Val Arg Val Asp Thr Ser Asn
                85                  90                  95

Asn Met Pro Thr Ala Ala Gly Leu Ser Ser Ser Ser Gly Leu Ser
            100                 105                 110

Ala Leu Val Lys Ala Cys Asn Ala Tyr Phe Gln Thr Gly Tyr Gln Thr
        115                 120                 125

Glu Glu Leu Ala Gln Leu Ala Lys Phe Ala Ser Gly Ser Ser Ala Arg
    130                 135                 140

Ser Phe Phe Gly Pro Leu Ala Ala Trp Asp Lys Asp Ser Gly Ala Ile
145                 150                 155                 160

Tyr Pro Val Lys Thr Asp Leu Lys Leu Ala Met Ile Met Leu Val Leu
                165                 170                 175

His Asp Glu Lys Lys Pro Ile Ser Ser Arg Asp Gly Met Glu Leu Cys
            180                 185                 190

Ala Lys Thr Ser Thr Ile Phe Pro Asp Trp Ile Ala Gln Ser Ala Leu
        195                 200                 205

Asp Tyr Gln Ala Met Leu Gly Tyr Leu Gln Asp Asn Asp Phe Ala Lys
    210                 215                 220

Val Gly Gln Leu Thr Glu Glu Asn Ala Leu Arg Met His Ala Thr Thr
225                 230                 235                 240

Glu Lys Ala Tyr Pro Pro Phe Ser Tyr Leu Thr Glu Glu Ser Tyr Gln
                245                 250                 255
```

Ala Met Asp Ala Val Arg Lys Leu Arg Glu Gln Gly Glu Arg Cys Tyr
            260                 265                 270

Phe Thr Met Asp Ala Gly Pro Asn Val Lys Val Leu Cys Leu Glu Glu
        275                 280                 285

Asp Leu Asp His Leu Ala Ala Ile Phe Glu Lys Asp Tyr Arg Leu Ile
        290                 295                 300

Val Ser Lys Thr Lys Asp Leu Ser Asp Glu Ser
305                 310                 315

<210> SEQ ID NO 122
<211> LENGTH: 1476
<212> TYPE: DNA
<213> ORGANISM: Saccharomyces cerevisiae

<400> SEQUENCE: 122

```
atgaaactct caactaaact tgttggtgt ggtattaaag aagacttag gccgcaaaag      60
caacaacaat tacacaatac aaacttgcaa atgactgaac taaaaaaaca aaagaccgct    120
gaacaaaaaa ccagacctca aaatgtcggt attaaaggta tccaaattta catcccaact    180
caatgtgtca accaatctga gctagagaaa tttgatggcg tttctcaagg taaatacaca    240
attggtctgg gccaaaccaa catgtctttt gtcaatgaca gagaagatat ctactcgatg    300
tccctaactg ttttgtctaa gttgatcaag agttacaaca tcgacaccaa caaaattggt    360
agattagaag tcggtactga aactctgatt gacaagtcca gtctgtcaa gtctgtcttg     420
atgcaattgt ttggtgaaaa cactgacgtc gaaggtattg acacgcttaa tgcctgttac    480
ggtggtacca acgcgttgtt caactctttg aactggattg aatctaacgc atgggatggt    540
agagacgcca ttgtagtttg cggtgatatt gccatctacg ataagggtgc cgcaagacca    600
accggtggtg ccgtactgtg tgctatgtgg atcggtcctg atgctccaat tgtatttgac    660
tctgtaagag cttcttacat ggaacacgcc tacgattttt acaagccaga tttcaccagc    720
gaatatcctt acgtcgatgg tcattttca ttaacttgtt acgtcaaggc tcttgatcaa     780
gtttacaaga gttattccaa gaaggctatt tctaaagggt tggttagcga tcccgctggt    840
tcggatgctt tgaacgtttt gaaatatttc gactacaacg ttttccatgt tccaacctgt    900
aaattggtca caaaatcata cggtagatta ctatataacg atttcagagc caatcctcaa    960
ttgttcccag aagttgacgc cgaattagct actcgcgatt atgacgaatc tttaaccgat   1020
aagaacattg aaaaaacttt tgttaatgtt gctaagccat tccacaaaga gagagttgcc   1080
caatctttga ttgttccaac aaacacaggt aacatgtaca ccgcatctgt ttatgccgcc   1140
tttgcatctc tattaaacta tgttggatct gacgacttac aaggcaagcg tgttggttta   1200
ttttcttacg gttccggttt agctgcatct ctatattctt gcaaaattgt tggtgacgtc   1260
caacatatta tcaaggaatt agatattact aacaaattag ccaagagaat caccgaaact   1320
ccaaaggatt acgaagctgc catcgaattg agagaaaatg cccatttgaa gaagaacttc   1380
aaacctcaag ttccattga gcatttgcaa agtggtgttt actacttgac caacatcgat   1440
gacaaattta aagatctta cgatgttaaa aaataa                              1476
```

<210> SEQ ID NO 123
<211> LENGTH: 491
<212> TYPE: PRT
<213> ORGANISM: Saccharomyces cerevisiae

<400> SEQUENCE: 123

Met Lys Leu Ser Thr Lys Leu Cys Trp Cys Gly Ile Lys Gly Arg Leu

-continued

```
1               5                   10                  15
Arg Pro Gln Lys Gln Gln Gln Leu His Asn Thr Asn Leu Gln Met Thr
                20                  25                  30
Glu Leu Lys Lys Gln Lys Thr Ala Glu Gln Lys Thr Arg Pro Gln Asn
                35                  40                  45
Val Gly Ile Lys Gly Ile Gln Ile Tyr Ile Pro Thr Gln Cys Val Asn
                50                  55                  60
Gln Ser Glu Leu Glu Lys Phe Asp Gly Val Ser Gln Gly Lys Tyr Thr
65                              70                  75              80
Ile Gly Leu Gly Gln Thr Asn Met Ser Phe Val Asn Asp Arg Glu Asp
                        85                  90                  95
Ile Tyr Ser Met Ser Leu Thr Val Leu Ser Lys Leu Ile Lys Ser Tyr
                100                 105                 110
Asn Ile Asp Thr Asn Lys Ile Gly Arg Leu Glu Val Gly Thr Glu Thr
                115                 120                 125
Leu Ile Asp Lys Ser Lys Ser Val Lys Ser Val Leu Met Gln Leu Phe
            130                 135                 140
Gly Glu Asn Thr Asp Val Glu Gly Ile Asp Thr Leu Asn Ala Cys Tyr
145                 150                 155                 160
Gly Gly Thr Asn Ala Leu Phe Asn Ser Leu Asn Trp Ile Glu Ser Asn
                    165                 170                 175
Ala Trp Asp Gly Arg Asp Ala Ile Val Val Cys Gly Asp Ile Ala Ile
                180                 185                 190
Tyr Asp Lys Gly Ala Ala Arg Pro Thr Gly Gly Ala Gly Thr Val Ala
                195                 200                 205
Met Trp Ile Gly Pro Asp Ala Pro Ile Val Phe Asp Ser Val Arg Ala
        210                 215                 220
Ser Tyr Met Glu His Ala Tyr Asp Phe Tyr Lys Pro Asp Phe Thr Ser
225                 230                 235                 240
Glu Tyr Pro Tyr Val Asp Gly His Phe Ser Leu Thr Cys Tyr Val Lys
                    245                 250                 255
Ala Leu Asp Gln Val Tyr Lys Ser Tyr Ser Lys Lys Ala Ile Ser Lys
                260                 265                 270
Gly Leu Val Ser Asp Pro Ala Gly Ser Asp Ala Leu Asn Val Leu Lys
            275                 280                 285
Tyr Phe Asp Tyr Asn Val Phe His Val Pro Thr Cys Lys Leu Val Thr
        290                 295                 300
Lys Ser Tyr Gly Arg Leu Leu Tyr Asn Asp Phe Arg Ala Asn Pro Gln
305                 310                 315                 320
Leu Phe Pro Glu Val Asp Ala Glu Leu Ala Thr Arg Asp Tyr Asp Glu
                325                 330                 335
Ser Leu Thr Asp Lys Asn Ile Glu Lys Thr Phe Val Asn Val Ala Lys
                340                 345                 350
Pro Phe His Lys Glu Arg Val Ala Gln Ser Leu Ile Val Pro Thr Asn
                355                 360                 365
Thr Gly Asn Met Tyr Thr Ala Ser Val Tyr Ala Ala Phe Ala Ser Leu
370                 375                 380
Leu Asn Tyr Val Gly Ser Asp Leu Gln Gly Lys Arg Val Gly Leu
385                 390                 395                 400
Phe Ser Tyr Gly Ser Gly Leu Ala Ala Ser Leu Tyr Ser Cys Lys Ile
                    405                 410                 415
Val Gly Asp Val Gln His Ile Ile Lys Glu Leu Asp Ile Thr Asn Lys
                420                 425                 430
```

Leu Ala Lys Arg Ile Thr Glu Thr Pro Lys Asp Tyr Glu Ala Ala Ile
        435                 440                 445

Glu Leu Arg Glu Asn Ala His Leu Lys Lys Asn Phe Lys Pro Gln Gly
    450                 455                 460

Ser Ile Glu His Leu Gln Ser Gly Val Tyr Tyr Leu Thr Asn Ile Asp
465                 470                 475                 480

Asp Lys Phe Arg Arg Ser Tyr Asp Val Lys Lys
                485                 490

<210> SEQ ID NO 124
<211> LENGTH: 816
<212> TYPE: DNA
<213> ORGANISM: Pseudomonas putida

<400> SEQUENCE: 124

```
atgagcgatt tcagcaccct cgaagtgatc cgcgacccgc gcggcttcgc caccctgtgg      60
ttaagccgtg aggacaagaa caacgccttc aatgcgcaga tgatccgcga gctgatcgtg     120
gccatcgacc agttggccga agacgccagc ctgcgctttg tgctgctgcg cggccgtggc     180
cggcacttca gcgccggtgc cgacctggcc tggatgcagc agtcggcgca actggacttc     240
aacaccaacc tggatgatgc ccacgaactg ggcgagctga tgtacgccct gcatcgcctc     300
aaggccccga ccctggccgt ggtgcaaggt gcagcctttg gcggcgcgct gggcctgatc     360
agctgctgcg acatggccat cggcgccgaa gacgcccaac tgtgcctgtc ggaagtacgc     420
atcggcctgg ccccggcggt catcagcccg ttcgtggtca aggccattgg cgaacgcgcc     480
gcgcgccgct acgccctcac cgccgagcgt ttcactggcg tgcgcgcacg cgagctgggc     540
ctgctggccg aggtgtaccc ggccagcgaa ctggacgacc acgtcgaagc ctgggtaagc     600
aacctgctgc agaacagccc gcaagcattg cgcgccacca aggacttgct gcgcgaagtg     660
gacgacggcg aactcagccc ggccctgcgc cgttactgcg aaaacaccat cgcccgtatc     720
cgcgtcagcg ccgaaggcca ggagggcctg cgcgcttttc ctggaaaaacg ccgccctgcc     780
tggcaaaccg ttgacaagaa ggagccgcgc ccatga                              816
```

<210> SEQ ID NO 125
<211> LENGTH: 271
<212> TYPE: PRT
<213> ORGANISM: Pseudomonas putida

<400> SEQUENCE: 125

Met Ser Asp Phe Ser Thr Leu Glu Val Ile Arg Asp Pro Arg Gly Phe
1               5                   10                  15

Ala Thr Leu Trp Leu Ser Arg Glu Asp Lys Asn Asn Ala Phe Asn Ala
            20                  25                  30

Gln Met Ile Arg Glu Leu Ile Val Ala Ile Asp Gln Leu Ala Glu Asp
        35                  40                  45

Ala Ser Leu Arg Phe Val Leu Leu Arg Gly Arg Gly Arg His Phe Ser
    50                  55                  60

Ala Gly Ala Asp Leu Ala Trp Met Gln Gln Ser Ala Gln Leu Asp Phe
65                  70                  75                  80

Asn Thr Asn Leu Asp Asp Ala His Glu Leu Gly Glu Leu Met Tyr Ala
                85                  90                  95

Leu His Arg Leu Lys Ala Pro Thr Leu Ala Val Val Gln Gly Ala Ala
            100                 105                 110

Phe Gly Gly Ala Leu Gly Leu Ile Ser Cys Cys Asp Met Ala Ile Gly

```
                115                 120                 125
Ala Glu Asp Ala Gln Leu Cys Leu Ser Glu Val Arg Ile Gly Leu Ala
            130                 135                 140

Pro Ala Val Ile Ser Pro Phe Val Lys Ala Ile Gly Glu Arg Ala
145                 150                 155                 160

Ala Arg Arg Tyr Ala Leu Thr Ala Glu Arg Phe Thr Gly Val Arg Ala
                165                 170                 175

Arg Glu Leu Gly Leu Leu Ala Glu Val Tyr Pro Ala Ser Glu Leu Asp
            180                 185                 190

Asp His Val Glu Ala Trp Val Ser Asn Leu Leu Gln Asn Ser Pro Gln
        195                 200                 205

Ala Leu Arg Ala Thr Lys Asp Leu Leu Arg Glu Val Asp Asp Gly Glu
    210                 215                 220

Leu Ser Pro Ala Leu Arg Arg Tyr Cys Glu Asn Thr Ile Ala Arg Ile
225                 230                 235                 240

Arg Val Ser Ala Glu Gly Gln Glu Gly Leu Arg Ala Phe Leu Glu Lys
                245                 250                 255

Arg Arg Pro Ala Trp Gln Thr Val Asp Lys Lys Glu Pro Arg Pro
            260                 265                 270

<210> SEQ ID NO 126
<211> LENGTH: 1608
<212> TYPE: DNA
<213> ORGANISM: Pseudomonas aeruginosa

<400> SEQUENCE: 126
atggccatcc tgcacaccca gatcaatcca cgctccgccg agttcgcggc caacgccgcg      60
accatgctgg aacaggtcaa cgccctgcgc accctcctcg gccgcatcca cgaaggcggc     120
ggtagcgccg cccaggcccg gcacagcgcg cgcggcaagc tgctggtgcg cgaacgcatc     180
aaccgcctgc tcgaccccgg ctcgccgttc ctcgagcttt ccgccctcgc cgcccacgaa     240
gtctacggcg aagaggtcgc cgccgccggc atcgtcgccg ggatcggccg ggtcgaaggg     300
gtggaatgca tgatcgtcgg caacgatgcc acggtgaagg cggcaccta ctatccgctg      360 accgtgaaga agcacctgcg ggcccaggcc atcgccctgg agaaccgcct gcatgcatc      420 tacctggtgg actctggcgg cgccaacctg ccgcgccagg acgaggtgtt ccccgaccgc     480
gagcacttcg gccggatctt cttcaaccag gccaacatga gtgcccgcgg catcccgcag     540
atcgccgtgg tcatgggctc ctgcaccgcc ggcggggcct acgtgccggc gatgtccgac     600
gaaaccgtga tggtgcgcga acaggccacc atcttcctcg ccgggccgcc gctggtgaag     660
gccgctaccg gcgaggtggt cagcgccgag gaacttggcg gcgccgacgt gcactgcaag     720
gtctcagggg tcgccgacca ctatgccgag gacgatgacc atgccctggc catcgcccgc     780
cgctgcgtcg ccaacctcaa ctggcgcaag cagggccagc tgcaatgccg tgcaccgcgc     840
gcgccgctgt accccgccga ggagctgtac ggggtgattc cgccgacag caagcagccc      900 tacgacgtgc gcgaagtgat cgcacggctg gtggacggct ccgagttcga cgaattcaag     960
gcgctgttcg gcaccaccct ggtctgcggc ttcgcccacc tgcacggcta tccgatcgcc    1020
atcctggcca acaacgggat cctcttcgcc gaggccgcgc agaaaggcgc gcacttcatc    1080
gagttggcct gccagcgtgg catcccgctg ctgttcctgc agaacatcac cggtttcatg    1140
gtcggccaga agtacgaggc tgcggcatc gccaagcacg cgccaagct ggtgaccgcg      1200 gtggcctgcg cgcgggtgcc gaagttcacc gtgctgatcg cggcagctt cggcgccggc    1260
```

```
aactacggca tgtgcggacg cgcctacgac ccgcgcttcc tgtggatgtg gccgaacgcg    1320
aggatcggcg tgatgggcgg cgaacaggcc gccggggtgc tcgcccaggt caagcgcgag    1380
caggccgagc gcgccggcca gcagctcggc gtcgaagagg aggcgaagat caaggcgccg    1440
atcctcgagc agtacgagca ccagggccat ccctactact ccagcgcgcg actgtgggac    1500
gacggcgtga tcgatccggc gcagacccgc gaggtcctcg ccctggcgct ttccgccgcc    1560
ctcaacgccc ccatcgagcc gaccgccttc ggcgtgttcc gcatgtga                1608
```

<210> SEQ ID NO 127
<211> LENGTH: 535
<212> TYPE: PRT
<213> ORGANISM: Pseudomonas aeruginosa

<400> SEQUENCE: 127

```
Met Ala Ile Leu His Thr Gln Ile Asn Pro Arg Ser Ala Glu Phe Ala
1               5                  10                  15

Ala Asn Ala Ala Thr Met Leu Glu Gln Val Asn Ala Leu Arg Thr Leu
            20                  25                  30

Leu Gly Arg Ile His Glu Gly Gly Ser Ala Ala Gln Ala Arg His
        35                  40                  45

Ser Ala Arg Gly Lys Leu Leu Val Arg Glu Arg Ile Asn Arg Leu Leu
    50                  55                  60

Asp Pro Gly Ser Pro Phe Leu Glu Leu Ser Ala Leu Ala Ala His Glu
65                  70                  75                  80

Val Tyr Gly Glu Glu Val Ala Ala Ala Gly Ile Val Ala Gly Ile Gly
                85                  90                  95

Arg Val Glu Gly Val Glu Cys Met Ile Val Gly Asn Asp Ala Thr Val
            100                 105                 110

Lys Gly Gly Thr Tyr Tyr Pro Leu Thr Val Lys Lys His Leu Arg Ala
        115                 120                 125

Gln Ala Ile Ala Leu Glu Asn Arg Leu Pro Cys Ile Tyr Leu Val Asp
    130                 135                 140

Ser Gly Gly Ala Asn Leu Pro Arg Gln Asp Glu Val Phe Pro Asp Arg
145                 150                 155                 160

Glu His Phe Gly Arg Ile Phe Phe Asn Gln Ala Asn Met Ser Ala Arg
                165                 170                 175

Gly Ile Pro Gln Ile Ala Val Val Met Gly Ser Cys Thr Ala Gly Gly
            180                 185                 190

Ala Tyr Val Pro Ala Met Ser Asp Glu Thr Val Met Val Arg Glu Gln
        195                 200                 205

Ala Thr Ile Phe Leu Ala Gly Pro Pro Leu Val Lys Ala Ala Thr Gly
    210                 215                 220

Glu Val Val Ser Ala Glu Leu Gly Gly Ala Asp Val His Cys Lys
225                 230                 235                 240

Val Ser Gly Val Ala Asp His Tyr Ala Glu Asp Asp His Ala Leu
                245                 250                 255

Ala Ile Ala Arg Arg Cys Val Ala Asn Leu Asn Trp Arg Lys Gln Gly
            260                 265                 270

Gln Leu Gln Cys Arg Ala Pro Arg Ala Pro Leu Tyr Pro Ala Glu Glu
        275                 280                 285

Leu Tyr Gly Val Ile Pro Ala Asp Ser Lys Gln Pro Tyr Asp Val Arg
    290                 295                 300

Glu Val Ile Ala Arg Leu Val Asp Gly Ser Glu Phe Asp Glu Phe Lys
305                 310                 315                 320
```

```
Ala Leu Phe Gly Thr Thr Leu Val Cys Gly Phe Ala His Leu His Gly
                325                 330                 335

Tyr Pro Ile Ala Ile Leu Ala Asn Asn Gly Ile Leu Phe Ala Glu Ala
            340                 345                 350

Ala Gln Lys Gly Ala His Phe Ile Glu Leu Ala Cys Gln Arg Gly Ile
        355                 360                 365

Pro Leu Leu Phe Leu Gln Asn Ile Thr Gly Phe Met Val Gly Gln Lys
    370                 375                 380

Tyr Glu Ala Gly Gly Ile Ala Lys His Gly Ala Lys Leu Val Thr Ala
385                 390                 395                 400

Val Ala Cys Ala Arg Val Pro Lys Phe Thr Val Leu Ile Gly Gly Ser
                405                 410                 415

Phe Gly Ala Gly Asn Tyr Gly Met Cys Gly Arg Ala Tyr Asp Pro Arg
            420                 425                 430

Phe Leu Trp Met Trp Pro Asn Ala Arg Ile Gly Val Met Gly Gly Glu
        435                 440                 445

Gln Ala Ala Gly Val Leu Ala Gln Val Lys Arg Glu Gln Ala Glu Arg
    450                 455                 460

Ala Gly Gln Gln Leu Gly Val Glu Glu Ala Lys Ile Lys Ala Pro
465                 470                 475                 480

Ile Leu Glu Gln Tyr Glu His Gln Gly His Pro Tyr Tyr Ser Ser Ala
                485                 490                 495

Arg Leu Trp Asp Asp Gly Val Ile Asp Pro Ala Gln Thr Arg Glu Val
            500                 505                 510

Leu Ala Leu Ala Leu Ser Ala Ala Leu Asn Ala Pro Ile Glu Pro Thr
        515                 520                 525

Ala Phe Gly Val Phe Arg Met
    530                 535

<210> SEQ ID NO 128
<211> LENGTH: 1968
<212> TYPE: DNA
<213> ORGANISM: Pseudomonas aeruginosa

<400> SEQUENCE: 128
atgaacccgg actaccgcag catccagcgc ctcctggtcg ccaaccgcgg cgagatcgcc    60
tgccgggtga tgcgcagcgc gcgcgccctc ggcatcggca gcgtcgccgt gcacagcgac   120
atcgaccgcc acgcccgcca cgtcgccgaa gccgacatcg ccgtcgacct gggcggcgcc   180
aagcccgccg acagctacct gcgcggcgac aggatcatcg cagctgccct cgccagcggc   240
gcccaggcga tccaccccgg ctacggcttc ctctcggaga cgccgacttc gcccgcgcc    300 tgcgaggaag ccgccctgct cttcctcgga ccgccggcgg cggccatcga cgccatgggc   360
agcaagtcgg ccgccaaggc gctgatggaa gaagccggcg tgccgctggt gcccggctat   420
cacggcgaag cccaggacct cgagactttc gccggaag ccgggcgcat cggctacccg    480
gtgctgctca aggccgccgc tggcggcggc ggcaagggca tgaaggtggt ggagcgcgag   540
gccgagctgg ccgaggccct ttcctccgcc cagcgcgagg ccaaggccgc cttcggcgac   600
gcgcgtatgc tggtggagaa atacctgctg aagccgcgcc acgtggagat ccaggtattc   660
gccgaccgcc atggccactg cctgtacctc aacgaacgcg actgttcgat ccagcgccgc   720
caccagaagg tcgtcgagga agccccgcc ccggtctcg gcgcggaact gccggggcc    780 atgggcgagg ccgcggtacg cgcggcgcag gcgatcggct acgtcggcgc cggtaccgtc   840
```

```
gaattcctcc tcgacgaacg cggccagttc ttcttcatgg aaatgaacac ccgcctgcag    900
gtggaacacc cggtcaccga ggccatcacc ggcctcgacc tggtcgcctg cagatccgc    960
gtcgctcgcg gcgaggcgct accgctgacg caggaacagg taccgctgaa cggccacgcc   1020
atcgaagtac ggctctatgc ggaagacccc gagggcgact tcctcccgcc agcggccgc    1080
ctgatgctat accgcgaagc ggccgccggc cccggccggc gggtcgacag cggggtacgc   1140
gaaggcgacg aggtctcgcc gttctacgac ccgatgctgg ccaagctgat cgcctggggc   1200
gaaacccgcg aggaagcccg ccagcgcctg ctggcgatgc tggcggaaac ctcggtcggc   1260
ggcctgcgca ccaacctggc gttcctccgc cgcatcctcg gccatccggc gttcgccgcc   1320
gccgaactgg acaccggggtt catcgcgcgc caccaagacg acctgctgcc ggcgccgcaa   1380
gcgctgccgg agcatttctg gaagccgcc gccgaagcct ggctgcagag cgaaccgggc    1440
caccgtcgcg acgacgaccc gcattcgccg tggagccgca cgacggctg gcgcagcgcc    1500
ctggcgcggg agtccgacct gatgctgcgc tgccgcgacg aacgccgctg cgtccgcctg   1560
cgccacgcca gccccagcca gtatcgcctc gacggcgacg acctggtcag ccgggtggac   1620
ggtgtcaccc gtcgctcggc ggcgttgcgc gcggacgcc aattgttcct cgaatgggag    1680
ggcgaactgc tggccatcga agccgtcgac ccgatcgccg aggccgaggc cgcccatgcc   1740
caccagggcg gtttgagcgc gccgatgaac ggcagtatcg tgcgggtcct ggtcgagccc   1800
ggccagacgg tcgaagccgg cgccacccctg gtggtgctgg aggcgatgaa gatggaacac   1860
agcatccgcg cgccccacgc cggggtagtg aaggcgctgt attgcagcga gggcgaactg   1920
gtcgaggaag gcacgccgct ggtggagctg gacgagaacc aggcctga              1968

<210> SEQ ID NO 129
<211> LENGTH: 655
<212> TYPE: PRT
<213> ORGANISM: Pseudomonas aeruginosa

<400> SEQUENCE: 129

Met Asn Pro Asp Tyr Arg Ser Ile Gln Arg Leu Leu Val Ala Asn Arg
1               5                   10                  15

Gly Glu Ile Ala Cys Arg Val Met Arg Ser Ala Arg Ala Leu Gly Ile
            20                  25                  30

Gly Ser Val Ala Val His Ser Asp Ile Asp Arg His Ala Arg His Val
        35                  40                  45

Ala Glu Ala Asp Ile Ala Val Asp Leu Gly Gly Ala Lys Pro Ala Asp
    50                  55                  60

Ser Tyr Leu Arg Gly Asp Arg Ile Ile Ala Ala Leu Ala Ser Gly
65                  70                  75                  80

Ala Gln Ala Ile His Pro Gly Tyr Gly Phe Leu Ser Glu Asn Ala Asp
                85                  90                  95

Phe Ala Arg Ala Cys Glu Glu Ala Gly Leu Leu Phe Leu Gly Pro Pro
            100                 105                 110

Ala Ala Ala Ile Asp Ala Met Gly Ser Lys Ser Ala Ala Lys Ala Leu
        115                 120                 125

Met Glu Glu Ala Gly Val Pro Leu Val Pro Gly Tyr His Gly Glu Ala
    130                 135                 140

Gln Asp Leu Glu Thr Phe Arg Arg Glu Ala Gly Arg Ile Gly Tyr Pro
145                 150                 155                 160

Val Leu Leu Lys Ala Ala Gly Gly Gly Lys Gly Met Lys Val
                165                 170                 175
```

```
Val Glu Arg Glu Ala Glu Leu Ala Glu Ala Leu Ser Ser Ala Gln Arg
            180                 185                 190

Glu Ala Lys Ala Ala Phe Gly Asp Ala Arg Met Leu Val Glu Lys Tyr
        195                 200                 205

Leu Leu Lys Pro Arg His Val Glu Ile Gln Val Phe Ala Asp Arg His
    210                 215                 220

Gly His Cys Leu Tyr Leu Asn Glu Arg Asp Cys Ser Ile Gln Arg Arg
225                 230                 235                 240

His Gln Lys Val Val Glu Glu Ala Pro Ala Pro Gly Leu Gly Ala Glu
                245                 250                 255

Leu Arg Arg Ala Met Gly Glu Ala Ala Val Arg Ala Ala Gln Ala Ile
            260                 265                 270

Gly Tyr Val Gly Ala Gly Thr Val Glu Phe Leu Leu Asp Glu Arg Gly
        275                 280                 285

Gln Phe Phe Phe Met Glu Met Asn Thr Arg Leu Gln Val Glu His Pro
    290                 295                 300

Val Thr Glu Ala Ile Thr Gly Leu Asp Leu Val Ala Trp Gln Ile Arg
305                 310                 315                 320

Val Ala Arg Gly Glu Ala Leu Pro Leu Thr Gln Glu Gln Val Pro Leu
                325                 330                 335

Asn Gly His Ala Ile Glu Val Arg Leu Tyr Ala Glu Asp Pro Glu Gly
            340                 345                 350

Asp Phe Leu Pro Ala Ser Gly Arg Leu Met Leu Tyr Arg Glu Ala Ala
        355                 360                 365

Ala Gly Pro Gly Arg Arg Val Asp Ser Gly Val Arg Glu Gly Asp Glu
    370                 375                 380

Val Ser Pro Phe Tyr Asp Pro Met Leu Ala Lys Leu Ile Ala Trp Gly
385                 390                 395                 400

Glu Thr Arg Glu Glu Ala Arg Gln Arg Leu Leu Ala Met Leu Ala Glu
                405                 410                 415

Thr Ser Val Gly Gly Leu Arg Thr Asn Leu Ala Phe Leu Arg Arg Ile
            420                 425                 430

Leu Gly His Pro Ala Phe Ala Ala Ala Glu Leu Asp Thr Gly Phe Ile
        435                 440                 445

Ala Arg His Gln Asp Asp Leu Leu Pro Ala Pro Gln Ala Leu Pro Glu
    450                 455                 460

His Phe Trp Gln Ala Ala Ala Glu Ala Trp Leu Gln Ser Glu Pro Gly
465                 470                 475                 480

His Arg Arg Asp Asp Pro His Ser Pro Trp Ser Arg Asn Asp Gly
                485                 490                 495

Trp Arg Ser Ala Leu Ala Arg Glu Ser Asp Leu Met Leu Arg Cys Arg
            500                 505                 510

Asp Glu Arg Arg Cys Val Arg Leu Arg His Ala Ser Pro Ser Gln Tyr
        515                 520                 525

Arg Leu Asp Gly Asp Leu Val Ser Arg Val Asp Gly Val Thr Arg
    530                 535                 540

Arg Ser Ala Ala Leu Arg Gly Arg Gln Leu Phe Leu Glu Trp Glu
545                 550                 555                 560

Gly Glu Leu Leu Ala Ile Glu Ala Val Asp Pro Ile Ala Glu Ala Glu
                565                 570                 575

Ala Ala His Ala His Gln Gly Gly Leu Ser Ala Pro Met Asn Gly Ser
            580                 585                 590

Ile Val Arg Val Leu Val Glu Pro Gly Gln Thr Val Glu Ala Gly Ala
```

```
            595                 600                 605
Thr Leu Val Val Leu Glu Ala Met Lys Met Glu His Ser Ile Arg Ala
            610                 615                 620

Pro His Ala Gly Val Val Lys Ala Leu Tyr Cys Ser Glu Gly Glu Leu
625                 630                 635                 640

Val Glu Glu Gly Thr Pro Leu Val Glu Leu Asp Glu Asn Gln Ala
                    645                 650                 655

<210> SEQ ID NO 130
<211> LENGTH: 1164
<212> TYPE: DNA
<213> ORGANISM: Escherichia coli

<400> SEQUENCE: 130
atggaacagg ttgtcattgt cgatgcaatt cgcaccccga tgggccgttc gaagggcggt     60
gcttttcgta acgtgcgtgc agaagatctc tccgctcatt taatgcgtag cctgctggcg    120
cgtaacccgg cgctggaagc ggcggccctc gacgatattt actggggttg tgtgcagcag    180
acgctggagc agggttttaa tatcgcccgt aacgcggcgc tgctggcaga agtaccacac    240
tctgtcccgg cggttaccgt taatcgcttg tgtggttcat ccatgcaggc actgcatgac    300
gcagcacgaa tgatcatgac tggcgatgcg caggcatgtc tggttggcgg cgtggagcat    360
atgggccatg tgccgatgag tcacggcgtc gattttcacc ccggcctgag ccgcaatgtc    420
gccaaagcgg cgggcatgat gggcttaacg gcagaaatgc tggcgcgtat gcacggtatc    480
agccgtgaaa tgcaggatgc ctttgccgcg cggtcacacg cccgcgcctg gccgccacg    540 cagtcggccg catttaaaaa tgaaatcatc ccgaccggtg gtcacgatgc cgacggcgtc    600
ctgaagcagt ttaattacga cgaagtgatt cgcccggaaa ccaccgtgga agccctcgcc    660
acgctgcgtc cggcgtttga tccagtaaac ggtatggtaa cggcgggcac atcttctgca    720
ctttccgatg gcgcagctgc catgctggtg atgagtgaaa gccgcgccca tgaattaggt    780
cttaagccgc gcgctcgtgt gcgttcgatg gcggtcgttg ttgtgaccc atcgattatg    840 ggttacggcc cggttccggc ctcgaaactg gcgctgaaaa agcggggct ttctgccagc    900 gatatcggcg tgtttgaaat gaacgaagcc tttgccgcgc agatcctgcc atgtattaaa    960
gatctgggac taattgagca gattgacgag aagatcaacc tcaacggtgg cgcgatcgcg   1020
ctgggtcatc cgctgggttg ttccggtgcg cgtatcagca ccacgctgct gaatctgatg   1080
gaacgcaaag acgttcagtt tggtctggcg acgatgtgta tcggtctggg tcagggtatt   1140
gcgacggtgt tgagcgggt ttaa                                           1164

<210> SEQ ID NO 131
<211> LENGTH: 387
<212> TYPE: PRT
<213> ORGANISM: Escherichia coli

<400> SEQUENCE: 131

Met Glu Gln Val Val Ile Val Asp Ala Ile Arg Thr Pro Met Gly Arg
1               5                   10                  15

Ser Lys Gly Gly Ala Phe Arg Asn Val Arg Ala Glu Asp Leu Ser Ala
            20                  25                  30

His Leu Met Arg Ser Leu Leu Ala Arg Asn Pro Ala Leu Glu Ala Ala
        35                  40                  45

Ala Leu Asp Asp Ile Tyr Trp Gly Cys Val Gln Gln Thr Leu Glu Gln
    50                  55                  60
```

```
Gly Phe Asn Ile Ala Arg Asn Ala Ala Leu Leu Ala Glu Val Pro His
 65                  70                  75                  80
Ser Val Pro Ala Val Thr Val Asn Arg Leu Cys Gly Ser Ser Met Gln
                 85                  90                  95
Ala Leu His Asp Ala Ala Arg Met Ile Met Thr Gly Asp Ala Gln Ala
            100                 105                 110
Cys Leu Val Gly Gly Val Glu His Met Gly His Val Pro Met Ser His
        115                 120                 125
Gly Val Asp Phe His Pro Gly Leu Ser Arg Asn Val Ala Lys Ala Ala
    130                 135                 140
Gly Met Met Gly Leu Thr Ala Glu Met Leu Ala Arg Met His Gly Ile
145                 150                 155                 160
Ser Arg Glu Met Gln Asp Ala Phe Ala Ala Arg Ser His Ala Arg Ala
                165                 170                 175
Trp Ala Ala Thr Gln Ser Ala Ala Phe Lys Asn Glu Ile Ile Pro Thr
            180                 185                 190
Gly Gly His Asp Ala Asp Gly Val Leu Lys Gln Phe Asn Tyr Asp Glu
        195                 200                 205
Val Ile Arg Pro Glu Thr Thr Val Glu Ala Leu Ala Thr Leu Arg Pro
    210                 215                 220
Ala Phe Asp Pro Val Asn Gly Met Val Thr Ala Gly Thr Ser Ser Ala
225                 230                 235                 240
Leu Ser Asp Gly Ala Ala Met Leu Val Met Ser Glu Ser Arg Ala
                245                 250                 255
His Glu Leu Gly Leu Lys Pro Arg Ala Arg Val Arg Ser Met Ala Val
            260                 265                 270
Val Gly Cys Asp Pro Ser Ile Met Gly Tyr Gly Pro Val Pro Ala Ser
        275                 280                 285
Lys Leu Ala Leu Lys Lys Ala Gly Leu Ser Ala Ser Asp Ile Gly Val
    290                 295                 300
Phe Glu Met Asn Glu Ala Phe Ala Ala Gln Ile Leu Pro Cys Ile Lys
305                 310                 315                 320
Asp Leu Gly Leu Ile Glu Gln Ile Asp Glu Lys Ile Asn Leu Asn Gly
                325                 330                 335
Gly Ala Ile Ala Leu Gly His Pro Leu Gly Cys Ser Gly Ala Arg Ile
            340                 345                 350
Ser Thr Thr Leu Leu Asn Leu Met Glu Arg Lys Asp Val Gln Phe Gly
        355                 360                 365
Leu Ala Thr Met Cys Ile Gly Leu Gly Gln Gly Ile Ala Thr Val Phe
    370                 375                 380
Glu Arg Val
385

<210> SEQ ID NO 132
<211> LENGTH: 2190
<212> TYPE: DNA
<213> ORGANISM: Escherichia coli

<400> SEQUENCE: 132
atgctttaca aaggcgacac cctgtacctt gactggctgg aagatggcat tgccgaactg      60
gtatttgatg ccccaggttc agttaataaa ctcgacactg cgaccgtcgc cagcctcggc     120
gaggccatcg cgtgctgga acagcaatca gatctaaaag gctgctgct gcgttcgaac       180 aaagcagcct ttatcgtcgg tgctgatatc accgaatttt gtccctgtt cctcgttcct     240
```

| | |
|---|---|
| gaagaacagt taagtcagtg gctgcacttt gccaatagcg tgtttaatcg cctggaagat | 300 |
| ctgccggtgc cgaccattgc tgccgtcaat ggctatgcgc tgggcggtgg ctgcgaatgc | 360 |
| gtgctggcga ccgattatcg tctggcgacg ccggatctgc gcatcggtct gccggaaacc | 420 |
| aaactgggca tcatgcctgg ctttggcggt tctgtacgta tgccacgtat gctgggcgct | 480 |
| gacagtgcgc tggaaatcat tgccgccggt aaagatgtcg gcgcggatca ggcgctgaaa | 540 |
| atcggtctgg tggatggcgt agtcaaagca gaaaaactgg ttgaaggcgc aaaggcggtt | 600 |
| ttacgccagg ccattaacgg cgacctcgac tggaaagcaa acgtcagcc gaagctggaa | 660 |
| ccactaaaac tgagcaagat gaagccacc atgagcttca ccatcgctaa agggatggtc | 720 |
| gcacaaacag cggggaaaca ttatccggcc cccatcaccg cagtaaaaac cattgaagct | 780 |
| gcggcccgtt ttggtcgtga agaagcctta aacctggaaa acaaaagttt tgtcccgctg | 840 |
| gcgcatacca acgaagcccg cgcactggtc ggcattttcc ttaacgatca atatgtaaaa | 900 |
| ggcaaagcga gaaactcac caaagacgtt gaaaccccga acaggccgc ggtgctgggt | 960 |
| gcaggcatta tgggcggcgg catcgcttac cagtctgcgt ggaaaggcgt gccggttgtc | 1020 |
| atgaaagata tcaacgacaa gtcgttaacc ctcggcatga ccgaagccgc gaaactgctg | 1080 |
| aacaagcagc ttgagcgcgg caagatcgat ggtctgaaac tggctggcgt gatctccaca | 1140 |
| atccacccaa cgctcgacta cgccggatt gaccgcgtgg atattgtggt agaagcggtt | 1200 |
| gttgaaaacc cgaaagtgaa aaaagccgta ctggcagaaa ccgaacaaaa agtacgccag | 1260 |
| gataccgtgc tggcgtctaa cacttcaacc attcctatca gcgaactggc caacgcgctg | 1320 |
| gaacgcccga aaaacttctg cgggatgcac ttctttaacc cggtccaccg aatgccgttg | 1380 |
| gtagaaatta ttcgcggcga gaaaagctcc gacgaaacca tcgcgaaagt tgtcgcctgg | 1440 |
| gcgagcaaga tgggcaagac gccgattgtg gttaacgact gccccggctt ctttgttaac | 1500 |
| cgcgtgctgt tcccgtattt cgccggtttc agccagctgc tgcgcgacgg cgcggatttc | 1560 |
| cgcaagatcg acaaagtgat ggaaaaacag tttggctggc cgatgggccc ggcatatctg | 1620 |
| ctggacgttg tgggcattga taccgcgcat cacgctcagg ctgtcatggc agcaggcttc | 1680 |
| ccgcagcgga tgcagaaaga ttaccgcgat gccatcgacg cgctgtttga tgccaaccgc | 1740 |
| tttggtcaga gaacggcct cggtttctgg cgttataaag aagacagcaa aggtaagccg | 1800 |
| aagaaagaag aagacgccgc cgttgaagac ctgctggcag aagtgagcca gccgaagcgc | 1860 |
| gatttcagcg aagaagagat tatcgcccgc atgatgatcc cgatggtcaa cgaagtggtg | 1920 |
| cgctgtctgg aggaaggcat tatcgccact ccggcggaag cggatatggc gctggtctac | 1980 |
| ggcctgggct tccctccgtt ccacggcggc gcgttccgct ggctggacac cctcggtagc | 2040 |
| gcaaaatacc tcgatatggc acagcaatat cagcacctcg gcccgctgta tgaagtgccg | 2100 |
| gaaggtctgc gtaataaagc gcgtcataac gaaccgtact atcctccggt tgagccagcc | 2160 |
| cgtccggttg cgacctgaa aacggcttaa | 2190 |

<210> SEQ ID NO 133
<211> LENGTH: 729
<212> TYPE: PRT
<213> ORGANISM: Escherichia coli

<400> SEQUENCE: 133

Met Leu Tyr Lys Gly Asp Thr Leu Tyr Leu Asp Trp Leu Glu Asp Gly
1               5                   10                  15

Ile Ala Glu Leu Val Phe Asp Ala Pro Gly Ser Val Asn Lys Leu Asp
            20                  25                  30

```
Thr Ala Thr Val Ala Ser Leu Gly Glu Ala Ile Gly Val Leu Glu Gln
         35                  40                  45

Gln Ser Asp Leu Lys Gly Leu Leu Arg Ser Asn Lys Ala Ala Phe
     50                  55                  60

Ile Val Gly Ala Asp Ile Thr Glu Phe Leu Ser Leu Phe Leu Val Pro
 65                  70                  75                  80

Glu Glu Gln Leu Ser Gln Trp Leu His Phe Ala Asn Ser Val Phe Asn
                     85                  90                  95

Arg Leu Glu Asp Leu Pro Val Pro Thr Ile Ala Ala Val Asn Gly Tyr
                100                 105                 110

Ala Leu Gly Gly Cys Glu Cys Val Leu Ala Thr Asp Tyr Arg Leu
             115                 120                 125

Ala Thr Pro Asp Leu Arg Ile Gly Leu Pro Glu Thr Lys Leu Gly Ile
         130                 135                 140

Met Pro Gly Phe Gly Gly Ser Val Arg Met Pro Arg Met Leu Gly Ala
145                 150                 155                 160

Asp Ser Ala Leu Glu Ile Ile Ala Ala Gly Lys Asp Val Gly Ala Asp
                165                 170                 175

Gln Ala Leu Lys Ile Gly Leu Val Asp Gly Val Val Lys Ala Glu Lys
                180                 185                 190

Leu Val Glu Gly Ala Lys Ala Val Leu Arg Gln Ala Ile Asn Gly Asp
                195                 200                 205

Leu Asp Trp Lys Ala Lys Arg Gln Pro Lys Leu Glu Pro Leu Lys Leu
        210                 215                 220

Ser Lys Ile Glu Ala Thr Met Ser Phe Thr Ile Ala Lys Gly Met Val
225                 230                 235                 240

Ala Gln Thr Ala Gly Lys His Tyr Pro Ala Pro Ile Thr Ala Val Lys
                245                 250                 255

Thr Ile Glu Ala Ala Ala Arg Phe Gly Arg Glu Glu Ala Leu Asn Leu
                260                 265                 270

Glu Asn Lys Ser Phe Val Pro Leu Ala His Thr Asn Glu Ala Arg Ala
        275                 280                 285

Leu Val Gly Ile Phe Leu Asn Asp Gln Tyr Val Lys Gly Lys Ala Lys
        290                 295                 300

Lys Leu Thr Lys Asp Val Glu Thr Pro Lys Gln Ala Ala Val Leu Gly
305                 310                 315                 320

Ala Gly Ile Met Gly Gly Gly Ile Ala Tyr Gln Ser Ala Trp Lys Gly
                325                 330                 335

Val Pro Val Val Met Lys Asp Ile Asn Asp Lys Ser Leu Thr Leu Gly
                340                 345                 350

Met Thr Glu Ala Ala Lys Leu Leu Asn Lys Gln Leu Glu Arg Gly Lys
        355                 360                 365

Ile Asp Gly Leu Lys Leu Ala Gly Val Ile Ser Thr Ile His Pro Thr
        370                 375                 380

Leu Asp Tyr Ala Gly Phe Asp Arg Val Asp Ile Val Val Glu Ala Val
385                 390                 395                 400

Val Glu Asn Pro Lys Val Lys Lys Ala Val Leu Ala Glu Thr Glu Gln
                405                 410                 415

Lys Val Arg Gln Asp Thr Val Leu Ala Ser Asn Thr Ser Thr Ile Pro
                420                 425                 430

Ile Ser Glu Leu Ala Asn Ala Leu Glu Arg Pro Glu Asn Phe Cys Gly
        435                 440                 445
```

```
Met His Phe Phe Asn Pro Val His Arg Met Pro Leu Val Glu Ile Ile
            450                 455                 460

Arg Gly Glu Lys Ser Ser Asp Glu Thr Ile Ala Lys Val Val Ala Trp
465                 470                 475                 480

Ala Ser Lys Met Gly Lys Thr Pro Ile Val Asn Asp Cys Pro Gly
                485                 490                 495

Phe Phe Val Asn Arg Val Leu Phe Pro Tyr Phe Ala Gly Phe Ser Gln
            500                 505                 510

Leu Leu Arg Asp Gly Ala Asp Phe Arg Lys Ile Asp Lys Val Met Glu
            515                 520                 525

Lys Gln Phe Gly Trp Pro Met Gly Pro Ala Tyr Leu Leu Asp Val Val
            530                 535                 540

Gly Ile Asp Thr Ala His His Ala Gln Ala Val Met Ala Ala Gly Phe
545                 550                 555                 560

Pro Gln Arg Met Gln Lys Asp Tyr Arg Asp Ala Ile Asp Ala Leu Phe
                565                 570                 575

Asp Ala Asn Arg Phe Gly Gln Lys Asn Gly Leu Gly Phe Trp Arg Tyr
            580                 585                 590

Lys Glu Asp Ser Lys Gly Lys Pro Lys Lys Glu Glu Asp Ala Ala Val
            595                 600                 605

Glu Asp Leu Leu Ala Glu Val Ser Gln Pro Lys Arg Asp Phe Ser Glu
610                 615                 620

Glu Glu Ile Ile Ala Arg Met Met Ile Pro Met Val Asn Glu Val Val
625                 630                 635                 640

Arg Cys Leu Glu Glu Gly Ile Ile Ala Thr Pro Ala Glu Ala Asp Met
                645                 650                 655

Ala Leu Val Tyr Gly Leu Gly Phe Pro Pro Phe His Gly Gly Ala Phe
            660                 665                 670

Arg Trp Leu Asp Thr Leu Gly Ser Ala Lys Tyr Leu Asp Met Ala Gln
            675                 680                 685

Gln Tyr Gln His Leu Gly Pro Leu Tyr Glu Val Pro Glu Gly Leu Arg
            690                 695                 700

Asn Lys Ala Arg His Asn Glu Pro Tyr Tyr Pro Pro Val Glu Pro Ala
705                 710                 715                 720

Arg Pro Val Gly Asp Leu Lys Thr Ala
                725

<210> SEQ ID NO 134
<211> LENGTH: 861
<212> TYPE: DNA
<213> ORGANISM: Escherichia coli

<400> SEQUENCE: 134
atgagtcagg cgctaaaaaa tttactgaca ttgttaaatc tggaaaaaat tgaggaagga    60
ctctttcgcg ccagagtga agatttaggt ttacgccagg tgtttggcgg ccaggtcgtg   120
ggtcaggcct tgtatgctgc aaaagagacc gtccctgaag agcggctggt acattcgttt   180
cacagctact tcttcgccc tggcgatagt aagaagccga ttatttatga tgtcgaaacg   240
ctgcgtgacg gtaacagctt cagcgcccgc cgggttgctg ctattcaaaa cggcaaaccg   300
attttttata tgactgcctc tttccaggca ccagaagcgg tttcgaaca tcaaaaaaca   360 atgccgtccg cgccagcgcc tgatggcctc ccttcggaaa cgcaaatcgc ccaatcgctg   420
gcgcacctgc tgccgccagt gctgaaagat aaattcatct cgatcgtcc gctgaaagtc   480 cgtccggtgg agtttcataa cccactgaaa ggtcacgtcg cagaaccaca tcgtcaggtg   540
```

```
tggatccgcg caaatggtag cgtgccggat gacctgcgcg ttcatcagta tctgctcggt    600
tacgcttctg atcttaactt cctgccggta gctctacagc cgcacggcat cggttttctc    660
gaaccgggga ttcagattgc caccattgac cattccatgt ggttccatcg cccgtttaat    720
ttgaatgaat ggctgctgta tagcgtggag agcacctcgg cgtccagcgc acgtggcttt    780
gtgcgcggtg agttttatac ccaagacggc gtactggttg cctcgaccgt tcaggaaggg    840
gtgatgcgta atcacaatta a                                              861
```

<210> SEQ ID NO 135
<211> LENGTH: 286
<212> TYPE: PRT
<213> ORGANISM: Escherichia coli

<400> SEQUENCE: 135

```
Met Ser Gln Ala Leu Lys Asn Leu Leu Thr Leu Leu Asn Leu Glu Lys
1               5                   10                  15

Ile Glu Glu Gly Leu Phe Arg Gly Gln Ser Glu Asp Leu Gly Leu Arg
            20                  25                  30

Gln Val Phe Gly Gly Gln Val Val Gly Gln Ala Leu Tyr Ala Ala Lys
        35                  40                  45

Glu Thr Val Pro Glu Glu Arg Leu Val His Ser Phe His Ser Tyr Phe
    50                  55                  60

Leu Arg Pro Gly Asp Ser Lys Lys Pro Ile Ile Tyr Asp Val Glu Thr
65                  70                  75                  80

Leu Arg Asp Gly Asn Ser Phe Ser Ala Arg Arg Val Ala Ala Ile Gln
                85                  90                  95

Asn Gly Lys Pro Ile Phe Tyr Met Thr Ala Ser Phe Gln Ala Pro Glu
            100                 105                 110

Ala Gly Phe Glu His Gln Lys Thr Met Pro Ser Ala Pro Ala Pro Asp
        115                 120                 125

Gly Leu Pro Ser Glu Thr Gln Ile Ala Gln Ser Leu Ala His Leu Leu
    130                 135                 140

Pro Pro Val Leu Lys Asp Lys Phe Ile Cys Asp Arg Pro Leu Glu Val
145                 150                 155                 160

Arg Pro Val Glu Phe His Asn Pro Leu Lys Gly His Val Ala Glu Pro
                165                 170                 175

His Arg Gln Val Trp Ile Arg Ala Asn Gly Ser Val Pro Asp Asp Leu
            180                 185                 190

Arg Val His Gln Tyr Leu Leu Gly Tyr Ala Ser Asp Leu Asn Phe Leu
        195                 200                 205

Pro Val Ala Leu Gln Pro His Gly Ile Gly Phe Leu Glu Pro Gly Ile
    210                 215                 220

Gln Ile Ala Thr Ile Asp His Ser Met Trp Phe His Arg Pro Phe Asn
225                 230                 235                 240

Leu Asn Glu Trp Leu Leu Tyr Ser Val Glu Ser Thr Ser Ala Ser Ser
                245                 250                 255

Ala Arg Gly Phe Val Arg Gly Glu Phe Tyr Thr Gln Asp Gly Val Leu
            260                 265                 270

Val Ala Ser Thr Val Gln Glu Gly Val Met Arg Asn His Asn
        275                 280                 285
```

<210> SEQ ID NO 136
<211> LENGTH: 1056
<212> TYPE: DNA

<213> ORGANISM: Clostridium beijerinckii

<400> SEQUENCE: 136
atgaaaggtt ttgcaatgct aggtattaat aagttaggat ggatcgaaaa agaaaggcca 60
gttgcgggtt catatgatgc tattgtacgc ccattagcag tatctccgtg tacatcagat 120
atacatactg tttttgaggg agctcttgga gataggaaga atatgatttt agggcatgaa 180
gctgtaggtg aagttgttga agtaggaagt gaagtgaagg attttaaacc tggtgacaga 240
gttatagttc cttgtacaac tccagattgg agatctttgg aagttcaagc tggttttcaa 300
cagcactcaa acggtatgct cgcaggatgg aaattttcaa atttcaagga tggagttttt 360
ggtgaatatt ttcatgtaaa tgatgcggat atgaatcttg cgattctacc taaagacatg 420
ccattagaaa atgctgttat gataacagat atgatgacta ctggatttca tggagcagaa 480
cttgcagata ttcaaatggg ttcaagtgtt gtggtaattg gcattggagc tgttggctta 540
atgggaatag caggtgctaa attacgtgga gcaggtagaa taattggagt ggggagcagg 600
ccgatttgtg ttgaggctgc aaaattttat ggagcaacag atattctaaa ttataaaaat 660
ggtcatatag ttgatcaagt tatgaaatta acgaatggaa aaggcgttga ccgcgtaatt 720
atggcaggcg gtggttctga aacattatcc caagcagtat ctatggttaa accaggagga 780
ataatttcta atataaatta tcatggaagt ggagatgctt tactaatacc acgtgtagaa 840
tggggatgtg gaatggctca caagactata aaaggaggtc tttgtcctgg gggacgtttg 900
agagcagaaa tgttaagaga tatggtagta tataatcgtg ttgatctaag taaattagtt 960
acacatgtat atcatggatt tgatcacata gaagaagcac tgttattaat gaaagacaag 1020
ccaaaagact taattaaagc agtagttata ttataa 1056

<210> SEQ ID NO 137
<211> LENGTH: 1056
<212> TYPE: DNA
<213> ORGANISM: Clostridium beijerinckii

<400> SEQUENCE: 137
atgaaagggt ttgccatgtt aggtatcaat aaactgggct ggattgaaaa agagcgcccg 60
gtggcgggtt catacgatgc aattgttcgt ccgctggccg tcagtccgtg caccagcgac 120
atccatacag tctttgaagg tgccctgggt gatcggaaaa acatgattct gggccatgaa 180
gccgtaggcg aagtagtgga agtgggcagc gaggtaaagg atttcaaacc gggtgatcgc 240
gtaattgttc cttgcacgac cccagattgg cgctcactgg aagttcaggc tggttttcag 300
cagcatagta acggtatgtt agcaggctgg aagtttagca attttaaaga cggggtgttc 360
ggggagtatt ttcatgtcaa cgatgcggac atgaatctgg ctattttacc taaagatatg 420
ccgctggaga acgcagtgat gattaccgac atgatgacga caggctttca cggtgcagaa 480
ctggctgaca tccaaatggg ctccagtgtg gtggttatcg gtattggtgc ggtcgggctg 540
atgggtatcg cgggcgcgaa attacggggc gctggtcgca tcatcggtgt cggcagccgt 600
ccaatttgcg ttgaagcagc taaattctat ggtgccacgg acattctgaa ctataaaaat 660
ggtcacatcg tcgatcaggt gatgaaactg accaatggca aaggtgtgga ccgcgtgatc 720
atggcgggcg gcggctcaga gactttatct caagcggtgt ctatggttaa acctgggggc 780
atcatttcta atattaacta tcatggctcc ggcgacgcat tactgatccc gcgtgttgaa 840
tggggctgtg ggatggccca caaaaccatt aaagggggt tatgtccggg tggtcgcctg 900
cgtgccgaaa tgctgcgtga catggtggtt tacaaccgtg tggatctgtc caaactggta 960

```
actcacgtat accacggttt cgatcacatt gaagaggcgc tgctgctgat gaaggataag    1020
ccaaaggatc tgattaaggc ggttgttatc ctgtaa                              1056
```

<210> SEQ ID NO 138
<211> LENGTH: 351
<212> TYPE: PRT
<213> ORGANISM: Clostridium beijerinckii

<400> SEQUENCE: 138

| | | | | | | | | | | | | | | |
|---|---|---|---|---|---|---|---|---|---|---|---|---|---|---|
| Met | Lys | Gly | Phe | Ala | Met | Leu | Gly | Ile | Asn | Lys | Leu | Gly | Trp | Ile | Glu |
| 1 | | | | 5 | | | | | 10 | | | | | 15 | |
| Lys | Glu | Arg | Pro | Val | Ala | Gly | Ser | Tyr | Asp | Ala | Ile | Val | Arg | Pro | Leu |
| | | | 20 | | | | | 25 | | | | | 30 | | |
| Ala | Val | Ser | Pro | Cys | Thr | Ser | Asp | Ile | His | Thr | Val | Phe | Glu | Gly | Ala |
| | | 35 | | | | | 40 | | | | | 45 | | | |
| Leu | Gly | Asp | Arg | Lys | Asn | Met | Ile | Leu | Gly | His | Glu | Ala | Val | Gly | Glu |
| | 50 | | | | | 55 | | | | | 60 | | | | |
| Val | Val | Glu | Val | Gly | Ser | Glu | Val | Lys | Asp | Phe | Lys | Pro | Gly | Asp | Arg |
| 65 | | | | | 70 | | | | | 75 | | | | | 80 |
| Val | Ile | Val | Pro | Cys | Thr | Thr | Pro | Asp | Trp | Arg | Ser | Leu | Glu | Val | Gln |
| | | | | 85 | | | | | 90 | | | | | 95 | |
| Ala | Gly | Phe | Gln | Gln | His | Ser | Asn | Gly | Met | Leu | Ala | Gly | Trp | Lys | Phe |
| | | | 100 | | | | | 105 | | | | | 110 | | |
| Ser | Asn | Phe | Lys | Asp | Gly | Val | Phe | Gly | Glu | Tyr | Phe | His | Val | Asn | Asp |
| | | 115 | | | | | 120 | | | | | 125 | | | |
| Ala | Asp | Met | Asn | Leu | Ala | Ile | Leu | Pro | Lys | Asp | Met | Pro | Leu | Glu | Asn |
| | 130 | | | | | 135 | | | | | 140 | | | | |
| Ala | Val | Met | Ile | Thr | Asp | Met | Met | Thr | Thr | Gly | Phe | His | Gly | Ala | Glu |
| 145 | | | | | 150 | | | | | 155 | | | | | 160 |
| Leu | Ala | Asp | Ile | Gln | Met | Gly | Ser | Ser | Val | Val | Ile | Gly | Ile | Gly |
| | | | | 165 | | | | | 170 | | | | | 175 |
| Ala | Val | Gly | Leu | Met | Gly | Ile | Ala | Gly | Ala | Lys | Leu | Arg | Gly | Ala | Gly |
| | | | 180 | | | | | 185 | | | | | 190 | | |
| Arg | Ile | Ile | Gly | Val | Gly | Ser | Arg | Pro | Ile | Cys | Val | Glu | Ala | Ala | Lys |
| | | 195 | | | | | 200 | | | | | 205 | | | |
| Phe | Tyr | Gly | Ala | Thr | Asp | Ile | Leu | Asn | Tyr | Lys | Asn | Gly | His | Ile | Val |
| | 210 | | | | | 215 | | | | | 220 | | | | |
| Asp | Gln | Val | Met | Lys | Leu | Thr | Asn | Gly | Lys | Gly | Val | Asp | Arg | Val | Ile |
| 225 | | | | | 230 | | | | | 235 | | | | | 240 |
| Met | Ala | Gly | Gly | Gly | Ser | Glu | Thr | Leu | Ser | Gln | Ala | Val | Ser | Met | Val |
| | | | | 245 | | | | | 250 | | | | | 255 | |
| Lys | Pro | Gly | Gly | Ile | Ile | Ser | Asn | Ile | Asn | Tyr | His | Gly | Ser | Gly | Asp |
| | | | 260 | | | | | 265 | | | | | 270 | | |
| Ala | Leu | Leu | Ile | Pro | Arg | Val | Glu | Trp | Gly | Cys | Gly | Met | Ala | His | Lys |
| | | 275 | | | | | 280 | | | | | 285 | | | |
| Thr | Ile | Lys | Gly | Gly | Leu | Cys | Pro | Gly | Gly | Arg | Leu | Arg | Ala | Glu | Met |
| | 290 | | | | | 295 | | | | | 300 | | | | |
| Leu | Arg | Asp | Met | Val | Val | Tyr | Asn | Arg | Val | Asp | Leu | Ser | Lys | Leu | Val |
| 305 | | | | | 310 | | | | | 315 | | | | | 320 |
| Thr | His | Val | Tyr | His | Gly | Phe | Asp | His | Ile | Glu | Glu | Ala | Leu | Leu | Leu |
| | | | | 325 | | | | | 330 | | | | | 335 | |
| Met | Lys | Asp | Lys | Pro | Lys | Asp | Leu | Ile | Lys | Ala | Val | Val | Ile | Leu |
| | | | 340 | | | | | 345 | | | | | 350 | |

<210> SEQ ID NO 139
<211> LENGTH: 2580
<212> TYPE: DNA
<213> ORGANISM: Unknown
<220> FEATURE:
<223> OTHER INFORMATION: Clostridium carboxidivorans Sequence

<400> SEQUENCE: 139
atgaaggtaa ctaatgttga agaactgatg aaaaaaatgc aggaagtgca aaatgctcaa 60
aaaaaatttg ggagttttac tcaggaacaa gtagatgaaa ttttcaggca agcagcacta 120
gcagctaaca gtgccagaat agatctagct aaaatggcag tggaagaaac taaaatggga 180
attgtagagg ataaggttat aaaaaatcat tttgttgcag aatacatata taataagtat 240
aaaaatgaaa aaacttgtgg gattttggaa gaagatgaag gctttggaat ggttaaaatt 300
gcagaacctg taggtgtgat tgcagcagta attccaacaa caaatccaac atctacagca 360
atatttaaag cattattagc tttgaaaaca agaaatggta taattttttc accacatcca 420
agagcaaaaa agtgtactat tgcagcagct aagttagttc ttgatgctgc agttaaagca 480
ggtgctccta aaggaattat aggttggata gatgaacctt ctattgaact ttcacagata 540
gtaatgaaag aagctgatat aatccttgca acaggtggtc caggtatggt taaagcagct 600
tattcttcag gtaaacctgc tataggggtt ggtcctggta acacacctgc tttaattgat 660
gaaagtgctg atattaaaat ggcagtaaat tcaatacttc tttccaaaac ttttgataat 720
ggtatgattt gtgcttcaga gcagtcggta gtagttgtag attcaatata tgaagaagtt 780
aagaaagaat ttgctcatag aggagcttat attttaagta aggatgaaac aactaaagtt 840
ggaaaaatac tcttagttaa tggtacatta aatgctggta tcgttggtca gagtgcttat 900
aaaatagcag aaatggcagg agttaaagtt ccagaagatg ctaaagttct tataggagaa 960
gtaaaatcag tggagcattc agaagagcca ttttcacatg aaaagttatc tccagtttta 1020
gctatgtata gagctaaaaa ttttgatgaa gctcttttaa aagctggaag attagttgaa 1080
ctcggtggaa tgggtcatac atctgtatta tatgtaaatg caataactga aaaagtaaaa 1140
gtagaaaaat ttagagaaac tatgaagact ggtagaacat taataaatat gccttcagca 1200
caaggtgcta taggagacat atataacttt aaactagctc cttcattaac attaggttgt 1260
ggttcatggg gaggaaactc cgtatcagaa aatgttggac ctaaacactt attaaatata 1320
aaaagtgttg ctgagaggag agaaaatatg ctttggttta gagttcctga aaaggtttat 1380
tttaaatatg gtagtcttgg agttgcatta aaagaattag atattttgga taagaaaaaa 1440
gtatttatag taacagataa agttctttat caattaggtt atatagatag agttacaaag 1500
attcttgaag aattgaaaat ttcatataaa atatttacag atgtagaacc agatccaacc 1560
ctagctacag ctaaaaaagg tgcagaagaa ttgttatcat ttaatccaga tactattata 1620
gcagttggtg gtggttcagc aatggatgct gctaagatta tgtgggtaat gtatgaacat 1680
ccggaagtaa gatttgaaga tttagctatg agatttatgg atataagaaa gagagtatat 1740
acttttccta agatgggtga aaaagcaatg atgatttctg ttgcaacatc agcaggaaca 1800
ggatcagaag taacaccttt tgcagtaatt actgatgaaa aaacaggagc taaatatcca 1860
ttagctgatt atgaattaac tccaaatatg gctataattg atgctgaact tatgatgggt 1920
atgccaaaag gattaacagc agcttcagga atagatgcac taactcatgc aatagaagct 1980
tatgtatcaa taatggcttc agaatatact aatggattag cgttagaagc aataagattg 2040
atatttaagt atttaccaat agcttacagt gaaggaacaa caagtataaa ggcaagagaa 2100

```
aaaatggcgc atgcttcaac aatagctggt atggcatttg ctaatgcatt tttaggagta    2160
tgtcattcaa tggcacataa attaggatca actcatcacg taccacatgg cattgccaat    2220
gcactactta taaatgaagt tataaaattt aatgcagtag aaaatccaag aaaacaagct    2280
gcatttccac aatataagta tccaaatata aaaagagag atgctagaat agcagattac     2340
cttaacttag gtgggtcaac agacgatgaa aaagtacaat tattaataaa tgctatagat    2400
gaattaaaag ctaagataaa tattccagaa agtattaaag aagcaggagt aacagaagaa    2460 aaatttatg ctactttaga taaaatgtca gaattagctt ttgatgatca atgtacaggt     2520 gcaaaccta gatatccatt aataagtgaa ataaaacaaa tgtatgtaaa tgcattttaa     2580
```

<210> SEQ ID NO 140
<211> LENGTH: 859
<212> TYPE: PRT
<213> ORGANISM: Unknown
<220> FEATURE:
<223> OTHER INFORMATION: Clostridium carboxidivorans Sequence

<400> SEQUENCE: 140

```
Met Lys Val Thr Asn Val Glu Glu Leu Met Lys Met Gln Glu Val
1               5                   10                  15

Gln Asn Ala Gln Lys Lys Phe Gly Ser Phe Thr Gln Glu Gln Val Asp
            20                  25                  30

Glu Ile Phe Arg Gln Ala Ala Leu Ala Ala Asn Ser Ala Arg Ile Asp
        35                  40                  45

Leu Ala Lys Met Ala Val Glu Glu Thr Lys Met Gly Ile Val Glu Asp
    50                  55                  60

Lys Val Ile Lys Asn His Phe Val Ala Glu Tyr Ile Tyr Asn Lys Tyr
65              70                  75                  80

Lys Asn Glu Lys Thr Cys Gly Ile Leu Glu Glu Asp Glu Gly Phe Gly
                85                  90                  95

Met Val Lys Ile Ala Glu Pro Val Gly Val Ile Ala Ala Val Ile Pro
            100                 105                 110

Thr Thr Asn Pro Thr Ser Thr Ala Ile Phe Lys Ala Leu Leu Ala Leu
        115                 120                 125

Lys Thr Arg Asn Gly Ile Ile Phe Ser Pro His Pro Arg Ala Lys Lys
    130                 135                 140

Cys Thr Ile Ala Ala Ala Lys Leu Val Leu Asp Ala Ala Val Lys Ala
145             150                 155                 160

Gly Ala Pro Lys Gly Ile Ile Gly Trp Ile Asp Glu Pro Ser Ile Glu
                165                 170                 175

Leu Ser Gln Ile Val Met Lys Glu Ala Asp Ile Ile Leu Ala Thr Gly
            180                 185                 190

Gly Pro Gly Met Val Lys Ala Ala Tyr Ser Ser Gly Lys Pro Ala Ile
        195                 200                 205

Gly Val Gly Pro Gly Asn Thr Pro Ala Leu Ile Asp Glu Ser Ala Asp
    210                 215                 220

Ile Lys Met Ala Val Asn Ser Ile Leu Leu Ser Lys Thr Phe Asp Asn
225             230                 235                 240

Gly Met Ile Cys Ala Ser Glu Gln Ser Val Val Val Asp Ser Ile
                245                 250                 255

Tyr Glu Glu Val Lys Lys Glu Phe Ala His Arg Gly Ala Tyr Ile Leu
            260                 265                 270

Ser Lys Asp Glu Thr Thr Lys Val Gly Lys Ile Leu Leu Val Asn Gly
```

```
              275                 280                 285
Thr Leu Asn Ala Gly Ile Val Gly Gln Ser Ala Tyr Lys Ile Ala Glu
290                 295                 300

Met Ala Gly Val Lys Val Pro Glu Asp Ala Lys Val Leu Ile Gly Glu
305                 310                 315                 320

Val Lys Ser Val Glu His Ser Glu Glu Pro Phe Ser His Glu Lys Leu
                325                 330                 335

Ser Pro Val Leu Ala Met Tyr Arg Ala Lys Asn Phe Asp Glu Ala Leu
            340                 345                 350

Leu Lys Ala Gly Arg Leu Val Glu Leu Gly Gly Met Gly His Thr Ser
        355                 360                 365

Val Leu Tyr Val Asn Ala Ile Thr Glu Lys Val Lys Val Glu Lys Phe
370                 375                 380

Arg Glu Thr Met Lys Thr Gly Arg Thr Leu Ile Asn Met Pro Ser Ala
385                 390                 395                 400

Gln Gly Ala Ile Gly Asp Ile Tyr Asn Phe Lys Leu Ala Pro Ser Leu
                405                 410                 415

Thr Leu Gly Cys Gly Ser Trp Gly Gly Asn Ser Val Ser Glu Asn Val
            420                 425                 430

Gly Pro Lys His Leu Leu Asn Ile Lys Ser Val Ala Glu Arg Arg Glu
        435                 440                 445

Asn Met Leu Trp Phe Arg Val Pro Glu Lys Val Tyr Phe Lys Tyr Gly
450                 455                 460

Ser Leu Gly Val Ala Leu Lys Glu Leu Asp Ile Leu Asp Lys Lys Lys
465                 470                 475                 480

Val Phe Ile Val Thr Asp Lys Val Leu Tyr Gln Leu Gly Tyr Ile Asp
                485                 490                 495

Arg Val Thr Lys Ile Leu Glu Glu Leu Lys Ile Ser Tyr Lys Ile Phe
            500                 505                 510

Thr Asp Val Glu Pro Asp Pro Thr Leu Ala Thr Ala Lys Lys Gly Ala
        515                 520                 525

Glu Glu Leu Leu Ser Phe Asn Pro Asp Thr Ile Ile Ala Val Gly Gly
530                 535                 540

Gly Ser Ala Met Asp Ala Ala Lys Ile Met Trp Val Met Tyr Glu His
545                 550                 555                 560

Pro Glu Val Arg Phe Glu Asp Leu Ala Met Arg Phe Met Asp Ile Arg
                565                 570                 575

Lys Arg Val Tyr Thr Phe Pro Lys Met Gly Glu Lys Ala Met Met Ile
            580                 585                 590

Ser Val Ala Thr Ser Ala Gly Thr Gly Ser Glu Val Thr Pro Phe Ala
        595                 600                 605

Val Ile Thr Asp Glu Lys Thr Gly Ala Lys Tyr Pro Leu Ala Asp Tyr
610                 615                 620

Glu Leu Thr Pro Asn Met Ala Ile Ile Asp Ala Glu Leu Met Met Gly
625                 630                 635                 640

Met Pro Lys Gly Leu Thr Ala Ala Ser Gly Ile Asp Ala Leu Thr His
                645                 650                 655

Ala Ile Glu Ala Tyr Val Ser Ile Met Ala Ser Glu Tyr Thr Asn Gly
            660                 665                 670

Leu Ala Leu Glu Ala Ile Arg Leu Ile Phe Lys Tyr Leu Pro Ile Ala
        675                 680                 685

Tyr Ser Glu Gly Thr Thr Ser Ile Lys Ala Arg Glu Lys Met Ala His
690                 695                 700
```

```
Ala Ser Thr Ile Ala Gly Met Ala Phe Ala Asn Ala Phe Leu Gly Val
705                 710                 715                 720

Cys His Ser Met Ala His Lys Leu Gly Ser Thr His His Val Pro His
            725                 730                 735

Gly Ile Ala Asn Ala Leu Leu Ile Asn Glu Val Ile Lys Phe Asn Ala
        740                 745                 750

Val Glu Asn Pro Arg Lys Gln Ala Ala Phe Pro Gln Tyr Lys Tyr Pro
    755                 760                 765

Asn Ile Lys Lys Arg Tyr Ala Arg Ile Ala Asp Tyr Leu Asn Leu Gly
770                 775                 780

Gly Ser Thr Asp Asp Glu Lys Val Gln Leu Leu Ile Asn Ala Ile Asp
785                 790                 795                 800

Glu Leu Lys Ala Lys Ile Asn Ile Pro Glu Ser Ile Lys Glu Ala Gly
                805                 810                 815

Val Thr Glu Glu Lys Phe Tyr Ala Thr Leu Asp Lys Met Ser Glu Leu
            820                 825                 830

Ala Phe Asp Asp Gln Cys Thr Gly Ala Asn Pro Arg Tyr Pro Leu Ile
        835                 840                 845

Ser Glu Ile Lys Gln Met Tyr Val Asn Ala Phe
    850                 855
```

<210> SEQ ID NO 141
<211> LENGTH: 1401
<212> TYPE: DNA
<213> ORGANISM: Escherichia coli

<400> SEQUENCE: 141

```
atgccacatt cctacgatta cgatgccata gtaataggtt ccggccccgg cggcgaaggc      60
gctgcaatgg gcctggttaa gcaaggtgcg cgcgtcgcag ttatcgagcg ttatcaaaat     120
gttggcggcg ttgcaccca  ctggggcacc atcccgtcga aagctctccg tcacgccgtc     180
agccgcatta tagaattcaa tcaaaaccca ctttacagcg accattcccg actgctccgc     240
tcttcttttg ccgatatcct taaccatgcc gataacgtga ttaatcaaca acgcgcatg      300
cgtcagggat tttacgaacg taatcactgt gaaatattgc agggaaacgc tcgctttgtt     360
gacgagcata cgttggcgct ggattgcccg gacggcagcg ttgaaacact aaccgctgaa     420
aaatttgtta ttgcctgcgg ctctcgtcca tatcatccaa cagatgttga tttcacccat     480
ccacgcattt acgacagcga ctcaattctc agcatgcacc acgaaccgcg ccatgtactt     540
atctatggtc tggagtgat  cggctgtgaa atgcgtcga  tcttccgcgg tatggatgta     600
aaagtggatc tgatcaacac ccgcgatcgc ctgctggcat ttctcgatca agagatgtca     660
gattctctct cctatcactt ctggaacagt ggcgtagtga ttcgtcacaa cgaagagtac     720
gagaagatcg aaggctgtga cgatggtgtg atcatgcatc tgaagtcggg taaaaaactg     780
aaagctgact gcctgctcta tgccaacggt cgcaccggta ataccgattc gctggcgtta     840
cagaacattg gctagaaac  tgacagccgc ggacagctga aggtcaacag catgtatcag     900
accgcacagc cacacgttta cgcggtgggc gacgtgattg ttatccgag  cctggcgtcg     960
gcggcctatg accaggggcg cattgccgcg caggcgctgg taaaaggcga agccaccgca    1020
catctgattg aagatatccc taccggtatt tacaccatcc cggaaatcag ctctgtgggc    1080
aaaaccgaac agcagctgac cgcaatgaaa gtgccatatg aagtgggccg cgcccagttt    1140
aaacatctgg cacgcgcaca aatcgtcggc atgaacgtgg gcacgctgaa aattttgttc    1200
```

```
catcgggaaa caaaagagat tctgggtatt cactgctttg gcgagcgcgc tgccgaaatt    1260
attcatatcg gtcaggcgat tatggaacag aaaggtggcg gcaacactat tgagtacttc    1320
gtcaacacca cctttaacta cccgacgatg gcggaagcct atcgggtagc tgcgttaaac    1380
ggtttaaacc gcctgtttta a                                              1401
```

<210> SEQ ID NO 142
<211> LENGTH: 466
<212> TYPE: PRT
<213> ORGANISM: Escherichia coli

<400> SEQUENCE: 142

```
Met Pro His Ser Tyr Asp Tyr Asp Ala Ile Val Ile Gly Ser Gly Pro
1               5                   10                  15

Gly Gly Glu Gly Ala Ala Met Gly Leu Val Lys Gln Gly Ala Arg Val
            20                  25                  30

Ala Val Ile Glu Arg Tyr Gln Asn Val Gly Gly Gly Cys Thr His Trp
        35                  40                  45

Gly Thr Ile Pro Ser Lys Ala Leu Arg His Ala Val Ser Arg Ile Ile
    50                  55                  60

Glu Phe Asn Gln Asn Pro Leu Tyr Ser Asp His Ser Arg Leu Leu Arg
65                  70                  75                  80

Ser Ser Phe Ala Asp Ile Leu Asn His Ala Asp Asn Val Ile Asn Gln
                85                  90                  95

Gln Thr Arg Met Arg Gln Gly Phe Tyr Glu Arg Asn His Cys Glu Ile
            100                 105                 110

Leu Gln Gly Asn Ala Arg Phe Val Asp Glu His Thr Leu Ala Leu Asp
        115                 120                 125

Cys Pro Asp Gly Ser Val Glu Thr Leu Thr Ala Glu Lys Phe Val Ile
    130                 135                 140

Ala Cys Gly Ser Arg Pro Tyr His Pro Thr Asp Val Asp Phe Thr His
145                 150                 155                 160

Pro Arg Ile Tyr Asp Ser Asp Ser Ile Leu Ser Met His His Glu Pro
                165                 170                 175

Arg His Val Leu Ile Tyr Gly Ala Gly Val Ile Gly Cys Glu Tyr Ala
            180                 185                 190

Ser Ile Phe Arg Gly Met Asp Val Lys Val Asp Leu Ile Asn Thr Arg
        195                 200                 205

Asp Arg Leu Leu Ala Phe Leu Asp Gln Glu Met Ser Asp Ser Leu Ser
    210                 215                 220

Tyr His Phe Trp Asn Ser Gly Val Val Ile Arg His Asn Glu Glu Tyr
225                 230                 235                 240

Glu Lys Ile Glu Gly Cys Asp Asp Gly Val Ile Met His Leu Lys Ser
                245                 250                 255

Gly Lys Lys Leu Lys Ala Asp Cys Leu Leu Tyr Ala Asn Gly Arg Thr
            260                 265                 270

Gly Asn Thr Asp Ser Leu Ala Leu Gln Asn Ile Gly Leu Glu Thr Asp
        275                 280                 285

Ser Arg Gly Gln Leu Lys Val Asn Ser Met Tyr Gln Thr Ala Gln Pro
    290                 295                 300

His Val Tyr Ala Val Gly Asp Val Ile Gly Tyr Pro Ser Leu Ala Ser
305                 310                 315                 320

Ala Ala Tyr Asp Gln Gly Arg Ile Ala Ala Gln Ala Leu Val Lys Gly
                325                 330                 335
```

```
Glu Ala Thr Ala His Leu Ile Glu Asp Ile Pro Thr Gly Ile Tyr Thr
                340                 345                 350

Ile Pro Glu Ile Ser Ser Val Gly Lys Thr Glu Gln Gln Leu Thr Ala
            355                 360                 365

Met Lys Val Pro Tyr Glu Val Gly Arg Ala Gln Phe Lys His Leu Ala
    370                 375                 380

Arg Ala Gln Ile Val Gly Met Asn Val Gly Thr Leu Lys Ile Leu Phe
385                 390                 395                 400

His Arg Glu Thr Lys Glu Ile Leu Gly Ile His Cys Phe Gly Glu Arg
                405                 410                 415

Ala Ala Glu Ile Ile His Ile Gly Gln Ala Ile Met Glu Gln Lys Gly
                420                 425                 430

Gly Gly Asn Thr Ile Glu Tyr Phe Val Asn Thr Thr Phe Asn Tyr Pro
            435                 440                 445

Thr Met Ala Glu Ala Tyr Arg Val Ala Ala Leu Asn Gly Leu Asn Arg
    450                 455                 460

Leu Phe
465

<210> SEQ ID NO 143
<211> LENGTH: 1323
<212> TYPE: DNA
<213> ORGANISM: Escherichia coli

<400> SEQUENCE: 143
atgcaagcct attttgacca gctcgatcgc gttcgttatg aaggctcaaa atcctcaaac      60
ccgttagcat tccgtcacta caatcccgac gaactggtgt tgggtaagcg tatggaagag     120
cacttgcgtt ttgccgcctg ctactggcac accttctgct ggaacggggc ggatatgttt     180
ggtgtggggg cgtttaatcg tccgtggcag cagcctggtg aggcactggc gttggcgaag     240
cgtaaagcag atgtcgcatt tgagtttttc cacaagttac atgtgccatt ttattgcttc     300
cacgatgtgg atgtttcccc tgagggcgcg tcgttaaaag agtacatcaa taattttgcg     360
caaatggttg atgtcctggc aggcaagcaa gaagagagcg gcgtgaagct gctgtgggga     420
acggccaact gctttacaaa ccctcgctac ggcgcgggtg cggcgacgaa cccagatcct     480
gaagtcttca gctgggcggc aacgcaagtt gttacagcga tggaagcaac ccataaattg     540
ggcggtgaaa actatgtcct gtggggcggt cgtgaaggtt acgaaacgct gttaaatacc     600
gacttgcgtc aggagcgtga caactgggcg cgctttatgc agatggtggt tgagcataaa     660
cataaaatcg gttccagggg cacgttgctt atcgaaccga aaccgcaaga accgaccaaa     720
catcaatatg attacgatgc cgcgacggtc tatggcttcc tgaaacagtt tggtctggaa     780
aaagagatta aactgaacat tgaagctaac cacgcgacgc tggcaggtca ctcttttccat    840 catgaaatag ccaccgccat tgcgcttggc ctgttcggtt ctgtcgacgc caaccgtggc     900
gatgcgcaac tgggctggga caccgaccag ttcccgaaca gtgtggaaga aatgcgctg     960 gtgatgtatg aaattctcaa agcaggcggt ttcaccaccg gtggtctgaa cttcgatgcc    1020
aaagtacgtc gtcaaagtac tgataaatat gatctgttttt acggtcatat cggcgcgatg    1080
gatacgatgg cactggcgct gaaaattgca gcgcgcatga ttgaagatgg cgagctggat    1140
aaacgcatcg cgcagcgtta ttccggctgg aatagcgaat gggccagca atcctgaaa    1200 ggccaaatgt cactggcaga tttagccaaa tatgctcagg acatcatttt gtctccggtg    1260
catcagagtg gtcgccagga acaactggaa aatctggtaa accattatct gttcgacaaa    1320
```

```
taa                                                                    1323
```

<210> SEQ ID NO 144
<211> LENGTH: 440
<212> TYPE: PRT
<213> ORGANISM: Escherichia coli

<400> SEQUENCE: 144

Met Gln Ala Tyr Phe Asp Gln Leu Asp Arg Val Arg Tyr Glu Gly Ser
1               5                   10                  15

Lys Ser Ser Asn Pro Leu Ala Phe Arg His Tyr Asn Pro Asp Glu Leu
            20                  25                  30

Val Leu Gly Lys Arg Met Glu His Leu Arg Phe Ala Ala Cys Tyr
        35                  40                  45

Trp His Thr Phe Cys Trp Asn Gly Ala Asp Met Phe Gly Val Gly Ala
    50                  55                  60

Phe Asn Arg Pro Trp Gln Gln Pro Gly Glu Ala Leu Ala Leu Ala Lys
65                  70                  75                  80

Arg Lys Ala Asp Val Ala Phe Glu Phe Phe His Lys Leu His Val Pro
                85                  90                  95

Phe Tyr Cys Phe His Asp Val Asp Val Ser Pro Glu Gly Ala Ser Leu
            100                 105                 110

Lys Glu Tyr Ile Asn Asn Phe Ala Gln Met Val Asp Val Leu Ala Gly
        115                 120                 125

Lys Gln Glu Glu Ser Gly Val Lys Leu Leu Trp Gly Thr Ala Asn Cys
130                 135                 140

Phe Thr Asn Pro Arg Tyr Gly Ala Gly Ala Ala Thr Asn Pro Asp Pro
145                 150                 155                 160

Glu Val Phe Ser Trp Ala Ala Thr Gln Val Val Thr Ala Met Glu Ala
                165                 170                 175

Thr His Lys Leu Gly Gly Glu Asn Tyr Val Leu Trp Gly Gly Arg Glu
            180                 185                 190

Gly Tyr Glu Thr Leu Leu Asn Thr Asp Leu Arg Gln Glu Arg Glu Gln
        195                 200                 205

Leu Gly Arg Phe Met Gln Met Val Val Glu His Lys His Lys Ile Gly
210                 215                 220

Phe Gln Gly Thr Leu Leu Ile Glu Pro Lys Pro Gln Glu Pro Thr Lys
225                 230                 235                 240

His Gln Tyr Asp Tyr Asp Ala Ala Thr Val Tyr Gly Phe Leu Lys Gln
                245                 250                 255

Phe Gly Leu Glu Lys Glu Ile Lys Leu Asn Ile Glu Ala Asn His Ala
            260                 265                 270

Thr Leu Ala Gly His Ser Phe His His Glu Ile Ala Thr Ala Ile Ala
        275                 280                 285

Leu Gly Leu Phe Gly Ser Val Asp Ala Asn Arg Gly Asp Ala Gln Leu
290                 295                 300

Gly Trp Asp Thr Asp Gln Phe Pro Asn Ser Val Glu Glu Asn Ala Leu
305                 310                 315                 320

Val Met Tyr Glu Ile Leu Lys Ala Gly Gly Phe Thr Thr Gly Gly Leu
                325                 330                 335

Asn Phe Asp Ala Lys Val Arg Arg Gln Ser Thr Asp Lys Tyr Asp Leu
            340                 345                 350

Phe Tyr Gly His Ile Gly Ala Met Asp Thr Met Ala Leu Ala Leu Lys
        355                 360                 365

```
Ile Ala Ala Arg Met Ile Glu Asp Gly Glu Leu Asp Lys Arg Ile Ala
        370                 375                 380

Gln Arg Tyr Ser Gly Trp Asn Ser Glu Leu Gly Gln Gln Ile Leu Lys
385                 390                 395                 400

Gly Gln Met Ser Leu Ala Asp Leu Ala Lys Tyr Ala Gln Glu His His
                405                 410                 415

Leu Ser Pro Val His Gln Ser Gly Arg Gln Glu Gln Leu Glu Asn Leu
            420                 425                 430

Val Asn His Tyr Leu Phe Asp Lys
            435                 440

<210> SEQ ID NO 145
<211> LENGTH: 1455
<212> TYPE: DNA
<213> ORGANISM: Escherichia coli

<400> SEQUENCE: 145
atgtatatcg ggatagatct tggcacctcg ggcgtaaaag ttattttgct caacgagcag      60
ggtgaggtgg ttgctgcgca acggaaaag ctgaccgttt cgcgcccgca tccactctgg     120
tcggaacaag acccggaaca gtggtggcag gcaactgatc gcgcaatgaa agctctgggc    180
gatcagcatt ctctgcagga cgttaaagca ttgggtattg ccggccagat gcacggagca    240
accttgctgg atgctcagca acgggtgtta cgccctgcca ttttgtggaa cgacgggcgc    300
tgtgcgcaag agtgcacttt gctggaagcg cgagttccgc aatcgcgggt gattaccggc    360
aacctgatga tgcccggatt tactgcgcct aaattgctat gggttcagcg gcatgagccg    420
gagatattcc gtcaaatcga caaagtatta ttaccgaaag attacttgcg tctgcgtatg    480
acggggagt tgccagcga tatgtctgac gcagctggca ccatgtggct ggatgtcgca    540
aagcgtgact ggagtgacgt catgctgcag gcttgcgact tatctcgtga ccagatgccc    600
gcattatacg aaggcagcga aattactggt gctttgttac ctgaagttgc gaaagcgtgg    660
ggtatggcga cggtgccagt tgtcgcaggc ggtggcgaca atgcagctgg tgcagttggt    720
gtgggaatgg ttgatgctaa tcaggcaatg ttatcgctgg ggacgtcggg ggtctatttt    780
gctgtcagcg aagggttctt aagcaagcca gaaagcgccg tacatagctt tgccatgcg    840
ctaccgcaac gttggcattt aatgtctgtg atgctgagtg cagcgtcgtg tctggattgg    900
gccgcgaaat taaccggcct gagcaatgtc cagcttaa tcgctgcagc tcaacaggct    960
gatgaaagtg ccgagccagt ttggtttctg ccttatcttt ccggcgagcg tacgccacac   1020
aataatcccc aggcgaaggg ggttttcttt ggtttgactc atcaacatgg ccccaatgaa   1080
ctggcgcgag cagtgctgga aggcgtgggt tatgcgctgg cagatggcat ggatgtcgtg   1140
catgcctgcg gtattaaacc gcaaagtgtt acgttgattg ggggcgggc gcgtagtgag   1200
tactggcgtc agatgctggc ggatatcagc ggtcagcagc tcgattaccg tacgggggg   1260
gatgtggggc cagcactggg cgcagcaagg ctggcgcaga tcgcggcgaa tccagagaaa   1320
tcgctcattg aattgttgcc gcaactaccg ttagaacagt cgcatctacc agatgcgcag   1380
cgttatgccg cttatcagcc acgacgagaa acgttccgtc gcctctatca gcaacttctg   1440
ccattaatgg cgtaa                                                    1455

<210> SEQ ID NO 146
<211> LENGTH: 484
<212> TYPE: PRT
<213> ORGANISM: Escherichia coli
```

```
<400> SEQUENCE: 146

Met Tyr Ile Gly Ile Asp Leu Gly Thr Ser Gly Val Lys Val Ile Leu
1               5                   10                  15

Leu Asn Glu Gln Gly Glu Val Val Ala Ala Gln Thr Glu Lys Leu Thr
            20                  25                  30

Val Ser Arg Pro His Pro Leu Trp Ser Glu Gln Asp Pro Glu Gln Trp
        35                  40                  45

Trp Gln Ala Thr Asp Arg Ala Met Lys Ala Leu Gly Asp Gln His Ser
    50                  55                  60

Leu Gln Asp Val Lys Ala Leu Gly Ile Ala Gly Gln Met His Gly Ala
65                  70                  75                  80

Thr Leu Leu Asp Ala Gln Gln Arg Val Leu Arg Pro Ala Ile Leu Trp
                85                  90                  95

Asn Asp Gly Arg Cys Ala Gln Glu Cys Thr Leu Leu Glu Ala Arg Val
            100                 105                 110

Pro Gln Ser Arg Val Ile Thr Gly Asn Leu Met Met Pro Gly Phe Thr
        115                 120                 125

Ala Pro Lys Leu Leu Trp Val Gln Arg His Glu Pro Glu Ile Phe Arg
    130                 135                 140

Gln Ile Asp Lys Val Leu Leu Pro Lys Asp Tyr Leu Arg Leu Arg Met
145                 150                 155                 160

Thr Gly Glu Phe Ala Ser Asp Met Ser Asp Ala Ala Gly Thr Met Trp
                165                 170                 175

Leu Asp Val Ala Lys Arg Asp Trp Ser Asp Val Met Leu Gln Ala Cys
            180                 185                 190

Asp Leu Ser Arg Asp Gln Met Pro Ala Leu Tyr Glu Gly Ser Glu Ile
        195                 200                 205

Thr Gly Ala Leu Leu Pro Glu Val Ala Lys Ala Trp Gly Met Ala Thr
210                 215                 220

Val Pro Val Val Ala Gly Gly Asp Asn Ala Ala Gly Ala Val Gly
225                 230                 235                 240

Val Gly Met Val Asp Ala Asn Gln Ala Met Leu Ser Leu Gly Thr Ser
                245                 250                 255

Gly Val Tyr Phe Ala Val Ser Glu Gly Phe Leu Ser Lys Pro Glu Ser
            260                 265                 270

Ala Val His Ser Phe Cys His Ala Leu Pro Gln Arg Trp His Leu Met
        275                 280                 285

Ser Val Met Leu Ser Ala Ala Ser Cys Leu Asp Trp Ala Ala Lys Leu
    290                 295                 300

Thr Gly Leu Ser Asn Val Pro Ala Leu Ile Ala Ala Gln Gln Ala
305                 310                 315                 320

Asp Glu Ser Ala Glu Pro Val Trp Phe Leu Pro Tyr Leu Ser Gly Glu
                325                 330                 335

Arg Thr Pro His Asn Asn Pro Gln Ala Lys Gly Val Phe Phe Gly Leu
            340                 345                 350

Thr His Gln His Gly Pro Asn Glu Leu Ala Arg Ala Val Leu Glu Gly
        355                 360                 365

Val Gly Tyr Ala Leu Ala Asp Gly Met Asp Val His Ala Cys Gly
    370                 375                 380

Ile Lys Pro Gln Ser Val Thr Leu Ile Gly Gly Gly Ala Arg Ser Glu
385                 390                 395                 400

Tyr Trp Arg Gln Met Leu Ala Asp Ile Ser Gly Gln Gln Leu Asp Tyr
                405                 410                 415
```

```
Arg Thr Gly Gly Asp Val Gly Pro Ala Leu Gly Ala Ala Arg Leu Ala
            420                 425                 430

Gln Ile Ala Ala Asn Pro Glu Lys Ser Leu Ile Glu Leu Leu Pro Gln
            435                 440                 445

Leu Pro Leu Glu Gln Ser His Leu Pro Asp Ala Gln Arg Tyr Ala Ala
450                 455                 460

Tyr Gln Pro Arg Arg Glu Thr Phe Arg Arg Leu Tyr Gln Gln Leu Leu
465                 470                 475                 480

Pro Leu Met Ala

<210> SEQ ID NO 147
<211> LENGTH: 1992
<212> TYPE: DNA
<213> ORGANISM: Escherichia coli

<400> SEQUENCE: 147
```

| | | | | |
|---|---|---|---|---|
| atgtcctcac | gtaaagagct | tgccaatgct | attcgtgcgc | tgagcatgga | cgcagtacag | 60 |
| aaagccaaat | ccggtcaccc | gggtgcccct | atgggtatgg | ctgacattgc | cgaagtcctg | 120 |
| tggcgtgatt | tcctgaaaca | caacccgcag | aatccgtcct | gggctgaccg | tgaccgcttc | 180 |
| gtgctgtcca | acggccacgg | ctccatgctg | atctacagcc | tgctgcacct | caccggttac | 240 |
| gatctgccga | tggaagaact | gaaaaacttc | cgtcagctgc | actctaaaac | tccgggtcac | 300 |
| ccggaagtgg | gttacaccgc | tggtgtggaa | accaccaccg | gtccgctggg | tcagggtatt | 360 |
| gccaacgcag | tcggtatggc | gattgcagaa | aaaacgctgg | cggcgcagtt | taaccgtccg | 420 |
| ggccacgaca | ttgtcgacca | ctacacctac | gccttcatgg | gcgacggctg | catgatggaa | 480 |
| ggcatctccc | acgaagtttg | ctctctggcg | ggtacgctga | gctgggtaa | actgattgca | 540 |
| ttctacgatg | acaacggtat | ttctatcgat | ggtcacgttg | aaggctggtt | caccgacgac | 600 |
| accgcaatgc | gtttcgaagc | ttacggctgg | cacgttattc | gcgacatcga | cggtcatgac | 660 |
| gcggcatcta | tcaaacgcgc | agtagaagaa | gcgcgcgcag | tgactgacaa | accttccctg | 720 |
| ctgatgtgca | aaaccatcat | cggtttcggt | tccccgaaca | aagccggtac | ccacgactcc | 780 |
| cacggtgcgc | cgctgggcga | cgctgaaatt | gccctgaccc | gcaacaact | gggctggaaa | 840 |
| tatgcgccgt | tcgaaatccc | gtctgaaatc | tatgctcagt | gggatgcgaa | agaagcaggc | 900 |
| caggcgaaag | aatccgcatg | gaacgagaaa | ttcgctgctt | acgcgaaagc | ttatccgcag | 960 |
| gaagccgctg | aatttacccg | ccgtatgaaa | ggcgaaatgc | cgtctgactt | cgacgctaaa | 1020 |
| gcgaaagagt | tcatcgctaa | actgcaggct | aatccggcga | aaatcgccag | ccgtaaagcg | 1080 |
| tctcagaatg | ctatcgaagc | gttcggtccg | ctgttgccgg | aattcctcgg | cggttctgct | 1140 |
| gacctggcgc | cgtctaacct | gaccctgtgg | tctggttcta | agcaatcaa | cgaagatgct | 1200 |
| gcgggtaact | acatccacta | cggtgttcgc | gagttcggta | tgaccgcgat | tgctaacggt | 1260 |
| atctccctgc | acggtggctt | cctgccgtac | acctccacct | tcctgatgtt | cgtggaatac | 1320 |
| gcacgtaacg | ccgtacgtat | ggctgcgctg | atgaaacagc | gtcaggtgat | ggtttacacc | 1380 |
| cacgactcca | tcggtctggg | cgaagacggc | ccgactcacc | agccggttga | gcaggtcgct | 1440 |
| tctctgcgcg | taaccccgaa | catgtctaca | tggcgtccgt | gtgaccaggt | tgaatccgcg | 1500 |
| gtcgcgtgga | aatacggtgt | tgagcgtcag | gacgcccga | ccgcactgat | cctctcccgt | 1560 |
| cagaacctgg | cgcagcagga | acgaactgaa | gagcaactgg | caaacatcgc | gcgcggtggt | 1620 |
| tatgtgctga | aagactgcgc | cggtcagccg | gaactgattt | tcatcgctac | cggttcagaa | 1680 |

-continued

```
gttgaactgg ctgttgctgc ctacgaaaaa ctgactgccg aaggcgtgaa agcgcgcgtg    1740
gtgtccatgc cgtctaccga cgcatttgac aagcaggatg ctgcttaccg tgaatccgta    1800
ctgccgaaag cggttactgc acgcgttgct gtagaagcgg gtattgctga ctactggtac    1860
aagtatgttg gcctgaacgg tgctatcgtc ggtatgacca ccttcggtga atctgctccg    1920
gcagagctgc tgtttgaaga gttcggcttc actgttgata cgttgttgc gaaagcaaaa    1980 gaactgctgt aa                                                        1992

<210> SEQ ID NO 148
<211> LENGTH: 663
<212> TYPE: PRT
<213> ORGANISM: Escherichia coli

<400> SEQUENCE: 148

Met Ser Ser Arg Lys Glu Leu Ala Asn Ala Ile Arg Ala Leu Ser Met
1               5                   10                  15

Asp Ala Val Gln Lys Ala Lys Ser Gly His Pro Gly Ala Pro Met Gly
                20                  25                  30

Met Ala Asp Ile Ala Glu Val Leu Trp Arg Asp Phe Leu Lys His Asn
            35                  40                  45

Pro Gln Asn Pro Ser Trp Ala Asp Arg Asp Arg Phe Val Leu Ser Asn
        50                  55                  60

Gly His Gly Ser Met Leu Ile Tyr Ser Leu Leu His Leu Thr Gly Tyr
65                  70                  75                  80

Asp Leu Pro Met Glu Glu Leu Lys Asn Phe Arg Gln Leu His Ser Lys
                85                  90                  95

Thr Pro Gly His Pro Glu Val Gly Tyr Thr Ala Gly Val Glu Thr Thr
            100                 105                 110

Thr Gly Pro Leu Gly Gln Gly Ile Ala Asn Ala Val Gly Met Ala Ile
        115                 120                 125

Ala Glu Lys Thr Leu Ala Ala Gln Phe Asn Arg Pro Gly His Asp Ile
    130                 135                 140

Val Asp His Tyr Thr Tyr Ala Phe Met Gly Asp Gly Cys Met Met Glu
145                 150                 155                 160

Gly Ile Ser His Glu Val Cys Ser Leu Ala Gly Thr Leu Lys Leu Gly
                165                 170                 175

Lys Leu Ile Ala Phe Tyr Asp Asp Asn Gly Ile Ser Ile Asp Gly His
            180                 185                 190

Val Glu Gly Trp Phe Thr Asp Thr Ala Met Arg Phe Glu Ala Tyr
        195                 200                 205

Gly Trp His Val Ile Arg Asp Ile Asp Gly His Asp Ala Ala Ser Ile
    210                 215                 220

Lys Arg Ala Val Glu Glu Ala Arg Ala Val Thr Asp Lys Pro Ser Leu
225                 230                 235                 240

Leu Met Cys Lys Thr Ile Ile Gly Phe Gly Ser Pro Asn Lys Ala Gly
                245                 250                 255

Thr His Asp Ser His Gly Ala Pro Leu Gly Asp Ala Glu Ile Ala Leu
            260                 265                 270

Thr Arg Glu Gln Leu Gly Trp Lys Tyr Ala Pro Phe Glu Ile Pro Ser
        275                 280                 285

Glu Ile Tyr Ala Gln Trp Asp Ala Lys Glu Ala Gly Gln Ala Lys Glu
    290                 295                 300

Ser Ala Trp Asn Glu Lys Phe Ala Ala Tyr Ala Lys Ala Tyr Pro Gln
305                 310                 315                 320
```

Glu Ala Ala Glu Phe Thr Arg Arg Met Lys Gly Met Pro Ser Asp
            325                 330                 335

Phe Asp Ala Lys Ala Lys Glu Phe Ile Ala Lys Leu Gln Ala Asn Pro
            340                 345                 350

Ala Lys Ile Ala Ser Arg Lys Ala Ser Gln Asn Ala Ile Glu Ala Phe
            355                 360                 365

Gly Pro Leu Leu Pro Glu Phe Leu Gly Gly Ser Ala Asp Leu Ala Pro
        370                 375                 380

Ser Asn Leu Thr Leu Trp Ser Gly Ser Lys Ala Ile Asn Glu Asp Ala
385                 390                 395                 400

Ala Gly Asn Tyr Ile His Tyr Gly Val Arg Glu Phe Gly Met Thr Ala
            405                 410                 415

Ile Ala Asn Gly Ile Ser Leu His Gly Gly Phe Leu Pro Tyr Thr Ser
            420                 425                 430

Thr Phe Leu Met Phe Val Glu Tyr Ala Arg Asn Ala Val Arg Met Ala
        435                 440                 445

Ala Leu Met Lys Gln Arg Gln Val Met Val Tyr Thr His Asp Ser Ile
        450                 455                 460

Gly Leu Gly Glu Asp Gly Pro Thr His Gln Pro Val Glu Gln Val Ala
465                 470                 475                 480

Ser Leu Arg Val Thr Pro Asn Met Ser Thr Trp Arg Pro Cys Asp Gln
            485                 490                 495

Val Glu Ser Ala Val Ala Trp Lys Tyr Gly Val Glu Arg Gln Asp Gly
            500                 505                 510

Pro Thr Ala Leu Ile Leu Ser Arg Gln Asn Leu Ala Gln Gln Glu Arg
        515                 520                 525

Thr Glu Glu Gln Leu Ala Asn Ile Ala Arg Gly Gly Tyr Val Leu Lys
        530                 535                 540

Asp Cys Ala Gly Gln Pro Glu Leu Ile Phe Ile Ala Thr Gly Ser Glu
545                 550                 555                 560

Val Glu Leu Ala Val Ala Ala Tyr Glu Lys Leu Thr Ala Glu Gly Val
            565                 570                 575

Lys Ala Arg Val Val Ser Met Pro Ser Thr Asp Ala Phe Asp Lys Gln
            580                 585                 590

Asp Ala Ala Tyr Arg Glu Ser Val Leu Pro Lys Ala Val Thr Ala Arg
        595                 600                 605

Val Ala Val Glu Ala Gly Ile Ala Asp Tyr Trp Tyr Lys Tyr Val Gly
        610                 615                 620

Leu Asn Gly Ala Ile Val Gly Met Thr Thr Phe Gly Glu Ser Ala Pro
625                 630                 635                 640

Ala Glu Leu Leu Phe Glu Glu Phe Gly Phe Thr Val Asp Asn Val Val
            645                 650                 655

Ala Lys Ala Lys Glu Leu Leu
            660

<210> SEQ ID NO 149
<211> LENGTH: 2004
<212> TYPE: DNA
<213> ORGANISM: Escherichia coli

<400> SEQUENCE: 149
atgtcccgaa aagaccttgc caatgcgatt cgcgcactca gtatggatgc ggtacaaaaa    60
gccaactctg gtcatcccgg cgcgccgatg ggcatggctg atattgccga agtgctgtgg   120

```
aacgattttc ttaaacataa ccctaccgac ccaacctggt atgatcgcga ccgctttatt   180
ctttccaacg gtcacgcgtc gatgctgctc tacagtttgc tacatctgac cggttacgac   240
ctgccgctgg aagaactgaa gaacttccgt cagttgcatt cgaaaacccc aggccacccg   300
gagattggct atacgccagg cgttgaaacc accaccggcc cgcttggaca ggttttggcg   360
aacgccgtcg ggctggcgat agcagagcgt acactggcgg cgcagtttaa ccagccagac   420
catgagatcg tcgatcactt cacctatgtg tttatgggcg acggctgcct gatgaaggt    480
atttcccacg aagtctgttc gctggcaggc acgctgggac tgggcaagct gattggtttt   540
tacgatcaca acgtatttc catcgacggt gaaacagaag ctggtttac cgacgatacg    600
gcaaaacgtt ttgaagccta tcactggcat gtgatccatg aaatcgacgg tcacgatccg   660
caggcggtga aggaagcgat ccttgaagcg caaagcgtga agataagcc gtcgctgatt    720
atctgccgta cggtgattgg ctttggttcg ccgaataaag caggtaagga agaggcgcac   780
ggcgcaccac tgggggaaga agaagtggcg ctggcacggc aaaaactggg ctggcaccat   840
ccgccatttg agatccctaa agagatttat cacgcctggg atgcccgtga aaaggcgaa    900
aaagcgcagc agagctggaa tgagaagttt gccgcctata aaaaggctca tccgcaactg   960
gcagaagagt ttacccgacg gatgagcggt ggtttaccga aggactggga gaaaacgact  1020
cagaaatata tcaatgagtt acaggcaaat ccggcgaaaa tcgctacccg taaggcttcg  1080
caaaatacgc ttaacgctta cgggccgatg ctgcctgagt tgctcggcgg ttcggcggat  1140
ctggctccca gcaacctgac catctggaaa ggttctgttt cgctgaagga agatccagcg  1200
ggcaactaca ttcactacgg ggtgcgtgaa tttggcatga ccgctatcgc caacggcatc  1260
gcgcaccacg gcggctttgt gccgtatacc gcgacgttcc tgatgtttgt tgaatacgcc  1320
cgtaacgccg cgcggatggc ggcactgatg aaagcgcggc agattatggt ttataccccac  1380
gactcaattg gcctgggcga agatggtccg acgcaccagg ctgttgagca actggccagc  1440
ctgccgctta cgccaaattt cagcacctgg cgaccgtgcg atcaggtgga agcggcggtg  1500
ggctggaagc tggcggttga gcgccacaac ggaccgacgg cactgatcct ctcaaggcag  1560
aatctggccc aggtggaacg tacgccggat caggttaaag agattgctcg tggcggttat  1620
gtgctgaaag acagcggcgg taagccagat attattctga ttgccaccgg ttcagagatg  1680
gaaattaccc tgcaagcggc agagaaatta gcaggagaag gtcgcaatgt acgcgtagtt  1740
tccctgccct cgaccgatat tttcgacgcc caggatgagg aatatcggga gtcggtgttg  1800
ccttctaacg ttgcggctcg cgtggcggtg aagcaggta ttgccgatta ctggtacaag   1860
tatgttggtc tgaaaggggc aattgtcggg atgacgggtt acggggaatc tgctccggcg  1920
gataagctgt tcccgttctt tggctttacc gccgagaata ttgtggcaaa agcgcataag  1980
gtgctgggag tgaaaggtgc ctga                                          2004
```

<210> SEQ ID NO 150
<211> LENGTH: 667
<212> TYPE: PRT
<213> ORGANISM: Escherichia coli

<400> SEQUENCE: 150

Met Ser Arg Lys Asp Leu Ala Asn Ala Ile Arg Ala Leu Ser Met Asp
1               5                   10                  15

Ala Val Gln Lys Ala Asn Ser Gly His Pro Gly Ala Pro Met Gly Met
            20                  25                  30

Ala Asp Ile Ala Glu Val Leu Trp Asn Asp Phe Leu Lys His Asn Pro

-continued

```
                35                  40                  45
Thr Asp Pro Thr Trp Tyr Asp Arg Asp Arg Phe Ile Leu Ser Asn Gly
 50                  55                  60
His Ala Ser Met Leu Leu Tyr Ser Leu Leu His Leu Thr Gly Tyr Asp
 65                  70                  75                  80
Leu Pro Leu Glu Glu Leu Lys Asn Phe Arg Gln Leu His Ser Lys Thr
                 85                  90                  95
Pro Gly His Pro Glu Ile Gly Tyr Thr Pro Gly Val Glu Thr Thr Thr
                100                 105                 110
Gly Pro Leu Gly Gln Gly Leu Ala Asn Ala Val Gly Leu Ala Ile Ala
                115                 120                 125
Glu Arg Thr Leu Ala Ala Gln Phe Asn Gln Pro Asp His Glu Ile Val
130                 135                 140
Asp His Phe Thr Tyr Val Phe Met Gly Asp Gly Cys Leu Met Glu Gly
145                 150                 155                 160
Ile Ser His Glu Val Cys Ser Leu Ala Gly Thr Leu Gly Leu Gly Lys
                165                 170                 175
Leu Ile Gly Phe Tyr Asp His Asn Gly Ile Ser Ile Asp Gly Glu Thr
                180                 185                 190
Glu Gly Trp Phe Thr Asp Asp Thr Ala Lys Arg Phe Glu Ala Tyr His
            195                 200                 205
Trp His Val Ile His Glu Ile Asp Gly His Asp Pro Gln Ala Val Lys
210                 215                 220
Glu Ala Ile Leu Glu Ala Gln Ser Val Lys Asp Lys Pro Ser Leu Ile
225                 230                 235                 240
Ile Cys Arg Thr Val Ile Gly Phe Gly Ser Pro Asn Lys Ala Gly Lys
                245                 250                 255
Glu Glu Ala His Gly Ala Pro Leu Gly Glu Glu Val Ala Leu Ala
                260                 265                 270
Arg Gln Lys Leu Gly Trp His His Pro Pro Phe Glu Ile Pro Lys Glu
            275                 280                 285
Ile Tyr His Ala Trp Asp Ala Arg Glu Lys Gly Glu Lys Ala Gln Gln
        290                 295                 300
Ser Trp Asn Glu Lys Phe Ala Ala Tyr Lys Lys Ala His Pro Gln Leu
305                 310                 315                 320
Ala Glu Glu Phe Thr Arg Arg Met Ser Gly Gly Leu Pro Lys Asp Trp
                325                 330                 335
Glu Lys Thr Thr Gln Lys Tyr Ile Asn Glu Leu Gln Ala Asn Pro Ala
                340                 345                 350
Lys Ile Ala Thr Arg Lys Ala Ser Gln Asn Thr Leu Asn Ala Tyr Gly
                355                 360                 365
Pro Met Leu Pro Glu Leu Leu Gly Gly Ser Ala Asp Leu Ala Pro Ser
            370                 375                 380
Asn Leu Thr Ile Trp Lys Gly Ser Val Ser Leu Lys Glu Asp Pro Ala
385                 390                 395                 400
Gly Asn Tyr Ile His Tyr Gly Val Arg Glu Phe Gly Met Thr Ala Ile
                405                 410                 415
Ala Asn Gly Ile Ala His His Gly Gly Phe Val Pro Tyr Thr Ala Thr
                420                 425                 430
Phe Leu Met Phe Val Glu Tyr Ala Arg Asn Ala Ala Arg Met Ala Ala
            435                 440                 445
Leu Met Lys Ala Arg Gln Ile Met Val Tyr Thr His Asp Ser Ile Gly
450                 455                 460
```

```
Leu Gly Glu Asp Gly Pro Thr His Gln Ala Val Gln Leu Ala Ser
465                 470                 475                 480

Leu Arg Leu Thr Pro Asn Phe Ser Thr Trp Arg Pro Cys Asp Gln Val
                485                 490                 495

Glu Ala Ala Val Gly Trp Lys Leu Ala Val Glu Arg His Asn Gly Pro
            500                 505                 510

Thr Ala Leu Ile Leu Ser Arg Gln Asn Leu Ala Gln Val Glu Arg Thr
        515                 520                 525

Pro Asp Gln Val Lys Glu Ile Ala Arg Gly Gly Tyr Val Leu Lys Asp
    530                 535                 540

Ser Gly Gly Lys Pro Asp Ile Ile Leu Ile Ala Thr Gly Ser Glu Met
545                 550                 555                 560

Glu Ile Thr Leu Gln Ala Ala Glu Lys Leu Ala Gly Glu Gly Arg Asn
                565                 570                 575

Val Arg Val Val Ser Leu Pro Ser Thr Asp Ile Phe Asp Ala Gln Asp
            580                 585                 590

Glu Glu Tyr Arg Glu Ser Val Leu Pro Ser Asn Val Ala Ala Arg Val
        595                 600                 605

Ala Val Glu Ala Gly Ile Ala Asp Tyr Trp Tyr Lys Tyr Val Gly Leu
    610                 615                 620

Lys Gly Ala Ile Val Gly Met Thr Gly Tyr Gly Glu Ser Ala Pro Ala
625                 630                 635                 640

Asp Lys Leu Phe Pro Phe Phe Gly Phe Thr Ala Glu Asn Ile Val Ala
                645                 650                 655

Lys Ala His Lys Val Leu Gly Val Lys Gly Ala
            660                 665
```

<210> SEQ ID NO 151
<211> LENGTH: 951
<212> TYPE: DNA
<213> ORGANISM: Escherichia coli

<400> SEQUENCE: 151

| | | | | | |
|---|---|---|---|---|---|
| atgaacgagt | tagacggcat | caaacagttc | accactgtcg | tggcagacag | cggcgatatt | 60 |
| gagtccattc | gccattatca | tccccaggat | gccaccacca | atccttcgct | gttactcaaa | 120 |
| gctgccggat | tatcacaata | tgagcattta | atagacgatg | ctatcgcctg | ggtaaaaaa | 180 |
| aatggcaaga | cccaggaaca | acaggtggtc | gcagcgtgtg | acaaactggc | ggtcaatttc | 240 |
| ggtgctgaaa | tcctcaaaat | cgtacccggt | cgcgtgtcaa | cagaagttga | tgcacgcctc | 300 |
| tcttttgata | agaaaagag | tattgagaag | gcgcgccatc | tggtggactt | gtatcagcaa | 360 |
| caaggcgttg | agaaatcacg | cattctgatc | aagctggctt | cgacctggga | aggaattcgc | 420 |
| gcggcagaag | agctggaaaa | agaaggtatt | aactgcaacc | tgacgctgct | gttttctttt | 480 |
| gcacaggcac | gggcctgtgc | ggaagcaggc | gttttctga | tttcgccgtt | tgtcgggcgt | 540 |
| atttatgact | ggtatcaggc | acgcaagccg | atggacccgt | atgtggtgga | agaagatccg | 600 |
| ggcgttaaat | cggtgcgcaa | tatctacgac | tactataagc | aacaccacta | tgaaaccatt | 660 |
| gtgatgggcg | cgagcttccg | tcgcaccgaa | caaatcctcg | ccttaaccgg | ctgcgatcga | 720 |
| ctgactatcg | caccgaattt | actgaaggag | ctgcaggaaa | aagtttcgcc | agtggtacgt | 780 |
| aaattaatcc | caccttctca | gacgttccca | cgcccagctc | ccatgagcga | agcggagttc | 840 |
| cgttgggagc | acaatcagga | tgcgatggcg | gtagaaaaac | tgtctgaagg | cattcgtctg | 900 |
| ttcgccgttg | atcaacgcaa | actggaagat | cttcttgccg | ccaaactata | a | 951 |

<210> SEQ ID NO 152
<211> LENGTH: 316
<212> TYPE: PRT
<213> ORGANISM: Escherichia coli

<400> SEQUENCE: 152

Met Asn Glu Leu Asp Gly Ile Lys Gln Phe Thr Thr Val Val Ala Asp
1               5                   10                  15

Ser Gly Asp Ile Glu Ser Ile Arg His Tyr His Pro Gln Asp Ala Thr
            20                  25                  30

Thr Asn Pro Ser Leu Leu Leu Lys Ala Ala Gly Leu Ser Gln Tyr Glu
        35                  40                  45

His Leu Ile Asp Asp Ala Ile Ala Trp Gly Lys Lys Asn Gly Lys Thr
    50                  55                  60

Gln Glu Gln Gln Val Val Ala Ala Cys Asp Lys Leu Ala Val Asn Phe
65                  70                  75                  80

Gly Ala Glu Ile Leu Lys Ile Val Pro Gly Arg Val Ser Thr Glu Val
                85                  90                  95

Asp Ala Arg Leu Ser Phe Asp Lys Glu Lys Ser Ile Glu Lys Ala Arg
            100                 105                 110

His Leu Val Asp Leu Tyr Gln Gln Gln Gly Val Glu Lys Ser Arg Ile
        115                 120                 125

Leu Ile Lys Leu Ala Ser Thr Trp Glu Gly Ile Arg Ala Ala Glu Glu
    130                 135                 140

Leu Glu Lys Glu Gly Ile Asn Cys Asn Leu Thr Leu Leu Phe Ser Phe
145                 150                 155                 160

Ala Gln Ala Arg Ala Cys Ala Glu Ala Gly Val Phe Leu Ile Ser Pro
                165                 170                 175

Phe Val Gly Arg Ile Tyr Asp Trp Tyr Gln Ala Arg Lys Pro Met Asp
            180                 185                 190

Pro Tyr Val Val Glu Glu Asp Pro Gly Val Lys Ser Val Arg Asn Ile
        195                 200                 205

Tyr Asp Tyr Tyr Lys Gln His His Tyr Glu Thr Ile Val Met Gly Ala
    210                 215                 220

Ser Phe Arg Arg Thr Glu Gln Ile Leu Ala Leu Thr Gly Cys Asp Arg
225                 230                 235                 240

Leu Thr Ile Ala Pro Asn Leu Leu Lys Glu Leu Gln Glu Lys Val Ser
                245                 250                 255

Pro Val Val Arg Lys Leu Ile Pro Pro Ser Gln Thr Phe Pro Arg Pro
            260                 265                 270

Ala Pro Met Ser Glu Ala Glu Phe Arg Trp Glu His Asn Gln Asp Ala
        275                 280                 285

Met Ala Val Glu Lys Leu Ser Glu Gly Ile Arg Leu Phe Ala Val Asp
    290                 295                 300

Gln Arg Lys Leu Glu Asp Leu Leu Ala Ala Lys Leu
305                 310                 315

<210> SEQ ID NO 153
<211> LENGTH: 954
<212> TYPE: DNA
<213> ORGANISM: Escherichia coli

<400> SEQUENCE: 153
atgacggaca aattgacctc ccttcgtcag tacaccaccg tagtggccga cactggggac     60

```
atcgcggcaa tgaagctgta tcaaccgcag gatgccacaa ccaacccttc tctcattctt    120
aacgcagcgc agattccgga ataccgtaag ttgattgatg atgctgtcgc ctgggcgaaa    180
cagcagagca acgatcgcgc gcagcagatc gtggacgcga ccgacaaact ggcagtaaat    240
attggtctgg aaatcctgaa actggttccg ggccgtatct caactgaagt tgatgcgcgt    300
ctttcctatg acaccgaagc gtcaattgcg aaagcaaaac gcctgatcaa actctacaac    360
gatgctggta ttagcaacga tcgtattctg atcaaactgg cttctacctg caggggtatc    420
cgtgctgcag aacagctgga aaagaaggc atcaactgta acctgaccct gctgttctcc     480
ttcgctcagg ctcgtgcttg tgcggaagcg ggcgtgttcc tgatctcgcc gtttgttggc    540
cgtattcttg actggtacaa agcgaatacc gataagaaag agtacgctcc ggcagaagat    600
ccgggcgtgg tttctgtatc tgaaatctac cagtactaca aagagcacgg ttatgaaacc    660
gtggttatgg gcgcaagctt ccgtaacatc ggcgaaattc tggaactggc aggctgcgac    720
cgtctgacca tcgcaccggc actgctgaaa gagctggcgg agagcgaagg ggctatcgaa    780
cgtaaactgt cttacaccgg cgaagtgaaa gcgcgtccgg cgcgtatcac tgagtccgag    840
ttcctgtggc agcacaacca ggatccaatg gcagtagata aactggcgga aggtatccgt    900
aagtttgcta ttgaccagga aaaactggaa aaaatgatcg gcgatctgct gtaa          954

<210> SEQ ID NO 154
<211> LENGTH: 317
<212> TYPE: PRT
<213> ORGANISM: Escherichia coli

<400> SEQUENCE: 154

Met Thr Asp Lys Leu Thr Ser Leu Arg Gln Tyr Thr Thr Val Val Ala
1               5                   10                  15

Asp Thr Gly Asp Ile Ala Ala Met Lys Leu Tyr Gln Pro Gln Asp Ala
                20                  25                  30

Thr Thr Asn Pro Ser Leu Ile Leu Asn Ala Ala Gln Ile Pro Glu Tyr
            35                  40                  45

Arg Lys Leu Ile Asp Asp Ala Val Ala Trp Ala Lys Gln Gln Ser Asn
        50                  55                  60

Asp Arg Ala Gln Gln Ile Val Asp Ala Thr Asp Lys Leu Ala Val Asn
65                  70                  75                  80

Ile Gly Leu Glu Ile Leu Lys Leu Val Pro Gly Arg Ile Ser Thr Glu
                85                  90                  95

Val Asp Ala Arg Leu Ser Tyr Asp Thr Glu Ala Ser Ile Ala Lys Ala
            100                 105                 110

Lys Arg Leu Ile Lys Leu Tyr Asn Asp Ala Gly Ile Ser Asn Asp Arg
        115                 120                 125

Ile Leu Ile Lys Leu Ala Ser Thr Trp Gln Gly Ile Arg Ala Ala Glu
130                 135                 140

Gln Leu Glu Lys Glu Gly Ile Asn Cys Asn Leu Thr Leu Leu Phe Ser
145                 150                 155                 160

Phe Ala Gln Ala Arg Ala Cys Ala Glu Ala Gly Val Phe Leu Ile Ser
                165                 170                 175

Pro Phe Val Gly Arg Ile Leu Asp Trp Tyr Lys Ala Asn Thr Asp Lys
            180                 185                 190

Lys Glu Tyr Ala Pro Ala Glu Asp Pro Gly Val Val Ser Val Ser Glu
        195                 200                 205

Ile Tyr Gln Tyr Tyr Lys Glu His Gly Tyr Glu Thr Val Val Met Gly
210                 215                 220
```

Ala Ser Phe Arg Asn Ile Gly Glu Ile Leu Glu Leu Ala Gly Cys Asp
225                 230                 235                 240

Arg Leu Thr Ile Ala Pro Ala Leu Leu Lys Glu Leu Ala Glu Ser Glu
            245                 250                 255

Gly Ala Ile Glu Arg Lys Leu Ser Tyr Thr Gly Glu Val Lys Ala Arg
        260                 265                 270

Pro Ala Arg Ile Thr Glu Ser Glu Phe Leu Trp Gln His Asn Gln Asp
    275                 280                 285

Pro Met Ala Val Asp Lys Leu Ala Glu Gly Ile Arg Lys Phe Ala Ile
290                 295                 300

Asp Gln Glu Lys Leu Glu Lys Met Ile Gly Asp Leu Leu
305                 310                 315

<210> SEQ ID NO 155
<211> LENGTH: 954
<212> TYPE: DNA
<213> ORGANISM: Escherichia coli

<400> SEQUENCE: 155
atgacggaca aattgacctc ccttcgtcag tacaccaccg tagtggccga cactggggac        60
atcgcggcaa tgaagctgta tcaaccgcag gatgccacaa ccaacccttc tctcattctt       120
aacgcagcgc agattccgga ataccgtaag ttgattgatg atgctgtcgc ctgggcgaaa       180
cagcagagca acgatcgcgc gcagcagatc gtggacgcga ccgacaaact ggcagtaaat       240
attggtctgg aaatcctgaa actggttccg ggccgtatct caactgaagt tgatgcgcgt       300
ctttcctatg acaccgaagc gtcaattgcg aaagcaaaac gcctgatcaa actctacaac       360
gatgctggta ttagcaacga tcgtattctg atcaaactgg cttctacctg cagggtatc       420
cgtgctgcag aacagctgga aaagaaggc atcaactgta acctgaccct gctgttctcc       480
ttcgctcagg ctcgtgcttg tgcggaagcg ggcgtgttcc tgatctcgcc gtttgttggc       540
cgtattcttg actggtacaa agcgaatacc gataagaaag agtacgctcc ggcagaagat       600
ccgggcgtgg tttctgtatc tgaaatctac cagtactaca agagcacgg ttatgaaacc       660
gtggttatgg gcgcaagctt ccgtaacatc ggcgaaattc tggaactggc aggctgcgac       720
cgtctgacca tcgcaccggc actgctgaaa gagctggcgg agagcgaagg gctatcgaa       780
cgtaaactgt cttacaccgg cgaagtgaaa gcgcgtccgg cgcgtatcac tgagtccgag       840
ttcctgtggc agcacaacca ggatccaatg gcagtagata aactggcgga aggtatccgt       900
aagtttgcta ttgaccagga aaaactggaa aaatgatcg gcgatctgct gtaa            954

<210> SEQ ID NO 156
<211> LENGTH: 317
<212> TYPE: PRT
<213> ORGANISM: Escherichia coli

<400> SEQUENCE: 156

Met Thr Asp Lys Leu Thr Ser Leu Arg Gln Tyr Thr Thr Val Val Ala
1               5                   10                  15

Asp Thr Gly Asp Ile Ala Ala Met Lys Leu Tyr Gln Pro Gln Asp Ala
            20                  25                  30

Thr Thr Asn Pro Ser Leu Ile Leu Asn Ala Ala Gln Ile Pro Glu Tyr
        35                  40                  45

Arg Lys Leu Ile Asp Asp Ala Val Ala Trp Ala Lys Gln Gln Ser Asn
    50                  55                  60

Asp Arg Ala Gln Gln Ile Val Asp Ala Thr Asp Lys Leu Ala Val Asn
65                  70                  75                  80

Ile Gly Leu Glu Ile Leu Lys Leu Val Pro Gly Arg Ile Ser Thr Glu
                85                  90                  95

Val Asp Ala Arg Leu Ser Tyr Asp Thr Glu Ala Ser Ile Ala Lys Ala
            100                 105                 110

Lys Arg Leu Ile Lys Leu Tyr Asn Asp Ala Gly Ile Ser Asn Asp Arg
        115                 120                 125

Ile Leu Ile Lys Leu Ala Ser Thr Trp Gln Gly Ile Arg Ala Ala Glu
130                 135                 140

Gln Leu Glu Lys Glu Gly Ile Asn Cys Asn Leu Thr Leu Leu Phe Ser
145                 150                 155                 160

Phe Ala Gln Ala Arg Ala Cys Ala Glu Ala Gly Val Phe Leu Ile Ser
                165                 170                 175

Pro Phe Val Gly Arg Ile Leu Asp Trp Tyr Lys Ala Asn Thr Asp Lys
            180                 185                 190

Lys Glu Tyr Ala Pro Ala Glu Asp Pro Gly Val Val Ser Val Ser Glu
        195                 200                 205

Ile Tyr Gln Tyr Tyr Lys Glu His Gly Tyr Glu Thr Val Val Met Gly
210                 215                 220

Ala Ser Phe Arg Asn Ile Gly Glu Ile Leu Glu Leu Ala Gly Cys Asp
225                 230                 235                 240

Arg Leu Thr Ile Ala Pro Ala Leu Leu Lys Glu Leu Ala Glu Ser Glu
                245                 250                 255

Gly Ala Ile Glu Arg Lys Leu Ser Tyr Thr Gly Glu Val Lys Ala Arg
            260                 265                 270

Pro Ala Arg Ile Thr Glu Ser Glu Phe Leu Trp Gln His Asn Gln Asp
        275                 280                 285

Pro Met Ala Val Asp Lys Leu Ala Glu Gly Ile Arg Lys Phe Ala Ile
290                 295                 300

Asp Gln Glu Lys Leu Glu Lys Met Ile Gly Asp Leu Leu
305                 310                 315

<210> SEQ ID NO 157
<211> LENGTH: 678
<212> TYPE: DNA
<213> ORGANISM: Escherichia coli

<400> SEQUENCE: 157
atgaaacagt atttgattgc cccctcaatt ctgtcggctg attttgcccg cctgggtgaa      60
gataccgcaa agccctggc agctggcgct gatgtcgtgc attttgacgt catggataac     120
cactatgttc ccaatctgac gattgggcca atggtgctga atccttgcg taactatggc     180 attaccgccc ctatcgacgt acacctgatg gtgaaacccg tcgatcgcat tgtgcctgat     240
ttcgctgccg ctggtgccag catcattacc tttcatccag aagcctccga gcatgttgac     300
cgcacgctgc aactgattaa agaaaatggc tgtaaagcgg gtctggtatt aacccggcg     360 acacctctga gctatctgga ttacgtgatg gataagctgg atgtgatcct gctgatgtcc     420
gtcaaccctg gtttcggcgg tcagtctttc attcctcaaa cactggataa actgcgcgaa     480
gtacgtcgcc gtatcgacga gtctggcttt gacattcgac tagaagtgga cggtggcgtg     540
aaggtgaaca acattggcga aatcgctgcg gcgggcgcgg atatgttcgt cgccggttcg     600
gcaatcttcg accagccaga ctacaaaaaa gtcattgatg aaatgcgcag tgaactggca     660
aaggtaagtc atgaataa                                                   678

<210> SEQ ID NO 158
<211> LENGTH: 225
<212> TYPE: PRT
<213> ORGANISM: Escherichia coli

<400> SEQUENCE: 158

Met Lys Gln Tyr Leu Ile Ala Pro Ser Ile Leu Ser Ala Asp Phe Ala
1               5                   10                  15

Arg Leu Gly Glu Asp Thr Ala Lys Ala Leu Ala Ala Gly Ala Asp Val
            20                  25                  30

Val His Phe Asp Val Met Asp Asn His Tyr Val Pro Asn Leu Thr Ile
        35                  40                  45

Gly Pro Met Val Leu Lys Ser Leu Arg Asn Tyr Gly Ile Thr Ala Pro
    50                  55                  60

Ile Asp Val His Leu Met Val Lys Pro Val Asp Arg Ile Val Pro Asp
65                  70                  75                  80

Phe Ala Ala Ala Gly Ala Ser Ile Ile Thr Phe His Pro Glu Ala Ser
                85                  90                  95

Glu His Val Asp Arg Thr Leu Gln Leu Ile Lys Glu Asn Gly Cys Lys
            100                 105                 110

Ala Gly Leu Val Phe Asn Pro Ala Thr Pro Leu Ser Tyr Leu Asp Tyr
        115                 120                 125

Val Met Asp Lys Leu Asp Val Ile Leu Leu Met Ser Val Asn Pro Gly
    130                 135                 140

Phe Gly Gly Gln Ser Phe Ile Pro Gln Thr Leu Asp Lys Leu Arg Glu
145                 150                 155                 160

Val Arg Arg Arg Ile Asp Glu Ser Gly Phe Asp Ile Arg Leu Glu Val
                165                 170                 175

Asp Gly Gly Val Lys Val Asn Asn Ile Gly Glu Ile Ala Ala Ala Gly
            180                 185                 190

Ala Asp Met Phe Val Ala Gly Ser Ala Ile Phe Asp Gln Pro Asp Tyr
        195                 200                 205

Lys Lys Val Ile Asp Glu Met Arg Ser Glu Leu Ala Lys Val Ser His
    210                 215                 220

Glu
225

<210> SEQ ID NO 159
<211> LENGTH: 1416
<212> TYPE: DNA
<213> ORGANISM: Escherichia coli

<400> SEQUENCE: 159
gtgaaacaaa gcactattgc actggcactc ttaccgttac tgtttacccc tgtgacaaaa      60
gcccggacac cagaaatgcc tgttctggaa aaccgggctg tcagggcga ttattactgca     120 cccggcggtg ctcgccgttt aacgggtgat cagactgccg ctctgcgtga ttctcttagc     180
gataaacctg caaaaaatat tattttgctg attggcgatg ggatggggga ctcggaaatt     240
actgccgcac gtaattatgc cgaaggtgcg ggcggctttt ttaaaggtat agatgcctta     300
ccgcttaccg ggcaatacac tcactatgcg ctgaataaaa aaaccggcaa accggactac     360
gtcaccgact cggctgcatc agcaaccgcc tggtcaaccg tgtcaaaac ctataacggc     420 gcgctgggcg tcgatattca cgaaaaagat caccccaacga ttctggaaat ggcaaaagcc     480
gcaggtctgg cgaccggtaa cgtttctacc gcagagttgc aggatgccac gcccgctgcg     540

-continued

```
ctggtggcac atgtgacctc gcgcaaatgc tacggtccga gcgcgaccag tgaaaaatgt    600
ccgggtaacg ctctggaaaa aggcggaaaa ggatcgatta ccgaacagct gcttaacgct    660
cgtgccgacg ttacgcttgg cggcggcgca aaacctttg ctgaaacggc aaccgctggt     720
gaatggcagg aaaaacgct gcgtgaacag gcacaggcgc gtggttatca gttggtgagc     780
gatgctgcct cactgaattc ggtgacggaa gcgaatcagc aaaaacccct gcttggcctg    840
tttgctgacg caatatgcc agtgcgctgg ctaggaccga agcaacgta ccatggcaat      900 atcgataagc ccgcagtcac ctgtacgcca aatccgcaac gtaatgacag tgtaccaacc    960
ctggcgcaga tgaccgacaa agccattgaa ttgttgagta aaatgagaa aggcttttc     1020 ctgcaagttg aaggtgcgtc aatcgataaa caggatcatg ctgcgaatcc ttgtgggcaa   1080
attggcgaga cggtcgatct cgatgaagcc gtacaacggg cgctggaatt cgctaaaaag   1140
gagggtaaca cgctggtcat agtcaccgct gatcacgccc acgccagcca gattgttgcg   1200
ccggatacca aagctccggg cctcacccag gcgctaaata ccaaagatgg cgcagtgatg   1260
gtgatgagtt acgggaactc cgaagaggat tcacaagaac ataccggcag tcagttgcgt   1320
attgcggcgt atggcccgca tgccgccaat gttgttggac tgaccgacca gaccgatctc   1380
ttctacacca tgaaagccgc tctggggctg aaataa                             1416
```

<210> SEQ ID NO 160
<211> LENGTH: 471
<212> TYPE: PRT
<213> ORGANISM: Escherichia coli

<400> SEQUENCE: 160

```
Met Lys Gln Ser Thr Ile Ala Leu Ala Leu Leu Pro Leu Leu Phe Thr
1               5                   10                  15

Pro Val Thr Lys Ala Arg Thr Pro Glu Met Pro Val Leu Glu Asn Arg
            20                  25                  30

Ala Ala Gln Gly Asp Ile Thr Ala Pro Gly Gly Ala Arg Arg Leu Thr
        35                  40                  45

Gly Asp Gln Thr Ala Ala Leu Arg Asp Ser Leu Ser Asp Lys Pro Ala
    50                  55                  60

Lys Asn Ile Ile Leu Leu Ile Gly Asp Gly Met Gly Asp Ser Glu Ile
65                  70                  75                  80

Thr Ala Ala Arg Asn Tyr Ala Glu Gly Ala Gly Gly Phe Phe Lys Gly
                85                  90                  95

Ile Asp Ala Leu Pro Leu Thr Gly Gln Tyr Thr His Tyr Ala Leu Asn
            100                 105                 110

Lys Lys Thr Gly Lys Pro Asp Tyr Val Thr Asp Ser Ala Ala Ser Ala
        115                 120                 125

Thr Ala Trp Ser Thr Gly Val Lys Thr Tyr Asn Gly Ala Leu Gly Val
    130                 135                 140

Asp Ile His Glu Lys Asp His Pro Thr Ile Leu Glu Met Ala Lys Ala
145                 150                 155                 160

Ala Gly Leu Ala Thr Gly Asn Val Ser Thr Ala Glu Leu Gln Asp Ala
                165                 170                 175

Thr Pro Ala Ala Leu Val Ala His Val Thr Ser Arg Lys Cys Tyr Gly
            180                 185                 190

Pro Ser Ala Thr Ser Glu Lys Cys Pro Gly Asn Ala Leu Glu Lys Gly
        195                 200                 205

Gly Lys Gly Ser Ile Thr Glu Gln Leu Leu Asn Ala Arg Ala Asp Val
```

```
                  210                 215                 220
Thr Leu Gly Gly Gly Ala Lys Thr Phe Ala Glu Thr Ala Thr Ala Gly
225                 230                 235                 240

Glu Trp Gln Gly Lys Thr Leu Arg Glu Gln Ala Gln Ala Arg Gly Tyr
                245                 250                 255

Gln Leu Val Ser Asp Ala Ala Ser Leu Asn Ser Val Thr Glu Ala Asn
                260                 265                 270

Gln Gln Lys Pro Leu Leu Gly Leu Phe Ala Asp Gly Asn Met Pro Val
                275                 280                 285

Arg Trp Leu Gly Pro Lys Ala Thr Tyr His Gly Asn Ile Asp Lys Pro
                290                 295                 300

Ala Val Thr Cys Thr Pro Asn Pro Gln Arg Asn Asp Ser Val Pro Thr
305                 310                 315                 320

Leu Ala Gln Met Thr Asp Lys Ala Ile Glu Leu Leu Ser Lys Asn Glu
                325                 330                 335

Lys Gly Phe Phe Leu Gln Val Glu Gly Ala Ser Ile Asp Lys Gln Asp
                340                 345                 350

His Ala Ala Asn Pro Cys Gly Gln Ile Gly Glu Thr Val Asp Leu Asp
                355                 360                 365

Glu Ala Val Gln Arg Ala Leu Glu Phe Ala Lys Lys Glu Gly Asn Thr
370                 375                 380

Leu Val Ile Val Thr Ala Asp His Ala His Ala Ser Gln Ile Val Ala
385                 390                 395                 400

Pro Asp Thr Lys Ala Pro Gly Leu Thr Gln Ala Leu Asn Thr Lys Asp
                405                 410                 415

Gly Ala Val Met Val Met Ser Tyr Gly Asn Ser Glu Glu Asp Ser Gln
                420                 425                 430

Glu His Thr Gly Ser Gln Leu Arg Ile Ala Ala Tyr Gly Pro His Ala
                435                 440                 445

Ala Asn Val Val Gly Leu Thr Asp Gln Thr Asp Leu Phe Tyr Thr Met
                450                 455                 460

Lys Ala Ala Leu Gly Leu Lys
465                 470

<210> SEQ ID NO 161
<211> LENGTH: 1858
<212> TYPE: DNA
<213> ORGANISM: Arabidopsis thaliana

<400> SEQUENCE: 161
cacgtggcga agaatagtcc ccgaatcttc ctctgacgac catttgatac ttttttttct    60
tcagtttgtt ggttttgtcc tcttaacaaa atattcttca aactctctct gttgtttgtt   120
tgttgacaaa tctctcaaaa ccatttgttt tgcaatcgca gatccgtttt tcttcgggtc   180
tcatcacaat gaatggcttc tctgatctta atccttctga gaggtacgct ttgtctgatc   240
atcaatgatg cttataataa tctcatttat acatgatctt gcctctatat atttgttcat   300
cttagtaatc ttcggtctca gcttccattt tcgtctccca ctatgtttct aggattttgt   360
gttacttttg ttagaaaact gcgattttg tgctagtgtt tgtttctcca agatcaatgg   420
aactcgttgc ctaaaattcc tgattatagt tacataaaca tcaaatggtt ctaattggtc   480
tttgatctta aacccatttg attatggtat ctaaagtttg atccttttga tgcactctca   540
tcgcagtttc tcgtgatttt aatattattg aactcttttg atttgtggtg aagcaaacct   600
tctctgtcac aactagctcc attagaagcc attctgtttg atgttgatgg aacactctgt   660
```

```
gactcagatc ccatccacct tattgccttc aagaactgc ttcaagaggt tccttgcttt    720
ttttaatgtc attataactt ccaaatttac aacaagactt tagaaaactg tgaataatat    780
gctatggaac cttgctatta ctcagtttca agctctcgtg tcaatcaatt ttgtttcttt    840
ctatcattcg cagattggtt ttaacaatgg tgtcccaatc gatgagaaat tctttgttga    900
gaacattgct ggaaaacaca attctgaaat tgctctactt ctgttccctg atgatgtttc    960
aagagggtta aaattctgtg atgaaaagga agctctttac cgcaagtaag ctattttttct   1020 gtgtttcctc cattcttta atgtcacaaa ctcttttcag gtctgagttc atttggagta    1080
actttgtttt gttctttttt cttgatgatt agaattgttg cagagaagat aaagccactt    1140
gatgggctta taaaactgac caaatggatc gaagatcgtg gattgaaacg agctgcggta    1200
acaaacgctc caaagaaaaa cgcagagctc atgatatcga acttggtct gactgatttc    1260 tttcaagcag tgattcttgg ctctgaatgt gaatttccca aaccacaccc tggaccttac    1320
ttgaaggctc ttgaagtgct taacgtgtca aaggagcaca cgctagtttt cgaagactcg    1380
atctctggga taaaagctgg agttgcagct ggaatgccag tgattggact gactacaggg    1440
aatccagcaa gcctgcttat gcaagcaaaa cccgcttttc tcatcgagaa ctatgcggat    1500
ccaaaactgt gggctgtgtt ggaagaactt gataacaagt cttaagtctc acttgtttgg    1560
cttatggaaa cccacacatg catgagcagc tctgaagtt taccttatgt cttagatgat    1620
cattgttgaa taattcattg ggagtttatg acaatgggag ctttcaaata tctgattatt    1680
ttgtattgat acatgcacaa tgctagattt gtatccagga gatagttgca taaaccaata    1740
tactataccc tcggatctta gcttattttc attgatatct tgttgtttg tgctgtaaac    1800 atatcagctt ttgaatacat ttggtccatg gcgcaaaata agactttttt tttttttt     1858
```

<210> SEQ ID NO 162
<211> LENGTH: 244
<212> TYPE: PRT
<213> ORGANISM: Arabidopsis thaliana

<400> SEQUENCE: 162

```
Met Asn Gly Phe Ser Asp Leu Asn Pro Ser Glu Ser Lys Pro Ser Leu
1               5                   10                  15

Ser Gln Leu Ala Pro Leu Glu Ala Ile Leu Phe Asp Val Asp Gly Thr
            20                  25                  30

Leu Cys Asp Ser Asp Pro Ile His Leu Ile Ala Phe Gln Glu Leu Leu
        35                  40                  45

Gln Glu Ile Gly Phe Asn Asn Gly Val Pro Ile Asp Glu Lys Phe Phe
    50                  55                  60

Val Glu Asn Ile Ala Gly Lys His Asn Ser Glu Ile Ala Leu Leu Leu
65                  70                  75                  80

Phe Pro Asp Asp Val Ser Arg Gly Leu Lys Phe Cys Asp Glu Lys Glu
                85                  90                  95

Ala Leu Tyr Arg Lys Ile Val Ala Glu Lys Ile Lys Pro Leu Asp Gly
            100                 105                 110

Leu Ile Lys Leu Thr Lys Trp Ile Glu Asp Arg Gly Leu Lys Arg Ala
        115                 120                 125

Ala Val Thr Asn Ala Pro Lys Glu Asn Ala Glu Leu Met Ile Ser Lys
    130                 135                 140

Leu Gly Leu Thr Asp Phe Phe Gln Ala Val Ile Leu Gly Ser Glu Cys
145                 150                 155                 160
```

```
Glu Phe Pro Lys Pro His Pro Gly Pro Tyr Leu Lys Ala Leu Glu Val
            165                 170                 175

Leu Asn Val Ser Lys Glu His Thr Leu Val Phe Glu Asp Ser Ile Ser
        180                 185                 190

Gly Ile Lys Ala Gly Val Ala Ala Gly Met Pro Val Ile Gly Leu Thr
        195                 200                 205

Thr Gly Asn Pro Ala Ser Leu Leu Met Gln Ala Lys Pro Ala Phe Leu
    210                 215                 220

Ile Glu Asn Tyr Ala Asp Pro Lys Leu Trp Ala Val Leu Glu Glu Leu
225                 230                 235                 240

Asp Asn Lys Ser

<210> SEQ ID NO 163
<211> LENGTH: 819
<212> TYPE: DNA
<213> ORGANISM: Bacillus subtilis

<400> SEQUENCE: 163
atgcgtatta tggccagtca tgatacgcct gtgtcaccgg ctggcattct gattgacttg      60
gacggtactg tattcagagg aaatgagttg atcgaaggag caagagaagc gatcaaaacg     120
cttaggagaa tgggaaagaa aatcgtcttt ttaagcaacc gggggaatat ctcccgtgcc     180
atgtgcagaa aaaacttct tggcgcgggg attgaaacgg acgtaaacga cattgttctg     240
tcatcaagcg tgacagcggc tttctgaaa aaacattatc gttttcaaa ggtatgggtg      300 cttggggagc aaggcttggt tgacgagctg aggctggccg tgtgcagaa cgcgagcgaa     360 ccgaaggaag cggattggct cgtgatctcc cttcatgaaa cgctcacgta cgacgattta     420
aatcaagcct ttcaagcggc tgccggcggc gctcgtatta cgctacaaa caaagaccgc     480 tcttttccga cgaagacgg aaatgccatt gatgtggccg gaatgatcgg ggcaattgag     540
acttctgcac aagcgaagac tgaacttgtt gtcggaaaac cgtcatggct gatggcggag     600
gctgcctgta cagcaatggg gctgtccgca catgaatgca tgattataggagacagcatt     660 gaatctgaca ttgcgatggg gaagctttat ggcatgaaa gcgccttagt gctaactggt     720
tctgcgaaac agggtgaaca cgtttgtac acgccggatt atgtgctgga ttctattaag     780
gatgtaacca aattggctga ggaggggatt ctgatatga                          819

<210> SEQ ID NO 164
<211> LENGTH: 272
<212> TYPE: PRT
<213> ORGANISM: Bacillus subtilis

<400> SEQUENCE: 164

Met Arg Ile Met Ala Ser His Asp Thr Pro Val Ser Pro Ala Gly Ile
1               5                   10                  15

Leu Ile Asp Leu Asp Gly Thr Val Phe Arg Gly Asn Glu Leu Ile Glu
            20                  25                  30

Gly Ala Arg Glu Ala Ile Lys Thr Leu Arg Arg Met Gly Lys Lys Ile
        35                  40                  45

Val Phe Leu Ser Asn Arg Gly Asn Ile Ser Arg Ala Met Cys Arg Lys
    50                  55                  60

Lys Leu Leu Gly Ala Gly Ile Glu Thr Asp Val Asn Asp Ile Val Leu
65                  70                  75                  80

Ser Ser Ser Val Thr Ala Ala Phe Leu Lys Lys His Tyr Arg Phe Ser
                85                  90                  95
```

```
Lys Val Trp Val Leu Gly Glu Gln Gly Leu Val Asp Glu Leu Arg Leu
            100                 105                 110

Ala Gly Val Gln Asn Ala Ser Glu Pro Lys Glu Ala Asp Trp Leu Val
            115                 120                 125

Ile Ser Leu His Glu Thr Leu Thr Tyr Asp Asp Leu Asn Gln Ala Phe
        130                 135                 140

Gln Ala Ala Ala Gly Gly Ala Arg Ile Ile Ala Thr Asn Lys Asp Arg
145                 150                 155                 160

Ser Phe Pro Asn Glu Asp Gly Asn Ala Ile Asp Val Ala Gly Met Ile
                165                 170                 175

Gly Ala Ile Glu Thr Ser Ala Gln Ala Lys Thr Glu Leu Val Val Gly
            180                 185                 190

Lys Pro Ser Trp Leu Met Ala Glu Ala Ala Cys Thr Ala Met Gly Leu
            195                 200                 205

Ser Ala His Glu Cys Met Ile Ile Gly Asp Ser Ile Glu Ser Asp Ile
        210                 215                 220

Ala Met Gly Lys Leu Tyr Gly Met Lys Ser Ala Leu Val Leu Thr Gly
225                 230                 235                 240

Ser Ala Lys Gln Gly Glu Gln Arg Leu Tyr Thr Pro Asp Tyr Val Leu
                245                 250                 255

Asp Ser Ile Lys Asp Val Thr Lys Leu Ala Glu Glu Gly Ile Leu Ile
            260                 265                 270

<210> SEQ ID NO 165
<211> LENGTH: 825
<212> TYPE: DNA
<213> ORGANISM: Pseudomonas fluorescens

<400> SEQUENCE: 165
atgagtgacg cagcgattca tcccatccgt tttatcctca gtgacgtgga cggcaccttg     60
ctgcatcccg atcatagcct cagccaacgc accgccgacg cggtgcgcgc cttgcgcgaa    120
gccggagtgt tgttcagcct ggccagcggg cgcccgccca aggccatgct gcacctgatc    180
gaaacctttg gatcgatgt gccggtggcg ggcttcaatg gcggtaccct gatcaacccg    240
gatggcagca tcctggttgc ccatcatctg ccggcggaag cggcgctggt taccctggcg    300
ctgttttcag cggagccgga ggtgaagtg tgggtgtttg ccgatggcga ctggctgcgc    360
cgtgacccgt cagggccgat ggagccgcgc gaggcgaatg gcctgggcta tgggccggtg    420
gtggtggaga gtttcgagcc ctacctggac cgggtcgaca agatcgtcgc cgcgagtcac    480
aacacgcaat tattggtaga gctggaggcg cgattgcaac ccaaggtgca ggggctggcc    540
caggtgtcgc gttcgcaacc ggtgtacttg gacgtgaccg cgatgctggc caacaagggc    600
gaggccttga agaccttggc ggcacacctg ggtgtgccca tggagcaaac ggcggcgatt    660
ggcgatggtg gcaatgaccc ggcgatgttt caggtggccg ggttgtcgat tgccatgggg    720
caggcggaag aaaccgtcaa gcgccaggcc agtgtggtga cgggcagcaa catcgaagat    780
ggcgccgccg aagcaatcga acggtttatt ctcgcggcac cttaa                   825

<210> SEQ ID NO 166
<211> LENGTH: 274
<212> TYPE: PRT
<213> ORGANISM: Pseudomonas fluorescens

<400> SEQUENCE: 166

Met Ser Asp Ala Ala Ile His Pro Ile Arg Phe Ile Leu Ser Asp Val
1               5                   10                  15
```

```
Asp Gly Thr Leu Leu His Pro Asp His Ser Leu Ser Gln Arg Thr Ala
            20                  25                  30

Asp Ala Val Arg Ala Leu Arg Glu Ala Gly Val Leu Phe Ser Leu Ala
        35                  40                  45

Ser Gly Arg Pro Pro Lys Ala Met Leu His Leu Ile Glu Thr Phe Gly
 50                  55                  60

Ile Asp Val Pro Val Ala Gly Phe Asn Gly Gly Thr Leu Ile Asn Pro
 65                  70                  75                  80

Asp Gly Ser Ile Leu Val Ala His His Leu Pro Ala Glu Ala Ala Leu
                 85                  90                  95

Val Thr Leu Ala Leu Phe Ser Ala Glu Pro Glu Val Glu Val Trp Val
            100                 105                 110

Phe Ala Asp Gly Asp Trp Leu Arg Arg Asp Pro Ser Gly Pro Met Glu
        115                 120                 125

Pro Arg Glu Ala Asn Gly Leu Gly Tyr Gly Pro Val Val Val Glu Ser
130                 135                 140

Phe Glu Pro Tyr Leu Asp Arg Val Asp Lys Ile Val Ala Ala Ser His
145                 150                 155                 160

Asn Thr Gln Leu Leu Val Glu Leu Glu Ala Arg Leu Gln Pro Lys Val
                165                 170                 175

Gln Gly Leu Ala Gln Val Ser Arg Ser Gln Pro Val Tyr Leu Asp Val
            180                 185                 190

Thr Ala Met Leu Ala Asn Lys Gly Glu Ala Leu Lys Thr Leu Ala Ala
        195                 200                 205

His Leu Gly Val Pro Met Glu Gln Thr Ala Ala Ile Gly Asp Gly Gly
    210                 215                 220

Asn Asp Pro Ala Met Phe Gln Val Ala Gly Leu Ser Ile Ala Met Gly
225                 230                 235                 240

Gln Ala Glu Glu Thr Val Lys Arg Gln Ala Ser Val Val Thr Gly Ser
                245                 250                 255

Asn Ile Glu Asp Gly Ala Ala Glu Ala Ile Glu Arg Phe Ile Leu Ala
            260                 265                 270

Ala Pro

<210> SEQ ID NO 167
<211> LENGTH: 651
<212> TYPE: DNA
<213> ORGANISM: Escherichia coli

<400> SEQUENCE: 167
gtgcggtgca aaggttttct gtttgatctt gatggaacgc tggtggattc cctgcctgcg    60
gtagaacggg cgtggagcaa ctgggccaga cgtcatgggt tagcgccgga agaggtgctg   120
gctttcattc acggtaaaca ggcgatcacc tctctgcgcc attttatggc gggcaaatcc   180
gaggctgata ttgccgccga gtttacgcgt ctggagcaca tcgaggccac ggaaaccgaa   240
ggtattaccg cgcttccggg ggcaatcgcc ttactcagtc atttgaataa agcaggtatt   300
ccgtgggcca ttgtgacttc tggctccatg ccggtagcgc gagcgcgcca taaaatagct   360
gggcttcccg caccagaggt gtttgtaacc gctgagcgag tgaagcgcgg aaaaccagaa   420
cctgatgcgt atctgttagg cgcgcagctg ctggggcttg cgccgcagga gtgtgtggtg   480
gtggaagatg ctcccgctgg cgtgctttct ggcctggcgg cgggttgtca tgtcattgcg   540
gttaacgctc cggcagatac cccgcgcctg aatgaggtcg atttggtcct ccacagtctg   600
```
gagcaaatta ctgtgaccaa acagccaaat ggcgatgtta ttattcagtg a  651

<210> SEQ ID NO 168
<211> LENGTH: 216
<212> TYPE: PRT
<213> ORGANISM: Escherichia coli

<400> SEQUENCE: 168

Met Arg Cys Lys Gly Phe Leu Phe Asp Leu Asp Gly Thr Leu Val Asp
1               5                   10                  15

Ser Leu Pro Ala Val Glu Arg Ala Trp Ser Asn Trp Ala Arg Arg His
            20                  25                  30

Gly Leu Ala Pro Glu Glu Val Leu Ala Phe Ile His Gly Lys Gln Ala
        35                  40                  45

Ile Thr Ser Leu Arg His Phe Met Ala Gly Lys Ser Glu Ala Asp Ile
    50                  55                  60

Ala Ala Glu Phe Thr Arg Leu Glu His Ile Glu Ala Thr Glu Thr Glu
65                  70                  75                  80

Gly Ile Thr Ala Leu Pro Gly Ala Ile Ala Leu Leu Ser His Leu Asn
                85                  90                  95

Lys Ala Gly Ile Pro Trp Ala Ile Val Thr Ser Gly Ser Met Pro Val
            100                 105                 110

Ala Arg Ala Arg His Lys Ile Ala Gly Leu Pro Ala Pro Glu Val Phe
        115                 120                 125

Val Thr Ala Glu Arg Val Lys Arg Gly Lys Pro Glu Pro Asp Ala Tyr
    130                 135                 140

Leu Leu Gly Ala Gln Leu Leu Gly Leu Ala Pro Gln Glu Cys Val Val
145                 150                 155                 160

Val Glu Asp Ala Pro Ala Gly Val Leu Ser Gly Leu Ala Ala Gly Cys
                165                 170                 175

His Val Ile Ala Val Asn Ala Pro Ala Asp Thr Pro Arg Leu Asn Glu
            180                 185                 190

Val Asp Leu Val Leu His Ser Leu Glu Gln Ile Thr Val Thr Lys Gln
        195                 200                 205

Pro Asn Gly Asp Val Ile Ile Gln
    210                 215

<210> SEQ ID NO 169
<211> LENGTH: 816
<212> TYPE: DNA
<213> ORGANISM: Escherichia coli

<400> SEQUENCE: 169
atgagcgtaa aagttatcgt cacagacatg gacggtactt ttcttaacga cgccaaaacg    60
tacaaccaac cacgttttat ggcgcaatat caggaactga aaagcgcgg cattaagttc    120 gttgttgcca gcggtaatca gtattaccag cttatttcat tctttcctga gctaaaggat    180
gagatctctt ttgtcgcgga aaacggcgca ctggtttacg aacatggcaa gcagttgttc    240
cacggcgaac tgacccgaca tgaatcgcgg attgttattg gcgagttgct aaaagataag    300
caactcaatt ttgtcgcctg cggtctgcaa agtgcatatg tcagcgaaaa tgccccgaa    360 gcatttgtcg cactgatggc aaaacactac catcgcctga acctgtaaa agattatcag    420 gagattgacg acgtactgtt caagttttcg ctcaacctgc cggatgaaca atcccgtta    480 gtgatcgaca aactgcacgt agcgctcgat ggcattatga aacccgttac cagtggtttt    540
ggctttatcg acctgattat tcccggtcta cataaagcaa acggtatttc gcggttactg    600

```
aaacgctggg atctgtcacc gcaaaatgtg gtagcgattg gcgacagcgg taacgatgcg    660
gagatgctga aaatggcgcg ttattccttt gcgatgggca atgctgcgga aacattaaa     720 caaatcgccc gttacgctac cgatgataat aatcatgaag gcgcgctgaa tgtgattcag    780
gcggtgctgg ataacacatc ccctttttaac agctga                             816
```

<210> SEQ ID NO 170
<211> LENGTH: 271
<212> TYPE: PRT
<213> ORGANISM: Escherichia coli

<400> SEQUENCE: 170

```
Met Ser Val Lys Val Ile Val Thr Asp Met Asp Gly Thr Phe Leu Asn
1               5                   10                  15

Asp Ala Lys Thr Tyr Asn Gln Pro Arg Phe Met Ala Gln Tyr Gln Glu
            20                  25                  30

Leu Lys Lys Arg Gly Ile Lys Phe Val Val Ala Ser Gly Asn Gln Tyr
        35                  40                  45

Tyr Gln Leu Ile Ser Phe Phe Pro Glu Leu Lys Asp Glu Ile Ser Phe
    50                  55                  60

Val Ala Glu Asn Gly Ala Leu Val Tyr Glu His Gly Lys Gln Leu Phe
65                  70                  75                  80

His Gly Glu Leu Thr Arg His Glu Ser Arg Ile Val Ile Gly Glu Leu
                85                  90                  95

Leu Lys Asp Lys Gln Leu Asn Phe Val Ala Cys Gly Leu Gln Ser Ala
            100                 105                 110

Tyr Val Ser Glu Asn Ala Pro Glu Ala Phe Val Ala Leu Met Ala Lys
        115                 120                 125

His Tyr His Arg Leu Lys Pro Val Lys Asp Tyr Gln Glu Ile Asp Asp
    130                 135                 140

Val Leu Phe Lys Phe Ser Leu Asn Leu Pro Asp Glu Gln Ile Pro Leu
145                 150                 155                 160

Val Ile Asp Lys Leu His Val Ala Leu Asp Gly Ile Met Lys Pro Val
                165                 170                 175

Thr Ser Gly Phe Gly Phe Ile Asp Leu Ile Ile Pro Gly Leu His Lys
            180                 185                 190

Ala Asn Gly Ile Ser Arg Leu Leu Lys Arg Trp Asp Leu Ser Pro Gln
        195                 200                 205

Asn Val Val Ala Ile Gly Asp Ser Gly Asn Asp Ala Glu Met Leu Lys
    210                 215                 220

Met Ala Arg Tyr Ser Phe Ala Met Gly Asn Ala Ala Glu Asn Ile Lys
225                 230                 235                 240

Gln Ile Ala Arg Tyr Ala Thr Asp Asp Asn Asn His Glu Gly Ala Leu
                245                 250                 255

Asn Val Ile Gln Ala Val Leu Asp Asn Thr Ser Pro Phe Asn Ser
            260                 265                 270
```

<210> SEQ ID NO 171
<211> LENGTH: 813
<212> TYPE: DNA
<213> ORGANISM: Escherichia coli

<400> SEQUENCE: 171

```
atggctatta aactcattgc tatcgatatg gatggcaccc ttctgctgcc cgatcacacc    60
atttcacccg ccgttaaaaa tgcgattgcc gcagctcgcg cccgtggcgt gaatgtcgtg   120
```

```
ctaacgacgg gtcgcccgta tgcaggtgtg cacaactacc tgaaagagct gcatatggaa      180
cagccgggcg actactgcat tacttataac ggcgcgctgg tacagaaggc cgctgatggt      240
agcaccgtgg cgcaaactgc tctcagctat gacgactatc gtttcctgga aaaactctct      300
cgcgaagtcg gttctcattt ccacgccctg accgcacca cgctgtacac cgccaaccgt       360
gatatcagct actacacggt gcatgaatcc ttcgttgcca ccattccgct ggtgttctgc      420
gaagcggaga aaatggaccc caataccag ttcctgaaag tgatgatgat tgatgaaccc       480
gccatcctcg accaggctat cgcgcgtatt ccgcaggaag tgaaagagaa atataccgtg      540
ctgaaaagtg cgccgtactt cctcgaaatc ctcgataaac gcgttaacaa aggtacgggg      600
gtgaaatcac tggccgacgt gttaggtatt aaaccggaag aaatcatggc gattggcgat      660
caggaaaacg atatcgcaat gattgaatat gcaggcgtcg gtgtggcgat ggataacgct      720
attccttcag tgaaagaagt ggcgaacttt gtcaccaaat ctaaccttga agatggcgtg      780
gcgtttgcta ttgagaagta tgtgctgaat taa                                  813
```

<210> SEQ ID NO 172
<211> LENGTH: 270
<212> TYPE: PRT
<213> ORGANISM: Escherichia coli

<400> SEQUENCE: 172

```
Met Ala Ile Lys Leu Ile Ala Ile Asp Met Asp Gly Thr Leu Leu
1               5                   10                  15

Pro Asp His Thr Ile Ser Pro Ala Val Lys Asn Ala Ile Ala Ala
                20                  25                  30

Arg Ala Arg Gly Val Asn Val Val Leu Thr Thr Gly Arg Pro Tyr Ala
            35                  40                  45

Gly Val His Asn Tyr Leu Lys Glu Leu His Met Glu Gln Pro Gly Asp
        50                  55                  60

Tyr Cys Ile Thr Tyr Asn Gly Ala Leu Val Gln Lys Ala Ala Asp Gly
65                  70                  75                  80

Ser Thr Val Ala Gln Thr Ala Leu Ser Tyr Asp Asp Tyr Arg Phe Leu
                85                  90                  95

Glu Lys Leu Ser Arg Glu Val Gly Ser His Phe His Ala Leu Asp Arg
            100                 105                 110

Thr Thr Leu Tyr Thr Ala Asn Arg Asp Ile Ser Tyr Tyr Thr Val His
        115                 120                 125

Glu Ser Phe Val Ala Thr Ile Pro Leu Val Phe Cys Glu Ala Glu Lys
    130                 135                 140

Met Asp Pro Asn Thr Gln Phe Leu Lys Val Met Met Ile Asp Glu Pro
145                 150                 155                 160

Ala Ile Leu Asp Gln Ala Ile Ala Arg Ile Pro Gln Glu Val Lys Glu
                165                 170                 175

Lys Tyr Thr Val Leu Lys Ser Ala Pro Tyr Phe Leu Glu Ile Leu Asp
            180                 185                 190

Lys Arg Val Asn Lys Gly Thr Gly Val Lys Ser Leu Ala Asp Val Leu
        195                 200                 205

Gly Ile Lys Pro Glu Glu Ile Met Ala Ile Gly Asp Gln Glu Asn Asp
    210                 215                 220

Ile Ala Met Ile Glu Tyr Ala Gly Val Gly Val Ala Met Asp Asn Ala
225                 230                 235                 240

Ile Pro Ser Val Lys Glu Val Ala Asn Phe Val Thr Lys Ser Asn Leu
```

```
                    245                 250                 255
Glu Asp Gly Val Ala Phe Ala Ile Glu Lys Tyr Val Leu Asn
            260                 265                 270

<210> SEQ ID NO 173
<211> LENGTH: 867
<212> TYPE: DNA
<213> ORGANISM: Plasmodium falciparum

<400> SEQUENCE: 173
atgcacgaaa ttgtagataa gaatggtaag aaagttcaaa agaataattt gaatgatgaa      60
ataaaaataa tctttacgga tttagatgga acattgttaa atagtgagaa taaggtttca     120
gaacagaatt tggagagttt aataagagct caagaaaaag cataaaggt tgttatagca      180
acaggtagat ctatatttc tgtagagaat gttataggag agcatgtaaa aagaataga      240
ataagtttat taccagggat atatatgaat ggatgtgtaa catttgatga aaaaggttca     300
agggtgatag ataggattat gaacaatgac ttgaaaatgg agatacatga attttctaaa     360
caaataaata tatcaaaata tgctatatgg ttttgtttag aaaaaacata ttgttttgaa     420
ataaatgatt gtatacgtga atatatggag gttgaagcat taaatcctga tgttattgaa     480
gataatatgt tagaaggttt gacagtatat aaagtattat tttcattacc agaaaatata     540
ttagaaaata cgttaaaatt atgtagagag aaatttttctc atcgtattaa tgtagctaat    600
acttttcaaa gttatgttga attatttcat caacatacta taaaattcga aggtgtaaaa     660
gaaatttgta atattataa atataagtcta acaatgcgc tagctatggg agatggagaa     720
aatgatattg aaatgttaag tggtttaaca cattcagtgg gtgtacataa tgcttcagaa     780
aaagtaaaaa attcagctgc ttatgttgga ccttcgaata tgaacatgc tatatctcat     840
gtcttgaaga cattctgtga catataa                                         867

<210> SEQ ID NO 174
<211> LENGTH: 288
<212> TYPE: PRT
<213> ORGANISM: Plasmodium falciparum

<400> SEQUENCE: 174

Met His Glu Ile Val Asp Lys Asn Gly Lys Lys Val Gln Lys Asn Asn
1               5                   10                  15

Leu Asn Asp Glu Ile Lys Ile Ile Phe Thr Asp Leu Asp Gly Thr Leu
            20                  25                  30

Leu Asn Ser Glu Asn Lys Val Ser Glu Gln Asn Leu Glu Ser Leu Ile
        35                  40                  45

Arg Ala Gln Glu Lys Gly Ile Lys Val Val Ile Ala Thr Gly Arg Ser
    50                  55                  60

Ile Phe Ser Val Glu Asn Val Ile Gly Glu His Val Lys Lys Asn Arg
65                  70                  75                  80

Ile Ser Leu Leu Pro Gly Ile Tyr Met Asn Gly Cys Val Thr Phe Asp
                85                  90                  95

Glu Lys Gly Ser Arg Val Ile Asp Arg Ile Met Asn Asn Asp Leu Lys
            100                 105                 110

Met Glu Ile His Glu Phe Ser Lys Gln Ile Asn Ile Ser Lys Tyr Ala
        115                 120                 125

Ile Trp Phe Cys Leu Glu Lys Thr Tyr Cys Phe Glu Ile Asn Asp Cys
    130                 135                 140

Ile Arg Glu Tyr Met Glu Val Glu Ala Leu Asn Pro Asp Val Ile Glu
```

```
                    145                 150                 155                 160
Asp Asn Met Leu Glu Gly Leu Thr Val Tyr Lys Val Leu Phe Ser Leu
                165                 170                 175

Pro Glu Asn Ile Leu Glu Asn Thr Leu Lys Leu Cys Arg Glu Lys Phe
            180                 185                 190

Ser His Arg Ile Asn Val Ala Asn Thr Phe Gln Ser Tyr Val Glu Leu
        195                 200                 205

Phe His Gln His Thr Asn Lys Phe Glu Gly Val Lys Glu Ile Cys Lys
    210                 215                 220

Tyr Tyr Asn Ile Ser Leu Asn Ala Leu Ala Met Gly Asp Gly Glu
225                 230                 235                 240

Asn Asp Ile Glu Met Leu Ser Gly Leu Thr His Ser Val Gly Val His
                245                 250                 255

Asn Ala Ser Glu Lys Val Lys Asn Ser Ala Ala Tyr Val Gly Pro Ser
            260                 265                 270

Asn Asn Glu His Ala Ile Ser His Val Leu Lys Thr Phe Cys Asp Ile
        275                 280                 285

<210> SEQ ID NO 175
<211> LENGTH: 1059
<212> TYPE: DNA
<213> ORGANISM: Enterococcus avium

<400> SEQUENCE: 175
atgagtaaaa caatgaaggg tgtttccaag caggcacccg gttatgacca atggcattt        60 atcgatttat ctgttccaga agcaacagat gacaaggtct tgattaaagt cgcttataca      120
ggtatttgcg atcagatat  ccatacgttt aaaggtgaat acaaaaatcc cactactccc      180
gtcgtcctag acatgaatt  ttctgggcag gtagttgaag tcggagccaa tgtaccaaag      240
gtcaaggttg gtgatcgggt aaccagtgag acgacctttt atgtctgcgg cgaatgcgat      300
tattgcaagg aaaagcagta taatttgtgt ccccatcgaa aaggaatcgg cacgcagcaa      360
aatggctcca tggcgaacta tgtgttggct cgagaagaaa gcattcattt actgccggat      420
catttaagct atgaaggtgc ggcgatgagc gaaccattag cgtgctgtgt ccacgcgatg      480
tatcaaaaga gtcacttgga attaaaagac acgatcatta tcatgggccc tggaccaatc      540
ggactgtatc ttttgcagat tgccaaggaa attggagcct tcgtcattat gacggggatc      600
acaaaagatg ctcatcgctt agcattagca aaaaaactag cgcgcgatgt gatcgttgat      660
acgatgaagg aagatctagc gaaagtcgtc aatgagatca cggatggcta cggtgtcgat      720
aaagtgtatg atgcctcagg agcagttcct gctgttaatg ctagtctgcc attgattcgc      780
aagcaggggc aatttattca gtaggcttg  ttcgctaata aaatggtgga tttagacact      840
gaatcgatca ttcaacgaga gatcgaatac atcggcagtc gttcacagaa cccttatgac      900
tggccgattg cgatccactt attagcgaaa ggtgcgatca atatcgatga gatgattacg      960
aaaaaatacc cgttgactga atggcgggaa gcctttgata aagtgatgga aggcaatgaa     1020
atcaaggtaa tgatcgaatc caatccagaa gaattttaa                            1059

<210> SEQ ID NO 176
<211> LENGTH: 352
<212> TYPE: PRT
<213> ORGANISM: Enterococcus avium

<400> SEQUENCE: 176

Met Ser Lys Thr Met Lys Gly Val Ser Lys Gln Ala Pro Gly Tyr Asp
```

```
  1               5                  10                 15
Gln Met Ala Phe Ile Asp Leu Ser Val Pro Glu Ala Thr Asp Lys
                 20                 25                 30

Val Leu Ile Lys Val Ala Tyr Thr Gly Ile Cys Gly Ser Asp Ile His
                 35                 40                 45

Thr Phe Lys Gly Glu Tyr Lys Asn Pro Thr Thr Pro Val Val Leu Gly
         50                 55                 60

His Glu Phe Ser Gly Gln Val Glu Val Gly Ala Asn Val Pro Lys
65                  70                 75                 80

Val Lys Val Gly Asp Arg Val Thr Ser Glu Thr Thr Phe Tyr Val Cys
                 85                 90                 95

Gly Glu Cys Asp Tyr Cys Lys Glu Lys Gln Tyr Asn Leu Cys Pro His
                 100                105                110

Arg Lys Gly Ile Gly Thr Gln Gln Asn Gly Ser Met Ala Asn Tyr Val
                 115                120                125

Leu Ala Arg Glu Glu Ser Ile His Leu Leu Pro Asp His Leu Ser Tyr
        130                135                140

Glu Gly Ala Ala Met Ser Glu Pro Leu Ala Cys Cys Val His Ala Met
145                 150                155                160

Tyr Gln Lys Ser His Leu Glu Leu Lys Asp Thr Ile Ile Met Gly
                 165                170                175

Pro Gly Pro Ile Gly Leu Tyr Leu Leu Gln Ile Ala Lys Glu Ile Gly
                 180                185                190

Ala Phe Val Ile Met Thr Gly Ile Thr Lys Asp Ala His Arg Leu Ala
                 195                200                205

Leu Ala Lys Lys Leu Gly Ala Asp Val Ile Val Asp Thr Met Lys Glu
         210                215                220

Asp Leu Ala Lys Val Val Asn Glu Ile Thr Asp Gly Tyr Gly Val Asp
225                 230                235                240

Lys Val Tyr Asp Ala Ser Gly Ala Val Pro Ala Val Asn Ala Ser Leu
                 245                250                255

Pro Leu Ile Arg Lys Gln Gly Gln Phe Ile Gln Val Gly Leu Phe Ala
                 260                265                270

Asn Lys Met Val Asp Leu Asp Thr Glu Ser Ile Ile Gln Arg Glu Ile
                 275                280                285

Glu Tyr Ile Gly Ser Arg Ser Gln Asn Pro Tyr Asp Trp Pro Ile Ala
                 290                295                300

Ile His Leu Leu Ala Lys Gly Ala Ile Asn Ile Asp Glu Met Ile Thr
305                 310                315                320

Lys Lys Tyr Pro Leu Thr Glu Trp Arg Glu Ala Phe Asp Lys Val Met
                 325                330                335

Glu Gly Asn Glu Ile Lys Val Met Ile Glu Ser Asn Pro Glu Glu Phe
                 340                345                350

<210> SEQ ID NO 177
<211> LENGTH: 846
<212> TYPE: DNA
<213> ORGANISM: Candida albicans

<400> SEQUENCE: 177
atggattccg catactggtc atacgataac atagtcccaa gcttccgttt ggatggaaaa      60
ctagtcatat taaccggtgg ctctggtggt ttggctgccg tggtatcaag agctttatta     120
gccaaaggtg ccgatgttgc attagtcgat atgaacttgg aagaacacac acaagctgct     180
```

```
agagacgtct tacaatgggg cgaagagcaa atgaaaggta aatacgaatc accaatcggt    240
caggtgagtg cttggtcatg taatattggc gatgctgaag ctgtcgactt gacattcaaa    300
gccatcaacg aacaccacgg caaaatctca agtgtcttgg tcaacactgc cggttacgct    360
gaaaacttcc cagctgaaga gtacccagcc aagaacgctg aaaaccttat gaaagttaac    420
gggttggggt cattctacgt ttcccaagct tttgctagac cattaatcca aaacaacatg    480
accggatcga tcattttgat cgggtcaatg tccggtacca tcgtcaacga cccacaacca    540
caatgcatgt acaacatgtc caaagccggt gtcattcatt tagccagatc attggcctgt    600
gaatgggcta aatacaatat cagagtcaac acattgtcgc cagggtacat cttaaccccca    660 ttgacaagaa acgttattag tggacacacc gaaatgaaga cagaatggga atcaaagatc    720
ccaatgaaga gaatggcaga accaaaagag tttgttggtt ctatcttata cttggcctca    780
gaatctgctt catcatacac tactggtcac aacttggtcg ttgacgggg ttacgagtgc    840 tggtaa                                                               846
```

<210> SEQ ID NO 178
<211> LENGTH: 281
<212> TYPE: PRT
<213> ORGANISM: Candida albicans

<400> SEQUENCE: 178

```
Met Asp Ser Ala Tyr Trp Ser Tyr Asp Asn Ile Val Pro Ser Phe Arg
1               5                   10                  15

Leu Asp Gly Lys Leu Val Ile Leu Thr Gly Gly Ser Gly Gly Leu Ala
            20                  25                  30

Ala Val Val Ser Arg Ala Leu Leu Ala Lys Gly Ala Asp Val Ala Leu
        35                  40                  45

Val Asp Met Asn Leu Glu Arg Thr Gln Gln Ala Ala Arg Asp Val Leu
    50                  55                  60

Gln Trp Gly Glu Glu Gln Met Lys Gly Lys Tyr Glu Ser Pro Ile Gly
65                  70                  75                  80

Gln Val Ser Ala Trp Ser Cys Asn Ile Gly Asp Ala Glu Ala Val Asp
                85                  90                  95

Leu Thr Phe Lys Ala Ile Asn Glu His His Gly Lys Ile Ser Ser Val
            100                 105                 110

Leu Val Asn Thr Ala Gly Tyr Ala Glu Asn Phe Pro Ala Glu Glu Tyr
        115                 120                 125

Pro Ala Lys Asn Ala Glu Asn Leu Met Lys Val Asn Gly Leu Gly Ser
    130                 135                 140

Phe Tyr Val Ser Gln Ala Phe Ala Arg Pro Leu Ile Gln Asn Asn Met
145                 150                 155                 160

Thr Gly Ser Ile Ile Leu Ile Gly Ser Met Ser Gly Thr Ile Val Asn
                165                 170                 175

Asp Pro Gln Pro Gln Cys Met Tyr Asn Met Ser Lys Ala Gly Val Ile
            180                 185                 190

His Leu Ala Arg Ser Leu Ala Cys Glu Trp Ala Lys Tyr Asn Ile Arg
        195                 200                 205

Val Asn Thr Leu Ser Pro Gly Tyr Ile Leu Thr Pro Leu Thr Arg Asn
    210                 215                 220

Val Ile Ser Gly His Thr Glu Met Lys Thr Glu Trp Glu Ser Lys Ile
225                 230                 235                 240

Pro Met Lys Arg Met Ala Glu Pro Lys Glu Phe Val Gly Ser Ile Leu
                245                 250                 255
```

Tyr Leu Ala Ser Glu Ser Ala Ser Ser Tyr Thr Thr Gly His Asn Leu
                    260                 265                 270

Val Val Asp Gly Gly Tyr Glu Cys Trp
        275                 280

<210> SEQ ID NO 179
<211> LENGTH: 849
<212> TYPE: DNA
<213> ORGANISM: Candida tropicalis

<400> SEQUENCE: 179
atggactcct catcatactg gtcatacgac aacattgttc caagttttag attggatgga    60
aaattagtaa ttatcactgg tggttctggt ggtttgtccg ctgttgtttc cagagccttg   120
ttagcaaaag gtgctgatat tgctttgatt gatatgaact tggaaagaac ccaacaagcc   180
gcaagagatg ttttacaatg gggtgaagaa caaatgaaag gaaaacacga atctccaatt   240
ggtcaagtca gtgcttggtc ctgtaacatt ggtgatgctg aagctgttga attgacattc   300
aaagccatca acgaacacca cggtaaagtt gccagtgttt tgattaacac agctggttat   360
gctgaaaatt tccctgctga agaataccca gccaagaatg ccgaaaatat catgaaggtc   420
aatggtttag atccttttta cgtctcacaa gctttcgcca gacctttgat tcaaaataac   480
atgactggct ctattatctt gattggttct atgtctggta ccattgtcaa cgatccacaa   540
ccacaatgta tgtacaacat gtccaaagct ggtgtcattc acttggccag atctttagca   600
tgtgaatggg ccaaatacaa catcagagtc aataccttgt ccccaggtta tattttgact   660
ccattgacaa gaaatgttat tagtggtcac actgaaatga gacagaatg ggaatccaag   720 attccaatga agagaatggc cgagccaaaa gaatttgtcg gttctatttt gtacttggct   780
tctgattctg cctcttccta cactactggt cacaatttgg tagtggatgg tggttacgaa   840
tgttggtaa                                                           849

<210> SEQ ID NO 180
<211> LENGTH: 282
<212> TYPE: PRT
<213> ORGANISM: Candida tropicalis

<400> SEQUENCE: 180

Met Asp Ser Ser Tyr Trp Ser Tyr Asp Asn Ile Val Pro Ser Phe
1               5                   10                  15

Arg Leu Asp Gly Lys Leu Val Ile Ile Thr Gly Gly Ser Gly Gly Leu
                20                  25                  30

Ser Ala Val Val Ser Arg Ala Leu Leu Ala Lys Gly Ala Asp Ile Ala
            35                  40                  45

Leu Ile Asp Met Asn Leu Glu Arg Thr Gln Gln Ala Ala Arg Asp Val
        50                  55                  60

Leu Gln Trp Gly Glu Glu Gln Met Lys Gly Lys His Glu Ser Pro Ile
65                  70                  75                  80

Gly Gln Val Ser Ala Trp Ser Cys Asn Ile Gly Asp Ala Glu Ala Val
                85                  90                  95

Glu Leu Thr Phe Lys Ala Ile Asn Glu His His Gly Lys Val Ala Ser
            100                 105                 110

Val Leu Ile Asn Thr Ala Gly Tyr Ala Glu Asn Phe Pro Ala Glu Glu
        115                 120                 125

Tyr Pro Ala Lys Asn Ala Glu Asn Ile Met Lys Val Asn Gly Leu Gly
    130                 135                 140

Ser Phe Tyr Val Ser Gln Ala Phe Ala Arg Pro Leu Ile Gln Asn Asn
145                 150                 155                 160

Met Thr Gly Ser Ile Ile Leu Ile Gly Ser Met Ser Gly Thr Ile Val
            165                 170                 175

Asn Asp Pro Gln Pro Gln Cys Met Tyr Asn Met Ser Lys Ala Gly Val
        180                 185                 190

Ile His Leu Ala Arg Ser Leu Ala Cys Glu Trp Ala Lys Tyr Asn Ile
    195                 200                 205

Arg Val Asn Thr Leu Ser Pro Gly Tyr Ile Leu Thr Pro Leu Thr Arg
210                 215                 220

Asn Val Ile Ser Gly His Thr Glu Met Lys Thr Glu Trp Glu Ser Lys
225                 230                 235                 240

Ile Pro Met Lys Arg Met Ala Glu Pro Lys Glu Phe Val Gly Ser Ile
                245                 250                 255

Leu Tyr Leu Ala Ser Asp Ser Ala Ser Ser Tyr Thr Thr Gly His Asn
            260                 265                 270

Leu Val Val Asp Gly Gly Tyr Glu Cys Trp
            275                 280

```
<210> SEQ ID NO 181
<211> LENGTH: 1158
<212> TYPE: DNA
<213> ORGANISM: Unknown
<220> FEATURE:
<223> OTHER INFORMATION: Scheffersomyces stipitis Sequence

<400> SEQUENCE: 181
aatttctata gattggtaca aatcatagaa tagagaatcc caatagcaca agctcctgat      60
ttccttgcat tatttgcccg cgctcaagta tttttagac tgagtcttcc atacttcgta     120
ctgatataaa caaatattgc acaaactact actagtgaat tactaatagt ttccaccaaa    180
tacagccact acacactaca tatactacaa tggactactc atacgctaac gttgttccca    240
acttcagatt ggacggaaga ttggctatta ttaccggagg ttctggtggt ttggccgcag    300
tcatttcgcg tgccttgttg gcccagggcg ctgatgttgc tctcattgac atgaacttgg    360
aaagaaccaa gtccgctgcc aaagaagttt tgggctgggg tgaagagacg ttgaagggtg    420
aacacgcttc agccatcggc caagtttccg cctggtcctg aacattggg gatgctgagg     480 cagtagacgc tactttcagc tccatcaacg aacaccacgg caagatcgct gacttgttga    540
ttaacaccgc tggatactgt gaaaacttcc ctgccgaaac gtacccggct actaacgctg    600
aaagcatcat gaaggtgaac ggtttgggct cattctacgt ttcgcaatcg ttcgctagac    660
cattgatcca gaacaacttg agaggctcta tcatcttgat tggctcaatg tctggaacaa    720
ttgtcaacga cccacaaccc caatgtatgt acaacatgtc caaggctgga gtgatccact    780
tggtcagatc gttggcctgc gaatgggcca agtacaacat cagagtcaac accttatcac    840
caggctatat tttgactcct ttaaccagaa acgtgatttc tggccacaca gagatgaagg    900
aagcctggga atccaagatc cccatgaaga gaatggccga acccaaggaa ttcgtggggt    960
ccatcttata cttggcaagc gagactgctt cttcctacac tacgggccac aatttggttg   1020
tggacggagg atatgaatgc tggtagatac cgctcccatt ttaatgaaac gaccacgata   1080
cgacccacag tttaatttca caagtataaa gtttatatgt cgctactgtt ttatagagaa   1140
agccaaaatt gacgaaac                                                 1158
```

```
<210> SEQ ID NO 182
<211> LENGTH: 278
<212> TYPE: PRT
<213> ORGANISM: Unknown
<220> FEATURE:
<223> OTHER INFORMATION: Scheffersomyces stipitis Sequence

<400> SEQUENCE: 182

Met Asp Tyr Ser Tyr Ala Asn Val Val Pro Asn Phe Arg Leu Asp Gly
1               5                   10                  15

Arg Leu Ala Ile Ile Thr Gly Gly Ser Gly Gly Leu Ala Ala Val Ile
            20                  25                  30

Ser Arg Ala Leu Leu Ala Gln Gly Ala Asp Val Ala Leu Ile Asp Met
        35                  40                  45

Asn Leu Glu Arg Thr Lys Ser Ala Ala Lys Glu Val Leu Gly Trp Gly
    50                  55                  60

Glu Glu Thr Leu Lys Gly Glu His Ala Ser Ala Ile Gly Gln Val Ser
65                  70                  75                  80

Ala Trp Ser Cys Asn Ile Gly Asp Ala Glu Ala Val Asp Ala Thr Phe
                85                  90                  95

Ser Ser Ile Asn Glu His His Gly Lys Ile Ala Asp Leu Leu Ile Asn
            100                 105                 110

Thr Ala Gly Tyr Cys Glu Asn Phe Pro Ala Glu Thr Tyr Pro Ala Thr
        115                 120                 125

Asn Ala Glu Ser Ile Met Lys Val Asn Gly Leu Gly Ser Phe Tyr Val
    130                 135                 140

Ser Gln Ser Phe Ala Arg Pro Leu Ile Gln Asn Asn Leu Arg Gly Ser
145                 150                 155                 160

Ile Ile Leu Ile Gly Ser Met Ser Gly Thr Ile Val Asn Asp Pro Gln
                165                 170                 175

Pro Gln Cys Met Tyr Asn Met Ser Lys Ala Gly Val Ile His Leu Val
            180                 185                 190

Arg Ser Leu Ala Cys Glu Trp Ala Lys Tyr Asn Ile Arg Val Asn Thr
        195                 200                 205

Leu Ser Pro Gly Tyr Ile Leu Thr Pro Leu Thr Arg Asn Val Ile Ser
    210                 215                 220

Gly His Thr Glu Met Lys Glu Ala Trp Glu Ser Lys Ile Pro Met Lys
225                 230                 235                 240

Arg Met Ala Glu Pro Lys Glu Phe Val Gly Ser Ile Leu Tyr Leu Ala
                245                 250                 255

Ser Glu Thr Ala Ser Ser Tyr Thr Thr Gly His Asn Leu Val Val Asp
            260                 265                 270

Gly Gly Tyr Glu Cys Trp
        275

<210> SEQ ID NO 183
<211> LENGTH: 1482
<212> TYPE: DNA
<213> ORGANISM: Pseudomonas fluorescens

<400> SEQUENCE: 183
atgaaactga ataagcagaa cctcacccag ctggcgcccg aagtgaaatt gccagcctat    60
acgcttgccg acacacgcca gggcatcgcc catatcggcg tcggcggctt ccatcgcgcg   120
caccaggcgt attaccacga tgcgctgatg aataccggcg agggcctgga ctggagcatc   180
tgcggcgttg gcctgcgcag cgaggaccgc aaggcccgcg atgacctggc cggccaggac   240
```

-continued

```
tacctgttca ccctgtacga actgggcgac accgacgaca ccgaagtgcg cgtgatcggc      300
tcgatcagcg acatgctgct ggccgaagac agcgcccagg cattgatcga taaactggcc      360
agccccgaga ttcgcatcgt ctcgctgacc atcaccgaag cggctactg catcgacgac       420
agcaacggcg aattcatggc ccacttgccg cagatccagc acgacctggc tcatccgtcg      480
tcgccaaaaa ccgtgttcgg ctttatctgc gcggcattga cccagcgccg cgcggccggc      540
atcccggcgt ttaccgtgat gtcctgcgat aacctgcccc acaatggcgc tgtcacgcgc      600
aaggcactgc tggcgttcgc cgccctgcac aacgccgagc tgcatgactg gatcaaggcc      660
catgtgagct tcccgaacgc catggtcgac cgcatcacgc cgatgaccag caccgcccac      720
cgcctgcaac tgcacgatga acacggcatc gacgatgcct ggccagttgt ttgcgaaccc      780
tttgtgcagt gggtactgga agacaaattc gtcaacggcc gccggcgtg ggaaaaggtt       840
ggcgtgcagt tcaccgacga tgtgacaccc tatgaagaga tgaagatcgg cttgctcaac      900
ggcagccacc tggccctgac ctacctgggt tttctcaagg ctatcggtt tgtgcacgag       960
accatgaacg accgctgtt cgtggcctac atgcgcgcct acatggacct cgacgtcacg       1020
ccaaacctcg cgccggtacc gggcatcgac ctgaccgact acaagcagac cctggtggac     1080
cgcttctcca accaggcgat tgccgaccag ttggaacggg tgtgttcgga tggctcgtcg     1140
aagtttccca gttcaccgt gccgaccatc aaccgcctga ttgccgacgg ccgtgagacc      1200
gagcgtgcag cactggtcgt cgcggcctgg gccttgtatt tgaagggtgt ggatgagaat    1260
ggcgtgagct acacaatccc cgatccgcgc gccgagttct gccaggggct ggtgagtgac   1320
gatgcactga tcagccagcg gttgctggca gtggaagaga ttttcggtac ggctattccc    1380
aactcgcctg agtttgtggc agcgttcgag cggtgctatg ggagcctgcg tgataacggc   1440
gtcaccacta ccctgaagca cctcctgaag aaaccggttt aa                        1482
```

<210> SEQ ID NO 184
<211> LENGTH: 493
<212> TYPE: PRT
<213> ORGANISM: Pseudomonas fluorescens

<400> SEQUENCE: 184

```
Met Lys Leu Asn Lys Gln Asn Leu Thr Gln Leu Ala Pro Glu Val Lys
1               5                   10                  15

Leu Pro Ala Tyr Thr Leu Ala Asp Thr Arg Gln Gly Ile Ala His Ile
            20                  25                  30

Gly Val Gly Gly Phe His Arg Ala His Gln Ala Tyr Tyr Thr Asp Ala
        35                  40                  45

Leu Met Asn Thr Gly Glu Gly Leu Asp Trp Ser Ile Cys Gly Val Gly
    50                  55                  60

Leu Arg Ser Glu Asp Arg Lys Ala Arg Asp Leu Ala Gly Gln Asp
65                  70                  75                  80

Tyr Leu Phe Thr Leu Tyr Glu Leu Gly Asp Thr Asp Thr Glu Val
                85                  90                  95

Arg Val Ile Gly Ser Ile Ser Asp Met Leu Leu Ala Glu Asp Ser Ala
            100                 105                 110

Gln Ala Leu Ile Asp Lys Leu Ala Ser Pro Glu Ile Arg Ile Val Ser
        115                 120                 125

Leu Thr Ile Thr Glu Gly Gly Tyr Cys Ile Asp Asp Ser Asn Gly Glu
    130                 135                 140

Phe Met Ala His Leu Pro Gln Ile Gln His Asp Leu Ala His Pro Ser
145                 150                 155                 160
```

Ser Pro Lys Thr Val Phe Gly Phe Ile Cys Ala Ala Leu Thr Gln Arg
                165                 170                 175

Arg Ala Ala Gly Ile Pro Ala Phe Thr Val Met Ser Cys Asp Asn Leu
            180                 185                 190

Pro His Asn Gly Ala Val Thr Arg Lys Ala Leu Leu Ala Phe Ala Ala
        195                 200                 205

Leu His Asn Ala Glu Leu His Asp Trp Ile Lys Ala His Val Ser Phe
    210                 215                 220

Pro Asn Ala Met Val Asp Arg Ile Thr Pro Met Thr Ser Thr Ala His
225                 230                 235                 240

Arg Leu Gln Leu His Asp Glu His Gly Ile Asp Asp Ala Trp Pro Val
                245                 250                 255

Val Cys Glu Pro Phe Val Gln Trp Val Leu Glu Asp Lys Phe Val Asn
            260                 265                 270

Gly Arg Pro Ala Trp Glu Lys Val Gly Val Gln Phe Thr Asp Asp Val
        275                 280                 285

Thr Pro Tyr Glu Glu Met Lys Ile Gly Leu Leu Asn Gly Ser His Leu
    290                 295                 300

Ala Leu Thr Tyr Leu Gly Phe Leu Lys Gly Tyr Arg Phe Val His Glu
305                 310                 315                 320

Thr Met Asn Asp Pro Leu Phe Val Ala Tyr Met Arg Ala Tyr Met Asp
                325                 330                 335

Leu Asp Val Thr Pro Asn Leu Ala Pro Val Pro Gly Ile Asp Leu Thr
            340                 345                 350

Asp Tyr Lys Gln Thr Leu Val Asp Arg Phe Ser Asn Gln Ala Ile Ala
        355                 360                 365

Asp Gln Leu Glu Arg Val Cys Ser Asp Gly Ser Ser Lys Phe Pro Lys
    370                 375                 380

Phe Thr Val Pro Thr Ile Asn Arg Leu Ile Ala Asp Gly Arg Glu Thr
385                 390                 395                 400

Glu Arg Ala Ala Leu Val Val Ala Ala Trp Ala Leu Tyr Leu Lys Gly
                405                 410                 415

Val Asp Glu Asn Gly Val Ser Tyr Thr Ile Pro Asp Pro Arg Ala Glu
            420                 425                 430

Phe Cys Gln Gly Leu Val Ser Asp Asp Ala Leu Ile Ser Gln Arg Leu
        435                 440                 445

Leu Ala Val Glu Glu Ile Phe Gly Thr Ala Ile Pro Asn Ser Pro Glu
    450                 455                 460

Phe Val Ala Ala Phe Glu Arg Cys Tyr Gly Ser Leu Arg Asp Asn Gly
465                 470                 475                 480

Val Thr Thr Thr Leu Lys His Leu Leu Lys Lys Pro Val
                485                 490

<210> SEQ ID NO 185
<211> LENGTH: 1368
<212> TYPE: DNA
<213> ORGANISM: Klebsiella pneumoniae

<400> SEQUENCE: 185
ttagttaatc agcgtgtaaa cggcggcgac tttctcgcgc atcagcgcca ggaaatccgc      60
gttgttggcg agatcaccaa acagggcttt atcacgggcg aagacagcca ccggatcctg    120
agcctcgaac atctcatgca ccgcctgcgc atccaggatg ccgtcctggt actgatatgg    180
cagagttccc ttgtgccact gctccataaa gacgaagaac agcgccggca gcatggcggt    240

```
cgcttccggg cggacgccgc gctggtagca ctcctgcaag gttggcgcga tcatcgccgg    300
aattttcgag aagccgtcgg cggcgacgcg ctggttggtg tcctggatat aggggttggt    360
aaagcgctta agcaccacat cccggtaggt cggcagatca atgccgttgt cgccgagaca    420
cggaataacg tcctccgtaa cgtagcggtc ggcaatggcg tagataacat cggtcagcgt    480
gctttcatga atatactgct ggccgattaa ggttcccgcc caggcaatgc agctgtgcga    540
cgcgttcaaa atacggattt cgcctcttc atacgggatg accgactcca ccatctccac     600
gccgactgcc tccagattcg gcggacatc gcggaagttg ttctccacta cccactggat      660
aaaggtctcc cccatcaccg gcgctttgtc atcaattccg gcttgcgctt tgatgcgggc    720
cggcagatcg gccgccggac gcggggtgat gcggtccacc atggtgttcg acaggtggt     780 attggccgcc atccagtcaa tcaccgcctg tttgccggtg agctgcagga actcgaccat    840
accgtcgtgg aaacgctcgc cgttatggcg cacgttatcg cagttgagca gggtcagcgg    900
cccggcgttg tcggccatgc gcttttccag gatccgcgcg agggtgccgt aaatggtttt    960
gcactcgcct tgcaggtcgg cctgcagatc ggggttgctg gtttccagcc gatggcgagt   1020
gttcaggtag taccccccctt ccgtcacggt aaaggcgata actttggtct gcgggtttgc   1080
cccttcgtta atcagcggct gtagcccggc ctgccacggt agcagtttct ggattgaggt   1140
gatctcttca tattcgcgct ccccttccgg gctgacggtc tcgaggacgt aacgtcctcc   1200
ctgcgccgcc agcgcctgga ccacctgctc ggcgtcgttg cgaatattcc ccgccgcgat   1260
gcgccagcga ttatccccgg aagcaatcag acgatgcaga taccacgcct gatgcgcgcg   1320
atgaaaagaa cccagaccga tatgaagcca tgtgaattga ttgttcat              1368
```

<210> SEQ ID NO 186
<211> LENGTH: 455
<212> TYPE: PRT
<213> ORGANISM: Klebsiella pneumoniae

<400> SEQUENCE: 186

```
Met Asn Asn Gln Phe Thr Trp Leu His Ile Gly Leu Gly Ser Phe His
1               5                   10                  15

Arg Ala His Gln Ala Trp Tyr Leu His Arg Leu Ile Ala Ser Gly Asp
                20                  25                  30

Asn Arg Trp Arg Ile Ala Ala Gly Asn Ile Arg Asn Asp Ala Glu Gln
            35                  40                  45

Val Val Gln Ala Leu Ala Ala Gln Gly Gly Arg Tyr Val Leu Glu Thr
        50                  55                  60

Val Ser Pro Glu Gly Glu Arg Glu Tyr Glu Glu Ile Thr Ser Ile Gln
65                  70                  75                  80

Lys Leu Leu Pro Trp Gln Ala Gly Leu Gln Pro Leu Ile Asn Glu Gly
                85                  90                  95

Ala Asn Pro Gln Thr Lys Val Ile Ala Phe Thr Val Thr Glu Gly Gly
            100                 105                 110

Tyr Tyr Leu Asn Thr Arg His Arg Leu Glu Thr Ser Asn Pro Asp Leu
        115                 120                 125

Gln Ala Asp Leu Gln Gly Glu Cys Lys Thr Ile Tyr Gly Thr Leu Ala
    130                 135                 140

Arg Ile Leu Glu Lys Arg Met Ala Asp Asn Ala Gly Pro Leu Thr Leu
145                 150                 155                 160

Leu Asn Cys Asp Asn Val Arg His Asn Gly Glu Arg Phe His Asp Gly
                165                 170                 175
```

```
Met Val Glu Phe Leu Gln Leu Thr Gly Lys Gln Ala Val Ile Asp Trp
            180                 185                 190

Met Ala Ala Asn Thr Thr Cys Pro Asn Thr Met Val Asp Arg Ile Thr
        195                 200                 205

Pro Arg Pro Ala Ala Asp Leu Pro Ala Arg Ile Lys Ala Gln Ala Gly
    210                 215                 220

Ile Asp Asp Lys Ala Pro Val Met Gly Glu Thr Phe Ile Gln Trp Val
225                 230                 235                 240

Val Glu Asn Asn Phe Arg Asp Val Arg Pro Asn Leu Glu Ala Val Gly
                245                 250                 255

Val Glu Met Val Glu Ser Val Ile Pro Tyr Glu Glu Ala Lys Ile Arg
            260                 265                 270

Ile Leu Asn Ala Ser His Ser Cys Ile Ala Trp Ala Gly Thr Leu Ile
        275                 280                 285

Gly Gln Gln Tyr Ile His Glu Ser Thr Leu Thr Asp Val Ile Tyr Ala
    290                 295                 300

Ile Ala Asp Arg Tyr Val Thr Glu Asp Val Ile Pro Cys Leu Gly Asp
305                 310                 315                 320

Asn Gly Ile Asp Leu Pro Thr Tyr Arg Asp Val Val Leu Lys Arg Phe
                325                 330                 335

Thr Asn Pro Tyr Ile Gln Asp Thr Asn Gln Arg Val Ala Ala Asp Gly
            340                 345                 350

Phe Ser Lys Ile Pro Ala Met Ile Ala Pro Thr Leu Gln Glu Cys Tyr
        355                 360                 365

Gln Arg Gly Val Arg Pro Glu Ala Thr Ala Met Leu Pro Ala Leu Phe
    370                 375                 380

Phe Val Phe Met Glu Gln Trp His Lys Gly Thr Leu Pro Tyr Gln Tyr
385                 390                 395                 400

Gln Asp Gly Ile Leu Asp Ala Gln Ala Val His Glu Met Phe Glu Ala
                405                 410                 415

Gln Asp Pro Val Ala Val Phe Ala Arg Asp Lys Ala Leu Phe Gly Asp
            420                 425                 430

Leu Ala Asn Asn Ala Asp Phe Leu Ala Leu Met Arg Glu Lys Val Ala
        435                 440                 445

Ala Val Tyr Thr Leu Ile Asn
    450                 455
```

<210> SEQ ID NO 187
<211> LENGTH: 1398
<212> TYPE: DNA
<213> ORGANISM: Ralstonia solanacearum

<400> SEQUENCE: 187

```
atgacgcggt cgtccctcgc gcgtgcgcca gtgctgctgc atattggcgc cggatctttc      60
catcgtgcgc accaggcgtg gtatctgcat cgcgtcaacg cggccgtgcc tcccggcgag     120
cgctggacgc tgacggtcgg gaacattcgc gacgacatgc acgcgacact cgccgcgctg     180
gccgcgcagc agggtgccta cacgctcgag accgtcacgc cgcaaggcga gcgtgcgtat     240
gagacgatcc gctcgatcgc gcgggtgctg ccctggtccg ccgatcttgc cgcgctcatc     300
aatacgggcg ccgatcccgc gtgccggatc gtgtcgttta cggtcaccga aggcgggtat     360
tacctcgacg agcacgatcg tctcgatgtc acgcatcccg atctcgcggc cgacctgcgg     420
ggcgcccgct cgacgctata cggcgcattg gccgcgttgc tcgccgagcg ccgccagcgc     480
```

```
ggagccgggc cgctcacgct gcagagttgc gacaatctgc gcagcaacgg cgcgcgtttt    540
cgcgcgggca tgcgcgcgtt cctcgcgctg cgcggcgacg cagcgctcct cgcgtggttc    600
gatgccaacg tatcgtgccc gagcgcgatg gtcgaccgga tcacgccgcg gccgaccgac    660
gacgtccgca cgcgcgtgca cgcggccacc ggcgtcgacg accgctgccc ggtcatgggc    720
gaatccttca tccaatgggt gatcgaggac aacttcatcg ccggccggcc ggcatgggag    780
atcgcgggcg cggagatcgt cgccgatgtg catccgtacg aagaggcgaa gatccggatc    840
ctgaatgcga cgcacagctg catcgcctgg gcgggcacgc tcgcgggact cacctacatt    900
cacgaaggga tgcgtgatgc ggccatttat cgcttcgcct acgactacgt caccgacgac    960
gtgattccct gcctgacgcc gagcccgctg gatctcgagc gctatcggga cgtcgtgctc   1020
gagcgcttcg gcaatccgta cgtgctcgac accaaccagc gtgtcgccgc cgatggcttc   1080
tcgaaaatcc ccggcttcat cgcaccgacg ctcgccgaat gctttgcgcg cggcgccgat   1140
ccggtcgcga ccgcggtgtt gccggcgctg tttctgggct tccttgaagg ttgggcgcgc   1200
ggcaccttgc cctacgtata ccaggacggc gtgatggatg cgccgccgc acgcagcatc    1260 gtcgaggctc cggattccgt tgccgcgttc tgttcagatc gccaattgtg gggttcgctt   1320
gcgggccgcg acgcgcttgt ccaggcggtg cgtgcgggac gcgcgcgcgt tgaagcatgg   1380
cgagccgcac gccgctga                                                 1398
```

<210> SEQ ID NO 188
<211> LENGTH: 465
<212> TYPE: PRT
<213> ORGANISM: Ralstonia solanacearum

<400> SEQUENCE: 188

Met Thr Arg Ser Ser Leu Ala Arg Ala Pro Val Leu Leu His Ile Gly
1               5                   10                  15

Ala Gly Ser Phe His Arg Ala His Gln Ala Trp Tyr Leu His Arg Val
            20                  25                  30

Asn Ala Ala Val Pro Pro Gly Glu Arg Trp Thr Leu Thr Val Gly Asn
        35                  40                  45

Ile Arg Asp Asp Met His Ala Thr Leu Ala Ala Leu Ala Ala Gln Gln
    50                  55                  60

Gly Ala Tyr Thr Leu Glu Thr Val Thr Pro Gln Gly Glu Arg Ala Tyr
65                  70                  75                  80

Glu Thr Ile Arg Ser Ile Ala Arg Val Leu Pro Trp Ser Ala Asp Leu
                85                  90                  95

Ala Ala Leu Ile Asn Thr Gly Ala Asp Pro Ala Cys Arg Ile Val Ser
            100                 105                 110

Phe Thr Val Thr Glu Gly Gly Tyr Tyr Leu Asp Glu His Asp Arg Leu
        115                 120                 125

Asp Val Thr His Pro Asp Leu Ala Ala Asp Leu Arg Gly Ala Arg Ser
    130                 135                 140

Thr Leu Tyr Gly Ala Leu Ala Ala Leu Ala Glu Arg Arg Gln Arg
145                 150                 155                 160

Gly Ala Gly Pro Leu Thr Leu Gln Ser Cys Asp Asn Leu Arg Ser Asn
                165                 170                 175

Gly Ala Arg Phe Arg Ala Gly Met Arg Ala Phe Leu Ala Leu Arg Gly
            180                 185                 190

Asp Ala Ala Leu Leu Ala Trp Phe Asp Ala Asn Val Ser Cys Pro Ser
        195                 200                 205

Ala Met Val Asp Arg Ile Thr Pro Arg Pro Thr Asp Asp Val Arg Thr
    210                 215                 220

Arg Val His Ala Ala Thr Gly Val Asp Asp Arg Cys Pro Val Met Gly
225                 230                 235                 240

Glu Ser Phe Ile Gln Trp Val Ile Glu Asp Asn Phe Ile Ala Gly Arg
                245                 250                 255

Pro Ala Trp Glu Ile Ala Gly Ala Glu Ile Val Ala Asp Val His Pro
                260                 265                 270

Tyr Glu Glu Ala Lys Ile Arg Ile Leu Asn Ala Thr His Ser Cys Ile
                275                 280                 285

Ala Trp Ala Gly Thr Leu Ala Gly Leu Thr Tyr Ile His Glu Gly Met
    290                 295                 300

Arg Asp Ala Ala Ile Tyr Arg Phe Ala Tyr Asp Tyr Val Thr Asp Asp
305                 310                 315                 320

Val Ile Pro Cys Leu Thr Pro Ser Pro Leu Asp Leu Glu Arg Tyr Arg
                325                 330                 335

Asp Val Val Leu Glu Arg Phe Gly Asn Pro Tyr Val Leu Asp Thr Asn
                340                 345                 350

Gln Arg Val Ala Ala Asp Gly Phe Ser Lys Ile Pro Gly Phe Ile Ala
                355                 360                 365

Pro Thr Leu Ala Glu Cys Phe Ala Arg Gly Ala Asp Pro Val Ala Thr
    370                 375                 380

Ala Val Leu Pro Ala Leu Phe Leu Gly Phe Leu Glu Gly Trp Ala Arg
385                 390                 395                 400

Gly Thr Leu Pro Tyr Val Tyr Gln Asp Gly Val Met Asp Gly Ala Ala
                405                 410                 415

Ala Arg Ser Ile Val Glu Ala Pro Asp Ser Val Ala Ala Phe Cys Ser
                420                 425                 430

Asp Arg Gln Leu Trp Gly Ser Leu Ala Gly Arg Asp Ala Leu Val Gln
                435                 440                 445

Ala Val Arg Ala Gly Arg Ala Arg Val Glu Ala Trp Arg Ala Ala Arg
    450                 455                 460

Arg
465

<210> SEQ ID NO 189
<211> LENGTH: 1185
<212> TYPE: DNA
<213> ORGANISM: Bacillus subtilis

<400> SEQUENCE: 189
atgaatcgta tcgcagctga cgttcagcgt gcttttgaaa acgccggaga aaagacgttg      60
cctataaaag ttgaagaaat tgttctcggt aagcaagcag ctgattcgct tttggattat     120
gtaaaacgaa aaacaatca acatattgtc cttgtctgcg acgcgaatac acaccgcatt      180
gcaggaattg atttagaaaa ccgactgaat caagaaggat ttcaggccga gtgcctgatc     240
attccagaaa atgaagccgg agatgtgaca gctgatgaac gatcgctcat tcatgtgctg     300
atccatacga aacaaccaac ggatgtcatg atcgcagtcg gttcgggcac gattcatgat     360
atcgtccgct ttgcggcgtt tcaaagagat ttgccgtttta tttcttatcc gactgctcca     420
tctgtagacg gttttacatc agccggtgcg ccgattattt tatacggcac gaaaacaacc    480
attcaaacga aggccccatc tgcgctgttc gctgatctgg atctattaaa agcggcaccg    540
cagtcaatgg tggcggctgg ctttggtgac atgctcggta aaatcacgtc tttagcagat    600

```
tgggaaatat cccggcatct tgccggtgag ccttattcgc ctgcaggagc taagatcgtt    660
caggaggcgc ttgctgcctg cattgaacac acagaagaca ttgcgatgaa aacggaaact    720
ggcatacggg ttttgatgga gtctttactt gtatcggggc ttgtcatgct ggcattagat    780
cattcccgac cggcatcagg cggcgagcat catatttcac attggattga aatggagtta    840
atggagaaaa aacggcctca gattcttcat ggggcaaagg tgggctgtgc cgctgtttta    900
ttaactgaca catacagaaa gctcgctcag gatgacgggc tgaacgaatt ttcaccaagc    960
cgccgggaag ccatccaatc ggcttatcaa acactcccga gaggagaagt gctggctgat   1020
tggctgagat cagccggagg ccctgcgtat tttgacgaaa tcggtgtcgg gcaggattcc   1080
gtcaaaaatg ccttcagaca cgcgcacacc ttaagagacc gatgcaccgg attaagaatc   1140
atcaatgaaa acaaaacgct gatcaaccat ggtctatatg aatag                   1185
```

<210> SEQ ID NO 190
<211> LENGTH: 394
<212> TYPE: PRT
<213> ORGANISM: Bacillus subtilis

<400> SEQUENCE: 190

```
Met Asn Arg Ile Ala Ala Asp Val Gln Arg Ala Phe Glu Asn Ala Gly
1               5                   10                  15

Glu Lys Thr Leu Pro Ile Lys Val Glu Glu Ile Val Leu Gly Lys Gln
            20                  25                  30

Ala Ala Asp Ser Leu Leu Asp Tyr Val Lys Arg Lys Asn Asn Gln His
        35                  40                  45

Ile Val Leu Val Cys Asp Ala Asn Thr His Arg Ile Ala Gly Ile Asp
    50                  55                  60

Leu Glu Asn Arg Leu Asn Gln Glu Gly Phe Gln Ala Glu Cys Leu Ile
65                  70                  75                  80

Ile Pro Glu Asn Glu Ala Gly Asp Val Thr Ala Asp Glu Arg Ser Leu
                85                  90                  95

Ile His Val Leu Ile His Thr Lys Gln Pro Thr Asp Val Met Ile Ala
            100                 105                 110

Val Gly Ser Gly Thr Ile His Asp Ile Val Arg Phe Ala Ala Phe Gln
        115                 120                 125

Arg Asp Leu Pro Phe Ile Ser Tyr Pro Thr Ala Pro Ser Val Asp Gly
    130                 135                 140

Phe Thr Ser Ala Gly Ala Pro Ile Ile Leu Tyr Gly Thr Lys Thr Thr
145                 150                 155                 160

Ile Gln Thr Lys Ala Pro Ser Ala Leu Phe Ala Asp Leu Asp Leu Leu
                165                 170                 175

Lys Ala Ala Pro Gln Ser Met Val Ala Ala Gly Phe Gly Asp Met Leu
            180                 185                 190

Gly Lys Ile Thr Ser Leu Ala Asp Trp Glu Ile Ser Arg His Leu Ala
        195                 200                 205

Gly Glu Pro Tyr Ser Pro Ala Gly Lys Ile Val Gln Glu Ala Leu
    210                 215                 220

Ala Ala Cys Ile Glu His Thr Glu Asp Ile Ala Met Lys Thr Glu Thr
225                 230                 235                 240

Gly Ile Arg Val Leu Met Glu Ser Leu Leu Val Ser Gly Leu Val Met
                245                 250                 255

Leu Ala Leu Asp His Ser Arg Pro Ala Ser Gly Gly Glu His His Ile
            260                 265                 270
```

Ser His Trp Ile Glu Met Glu Leu Met Glu Lys Lys Arg Pro Gln Ile
          275                 280                 285

Leu His Gly Ala Lys Val Gly Cys Ala Ala Val Leu Leu Thr Asp Thr
          290                 295                 300

Tyr Arg Lys Leu Ala Gln Asp Asp Gly Leu Asn Glu Phe Ser Pro Ser
305                 310                 315                 320

Arg Arg Glu Ala Ile Gln Ser Ala Tyr Gln Thr Leu Pro Arg Gly Glu
                325                 330                 335

Val Leu Ala Asp Trp Leu Arg Ser Gly Gly Pro Ala Tyr Phe Asp
                340                 345                 350

Glu Ile Gly Val Gly Gln Asp Ser Val Lys Asn Ala Phe Arg His Ala
          355                 360                 365

His Thr Leu Arg Asp Arg Cys Thr Gly Leu Arg Ile Ile Asn Glu Asn
          370                 375                 380

Lys Thr Leu Ile Asn His Gly Leu Tyr Glu
385                 390

<210> SEQ ID NO 191
<211> LENGTH: 1059
<212> TYPE: DNA
<213> ORGANISM: Aeropyrum pernix

<400> SEQUENCE: 191 ttgtataacct cgttccacag gatagacctc ccgaggacta tagtagtcgg cggaggcgtt       60
ctcgacaagg cgggcggcta tgtatctggg gtggctcagc gaggcagcta tgtgctcgtc      120
gtatccggcc caacggtgtc ctcgaaatac ttcgagaggc ttagagccag cctcgaggcc      180
gagggcctta cagtcggcct gaagataatc agggacgcca cggttgagac tgctgaggag      240
gtggcccgtg aggctcttga gagcaggata gaggttgtgg cgggcctggg aggtgggaag      300
tcgatagacg ttgctaagta cgcttcaaaa agggcgggct cggttttcgt cagcataccc      360
accgtggcta gccacgacgg gataacatcg ccattctcaa gcctgaaggg gttcgacaag      420
cctatatcga ggcccgctaa ggctccggag gcgataatta tagatgtgga tgtgatagcg      480
gaggctccca gcgctacaa catcgctggc ttcggagacc tgataggcaa gtatactgca      540
gtcctcgact ggaggctggc ccacaagctc aggctggaat actatggcga atacgccgcc      600
agtctcgccc tcctgagcgc caaacatgtg agccagtacg ccgaggagat agcgctgggt      660
acgagggagg gctatagagt gctgctggag gctctcgtga gcagcggggt gtcgatgtgt      720
atagccggta gcacgaggcc tgcaagcggc agtgaacacc tcttcgccca cgccctccac      780
atagtcgcta ggaacaagcc tctccacggc gaggcggttg gggtggggac tataatgatg      840
gcctacctcc acggtaagaa ctggaggagg ataaggggcc tgctgaagac ggtcggcgcc      900
cccactaacg ccaaggagct tggtgtcgag gatgatgagg ttgttgaggc cctcactata      960
gcagccagga tcagaccgga gaggtacacc atactaggtg aaaaggggct cacgagagag     1020
gcggctgagg cgctggcgcg caagacgggc gttatatag                            1059

<210> SEQ ID NO 192
<211> LENGTH: 352
<212> TYPE: PRT
<213> ORGANISM: Aeropyrum pernix

<400> SEQUENCE: 192

Met Tyr Thr Ser Phe His Arg Ile Asp Leu Pro Arg Thr Ile Val Val
1               5                   10                  15

```
Gly Gly Gly Val Leu Asp Lys Ala Gly Tyr Val Ser Gly Val Ala
             20                  25                  30

Gln Arg Gly Ser Tyr Val Leu Val Val Ser Gly Pro Thr Val Ser Ser
         35                  40                  45

Lys Tyr Phe Glu Arg Leu Arg Ala Ser Leu Glu Ala Glu Gly Leu Thr
 50                  55                  60

Val Gly Leu Lys Ile Ile Arg Asp Ala Thr Val Thr Ala Glu Glu
 65                  70                  75                  80

Val Ala Arg Glu Ala Leu Glu Ser Arg Ile Glu Val Val Ala Gly Leu
                 85                  90                  95

Gly Gly Gly Lys Ser Ile Asp Val Ala Lys Tyr Ala Ser Lys Arg Ala
             100                 105                 110

Gly Ser Val Phe Val Ser Ile Pro Thr Val Ala Ser His Asp Gly Ile
         115                 120                 125

Thr Ser Pro Phe Ser Ser Leu Lys Gly Phe Asp Lys Pro Ile Ser Arg
130                 135                 140

Pro Ala Lys Ala Pro Glu Ala Ile Ile Ile Asp Val Asp Val Ile Ala
145                 150                 155                 160

Glu Ala Pro Arg Arg Tyr Asn Ile Ala Gly Phe Gly Asp Leu Ile Gly
                 165                 170                 175

Lys Tyr Thr Ala Val Leu Asp Trp Arg Leu Ala His Lys Leu Arg Leu
             180                 185                 190

Glu Tyr Gly Glu Tyr Ala Ala Ser Leu Ala Leu Leu Ser Ala Lys
         195                 200                 205

His Val Ser Gln Tyr Ala Glu Glu Ile Ala Leu Gly Thr Arg Glu Gly
210                 215                 220

Tyr Arg Val Leu Leu Glu Ala Leu Val Ser Ser Gly Val Ser Met Cys
225                 230                 235                 240

Ile Ala Gly Ser Thr Arg Pro Ala Ser Gly Ser Glu His Leu Phe Ala
                 245                 250                 255

His Ala Leu His Ile Val Ala Arg Asn Lys Pro Leu His Gly Glu Ala
             260                 265                 270

Val Gly Val Gly Thr Ile Met Met Ala Tyr Leu His Gly Lys Asn Trp
         275                 280                 285

Arg Arg Ile Arg Gly Leu Leu Lys Thr Val Gly Ala Pro Thr Asn Ala
290                 295                 300

Lys Glu Leu Gly Val Glu Asp Asp Glu Val Val Glu Ala Leu Thr Ile
305                 310                 315                 320

Ala Ala Arg Ile Arg Pro Glu Arg Tyr Thr Ile Leu Gly Glu Lys Gly
                 325                 330                 335

Leu Thr Arg Glu Ala Glu Ala Leu Ala Arg Lys Thr Gly Val Ile
             340                 345                 350

<210> SEQ ID NO 193
<211> LENGTH: 1020
<212> TYPE: DNA
<213> ORGANISM: Escherichia coli

<400> SEQUENCE: 193
atgaaccaac gtaatgcttc aatgactgtg atcggtgccg gctcgtacgg caccgctctt      60
gccatcaccc tggcaagaaa tggccacgag gttgtcctct ggggccatga ccctgaacat     120
atcgcaacgc ttgaacgcga ccgctgtaac gccgcgtttc tccccgatgt gccttttccc     180
gatacgctcc atcttgaaag cgatctcgcc actgcgctgg cagccagccg taatattctc     240
```

-continued

```
gtcgtcgtac ccagccatgt ctttggtgaa gtgctgcgcc agattaaacc actgatgcgt    300
cctgatgcgc gtctggtgtg ggcgaccaaa gggctggaag cggaaaccgg acgtctgtta    360
caggacgtgg cgcgtgaggc cttaggcgat caaattccgc tggcggttat ctctggccca    420
acgtttgcga agaactggcg gcaggtttta ccgacagcta tttcgctggc ctcgaccgat    480
cagacctttg ccgatgatct ccagcagctg ctgcactgcg gcaaaagttt ccgcgtttac    540
agcaatccgg atttcattgg cgtgcagctt ggcggcgcgg tgaaaaacgt tattgccatt    600
ggtgcgggga tgtccgacgg tatcggtttt ggtgcgaatg cgcgtacggc gctgatcacc    660
cgtgggctgg ctgaaatgtc gcgtcttggt gcggcgctgg gtgccgaccc tgccaccttt    720
atgggcatgg cggggcttgg cgatctggtg cttacctgta ccgacaacca gtcgcgtaac    780
cgccgttttg gcatgatgct cggtcagggc atggatgtac aaagcgcgca ggagaagatt    840
ggtcaggtgg tggaaggcta ccgcaatacg aaagaagtcc gcgaactggc gcatcgcttc    900
ggcgttgaaa tgccaataac cgaggaaatt tatcaagtat tatattgcgg aaaaaacgcg    960
cgcgaggcag cattgacttt actaggtcgt gcacgcaagg acgagcgcag cagccactaa  1020
```

<210> SEQ ID NO 194
<211> LENGTH: 339
<212> TYPE: PRT
<213> ORGANISM: Escherichia coli

<400> SEQUENCE: 194

```
Met Asn Gln Arg Asn Ala Ser Met Thr Val Ile Gly Ala Gly Ser Tyr
1               5                   10                  15

Gly Thr Ala Leu Ala Ile Thr Leu Ala Arg Asn Gly His Glu Val Val
            20                  25                  30

Leu Trp Gly His Asp Pro Glu His Ile Ala Thr Leu Glu Arg Asp Arg
        35                  40                  45

Cys Asn Ala Ala Phe Leu Pro Asp Val Pro Phe Pro Asp Thr Leu His
    50                  55                  60

Leu Glu Ser Asp Leu Ala Thr Ala Leu Ala Ala Ser Arg Asn Ile Leu
65                  70                  75                  80

Val Val Val Pro Ser His Val Phe Gly Glu Val Leu Arg Gln Ile Lys
                85                  90                  95

Pro Leu Met Arg Pro Asp Ala Arg Leu Val Trp Ala Thr Lys Gly Leu
            100                 105                 110

Glu Ala Glu Thr Gly Arg Leu Leu Gln Asp Val Ala Arg Glu Ala Leu
        115                 120                 125

Gly Asp Gln Ile Pro Leu Ala Val Ile Ser Gly Pro Thr Phe Ala Lys
    130                 135                 140

Glu Leu Ala Ala Gly Leu Pro Thr Ala Ile Ser Leu Ala Ser Thr Asp
145                 150                 155                 160

Gln Thr Phe Ala Asp Asp Leu Gln Gln Leu Leu His Cys Gly Lys Ser
                165                 170                 175

Phe Arg Val Tyr Ser Asn Pro Asp Phe Ile Gly Val Gln Leu Gly Gly
            180                 185                 190

Ala Val Lys Asn Val Ile Ala Ile Gly Ala Gly Met Ser Asp Gly Ile
        195                 200                 205

Gly Phe Gly Ala Asn Ala Arg Thr Ala Leu Ile Thr Arg Gly Leu Ala
    210                 215                 220

Glu Met Ser Arg Leu Gly Ala Ala Leu Gly Ala Asp Pro Ala Thr Phe
225                 230                 235                 240
```

Met Gly Met Ala Gly Leu Gly Asp Leu Val Leu Thr Cys Thr Asp Asn
            245                 250                 255

Gln Ser Arg Asn Arg Arg Phe Gly Met Met Leu Gly Gln Gly Met Asp
        260                 265                 270

Val Gln Ser Ala Gln Glu Lys Ile Gly Gln Val Val Glu Gly Tyr Arg
    275                 280                 285

Asn Thr Lys Glu Val Arg Glu Leu Ala His Arg Phe Gly Val Glu Met
290                 295                 300

Pro Ile Thr Glu Glu Ile Tyr Gln Val Leu Tyr Cys Gly Lys Asn Ala
305                 310                 315                 320

Arg Glu Ala Ala Leu Thr Leu Leu Gly Arg Ala Arg Lys Asp Glu Arg
            325                 330                 335

Ser Ser His

<210> SEQ ID NO 195
<211> LENGTH: 1176
<212> TYPE: DNA
<213> ORGANISM: Saccharomyces cerevisiae

<400> SEQUENCE: 195

```
atgtctgctg ctgctgatag attaaactta acttccggcc acttgaatgc tggtagaaag      60
agaagttcct cttctgtttc tttgaaggct gccgaaaagc ctttcaaggt tactgtgatt     120
ggatctggta actggggtac tactattgcc aaggtggttg ccgaaaattg taagggatac     180
ccagaagttt tcgctccaat agtacaaatg tgggtgttcg aagaagagat caatggtgaa     240
aaattgactg aaatcataaa tactagacat caaaacgtga atacttgcc tggcatcact      300 ctacccgaca atttggttgc taatccagac ttgattgatt cagtcaagga tgtcgacatc     360
atcgttttca acattccaca tcaatttttg ccccgtatct gtagccaatt gaaaggtcat     420
gttgattcac acgtcagagc tatctcctgt ctaaagggtt ttgaagttgg tgctaaaggt     480
gtccaattgc tatcctctta catcactgag gaactaggta ttcaatgtgg tgctctatct     540
ggtgctaaca ttgccaccga agtcgctcaa gaacactggt ctgaaacaac agttgcttac     600
cacattccaa aggatttcag aggcgagggc aaggacgtcg accataaggt tctaaaggcc     660
ttgttccaca gaccttactt ccacgttagt gtcatcgaag atgttgctgg tatctccatc     720
tgtggtgctt tgaagaacgt tgttgcctta ggttgtggtt tcgtcgaagg tctaggctgg     780
ggtaacaacg cttctgctgc catccaaaga gtcggtttgg gtgagatcat cagattcggt     840
caaatgtttt tcccagaatc tagagaagaa acatactacc aagagtctgc tggtgttgct     900
gatttgatca ccacctgcgc tggtggtaga aacgtcaagg ttgctaggct aatggctact     960
tctggtaagg acgcctggga atgtgaaaag gagttgttga atggccaatc cgctcaaggt    1020
ttaattacct gcaaagaagt tcacgaatgg ttggaaacat gtggctctgt cgaagacttc    1080
ccattatttg aagccgtata ccaaatcgtt tacaacaact acccaatgaa gaacctgccg    1140
gacatgattg aagaattaga tctacatgaa gattag                              1176
```

<210> SEQ ID NO 196
<211> LENGTH: 391
<212> TYPE: PRT
<213> ORGANISM: Saccharomyces cerevisiae

<400> SEQUENCE: 196

Met Ser Ala Ala Ala Asp Arg Leu Asn Leu Thr Ser Gly His Leu Asn
1               5                   10                  15

```
Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
50                  55                  60

Ala Pro Ile Val Gln Met Trp Val Phe Glu Glu Ile Asn Gly Glu
65                  70                  75              80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
            115                 120                 125

Phe Leu Pro Arg Ile Cys Ser Gln Leu Lys Gly His Val Asp Ser His
130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
            195                 200                 205

Glu Gly Lys Asp Val Asp His Lys Val Leu Lys Ala Leu Phe His Arg
210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
            275                 280                 285

Glu Glu Thr Tyr Tyr Gln Glu Ser Ala Gly Val Ala Asp Leu Ile Thr
290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
            355                 360                 365

Ile Val Tyr Asn Asn Tyr Pro Met Lys Asn Leu Pro Asp Met Ile Glu
370                 375                 380

Glu Leu Asp Leu His Glu Asp
385                 390

<210> SEQ ID NO 197
<211> LENGTH: 1224
<212> TYPE: DNA
<213> ORGANISM: Escherichia coli

<400> SEQUENCE: 197
```

```
atgaaacgtg catttattat ggtgctggac tcattcggca tcggcgctac agaagatgca    60
gaacgctttg gtgacgtcgg ggctgacacc ctgggtcata tcgcagaagc ttgtgccaaa   120
ggcgaagctg ataacggtcg taaaggcccg ctcaatctgc caaatctgac ccgtctgggg   180
ctggcgaaag cacacgaagg ttctaccggt ttcattccgg cgggaatgga cggcaacgct   240
gaagttatcg gcgcgtacgc atgggcgcac gaaatgtcat ccggtaaaga taccccgtct   300
ggtcactggg aaattgccgg tgtcccggtt ctgtttgagt ggggatattt ctccgatcac   360
gaaaacagct tcccgcaaga gctgctggat aaactggtcg aacgcgctaa tctgccgggt   420
tacctcggta actgccactc ttccggtacg gtcattctgg atcaactggg cgaagagcac   480
atgaaaaccg gcaagccgat tttctatacc tccgctgact ccgtgttcca gattgcctgc   540
catgaagaaa ctttcggtct ggataaactc tacgaactgt gcgaaatcgc ccgtgaagag   600
ctgaccaacg gcggctacaa tatcggtcgt gttatcgctc gtccgtttat cggcgacaaa   660
gccggtaact tccagcgtac cggtaaccgt cacgacctgg ctgttgagcc gccagcaccg   720
accgtgctgc agaaactggt tgatgaaaaa cacggccagg tggtttctgt cggtaaaatt   780
gcggacatct acgccaactg cggtatcacc aaaaaagtga agcgactgg cctgacgcg   840
ctgtttgacg ccaccatcaa agagatgaaa gaagcgggtg ataacaccat cgtcttcacc   900
aacttcgttg acttcgactc ttcctggggc accgtcgcg acgtcgcgg ttatgccgcg   960
ggtctggaac tgttcgaccg ccgtctgccg gagctgatgt ctctgctgcg cgatgacgac  1020
atcctgatcc tcaccgctga ccacggttgc gatccgacct ggaccggtac tgaccacacg  1080
cgtgaacaca ttccggtact ggtatatggc ccgaaagtaa aaccgggctc actgggtcat  1140
cgtgaaacct tcgcggatat cggccagact ctggcaaaat attttggtac ttctgatatg  1200
gaatatggca aagccatgtt ctga                                         1224
```

<210> SEQ ID NO 198
<211> LENGTH: 407
<212> TYPE: PRT
<213> ORGANISM: Escherichia coli

<400> SEQUENCE: 198

Met Lys Arg Ala Phe Ile Met Val Leu Asp Ser Phe Gly Ile Gly Ala
1               5                   10                  15

Thr Glu Asp Ala Glu Arg Phe Gly Asp Val Gly Ala Asp Thr Leu Gly
                20                  25                  30

His Ile Ala Glu Ala Cys Ala Lys Gly Glu Ala Asp Asn Gly Arg Lys
            35                  40                  45

Gly Pro Leu Asn Leu Pro Asn Leu Thr Arg Leu Gly Leu Ala Lys Ala
        50                  55                  60

His Glu Gly Ser Thr Gly Phe Ile Pro Ala Gly Met Asp Gly Asn Ala
65                  70                  75                  80

Glu Val Ile Gly Ala Tyr Ala Trp Ala His Glu Met Ser Ser Gly Lys
                85                  90                  95

Asp Thr Pro Ser Gly His Trp Glu Ile Ala Gly Val Pro Val Leu Phe
            100                 105                 110

Glu Trp Gly Tyr Phe Ser Asp His Glu Asn Ser Phe Pro Gln Glu Leu
        115                 120                 125

Leu Asp Lys Leu Val Glu Arg Ala Asn Leu Pro Gly Tyr Leu Gly Asn
    130                 135                 140

Cys His Ser Ser Gly Thr Val Ile Leu Asp Gln Leu Gly Glu Glu His

```
                145                 150                 155                 160
Met Lys Thr Gly Lys Pro Ile Phe Tyr Thr Ser Ala Asp Ser Val Phe
                    165                 170                 175

Gln Ile Ala Cys His Glu Glu Thr Phe Gly Leu Asp Lys Leu Tyr Glu
                    180                 185                 190

Leu Cys Glu Ile Ala Arg Glu Leu Thr Asn Gly Tyr Asn Ile
                195                 200                 205

Gly Arg Val Ile Ala Arg Pro Phe Ile Gly Asp Lys Ala Gly Asn Phe
210                 215                 220

Gln Arg Thr Gly Asn Arg His Asp Leu Ala Val Glu Pro Pro Ala Pro
225                 230                 235                 240

Thr Val Leu Gln Lys Leu Val Asp Glu Lys His Gly Gln Val Val Ser
                245                 250                 255

Val Gly Lys Ile Ala Asp Ile Tyr Ala Asn Cys Gly Ile Thr Lys Lys
                260                 265                 270

Val Lys Ala Thr Gly Leu Asp Ala Leu Phe Asp Ala Thr Ile Lys Glu
                275                 280                 285

Met Lys Glu Ala Gly Asp Asn Thr Ile Val Phe Thr Asn Phe Val Asp
290                 295                 300

Phe Asp Ser Ser Trp Gly His Arg Arg Asp Val Ala Gly Tyr Ala Ala
305                 310                 315                 320

Gly Leu Glu Leu Phe Asp Arg Arg Leu Pro Glu Leu Met Ser Leu Leu
                325                 330                 335

Arg Asp Asp Asp Ile Leu Ile Leu Thr Ala Asp His Gly Cys Asp Pro
                340                 345                 350

Thr Trp Thr Gly Thr Asp His Thr Arg Glu His Ile Pro Val Leu Val
                355                 360                 365

Tyr Gly Pro Lys Val Lys Pro Gly Ser Leu Gly His Arg Glu Thr Phe
                370                 375                 380

Ala Asp Ile Gly Gln Thr Leu Ala Lys Tyr Phe Gly Thr Ser Asp Met
385                 390                 395                 400

Glu Tyr Gly Lys Ala Met Phe
                405

<210> SEQ ID NO 199
<211> LENGTH: 1641
<212> TYPE: DNA
<213> ORGANISM: Escherichia coli

<400> SEQUENCE: 199
atggcaatcc acaatcgtgc aggccaacct gcacaacaga gtgatttgat taacgtcgcc      60
caactgacgg cgcaatatta tgtactgaaa ccagaagcag ggaatgcgga gcacgcggtg     120
aaattcggta cttccggtca ccgtggcagt gcagcgcgcc acagctttaa cgagccgcac     180
attctggcga tcgctcaggc aattgctgaa gaacgtgcga aaaacggcat cactggccct     240
tgctatgtgg gtaaagatac tcacgccctg tccgaacctg cattcatttc cgttctggaa     300
gtgctggcag cgaacggcgt tgatgtcatt gtgcaggaaa acaatggctt cacccccgacg   360 cctgccgttt ccaatgccat cctggttcac aataaaaaag gtgcccgct ggcagacggt      420 atcgtgatta caccgtccca taacccgccg gaagatggtg gaatcaaata caatccgcca     480
aatggtggcc cggctgatac caacgtcact aaagtggtgg aagacagggc caacgcactg     540
ctggccgatg gcctgaaagg cgtgaagcgt atctccctcg acgaagcgat ggcatccggt     600
catgtgaaag agcaggatct ggtgcagccg ttcgtggaag gtctggccga tatcgttgat     660
```

-continued

```
atggccgcga ttcagaaagc gggcctgacg ctgggcgttg atccgctggg cggttccggt      720
atcgaatact ggaagcgtat tggcgagtat tacaacctca acctgactat cgttaacgat      780
caggtcgatc aaaccttccg ctttatgcac cttgataaag acggcgcgat ccgtatggac      840
tgctcctccg agtgtgcgat ggcgggcctg ctggcactgc gtgataagtt cgatctggcg      900
tttgctaacg acccggatta tgaccgtcac ggtatcgtca ctccggcagg tttgatgaat      960
ccgaaccact acctggcggt ggcaatcaat tacctgttcc agcatcgtcc gcagtggggc     1020
aaagatgttg ccgtcggtaa aacgctggtt tcatctgcga tgatcgaccg tgtggtcaac     1080
gacttgggcc gtaaactggt agaagtcccg gtaggtttca aatggtttgt cgatggtctg     1140
ttcgacggca gcttcggctt tggcggcgaa gagagtgcag gggcttcctt cctgcgtttc     1200
gacggcacgc cgtggtccac cgacaaagac ggcatcatca tgtgtctgct ggcggcggaa     1260
atcaccgctg tcaccggtaa gaacccgcag gaacactaca cgaactggc aaaacgcttt      1320 ggtgcgccga gctacaaccg tttgcaggca gctgcgactt ccgcacaaaa agcggcgctg     1380
tctaagctgt ctccggaaat ggtgagcgcc agcaccctgg caggtgaccc gatcaccgcg     1440
cgcctgactg ctgctccggg caacggtgct tctattggcg gtctgaaagt gatgactgac     1500
aacggctggt tcgccgcgcg tccgtcaggc acggaagacg catataagat ctactgcgaa     1560
agcttcctcg gtgaagaaca tcgcaagcag attgagaaag aagcggttga gattgttagc     1620
gaagttctga aaaacgcgta a                                                1641
```

<210> SEQ ID NO 200
<211> LENGTH: 546
<212> TYPE: PRT
<213> ORGANISM: Escherichia coli

<400> SEQUENCE: 200

```
Met Ala Ile His Asn Arg Ala Gly Gln Pro Ala Gln Gln Ser Asp Leu
1               5                   10                  15

Ile Asn Val Ala Gln Leu Thr Ala Gln Tyr Tyr Val Leu Lys Pro Glu
            20                  25                  30

Ala Gly Asn Ala Glu His Ala Val Lys Phe Gly Thr Ser Gly His Arg
        35                  40                  45

Gly Ser Ala Ala Arg His Ser Phe Asn Glu Pro His Ile Leu Ala Ile
    50                  55                  60

Ala Gln Ala Ile Ala Glu Glu Arg Ala Lys Asn Gly Ile Thr Gly Pro
65                  70                  75                  80

Cys Tyr Val Gly Lys Asp Thr His Ala Leu Ser Glu Pro Ala Phe Ile
                85                  90                  95

Ser Val Leu Glu Val Leu Ala Ala Asn Gly Val Asp Val Ile Val Gln
            100                 105                 110

Glu Asn Asn Gly Phe Thr Pro Thr Pro Ala Val Ser Asn Ala Ile Leu
        115                 120                 125

Val His Asn Lys Lys Gly Gly Pro Leu Ala Asp Gly Ile Val Ile Thr
    130                 135                 140

Pro Ser His Asn Pro Pro Glu Asp Gly Gly Ile Lys Tyr Asn Pro Pro
145                 150                 155                 160

Asn Gly Gly Pro Ala Asp Thr Asn Val Thr Lys Val Val Glu Asp Arg
                165                 170                 175

Ala Asn Ala Leu Leu Ala Asp Gly Leu Lys Gly Val Lys Arg Ile Ser
            180                 185                 190
```

| | | | | | | | | | | | |
|---|---|---|---|---|---|---|---|---|---|---|---|
| Leu | Asp | Glu | Ala | Met | Ala | Ser | Gly | His | Val | Lys | Glu | Gln | Asp | Leu | Val |
| | | 195 | | | | | 200 | | | | 205 | | | | |
| Gln | Pro | Phe | Val | Glu | Gly | Leu | Ala | Asp | Ile | Val | Asp | Met | Ala | Ala | Ile |
| 210 | | | | | 215 | | | | | 220 | | | | | |

Gln Lys Ala Gly Leu Thr Leu Gly Val Asp Pro Leu Gly Gly Ser Gly
225                 230                 235                 240

Ile Glu Tyr Trp Lys Arg Ile Gly Glu Tyr Tyr Asn Leu Asn Leu Thr
            245                 250                 255

Ile Val Asn Asp Gln Val Asp Gln Thr Phe Arg Phe Met His Leu Asp
                260                 265                 270

Lys Asp Gly Ala Ile Arg Met Asp Cys Ser Ser Glu Cys Ala Met Ala
        275                 280                 285

Gly Leu Leu Ala Leu Arg Asp Lys Phe Asp Leu Ala Phe Ala Asn Asp
    290                 295                 300

Pro Tyr Asp Arg His Gly Ile Val Thr Pro Ala Gly Leu Met Asn
305                 310                 315                 320

Pro Asn His Tyr Leu Ala Val Ala Ile Asn Tyr Leu Phe Gln His Arg
                325                 330                 335

Pro Gln Trp Gly Lys Asp Val Ala Val Gly Lys Thr Leu Val Ser Ser
            340                 345                 350

Ala Met Ile Asp Arg Val Val Asn Asp Leu Gly Arg Lys Leu Val Glu
        355                 360                 365

Val Pro Val Gly Phe Lys Trp Phe Val Asp Gly Leu Phe Asp Gly Ser
    370                 375                 380

Phe Gly Phe Gly Gly Glu Glu Ser Ala Gly Ala Ser Phe Leu Arg Phe
385                 390                 395                 400

Asp Gly Thr Pro Trp Ser Thr Asp Lys Asp Gly Ile Ile Met Cys Leu
                405                 410                 415

Leu Ala Ala Glu Ile Thr Ala Val Thr Gly Lys Asn Pro Gln Glu His
            420                 425                 430

Tyr Asn Glu Leu Ala Lys Arg Phe Gly Ala Pro Ser Tyr Asn Arg Leu
        435                 440                 445

Gln Ala Ala Ala Thr Ser Ala Gln Lys Ala Ala Leu Ser Lys Leu Ser
    450                 455                 460

Pro Glu Met Val Ser Ala Ser Thr Leu Ala Gly Asp Pro Ile Thr Ala
465                 470                 475                 480

Arg Leu Thr Ala Ala Pro Gly Asn Gly Ala Ser Ile Gly Gly Leu Lys
                485                 490                 495

Val Met Thr Asp Asn Gly Trp Phe Ala Ala Arg Pro Ser Gly Thr Glu
            500                 505                 510

Asp Ala Tyr Lys Ile Tyr Cys Glu Ser Phe Leu Gly Glu Glu His Arg
        515                 520                 525

Lys Gln Ile Glu Lys Glu Ala Val Glu Ile Val Ser Glu Val Leu Lys
    530                 535                 540

Asn Ala
545

<210> SEQ ID NO 201
<211> LENGTH: 1746
<212> TYPE: DNA
<213> ORGANISM: Bacillus subtilis

<400> SEQUENCE: 201
atgacttgga gaaagagcta tgaacgctgg aaacagacag aacatttaga tctggaatta    60

-continued

```
aaagagcgcc ttattgaatt agagggagat gaacaggccc ttgaggactg tttctataaa    120
gaccttgaat tcggtaccgg cggaatgcgc ggggaaatcg gcgccgggac aaatcggatg    180
aatatttaca ctgtgcgcaa agcatcggcc gggtttgcgg catacatctc gaagcaaggt    240
gaggaagcga aaaacgggg cgttgtcatt gcttatgatt cccgccataa gtctccggag     300
ttcgcgatgg aagcggcaaa acacttgcg acacaaggca tccaaacata cgtgtttgat     360
gagcttcgcc cgacgccaga gctgtcattc gctgttagac agctgaacgc ttatggtgga    420
attgtggtaa cggcaagcca taacccgcct gaatataacg gctacaaagt atacggggat    480
gatggcggcc agctgcctcc aaaggaagcg gacatcgtca ttgagcaggt aaacgcgatt    540
gaaaatgagc tgacgatcac agtggacgaa gaaaataagt taaagaaaaa aggcttaatc    600
aaaatcatcg gtgaagatat tgataaagtt tatacagaaa aactgacgtc catttctgta    660
catcctgaat tatcggaaga agtagatgta aaggttgttt tcacaccgct gcatggaact    720
gcaaataaac cggtcagacg cggtcttgaa gcactcggct acaaaaatgt aacggttgtc    780
aaagaacagg aactgccgga ttcaaacttc tccactgtta catcgccgaa cccggaagag    840
catgcggcat tcgaatatgc cattaagctt ggggaggagc agaatgcaga tattctcatc    900
gcgacagatc ctgatgctga ccgcctcggc atcgcggtga aaaacgatca aggcaaatat    960
acagtgctga caggaaacca aaccggagcg ttgctgcttc attacctgct ttctgaaaag   1020
aaaaaacaag gcatcctgcc tgataacggt gttgttctca aaacgatcgt cacaagcgaa   1080
atcggccgtg ctgtagcttc ttcattcggc cttgatacga ttgatacgct gacaggcttt   1140
aagtttatcg gtgaaaagat taaggaatac gaagcatcag gccagtatac cttccaattc   1200
ggttatgaag agagctacgg ttatttaatc ggggattttg cccgcgataa ggacgccatt   1260
caggctgcgc ttttggcagt tgaagtttgc gcgttctata aaaaacaggg aatgtcattg   1320
tatgaggcgc tcatcaatct ctttaacgaa tatggttttt atcgtgaagg gctgaaatcc   1380
ctgacgctga aagcaaaaca aggagcagag caaattgaag cgattcttgc ttccttcaga   1440
caaaatccgc cgcagaaaat ggcgggcaaa caggttgtca cagcagaaga ttacgctgta   1500
agcaaacgga cgcttctgac tgaaagcaaa gaagaagcca tcgacttgcc aaaatcaaat   1560
gtattgaaat acttcctgga agacgggtct tggttctgtc tccgtccttc tggaactgag   1620
ccgaaggtta aattttattt cgccgtaaaa gggtcatctt tggaagacag tgaaaagcga   1680
cttgccgtcc tttctgaaga tgtaatgaag acggtggatg aaattgttga gtcaacagca   1740
aaataa                                                              1746
```

<210> SEQ ID NO 202
<211> LENGTH: 581
<212> TYPE: PRT
<213> ORGANISM: Bacillus subtilis

<400> SEQUENCE: 202

```
Met Thr Trp Arg Lys Ser Tyr Glu Arg Trp Lys Gln Thr Glu His Leu
 1               5                  10                  15

Asp Leu Glu Leu Lys Glu Arg Leu Ile Glu Leu Glu Gly Asp Glu Gln
            20                  25                  30

Ala Leu Glu Asp Cys Phe Tyr Lys Asp Leu Glu Phe Gly Thr Gly Gly
        35                  40                  45

Met Arg Gly Glu Ile Gly Ala Gly Thr Asn Arg Met Asn Ile Tyr Thr
    50                  55                  60

Val Arg Lys Ala Ser Ala Gly Phe Ala Ala Tyr Ile Ser Lys Gln Gly
```

```
                65                  70                  75                  80
Glu Glu Ala Lys Lys Arg Gly Val Val Ile Ala Tyr Asp Ser Arg His
                    85                  90                  95
Lys Ser Pro Glu Phe Ala Met Glu Ala Ala Lys Thr Leu Ala Thr Gln
                100                 105                 110
Gly Ile Gln Thr Tyr Val Phe Asp Glu Leu Arg Pro Thr Pro Glu Leu
                115                 120                 125
Ser Phe Ala Val Arg Gln Leu Asn Ala Tyr Gly Gly Ile Val Val Thr
            130                 135                 140
Ala Ser His Asn Pro Pro Glu Tyr Asn Gly Tyr Lys Val Tyr Gly Asp
145                 150                 155                 160
Asp Gly Gly Gln Leu Pro Pro Lys Glu Ala Asp Ile Val Ile Glu Gln
                165                 170                 175
Val Asn Ala Ile Glu Asn Glu Leu Thr Ile Thr Val Asp Glu Glu Asn
            180                 185                 190
Lys Leu Lys Glu Lys Gly Leu Ile Lys Ile Gly Glu Asp Ile Asp
            195                 200                 205
Lys Val Tyr Thr Glu Lys Leu Thr Ser Ile Ser Val His Pro Glu Leu
            210                 215                 220
Ser Glu Glu Val Asp Val Lys Val Val Phe Thr Pro Leu His Gly Thr
225                 230                 235                 240
Ala Asn Lys Pro Val Arg Arg Gly Leu Glu Ala Leu Gly Tyr Lys Asn
                245                 250                 255
Val Thr Val Val Lys Glu Gln Glu Leu Pro Asp Ser Asn Phe Ser Thr
                260                 265                 270
Val Thr Ser Pro Asn Pro Glu Glu His Ala Ala Phe Glu Tyr Ala Ile
            275                 280                 285
Lys Leu Gly Glu Glu Gln Asn Ala Asp Ile Leu Ile Ala Thr Asp Pro
            290                 295                 300
Asp Ala Asp Arg Leu Gly Ile Ala Val Lys Asn Asp Gln Gly Lys Tyr
305                 310                 315                 320
Thr Val Leu Thr Gly Asn Gln Thr Gly Ala Leu Leu Leu His Tyr Leu
                325                 330                 335
Leu Ser Glu Lys Lys Gln Gly Ile Leu Pro Asp Asn Gly Val Val
            340                 345                 350
Leu Lys Thr Ile Val Thr Ser Glu Ile Gly Arg Ala Val Ala Ser Ser
            355                 360                 365
Phe Gly Leu Asp Thr Ile Asp Thr Leu Thr Gly Phe Lys Phe Ile Gly
370                 375                 380
Glu Lys Ile Lys Glu Tyr Glu Ala Ser Gly Gln Tyr Thr Phe Gln Phe
385                 390                 395                 400
Gly Tyr Glu Glu Ser Tyr Gly Tyr Leu Ile Gly Asp Phe Ala Arg Asp
                405                 410                 415
Lys Asp Ala Ile Gln Ala Ala Leu Leu Ala Val Glu Val Cys Ala Phe
                420                 425                 430
Tyr Lys Lys Gln Gly Met Ser Leu Tyr Glu Ala Leu Ile Asn Leu Phe
            435                 440                 445
Asn Glu Tyr Gly Phe Tyr Arg Glu Gly Leu Lys Ser Leu Thr Leu Lys
            450                 455                 460
Gly Lys Gln Gly Ala Glu Gln Ile Glu Ala Ile Leu Ala Ser Phe Arg
465                 470                 475                 480
Gln Asn Pro Pro Gln Lys Met Ala Gly Lys Gln Val Val Thr Ala Glu
                485                 490                 495
```

Asp Tyr Ala Val Ser Lys Arg Thr Leu Leu Thr Glu Ser Lys Glu Glu
                500                 505                 510

Ala Ile Asp Leu Pro Lys Ser Asn Val Leu Lys Tyr Phe Leu Glu Asp
            515                 520                 525

Gly Ser Trp Phe Cys Leu Arg Pro Ser Gly Thr Glu Pro Lys Val Lys
        530                 535                 540

Phe Tyr Phe Ala Val Lys Gly Ser Ser Leu Glu Asp Ser Glu Lys Arg
545                 550                 555                 560

Leu Ala Val Leu Ser Glu Asp Val Met Lys Thr Val Asp Glu Ile Val
                565                 570                 575

Glu Ser Thr Ala Lys
            580

<210> SEQ ID NO 203
<211> LENGTH: 666
<212> TYPE: DNA
<213> ORGANISM: Lactococcus lactis

<400> SEQUENCE: 203
atgtttaaag cagtattgtt tgatttagat ggtgtaatta cagataccgc agagtatcat      60
tttagagctt ggaaagcttt ggctgaagaa attggcatta atggtgttga ccgccaattt     120
aatgagcaat aaaaggggt ctcacgagaa gactcgcttc agaaaattct agatttagct      180
gataaaaaag tatcagctga ggaatttaaa gaacttgcta agagaaaaaa tgataactat     240
gtgaaaatga ttcaggatgt gtcgccagcc gatgtctatc ctggaatttt acaattactc     300
aaagatttac gttcaaataa aatcaaaatt gctttagcat cggcttctaa gaatggtcca     360 ttttattag agaaaatgaa tttaactgga tattttgatg caattgctga tccggctgaa     420
gttgcagcat caaaaccagc accagatatt tttattgcag cagcacatgc agtgggtgtt     480 gcccctctg aatcaattgg gttagaggat tctcaagctg gaattcaagc catcaaagat      540 tcagggctt taccaattgg tgtagggcgc ccagaagatt tgggagatga tatcgtcatt     600
gtgcctgata cttcatacta tacattagaa ttttgaaag aagtttggct tcaaaagcaa      660
aaatga                                                                666

<210> SEQ ID NO 204
<211> LENGTH: 221
<212> TYPE: PRT
<213> ORGANISM: Lactococcus lactis

<400> SEQUENCE: 204

Met Phe Lys Ala Val Leu Phe Asp Leu Asp Gly Val Ile Thr Asp Thr
1               5                   10                  15

Ala Glu Tyr His Phe Arg Ala Trp Lys Ala Leu Ala Glu Glu Ile Gly
            20                  25                  30

Ile Asn Gly Val Asp Arg Gln Phe Asn Glu Gln Leu Lys Gly Val Ser
        35                  40                  45

Arg Glu Asp Ser Leu Gln Lys Ile Leu Asp Leu Ala Asp Lys Lys Val
    50                  55                  60

Ser Ala Glu Glu Phe Lys Glu Leu Ala Lys Arg Lys Asn Asp Asn Tyr
65                  70                  75                  80

Val Lys Met Ile Gln Asp Val Ser Pro Ala Asp Val Tyr Pro Gly Ile
                85                  90                  95

Leu Gln Leu Leu Lys Asp Leu Arg Ser Asn Lys Ile Lys Ile Ala Leu
            100                 105                 110

Ala Ser Ala Ser Lys Asn Gly Pro Phe Leu Leu Glu Lys Met Asn Leu
            115                 120                 125

Thr Gly Tyr Phe Asp Ala Ile Ala Asp Pro Ala Glu Val Ala Ala Ser
    130                 135                 140

Lys Pro Ala Pro Asp Ile Phe Ile Ala Ala His Ala Val Gly Val
145                 150                 155                 160

Ala Pro Ser Glu Ser Ile Gly Leu Glu Asp Ser Gln Ala Gly Ile Gln
                165                 170                 175

Ala Ile Lys Asp Ser Gly Ala Leu Pro Ile Gly Val Gly Arg Pro Glu
            180                 185                 190

Asp Leu Gly Asp Asp Ile Val Ile Val Pro Asp Thr Ser Tyr Tyr Thr
            195                 200                 205

Leu Glu Phe Leu Lys Glu Val Trp Leu Gln Lys Gln Lys
            210                 215                 220

<210> SEQ ID NO 205
<211> LENGTH: 660
<212> TYPE: DNA
<213> ORGANISM: Escherichia coli

<400> SEQUENCE: 205
atgaaactgc aagggtaat tttcgatctg gatggtgtaa tcaccgatac cgcgcatctg      60
catttccagg cgtggcagca gattgccgct gaaattggca tcagcattga tgcgcagttt     120
aacgaatccc taaaagggat cagccgcgat gagtctctgc ggcgcattct gcaacacggg     180
ggcaaagagg gcgactttaa ctcgcaggag agggcgcaac tggcgtatcg caaaaatctg     240
ctctatgtcc actcactacg cgagttgacg gtcaacgctg ttctacccgg cattcgctct     300
tgctggcag atctccgtgc acagcagatc tcggttgggc tggcttctgt ctccctgaat     360
gcgccgacga ttttagcggc gctggagctg cgcgagtttt tcaccttctg cgcggatgct     420
tcccaactta aaaactcgaa accggacccg gaaatctttc tcgccgcctg tgcagggctg     480
ggcgtgccgc cgcaggcatg tatcggcatt gaagatgcgc aggcgggcat tgacgccatt     540
aacgccagcg gtatgcgctc ggtgggatc ggcgcgggct taaccggggc gcaattactg     600
ttgccttcaa cggaatcact cacctggccg cggttatcgg ccttctggca aaacgtatag     660

<210> SEQ ID NO 206
<211> LENGTH: 219
<212> TYPE: PRT
<213> ORGANISM: Escherichia coli

<400> SEQUENCE: 206

Met Lys Leu Gln Gly Val Ile Phe Asp Leu Asp Gly Val Ile Thr Asp
1               5                   10                  15

Thr Ala His Leu His Phe Gln Ala Trp Gln Gln Ile Ala Ala Glu Ile
            20                  25                  30

Gly Ile Ser Ile Asp Ala Gln Phe Asn Glu Ser Leu Lys Gly Ile Ser
        35                  40                  45

Arg Asp Glu Ser Leu Arg Arg Ile Leu Gln His Gly Gly Lys Glu Gly
    50                  55                  60

Asp Phe Asn Ser Gln Glu Arg Ala Gln Leu Ala Tyr Arg Lys Asn Leu
65                  70                  75                  80

Leu Tyr Val His Ser Leu Arg Glu Leu Thr Val Asn Ala Val Leu Pro
                85                  90                  95

Gly Ile Arg Ser Leu Leu Ala Asp Leu Arg Ala Gln Gln Ile Ser Val

```
            100                 105                 110
Gly Leu Ala Ser Val Ser Leu Asn Ala Pro Thr Ile Leu Ala Ala Leu
        115                 120                 125

Glu Leu Arg Glu Phe Phe Thr Phe Cys Ala Asp Ala Ser Gln Leu Lys
        130                 135                 140

Asn Ser Lys Pro Asp Pro Glu Ile Phe Leu Ala Ala Cys Ala Gly Leu
145                 150                 155                 160

Gly Val Pro Pro Gln Ala Cys Ile Gly Ile Glu Asp Ala Gln Ala Gly
                165                 170                 175

Ile Asp Ala Ile Asn Ala Ser Gly Met Arg Ser Val Gly Ile Gly Ala
                180                 185                 190

Gly Leu Thr Gly Ala Gln Leu Leu Pro Ser Thr Glu Ser Leu Thr
            195                 200                 205

Trp Pro Arg Leu Ser Ala Phe Trp Gln Asn Val
        210                 215

<210> SEQ ID NO 207
<211> LENGTH: 1392
<212> TYPE: DNA
<213> ORGANISM: Pseudomonas aeruginosa

<400> SEQUENCE: 207
```

| | | | | | |
|---|---|---|---|---|---|
| atgagcactg | taaaagcacc | gacgctgccc | gccagcatct | tccgcgccta | cgacatccgt | 60 |
| cgcgtggtag | gcgataccct | caccgccgag | accgcctact | ggatcggtcg | cgccatcggc | 120 |
| tcggaaagcc | tcgcccgcgg | cgaaccgtgc | gtcgctgtcg | gccgcgatgg | ccgcctgtcc | 180 |
| ggtcccgagc | tggtcaagca | gctgatccag | ggcctggtgg | actgcggttg | ccaggtcagc | 240 |
| gacgtgggca | tggtgcctac | cccggtgctg | tactacgcgg | ccaacgtgct | cgagggcaag | 300 |
| tccggggtga | tgctgaccgg | cagccacaat | ccgccggact | acaacggctt | caagatcgtg | 360 |
| gtcgccggcg | agaccctggc | caacgagcag | atccaggccc | tgcgcgagcg | catcgagaaa | 420 |
| aacgacctgg | catccggcgt | cggcagcgta | gagcaggtcg | acatcctgcc | gcgctacttc | 480 |
| aagcagatcc | gcgacgacat | cgccatggcc | aagccgatga | aggtggtggt | cgactgcggc | 540 |
| aacggcgtgg | ccggggtgat | cgccccgcag | ttgatcgagg | ccctgggctg | cagcgtgatc | 600 |
| ccgctgtact | gcgaggtcga | cggcaacttc | ccgaaccacc | atccggaccc | gggcaagccg | 660 |
| gagaacctga | aggacctgat | cgccaaggtc | aaggccgaga | cgccgaccct | gggcctggcc | 720 |
| ttcgacggcg | acggcgatcg | cgtcggcgtg | gtcaccaata | ccggtaccat | catctatccg | 780 |
| gaccgtctgc | tgatgctgtt | cgccaaggac | gtggtctcgc | gcaacccggg | ggccgacatc | 840 |
| atcttcgacg | tcaagtgcac | ccgccgtctg | atcgccctga | tcagcggcta | cggcggccgt | 900 |
| ccggtgatgt | ggaagaccgg | ccactcgctg | atcaagaaga | agatgaagga | aaccggcgcc | 960 |
| ctgctggctg | gcgagatgag | cggccacgtg | ttcttcaagg | agcgctggtt | cggcttcgac | 1020 |
| gatggcatct | acagcgccgc | ccgcctgctg | gaaatcctca | gccaggatca | gcgtgacagc | 1080 |
| gagcacgtgt | tctcggcctt | cccgagcgac | atttccaccc | cggaaatcaa | catcaccgtc | 1140 |
| accgaggaca | gcaagttcgc | catcatcgag | gcgctgcaac | gcgacgccca | atggggcgaa | 1200 |
| ggcaacatca | ccaccctcga | cggcgtgcgg | gtcgactacc | ccaaaggctg | ggccctggta | 1260 |
| cgcgcctcca | acaccactcc | cgtgctggtc | ctgcgcttcg | aagcggaccc | cgaggaagag | 1320 |
| ctggagcgca | tcaagaccgt | cttccgtaac | caactgaagg | cagtggattc | ctcgctgccc | 1380 |
| gtgcccttct | ga | | | | | 1392 |

<210> SEQ ID NO 208
<211> LENGTH: 463
<212> TYPE: PRT
<213> ORGANISM: Pseudomonas aeruginosa

<400> SEQUENCE: 208

```
Met Ser Thr Ala Lys Ala Pro Thr Leu Pro Ala Ser Ile Phe Arg Ala
1               5                   10                  15

Tyr Asp Ile Arg Gly Val Val Gly Asp Thr Leu Thr Glu Thr Ala
            20                  25                  30

Tyr Trp Ile Gly Arg Ala Ile Gly Ser Glu Ser Leu Ala Arg Gly Glu
            35                  40                  45

Pro Cys Val Ala Val Gly Arg Asp Gly Arg Leu Ser Gly Pro Glu Leu
        50                  55                  60

Val Lys Gln Leu Ile Gln Gly Leu Val Asp Cys Gly Cys Gln Val Ser
65                  70                  75                  80

Asp Val Gly Met Val Pro Thr Pro Val Leu Tyr Tyr Ala Ala Asn Val
                85                  90                  95

Leu Glu Gly Lys Ser Gly Val Met Leu Thr Gly Ser His Asn Pro Pro
            100                 105                 110

Asp Tyr Asn Gly Phe Lys Ile Val Val Ala Gly Glu Thr Leu Ala Asn
        115                 120                 125

Glu Gln Ile Gln Ala Leu Arg Glu Arg Ile Glu Lys Asn Asp Leu Ala
130                 135                 140

Ser Gly Val Gly Ser Val Glu Gln Val Asp Ile Leu Pro Arg Tyr Phe
145                 150                 155                 160

Lys Gln Ile Arg Asp Asp Ile Ala Met Ala Lys Pro Met Lys Val Val
                165                 170                 175

Val Asp Cys Gly Asn Gly Val Ala Gly Val Ile Ala Pro Gln Leu Ile
            180                 185                 190

Glu Ala Leu Gly Cys Ser Val Ile Pro Leu Tyr Cys Glu Val Asp Gly
        195                 200                 205

Asn Phe Pro Asn His His Pro Asp Pro Gly Lys Pro Glu Asn Leu Lys
    210                 215                 220

Asp Leu Ile Ala Lys Val Lys Ala Glu Asn Ala Asp Leu Gly Leu Ala
225                 230                 235                 240

Phe Asp Gly Asp Gly Asp Arg Val Gly Val Val Thr Asn Thr Gly Thr
                245                 250                 255

Ile Ile Tyr Pro Asp Arg Leu Leu Met Leu Phe Ala Lys Asp Val Val
            260                 265                 270

Ser Arg Asn Pro Gly Ala Asp Ile Ile Phe Asp Val Lys Cys Thr Arg
        275                 280                 285

Arg Leu Ile Ala Leu Ile Ser Gly Tyr Gly Gly Arg Pro Val Met Trp
    290                 295                 300

Lys Thr Gly His Ser Leu Ile Lys Lys Met Lys Glu Thr Gly Ala
305                 310                 315                 320

Leu Leu Ala Gly Glu Met Ser Gly His Val Phe Lys Glu Arg Trp
                325                 330                 335

Phe Gly Phe Asp Asp Gly Ile Tyr Ser Ala Ala Arg Leu Leu Glu Ile
            340                 345                 350

Leu Ser Gln Asp Gln Arg Asp Ser Glu His Val Phe Ser Ala Phe Pro
        355                 360                 365

Ser Asp Ile Ser Thr Pro Glu Ile Asn Ile Thr Val Thr Glu Asp Ser
    370                 375                 380
```

```
Lys Phe Ala Ile Ile Glu Ala Leu Gln Arg Asp Ala Gln Trp Gly Glu
385                 390                 395                 400

Gly Asn Ile Thr Thr Leu Asp Gly Val Arg Val Asp Tyr Pro Lys Gly
                405                 410                 415

Trp Gly Leu Val Arg Ala Ser Asn Thr Thr Pro Val Leu Val Leu Arg
            420                 425                 430

Phe Glu Ala Asp Thr Glu Glu Glu Leu Glu Arg Ile Lys Thr Val Phe
        435                 440                 445

Arg Asn Gln Leu Lys Ala Val Asp Ser Ser Leu Pro Val Pro Phe
    450                 455                 460
```

<210> SEQ ID NO 209
<211> LENGTH: 1371
<212> TYPE: DNA
<213> ORGANISM: Escherichia coli

<400> SEQUENCE: 209

```
atgaaaaaat taacctgctt taaagcctat gatattcgcg ggaaattagg cgaagaactg      60
aatgaagata tcgcctggcg cattggtcgc gcctatggcg aatttctcaa accgaaaacc     120
attgtgttag gcggtgatgt ccgcctcacc agcgaaacct aaaactggc gctggcgaaa      180
ggtttacagg atgcgggcgt tgacgtgctg atattggta tgtccggcac cgaagagatc      240
tatttcgcca cgttccatct cggcgtggat ggcggcattg aagttaccgc cagccataat    300
ccgatggatt ataacggcat gaagctggtt cgcgagggg ctcgcccgat cagcggagat     360
accggactgc gcgacgtcca gcgtctggct gaagccaacg actttcctcc cgtcgatgaa    420
accaaacgcg gtcgctatca gcaaatcaac ctgcgtgacg cttacgttga tcacctgttc    480
ggttatatca atgtcaaaaa cctcacgccg ctcaagctgg tgatcaactc cgggaacggc    540
gcagcgggtc cggtggtgga cgccattgaa gcccgcttta aagccctcgg cgcgcccgtg    600
gaattaatca aagtgcacaa cacgccggac ggcaatttcc ccaacggtat tcctaaccca    660
ctactgccgg aatgccgcga cgacacccgc aatgcggtca tcaaacacgg cgcggatatg    720
ggcattgctt tgatggcga ttttgaccgc tgtttcctgt tgacgaaaaa agggcagttt    780
attgagggct actacattgt cggcctgttg gcagaagcat tcctcgaaaa aaatcccggc    840
gcgaagatca tccacgatcc acgtctctcc tggaacaccg ttgatgtggt gactgccgca    900
ggtggcacgc cggtaatgtc gaaaaccgga cacgccttta ttaaagaacg tatgcgcaag    960
gaagacgcca tctatggtgg cgaaatgagc gcccaccatt acttccgtga tttcgcttac   1020
tgcgacagcg gcatgatccc gtggctgctg gtcgccgaac tggtgtgcct gaaagataaa   1080
acgctgggcg aactggtacg cgaccggatg gcggcgtttc cggcaagcgg tgagatcaac   1140
agcaaactgg cgcaacccgt tgaggcgatt aaccgcgtgg aacagcattt tagccgtgag   1200
gcgctggcgg tggatcgcac cgatggcatc agcatgacct ttgccgactg gcgctttaac   1260
ctgcgcacct ccaataccga accggtggtg cgcctgaatg tggaatcgcg cggtgatgtg   1320
ccgctgatgg aagcgcgaac gcgaactctg ctgacgttgc tgaacgagta a             1371
```

<210> SEQ ID NO 210
<211> LENGTH: 456
<212> TYPE: PRT
<213> ORGANISM: Escherichia coli

<400> SEQUENCE: 210

Met Lys Lys Leu Thr Cys Phe Lys Ala Tyr Asp Ile Arg Gly Lys Leu

-continued

```
1               5                   10                  15
Gly Glu Glu Leu Asn Glu Asp Ile Ala Trp Arg Ile Gly Arg Ala Tyr
            20                  25                  30
Gly Glu Phe Leu Lys Pro Lys Thr Ile Val Leu Gly Gly Asp Val Arg
            35                  40                  45
Leu Thr Ser Glu Thr Leu Lys Leu Ala Leu Ala Lys Gly Leu Gln Asp
50                  55                  60
Ala Gly Val Asp Val Leu Asp Ile Gly Met Ser Gly Thr Glu Glu Ile
65                  70                  75                  80
Tyr Phe Ala Thr Phe His Leu Gly Val Asp Gly Ile Glu Val Thr
                85                  90                  95
Ala Ser His Asn Pro Met Asp Tyr Asn Gly Met Lys Leu Val Arg Glu
            100                 105                 110
Gly Ala Arg Pro Ile Ser Gly Asp Thr Gly Leu Arg Asp Val Gln Arg
            115                 120                 125
Leu Ala Glu Ala Asn Asp Phe Pro Pro Val Asp Glu Thr Lys Arg Gly
            130                 135                 140
Arg Tyr Gln Gln Ile Asn Leu Arg Asp Ala Tyr Val Asp His Leu Phe
145                 150                 155                 160
Gly Tyr Ile Asn Val Lys Asn Leu Thr Pro Leu Lys Leu Val Ile Asn
                165                 170                 175
Ser Gly Asn Gly Ala Ala Gly Pro Val Val Asp Ala Ile Glu Ala Arg
            180                 185                 190
Phe Lys Ala Leu Gly Ala Pro Val Glu Leu Ile Lys Val His Asn Thr
            195                 200                 205
Pro Asp Gly Asn Phe Pro Asn Gly Ile Pro Asn Pro Leu Leu Pro Glu
            210                 215                 220
Cys Arg Asp Asp Thr Arg Asn Ala Val Ile Lys His Gly Ala Asp Met
225                 230                 235                 240
Gly Ile Ala Phe Asp Gly Asp Phe Asp Arg Cys Phe Leu Phe Asp Glu
                245                 250                 255
Lys Gly Gln Phe Ile Glu Gly Tyr Tyr Ile Val Gly Leu Leu Ala Glu
            260                 265                 270
Ala Phe Leu Glu Lys Asn Pro Gly Ala Lys Ile Ile His Asp Pro Arg
            275                 280                 285
Leu Ser Trp Asn Thr Val Asp Val Val Thr Ala Gly Gly Thr Pro
            290                 295                 300
Val Met Ser Lys Thr Gly His Ala Phe Ile Lys Glu Arg Met Arg Lys
305                 310                 315                 320
Glu Asp Ala Ile Tyr Gly Gly Glu Met Ser Ala His His Tyr Phe Arg
                325                 330                 335
Asp Phe Ala Tyr Cys Asp Ser Gly Met Ile Pro Trp Leu Leu Val Ala
            340                 345                 350
Glu Leu Val Cys Leu Lys Asp Lys Thr Leu Gly Glu Leu Val Arg Asp
            355                 360                 365
Arg Met Ala Ala Phe Pro Ala Ser Gly Glu Ile Asn Ser Lys Leu Ala
            370                 375                 380
Gln Pro Val Glu Ala Ile Asn Arg Val Glu Gln His Phe Ser Arg Glu
385                 390                 395                 400
Ala Leu Ala Val Asp Arg Thr Asp Gly Ile Ser Met Thr Phe Ala Asp
                405                 410                 415
Trp Arg Phe Asn Leu Arg Thr Ser Asn Thr Glu Pro Val Val Arg Leu
            420                 425                 430
```

Asn Val Glu Ser Arg Gly Asp Val Pro Leu Met Glu Ala Arg Thr Arg
    435                 440                 445

Thr Leu Leu Thr Leu Leu Asn Glu
    450                 455

<210> SEQ ID NO 211
<211> LENGTH: 2478
<212> TYPE: DNA
<213> ORGANISM: Bifidobacterium dentium

<400> SEQUENCE: 211

| | | | | |
|---|---|---|---|---|
| atgacgagtc | ctgttattgg | cacccctttgg | aagaagctga | acgctccggt | ttccgaggaa | 60 |
| gctatcgaag | gtgtggataa | gtactggcgt | gcagccaact | acctctccat | cggccagatc | 120 |
| tatctgcgta | gcaacccgct | gatgaaggag | cccttcaccc | gcgaagacgt | caagcaccgt | 180 |
| ctggtcggcc | actggggcac | caccccgggc | ctgaacttcc | tcatcggcca | catcaaccgt | 240 |
| ctcatcgctg | atcaccagca | gaacaccgtg | atcatcatgg | gcccgggcca | cggcggcccg | 300 |
| gctggtaccg | ctcagtccta | cctggacggc | acctacaccg | agtacttccc | gaacatcacc | 360 |
| aaggatgaag | ctggcctgca | gaagttcttc | cgccagttct | cctacccggg | cggcatcccg | 420 |
| tcccactacg | ctccggagac | cccgggctcc | atccacgaag | gtggcgagct | gggttacgcc | 480 |
| ctgtcccacg | cctatggcgc | tgtgatgaac | aacccgagcc | tgttcgttcc | ggccatcgtc | 540 |
| ggcgacggcg | aagccgagac | cggcccgctg | gccaccggct | ggcagtccaa | caagctcgtc | 600 |
| aacccgcgca | ccgacggtat | cgtgctgccg | atcctgcacc | tcaatggcta | caagatcgcc | 660 |
| aacccgacca | tcctgtcccg | catctccgac | gaagagctgc | acgagttctt | ccacggcatg | 720 |
| ggctatgagc | cgtatgagtt | cgtcgccggc | ttcgacaacg | aggatcacct | gtcgatccac | 780 |
| cgtcgtttcg | ccgagttgtt | cgagaccgtc | ttcgacgaga | tctgcgacat | caaggccgcc | 840 |
| gctcagactg | acgacatgac | tcgtccgttc | tacccgatga | tcatcttccg | caccccgaag | 900 |
| ggctggaccct | gcccgaagtt | catcgacggc | aagaagaccg | aaggttcctg | gcgctcccac | 960 |
| caggttccgc | tggcttccgc | ccgcgatacc | gaggctcact | tcgaggtcct | caagaactgg | 1020 |
| ctcgagtcct | acaagccgga | agagctgttc | gacgccaacg | cgccgtgaa | gccggaagtc | 1080 |
| accgccttca | tgccgaccgg | cgaactgcgc | atcggtgaga | cccgaacgc | caacggtggc | 1140 |
| cgcatccgcg | aagagctgaa | cctgccggcc | ctcgaggact | acgaggtcaa | ggaagtcgcc | 1200 |
| gagtacggcc | acggctgggg | ccagctcgag | gccacccgtc | gtctgggcgt | ctacacccgc | 1260 |
| gacatcatca | gaacaaccc | ggactccttc | cgtatcttcg | accggacga | gaccgcttcc | 1320 |
| aaccgtctgc | aggccgcata | cgacgtcacc | aacaagcagt | gggacgccgg | ctacctgtcc | 1380 |
| gctcaggttg | atgagcacat | ggccgtcacc | ggtcaggtca | ccgagcagct | ctccgagcac | 1440 |
| cagatggaag | gcttcctcga | ggcctacctg | ctcaccggcc | gtcacggcat | ctggagctcc | 1500 |
| tacgagtcct | tcgtgcacgt | gatcgactcc | atgctgaacc | agcacgccaa | gtggctcgag | 1560 |
| gctaccgtcc | gcgagatccc | gtggcgcaag | ccgatctcct | ccatgaacct | gctcgtctcc | 1620 |
| tcccacgtgt | ggcgtcagga | tcacaacggc | ttctcccacc | aggatccggg | tgtcaccctcc | 1680 |
| gtcctgctga | acaagtgctt | caacaacgat | acgtgatcg | gcatctactt | cccggtggat | 1740 |
| tccaacatgc | tgctcgccgt | ggctgagaag | tgctacaagt | ccaccgacat | gatcaacgcc | 1800 |
| atcatcgccg | gcaagcagcc | ggccgccacc | tggctgaccc | tggacgaagc | tcgcgccgag | 1860 |
| ctcgagaagg | gtgccgccga | gtgggagtgg | gcctccaccg | ccaagtccaa | cgacgaagca | 1920 |

-continued

```
cagatcgtgc tcgcctccgc tggcgatgtc ccggctcagg agatcatggc cgctgccgac   1980
aagctcgatg ccatgggcat caagttcaag gtcgtcaacg ttgtggatct ggtcaagctg   2040
cagtccacca aggagaatga cgaagccatc tccgacgccg acttcgctga cctgttcacc   2100
gaggacaagc cggtcctgtt cgcctaccac tcctatgccc gcgacgtgcg tggtctgatc   2160
tacgatcgcc cgaaccacga caacttcaac gtccacggct acgaggagca gggctccacc   2220
accaccccgt acgacatggt cgcgtgaac aacatcgatc gctacgagct cgttgccgaa   2280
gctctgcgca tgatcgacgc tgacaagtac gccgacaaga tcgacgagct cgaggccttc   2340
cgcaaggaag ccttccagtt cgcagtcgac aacggctacg atcacccgga ttacaccgac   2400
tgggtgtact ccggcgtcaa caccaacaag cagggtgctg tctccgctac cgccgcaacc   2460
gccggcgata acgagtga                                                 2478
```

<210> SEQ ID NO 212
<211> LENGTH: 825
<212> TYPE: PRT
<213> ORGANISM: Bifidobacterium dentium

<400> SEQUENCE: 212

```
Met Thr Ser Pro Val Ile Gly Thr Pro Trp Lys Lys Leu Asn Ala Pro
1               5                  10                  15

Val Ser Glu Glu Ala Ile Glu Gly Val Asp Lys Tyr Trp Arg Ala Ala
            20                  25                  30

Asn Tyr Leu Ser Ile Gly Gln Ile Tyr Leu Arg Ser Asn Pro Leu Met
        35                  40                  45

Lys Glu Pro Phe Thr Arg Glu Asp Val Lys His Arg Leu Val Gly His
    50                  55                  60

Trp Gly Thr Thr Pro Gly Leu Asn Phe Leu Ile Gly His Ile Asn Arg
65                  70                  75                  80

Leu Ile Ala Asp His Gln Gln Asn Thr Val Ile Ile Met Gly Pro Gly
                85                  90                  95

His Gly Gly Pro Ala Gly Thr Ala Gln Ser Tyr Leu Asp Gly Thr Tyr
            100                 105                 110

Thr Glu Tyr Phe Pro Asn Ile Thr Lys Asp Glu Ala Gly Leu Gln Lys
        115                 120                 125

Phe Phe Arg Gln Phe Ser Tyr Pro Gly Gly Ile Pro Ser His Tyr Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Val Met Asn Asn Pro Ser Leu Phe Val
                165                 170                 175

Pro Ala Ile Val Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Ile
    210                 215                 220

Leu Ser Arg Ile Ser Asp Glu Glu Leu His Glu Phe Phe His Gly Met
225                 230                 235                 240

Gly Tyr Glu Pro Tyr Glu Phe Val Ala Gly Phe Asp Asn Glu Asp His
                245                 250                 255

Leu Ser Ile His Arg Arg Phe Ala Glu Leu Phe Glu Thr Val Phe Asp
            260                 265                 270
```

```
Glu Ile Cys Asp Ile Lys Ala Ala Gln Thr Asp Met Thr Arg
            275                 280                 285

Pro Phe Tyr Pro Met Ile Ile Phe Arg Thr Pro Lys Gly Trp Thr Cys
290                 295                 300

Pro Lys Phe Ile Asp Gly Lys Lys Thr Glu Gly Ser Trp Arg Ser His
305                 310                 315                 320

Gln Val Pro Leu Ala Ser Ala Arg Asp Thr Glu Ala His Phe Glu Val
                325                 330                 335

Leu Lys Asn Trp Leu Glu Ser Tyr Lys Pro Glu Glu Leu Phe Asp Ala
            340                 345                 350

Asn Gly Ala Val Lys Pro Glu Val Thr Ala Phe Met Pro Thr Gly Glu
            355                 360                 365

Leu Arg Ile Gly Glu Asn Pro Asn Ala Asn Gly Gly Arg Ile Arg Glu
370                 375                 380

Glu Leu Asn Leu Pro Ala Leu Glu Asp Tyr Glu Val Lys Glu Val Ala
385                 390                 395                 400

Glu Tyr Gly His Gly Trp Gly Gln Leu Glu Ala Thr Arg Arg Leu Gly
                405                 410                 415

Val Tyr Thr Arg Asp Ile Ile Lys Asn Asn Pro Asp Ser Phe Arg Ile
            420                 425                 430

Phe Gly Pro Asp Glu Thr Ala Ser Asn Arg Leu Gln Ala Ala Tyr Asp
            435                 440                 445

Val Thr Asn Lys Gln Trp Asp Ala Gly Tyr Leu Ser Ala Gln Val Asp
450                 455                 460

Glu His Met Ala Val Thr Gly Gln Val Thr Glu Gln Leu Ser Glu His
465                 470                 475                 480

Gln Met Glu Gly Phe Leu Glu Ala Tyr Leu Leu Thr Gly Arg His Gly
                485                 490                 495

Ile Trp Ser Ser Tyr Glu Ser Phe Val His Val Ile Asp Ser Met Leu
            500                 505                 510

Asn Gln His Ala Lys Trp Leu Glu Ala Thr Val Arg Glu Ile Pro Trp
            515                 520                 525

Arg Lys Pro Ile Ser Ser Met Asn Leu Leu Val Ser Ser His Val Trp
530                 535                 540

Arg Gln Asp His Asn Gly Phe Ser His Gln Asp Pro Gly Val Thr Ser
545                 550                 555                 560

Val Leu Leu Asn Lys Cys Phe Asn Asn Asp His Val Ile Gly Ile Tyr
                565                 570                 575

Phe Pro Val Asp Ser Asn Met Leu Leu Ala Val Ala Glu Lys Cys Tyr
            580                 585                 590

Lys Ser Thr Asp Met Ile Asn Ala Ile Ala Gly Lys Gln Pro Ala
            595                 600                 605

Ala Thr Trp Leu Thr Leu Asp Glu Ala Arg Ala Glu Leu Glu Lys Gly
            610                 615                 620

Ala Ala Glu Trp Glu Trp Ala Ser Thr Ala Lys Ser Asn Asp Glu Ala
625                 630                 635                 640

Gln Ile Val Leu Ala Ser Ala Gly Asp Val Pro Ala Gln Glu Ile Met
                645                 650                 655

Ala Ala Ala Asp Lys Leu Asp Ala Met Gly Ile Lys Phe Lys Val Val
            660                 665                 670

Asn Val Val Asp Leu Val Lys Leu Gln Ser Thr Lys Glu Asn Asp Glu
            675                 680                 685

Ala Ile Ser Asp Ala Asp Phe Ala Asp Leu Phe Thr Glu Asp Lys Pro
```

```
        690              695              700
Val Leu Phe Ala Tyr His Ser Tyr Ala Arg Asp Val Arg Gly Leu Ile
705              710              715              720

Tyr Asp Arg Pro Asn His Asp Asn Phe Asn Val His Gly Tyr Glu Glu
                 725              730              735

Gln Gly Ser Thr Thr Pro Tyr Asp Met Val Arg Val Asn Asn Ile
            740              745              750

Asp Arg Tyr Glu Leu Val Ala Glu Ala Leu Arg Met Ile Asp Ala Asp
            755              760              765

Lys Tyr Ala Asp Lys Ile Asp Glu Leu Glu Ala Phe Arg Lys Glu Ala
            770              775              780

Phe Gln Phe Ala Val Asp Asn Gly Tyr Asp His Pro Asp Tyr Thr Asp
785              790              795              800

Trp Val Tyr Ser Gly Val Asn Thr Asn Lys Gln Gly Ala Val Ser Ala
                 805              810              815

Thr Ala Thr Ala Gly Asp Asn Glu
            820              825

<210> SEQ ID NO 213
<211> LENGTH: 2478
<212> TYPE: DNA
<213> ORGANISM: Bifidobacterium lactis

<400> SEQUENCE: 213
atgactaatc ctgttattgg taccccatgg cagaagctgg atcgtccggt ttccgaagag    60
gccatcgaag gcatggacaa gtactggcgc gtcgccaact acatgtctat cggccagatc   120
tacctgcgta gcaacccgct gatgaaggag cccttcaccc gcgatgacgt gaagcaccgt   180
ctggtcggcc actggggcac caccccgggc ctgaacttcc ttctcgccca catcaaccgc   240
ctgatcgccg atcaccagca gaacaccgtg ttcatcatgg gtcctggcca cggcggccct   300
gcaggtaccg ctcagtccta catcgacggc acctacaccg agtactaccc gaacatcacc   360
aaggacgaag ctggcctgca gaagttcttc cgccagttct cctacccggg tggcattcct   420
tcccacttcg ctccggagac gccgggctcc atccacgaag cggcgagct gggctacgcc   480
ctgtcgcacg cctacggcgc gatcatggac aacccgagcc tcttcgtccc gtgcatcatc   540
ggtgacggcg aagccgagac cggccctctg ccaccggct ggcagtccaa caagctcgtc   600
aacccgcgca ccgacggcat cgtcctgccg atcctgcacc tcaacggcta caagatcgcc   660
aacccgacga tcctcgcccg catctccgac gaggagctgc acgacttctt ccgcggcatg   720
ggttaccacc gtacgagtt cgtcgccggc ttcgacaacg aggatcacct gtcgatccac   780
cgtcgcttcg ccgagctctt cgagaccatc ttcgacgaga tctgcgatat caaggctgcg   840
gctcagaccg acgacatgac ccgtccgttc tacccgatgc tcatcttccg caccccgaag   900
ggctggacct gcccgaagtt catcgacggc aagaagaccg aaggctcctg gcgtgcacac   960
caggtcccgc tggcttccgc ccgcgacacc gaggcccact tcgaagtcct caagggctgg  1020
atggaatcct acaagccgga ggagctcttc aacgccgacg gctccatcaa ggaggacgtc  1080
accgcattca tgcctaaggg cgaactgcgc atcggcgcca acccgaatgc aacggcggc   1140
cgcatccgcg aggatctgaa gctccctgag ctcgatcagt acgagatcac cggcgtcaag  1200
gaatacggcc acggttgggg ccaggtcgag gctccgcgtt ccctcggcgc gtactgccgc  1260
gacatcatca gaacaaccc ggattcgttc cgcgtcttcg acctgacga gaccgcgtcc  1320
aaccgtctga cgcgaccta cgaggtcacc aagaagcagt gggacaacgg ataccctctcg  1380
```

```
gctctcgtcg acgagaacat ggccgtcacc ggccaggttg tcgagcagct ctccgagcat    1440
cagtgcgaag gcttcctcga ggcctacctg ctcaccggcc gtcacggcat ctggagctcc    1500
tacgagtcct tcgtgcacgt gatcgactcc atgctgaacc agcatgcgaa gtggctcgag    1560
gccaccgtcc gcgagatccc gtggcgtaag ccgatctcct cggtgaacct cctggtctcc    1620
tcgcacgtgt ggcgtcagga tcacaacggc ttctcgcacc aggatccggg tgtgacctcc    1680
gtcctgctga acaagacgtt caacaacgac cacgtgacga acatctactt cgcgaccgat    1740
gccaacatgc tgctggccat cgccgagaag tgcttcaagt ccaccaacaa gatcaacgca    1800
atcttcgccg gcaagcagcc ggccgcgacg tggatcaccc tcgacgaggt acgcgccgag    1860
ctcgaggctg gtgccgccga gtggaagtgg gcttccaacg ccaagagcaa cgacgaggtc    1920
caggttgtcc tcgccgccgc cggcgacgtc ccgacccagg agatcatggc cgcttccgat    1980
gccctcaaca agatgggcat caagttcaag gtcgtcaacg tcgtggacct catcaagctg    2040
cagtcctcga aggagaacga cgaggccatg tctgacgagg acttcgccga cctgttcacc    2100
gcggacaagc cggtcctctt cgcctaccac tcctatgccc aggacgttcg tggcctcatc    2160
tacgaccgcc cgaaccacga caacttcacc gttgtcggat acaaggagca gggctccacg    2220
acgacgccgt tcgacatggt cgcgtgtcaac gacatggatc gctacgccct tcaggccaag    2280
gccctcgagc tcatcgacgc cgacaagtat gccgacaaga tcaacgagct caacgagttc    2340
cgcaagaccg cgttccagtt cgccgtcgac aatggctatg acattcctga gttcaccgat    2400
tgggtgtacc cggatgtcaa ggtcgacgag acctccatgc tctccgccac cgccgcgacc    2460
gccggcgaca acgagtga                                                   2478
```

<210> SEQ ID NO 214
<211> LENGTH: 825
<212> TYPE: PRT
<213> ORGANISM: Bifidobacterium lactis

<400> SEQUENCE: 214

```
Met Thr Asn Pro Val Ile Gly Thr Pro Trp Gln Lys Leu Asp Arg Pro
1               5                   10                  15

Val Ser Glu Glu Ala Ile Glu Gly Met Asp Lys Tyr Trp Arg Val Ala
            20                  25                  30

Asn Tyr Met Ser Ile Gly Gln Ile Tyr Leu Arg Ser Asn Pro Leu Met
        35                  40                  45

Lys Glu Pro Phe Thr Arg Asp Asp Val Lys His Arg Leu Val Gly His
    50                  55                  60

Trp Gly Thr Thr Pro Gly Leu Asn Phe Leu Ala His Ile Asn Arg
65                  70                  75                  80

Leu Ile Ala Asp His Gln Gln Asn Thr Val Phe Ile Met Gly Pro Gly
                85                  90                  95

His Gly Gly Pro Ala Gly Thr Ala Gln Ser Tyr Ile Asp Gly Thr Tyr
            100                 105                 110

Thr Glu Tyr Tyr Pro Asn Ile Thr Lys Asp Glu Ala Gly Leu Gln Lys
        115                 120                 125

Phe Phe Arg Gln Phe Ser Tyr Pro Gly Gly Ile Pro Ser His Phe Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Ile Met Asp Asn Pro Ser Leu Phe Val
                165                 170                 175
```

-continued

```
Pro Cys Ile Ile Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Ile
    210                 215                 220

Leu Ala Arg Ile Ser Asp Glu Glu Leu His Asp Phe Arg Gly Met
225                 230                 235                 240

Gly Tyr His Pro Tyr Glu Phe Val Ala Gly Phe Asp Asn Glu Asp His
                245                 250                 255

Leu Ser Ile His Arg Arg Phe Ala Glu Leu Phe Glu Thr Ile Phe Asp
            260                 265                 270

Glu Ile Cys Asp Ile Lys Ala Ala Ala Gln Thr Asp Asp Met Thr Arg
        275                 280                 285

Pro Phe Tyr Pro Met Leu Ile Phe Arg Thr Pro Lys Gly Trp Thr Cys
    290                 295                 300

Pro Lys Phe Ile Asp Gly Lys Lys Thr Glu Gly Ser Trp Arg Ala His
305                 310                 315                 320

Gln Val Pro Leu Ala Ser Ala Arg Asp Thr Glu Ala His Phe Glu Val
                325                 330                 335

Leu Lys Gly Trp Met Glu Ser Tyr Lys Pro Glu Glu Leu Phe Asn Ala
            340                 345                 350

Asp Gly Ser Ile Lys Glu Asp Val Thr Ala Phe Met Pro Lys Gly Glu
        355                 360                 365

Leu Arg Ile Gly Ala Asn Pro Asn Ala Asn Gly Gly Arg Ile Arg Glu
    370                 375                 380

Asp Leu Lys Leu Pro Glu Leu Asp Gln Tyr Glu Ile Thr Gly Val Lys
385                 390                 395                 400

Glu Tyr Gly His Gly Trp Gly Gln Val Glu Ala Pro Arg Ser Leu Gly
                405                 410                 415

Ala Tyr Cys Arg Asp Ile Ile Lys Asn Asn Pro Asp Ser Phe Arg Val
            420                 425                 430

Phe Gly Pro Asp Glu Thr Ala Ser Asn Arg Leu Asn Ala Thr Tyr Glu
        435                 440                 445

Val Thr Lys Lys Gln Trp Asp Asn Gly Tyr Leu Ser Ala Leu Val Asp
    450                 455                 460

Glu Asn Met Ala Val Thr Gly Gln Val Val Glu Gln Leu Ser Glu His
465                 470                 475                 480

Gln Cys Glu Gly Phe Leu Glu Ala Tyr Leu Leu Thr Gly Arg His Gly
                485                 490                 495

Ile Trp Ser Ser Tyr Glu Ser Phe Val His Val Ile Asp Ser Met Leu
            500                 505                 510

Asn Gln His Ala Lys Trp Leu Glu Ala Thr Val Arg Glu Ile Pro Trp
        515                 520                 525

Arg Lys Pro Ile Ser Ser Val Asn Leu Leu Val Ser Ser His Val Trp
    530                 535                 540

Arg Gln Asp His Asn Gly Phe Ser His Gln Asp Pro Gly Val Thr Ser
545                 550                 555                 560

Val Leu Leu Asn Lys Thr Phe Asn Asn Asp His Val Thr Asn Ile Tyr
                565                 570                 575

Phe Ala Thr Asp Ala Asn Met Leu Leu Ala Ile Ala Glu Lys Cys Phe
            580                 585                 590
```

| | | | | | | | | | | |
|---|---|---|---|---|---|---|---|---|---|---|
|Lys|Ser|Thr|Asn|Lys|Ile|Asn|Ala|Ile|Phe|Ala|Gly|Lys|Gln|Pro|Ala|
| | |595| | | |600| | | |605| | | | | |

Ala Thr Trp Ile Thr Leu Asp Glu Val Arg Ala Glu Leu Glu Ala Gly
    610             615             620

Ala Ala Glu Trp Lys Trp Ala Ser Asn Ala Lys Ser Asn Asp Glu Val
625             630             635             640

Gln Val Val Leu Ala Ala Ala Gly Asp Val Pro Thr Gln Glu Ile Met
            645             650             655

Ala Ala Ser Asp Ala Leu Asn Lys Met Gly Ile Lys Phe Lys Val Val
            660             665             670

Asn Val Val Asp Leu Ile Lys Leu Gln Ser Ser Lys Glu Asn Asp Glu
            675             680             685

Ala Met Ser Asp Glu Asp Phe Ala Asp Leu Phe Thr Ala Asp Lys Pro
690             695             700

Val Leu Phe Ala Tyr His Ser Tyr Ala Gln Asp Val Arg Gly Leu Ile
705             710             715             720

Tyr Asp Arg Pro Asn His Asp Asn Phe Thr Val Val Gly Tyr Lys Glu
            725             730             735

Gln Gly Ser Thr Thr Thr Pro Phe Asp Met Val Arg Val Asn Asp Met
            740             745             750

Asp Arg Tyr Ala Leu Gln Ala Lys Ala Leu Glu Leu Ile Asp Ala Asp
            755             760             765

Lys Tyr Ala Asp Lys Ile Asn Glu Leu Asn Glu Phe Arg Lys Thr Ala
            770             775             780

Phe Gln Phe Ala Val Asp Asn Gly Tyr Asp Ile Pro Glu Phe Thr Asp
785             790             795             800

Trp Val Tyr Pro Asp Val Lys Val Asp Glu Thr Ser Met Leu Ser Ala
            805             810             815

Thr Ala Ala Thr Ala Gly Asp Asn Glu
            820             825

<210> SEQ ID NO 215
<211> LENGTH: 2367
<212> TYPE: DNA
<213> ORGANISM: Unknown
<220> FEATURE:
<223> OTHER INFORMATION: Lactobacillus paraplantarum Sequence
<220> FEATURE:
<221> NAME/KEY: misc_feature
<222> LOCATION: (75)..(75)
<223> OTHER INFORMATION: n is a, c, g, or t

<400> SEQUENCE: 215

```
atgacaacag attactcatc accagcatat ttgcaaaaag ttgataagta ctggcgggca      60
gccaactact tatcngttgg gcaactttat ttaaaagatt atccattatt acaacagcca     120
ttgaaggcca gtgacgttaa ggttcatcca atttgtcact ggggacgat tgccggtcaa     180
aactctatct acgcgcacct taaccgggtt attaacaagt acgtttgaa gatgttctac     240
gttgaaggtc caggtcatgg tggtcaagtg atggtttcaa actcttatct tgacggtact     300
tacaccgata tttatccaga aattacgcag gatgttgaag gaatgcagaa actcttcaag     360
caattctcat tcccaggtgg ggttgcttcc catgcggcac ctgaaacacc tggttcaatc     420
cacgaaggtg gcgaactagg ttactcaatt tcacacgggg ttggggcaat tcttgacaat     480
cctgacgaaa ttgcagcggt cgttgttggt gatggggaat ccgaaacggg tccattagca     540
acttcatggc aatcaacgaa gttcattaac ccaatcaatg acggggcagt gttaccaatc     600
```

-continued

```
ttgaacttaa atggttttaa gatttctaac ccaacgattt ttggtcggac ttctgatgct      660
aagattaagg aatacttcga aagcatgagc tgggaaccaa tcttcgttga aggtgacgat      720
cctgaaaagg ttcacccagt cttagctaaa gccatggatg aagccgttga aaagatcaag      780
gcaatccaga agcatgctcg tgaaaatgac gatgcgacgt tgccagtatg gccaatgatc      840
gttttccgtg cacctaaggg ctggactggt cctaagtcat gggacggcga taagattgaa      900
ggttcattcc gggcccatca aattccgatt cctgttgatc aaaatgacat ggaacatgcg      960
gacgctttag ttgattggct tgaatcatat caaccaaagg aactcttcaa tgaagatggt     1020
tctttgaagg atgatattaa agaaattatt cctactgggg acagtcggat ggcagctaac     1080
ccaatcacca atggtggggt tgatccgaaa gccttgaact taccaaactt ccgggattat     1140
gcggtcgata cgtccaagga aggcgcgaat gttaagcaag atatgcttgt ttggtcagac     1200
tatttgcggg atgtcatcaa gaagaatcct gataacttcc ggttgttcgg acctgatgaa     1260
accatgtcta accgcttata tggtgtcttc gaaaccacta atcgtcaatg gatggaagac     1320
attcatcccg atagtgacca atatgaagct gcagctggcc gggtcttaga tgctcagtta     1380
tctgaacacc aagctgaagg ttggttagaa ggttacgtct taactggacg tcatgggtta     1440
tttgccagtt atgaagcctt cctacgcgtt gtggactcaa tgttgacgca acacttcaag     1500
tggttacgta aggccaatga acttgattgg cgtaaaaagt acccatcact taacattatc     1560
gcggcttcaa ctgtattcca acaagaccat aatggttaca cccaccaaga tccaggtgcg     1620
ttgactcatt tggccgaaaa gaaaccagaa tacattcgcg aatatttacc agccgatgcc     1680
aacacgttat tagctgtcgg tgacgtcatt ttccggagcc aagaaaagat caactacgtg     1740
gttacgtcaa acacccacg tcaacaatgg ttcagcattg aagaagctaa acaattagtt     1800
gacaatggtc ttggtatcat tgactgggca agcacggatc aaggtagcga accagacatc     1860
gtctttgcag ctgctgggac ggaaccaacg cttgaaacgt tggctgccat ccaattacta     1920
cacgacagtt tcccagagat gaagattcgt ttcgtgaacg tggtcgacat cttgaagtta     1980
cgtagtcctg aaaaggatcc acggggcttg tcagatgctg aatttgacca ttactttact     2040
aaggacaaac cagtggtctt tgctttccac ggttacgaag atttagttcg tgacatcttc     2100
ttcgatcgtc acaaccataa cttatacgtc cacggttacc gtgaaaatgg tgatattacc     2160
acaccattcg acgtacgggt catgaaccaa atggatcgtt tcgacttagc taagacggcg     2220
attgcggcgc aaccagcaat ggaaaacacc ggtgcggcct tgttcaatc catggataac      2280 atgcttgcta aacacaatgc atacattcgg gatgccggaa ccgacttgcc agaagttaac     2340
gactggcaat ggaaaggttt gaaataa                                         2367
```

<210> SEQ ID NO 216
<211> LENGTH: 788
<212> TYPE: PRT
<213> ORGANISM: Unknown
<220> FEATURE:
<223> OTHER INFORMATION: Lactobacillus paraplantarum Sequence

<400> SEQUENCE: 216

Met Thr Thr Asp Tyr Ser Ser Pro Ala Tyr Leu Gln Lys Val Asp Lys
1               5                   10                  15

Tyr Trp Arg Ala Ala Asn Tyr Leu Ser Val Gly Gln Leu Tyr Leu Lys
            20                  25                  30

Asp Tyr Pro Leu Leu Gln Gln Pro Leu Lys Ala Ser Asp Val Lys Val
        35                  40                  45

-continued

```
His Pro Ile Cys His Trp Gly Thr Ile Ala Gly Gln Asn Ser Ile Tyr
 50                  55                  60
Ala His Leu Asn Arg Val Ile Asn Lys Tyr Gly Leu Lys Met Phe Tyr
 65                  70                  75                  80
Val Glu Gly Pro Gly His Gly Gly Gln Val Met Val Ser Asn Ser Tyr
                 85                  90                  95
Leu Asp Gly Thr Tyr Thr Asp Ile Tyr Pro Glu Ile Thr Gln Asp Val
                100                 105                 110
Glu Gly Met Gln Lys Leu Phe Lys Gln Phe Ser Phe Pro Gly Gly Val
                115                 120                 125
Ala Ser His Ala Ala Pro Glu Thr Pro Gly Ser Ile His Glu Gly Gly
130                 135                 140
Glu Leu Gly Tyr Ser Ile Ser His Gly Val Gly Ala Ile Leu Asp Asn
145                 150                 155                 160
Pro Asp Glu Ile Ala Ala Val Val Gly Asp Gly Glu Ser Glu Thr
                165                 170                 175
Gly Pro Leu Ala Thr Ser Trp Gln Ser Thr Lys Phe Ile Asn Pro Ile
                180                 185                 190
Asn Asp Gly Ala Val Leu Pro Ile Leu Asn Leu Asn Gly Phe Lys Ile
                195                 200                 205
Ser Asn Pro Thr Ile Phe Gly Arg Thr Ser Asp Ala Lys Ile Lys Glu
210                 215                 220
Tyr Phe Glu Ser Met Ser Trp Glu Pro Ile Phe Val Glu Gly Asp Asp
225                 230                 235                 240
Pro Glu Lys Val His Pro Val Leu Ala Lys Ala Met Asp Glu Ala Val
                245                 250                 255
Glu Lys Ile Lys Ala Ile Gln Lys His Ala Arg Glu Asn Asp Asp Ala
                260                 265                 270
Thr Leu Pro Val Trp Pro Met Ile Val Phe Arg Ala Pro Lys Gly Trp
                275                 280                 285
Thr Gly Pro Lys Ser Trp Asp Gly Asp Lys Ile Glu Gly Ser Phe Arg
                290                 295                 300
Ala His Gln Ile Pro Ile Pro Val Asp Gln Asn Asp Met Glu His Ala
305                 310                 315                 320
Asp Ala Leu Val Asp Trp Leu Glu Ser Tyr Gln Pro Lys Glu Leu Phe
                325                 330                 335
Asn Glu Asp Gly Ser Leu Lys Asp Asp Ile Lys Glu Ile Ile Pro Thr
                340                 345                 350
Gly Asp Ser Arg Met Ala Ala Asn Pro Ile Thr Asn Gly Gly Val Asp
                355                 360                 365
Pro Lys Ala Leu Asn Leu Pro Asn Phe Arg Asp Tyr Ala Val Asp Thr
                370                 375                 380
Ser Lys Glu Gly Ala Asn Val Lys Gln Asp Met Leu Val Trp Ser Asp
385                 390                 395                 400
Tyr Leu Arg Asp Val Ile Lys Lys Asn Pro Asp Asn Phe Arg Leu Phe
                405                 410                 415
Gly Pro Asp Glu Thr Met Ser Asn Arg Leu Tyr Gly Val Phe Glu Thr
                420                 425                 430
Thr Asn Arg Gln Trp Met Glu Asp Ile His Pro Asp Ser Asp Gln Tyr
                435                 440                 445
Glu Ala Ala Ala Gly Arg Val Leu Asp Ala Gln Leu Ser Glu His Gln
450                 455                 460
Ala Glu Gly Trp Leu Glu Gly Tyr Val Leu Thr Gly Arg His Gly Leu
```

```
            465                 470                 475                 480
        Phe Ala Ser Tyr Glu Ala Phe Leu Arg Val Val Asp Ser Met Leu Thr
                        485                 490                 495
        Gln His Phe Lys Trp Leu Arg Lys Ala Asn Glu Leu Asp Trp Arg Lys
                        500                 505                 510
        Lys Tyr Pro Ser Leu Asn Ile Ile Ala Ala Ser Thr Val Phe Gln Gln
                        515                 520                 525
        Asp His Asn Gly Tyr Thr His Gln Asp Pro Gly Ala Leu Thr His Leu
                        530                 535                 540
        Ala Glu Lys Lys Pro Glu Tyr Ile Arg Glu Tyr Leu Pro Ala Asp Ala
        545                 550                 555                 560
        Asn Thr Leu Leu Ala Val Gly Asp Val Ile Phe Arg Ser Gln Glu Lys
                        565                 570                 575
        Ile Asn Tyr Val Val Thr Ser Lys His Pro Arg Gln Gln Trp Phe Ser
                        580                 585                 590
        Ile Glu Glu Ala Lys Gln Leu Val Asp Asn Gly Leu Gly Ile Ile Asp
                        595                 600                 605
        Trp Ala Ser Thr Asp Gln Gly Ser Glu Pro Asp Ile Val Phe Ala Ala
                        610                 615                 620
        Ala Gly Thr Glu Pro Thr Leu Glu Thr Leu Ala Ala Ile Gln Leu Leu
        625                 630                 635                 640
        His Asp Ser Phe Pro Glu Met Lys Ile Arg Phe Val Asn Val Val Asp
                        645                 650                 655
        Ile Leu Lys Leu Arg Ser Pro Glu Lys Asp Pro Arg Gly Leu Ser Asp
                        660                 665                 670
        Ala Glu Phe Asp His Tyr Phe Thr Lys Asp Lys Pro Val Val Phe Ala
                        675                 680                 685
        Phe His Gly Tyr Glu Asp Leu Val Arg Asp Ile Phe Phe Asp Arg His
                        690                 695                 700
        Asn His Asn Leu Tyr Val His Gly Tyr Arg Glu Asn Gly Asp Ile Thr
        705                 710                 715                 720
        Thr Pro Phe Asp Val Arg Val Met Asn Gln Met Asp Arg Phe Asp Leu
                        725                 730                 735
        Ala Lys Thr Ala Ile Ala Ala Gln Pro Ala Met Glu Asn Thr Gly Ala
                        740                 745                 750
        Ala Phe Val Gln Ser Met Asp Asn Met Leu Ala Lys His Asn Ala Tyr
                        755                 760                 765
        Ile Arg Asp Ala Gly Thr Asp Leu Pro Glu Val Asn Asp Trp Gln Trp
                        770                 775                 780
        Lys Gly Leu Lys
        785
```

<210> SEQ ID NO 217
<211> LENGTH: 2478
<212> TYPE: DNA
<213> ORGANISM: Bifidobacterium breve

<400> SEQUENCE: 217

| | | | | | |
|---|---|---|---|---|---|
| atgacaaatc | tgttattgg | caccccgtgg | cagaagctgg | atcgcccggt | ttccgaagaa | 60 |
| gccatcgaag | gcatggacaa | gtattggcgc | gtcaccaact | acatgtccat | cggccagatc | 120 |
| tatctgcgta | gcaacccgct | gatgaaggaa | cccttcaccc | gcgatgacgt | gaagcaccgt | 180 |
| ctggtcggcc | actggggcac | cacccgggc | ctgaacttcc | ttctcgccca | catcaaccgc | 240 |
| ctcatcgctg | accaccagca | gaacaccgtg | ttcatcatgg | gcccgggcca | cggcggcccg | 300 |

```
gctggcacct cccagtctta cgttgacggc acgtacaccg agtactaccc gaacatcacc      360
aaggacgaag ctggcctgca gaagttcttc cgccagttct cctacccggg cggcatcccg      420
tcgcacttcg ccccggagac cccgggatcg atccacgaag gtggcgagct ggctacgcg       480
ctctcccacg catacggcgc cgtgatgaac aacccgagcc tgttcgtgcc gtgcatcatc      540
ggcgacggcg aggccgagac cggcccgctc gccaccggct ggcagtccaa caagctcgtc      600
aacccgcgca ccgacggcat cgtgctgccg atcctgcacc tcaacggcta caagatcgcc      660
aacccgacca tcctcgctcg tatctccgac gaagagctgc atgacttctt ccgcggcatg      720
ggctaccacc cgtacgagtt cgttgccggc ttcgacaacg aggaccacat gtcgatccac      780
cgtcgtttcg ccgagctgtt cgagacgatc ttcgacgaga tctgcgacat caaggctgcg      840
gcccagaccg acgacatgac ccgtccgttc tacccgatgc tcatcttccg cacccccgaag    900
ggctggacct gcccgaagtt catcgacggc aagaagaccg aaggctcctg cgtgcgcac      960
caggtcccgc tggcttccgc ccgcgacacc gaagagcact cgaagtcct caagggctgg     1020
atggaatcct acaagccgga agagctcttc aacgccgacg gctccatcaa ggatgacgtc    1080
accgcgttca tgccgaaggg cgagctccgc atcggcgcca acccgaacgc caacggtggt    1140
gtgatccgcg aggacctgaa gctccccgag ctcgaccagt acgaggtcac cggcgtcaag    1200
gagtacggcc atggctgggg ccaggtcgag gctccgcgtg ccctcggtgc atactgccgc    1260
gacatcatca agaacaaccc ggattcgttc cgcatcttcg gaccggacga gaccgcttcc    1320
aaccgcctga cgcgaccta cgaggtcacc gacaagcagt gggacaacgg ctaccttcg     1380
ggtctcgtcg acgagcacat ggcggtcacc ggtcaggtca ccgagcagct ctccgagcac    1440
cagtgcgagg gcttcctcga ggcgtacctc ctcaccggcc gccacggcat ctggagctcc    1500
tacgagtcct tcgtccacgt catcgactcg atgctcaacc agcatgcgaa gtggctcgag    1560
gccaccgtcc gcgagatccc gtggcgcaag ccgatctcct cggtgaacct cctcgtctcc    1620
tcgcacgtgt ggcgtcagga tcacaacggc ttctcgcacc aggatccggg tgtcacctcg    1680
ctcctgatca acaagacgtt caacaacgat cacgtgacga acatctactt cgcgaccgac    1740
gcgaacatgc tgctcgcgat ctccgagaag tgcttcaagt ccaccaacaa gatcaatgcg    1800
atcttcgccg gcaagcagcc tgctccgacg tgggtcacgc tcgatgaggc ccgcgccgag    1860
ctcgaagccg gcgccgctga gtggaagtgg gcttccaacg ccgagaacaa cgatgaggtc    1920
caggtcgtcc tcgcttccgc tggcgatgtg ccgacccagg agctcatggc cgcctccgat    1980
gccctcaaca agatgggcat caagttcaag gtcgtcaacg ttgttgacct cctgaagctg    2040
cagtcccgcg agaacaacga cgaggccctc acggacgagg agttcaccga actcttcacc    2100
gccgacaagc cggttctgtt cgcataccac tcctacgctc aggatgttcg cggcctcatc    2160
tacgaccgcc gaaccacga caacttccac gtcgtcggct acaaggagca gggctccacg     2220
accacgccgt cgacatggt ccgcgtcaac gacatggatc gctatgcgct ccaggccgct     2280
gccctcaagc tgatcgatgc cgacaagtac gccgacaaga tcgacgagct caacgcgttc    2340
cgcaagaagg cgttccagtt cgctgtcgac aacggctacg acatcccgga gttcaccgac    2400
tgggtgtacc cggatgtcaa ggtcgacgag acgcagatgc tttccgcgac cgcggcgacc    2460
gcaggcgaca acgagtga                                                  2478
```

<210> SEQ ID NO 218
<211> LENGTH: 825
<212> TYPE: PRT

-continued

<213> ORGANISM: Bifidobacterium breve

<400> SEQUENCE: 218

```
Met Thr Asn Pro Val Ile Gly Thr Pro Trp Gln Lys Leu Asp Arg Pro
1               5                   10                  15

Val Ser Glu Glu Ala Ile Glu Gly Met Asp Lys Tyr Trp Arg Val Thr
            20                  25                  30

Asn Tyr Met Ser Ile Gly Gln Ile Tyr Leu Arg Ser Asn Pro Leu Met
        35                  40                  45

Lys Glu Pro Phe Thr Arg Asp Asp Val Lys His Arg Leu Val Gly His
    50                  55                  60

Trp Gly Thr Thr Pro Gly Leu Asn Phe Leu Ala His Ile Asn Arg
65                  70                  75                  80

Leu Ile Ala Asp His Gln Gln Asn Thr Val Phe Ile Met Gly Pro Gly
                85                  90                  95

His Gly Gly Pro Ala Gly Thr Ser Gln Ser Tyr Val Asp Gly Thr Tyr
            100                 105                 110

Thr Glu Tyr Tyr Pro Asn Ile Thr Lys Asp Glu Ala Gly Leu Gln Lys
        115                 120                 125

Phe Phe Arg Gln Phe Ser Tyr Pro Gly Gly Ile Pro Ser His Phe Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Val Met Asn Asn Pro Ser Leu Phe Val
                165                 170                 175

Pro Cys Ile Ile Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Ile
    210                 215                 220

Leu Ala Arg Ile Ser Asp Glu Glu Leu His Asp Phe Phe Arg Gly Met
225                 230                 235                 240

Gly Tyr His Pro Tyr Glu Phe Val Ala Gly Phe Asp Asn Glu Asp His
                245                 250                 255

Met Ser Ile His Arg Arg Phe Ala Glu Leu Phe Glu Thr Ile Phe Asp
            260                 265                 270

Glu Ile Cys Asp Ile Lys Ala Ala Gln Thr Asp Asp Met Thr Arg
        275                 280                 285

Pro Phe Tyr Pro Met Leu Ile Phe Arg Thr Pro Lys Gly Trp Thr Cys
    290                 295                 300

Pro Lys Phe Ile Asp Gly Lys Lys Thr Glu Gly Ser Trp Arg Ala His
305                 310                 315                 320

Gln Val Pro Leu Ala Ser Ala Arg Asp Thr Glu Glu His Phe Glu Val
                325                 330                 335

Leu Lys Gly Trp Met Glu Ser Tyr Lys Pro Glu Glu Leu Phe Asn Ala
            340                 345                 350

Asp Gly Ser Ile Lys Asp Val Thr Ala Phe Met Pro Lys Gly Glu
        355                 360                 365

Leu Arg Ile Gly Ala Asn Pro Asn Ala Asn Gly Gly Val Ile Arg Glu
    370                 375                 380

Asp Leu Lys Leu Pro Glu Leu Asp Gln Tyr Glu Val Thr Gly Val Lys
385                 390                 395                 400
```

```
Glu Tyr Gly His Gly Trp Gly Gln Val Glu Ala Pro Arg Ala Leu Gly
                405                 410                 415

Ala Tyr Cys Arg Asp Ile Ile Lys Asn Asn Pro Asp Ser Phe Arg Ile
                420                 425                 430

Phe Gly Pro Asp Glu Thr Ala Ser Asn Arg Leu Asn Ala Thr Tyr Glu
                435                 440                 445

Val Thr Asp Lys Gln Trp Asp Asn Gly Tyr Leu Ser Gly Leu Val Asp
450                 455                 460

Glu His Met Ala Val Thr Gly Gln Val Thr Glu Gln Leu Ser Glu His
465                 470                 475                 480

Gln Cys Glu Gly Phe Leu Glu Ala Tyr Leu Leu Thr Gly Arg His Gly
                485                 490                 495

Ile Trp Ser Ser Tyr Glu Ser Phe Val His Val Ile Asp Ser Met Leu
                500                 505                 510

Asn Gln His Ala Lys Trp Leu Glu Ala Thr Val Arg Glu Ile Pro Trp
                515                 520                 525

Arg Lys Pro Ile Ser Ser Val Asn Leu Leu Val Ser Ser His Val Trp
                530                 535                 540

Arg Gln Asp His Asn Gly Phe Ser His Gln Asp Pro Gly Val Thr Ser
545                 550                 555                 560

Leu Leu Ile Asn Lys Thr Phe Asn Asn Asp His Val Thr Asn Ile Tyr
                565                 570                 575

Phe Ala Thr Asp Ala Asn Met Leu Leu Ala Ile Ser Glu Lys Cys Phe
                580                 585                 590

Lys Ser Thr Asn Lys Ile Asn Ala Ile Phe Ala Gly Lys Gln Pro Ala
                595                 600                 605

Pro Thr Trp Val Thr Leu Asp Glu Ala Arg Ala Glu Leu Glu Ala Gly
                610                 615                 620

Ala Ala Glu Trp Lys Trp Ala Ser Asn Ala Glu Asn Asn Asp Glu Val
625                 630                 635                 640

Gln Val Val Leu Ala Ser Ala Gly Asp Val Pro Thr Gln Glu Leu Met
                645                 650                 655

Ala Ala Ser Asp Ala Leu Asn Lys Met Gly Ile Lys Phe Lys Val Val
                660                 665                 670

Asn Val Val Asp Leu Leu Lys Leu Gln Ser Arg Glu Asn Asn Asp Glu
                675                 680                 685

Ala Leu Thr Asp Glu Glu Phe Thr Glu Leu Phe Thr Ala Asp Lys Pro
                690                 695                 700

Val Leu Phe Ala Tyr His Ser Tyr Ala Gln Asp Val Arg Gly Leu Ile
705                 710                 715                 720

Tyr Asp Arg Pro Asn His Asp Asn Phe His Val Val Gly Tyr Lys Glu
                725                 730                 735

Gln Gly Ser Thr Thr Thr Pro Phe Asp Met Val Arg Val Asn Asp Met
                740                 745                 750

Asp Arg Tyr Ala Leu Gln Ala Ala Ala Leu Lys Leu Ile Asp Ala Asp
                755                 760                 765

Lys Tyr Ala Asp Lys Ile Asp Glu Leu Asn Ala Phe Arg Lys Lys Ala
                770                 775                 780

Phe Gln Phe Ala Val Asp Asn Gly Tyr Asp Ile Pro Glu Phe Thr Asp
785                 790                 795                 800

Trp Val Tyr Pro Asp Val Lys Val Asp Glu Thr Gln Met Leu Ser Ala
                805                 810                 815

Thr Ala Ala Thr Ala Gly Asp Asn Glu
```

<210> SEQ ID NO 219
<211> LENGTH: 2145
<212> TYPE: DNA
<213> ORGANISM: Escherichia coli

<400> SEQUENCE: 219

```
gtgtcccgta ttattatgct gatccctacc ggaaccagcg tcggtctgac cagcgtcagc      60
cttggcgtga tccgtgcaat ggaacgcaaa ggcgttcgtc tgagcgtttt caaacctatc     120
gctcagccgc gtaccggtgg cgatgcgccc gatcagacta cgactatcgt gcgtgcgaac     180
tcttccacca cgacggccgc tgaaccgctg aaaatgagct acgttgaagg tctgctttcc     240
agcaatcaga aagatgtgct gatggaagag atcgtcgcaa actaccacgc taacaccaaa     300
gacgctgaag tcgttctggt tgaaggtctg gtcccgacac gtaagcacca gtttgcccag     360
tctctgaact acgaaatcgc taaaacgctg aatgcgaaaa tcgtcttcgt tatgtctcag     420
ggcactgaca ccccggaaca gctgaaagag cgtatcgaac tgacccgcaa cagcttcggc     480
ggtgccaaaa acaccaacat caccggcgtt atcgttaaca aactgaacgc accggttgat     540
gaacagggtc gtactcgccc ggatctgtcc gagattttcg acgactcttc caaagctaaa     600
gtaaacaatg ttgatccggc gaagctgcaa gaatccagcc cgctgccggt tctcggcgct     660
gtgccgtgga gctttgacct gatcgcgact cgtgcgatcg atatggctcg ccacctgaat     720
gcgaccatca tcaacgaagg cgacatcaat actcgccgcg ttaaatccgt cactttctgc     780
gcacgcagca ttccgcacat gctggagcac ttccgtgccg gttctctgct ggtgacttcc     840
gcagaccgtc ctgacgtgct ggtggccgct tgcctggcag ccatgaacgg cgtagaaatc     900
ggtgccctgc tgctgactgg cggttacgaa atggacgcgc gcatttctaa actgtgcgaa     960
cgtgctttcg ctaccggcct gccggtattt atggtgaaca ccaacacctg gcagacctct    1020
ctgagcctgc agagcttcaa cctggaagtt ccggttgacg atcacgaacg tatcgagaaa    1080
gttcaggaat acgttgctaa ctacatcaac gctgactgga tcgaatctct gactgccact    1140
tctgagcgca gccgtcgtct gtctccgcct gcgttccgtt atcagctgac tgaacttgcg    1200
cgcaaagcgg gcaaacgtat cgtactgccg gaaggtgacg aaccgcgtac cgttaaagca    1260
gccgctatct gtgctgaacg tggtatcgca acttgcgtac tgctgggtaa tccggcagag    1320
atcaaccgtg ttgcagcgtc tcagggtgta gaactgggtg cagggattga aatcgttgat    1380
ccagaagtgg ttcgcgaaag ctatgttggt cgtctggtcg aactgcgtaa gaacaaaggc    1440
atgaccgaaa ccgttgcccg cgaacagctg gaagacaacg tggtgctcgg tacgctgatg    1500
ctggaacagg atgaagttga tggtctggtt ccggtgctg ttcacactac cgcaaacacc    1560
atccgtccgc cgctgcagct gatcaaaact gcaccgggca gctccctggt atcttccgtg    1620
ttcttcatgc tgctgccgga acaggtttac gtttacggtg actgtgcgat caacccggat    1680
ccgaccgctg aacagctggc agaaatcgcg attcagtccg ctgattccgc tgcggccttc    1740
ggtatcgaac gcgcgttgc tatgctctcc tactccaccg gtacttctgg tgcaggtagc    1800
gacgtagaaa aagttcgcga agcaactcgt ctggcgcagg aaaaacgtcc tgacctgatg    1860
atcgacggtc cgctgcagta cgacgctgcg gtaatggctg acgttgcgaa atccaaagcg    1920
ccgaactctc cggttgcagg tcgcgctacc gtgttcatct cccggatct gaacaccggt    1980
aacaccacct acaagcggt acagcgttct gccgacctga tctccatcgg gccgatgctg    2040
cagggtatgc gcaagccggt taacgacctg tcccgtggcg cactggttga cgatatcgtc    2100
```
tacaccatcg cgctgactgc gattcagtct gcacagcagc agtaa 2145

<210> SEQ ID NO 220
<211> LENGTH: 714
<212> TYPE: PRT
<213> ORGANISM: Escherichia coli

<400> SEQUENCE: 220

| Met | Ser | Arg | Ile | Ile | Met | Leu | Ile | Pro | Thr | Gly | Thr | Ser | Val | Gly | Leu |
|---|---|---|---|---|---|---|---|---|---|---|---|---|---|---|---|
| 1 | | | | 5 | | | | | 10 | | | | | 15 | |

| Thr | Ser | Val | Ser | Leu | Gly | Val | Ile | Arg | Ala | Met | Glu | Arg | Lys | Gly | Val |
| | | | 20 | | | | | 25 | | | | | 30 | | |

| Arg | Leu | Ser | Val | Phe | Lys | Pro | Ile | Ala | Gln | Pro | Arg | Thr | Gly | Gly | Asp |
| | | 35 | | | | | 40 | | | | | 45 | | | |

| Ala | Pro | Asp | Gln | Thr | Thr | Thr | Ile | Val | Arg | Ala | Asn | Ser | Ser | Thr | Thr |
| | 50 | | | | | 55 | | | | | 60 | | | | |

| Thr | Ala | Ala | Glu | Pro | Leu | Lys | Met | Ser | Tyr | Val | Glu | Gly | Leu | Leu | Ser |
| 65 | | | | | 70 | | | | | 75 | | | | | 80 |

| Ser | Asn | Gln | Lys | Asp | Val | Leu | Met | Glu | Glu | Ile | Val | Ala | Asn | Tyr | His |
| | | | | 85 | | | | | 90 | | | | | 95 | |

| Ala | Asn | Thr | Lys | Asp | Ala | Glu | Val | Val | Leu | Val | Glu | Gly | Leu | Val | Pro |
| | | | 100 | | | | | 105 | | | | | 110 | | |

| Thr | Arg | Lys | His | Gln | Phe | Ala | Gln | Ser | Leu | Asn | Tyr | Glu | Ile | Ala | Lys |
| | | 115 | | | | | 120 | | | | | 125 | | | |

| Thr | Leu | Asn | Ala | Glu | Ile | Val | Phe | Val | Met | Ser | Gln | Gly | Thr | Asp | Thr |
| | 130 | | | | | 135 | | | | | 140 | | | | |

| Pro | Glu | Gln | Leu | Lys | Glu | Arg | Ile | Glu | Leu | Thr | Arg | Asn | Ser | Phe | Gly |
| 145 | | | | | 150 | | | | | 155 | | | | | 160 |

| Gly | Ala | Lys | Asn | Thr | Asn | Ile | Thr | Gly | Val | Ile | Val | Asn | Lys | Leu | Asn |
| | | | | 165 | | | | | 170 | | | | | 175 | |

| Ala | Pro | Val | Asp | Glu | Gln | Gly | Arg | Thr | Arg | Pro | Asp | Leu | Ser | Glu | Ile |
| | | | 180 | | | | | 185 | | | | | 190 | | |

| Phe | Asp | Asp | Ser | Ser | Lys | Ala | Lys | Val | Asn | Asn | Val | Asp | Pro | Ala | Lys |
| | | 195 | | | | | 200 | | | | | 205 | | | |

| Leu | Gln | Glu | Ser | Ser | Pro | Leu | Pro | Val | Leu | Gly | Ala | Val | Pro | Trp | Ser |
| | 210 | | | | | 215 | | | | | 220 | | | | |

| Phe | Asp | Leu | Ile | Ala | Thr | Arg | Ala | Ile | Asp | Met | Ala | Arg | His | Leu | Asn |
| 225 | | | | | 230 | | | | | 235 | | | | | 240 |

| Ala | Thr | Ile | Ile | Asn | Glu | Gly | Asp | Ile | Asn | Thr | Arg | Arg | Val | Lys | Ser |
| | | | | 245 | | | | | 250 | | | | | 255 | |

| Val | Thr | Phe | Cys | Ala | Arg | Ser | Ile | Pro | His | Met | Leu | Glu | His | Phe | Arg |
| | | | 260 | | | | | 265 | | | | | 270 | | |

| Ala | Gly | Ser | Leu | Leu | Val | Thr | Ser | Ala | Asp | Arg | Pro | Asp | Val | Leu | Val |
| | | 275 | | | | | 280 | | | | | 285 | | | |

| Ala | Ala | Cys | Leu | Ala | Ala | Met | Asn | Gly | Val | Glu | Ile | Gly | Ala | Leu | Leu |
| | 290 | | | | | 295 | | | | | 300 | | | | |

| Leu | Thr | Gly | Gly | Tyr | Glu | Met | Asp | Ala | Arg | Ile | Ser | Lys | Leu | Cys | Glu |
| 305 | | | | | 310 | | | | | 315 | | | | | 320 |

| Arg | Ala | Phe | Ala | Thr | Gly | Leu | Pro | Val | Phe | Met | Val | Asn | Thr | Asn | Thr |
| | | | | 325 | | | | | 330 | | | | | 335 | |

| Trp | Gln | Thr | Ser | Leu | Ser | Leu | Gln | Ser | Phe | Asn | Leu | Glu | Val | Pro | Val |
| | | | 340 | | | | | 345 | | | | | 350 | | |

| Asp | Asp | His | Glu | Arg | Ile | Glu | Lys | Val | Gln | Glu | Tyr | Val | Ala | Asn | Tyr |
| | | 355 | | | | | 360 | | | | | 365 | | | |

```
Ile Asn Ala Asp Trp Ile Glu Ser Leu Thr Ala Thr Ser Glu Arg Ser
        370                 375                 380

Arg Arg Leu Ser Pro Pro Ala Phe Arg Tyr Gln Leu Thr Glu Leu Ala
385                 390                 395                 400

Arg Lys Ala Gly Lys Arg Ile Val Leu Pro Glu Gly Asp Glu Pro Arg
                405                 410                 415

Thr Val Lys Ala Ala Ala Ile Cys Ala Glu Arg Gly Ile Ala Thr Cys
            420                 425                 430

Val Leu Leu Gly Asn Pro Ala Glu Ile Asn Arg Val Ala Ala Ser Gln
        435                 440                 445

Gly Val Glu Leu Gly Ala Gly Ile Glu Ile Val Asp Pro Glu Val Val
450                 455                 460

Arg Glu Ser Tyr Val Gly Arg Leu Val Glu Leu Arg Lys Asn Lys Gly
465                 470                 475                 480

Met Thr Glu Thr Val Ala Arg Glu Gln Leu Glu Asp Asn Val Val Leu
                485                 490                 495

Gly Thr Leu Met Leu Glu Gln Asp Glu Val Asp Gly Leu Val Ser Gly
            500                 505                 510

Ala Val His Thr Thr Ala Asn Thr Ile Arg Pro Pro Leu Gln Leu Ile
        515                 520                 525

Lys Thr Ala Pro Gly Ser Ser Leu Val Ser Ser Val Phe Phe Met Leu
530                 535                 540

Leu Pro Glu Gln Val Tyr Val Tyr Gly Asp Cys Ala Ile Asn Pro Asp
545                 550                 555                 560

Pro Thr Ala Glu Gln Leu Ala Glu Ile Ala Ile Gln Ser Ala Asp Ser
                565                 570                 575

Ala Ala Ala Phe Gly Ile Glu Pro Arg Val Ala Met Leu Ser Tyr Ser
            580                 585                 590

Thr Gly Thr Ser Gly Ala Gly Ser Asp Val Glu Lys Val Arg Glu Ala
        595                 600                 605

Thr Arg Leu Ala Gln Glu Lys Arg Pro Asp Leu Met Ile Asp Gly Pro
610                 615                 620

Leu Gln Tyr Asp Ala Ala Val Met Ala Asp Val Ala Lys Ser Lys Ala
625                 630                 635                 640

Pro Asn Ser Pro Val Ala Gly Arg Ala Thr Val Phe Ile Phe Pro Asp
                645                 650                 655

Leu Asn Thr Gly Asn Thr Thr Tyr Lys Ala Val Gln Arg Ser Ala Asp
            660                 665                 670

Leu Ile Ser Ile Gly Pro Met Leu Gln Gly Met Arg Lys Pro Val Asn
        675                 680                 685

Asp Leu Ser Arg Gly Ala Leu Val Asp Asp Ile Val Tyr Thr Ile Ala
690                 695                 700

Leu Thr Ala Ile Gln Ser Ala Gln Gln Gln
705                 710

<210> SEQ ID NO 221
<211> LENGTH: 1002
<212> TYPE: DNA
<213> ORGANISM: Clostridium acetobutylicum

<400> SEQUENCE: 221
atggatttaa tagaaagcat atgggagtgt gctaagcaag acaaaaaaag gataatatta      60
gctgaaggtg aagaaaaaag aaatctaatt gccgcagata aaattatcaa agagggatta     120
```

-continued

```
gcagagcttg ttcttgtagg tgatgaaaat aaaattaaag aaaaagcaag tgagttgaat        180
cttgacattt cgaaggctga aataatggat ccagagacat cactaaaaac agaaacatat        240
gctagagatt tttatgaact tagaaaacac aaaggaatga ctattgaaaa atctgaaaaa        300
atggtaagag atcctctttta ttttgcaaca atggctttaa agatggcta tgttgatgga        360 atggtttcag gagctgttca cacaactgga gatttattaa gaccaggact tcaaattata        420
aaaactgcac caggagttaa aatagtatca ggattctttg ttatgataat acctgactgc        480
gattatggtg aagagggtct tttattattt gcagattgtg ctgtaaatcc taacccaaca        540
tcagatgaac tagctgatat tgctataact acagctgaaa cagctagaaa attatgtaac        600
gtagagccta agttgcgat gctttcattc tcaactatgg aagtgcaaa aggcgaaatg        660 gtagataagg ttaaaaatgc tgttgaaatc acaaagaaat tcagaccgga tcttgctatt        720
gatggtgagc ttcagcttga tgctgcaata gatagtgaag tagcggcttt aaaaagcacct        780 tctagtaatg ttgcaggaaa tgcaaatgtt cttgtattcc cagatcttca aacaggaaac        840
attgggtaca agcttgttca aagatttgca aaagcaaaag caataggacc tatatgtcaa        900
ggatttgcaa aacctattaa tgatttatca agaggctgta gctcagagga tatagtaaat        960
gttgttgcta taactgttgt tcaggctcaa agaggtatat aa                        1002
```

<210> SEQ ID NO 222
<211> LENGTH: 333
<212> TYPE: PRT
<213> ORGANISM: Clostridium acetobutylicum

<400> SEQUENCE: 222

```
Met Asp Leu Ile Glu Ser Ile Trp Glu Cys Ala Lys Gln Asp Lys Lys
1               5                   10                  15

Arg Ile Ile Leu Ala Glu Gly Glu Lys Arg Asn Leu Ile Ala Ala
            20                  25                  30

Asp Lys Ile Ile Lys Glu Gly Leu Ala Glu Leu Val Leu Val Gly Asp
        35                  40                  45

Glu Asn Lys Ile Lys Glu Lys Ala Ser Glu Leu Asn Leu Asp Ile Ser
    50                  55                  60

Lys Ala Glu Ile Met Asp Pro Glu Thr Ser Leu Lys Thr Glu Thr Tyr
65                  70                  75                  80

Ala Arg Asp Phe Tyr Glu Leu Arg Lys His Lys Gly Met Thr Ile Glu
                85                  90                  95

Lys Ser Glu Lys Met Val Arg Asp Pro Leu Tyr Phe Ala Thr Met Ala
            100                 105                 110

Leu Lys Asp Gly Tyr Val Asp Gly Met Val Ser Gly Ala Val His Thr
        115                 120                 125

Thr Gly Asp Leu Leu Arg Pro Gly Leu Gln Ile Ile Lys Thr Ala Pro
    130                 135                 140

Gly Val Lys Ile Val Ser Gly Phe Phe Val Met Ile Ile Pro Asp Cys
145                 150                 155                 160

Asp Tyr Gly Glu Glu Gly Leu Leu Leu Phe Ala Asp Cys Ala Val Asn
                165                 170                 175

Pro Asn Pro Thr Ser Asp Glu Leu Ala Asp Ile Ala Ile Thr Thr Ala
            180                 185                 190

Glu Thr Ala Arg Lys Leu Cys Asn Val Glu Pro Lys Val Ala Met Leu
        195                 200                 205

Ser Phe Ser Thr Met Gly Ser Ala Lys Gly Glu Met Val Asp Lys Val
    210                 215                 220
```

```
Lys Asn Ala Val Glu Ile Thr Lys Lys Phe Arg Pro Asp Leu Ala Ile
225                 230                 235                 240

Asp Gly Glu Leu Gln Leu Asp Ala Ala Ile Asp Ser Glu Val Ala Ala
            245                 250                 255

Leu Lys Ala Pro Ser Ser Asn Val Ala Gly Asn Ala Asn Val Leu Val
        260                 265                 270

Phe Pro Asp Leu Gln Thr Gly Asn Ile Gly Tyr Lys Leu Val Gln Arg
    275                 280                 285

Phe Ala Lys Ala Lys Ala Ile Gly Pro Ile Cys Gln Gly Phe Ala Lys
290                 295                 300

Pro Ile Asn Asp Leu Ser Arg Gly Cys Ser Ser Glu Asp Ile Val Asn
305                 310                 315                 320

Val Val Ala Ile Thr Val Val Gln Ala Gln Arg Gly Ile
                325                 330
```

<210> SEQ ID NO 223
<211> LENGTH: 1647
<212> TYPE: DNA
<213> ORGANISM: Lactococcus lactis

<400> SEQUENCE: 223

| | |
|---|---|
| atgtatacag taggagatta cctattagac cgattacacg agttaggaat tgaagaaatt | 60 |
| tttggagtcc ctggagacta taacttacaa tttttagatc aaattatttc ccacaaggat | 120 |
| atgaaatggg tcggaaatgc taatgaatta atgcttcat atatggctga tggctatgct | 180 |
| cgtactaaaa aagctgccgc atttcttaca acctttggag taggtgaatt gagtgcagtt | 240 |
| aatggattag caggaagtta cgccgaaaat ttaccagtag tagaaatagt gggatcacct | 300 |
| acatcaaaag ttcaaaatga aggaaaattt gttcatcata cgctggctga cggtgatttt | 360 |
| aaacactta tgaaaatgca cgaacctgtt acagcagctc gaactttact gacagcagaa | 420 |
| aatgcaaccg ttgaaattga ccgagtactt tctgcactat aaaagaaag aaaacctgtc | 480 |
| tatatcaact taccagttga tgttgctgct gcaaaagcag agaaaccctc actcccttg | 540 |
| aaaaaggaaa actcaacttc aaatacaagt gaccaagaaa ttttgaacaa aattcaagaa | 600 |
| agcttgaaaa atgccaaaaa accaatcgtg attacaggac atgaaataat tagttttggc | 660 |
| ttagaaaaaa cagtcactca atttatttca aagacaaaac tacctattac gacattaaac | 720 |
| tttggtaaaa gttcagttga tgaagccctc ccttcatttt taggaatcta taatggtaca | 780 |
| ctctcagagc ctaatcttaa agaattcgtg gaatcagccg acttcatctt gatgcttgga | 840 |
| gttaaactca cagactcttc aacaggagcc ttcactcatc attaaatga aaataaatg | 900 |
| atttcactga atatagatga aggaaaaata tttaacgaaa gaatccaaaa ttttgatttt | 960 |
| gaatccctca tctcctctct cttagaccta agcgaaatag aatacaaagg aaaatatatc | 1020 |
| gataaaaagc aagaagactt tgttccatca aatgcgcttt tatcacaaga ccgcctatgg | 1080 |
| caagcagttg aaaacctaac tcaaagcaat gaaacaatcg ttgctgaaca agggacatca | 1140 |
| ttctttggcg cttcatcaat tttcttaaaa tcaagagtc atttattgg tcaacccta | 1200 |
| tggggatcaa ttggatatac attcccagca gcattaggaa gccaaattgc agataaagaa | 1260 |
| agcagacacc tttatttat tggtgatggt tcacttcaac ttacagtgca agaattagga | 1320 |
| ttagcaatca gagaaaaaat taatccaatt gctttatta tcaataatga tggttataca | 1380 |
| gtcgaaagag aaattcatgg accaaatcaa agctacaatg atattccaat gtggaattac | 1440 |
| tcaaaattac cagaatcgtt tggagcaaca gaagatcgag tagtctcaaa aatcgttaga | 1500 |

```
actgaaaatg aatttgtgtc tgtcatgaaa gaagctcaag cagatccaaa tagaatgtac   1560
tggattgagt taattttggc aaaagaaggt gcaccaaaag tactgaaaaa aatgggcaaa   1620
ctatttgctg aacaaaataa atcataa                                      1647
```

<210> SEQ ID NO 224
<211> LENGTH: 548
<212> TYPE: PRT
<213> ORGANISM: Lactococcus lactis

<400> SEQUENCE: 224

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
                20                  25                  30

Asp Gln Ile Ile Ser His Lys Asp Met Lys Trp Val Gly Asn Ala Asn
            35                  40                  45

Glu Leu Asn Ala Ser Tyr Met Ala Asp Gly Tyr Ala Arg Thr Lys Lys
        50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
                100                 105                 110

His Thr Leu Ala Asp Gly Asp Phe Lys His Phe Met Lys Met His Glu
            115                 120                 125

Pro Val Thr Ala Ala Arg Thr Leu Leu Thr Ala Glu Asn Ala Thr Val
        130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
```

```
        340             345             350
Leu Leu Ser Gln Asp Arg Leu Trp Gln Ala Val Glu Asn Leu Thr Gln
            355                 360                 365

Ser Asn Glu Thr Ile Val Ala Glu Gln Gly Thr Ser Phe Phe Gly Ala
        370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
    450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Gly Ala Pro Lys Val Leu Lys Lys Met Gly Lys Leu Phe Ala Glu
    530                 535                 540

Gln Asn Lys Ser
545

<210> SEQ ID NO 225
<211> LENGTH: 2802
<212> TYPE: DNA
<213> ORGANISM: Escherichia coli

<400> SEQUENCE: 225
atgcagaaca gcgctttgaa agcctggttg gactcttctt acctctctgg cgcaaaccag     60
agctggatag aacagctcta tgaagacttc ttaaccgatc ctgactcggt tgacgctaac    120
tggcgttcga cgttccagca gttacctggt acgggagtca aaccggatca attccactct    180
caaacgcgtg aatatttccg ccgcctggcg aaagacgctt cacgttactc ttcaacgatc    240
tccgaccctg acaccaatgt gaagcaggtt aaagtcctgc agctcattaa cgcataccgc    300
ttccgtggtc accagcatgc gaatctcgat ccgctgggac tgtggcagca agataaagtg    360
gccgatctgg atccgtcttt ccacgatctg accgaagcag acttccagga ccttcaaac    420 gtcggttcat tgccagcgg caaagaaacc atgaaactcg gcgagctgct ggaagccctc    480
aagcaaacct actgcggccc gattggtgcc gagtatatgc acattaccag caccgaagaa    540
aaacgctgga tccaacagcg tatcgagtct ggtcgcgcga ctttcaatag cgaagagaaa    600
aaacgcttct taagcgaact gaccgccgct gaaggtcttg aacgttacct cggcgcaaaa    660
ttccctggcg caaaacgctt ctcgctggaa ggcggtgacg cgttaatccc gatgcttaaa    720
gagatgatcc gccacgctgg caacagcggc acccgcgaag tggttctcgg gatggcgcac    780
cgtggtcgtc tgaacgtgct ggtgaacgtg ctgggtaaaa aaccgcaaga cttgttcgac    840
gagttcgccg gtaaacataa agaacacctc ggcacgggtg acgtgaaata ccacatgggc    900
```

| | | |
|---|---|---|
| ttctcgtctg acttccagac cgatggcggc ctggtgcacc tggcgctggc gtttaacccg | 960 | |
| tctcaccttg agattgtaag cccggtagtt atcggttctg ttcgtgcccg tctggacaga | 1020 | |
| cttgatgagc cgagcagcaa caaagtgctg ccaatcacca tccacggtga cgccgcagtg | 1080 | |
| accgggcagg gcgtggttca ggaaaccctg aacatgtcga aagcgcgtgg ttatgaagtt | 1140 | |
| ggcggtacgg tacgtatcgt tatcaacaac caggttggtt tcaccacctc taatccgctg | 1200 | |
| gatgcccgtt ctacgccgta ctgtactgat atcggtaaga tggttcaggc cccgattttc | 1260 | |
| cacgttaacg cggacgatcc ggaagccgtt gcctttgtga cccgtctggc gctcgatttc | 1320 | |
| cgtaacacct ttaaacgtga tgtcttcatc gacctggtgt gctaccgccg tcacggccac | 1380 | |
| aacgaagccg acgagccgag cgcaacccag ccgctgatgt atcagaaaat caaaaaacat | 1440 | |
| ccgacaccgc gcaaaatcta cgctgacaag ctggagcagg aaaaagtggc gacgctggaa | 1500 | |
| gatgccaccg agatggttaa cctgtaccgc gatgcgctgg atgctggcga ttgcgtagtg | 1560 | |
| gcagagtggc gtccgatgaa catgcactct ttcacctggt cgccgtacct caaccacgaa | 1620 | |
| tgggacgaag agtacccgaa caaagttgag atgaagcgcc tgcaggagct ggcgaaacgc | 1680 | |
| atcagcacgg tgccggaagc agttgaaatg cagtctcgcg ttgccaagat ttatggcgat | 1740 | |
| cgccaggcga tggctgccgg tgagaaactg ttcgactggg gcggtgcgga aaacctcgct | 1800 | |
| tacgccacgc tggttgatga aggcattccg gttcgcctgt cgggtgaaga ctccggtcgc | 1860 | |
| ggtaccttct tccaccgcca cgcggtgatc acaaccagt ctaacggttc cacttacacg | 1920 | |
| ccgctgcaac atatccataa cgggcagggc gcgttccgtg tctgggactc cgtactgtct | 1980 | |
| gaagaagcag tgctggcgtt tgaatatggt tatgccaccg cagaaccacg cactctgacc | 2040 | |
| atctgggaag cgcagttcgg tgacttcgcc aacggtgcgc aggtggttat cgaccagttc | 2100 | |
| atctcctctg cgaacagaa atggggccgg atgtgtggtc tggtgatgtt gctgccgcac | 2160 | |
| ggttacgaag gcaggggcc ggagcactcc tccgcgcgtc tggaacgtta tctgcaactt | 2220 | |
| tgtgctgagc aaaacatgca ggtttgcgta ccgtctaccc cggcacaggt ttaccacatg | 2280 | |
| ctgcgtcgtc aggcgctgcg cgggatgcgt cgtccgctgg tcgtgatgtc gccgaaatcc | 2340 | |
| ctgctgcgtc atccgctggc ggtttccagc ctcgaagaac tggcgaacgg cacctttctg | 2400 | |
| ccagccatcg gtgaaatcga cgagcttgat ccgaagggcg tgaagcgcgt agtgatgtgt | 2460 | |
| tctggtaagg tttattacga cctgctggaa cagcgtcgta agaacaatca acacgatgtc | 2520 | |
| gccattgtgc gtatcgagca actctacccg ttcccgcata aagcgatgca ggaagtgttg | 2580 | |
| cagcagtttg ctcacgtcaa ggattttgtc tggtgccagg aagagccgct caaccagggc | 2640 | |
| gcatggtact gcagccagca tcatttccgt gaagtgattc cgtttggggc ttctctgcgt | 2700 | |
| tatgcaggcc gccggcctc cgcctctccg gcgggtaggg tatatgtccgt tcaccagaaa | 2760 | |
| cagcaacaag atctggttaa tgacgcgctg aacgtcgaat aa | 2802 | |

<210> SEQ ID NO 226
<211> LENGTH: 933
<212> TYPE: PRT
<213> ORGANISM: Escherichia coli

<400> SEQUENCE: 226

Met Gln Asn Ser Ala Leu Lys Ala Trp Leu Asp Ser Ser Tyr Leu Ser
1               5                   10                  15

Gly Ala Asn Gln Ser Trp Ile Glu Gln Leu Tyr Glu Asp Phe Leu Thr
            20                  25                  30

Asp Pro Asp Ser Val Asp Ala Asn Trp Arg Ser Thr Phe Gln Gln Leu

```
              35                  40                  45
Pro Gly Thr Gly Val Lys Pro Asp Gln Phe His Ser Gln Thr Arg Glu
 50                  55                  60

Tyr Phe Arg Arg Leu Ala Lys Asp Ala Ser Arg Tyr Ser Ser Thr Ile
 65                  70                  75                  80

Ser Asp Pro Asp Thr Asn Val Lys Gln Val Lys Val Leu Gln Leu Ile
                 85                  90                  95

Asn Ala Tyr Arg Phe Arg Gly His Gln His Ala Asn Leu Asp Pro Leu
                100                 105                 110

Gly Leu Trp Gln Gln Asp Lys Val Ala Asp Leu Asp Pro Ser Phe His
                115                 120                 125

Asp Leu Thr Glu Ala Asp Phe Gln Glu Thr Phe Asn Val Gly Ser Phe
            130                 135                 140

Ala Ser Gly Lys Glu Thr Met Lys Leu Gly Leu Leu Glu Ala Leu
145                 150                 155                 160

Lys Gln Thr Tyr Cys Gly Pro Ile Gly Ala Glu Tyr Met His Ile Thr
                165                 170                 175

Ser Thr Glu Glu Lys Arg Trp Ile Gln Gln Arg Ile Glu Ser Gly Arg
                180                 185                 190

Ala Thr Phe Asn Ser Glu Glu Lys Lys Arg Phe Leu Ser Glu Leu Thr
            195                 200                 205

Ala Ala Glu Gly Leu Glu Arg Tyr Leu Gly Ala Lys Phe Pro Gly Ala
210                 215                 220

Lys Arg Phe Ser Leu Glu Gly Gly Asp Ala Leu Ile Pro Met Leu Lys
225                 230                 235                 240

Glu Met Ile Arg His Ala Gly Asn Ser Gly Thr Arg Glu Val Val Leu
                245                 250                 255

Gly Met Ala His Arg Gly Arg Leu Asn Val Leu Val Asn Val Leu Gly
                260                 265                 270

Lys Lys Pro Gln Asp Leu Phe Asp Glu Phe Ala Gly Lys His Lys Glu
            275                 280                 285

His Leu Gly Thr Gly Asp Val Lys Tyr His Met Gly Phe Ser Ser Asp
            290                 295                 300

Phe Gln Thr Asp Gly Gly Leu Val His Leu Ala Leu Ala Phe Asn Pro
305                 310                 315                 320

Ser His Leu Glu Ile Val Ser Pro Val Val Ile Gly Ser Val Arg Ala
                325                 330                 335

Arg Leu Asp Arg Leu Asp Glu Pro Ser Ser Asn Lys Val Leu Pro Ile
                340                 345                 350

Thr Ile His Gly Asp Ala Ala Val Thr Gly Gln Gly Val Val Gln Glu
            355                 360                 365

Thr Leu Asn Met Ser Lys Ala Arg Gly Tyr Glu Val Gly Gly Thr Val
            370                 375                 380

Arg Ile Val Ile Asn Asn Gln Val Gly Phe Thr Thr Ser Asn Pro Leu
385                 390                 395                 400

Asp Ala Arg Ser Thr Pro Tyr Cys Thr Asp Ile Gly Lys Met Val Gln
                405                 410                 415

Ala Pro Ile Phe His Val Asn Ala Asp Asp Pro Glu Ala Val Ala Phe
                420                 425                 430

Val Thr Arg Leu Ala Leu Asp Phe Arg Asn Thr Phe Lys Arg Asp Val
            435                 440                 445

Phe Ile Asp Leu Val Cys Tyr Arg Arg His Gly His Asn Glu Ala Asp
450                 455                 460
```

```
Glu Pro Ser Ala Thr Gln Pro Leu Met Tyr Gln Lys Ile Lys Lys His
465                 470                 475                 480

Pro Thr Pro Arg Lys Ile Tyr Ala Asp Lys Leu Glu Gln Glu Lys Val
                485                 490                 495

Ala Thr Leu Glu Asp Ala Thr Glu Met Val Asn Leu Tyr Arg Asp Ala
            500                 505                 510

Leu Asp Ala Gly Asp Cys Val Val Ala Glu Trp Arg Pro Met Asn Met
        515                 520                 525

His Ser Phe Thr Trp Ser Pro Tyr Leu Asn His Glu Trp Asp Glu Glu
    530                 535                 540

Tyr Pro Asn Lys Val Glu Met Lys Arg Leu Gln Glu Leu Ala Lys Arg
545                 550                 555                 560

Ile Ser Thr Val Pro Glu Ala Val Glu Met Gln Ser Arg Val Ala Lys
                565                 570                 575

Ile Tyr Gly Asp Arg Gln Ala Met Ala Ala Gly Glu Lys Leu Phe Asp
            580                 585                 590

Trp Gly Gly Ala Glu Asn Leu Ala Tyr Ala Thr Leu Val Asp Glu Gly
        595                 600                 605

Ile Pro Val Arg Leu Ser Gly Glu Asp Ser Gly Arg Gly Thr Phe Phe
    610                 615                 620

His Arg His Ala Val Ile His Asn Gln Ser Asn Gly Ser Thr Tyr Thr
625                 630                 635                 640

Pro Leu Gln His Ile His Asn Gly Gln Gly Ala Phe Arg Val Trp Asp
                645                 650                 655

Ser Val Leu Ser Glu Glu Ala Val Leu Ala Phe Glu Tyr Gly Tyr Ala
            660                 665                 670

Thr Ala Glu Pro Arg Thr Leu Thr Ile Trp Glu Ala Gln Phe Gly Asp
        675                 680                 685

Phe Ala Asn Gly Ala Gln Val Val Ile Asp Gln Phe Ile Ser Ser Gly
    690                 695                 700

Glu Gln Lys Trp Gly Arg Met Cys Gly Leu Val Met Leu Leu Pro His
705                 710                 715                 720

Gly Tyr Glu Gly Gln Gly Pro Glu His Ser Ser Ala Arg Leu Glu Arg
                725                 730                 735

Tyr Leu Gln Leu Cys Ala Glu Gln Asn Met Gln Val Cys Val Pro Ser
            740                 745                 750

Thr Pro Ala Gln Val Tyr His Met Leu Arg Arg Gln Ala Leu Arg Gly
        755                 760                 765

Met Arg Arg Pro Leu Val Val Met Ser Pro Lys Ser Leu Leu Arg His
    770                 775                 780

Pro Leu Ala Val Ser Ser Leu Glu Glu Leu Ala Asn Gly Thr Phe Leu
785                 790                 795                 800

Pro Ala Ile Gly Glu Ile Asp Glu Leu Asp Pro Lys Gly Val Lys Arg
                805                 810                 815

Val Val Met Cys Ser Gly Lys Val Tyr Tyr Asp Leu Leu Glu Gln Arg
            820                 825                 830

Arg Lys Asn Asn Gln His Asp Val Ala Ile Val Arg Ile Glu Gln Leu
        835                 840                 845

Tyr Pro Phe Pro His Lys Ala Met Gln Glu Val Leu Gln Gln Phe Ala
    850                 855                 860

His Val Lys Asp Phe Val Trp Cys Gln Glu Glu Pro Leu Asn Gln Gly
865                 870                 875                 880
```

Ala Trp Tyr Cys Ser Gln His His Phe Arg Glu Val Ile Pro Phe Gly
            885                 890                 895

Ala Ser Leu Arg Tyr Ala Gly Arg Pro Ala Ser Ala Ser Pro Ala Val
        900                 905                 910

Gly Tyr Met Ser Val His Gln Lys Gln Gln Gln Asp Leu Val Asn Asp
    915                 920                 925

Ala Leu Asn Val Glu
    930

<210> SEQ ID NO 227
<211> LENGTH: 1233
<212> TYPE: DNA
<213> ORGANISM: Escherichia coli

<400> SEQUENCE: 227

```
atggcaaagg tatcgctgga gaaagacaag attaagtttc tgctggtaga aggcgtgcac      60
caaaaggcgc tggaaagcct tcgtgcagct ggttacacca acatcgaatt tcacaaaggc     120
gcgctggatg atgaacaatt aaaagaatcc atccgcgatg cccacttcat cggcctgcga     180
tcccgtaccc atctgactga agacgtgatc aacgccgcag aaaaactggt cgctattggc     240
tgtttctgta tcggaacaaa ccaggttgat ctggatgcgg cggcaaagcg cgggatcccg     300
gtatttaacg caccgttctc aaatacgcgc tctgttgcgg agctggtgat ggcgaactg      360
ctgctgctat tgcgcggcgt gccggaagcc aatgctaaag cgcaccgtgg cgtgtggaac     420
aaactggcgg cgggttcttt tgaagcgcgc ggcaaaaagc tgggtatcat cggctacggt     480
catattggta cgcaattggg cattctggct gaatcgctgg aatgtatgt  ttacttttat     540
gatattgaaa ataaactgcc gctgggcaac gccactcagg tacagcatct ttctgacctg     600
ctgaatatga gcgatgtggt gagtctgcat gtaccagaga atccgtccac caaaaatatg     660
atgggcgcga agaaatttc  actaatgaag cccggctcgc tgctgattaa tgcttcgcgc     720
ggtactgtgg tggatattcc ggcgctgtgt gatgcgctgg cgagcaaaca tctggcgggg     780
gcggcaatcg acgtattccc gacggaaccg gcgaccaata gcgatccatt tacctctccg     840
ctgtgtgaat cgacaacgt  ccttctgacg ccacacattg gcggttcgac tcaggaagcg     900
caggagaata tcggcctgga agttgcgggt aaattgatca agtattctga caatggctca     960
acgctctctg cggtgaactt cccggaagtc tcgctgccac tgcacggtgg cgtcgtctg    1020
atgcacatcc acgaaaaccg tccgggcgtg ctaactgcgc tgaacaaaat cttcgccgag    1080
cagggcgtca acatcgccgc gcaatatctg caaacttccg cccagatggg ttatgtggtt    1140
attgatattg aagccgacga agacgttgcc gaaaaagcgc tgcaggcaat gaaagctatt    1200
ccgggtacca ttcgcgcccg tctgctgtac taa                                1233
```

<210> SEQ ID NO 228
<211> LENGTH: 410
<212> TYPE: PRT
<213> ORGANISM: Escherichia coli

<400> SEQUENCE: 228

Met Ala Lys Val Ser Leu Glu Lys Asp Lys Ile Lys Phe Leu Leu Val
1               5                   10                  15

Glu Gly Val His Gln Lys Ala Leu Glu Ser Leu Arg Ala Ala Gly Tyr
            20                  25                  30

Thr Asn Ile Glu Phe His Lys Gly Ala Leu Asp Asp Glu Gln Leu Lys
        35                  40                  45

Glu Ser Ile Arg Asp Ala His Phe Ile Gly Leu Arg Ser Arg Thr His
    50                  55                  60

Leu Thr Glu Asp Val Ile Asn Ala Ala Glu Lys Leu Val Ala Ile Gly
 65                  70                  75                  80

Cys Phe Cys Ile Gly Thr Asn Gln Val Asp Leu Asp Ala Ala Lys
                     85                  90                  95

Arg Gly Ile Pro Val Phe Asn Ala Pro Phe Ser Asn Thr Arg Ser Val
                100                 105                 110

Ala Glu Leu Val Ile Gly Glu Leu Leu Leu Leu Arg Gly Val Pro
            115                 120                 125

Glu Ala Asn Ala Lys Ala His Arg Gly Val Trp Asn Lys Leu Ala Ala
        130                 135                 140

Gly Ser Phe Glu Ala Arg Gly Lys Lys Leu Gly Ile Ile Gly Tyr Gly
145                 150                 155                 160

His Ile Gly Thr Gln Leu Gly Ile Leu Ala Glu Ser Leu Gly Met Tyr
                    165                 170                 175

Val Tyr Phe Tyr Asp Ile Glu Asn Lys Leu Pro Leu Gly Asn Ala Thr
                180                 185                 190

Gln Val Gln His Leu Ser Asp Leu Leu Asn Met Ser Asp Val Val Ser
            195                 200                 205

Leu His Val Pro Glu Asn Pro Ser Thr Lys Asn Met Met Gly Ala Lys
210                 215                 220

Glu Ile Ser Leu Met Lys Pro Gly Ser Leu Leu Ile Asn Ala Ser Arg
225                 230                 235                 240

Gly Thr Val Val Asp Ile Pro Ala Leu Cys Asp Ala Leu Ala Ser Lys
                    245                 250                 255

His Leu Ala Gly Ala Ala Ile Asp Val Phe Pro Thr Glu Pro Ala Thr
                260                 265                 270

Asn Ser Asp Pro Phe Thr Ser Pro Leu Cys Glu Phe Asp Asn Val Leu
            275                 280                 285

Leu Thr Pro His Ile Gly Gly Ser Thr Gln Glu Ala Gln Glu Asn Ile
290                 295                 300

Gly Leu Glu Val Ala Gly Lys Leu Ile Lys Tyr Ser Asp Asn Gly Ser
305                 310                 315                 320

Thr Leu Ser Ala Val Asn Phe Pro Glu Val Ser Leu Pro Leu His Gly
                    325                 330                 335

Gly Arg Arg Leu Met His Ile His Glu Asn Arg Pro Gly Val Leu Thr
                340                 345                 350

Ala Leu Asn Lys Ile Phe Ala Glu Gln Gly Val Asn Ile Ala Ala Gln
            355                 360                 365

Tyr Leu Gln Thr Ser Ala Gln Met Gly Tyr Val Val Ile Asp Ile Glu
370                 375                 380

Ala Asp Glu Asp Val Ala Glu Lys Ala Leu Gln Ala Met Lys Ala Ile
385                 390                 395                 400

Pro Gly Thr Ile Arg Ala Arg Leu Leu Tyr
                405                 410

<210> SEQ ID NO 229
<211> LENGTH: 1089
<212> TYPE: DNA
<213> ORGANISM: Escherichia coli

<400> SEQUENCE: 229
atggctcaaa tcttcaattt tagttctggt ccggcaatgc taccggcaga ggtgcttaaa      60

```
caggctcaac aggaactgcg cgactggaac ggtcttggta cgtcggtgat ggaagtgagt    120
caccgtggca aagagttcat tcaggttgca gaggaagccg agaaggattt tcgcgatctt    180
cttaatgtcc cctccaacta caaggtatta ttctgccatg gcggtggtcg cggtcagttt    240
gctgcggtac cgctgaatat tctcggtgat aaaaccaccg cagattatgt tgatgccggt    300
tactgggcgg caagtgccat taaagaagcg aaaaaatact gcacgcctaa tgtctttgac    360
gccaaagtga ctgttgatgg tctgcgcgcg gttaagccaa tgcgtgaatg caactctct    420 gataatgctg cttatatgca ttattgcccg aatgaaacca tcgatggtat cgccatcgac    480
gaaacgccag acttcggcgc agatgtggtg gtcgccgctg acttctcttc aaccattctt    540
tcccgtccga ttgacgtcag ccgttatggt gtaatttacg ctggcgcgca gaaaaatatc    600
ggcccggctg gcctgacaat cgtcatcgtt cgtgaagatt tgctgggcaa agcgaatatc    660
gcgtgtccgt cgattctgga ttattccatc ctcaacgata acggctccat gtttaacacg    720
ccgccgacat ttgcctggta tctatctggt ctggtcttta aatggctgaa agcgaacggc    780
ggtgtagctg aaatggataa aatcaatcag caaaaagcag aactgctata tggggtgatt    840
gataacagcg atttctaccg caatgacgtg gcgaaagcta accgttcgcg gatgaacgtg    900
ccgttccagt tggcggacag tgcgcttgac aaattgttcc ttgaagagtc ttttgctgct    960
ggccttcatg cactgaaagg tcaccgtgtg gtcggcggaa tgcgcgcttc tatttataac    1020
gccatgccgc tggaaggcgt taaagcgctg acagacttca tggttgagtt cgaacgccgt    1080
cacggttaa                                                             1089
```

<210> SEQ ID NO 230
<211> LENGTH: 362
<212> TYPE: PRT
<213> ORGANISM: Escherichia coli

<400> SEQUENCE: 230

```
Met Ala Gln Ile Phe Asn Phe Ser Ser Gly Pro Ala Met Leu Pro Ala
1               5                   10                  15

Glu Val Leu Lys Gln Ala Gln Gln Glu Leu Arg Asp Trp Asn Gly Leu
            20                  25                  30

Gly Thr Ser Val Met Glu Val Ser His Arg Gly Lys Glu Phe Ile Gln
        35                  40                  45

Val Ala Glu Glu Ala Glu Lys Asp Phe Arg Asp Leu Leu Asn Val Pro
    50                  55                  60

Ser Asn Tyr Lys Val Leu Phe Cys His Gly Gly Gly Arg Gly Gln Phe
65                  70                  75                  80

Ala Ala Val Pro Leu Asn Ile Leu Gly Asp Lys Thr Thr Ala Asp Tyr
                85                  90                  95

Val Asp Ala Gly Tyr Trp Ala Ala Ser Ala Ile Lys Glu Ala Lys Lys
            100                 105                 110

Tyr Cys Thr Pro Asn Val Phe Asp Ala Lys Val Thr Val Asp Gly Leu
        115                 120                 125

Arg Ala Val Lys Pro Met Arg Glu Trp Gln Leu Ser Asp Asn Ala Ala
    130                 135                 140

Tyr Met His Tyr Cys Pro Asn Glu Thr Ile Asp Gly Ile Ala Ile Asp
145                 150                 155                 160

Glu Thr Pro Asp Phe Gly Ala Asp Val Val Ala Ala Asp Phe Ser
                165                 170                 175

Ser Thr Ile Leu Ser Arg Pro Ile Asp Val Ser Arg Tyr Gly Val Ile
            180                 185                 190
```

Tyr Ala Gly Ala Gln Lys Asn Ile Gly Pro Ala Gly Leu Thr Ile Val
            195                 200                 205

Ile Val Arg Glu Asp Leu Leu Gly Lys Ala Asn Ile Ala Cys Pro Ser
210                 215                 220

Ile Leu Asp Tyr Ser Ile Leu Asn Asp Asn Gly Ser Met Phe Asn Thr
225                 230                 235                 240

Pro Pro Thr Phe Ala Trp Tyr Leu Ser Gly Leu Val Phe Lys Trp Leu
            245                 250                 255

Lys Ala Asn Gly Gly Val Ala Glu Met Asp Lys Ile Asn Gln Gln Lys
            260                 265                 270

Ala Glu Leu Leu Tyr Gly Val Ile Asp Asn Ser Asp Phe Tyr Arg Asn
            275                 280                 285

Asp Val Ala Lys Ala Asn Arg Ser Arg Met Asn Val Pro Phe Gln Leu
            290                 295                 300

Ala Asp Ser Ala Leu Asp Lys Leu Phe Leu Glu Ser Phe Ala Ala
305                 310                 315                 320

Gly Leu His Ala Leu Lys Gly His Arg Val Val Gly Met Arg Ala
            325                 330                 335

Ser Ile Tyr Asn Ala Met Pro Leu Glu Gly Val Lys Ala Leu Thr Asp
            340                 345                 350

Phe Met Val Glu Phe Glu Arg Arg His Gly
            355                 360

<210> SEQ ID NO 231
<211> LENGTH: 579
<212> TYPE: DNA
<213> ORGANISM: Escherichia coli

<400> SEQUENCE: 231
gtggaatacc gtagcctgac gcttgatgat ttttatcgc gctttcaact tttgcgcccg      60
caaattaacc gggaaaccct aaatcatcgt caggctgctg tgttaatccc catcgtccgt    120
cgaccgcaac cggggttgtt gctgactcag cgttcgattc atctgcgtaa acacgctgga    180
caagtggcat tccctggagg tgcagtcgat gacacggacg catcagctat cgccgccgcg    240
ctgcgcgaag ctgaagaaga ggtcgctata ccgccttccg ccgttgaagt tatcggcgtg    300
ctgccgcccg tcgatagcgt cactggctac caggtaaccc cagtggtcgg cattatcccg    360
cccgatctgc cgtatcgcgc cagtgaagat gaagtctcgg cggtgtttga aatgccgctc    420
gcccaggcat acatctgggt cgttatcac cctttagata tctaccgccg tggtgattca    480
catcgggtat ggctgtcctg gtacgaacag tattttgtat ggggaatgac cgcaggcata    540
attcgtgagc tggcgctgca aattggtgtg aaaccctga                           579

<210> SEQ ID NO 232
<211> LENGTH: 192
<212> TYPE: PRT
<213> ORGANISM: Escherichia coli

<400> SEQUENCE: 232

Met Glu Tyr Arg Ser Leu Thr Leu Asp Asp Phe Leu Ser Arg Phe Gln
1               5                   10                  15

Leu Leu Arg Pro Gln Ile Asn Arg Glu Thr Leu Asn His Arg Gln Ala
            20                  25                  30

Ala Val Leu Ile Pro Ile Val Arg Arg Pro Gln Pro Gly Leu Leu Leu
            35                  40                  45

| | | | | | | | | | | | |
|---|---|---|---|---|---|---|---|---|---|---|---|
|Thr|Gln|Arg|Ser|Ile|His|Leu|Arg|Lys|His|Ala|Gly|Gln|Val|Ala|Phe|
| |50| | | |55| | | |60| | |

Pro Gly Gly Ala Val Asp Asp Thr Asp Ala Ser Ala Ile Ala Ala Ala
65                  70                  75                  80

Leu Arg Glu Ala Glu Glu Val Ala Ile Pro Pro Ser Ala Val Glu
                85                  90                  95

Val Ile Gly Val Leu Pro Pro Val Asp Ser Val Thr Gly Tyr Gln Val
            100                 105                 110

Thr Pro Val Gly Ile Ile Pro Pro Asp Leu Pro Tyr Arg Ala Ser
            115                 120                 125

Glu Asp Glu Val Ser Ala Val Phe Glu Met Pro Leu Ala Gln Ala Leu
130                 135                 140

His Leu Gly Arg Tyr His Pro Leu Asp Ile Tyr Arg Arg Gly Asp Ser
145                 150                 155                 160

His Arg Val Trp Leu Ser Trp Tyr Glu Gln Tyr Phe Val Trp Gly Met
                165                 170                 175

Thr Ala Gly Ile Ile Arg Glu Leu Ala Leu Gln Ile Gly Val Lys Pro
            180                 185                 190

<210> SEQ ID NO 233
<211> LENGTH: 969
<212> TYPE: DNA
<213> ORGANISM: Escherichia coli

<400> SEQUENCE: 233

```
atgcctaaca ttacctggtg cgacctgcct gaagatgtct ctttatggcc gggtctgcct      60
ctttcattaa gtggtgatga agtgatgcca ctggattacc acgcaggtcg tagcggctgg     120
ctgctgtatg tcgtgggct ggataaacaa cgtctgaccc aataccgag caaactgggt       180
gcggcgatgg tgattgttgc cgcctggtgc gtggaagatt atcaggtgat cgtctggca     240
ggttcactca ccgcacgggc tacacgcctg cccacgaag cgcagctgga tgtcgccccg      300
ctggggaaaa tcccgcacct gcgcacgccg ggtttgctgg tgatggatat ggactccacc    360
gccatccaga ttgaatgtat tgatgaaatt gccaaactgg ccggaacggg cgagatggtg    420
gcggaagtaa ccgaacgggc gatgcgcggc gaactcgatt ttaccgccag cctgcgcagc    480
cgtgtggcga cgctgaaagg cgctgacgcc aatattctgc aacaggtgcg tgaaaatctg    540
ccgctgatgc caggcttaac gcaactggtg ctcaagctgg aaacgctggg ctggaaagtg    600
gcgattgcct ccggcggctt tactttcttt gctgaatacc tgcgcgacaa gctgcgcctg    660
accgccgtgg tagccaatga actggagatc atggacggta aatttaccgg caatgtgatc    720
ggcgacatcg tagacgcgca gtacaaagcg aaaactctga ctcgcctcgc gcaggagtat    780
gaaatcccgc tggcgcagac cgtggcgatt ggcgatggag ccaatgacct gccgatgatc    840
aaagcggcag gctggggat tgcctaccat gccaagccaa agtgaatga aaaggcggaa      900
gtcaccatcc gtcacgctga cctgatgggg gtattctgca tcctctcagg cagcctgaat    960
cagaagtaa                                                             969
```

<210> SEQ ID NO 234
<211> LENGTH: 322
<212> TYPE: PRT
<213> ORGANISM: Escherichia coli

<400> SEQUENCE: 234

Met Pro Asn Ile Thr Trp Cys Asp Leu Pro Glu Asp Val Ser Leu Trp
1               5                   10                  15

```
Pro Gly Leu Pro Leu Ser Leu Ser Gly Asp Glu Val Met Pro Leu Asp
        20                  25                  30

Tyr His Ala Gly Arg Ser Gly Trp Leu Leu Tyr Arg Gly Leu Asp
            35                  40                  45

Lys Gln Arg Leu Thr Gln Tyr Gln Ser Lys Leu Gly Ala Ala Met Val
 50                  55                  60

Ile Val Ala Ala Trp Cys Val Glu Asp Tyr Gln Val Ile Arg Leu Ala
 65                  70                  75                  80

Gly Ser Leu Thr Ala Arg Ala Thr Arg Leu Ala His Glu Ala Gln Leu
                85                  90                  95

Asp Val Ala Pro Leu Gly Lys Ile Pro His Leu Arg Thr Pro Gly Leu
                100                 105                 110

Leu Val Met Asp Met Asp Ser Thr Ala Ile Gln Ile Glu Cys Ile Asp
            115                 120                 125

Glu Ile Ala Lys Leu Ala Gly Thr Gly Glu Met Val Ala Glu Val Thr
130                 135                 140

Glu Arg Ala Met Arg Gly Glu Leu Asp Phe Thr Ala Ser Leu Arg Ser
145                 150                 155                 160

Arg Val Ala Thr Leu Lys Gly Ala Asp Ala Asn Ile Leu Gln Gln Val
                165                 170                 175

Arg Glu Asn Leu Pro Leu Met Pro Gly Leu Thr Gln Leu Val Leu Lys
            180                 185                 190

Leu Glu Thr Leu Gly Trp Lys Val Ala Ile Ala Ser Gly Gly Phe Thr
            195                 200                 205

Phe Phe Ala Glu Tyr Leu Arg Asp Lys Leu Arg Leu Thr Ala Val Val
210                 215                 220

Ala Asn Glu Leu Glu Ile Met Asp Gly Lys Phe Thr Gly Asn Val Ile
225                 230                 235                 240

Gly Asp Ile Val Asp Ala Gln Tyr Lys Ala Lys Thr Leu Thr Arg Leu
                245                 250                 255

Ala Gln Glu Tyr Glu Ile Pro Leu Ala Gln Thr Val Ala Ile Gly Asp
            260                 265                 270

Gly Ala Asn Asp Leu Pro Met Ile Lys Ala Ala Gly Leu Gly Ile Ala
            275                 280                 285

Tyr His Ala Lys Pro Lys Val Asn Glu Lys Ala Glu Val Thr Ile Arg
290                 295                 300

His Ala Asp Leu Met Gly Val Phe Cys Ile Leu Ser Gly Ser Leu Asn
305                 310                 315                 320

Gln Lys

<210> SEQ ID NO 235
<211> LENGTH: 2233
<212> TYPE: DNA
<213> ORGANISM: Arabidopsis thaliana

<400> SEQUENCE: 235
cgaaagggca aaaccaaaa agagaatcaa attttgcctc ttctatataa atcaaatcaa     60
cgacgaagcg tcgctctcgt tttctgtgtg tctctctctt tgtcccacca ttttcaccgc    120
ttctcctcca atcactcaga tctacagatt cctttaaaac aacaatggtt ggatctttgg    180
aatctgatca aactctttca atggccacct taatcgaaaa actcgacatc ttatctgacg    240
acttcgatcc aaccgccgta gtcaccgaac cgttacctcc tccggtaact aatggaatcg    300
gagctgataa aggaggagga ggaggagaaa gagagatggt tctcggtagg aatatacaca    360
```

```
caacgtcact cgctgtaacg gaaccggagg ttaacgatga attcaccgga gataagaag      420
cttatatggc tagtgttctt gctcgttacc ggaaaacttt ggttgaacga accaaaaacc     480
atttaggtaa aatttgatct gatctgatct ttttttttga atcggaatcg gaatctgaat    540
cggaatctgg tgtaggttat ccttataact tggatttcga ctatggtgcg cttggtcagt    600
tacaacattt ttcgattaat aatcttggag atccgtttat tgaaagtaac tatggtgtac    660
actcaagacc ttttgaagtt ggtgtgttgg attggtttgc tcgtctttgg gagattgaga    720
gagatgatta ttggggttac attaccaatt gtggtactga aggcaacctt catggcattt    780
tagtcgggta cgttttcga aaatcatcgg tgttttgatt cattcgaaaa accgaaaaaa     840
acggtgttt gatttgatgt gtgtttgtag agggagatg tttccggatg ggatattgta       900
tgcgtcgcgt gaatcgcatt actcggtgtt taaagctgct cgaatgtatc gaatggagtg    960
tgagaaggtt gatacgctta tgtcagggga gattgattgt gatgatttga ggaagaagtt   1020
gttggctaat aaagataaac cggcgattct taatgttaac ataggttggt ttatgtttta   1080
gtactttggc tttgtttgtt gtgttaggat tggtgctaat ggttgaaatc ttgttttctt   1140
taggaacgac ggttaaagga gctgttgatg atcttgacct tgttatcaaa actcttgaag   1200
agtgtggttt ctcacatgat aggttctata ttcattgtga tggagctttg tttggactta   1260
tgatgccttt tgtcaaacgt gtaagtgtat agtcttcagt ctaagcgaaa tcgttatgat   1320
aatctttgtt ctgctctgag atttgttgtt ttatctcctc tgtaggcacc gaaagtgacg   1380
tttaataaac cgatagggag tgtgagtgta tcgggccaca aatttgtcgg gtgtccaatg   1440
ccatgtggtg ttcagataac aagaatggaa catatcaaag tcctctccag taacgttgag   1500
taccttgctt caagggatgc aacaatcatg ggaagtcgta acgggcatgc tcctttgttc   1560
ctctggtaca ccttaaacag gaaaggttac aaaggattcc agaaagaagt tcagaaatgc   1620
ttgagaaacg cgcattacct caaagaccga cttcgtgaag ctgggattag cgccatgctt   1680
aatgagctta gcagcactgt ggtctttgaa cggcctaaag atgaagagtt tgttagaagg   1740
tggcagcttg cttgccaagg tgatatagct catgtggtgg ttatgccaag tgttacaatc   1800
gagaagcttg ataatttcct gaaagacctt gtcaaacaca gattgatctg gtacgaggat   1860
ggatctcagc ctccttgcct tgcatcggag gtaggaacca acaactgcat ctgtccagct   1920
cacaagtgac ggcaccattt tcatttgtt ggtattgttg ttttctagta agccacatct    1980
agtttaaatt cctcatcact gtattcctga acttggtttc aatcatcgta aaattttgtc   2040
agtttctctt atttacaagt taaggtttca aacagtgttt acaatttgta gctcaatctg   2100
gagcatgatc aaccttcact tcgtcgttcg caatcgttta ccgagtttta gcattatcgt   2160
aacagcaagt atgtgcctta agccgctgat ttagctgcgt gtttgatgat cggtgcttaa   2220
tgcctaggaa aag                                                     2233
```

<210> SEQ ID NO 236
<211> LENGTH: 482
<212> TYPE: PRT
<213> ORGANISM: Arabidopsis thaliana

<400> SEQUENCE: 236

```
Met Val Gly Ser Leu Glu Ser Asp Gln Thr Leu Ser Met Ala Thr Leu
1               5                   10                  15

Ile Glu Lys Leu Asp Ile Leu Ser Asp Asp Phe Asp Pro Thr Ala Val
            20                  25                  30
```

Val Thr Glu Pro Leu Pro Pro Val Thr Asn Gly Ile Gly Ala Asp
    35                  40                  45

Lys Gly Gly Gly Gly Glu Arg Glu Met Val Leu Gly Arg Asn Ile
 50                  55                  60

His Thr Thr Ser Leu Ala Val Thr Glu Pro Glu Val Asn Asp Glu Phe
 65                  70                  75                  80

Thr Gly Asp Lys Glu Ala Tyr Met Ala Ser Val Leu Ala Arg Tyr Arg
                 85                  90                  95

Lys Thr Leu Val Glu Arg Thr Lys Asn His Leu Gly Tyr Pro Tyr Asn
                100                 105                 110

Leu Asp Phe Asp Tyr Gly Ala Leu Gly Gln Leu Gln His Phe Ser Ile
             115                 120                 125

Asn Asn Leu Gly Asp Pro Phe Ile Glu Ser Asn Tyr Gly Val His Ser
130                 135                 140

Arg Pro Phe Glu Val Gly Val Leu Asp Trp Phe Ala Arg Leu Trp Glu
145                 150                 155                 160

Ile Glu Arg Asp Asp Tyr Trp Gly Tyr Ile Thr Asn Cys Gly Thr Glu
                165                 170                 175

Gly Asn Leu His Gly Ile Leu Val Gly Arg Glu Met Phe Pro Asp Gly
             180                 185                 190

Ile Leu Tyr Ala Ser Arg Glu Ser His Tyr Ser Val Phe Lys Ala Ala
         195                 200                 205

Arg Met Tyr Arg Met Glu Cys Glu Lys Val Asp Thr Leu Met Ser Gly
     210                 215                 220

Glu Ile Asp Cys Asp Asp Leu Arg Lys Lys Leu Leu Ala Asn Lys Asp
225                 230                 235                 240

Lys Pro Ala Ile Leu Asn Val Asn Ile Gly Thr Thr Val Lys Gly Ala
                245                 250                 255

Val Asp Asp Leu Asp Leu Val Ile Lys Thr Leu Glu Glu Cys Gly Phe
             260                 265                 270

Ser His Asp Arg Phe Tyr Ile His Cys Asp Gly Ala Leu Phe Gly Leu
         275                 280                 285

Met Met Pro Phe Val Lys Arg Ala Pro Lys Val Thr Phe Asn Lys Pro
     290                 295                 300

Ile Gly Ser Val Ser Val Ser Gly His Lys Phe Val Gly Cys Pro Met
305                 310                 315                 320

Pro Cys Gly Val Gln Ile Thr Arg Met Glu His Ile Lys Val Leu Ser
                325                 330                 335

Ser Asn Val Glu Tyr Leu Ala Ser Arg Asp Ala Thr Ile Met Gly Ser
             340                 345                 350

Arg Asn Gly His Ala Pro Leu Phe Leu Trp Tyr Thr Leu Asn Arg Lys
         355                 360                 365

Gly Tyr Lys Gly Phe Gln Lys Glu Val Gln Lys Cys Leu Arg Asn Ala
     370                 375                 380

His Tyr Leu Lys Asp Arg Leu Arg Glu Ala Gly Ile Ser Ala Met Leu
385                 390                 395                 400

Asn Glu Leu Ser Ser Thr Val Val Phe Glu Arg Pro Lys Asp Glu Glu
                405                 410                 415

Phe Val Arg Arg Trp Gln Leu Ala Cys Gln Gly Asp Ile Ala His Val
             420                 425                 430

Val Val Met Pro Ser Val Thr Ile Glu Lys Leu Asp Asn Phe Leu Lys
         435                 440                 445

Asp Leu Val Lys His Arg Leu Ile Trp Tyr Glu Asp Gly Ser Gln Pro

```
                450             455             460
Pro Cys Leu Ala Ser Glu Val Gly Thr Asn Asn Cys Ile Cys Pro Ala
465                 470             475                 480
His Lys

<210> SEQ ID NO 237
<211> LENGTH: 2274
<212> TYPE: DNA
<213> ORGANISM: Escherichia coli

<400> SEQUENCE: 237
atgggaagcc cctctctgta ttctgcccgt aaaacaaccc tggcgttggc agtcgcctta     60
agtttcgcct ggcaagcgcc ggtatttgcc cacggtggtg aagcgcatat ggtgccaatg    120
gataaaacgc ttaaagaatt tggtgccgat gtgcagtggg acgactacgc ccagctcttt    180
accctgatta agatggcgc gtacgtgaaa gtgaagcctg gtgcgcaaac agcaattgtt    240
aatggtcagc tctggcact gcaagtaccg tagtgatga agacaataa agcctgggtt    300 tctgacacct ttattaacga tgttttccag tccgggctgg atcaaacctt tcaggtagaa    360
aagcgccctc acccacttaa tgcgctaact gcggacgaaa ttaaacaggc cgttgaaatt    420
gttaaagctt ccgcggactt caaacccaat accgttttta ctgagatctc cctgctaccg    480
ccagataaag aagctgtctg gcgtttgcg ctggaaaaca accggttga ccagccgcgc    540 aaagccgacg tcattatgct cgacggcaaa catatcatcg aagcggtggt ggatctgcaa    600 acaacaaac tgctctcctg caacccatt aaagacgccc acggtatggt gttgctggat    660
gatttcgcca gtgtgcagaa cattattaac aacagtgaag aatttgccgc tgccgtgaag    720
aaacgcggta ttactgatgc gaaaaaagtg attaccacgc cgctgaccgt aggttatttc    780
gatggtaaag atggcctgaa acaagatgcc cggttgctca agtcatcag ctatcttgat    840 gtcggtgatg caactactg gcacatccc atcgaaaacc tggtggcggt cgttgattta    900
gaacagaaaa aaatcgttaa gattgaagaa ggtccggtag ttccggtgcc aatgaccgca    960
cgcccatttg atggccgtga ccgcgttgct ccggcagtta agcctatgca atcattgag    1020 cctgaaggta aaattacac cattactggc gatatgattc actggcggaa ctgggatttt    1080
cacctcagca tgaactctcg cgtcgggccg atgatctcca ccgtgactta taacgacaat    1140
ggcaccaaac gcaaagtcat gtacgaaggt tctctcggcg gcatgattgt gccttacggt    1200
gatcctgata ttggctggta ctttaaagcg tatctggact ctggtgacta cggtatgggc    1260
acgctaacct caccaattgc tcgtggtaaa gatgccccgt ctaacgcagt gctccttaat    1320
gaaaccatcg ccgactacac tggcgtgccg atggagatcc ctcgcgctat cgcggtattt    1380
gaacgttatg ccgggccgga gtataagcat caggaaatgg ccagcccaa cgtcagtacc    1440 gaacgccggg agttagtggt gcgctggatc agtacagtgg gtaactatga ctacattttt    1500
gactggatct tccatgaaaa cggcactatt ggcatcgatg ccggtgctac gggcatcgaa    1560
gcggtgaaag gtgttaaagc gaaaaccatg cacgatgaga cggcgaaaga tgacacgcgc    1620
tacggcacgc ttatcgatca aatatcgtg ggtactacac accaacatat ttataatttc    1680
cgcctcgatc tggatgtaga tggcgagaat aacagcctgg tggcgatgga cccagtggta    1740
aaaccgaata ctgccggtgg cccacgcacc agtaccatgc aagttaatca gtacaacatc    1800
ggcaatgaac aggatgccgc acagaaattt gatccgggca cgattcgtct gttgagtaac    1860
ccgaacaaag agaaccgcat gggcaatccg gtttcctatc aaattattcc ttatgcaggt    1920
```

-continued

```
ggtactcacc cggtagcaaa aggtgcccag ttcgcgccgg acgagtggat ctatcatcgt    1980
ttaagcttta tggacaagca gctctgggta acgcgttatc atcctggcga gcgtttcccg    2040
gaaggcaaat atccgaaccg ttctactcat gacaccggtc ttggacaata cagtaaggat    2100
aacgagtcgc tggacaacac cgacgccgtt gtctggatga ccaccggcac cacacatgtg    2160
gcccgcgccg aagagtggcc gattatgccg accgaatggg tacatactct gctgaaacca    2220
tggaacttct tgacgaaaac gccaacgcta ggggcgctga agaaagataa gtga          2274
```

<210> SEQ ID NO 238
<211> LENGTH: 757
<212> TYPE: PRT
<213> ORGANISM: Escherichia coli

<400> SEQUENCE: 238

```
Met Gly Ser Pro Ser Leu Tyr Ser Ala Arg Lys Thr Thr Leu Ala Leu
1               5                   10                  15

Ala Val Ala Leu Ser Phe Ala Trp Gln Ala Pro Val Phe Ala His Gly
            20                  25                  30

Gly Glu Ala His Met Val Pro Met Asp Lys Thr Leu Lys Glu Phe Gly
        35                  40                  45

Ala Asp Val Gln Trp Asp Asp Tyr Ala Gln Leu Phe Thr Leu Ile Lys
    50                  55                  60

Asp Gly Ala Tyr Val Lys Val Lys Pro Gly Ala Gln Thr Ala Ile Val
65                  70                  75                  80

Asn Gly Gln Pro Leu Ala Leu Gln Val Pro Val Val Met Lys Asp Asn
                85                  90                  95

Lys Ala Trp Val Ser Asp Thr Phe Ile Asn Asp Val Phe Gln Ser Gly
            100                 105                 110

Leu Asp Gln Thr Phe Gln Val Glu Lys Arg Pro His Pro Leu Asn Ala
        115                 120                 125

Leu Thr Ala Asp Glu Ile Lys Gln Ala Val Glu Ile Val Lys Ala Ser
    130                 135                 140

Ala Asp Phe Lys Pro Asn Thr Arg Phe Thr Glu Ile Ser Leu Leu Pro
145                 150                 155                 160

Pro Asp Lys Glu Ala Val Trp Ala Phe Ala Leu Glu Asn Lys Pro Val
                165                 170                 175

Asp Gln Pro Arg Lys Ala Asp Val Ile Met Leu Asp Gly Lys His Ile
            180                 185                 190

Ile Glu Ala Val Val Asp Leu Gln Asn Asn Lys Leu Leu Ser Trp Gln
        195                 200                 205

Pro Ile Lys Asp Ala His Gly Met Val Leu Leu Asp Asp Phe Ala Ser
    210                 215                 220

Val Gln Asn Ile Ile Asn Ser Glu Glu Phe Ala Ala Ala Val Lys
225                 230                 235                 240

Lys Arg Gly Ile Thr Asp Ala Lys Lys Val Ile Thr Thr Pro Leu Thr
                245                 250                 255

Val Gly Tyr Phe Asp Gly Lys Asp Gly Leu Lys Gln Asp Ala Arg Leu
            260                 265                 270

Leu Lys Val Ile Ser Tyr Leu Asp Val Gly Asp Gly Asn Tyr Trp Ala
        275                 280                 285

His Pro Ile Glu Asn Leu Val Ala Val Asp Leu Glu Gln Lys Lys
    290                 295                 300

Ile Val Lys Ile Glu Glu Gly Pro Val Val Pro Val Pro Met Thr Ala
305                 310                 315                 320
```

```
Arg Pro Phe Asp Gly Arg Asp Arg Val Ala Pro Ala Val Lys Pro Met
                325                 330                 335
Gln Ile Ile Glu Pro Glu Gly Lys Asn Tyr Thr Ile Thr Gly Asp Met
            340                 345                 350
Ile His Trp Arg Asn Trp Asp Phe His Leu Ser Met Asn Ser Arg Val
        355                 360                 365
Gly Pro Met Ile Ser Thr Val Thr Tyr Asn Asp Asn Gly Thr Lys Arg
    370                 375                 380
Lys Val Met Tyr Glu Gly Ser Leu Gly Gly Met Ile Val Pro Tyr Gly
385                 390                 395                 400
Asp Pro Asp Ile Gly Trp Tyr Phe Lys Ala Tyr Leu Asp Ser Gly Asp
                405                 410                 415
Tyr Gly Met Gly Thr Leu Thr Ser Pro Ile Ala Arg Gly Lys Asp Ala
            420                 425                 430
Pro Ser Asn Ala Val Leu Leu Asn Glu Thr Ile Ala Asp Tyr Thr Gly
        435                 440                 445
Val Pro Met Glu Ile Pro Arg Ala Ile Ala Val Phe Glu Arg Tyr Ala
    450                 455                 460
Gly Pro Glu Tyr Lys His Gln Glu Met Gly Gln Pro Asn Val Ser Thr
465                 470                 475                 480
Glu Arg Arg Glu Leu Val Val Arg Trp Ile Ser Thr Val Gly Asn Tyr
                485                 490                 495
Asp Tyr Ile Phe Asp Trp Ile Phe His Glu Asn Gly Thr Ile Gly Ile
            500                 505                 510
Asp Ala Gly Ala Thr Gly Ile Glu Ala Val Lys Gly Val Lys Ala Lys
        515                 520                 525
Thr Met His Asp Glu Thr Ala Lys Asp Asp Thr Arg Tyr Gly Thr Leu
    530                 535                 540
Ile Asp His Asn Ile Val Gly Thr Thr His Gln His Ile Tyr Asn Phe
545                 550                 555                 560
Arg Leu Asp Leu Asp Val Asp Gly Glu Asn Asn Ser Leu Val Ala Met
                565                 570                 575
Asp Pro Val Val Lys Pro Asn Thr Ala Gly Gly Pro Arg Thr Ser Thr
            580                 585                 590
Met Gln Val Asn Gln Tyr Asn Ile Gly Asn Glu Gln Asp Ala Ala Gln
        595                 600                 605
Lys Phe Asp Pro Gly Thr Ile Arg Leu Leu Ser Asn Pro Asn Lys Glu
    610                 615                 620
Asn Arg Met Gly Asn Pro Val Ser Tyr Gln Ile Ile Pro Tyr Ala Gly
625                 630                 635                 640
Gly Thr His Pro Val Ala Lys Gly Ala Gln Phe Ala Pro Asp Glu Trp
                645                 650                 655
Ile Tyr His Arg Leu Ser Phe Met Asp Lys Gln Leu Trp Val Thr Arg
            660                 665                 670
Tyr His Pro Gly Glu Arg Phe Pro Glu Gly Lys Tyr Pro Asn Arg Ser
        675                 680                 685
Thr His Asp Thr Gly Leu Gly Gln Tyr Ser Lys Asp Asn Glu Ser Leu
    690                 695                 700
Asp Asn Thr Asp Ala Val Val Trp Met Thr Thr Gly Thr Thr His Val
705                 710                 715                 720
Ala Arg Ala Glu Glu Trp Pro Ile Met Pro Thr Glu Trp Val His Thr
                725                 730                 735
```

-continued

```
Leu Leu Lys Pro Trp Asn Phe Phe Asp Glu Thr Pro Thr Leu Gly Ala
            740                 745                 750

Leu Lys Lys Asp Lys
        755

<210> SEQ ID NO 239
<211> LENGTH: 1218
<212> TYPE: DNA
<213> ORGANISM: Escherichia coli

<400> SEQUENCE: 239
atgtccccca ttgaaaaatc cagcaaatta gagaatgtct gttatgacat ccgtggtccg      60
gtgctgaaag aagcaaaacg cctggaagaa gaaggtaaca aggtactgaa actgaacatc     120
ggcaacccag ccccgttcgg ttttgacgcg ccagatgaaa tcctcgttga cgtgatacgc     180
aacctgccta ccgctcaagg gtattgcgat tccaaggtc tttactccgc gcgtaaagcc      240
atcatgcagc actaccaggc tcgtggcatg cgtgatgtta ccgtggaaga tatttacatc     300
ggcaatggtg tatcggagct tatcgttcag gcaatgcagg cattgctgaa cagcggggac     360
gaaatgttgg ttcctgcacc agattaccca ctctggaccg cggcggtttc gctttccagc     420 ggtaaagcg tgcattatct ttgcgatgaa tcctctgact ggttcccgga cctcgatgat      480
attcgcgcta aaattacgcc tcgtacgcgt gggatcgtta ttatcaaccc aaataaccca     540
accggcgcgg tatattccaa agagctttta atggagattg gagattgc acgtcagcat      600 aatctcatta tcttcgccga tgaaatttat gacaaaattc tctacgacga cgctgagcat     660
cactcaattg cgccgctggc acctgacctg ctgaccatta cctttaacgg actgtcgaaa     720
acgtaccgcg ttgcaggctt ccgtcagggg tggatggtgt gaacgggcc gaaaaaacac      780 gccaaaggct acatcgaagg tctggaaatg ctggcttcaa tgcgcctgtg tgctaacgtt     840
cctgcgcaac acgccattca gaccgcgcta ggtggttatc agagcatcag tgaatttatt     900 accctggcg tcgtcttta tgagcagcgt aaccgcgcgt gggaactgat caacgatatt      960
ccgggcgttt cctgcgtgaa acctcgtggt gcgctgtata tgttcccgaa atcgacgcc     1020 aaacgcttta acattcacga cgatcagaaa atggtgttgg atttcctgtt gcaggaaaaa    1080
gttctgttgg tgcaagggac ggcattcaac tggccgtggc cggatcactt ccgcattgtc    1140
acgctaccgc gtgtcgatga tatcgagctg tctttgagca gttcgcgcg tttcctttct    1200 ggttatcatc agctgtaa                                                  1218

<210> SEQ ID NO 240
<211> LENGTH: 405
<212> TYPE: PRT
<213> ORGANISM: Escherichia coli

<400> SEQUENCE: 240

Met Ser Pro Ile Glu Lys Ser Ser Lys Leu Glu Asn Val Cys Tyr Asp
1               5                   10                  15

Ile Arg Gly Pro Val Leu Lys Glu Ala Lys Arg Leu Glu Glu Glu Gly
            20                  25                  30

Asn Lys Val Leu Lys Leu Asn Ile Gly Asn Pro Ala Pro Phe Gly Phe
        35                  40                  45

Asp Ala Pro Asp Glu Ile Leu Val Asp Val Ile Arg Asn Leu Pro Thr
    50                  55                  60

Ala Gln Gly Tyr Cys Asp Ser Lys Gly Leu Tyr Ser Ala Arg Lys Ala
65                  70                  75                  80
```

Ile Met Gln His Tyr Gln Ala Arg Gly Met Arg Asp Val Thr Val Glu
            85                  90                  95

Asp Ile Tyr Ile Gly Asn Gly Val Ser Glu Leu Ile Val Gln Ala Met
        100                 105                 110

Gln Ala Leu Leu Asn Ser Gly Asp Glu Met Leu Val Pro Ala Pro Asp
        115                 120                 125

Tyr Pro Leu Trp Thr Ala Val Ser Leu Ser Ser Gly Lys Ala Val
    130                 135                 140

His Tyr Leu Cys Asp Glu Ser Ser Asp Trp Phe Pro Asp Leu Asp Asp
145                 150                 155                 160

Ile Arg Ala Lys Ile Thr Pro Arg Thr Arg Gly Ile Val Ile Ile Asn
                165                 170                 175

Pro Asn Asn Pro Thr Gly Ala Val Tyr Ser Lys Glu Leu Leu Met Glu
            180                 185                 190

Ile Val Glu Ile Ala Arg Gln His Asn Leu Ile Ile Phe Ala Asp Glu
        195                 200                 205

Ile Tyr Asp Lys Ile Leu Tyr Asp Asp Ala Glu His His Ser Ile Ala
    210                 215                 220

Pro Leu Ala Pro Asp Leu Leu Thr Ile Thr Phe Asn Gly Leu Ser Lys
225                 230                 235                 240

Thr Tyr Arg Val Ala Gly Phe Arg Gln Gly Trp Met Val Leu Asn Gly
                245                 250                 255

Pro Lys Lys His Ala Lys Gly Tyr Ile Glu Gly Leu Glu Met Leu Ala
            260                 265                 270

Ser Met Arg Leu Cys Ala Asn Val Pro Ala Gln His Ala Ile Gln Thr
    275                 280                 285

Ala Leu Gly Gly Tyr Gln Ser Ile Ser Glu Phe Ile Thr Pro Gly Gly
290                 295                 300

Arg Leu Tyr Glu Gln Arg Asn Arg Ala Trp Glu Leu Ile Asn Asp Ile
305                 310                 315                 320

Pro Gly Val Ser Cys Val Lys Pro Arg Gly Ala Leu Tyr Met Phe Pro
                325                 330                 335

Lys Ile Asp Ala Lys Arg Phe Asn Ile His Asp Asp Gln Lys Met Val
            340                 345                 350

Leu Asp Phe Leu Leu Gln Glu Lys Val Leu Leu Val Gln Gly Thr Ala
        355                 360                 365

Phe Asn Trp Pro Trp Pro Asp His Phe Arg Ile Val Thr Leu Pro Arg
    370                 375                 380

Val Asp Asp Ile Glu Leu Ser Leu Ser Lys Phe Ala Arg Phe Leu Ser
385                 390                 395                 400

Gly Tyr His Gln Leu
            405

<210> SEQ ID NO 241
<211> LENGTH: 975
<212> TYPE: DNA
<213> ORGANISM: Escherichia coli

<400> SEQUENCE: 241
atgaagccgt ccgttatcct ctacaaagcc ttacctgatg atttactgca acgcctgcaa     60
gagcatttca ccgttcacca ggtggcaaac ctcagcccac aaaccgtcga acaaaatgca    120 gcaattttg ccgaagctga aggtttactg ggttcaaacg agaatgtaaa tgccgcattg    180
ctggaaaaaa tgccgaaact gcgtgccaca tcaacgatct ccgtcggcta tgacaatttt    240

```
gatgtcgatg cgcttaccgc ccgaaaaatt ctgctgatgc acacgccaac cgtattaaca    300
gaaaccgtcg ccgatacgct gatggcgctg gtgttgtcta ccgctcgtcg ggttgtggag    360
gtagcagaac gggtaaaagc aggcgaatgg accgcgagca taggcccgga ctggtacggc    420
actgacgttc accataaaac actgggcatt gtcgggatgg gacggatcgg catggcgctg    480
gcacaacgtg cgcactttgg cttcaacatg cccatcctct ataacgcgcg ccgccaccat    540
aaagaagcag aagaacgctt caacgcccgc tactgcgatt tggatactct gttacaagag    600
tcagatttcg tttgcctgat cctgccgtta actgatgaga cgcatcatct gtttggcgca    660
gaacaattcg ccaaaatgaa atcctccgcc attttcatta atgccggacg tggcccggtg    720
gttgacgaaa atgcactgat cgcagcattg cagaaaggcg aaattcacgc tgccgggctg    780
gatgtcttcg aacaagagcc actgtccgta gattcgccgt tgctctcaat ggccaacgtc    840
gtcgcagtac cgcatattgg atctgccacc catgagacgc gttatggcat ggccgcctgt    900
gccgtggata atttgattga tgcgttacaa ggaaaggttg agaagaactg tgtgaatccg    960
cacgtcgcgg actaa                                                     975

<210> SEQ ID NO 242
<211> LENGTH: 324
<212> TYPE: PRT
<213> ORGANISM: Escherichia coli

<400> SEQUENCE: 242

Met Lys Pro Ser Val Ile Leu Tyr Lys Ala Leu Pro Asp Asp Leu Leu
1               5                   10                  15

Gln Arg Leu Gln Glu His Phe Thr Val His Gln Val Ala Asn Leu Ser
            20                  25                  30

Pro Gln Thr Val Glu Gln Asn Ala Ala Ile Phe Ala Glu Ala Glu Gly
        35                  40                  45

Leu Leu Gly Ser Asn Glu Asn Val Asn Ala Ala Leu Leu Glu Lys Met
    50                  55                  60

Pro Lys Leu Arg Ala Thr Ser Thr Ile Ser Val Gly Tyr Asp Asn Phe
65                  70                  75                  80

Asp Val Asp Ala Leu Thr Ala Arg Lys Ile Leu Leu Met His Thr Pro
                85                  90                  95

Thr Val Leu Thr Glu Thr Val Ala Asp Thr Leu Met Ala Leu Val Leu
            100                 105                 110

Ser Thr Ala Arg Arg Val Val Glu Val Ala Glu Arg Val Lys Ala Gly
        115                 120                 125

Glu Trp Thr Ala Ser Ile Gly Pro Asp Trp Tyr Gly Thr Asp Val His
    130                 135                 140

His Lys Thr Leu Gly Ile Val Gly Met Gly Arg Ile Gly Met Ala Leu
145                 150                 155                 160

Ala Gln Arg Ala His Phe Gly Phe Asn Met Pro Ile Leu Tyr Asn Ala
                165                 170                 175

Arg Arg His His Lys Glu Ala Glu Glu Arg Phe Asn Ala Arg Tyr Cys
            180                 185                 190

Asp Leu Asp Thr Leu Leu Gln Glu Ser Asp Phe Val Cys Leu Ile Leu
        195                 200                 205

Pro Leu Thr Asp Glu Thr His His Leu Phe Gly Ala Glu Gln Phe Ala
    210                 215                 220

Lys Met Lys Ser Ser Ala Ile Phe Ile Asn Ala Gly Arg Gly Pro Val
225                 230                 235                 240
```

```
Val Asp Glu Asn Ala Leu Ile Ala Ala Leu Gln Lys Gly Glu Ile His
                245                 250                 255

Ala Ala Gly Leu Asp Val Phe Glu Gln Glu Pro Leu Ser Val Asp Ser
            260                 265                 270

Pro Leu Leu Ser Met Ala Asn Val Val Ala Val Pro His Ile Gly Ser
        275                 280                 285

Ala Thr His Glu Thr Arg Tyr Gly Met Ala Ala Cys Ala Val Asp Asn
    290                 295                 300

Leu Ile Asp Ala Leu Gln Gly Lys Val Glu Lys Asn Cys Val Asn Pro
305                 310                 315                 320

His Val Ala Asp

<210> SEQ ID NO 243
<211> LENGTH: 1179
<212> TYPE: DNA
<213> ORGANISM: Homo sapiens

<400> SEQUENCE: 243
atggcctctc acaagctgct ggtgaccccc cccaaggccc tgctcaagcc cctctccatc      60
cccaaccagc tcctgctggg gcctggtcct tccaacctgc tcctcgcat catggcagcc      120 gggggggctgc agatgatcgg gtccatgagc aaggatatgt accagatcat ggacgagatc     180
aaggaaggca tccagtacgt gttccagacc aggaacccac tcacactggt catctctggc     240
tcgggacact gtgccctgga ggccgccctg gtcaatgtgc tggagcctgg ggactccttc     300
ctggttgggg ccaatggcat ttgggggcag cgagccgtgg acatcgggga gcgcatagga     360
gcccgagtgc acccgatgac caaggaccct ggaggccact acacactgca ggaggtggag     420
gagggcctgg cccagcacaa gccagtgctg ctgttcttaa cccacgggga gtcgtccacc     480
ggcgtgctgc agccccttga tggcttcggg aactctgcc acaggtacaa gtgcctgctc     540
ctggtggatt cggtggcatc cctgggcggg accccccttt acatgaccg gcaaggcatc     600 gacatcctgt actcgggctc ccagaaggcc ctgaacgccc tccagggac ctcgctcatc      660 tccttcagtg acaaggccaa aaagaagatg tactcccgca agacgaagcc cttctccttc    720
tacctggaca tcaagtggct ggccaacttc tggggctgtg acgaccagcc caggatgtac     780
catcacacaa tccccgtcat cagcctgtac agcctgagag agagcctggc cctcattgcg     840
gaacagggcc tggagaacag ctggcgccag caccgcgagg ccgcggcgta tctgcatggg     900
cgcctgcagg cactggggct gcagctcttc gtgaaggacc cggcgctccg gcttccaca     960 gtcaccactg tggctgtacc cgctggctat gactggagag acatcgtcag ctacgtcata    1020
gaccacttcg acattgagat catgggtggc cttgggccct ccacggggaa ggtgctgcgg    1080
atcggcctgc tgggctgcaa tgccaccccgc gagaatgtgg accgcgtgac ggaggccctg    1140
agggcggccc tgcagcactg ccccaagaag aagctgtga                           1179

<210> SEQ ID NO 244
<211> LENGTH: 392
<212> TYPE: PRT
<213> ORGANISM: Homo sapiens

<400> SEQUENCE: 244

Met Ala Ser His Lys Leu Leu Val Thr Pro Pro Lys Ala Leu Leu Lys
1               5                   10                  15

Pro Leu Ser Ile Pro Asn Gln Leu Leu Leu Gly Pro Gly Pro Ser Asn
            20                  25                  30
```

```
Leu Pro Pro Arg Ile Met Ala Ala Gly Gly Leu Gln Met Ile Gly Ser
        35                  40                  45
Met Ser Lys Asp Met Tyr Gln Ile Met Asp Glu Ile Lys Glu Gly Ile
 50                  55                  60
Gln Tyr Val Phe Gln Thr Arg Asn Pro Leu Thr Leu Val Ile Ser Gly
 65                  70                  75                  80
Ser Gly His Cys Ala Leu Glu Ala Ala Leu Val Asn Val Leu Glu Pro
                 85                  90                  95
Gly Asp Ser Phe Leu Val Gly Ala Asn Gly Ile Trp Gly Gln Arg Ala
            100                 105                 110
Val Asp Ile Gly Glu Arg Ile Gly Ala Arg Val His Pro Met Thr Lys
            115                 120                 125
Asp Pro Gly Gly His Tyr Thr Leu Gln Glu Val Glu Glu Gly Leu Ala
        130                 135                 140
Gln His Lys Pro Val Leu Leu Phe Leu Thr His Gly Glu Ser Ser Thr
145                 150                 155                 160
Gly Val Leu Gln Pro Leu Asp Gly Phe Gly Glu Leu Cys His Arg Tyr
                165                 170                 175
Lys Cys Leu Leu Leu Val Asp Ser Val Ala Ser Leu Gly Gly Thr Pro
            180                 185                 190
Leu Tyr Met Asp Arg Gln Gly Ile Asp Ile Leu Tyr Ser Gly Ser Gln
        195                 200                 205
Lys Ala Leu Asn Ala Pro Pro Gly Thr Ser Leu Ile Ser Phe Ser Asp
210                 215                 220
Lys Ala Lys Lys Lys Met Tyr Ser Arg Lys Thr Lys Pro Phe Ser Phe
225                 230                 235                 240
Tyr Leu Asp Ile Lys Trp Leu Ala Asn Phe Trp Gly Cys Asp Asp Gln
                245                 250                 255
Pro Arg Met Tyr His His Thr Ile Pro Val Ile Ser Leu Tyr Ser Leu
            260                 265                 270
Arg Glu Ser Leu Ala Leu Ile Ala Glu Gln Gly Leu Glu Asn Ser Trp
        275                 280                 285
Arg Gln His Arg Glu Ala Ala Ala Tyr Leu His Gly Arg Leu Gln Ala
290                 295                 300
Leu Gly Leu Gln Leu Phe Val Lys Asp Pro Ala Leu Arg Leu Pro Thr
305                 310                 315                 320
Val Thr Thr Val Ala Val Pro Ala Gly Tyr Asp Trp Arg Asp Ile Val
                325                 330                 335
Ser Tyr Val Ile Asp His Phe Asp Ile Glu Ile Met Gly Gly Leu Gly
            340                 345                 350
Pro Ser Thr Gly Lys Val Leu Arg Ile Gly Leu Leu Gly Cys Asn Ala
        355                 360                 365
Thr Arg Glu Asn Val Asp Arg Val Thr Glu Ala Leu Arg Ala Ala Leu
370                 375                 380
Gln His Cys Pro Lys Lys Lys Leu
385                 390
```

<210> SEQ ID NO 245
<211> LENGTH: 10
<212> TYPE: DNA
<213> ORGANISM: Escherichia coli

<400> SEQUENCE: 245
aaaaaaaaaa                                                            10

<210> SEQ ID NO 246
<211> LENGTH: 6
<212> TYPE: PRT
<213> ORGANISM: Escherichia coli

<400> SEQUENCE: 246

Leu Ala Asn Phe Trp Gly
1               5

<210> SEQ ID NO 247
<211> LENGTH: 10
<212> TYPE: DNA
<213> ORGANISM: Arabidopsis thaliana

<400> SEQUENCE: 247
aaaaaaaaaa                                                          10

<210> SEQ ID NO 248
<211> LENGTH: 5
<212> TYPE: PRT
<213> ORGANISM: Arabidopsis thaliana

<400> SEQUENCE: 248

Phe Val Lys Asp Pro
1               5

<210> SEQ ID NO 249
<211> LENGTH: 1146
<212> TYPE: DNA
<213> ORGANISM: Escherichia coli

<400> SEQUENCE: 249

| | | | | | |
|---|---|---|---|---|---|
| atgaagattg | tcattgcgcc | agactctttt | aaagagagct | taagtgcaga | aaaatgttgt | 60 |
| caggcaatta | aagccgggtt | ttcgaccctc | tttcccgatg | cgaactatat | ctgtttgccg | 120 |
| atagcggatg | gcggcgaagg | gacggtggat | gcgatggtcg | ccgcgacggg | cggcaacatc | 180 |
| gtgacgcttg | aagtctgcgg | gccgatgggc | gaaaaagtga | atgcttttta | tggccttacc | 240 |
| ggcgacggga | aaacggcggt | gattgagatg | cggcagcaa | gtggcctgat | gctggtcgcg | 300 |
| cctgaaaagc | gtaatccgtt | gctggcctcc | agttttggta | cggggagtt | aattcgtcat | 360 |
| gcgctggata | cgacattcg | ccatattatt | ctcggcattg | gcggcagtgc | gacggtcgac | 420 |
| ggcggtatgg | gcatggcgca | ggcgctcggt | gtgcgttttcc | ttgatgccga | cggtcaggcg | 480 |
| ctggcggcaa | acggtggtaa | tttagcgcgc | gtggcaagca | ttgagatgga | tgaatgcgat | 540 |
| ccgcgtctgg | cgaattgcca | tattgaagta | gcatgtgacg | ttgataaccc | gctggtaggg | 600 |
| gcacgcggcg | cggcggcggt | gtttggcccg | caaaaagggg | caacgccgga | gatggtcgaa | 660 |
| gaacttgaac | agggctgca | aaattacgcc | cgtgttttac | aacagcaaac | tgaaattaat | 720 |
| gtctgccaga | tggcgggcgg | cggcgctgcg | ggcggtatgg | gtattgcggc | ggcggtatt | 780 |
| ctcaatgcgg | atattaaacc | gggcattgaa | attgtgttga | atgcggtcaa | tcttgcgcag | 840 |
| gcagtgcagg | gcgcagcact | ggtgattacc | ggggaagggc | gcatcgactc | gcaaacggca | 900 |
| ggcggtaaag | cgccgctggg | tgtggcgtcg | gtggcgaagc | agtttaatgt | accggtgatt | 960 |
| gggattgctg | gcgtattggg | tgatggcgtg | gaagtggtgc | accagtacgg | cattgacgcg | 1020 |
| gtattcagca | ttttgcctcg | tctggcacct | ttagccgaag | tgctcgccag | cggtgaaacc | 1080 |
| aatctcttca | cagcgcgcg | aaatattgcc | tgcgccatta | aataggtca | gggaattaaa | 1140 |
| aactaa | | | | | | 1146 |

<210> SEQ ID NO 250
<211> LENGTH: 381
<212> TYPE: PRT
<213> ORGANISM: Escherichia coli

<400> SEQUENCE: 250

```
Met Lys Ile Val Ile Ala Pro Asp Ser Phe Lys Glu Ser Leu Ser Ala
1               5                   10                  15

Glu Lys Cys Cys Gln Ala Ile Lys Ala Gly Phe Ser Thr Leu Phe Pro
            20                  25                  30

Asp Ala Asn Tyr Ile Cys Leu Pro Ile Ala Asp Gly Gly Glu Gly Thr
        35                  40                  45

Val Asp Ala Met Val Ala Ala Thr Gly Gly Asn Ile Val Thr Leu Glu
    50                  55                  60

Val Cys Gly Pro Met Gly Glu Lys Val Asn Ala Phe Tyr Gly Leu Thr
65                  70                  75                  80

Gly Asp Gly Lys Thr Ala Val Ile Glu Met Ala Ala Ala Ser Gly Leu
                85                  90                  95

Met Leu Val Ala Pro Glu Lys Arg Asn Pro Leu Leu Ala Ser Ser Phe
            100                 105                 110

Gly Thr Gly Glu Leu Ile Arg His Ala Leu Asp Asn Asp Ile Arg His
        115                 120                 125

Ile Ile Leu Gly Ile Gly Gly Ser Ala Thr Val Asp Gly Gly Met Gly
    130                 135                 140

Met Ala Gln Ala Leu Gly Val Arg Phe Leu Asp Ala Asp Gly Gln Ala
145                 150                 155                 160

Leu Ala Ala Asn Gly Gly Asn Leu Ala Arg Val Ala Ser Ile Glu Met
                165                 170                 175

Asp Glu Cys Asp Pro Arg Leu Ala Asn Cys His Ile Glu Val Ala Cys
            180                 185                 190

Asp Val Asp Asn Pro Leu Val Gly Ala Arg Gly Ala Ala Ala Val Phe
        195                 200                 205

Gly Pro Gln Lys Gly Ala Thr Pro Glu Met Val Glu Glu Leu Glu Gln
    210                 215                 220

Gly Leu Gln Asn Tyr Ala Arg Val Leu Gln Gln Thr Glu Ile Asn
225                 230                 235                 240

Val Cys Gln Met Ala Gly Gly Ala Ala Gly Gly Met Gly Ile Ala
                245                 250                 255

Ala Ala Val Phe Leu Asn Ala Asp Ile Lys Pro Gly Ile Glu Ile Val
            260                 265                 270

Leu Asn Ala Val Asn Leu Ala Gln Ala Val Gln Gly Ala Ala Leu Val
        275                 280                 285

Ile Thr Gly Glu Gly Arg Ile Asp Ser Gln Thr Ala Gly Gly Lys Ala
    290                 295                 300

Pro Leu Gly Val Ala Ser Val Ala Lys Gln Phe Asn Val Pro Val Ile
305                 310                 315                 320

Gly Ile Ala Gly Val Leu Gly Asp Gly Val Glu Val Val His Gln Tyr
                325                 330                 335

Gly Ile Asp Ala Val Phe Ser Ile Leu Pro Arg Leu Ala Pro Leu Ala
            340                 345                 350

Glu Val Leu Ala Ser Gly Glu Thr Asn Leu Phe Asn Ser Ala Arg Asn
        355                 360                 365

Ile Ala Cys Ala Ile Lys Ile Gly Gln Gly Ile Lys Asn
```

```
              370            375            380
```

<210> SEQ ID NO 251
<211> LENGTH: 1146
<212> TYPE: DNA
<213> ORGANISM: Escherichia coli

<400> SEQUENCE: 251

```
atgaaaatcg taatcgcccc agactcttat aaagaaagtt tatctgccag cgaggttgcg    60
caggcgatag aaaaaggatt tcgggaaatt tttcctgatg cacagtacgt ttctgttccg   120
gttgccgacg gtggcgaagg aacggtggaa gcgatgattg cagccaccca ggggctgaa    180
cgtcacgcct gggttacagg gccgctgggc gagaaagtga atgccagttg ggggatctcc   240
ggcgatggca aaccgcgtt tattgaaatg cggcggcca gtgggctgga gctggtacct    300
gcggaaaaac gcgatccact cgtgaccact tcacgcggca caggcgagtt aatcctgcag   360
gcgctggaga gcggtgcgac aaacattatt atcggcattg cggcagcgc tacaaatgat   420
ggcggcgcag gcatggtaca ggcgctgggg gcgaaattat cgacgccaa cggcaatgaa   480
attggttttg cggcggtag tcttaatact ctgaatgata ttgatatttc cggcctcgat   540
ccgcgcttaa aagattgcgt cattcgcgtc gcttgtgatg tcaccaatcc gctggtgggc   600
gataacggcg catcgcgcat cttttggccca caaaagggag ccagtgaagc gatgattgtt   660
gagctggaca taacctctc tcactatgcc gaggtcatta aaaaagcgct gcatgttgat   720
gtgaaagatg tccccggtgc aggagctgcg ggtggtatgg gcgcggcgct aatggcgttt   780
cttggtgcgg aactgaaaag tggtattgaa atcgtcacta cggcgctgaa tctggaggaa   840
catattcacg attgtacgct ggtgatcacc ggtgaagggc gtattgacag ccagagtatt   900
cacgggaagg taccgattgg tgtcgcaaac gtggcgaaga agtaccataa accggtgatt   960
ggcattgcgg gtagcctgac cgatgatgtt ggcgttgtac atcagcatgg cattgatgcg  1020
gtcttcagcg tattgaccag cataggtacg ttggacgaag cattccgcgg ggcttatgac  1080
aatatctgcc gtgcttcacg taatatcgcc gcgacactgg cgattggaat gcgcaacgcg  1140
gggtga                                                             1146
```

<210> SEQ ID NO 252
<211> LENGTH: 381
<212> TYPE: PRT
<213> ORGANISM: Escherichia coli

<400> SEQUENCE: 252

```
Met Lys Ile Val Ile Ala Pro Asp Ser Tyr Lys Glu Ser Leu Ser Ala
1               5                   10                  15

Ser Glu Val Ala Gln Ala Ile Glu Lys Gly Phe Arg Glu Ile Phe Pro
            20                  25                  30

Asp Ala Gln Tyr Val Ser Val Pro Val Ala Asp Gly Gly Glu Gly Thr
        35                  40                  45

Val Glu Ala Met Ile Ala Ala Thr Gln Gly Ala Glu Arg His Ala Trp
    50                  55                  60

Val Thr Gly Pro Leu Gly Glu Lys Val Asn Ala Ser Trp Gly Ile Ser
65                  70                  75                  80

Gly Asp Gly Lys Thr Ala Phe Ile Glu Met Ala Ala Ala Ser Gly Leu
                85                  90                  95

Glu Leu Val Pro Ala Glu Lys Arg Asp Pro Leu Val Thr Thr Ser Arg
            100                 105                 110
```

```
Gly Thr Gly Glu Leu Ile Leu Gln Ala Leu Glu Ser Gly Ala Thr Asn
            115                 120                 125

Ile Ile Ile Gly Ile Gly Gly Ser Ala Thr Asn Asp Gly Gly Ala Gly
130                 135                 140

Met Val Gln Ala Leu Gly Ala Lys Leu Cys Asp Ala Asn Gly Asn Glu
145                 150                 155                 160

Ile Gly Phe Gly Gly Gly Ser Leu Asn Thr Leu Asn Asp Ile Asp Ile
                165                 170                 175

Ser Gly Leu Asp Pro Arg Leu Lys Asp Cys Val Ile Arg Val Ala Cys
            180                 185                 190

Asp Val Thr Asn Pro Leu Val Gly Asp Asn Gly Ala Ser Arg Ile Phe
        195                 200                 205

Gly Pro Gln Lys Gly Ala Ser Glu Ala Met Ile Val Glu Leu Asp Asn
210                 215                 220

Asn Leu Ser His Tyr Ala Glu Val Ile Lys Lys Ala Leu His Val Asp
225                 230                 235                 240

Val Lys Asp Val Pro Gly Ala Gly Ala Ala Gly Met Gly Ala Ala
                245                 250                 255

Leu Met Ala Phe Leu Gly Ala Glu Leu Lys Ser Gly Ile Glu Ile Val
                260                 265                 270

Thr Thr Ala Leu Asn Leu Glu Glu His Ile His Asp Cys Thr Leu Val
        275                 280                 285

Ile Thr Gly Glu Gly Arg Ile Asp Ser Gln Ser Ile His Gly Lys Val
        290                 295                 300

Pro Ile Gly Val Ala Asn Val Ala Lys Lys Tyr His Lys Pro Val Ile
305                 310                 315                 320

Gly Ile Ala Gly Ser Leu Thr Asp Asp Val Gly Val Val His Gln His
                325                 330                 335

Gly Ile Asp Ala Val Phe Ser Val Leu Thr Ser Ile Gly Thr Leu Asp
            340                 345                 350

Glu Ala Phe Arg Gly Ala Tyr Asp Asn Ile Cys Arg Ala Ser Arg Asn
        355                 360                 365

Ile Ala Ala Thr Leu Ala Ile Gly Met Arg Asn Ala Gly
370                 375                 380

<210> SEQ ID NO 253
<211> LENGTH: 450
<212> TYPE: DNA
<213> ORGANISM: Escherichia coli

<400> SEQUENCE: 253
atgaaaaaga ttgcatttgg ctgtgatcat gtcggtttca ttttaaaaca tgaaatagtg      60
gcacatttag ttgagcgtgg cgttgaagtg attgataaag aacctggtc gtcagagcgt      120 actgattatc cacattacgc cagtcaagtc gcactggctg ttgctggcgg agaggttgat      180
ggcgggattt tgatttgtgg tactggcgtc ggtatttcga tagcggcgaa caagtttgcc      240
ggaattcgcg cggtcgtctg tagcgaacct tattccgcgc aactttcgcg gcagcataac      300
gacaccaacg tgctggcttt tggttcacga gtggttggcc tcgaactggc aaaaatgatt      360
gtggatgcgt ggctgggcgc acagtacgaa ggcggtcgtc atcaacaacg cgtggaggcg      420
attacggcaa tagagcagcg gagaaattga                                      450

<210> SEQ ID NO 254
<211> LENGTH: 149
<212> TYPE: PRT
```

<213> ORGANISM: Escherichia coli

<400> SEQUENCE: 254

Met Lys Lys Ile Ala Phe Gly Cys Asp His Val Gly Phe Ile Leu Lys
1               5                   10                  15

His Glu Ile Val Ala His Leu Val Glu Arg Gly Val Glu Val Ile Asp
            20                  25                  30

Lys Gly Thr Trp Ser Ser Glu Arg Thr Asp Tyr Pro His Tyr Ala Ser
        35                  40                  45

Gln Val Ala Leu Ala Val Ala Gly Gly Glu Val Asp Gly Gly Ile Leu
    50                  55                  60

Ile Cys Gly Thr Gly Val Gly Ile Ser Ile Ala Ala Asn Lys Phe Ala
65                  70                  75                  80

Gly Ile Arg Ala Val Val Cys Ser Glu Pro Tyr Ser Ala Gln Leu Ser
                85                  90                  95

Arg Gln His Asn Asp Thr Asn Val Leu Ala Phe Gly Ser Arg Val Val
            100                 105                 110

Gly Leu Glu Leu Ala Lys Met Ile Val Asp Ala Trp Leu Gly Ala Gln
        115                 120                 125

Tyr Glu Gly Gly Arg His Gln Gln Arg Val Glu Ala Ile Thr Ala Ile
    130                 135                 140

Glu Gln Arg Arg Asn
145

<210> SEQ ID NO 255
<211> LENGTH: 1869
<212> TYPE: DNA
<213> ORGANISM: Saccharomyces cerevisiae PGM3

<400> SEQUENCE: 255
atgttgcaag gaattttaga accgtaccaa tctgacttga agatccgat atcattatgg     60
tttaagcaag accgcaaccc aaaaactata gaagaggtca ccgctctctg caaaaaatcc    120
gactggaatg agttacacaa agatttgat tctagaattc agtttggcac tgctggttta    180
agatcgcaaa tgcaagctgg ctttagcagg atgaatactt tagtagtcat acaagcgtct    240
cagggattgg caacttatgt aagacaacag tttccagaca atttggtagc tgttgtggga    300
cacgatcata gattccattc taaggagttc gctagagcta ctgctgctgc atttctttta    360
aaaggattta aggtacatta tttgaatcct gaccacgaat ttgttcatac ccctttagtt    420
cccttttgcag tggataagct aaaggcctcc gttggcgtaa tgataacagc aagtcacaac    480
ccaaaaatgg ataatggata taagtatac tattccaatg gatgccaaat cattccacct    540
cacgatcatg ccatctctga ttccattgac gcaaatttag aaccatgggc caatgtgtgg    600
gatttcgacg atgttctaaa taaggctctc aaacaaggga aattgatgta ttccagagaa    660
gaaatgctga gttatatttt agaggaggtt tctaaaaatc tggtagaaat caacccatta    720
aagcttgaag taaagccaa accttggttc gtttacactc caatgcatgg ggttggattt    780
gacattttca gcaccatcgt aaaaaaaaca ctgtgcctgg tagaaggtaa ggattaccta    840
tgtgttcctg aacaacaaaa tccagatcct tctttcccaa ctgttggatt tcctaaccct    900
gaagaaaaag gtgctttaga cattggtata aacttggctg aaaaacatga cattgactta    960
cttgttgcca acgaccctga cgctgataga ttctctgttg ctgttaaaga tatgcagtca   1020
ggcgaatggc gacaactaac aggtaacgaa atcggttttc tttttgcatt ttatgaatat   1080
cagaaatata aagtatgga caaagaattt cagcacgttc atccgttggc tatgttaaat   1140

-continued

```
tcaacagtgt cttcacaaat gataaaaaaa atggcagaaa tagaagggtt ccattatgag    1200
gatacattaa caggatttaa gtggatcgga atcgtgccca tactcttgga aaagaaaggc    1260
tattacgttc cttttggatt cgaggaagca ataggctaca tgtttccagc aatggagcat    1320
gataaggatg gtatcagtgc atccattgtc ttccttgcaag cctactgtaa gtggaaaata    1380
gaccacaatt tggacccgct aaatgtctta gaaatggct tcaaaaaata tggcgtgttc     1440
aaagagtaca atggctatta tgtcgttcca aatccaactg ttacaaaaga tatatttgac    1500
tacatcagga atgtctacac tcctgagggc gcgtcatatc cttcatctat tggtgaagaa    1560
atcgaagtac tttactatcg agatttaacc actggttacc aatcggatac cataaatcat    1620
aaacctactc tacccgtcga tcctacatca caaatgataa cagtatctgc tagaccaagt    1680
aacggtagtg agaatgagca tatccgcttc actattcgcg ggtccggaac agaaccaaaa    1740
cttaaagtat atattgaagc ttgcgcaaat gaagaacaaa gagcctcttt cttggcgaaa    1800
ttgacttgga atgtgctgag acgtgaatgg tttagaccag atgaaatgaa tatagttaca    1860
aaattttga                                                           1869
```

<210> SEQ ID NO 256
<211> LENGTH: 897
<212> TYPE: DNA
<213> ORGANISM: Homo sapiens cDNA khkC

<400> SEQUENCE: 256

```
atggtggaag agaagcagat cctgtgcgtg gggctagtgg tgctggacgt catcagcctg     60
gtggacaagt accctaagga ggactcggag ataaggtgtt tgtcccagag atggcagcgc    120
ggaggcaacg cgtccaactc ctgcaccgtt ctctccctgc tcggagcccc ctgtgccttc    180
atgggctcaa tggctcctgg ccatgttgct gacttcctgg tggccgactt caggcggcgg    240
ggcgtggacg tgtctcaggt ggcctggcag agcaaggggg acaccccag ctcctgctgc     300 atcatcaaca actccaatgg caaccgtacc attgtgctcc atgacacgag cctgccagat    360
gtgtctgcta cagactttga gaaggttgat ctgacccagt tcaagtggat ccacattgag    420
ggccggaacg catcggagca ggtgaagatg ctgcagcgga tagacgcaca caacaccagg    480
cagcctccag agcagaagat ccgggtgtcc gtggaggtgg agaagccacg agaggagctc    540
ttccagctgt ttggctacgg agacgtgtgt tttgtcagca agatgtggc caagcacttg    600 gggttccagt cagcagagga agccttgagg ggcttgtatg gtcgtgtgag gaaaggggct    660
gtgcttgtct gtgcctgggc tgaggagggc gccgacgccc tgggccctga tggcaaattg    720
ctccactcgg atgctttccc gccacccgc gtggtggata cactgggagc tggagacacc    780
ttcaatgcct ccgtcatctt cagcctctcc caggggagga gcgtgcagga agcactgaga    840
ttcgggtgcc aggtggccgg caagaagtgt ggcctgcagg gctttgatgg catcgtg      897
```

<210> SEQ ID NO 257
<211> LENGTH: 1419
<212> TYPE: DNA
<213> ORGANISM: Escherichia coli fucK

<400> SEQUENCE: 257

```
atgaaacaag aagttatcct ggtactcgac tgtggcgcga ccaatgtcag ggccatcgcg     60
gttaatcggc agggcaaaat tgttgcccgc gcctcaacgc ctaatgccag cgatatcgcg    120
atggaaaaca cacacctggca ccagtggtct ttagacgcca ttttgcaacg ctttgctgat    180
```

```
tgctgtcggc aaatcaatag tgaactgact gaatgccaca tccgcggtat cgccgtcacc      240
acctttggtg tggatggcgc tctggtagat aagcaaggca atctgctcta tccgattatt      300
agctggaaat gtccgcgaac agcagcggtt atggacaata ttgaacggtt aatctccgca      360
cagcggttgc aggctatttc tggcgtcgga gcctttagtt tcaatacgtt atataagttg      420
gtgtggttga agaaaatca tccacaactg ctggaacgcg cgcacgcctg gctctttatt       480
tcgtcgctga ttaaccaccg tttaaccggc gaattcacta ctgatatcac gatgccgga       540
accagccaga tgctggatat ccagcaacgc gatttcagtc gcaaatttt acaagccacc       600
ggtattccac gccgactctt ccctcgtctg gtggaagcgg gtgaacagat tggtacgcta      660
cagaacagcg ccgcagcaat gctcggctta cccgttggca taccggtgat ttccgcaggt      720
cacgataccc agttcgccct ttttggcgct ggtgctgaac aaaatgaacc cgtgctctct      780
tccggtacat gggaattttt aatggttcgc agcgcccagg ttgatacttc gctgttaagt      840
cagtacgccg gttccacctg cgaactggat agccaggcag ggttgtataa cccaggtatg      900
caatggctgg catccggcgt gctggaatgg gtgagaaaac tgttctggac ggctgaaaca      960
ccctggcaaa tgttgattga agaagctcgt ctgatcgcgc tggcgcgga tggcgtaaaa      1020
atgcagtgtg atttattgtc gtgtcagaac gctggctggc aaggagtgac gcttaatacc     1080
acgcgggggc atttctatcg cgcggcgctg aagggttaa ctgcgcaatt acagcgcaat      1140
ctacagatgc tggaaaaaat cgggcacttt aaggcctctg aattattgtt agtcggtgga     1200
ggaagtcgca acacattgtg gaatcagatt aaagccaata tgcttgatat tccggtaaaa     1260
gttctcgacg acgccgaaac gaccgtcgca ggagctgcgc tgttcggttg gtatggcgta     1320
ggggaattta acagcccgga agaagcccgc gcacagattc attatcagta ccgttatttc     1380
tacccgcaaa ctgaacctga atttatagag gaagtgtga                            1419
```

<210> SEQ ID NO 258
<211> LENGTH: 622
<212> TYPE: PRT
<213> ORGANISM: Saccharomyces cerevisiae PGM3

<400> SEQUENCE: 258

```
Met Leu Gln Gly Ile Leu Glu Thr Val Pro Ser Asp Leu Lys Asp Pro
1               5                   10                  15

Ile Ser Leu Trp Phe Lys Gln Asp Arg Asn Pro Lys Thr Ile Glu Glu
            20                  25                  30

Val Thr Ala Leu Cys Lys Lys Ser Asp Trp Asn Glu Leu His Lys Arg
        35                  40                  45

Phe Asp Ser Arg Ile Gln Phe Gly Thr Ala Gly Leu Arg Ser Gln Met
    50                  55                  60

Gln Ala Gly Phe Ser Arg Met Asn Thr Leu Val Ile Gln Ala Ser
65                  70                  75                  80

Gln Gly Leu Ala Thr Tyr Val Arg Gln Gln Phe Pro Asp Asn Leu Val
                85                  90                  95

Ala Val Val Gly His Asp His Arg Phe His Ser Lys Glu Phe Ala Arg
            100                 105                 110

Ala Thr Ala Ala Ala Phe Leu Leu Lys Gly Phe Lys Val His Tyr Leu
        115                 120                 125

Asn Pro Asp His Glu Phe Val His Thr Pro Leu Val Pro Phe Ala Val
    130                 135                 140

Asp Lys Leu Lys Ala Ser Val Gly Val Met Ile Thr Ala Ser His Asn
145                 150                 155                 160
```

```
Pro Lys Met Asp Asn Gly Tyr Lys Val Tyr Tyr Ser Asn Gly Cys Gln
                165                 170                 175

Ile Ile Pro Pro His Asp His Ala Ile Ser Asp Ser Ile Asp Ala Asn
            180                 185                 190

Leu Glu Pro Trp Ala Asn Val Trp Asp Phe Asp Val Leu Asn Lys
        195                 200                 205

Ala Leu Lys Gln Gly Lys Leu Met Tyr Ser Arg Glu Glu Met Leu Lys
    210                 215                 220

Leu Tyr Leu Glu Glu Val Ser Lys Asn Leu Val Glu Ile Asn Pro Leu
225                 230                 235                 240

Lys Leu Glu Val Lys Ala Lys Pro Trp Phe Val Tyr Thr Pro Met His
                245                 250                 255

Gly Val Gly Phe Asp Ile Phe Ser Thr Ile Val Lys Lys Thr Leu Cys
                260                 265                 270

Leu Val Glu Gly Lys Asp Tyr Leu Cys Val Pro Glu Gln Gln Asn Pro
            275                 280                 285

Asp Pro Ser Phe Pro Thr Val Gly Phe Pro Asn Pro Glu Glu Lys Gly
    290                 295                 300

Ala Leu Asp Ile Gly Ile Asn Leu Ala Glu Lys His Asp Ile Asp Leu
305                 310                 315                 320

Leu Val Ala Asn Asp Pro Asp Ala Asp Arg Phe Ser Val Ala Val Lys
                325                 330                 335

Asp Met Gln Ser Gly Glu Trp Arg Gln Leu Thr Gly Asn Glu Ile Gly
            340                 345                 350

Phe Leu Phe Ala Phe Tyr Glu Tyr Gln Lys Tyr Lys Ser Met Asp Lys
        355                 360                 365

Glu Phe Gln His Val His Pro Leu Ala Met Leu Asn Ser Thr Val Ser
    370                 375                 380

Ser Gln Met Ile Lys Lys Met Ala Glu Ile Glu Gly Phe His Tyr Glu
385                 390                 395                 400

Asp Thr Leu Thr Gly Phe Lys Trp Ile Gly Asn Arg Ala Ile Leu Leu
                405                 410                 415

Glu Lys Lys Gly Tyr Tyr Val Pro Phe Gly Phe Glu Glu Ala Ile Gly
            420                 425                 430

Tyr Met Phe Pro Ala Met Glu His Asp Lys Asp Gly Ile Ser Ala Ser
        435                 440                 445

Ile Val Phe Leu Gln Ala Tyr Cys Lys Trp Lys Ile Asp His Asn Leu
    450                 455                 460

Asp Pro Leu Asn Val Leu Glu Asn Gly Phe Lys Lys Tyr Gly Val Phe
465                 470                 475                 480

Lys Glu Tyr Asn Gly Tyr Tyr Val Val Pro Asn Pro Thr Val Thr Lys
                485                 490                 495

Asp Ile Phe Asp Tyr Ile Arg Asn Val Tyr Thr Pro Glu Gly Ala Ser
            500                 505                 510

Tyr Pro Ser Ser Ile Gly Glu Ile Glu Val Leu Tyr Tyr Arg Asp
        515                 520                 525

Leu Thr Thr Gly Tyr Gln Ser Asp Thr Ile Asn His Lys Pro Thr Leu
    530                 535                 540

Pro Val Asp Pro Thr Ser Gln Met Ile Thr Val Ser Ala Arg Pro Ser
545                 550                 555                 560

Asn Gly Ser Glu Asn Glu His Ile Arg Phe Thr Ile Arg Gly Ser Gly
                565                 570                 575
```

-continued

```
Thr Glu Pro Lys Leu Lys Val Tyr Ile Glu Ala Cys Ala Asn Glu Glu
            580                 585                 590

Gln Arg Ala Ser Phe Leu Ala Lys Leu Thr Trp Asn Val Leu Arg Arg
        595                 600                 605

Glu Trp Phe Arg Pro Asp Glu Met Asn Ile Val Thr Lys Phe
    610                 615                 620
```

MICROORGANISMS AND METHODS FOR THE PRODUCTION OF OXYGENATED COMPOUNDS FROM HEXOSES

CROSS-REFERENCE TO RELATED APPLICATIONS

This application claims priority to U.S. Provisional Application No. 62/808,247 filed Feb. 20, 2019, entitled "MICROORGANISMS AND METHODS FOR THE PRODUCTION OF OXYGENATED COMPOUNDS FROM HEXOSES", the disclosures of which are incorporated by reference herein.

TECHNICAL FIELD

This application relates to recombinant microorganisms useful in the biosynthesis of monoethylene glycol or monoethylene glycol and one or more co-product from one or more hexose feedstock. This application additionally relates to recombinant microorganisms useful in the biosynthesis of glycolic acid or glycolic acid and one or more co-product from one or more hexose feedstock. The application further relates to methods of producing monoethylene glycol or monoethylene glycol and one or more co-product from one or more hexose feedstock using the recombinant microorganisms, as well as methods of producing glycolic acid or glycolic acid and one or more co-product from one or more hexose feedstock using the recombinant microorganisms. The application further relates to compositions comprising one or more of these compounds and/or the recombinant microorganisms.

STATEMENT REGARDING SEQUENCE LISTING

The Sequence Listing associated with this application is provided in text format in lieu of a paper copy, and is hereby incorporated by reference into the specification. The name of the text file containing the Sequence Listing is BRSK-004_02US_ST25.txt. The text file is about 616 KB, was created on Feb. 18, 2020, and is being submitted electronically via EFS-Web.

BACKGROUND

A large number of chemical compounds are currently derived from petrochemicals. Compounds such as monoethylene glycol (MEG), glycolic acid, acetone, isopropanol (IPA), propene, serine, glycine, monoethanolamine, and ethylenediamine are valuable as raw material in the production of products like polyethylene terephthalate (PET) resins (from MEG), plastic polypropylene (from propene), polyglycolic acid and other biocompatible copolymers (from glycolic acid) and polyurethane fibers (from ethylenediamine). Alkenes (such as ethylene, propylene, different butenes, and pentenes, for example) are used in the plastics industry, fuels, and in other areas of the chemical industry. For example, isobutene is a small, highly reactive molecule that is used extensively as a platform chemical to manufacture a wide variety of products including fuel additives, rubber and rubber additives, and specialty chemicals.

However, the compounds are currently produced from precursors that originate from fossil fuels, which contribute to climate change. To develop more environmentally friendly processes for the production of MEG, researchers have engineered microorganisms with biosynthetic pathways to produce MEG. However, these pathways are challenging to implement, with loss of product yield, redox balance and excess biomass formation being some major obstacles to overcome.

Thus there exists a need for improved biosynthesis pathways for the production of MEG and other chemical compounds useful in industrial and pharmaceutical applications.

SUMMARY OF THE DISCLOSURE

The present application relates to recombinant microorganisms having one or more biosynthesis pathways for the production of monoethylene glycol (MEG) or glycolic acid (GA), or optionally, MEG (or GA) and one or more co-product from one or more hexose feedstock.

The recombinant microorganisms and methods of the present disclosure combine the advantages of glucose based, fermentative MEG production and xylose based, fermentative MEG production. In some embodiments, the recombinant microorganisms and methods of the present disclosure combine the advantages of xylose degradation biochemistry for high yielding MEG (or GA), or optionally, MEG (or GA) and one or more co-product, formation with the advantages of readily available pure hexose sugar feedstocks.

In some embodiments, the recombinant microorganisms and methods of the present disclosure solves the problem of xylose feedstock availability. In some embodiments, the recombinant microorganisms and methods of the present disclosure solves the problem of non-affordable xylose feedstock price. In some embodiments, the recombinant microorganisms and methods of the present disclosure solves the problem of xylose feedstock impurities. In some embodiments, the recombinant microorganisms and methods of the present disclosure solves the problem of inefficient xylose uptake by a microorganism. In some embodiments, the recombinant microorganisms and methods of the present disclosure solves the problem of glucose induced inhibition of xylose utilization. In some embodiments, the recombinant microorganisms and methods of the present disclosure solves the problem of a shortage of ATP in MEG (or GA) production pathways. In some embodiments, the recombinant microorganisms and methods of the present disclosure solves the problem of excess NADH in MEG (or GA) production pathways. In some embodiments, the recombinant microorganisms and methods of the present disclosure solves the problem of low overall product yield potential.

In some embodiments, the recombinant microorganisms and methods of the present disclosure provide a lossless conversion of one or more hexose feedstock to one or more pentose-5-phosphate intermediate. In some embodiments, the one or more pentose-5-phosphate intermediate is used for the production of MEG (or GA), or optionally, MEG (or GA) and one or more co-product, by one or more xylose based fermentation methods. In some embodiments, glucose flux is funneled into the pentose phosphate pathway instead of the glycolysis pathway.

In one aspect, the present disclosure provides a recombinant microorganism comprising one or more biochemical pathway that produces monoethylene glycol (MEG) (or glycolic acid) from one or more hexose feedstock via one or more pentose-5-phosphate intermediate. In one embodiment, one or more co-product is co-produced with MEG (or glycolic acid). In another embodiment, the one or more pentose-5-phosphate intermediate is one or more of D-xylulose-5-phosphate, D-ribulose-5-phosphate or D-ribose-5-phosphate.

Therefore, in one embodiment, the application relates to a recombinant microorganism comprising one or more biochemical pathway comprising the expression of at least one enzyme having an activity that converts one or more hexose feedstock in a lossless conversion to one or more pentose-5-phosphate intermediate.

In some embodiments, the recombinant microorganism comprises the expression of at least one enzyme having transketolase activity. In some embodiments, the enzyme having transketolase activity is encoded by an amino acid sequence having at least 70% sequence identity, at least 80% sequence identity, or at least 90% sequence identity to tktA from *E. coli*. In other embodiments, the enzyme having transketolase activity is tktA from *E. coli*. In some embodiments, the enzyme having transketolase activity is encoded by an amino acid sequence having at least 70% sequence identity at least 80% sequence identity, or at least 90% sequence identity to tktB from *E. coli*. In other embodiments, the enzyme having transketolase activity is tktB from *E. coli*. In another embodiment, the one or more nucleic acid molecules encoding the enzyme having transketolase activity comprises an amino acid sequence selected from the group consisting of SEQ ID NOs: 148 and 150. In some embodiments, the one or more nucleic acid molecules encoding the enzyme having transketolase activity is tktA, or homolog thereof. In some embodiments, the one or more nucleic acid molecules encoding the enzyme having transketolase activity is tktB, or homolog thereof. In a further embodiment, the one or more nucleic acid molecule encoding the enzyme having transketolase activity is encoded by a nucleic acid sequence selected from the group consisting of SEQ ID NOs: 147 and 149.

In some embodiments, the recombinant microorganism comprises the expression of at least one enzyme having transaldolase activity. In some embodiments, the enzyme having transaldolase activity is encoded by an amino acid sequence having at least 70% sequence identity, at least 80% sequence identity, or at least 90% sequence identity to talA or talB from *E. coli*. In some embodiments, the enzyme having transaldolase activity is talA from *E. coli*. In other embodiments, the enzyme having transaldolase activity is talB from *E. coli*. In another embodiment, the one or more nucleic acid molecules encoding the enzyme having transaldolase activity comprises an amino acid sequence selected from the group consisting of SEQ ID NOs: 152 and 154. In a further embodiment, the one or more nucleic acid molecule encoding the enzyme having transaldolase activity is encoded by a nucleic acid sequence selected from the group consisting of SEQ ID NOs: 151 and 153.

In some embodiments, the recombinant microorganism comprises the expression of at least one enzyme having ribulose-5-phosphate 3-epimerase activity. In some embodiments, the enzyme having ribulose-5-phosphate 3-epimerase activity is encoded by an amino acid sequence having at least 70% sequence identity, at least 80% sequence identity, or at least 90% sequence identity to rpe from *E. coli*. In other embodiments, the enzyme having ribulose-5-phosphate 3-epimerase activity is rpe from *E. coli*. In another embodiment, the one or more nucleic acid molecules encoding the enzyme having ribulose-5-phosphate 3-epimerase activity comprise an amino acid sequence set forth in SEQ ID NO: 158. In a further embodiment, the one or more nucleic acid molecule encoding the enzyme having ribulose-5-phosphate 3-epimerase activity is encoded by a nucleic acid sequence set forth in SEQ ID NO: 157.

In some embodiments, the recombinant microorganism comprises the expression of at least one enzyme having ribose-5-phosphate isomerase activity. In some embodiments, the enzyme having ribose-5-phosphate isomerase activity is encoded by an amino acid sequence having at least 70% sequence identity, at least 80% sequence identity, or at least 90% sequence identity to rpiA from *E. coli*. In other embodiments, the enzyme having ribose-5-phosphate isomerase activity is rpiA from *E. coli*. In other embodiments, the enzyme having ribose-5-phosphate isomerase activity is encoded by an amino acid sequence having at least 70% sequence identity, at least 80% sequence identity, or at least 90% sequence identity to rpiB from *E. coli*. In other embodiments, the enzyme having ribose-5-phosphate isomerase activity is rpiB from *E. coli*. In another embodiment, the one or more nucleic acid molecules encoding enzyme having ribose-5-phosphate isomerase activity comprise an amino acid sequence set forth in SEQ ID NO: 156. In a further embodiment, the one or more nucleic acid molecule encoding the enzyme having ribose-5-phosphate isomerase activity is encoded by a nucleic acid sequence set forth in SEQ ID NO: 155.

In some embodiments, the recombinant microorganism comprises the expression of at least one enzyme having a transketolase activity, a transaldolase activity, a ribulose-5-phosphate 3-epimerase activity, and a ribose-5-phosphate isomerase activity. In other embodiments, the recombinant microorganism further comprises a deleted or diminished activity in one or more endogenous enzymes selected from glyceraldehyde 3-phosphate dehydrogenase, phosphoglycerate kinase and phosphoglycerate mutase. In some embodiments, the endogenous glyceraldehyde 3-phosphate dehydrogenase enzyme is gapA, the phosphoglycerate kinase is pgk and the phosphoglycerate mutase is gpmA and/or gpmM.

In some embodiments, the recombinant microorganism comprises the expression of at least one enzyme having fructose-6-phosphate phosphoketolase activity. In some embodiments, an enzyme having fructose-6-phosphate phosphoketolase activity is encoded by an amino acid sequence having at least 70% sequence identity, at least 80% sequence identity, or at least 90% sequence identity to an enzyme having fructose-6-phosphate phosphoketolase activity selected from the group consisting of *Bifidobacterium dentium* BDP_1006, *Bifidobacterium lactis* xfp, *Lactobacillus paraplantarum* xpkA and *Bifidobacterium breve* xfp. In a preferred embodiment, an enzyme having fructose-6-phosphate phosphoketolase activity is selected from the group consisting of *Bifidobacterium dentium* BDP_1006, *Bifidobacterium lactis* xfp, *Lactobacillus paraplantarum* xpkA and *Bifidobacterium breve* xfp. In another embodiment, the one or more nucleic acid molecules encoding the enzyme having fructose-6-phosphate phosphoketolase activity comprise an amino acid sequence selected from the group consisting of SEQ ID NOs: 212, 214, 216 and 218. In a further embodiment, the one or more nucleic acid molecule encoding the enzyme having fructose-6-phosphate phosphoketolase activity is encoded by a nucleic acid sequence selected from the group consisting of SEQ ID NOs: 211, 213, 215 and 217.

In some embodiments, the recombinant microorganism comprises the expression of at least one enzyme having phosphate acetyltransferase activity. In some embodiments, an enzyme having phosphate acetyltransferase activity is encoded by an amino acid sequence having at least 70% sequence identity, at least 80% sequence identity, or at least 90% sequence identity to an enzyme having phosphate acetyltransferase activity selected from *E. coli* pta and *Clostridium acetobutylicum* pta. In a preferred embodiment, an enzyme having phosphate acetyltransferase activity is selected from *E. coli* pta and *Clostridium acetobutylicum* pta. In another embodiment, the one or more nucleic acid molecules encoding the enzyme having phosphate acetyltransferase activity comprise an amino acid sequence selected from SEQ ID NOs: 220 and 222. In a further embodiment, the one or more nucleic acid molecule encoding the enzyme having phosphate acetyltransferase activity is encoded by a nucleic acid sequence selected from SEQ ID NOs: 219 and 221.

In some embodiments, the recombinant microorganism comprises the expression of at least one enzyme having a fructose-6-phosphate phosphoketolase activity, a phosphate acetyltransferase activity, a transketolase activity, a transaldolase activity, a ribulose-5-phosphate 3-epimerase activity, and a ribose-5-phosphate isomerase activity. In other embodiments, the recombinant microorganism further comprises a deleted or diminished activity in an endogenous 6-phosphofructokinase enzyme. In some embodiments, the endogenous 6-phosphofructokinase enzyme is pfkA and/or pfkB.

In another embodiment, the one or more pentose-5-phosphate intermediate produced in the lossless conversion of one or more hexose feedstock can be connected with any one of the known C2 MEG or glycolic acid production pathways by conversion of the one or more pentose-5-phosphate intermediate to one or more pentose and/or pentose-1-phosphate intermediate. In some embodiments, the recombinant microorganism comprises the expression of at least one enzyme having a pentose phosphatase activity, an arabitol phosphate dehydrogenase activity, and/or a phosphopentomutase activity. In some embodiments, the phosphopentomutase is (Pgm3). In some embodiments, the phosphopentosemutase is Pgm3 from *Saccharomyces cerevisiae*. In some embodiments, the phosphopentosemutase is encoded by an aminoacid sequence having at least 70% sequence identity, at least 80% sequence identity or at least 90% sequence identity to the Pgm3 from *Saccharomyces cerevisiae*.

In some embodiments, the recombinant microorganism comprises the expression of at least one enzyme having pentose phosphatase activity. In other embodiments, the at least one enzyme having pentose phosphatase activity is selected from one or more of an enzyme having D-pentose-5-phosphatase activity, an enzyme having D-xylulose-5-phosphatase activity, an enzyme having D-ribose-5-phosphatase activity, and an enzyme having D-ribulose-5-phosphatase activity. In some embodiments, the pentose phosphatase is encoded by an amino acid sequence having at least 70% sequence identity, at least 80% sequence identity, or at least 90% sequence identity to a D-pentose-5-phosphatase selected from the group consisting of *E. coli* phoA, *E. coli* yfbT and *E. coli* yidA. In some embodiments, the enzyme having D-xylulose-5-phosphatase activity is encoded by an amino acid sequence having at least 70% sequence identity, at least 80% sequence identity, or at least 90% sequence identity to *Bacillus subtilis* araL. In some embodiments, the enzyme having D-ribose-5-phosphatase activity is encoded by an amino acid sequence having at least 70% sequence identity, at least 80% sequence identity, or at least 90% sequence identity to an enzyme having D-ribose-5-phosphatase activity selected from the group consisting of *Arabidopsis thaliana* SGPP, *Pseudomonas fluorescens* PFLU_2693, and *E. coli* ybiV. In some embodiments, the enzyme having D-ribulose-5-phosphatase activity is encoded by an amino acid sequence having at least 70% sequence identity, at least 80% sequence identity, or at least 90% sequence identity to *Plasmodium falciparum* PF10_0325. In some embodiments, the one or more nucleic acid molecules encoding the enzyme having D-pentose-5-phosphatase activity is selected from the group consisting of SEQ ID NOs: 159, 161, 163, 165, 167, 169, 171 and 173. In another embodiment, the one or more nucleic acid molecules encoding the enzyme having D-pentose-5-phosphatase activity comprise an amino acid sequence selected from the group consisting of SEQ ID NOs: 160, 162, 164, 166, 168, 170, 172 and 174.

In some embodiments, the recombinant microorganism comprises the expression of at least one enzyme having arabitol phosphate dehydrogenase activity. In some embodiments, the enzyme having arabitol phosphate dehydrogenase activity is selected from one or more of an enzyme having D-arabitol 1-phosphate 4-dehydrogenase activity, an enzyme having D-arabitol 5-phosphate 2-dehydrogenase activity, an enzyme having D-arabitol 1-phosphate 2-dehydrogenase activity and an enzyme having D-arabitol 5-phosphate 4-dehydrogenase activity.

In some embodiments, an enzyme having D-arabitol 1-phosphate 4-dehydrogenase activity is encoded by an amino acid sequence having at least 70% sequence identity, at least 80% sequence identity, or at least 90% sequence identity to APDH from *Enterococcus avium*. In a preferred embodiment, an enzyme having D-arabitol 1-phosphate 4-dehydrogenase activity is APDH from *Enterococcus avium*. In some embodiments, the one or more nucleic acid molecules encoding an enzyme having D-arabitol 1-phosphate 4-dehydrogenase activity is set forth in SEQ ID NO: 175. In another embodiment, the one or more nucleic acid molecules encoding an enzyme having D-arabitol 1-phosphate 4-dehydrogenase activity comprise an amino acid sequence set forth in SEQ ID NO: 176.

In some embodiments, an enzyme having D-arabitol 5-phosphate 2-dehydrogenase activity is encoded by an amino acid sequence having at least 70% sequence identity, at least 80% sequence identity, or at least 90% sequence identity to APDH from *Enterococcus avium*. In a preferred embodiment, an enzyme having D-arabitol 5-phosphate 2-dehydrogenase activity is APDH from *Enterococcus avium*. In some embodiments, the one or more nucleic acid molecules encoding an enzyme having D-arabitol 5-phosphate 2-dehydrogenase activity is set forth in SEQ ID NO: 175. In another embodiment, the one or more nucleic acid molecules encoding an enzyme having D-arabitol 5-phosphate 2-dehydrogenase activity comprise an amino acid sequence set forth in SEQ ID NO: 176.

In some embodiments, an enzyme having D-arabitol 1-phosphate 2-dehydrogenase activity is encoded by an amino acid sequence having at least 70% sequence identity, at least 80% sequence identity, or at least 90% sequence identity to an enzyme having D-arabitol 1-phosphate 2-dehydrogenase activity selected from the group consisting of *Candida albicans* ARD1, *Candida tropicalis* ARD1, *Scheffersomyces stipitis* ARDH, *Bacillus subtilis* egsA (araM), *Aeropyrum pernix* egsA, *E. coli* gpsA and *Saccharomyces cerevisiae* GPD1. In a preferred embodiment, an enzyme having D-arabitol 1-phosphate 2-dehydrogenase activity is selected from the group consisting of *Candida albicans* ARD1, *Candida tropicalis* ARD1, *Scheffersomyces stipitis* ARDH, *Bacillus subtilis* egsA (araM), *Aeropyrum pernix* egsA, *E. coli* gpsA and *Saccharomyces cerevisiae* GPD1. In some embodiments, the one or more nucleic acid molecules encoding an enzyme having D-arabitol 1-phosphate 2-dehydrogenase activity is selected from the group consisting of SEQ ID NOs: 177, 179, 181, 189, 191, 193 and 195. In another embodiment, the one or more nucleic acid molecules encoding an enzyme having D-arabitol 1-phosphate 2-dehydrogenase activity comprise an amino acid sequence selected from the group consisting of SEQ ID NOs: 178, 180, 182, 190, 192, 194 and 196.

In some embodiments, an enzyme having D-arabitol 5-phosphate 4-dehydrogenase activity is encoded by an amino acid sequence having at least 70% sequence identity, at least 80% sequence identity, or at least 90% sequence identity to an enzyme having D-arabitol 5-phosphate 4-dehydrogenase activity selected from the group consisting of *Pseudomonas fluorescens* mtlD, *Klebsiella pneumoniae* dalD, *Ralstonia solanacearum* dalD, *Bacillus subtilis* egsA (araM), *Aeropyrum pernix* egsA, *E. coli* gpsA and *Saccharomyces cerevisiae* GPD1. In a preferred embodiment, an enzyme having D-arabitol 5-phosphate 4-dehydrogenase activity is selected from the group consisting of *Pseudomonas fluorescens* mtlD, *Klebsiella pneumoniae* dalD, *Ralstonia solanacearum* dalD, *Bacillus subtilis* egsA (araM), *Aeropyrum pernix* egsA, *E. coli* gpsA and *Saccharomyces cerevisiae* GPD1. In some embodiments, the one or more nucleic acid molecules encoding an enzyme having D-arabitol 5-phosphate 4-dehydrogenase activity is selected from the group consisting of SEQ ID NOs: 183, 185, 187, 189, 191, 193 and 195. In another embodiment, the one or more nucleic acid molecules encoding an enzyme having D-arabitol 5-phosphate 4-dehydrogenase activity comprise an amino acid sequence selected from the group consisting of SEQ ID NOs: 184, 186, 188, 190, 192, 194 and 196.

In some embodiments, the recombinant microorganism comprises the expression of at least one enzyme having phosphopentomutase activity. In some embodiments, an enzyme having phosphopentomutase activity is encoded by an amino acid sequence having at least 70% sequence identity, at least 80% sequence identity, or at least 90% sequence identity to an enzyme having phosphopentomutase activity selected from the group consisting of *E. coli* deoB, *E. coli* pgm, *Bacillus subtilis* pgcA, *Lactococcus lactis* pgmB, *E. coli* ycjU, *Pseudomonas aeruginosa* algC, and *E. coli* cpsG. In a preferred embodiment, an enzyme having phosphopentomutase activity is selected from the group consisting of *E. coli* deoB, *E. coli* pgm, *Bacillus subtilis* pgcA, *Lactococcus lactis* pgmB, *E. coli* ycjU, *Pseudomonas aeruginosa* algC, and *E. coli* cpsG. In some embodiments, the one or more nucleic acid molecules encoding an enzyme having phosphopentomutase activity is selected from the group consisting of SEQ ID NOs: 197, 199, 201, 203, 205, 207 and 209. In another embodiment, the one or more nucleic acid molecules encoding an enzyme having phosphopentomutase activity comprise an amino acid sequence selected from the group consisting of SEQ ID NOs: 198, 200, 202, 204, 206, 208 and 210.

In some embodiments of any of the recombinant microorganisms described above, the recombinant microorganism further comprises a diminished activity in one or more endogenous enzymes selected from glucose 6-phosphate-1-dehydrogenase, 6-phosphogluconolactonase, and 6-phosphogluconate dehydrogenase. In further embodiments, the glucose 6-phosphate-1-dehydrogenase is zwf, the 6-phosphogluconolactonase is pgl, and the 6-phosphogluconate dehydrogenase is gnd.

In some embodiments, the application provides for a recombinant microorganism that co-produces MEG (or glycolic acid) and one or more co-product selected from acetone, isopropanol, propene, isobutene and one or more serine pathway compounds. In some preferred embodiments, the one or more serine pathway compounds is selected from serine, glycine, monoethanolamine (MEA) and ethylenediamine (EDA).

In some embodiments, the one or more hexose feedstock is selected from glucose or oligomers of glucose thereof. In other embodiments, the oligomers of glucose are selected from fructose, sucrose, starch, cellobiose, maltose, lactose and cellulose.

In some embodiments, the expression of an enzyme having transketolase activity or an enzyme having fructose-6-phosphate phosphoketolase activity in the recombinant microorganism enables a lossless conversion of one or more hexose feedstock to one or more pentose-5-phosphate intermediate.

In some embodiments, the recombinant microorganism produces MEG or glycolic acid (GA) through the conversion of glycolaldehyde in a C2 pathway and through the conversion of dihydroxyacetone phosphate (DHAP) or pyruvate in a C3 pathway. In other embodiments, the glycolaldehyde is oxidized to glycolic acid by a glycolaldehyde dehydrogenase.

In some embodiments, the at least one enzyme for the production of MEG or GA through the conversion of DHAP or pyruvate in a C3 pathway are selected from at least one enzyme having an activity selected from a 3-phosphoglycerate dehydrogenase activity, a phosphoserine aminotransferase activity, a 3-phosphohydroxypyruvate phosphatase activity, a phosphoserine phosphatase activity, a serine transaminase activity, a hydroxypyruvate decarboxylase activity, a 3-phosphohydroxypyruvate reductase activity, a glycolaldehyde reductase activity, a glycolaldehyde dehydrogenase activity, a serine oxidoreductase (deaminating) or serine-pyruvate aminotransferase activity, a serine decarboxylase activity, an ethanolamine aminotransferase or ethanolamine oxidoreductase (deaminating) activity, a glycerate decarboxylase activity, a hydroxypyruvate reductase activity, a 3-phosphoglycerate phosphatase activity, a 2-phosphoglycerate phosphatase activity, a glycerate 3-kinase activity, and a glycerate 2-kinase activity.

In some embodiments, the recombinant microorganism produces MEG or glycolic acid (GA) through the conversion of glycolaldehyde in a C2 pathway and produces one or more co-product through the conversion of dihydroxyacetone phosphate (DHAP) or pyruvate in a C3 pathway. In other embodiments, the one or more co-product is selected from acetone, isopropanol, propene, isobutene and one or more serine pathway compounds. In some preferred embodiments, the one or more serine pathway compounds is selected from serine, glycine, monoethanolamine (MEA) and ethylenediamine (EDA).

In some embodiments, the at least one enzyme for the production of one or more co-product through the conversion of DHAP or pyruvate in a C3 pathway are selected from at least one enzyme having an activity selected from a thiolase or acetyl coenzyme A acetyltransferase activity, an acetyl-CoA:acetoacetate transferase or acetate:acetoacetyl-CoA hydrolase activity, and an acetoacetate decarboxylase activity, and the one or more co-product comprises acetone.

In some embodiments, the at least one enzyme for the production of one or more co-product through the conversion of DHAP or pyruvate in a C3 pathway are selected from at least one enzyme having an activity selected from a thiolase or acetyl coenzyme A acetyltransferase activity, an acetyl-CoA:acetoacetate transferase or acetate:acetoacetyl-CoA hydrolase activity, an acetoacetate decarboxylase activity, and a secondary alcohol dehydrogenase activity, and the one or more co-product comprises isopropanol.

In some embodiments, the at least one enzyme for the production of one or more co-product through the conversion of DHAP or pyruvate in a C3 pathway are selected from at least one enzyme having an activity selected from a thiolase or acetyl coenzyme A acetyltransferase activity, an acetyl-CoA:acetoacetate transferase or acetate:acetoacetyl-CoA hydrolase activity, an acetoacetate decarboxylase activity, a secondary alcohol dehydrogenase activity, and a dehydratase activity, and the one or more co-product comprises propene.

In some embodiments, the at least one enzyme for the production of one or more co-product through the conversion of DHAP or pyruvate in a C3 pathway are selected from at least one enzyme having an activity selected from a thiolase or acetyl coenzyme A acetyltransferase activity, an acetyl-CoA:acetoacetate transferase or acetate:acetoacetyl-CoA hydrolase activity, an acetoacetate decarboxylase activity, a 3-hydroxyisovalerate (3HIV) synthase activity, a hydroxymethylglutaryl-CoA synthase activity, a methylglutaconyl-CoA hydratase activity, a methylcrotonyl-CoA carboxylase activity, a methylcrotonyl-CoA hydratase activity, a 3-hydroxyisovaleryl-CoA thioesterase activity, a 3HIV kinase activity, a 3HIV-3-phosphate decarboxylase activity, and a 3HIV decarboxylase activity, and the one or more co-product comprises isobutene.

In some embodiments, the at least one enzyme for the production of one or more co-product through the conversion of DHAP or pyruvate in a C3 pathway are selected from at least one enzyme having an activity selected from a 3-phosphoglycerate dehydrogenase activity, a phosphoserine aminotransferase activity, a 3-phosphohydroxypyruvate phosphatase activity, a phosphoserine phosphatase activity, a serine oxidoreductase (deaminating) or serine-pyruvate aminotransferase activity, a hydroxypyruvate reductase activity, a 3-phosphoglycerate phosphatase activity, a 2-phosphoglycerate phosphatase activity, a glycerate 3-kinase activity, and a glycerate 2-kinase activity, and wherein the one or more co-product comprises L-serine.

In some embodiments, the at least one enzyme for the production of one or more co-product through the conversion of DHAP or pyruvate in a C3 pathway are selected from at least one enzyme having an activity selected from a serine hydroxymethyltransferase activity, a transferase activity, a formaldehyde dehydrogenase activity, a formate dehydrogenase activity, an activity associated with glycine cleavage system, a 3-phosphoglycerate dehydrogenase activity, a phosphoserine aminotransferase activity, a 3-phosphohydroxypyruvate phosphatase activity, a phosphoserine phosphatase activity, a serine transaminase activity, a hydroxypyruvate decarboxylase activity, a serine oxidoreductase (deaminating) activity, a serine decarboxylase activity, an ethanolamine aminotransferase or ethanolamine oxidoreductase (deaminating) activity, a hydroxypyruvate reductase activity, a 3-phosphoglycerate phosphatase activity, a 2-phosphoglycerate phosphatase activity, a glycerate 3-kinase activity, a glycerate 2-kinase activity, a glycolaldehyde dehydrogenase activity, a glycolate dehydrogenase activity, an alanine-glyoxylate aminotransferase activity, an alanine transaminase activity, an NAD(P)H dependent glutamate dehydrogenase activity, and wherein the one or more co-product comprises glycine. In another embodiment, the activity associated with glycine cleavage system comprise an enzyme or protein selected from a glycine decarboxylase (P protein), an aminomethyltransferase (T protein), a dihydrolipoamide dehydrogenase (L protein), and an H protein.

In some embodiments, the at least one enzyme for the production of one or more co-product through the conversion of DHAP or pyruvate in a C3 pathway are selected from at least one enzyme having an activity selected from a 3-phosphoglycerate dehydrogenase activity, a phosphoserine aminotransferase activity, a 3-phosphohydroxypyruvate phosphatase activity, a phosphoserine phosphatase activity, a transaminase activity, a hydroxypyruvate decarboxylase activity, a serine oxidoreductase (deaminating) or serine-pyruvate aminotransferase activity, a serine decarboxylase activity, a hydroxypyruvate reductase activity, a 3-phosphoglycerate phosphatase activity, a 2-phosphoglycerate phosphatase activity, a glycerate 3-kinase activity, a glycerate 2-kinase activity, an acetaldehyde dehydrogenase activity, and an ethanolamine ammonia lyase activity, and the one or more co-product comprises monoethanolamine (MEA).

In some embodiments, the at least one enzyme for the production of one or more co-product through the conversion of DHAP or pyruvate in a C3 pathway are selected from at least one enzyme having an activity selected from a serine dehydrogenase activity, a 2-aminomalonate semialdehyde decarboxylase activity, an aminoacetaldehyde transaminase activity, a 2-aminomalonate semialdehyde transaminase activity, a 2,3-diaminopropanoate decarboxylase activity, a serine decarboxylase activity, an ethanolamine dehydrogenase activity, a serine hydroxymethyltransferase activity, an aldehyde oxidase activity, an N-acetyl transferase or O-acetyl transferase activity, an N-acetylserine dehydrogenase activity, a transaminase activity, a deacetylase activity, a serine aminase activity, and a 2,3-diaminopropanoate ammonia lyase activity, and the one or more co-product comprises ethylenediamine (EDA).

In some embodiments, the at least one enzyme for the production of MEG or GA from glycolaldehyde in a C2 pathway are selected from at least one enzyme having an activity selected from a D-tagatose 3-epimerase activity, a D-ribulokinase activity, a D-ribulose-1-phosphate aldolase activity, a D-xylulose 1-kinase activity, a D-xylulose-1-phosphate aldolase activity, a xylose reductase or aldose reductase activity, a xylitol dehydrogenase activity, a xylose isomerase activity, a xylose dehydrogenase activity, a xylonolactonase activity, a xylonate dehydrogenase activity, a 2-keto-3-deoxy-D-pentonate aldolase activity, a glycolaldehyde reductase activity and a glycolaldehyde dehydrogenase activity. In some embodiments, the enzyme having D-xylulose-1-phosphate aldolase activity is aldoB. In some embodiments, the enzyme having D-ribulose-1-phosphate aldolase activity is fucA.

In some embodiments of any of the recombinant microorganisms described above, the recombinant microorganism further comprises one or more modifications to diminish or delete activity in a glycolaldehyde dehydrogenase, a lactate dehydrogenase, a xylose isomerase, a xylulose kinase or combination thereof.

In one embodiment, at least a portion of the excess NADH produced in the C3 pathway is used as a source of reducing equivalents in the C2 pathway. In another embodiment, at least a portion of the excess NADH produced in the C3 pathway is used to produce ATP.

In one embodiment, excess biomass formation is minimized and production of MEG (or glycolic acid) or MEG (or glycolic acid) and one or more co-products is maximized.

In another aspect, the application provides for a method of producing MEG or glycolic acid (GA) using a recombinant microorganism of any of the above embodiments, wherein the method comprises cultivating the recombinant microorganism in a culture medium containing one or more hexose feedstock providing a carbon source until the MEG or GA is produced. In some embodiments, one or more co-product is co-produced with MEG or GA. In further embodiments, the one or more co-product is selected from acetone, isopropanol, propene, isobutene and one or more serine pathway compound. In yet further embodiments, the one or more serine pathway compound is selected from serine, glycine, monoethanolamine (MEA) and ethylenediamine (EDA).

In yet another aspect, a method of producing a recombinant microorganism that produces or accumulates MEG or glycolic acid (GA) from one or more exogenous hexose feedstock via one or more pentose-5-phosphate intermediate, comprising: introducing into or expressing in the recombinant microorganism one or more enzyme for the conversion of the one or more hexose feedstock to the one or more pentose-5-phosphate intermediate; introducing into or expressing in the recombinant microorganism one or more enzyme for the conversion of the one or more pentose-5-phosphate intermediate to one or more pentose or pentose-1-phosphate intermediate; introducing into or expressing in the recombinant microorganism one or more C2 pathway comprising one or more enzyme for the production of MEG or GA from glycolaldehyde; and introducing into or expressing in the recombinant microorganism one or more C3 pathway comprising one or more enzyme for the production of MEG or GA derived from DHAP or pyruvate; and culturing the recombinant microorganism in a culture medium containing the one or more hexose feedstock to produce or accumulate MEG or GA, wherein glycolaldehyde and DHAP (or pyruvate) are intermediates produced in the C2 pathway, and wherein MEG or GA are produced in both the C2 and C3 pathways.

In some embodiments, the application provides for a method of producing a recombinant microorganism that produces or accumulates MEG or glycolic acid (GA) and one or more co-product from one or more exogenous hexose feedstock via one or more pentose-5-phosphate intermediate, comprising: introducing into or expressing in the recombinant microorganism one or more enzyme for the conversion of the one or more hexose feedstock to the one or more pentose-5-phosphate intermediate; introducing into or expressing in the recombinant microorganism one or more enzyme for the conversion of the one or more pentose-5-phosphate intermediate to one or more pentose or pentose-1-phosphate intermediate; introducing into or expressing in the recombinant microorganism one or more C2 pathway comprising one or more enzyme for the production of MEG or GA from glycolaldehyde; and introducing into or expressing in the recombinant microorganism one or more C3 pathway comprising one or more enzyme for the production of one or more co-product derived from DHAP or pyruvate; and culturing the recombinant microorganism in a culture medium containing the one or more hexose feedstock to produce or accumulate MEG or GA and one or more co-product, wherein glycolaldehyde and DHAP (or pyruvate) are intermediates produced in the C2 pathway, and wherein MEG or GA is produced in the one or more C2 pathway and the one or more co-product is produced in the one or more C3 pathway.

BRIEF DESCRIPTION OF DRAWINGS

Illustrative embodiments of the disclosure are illustrated in the drawings, in which.

DETAILED DESCRIPTION

Definitions

Figure 1:
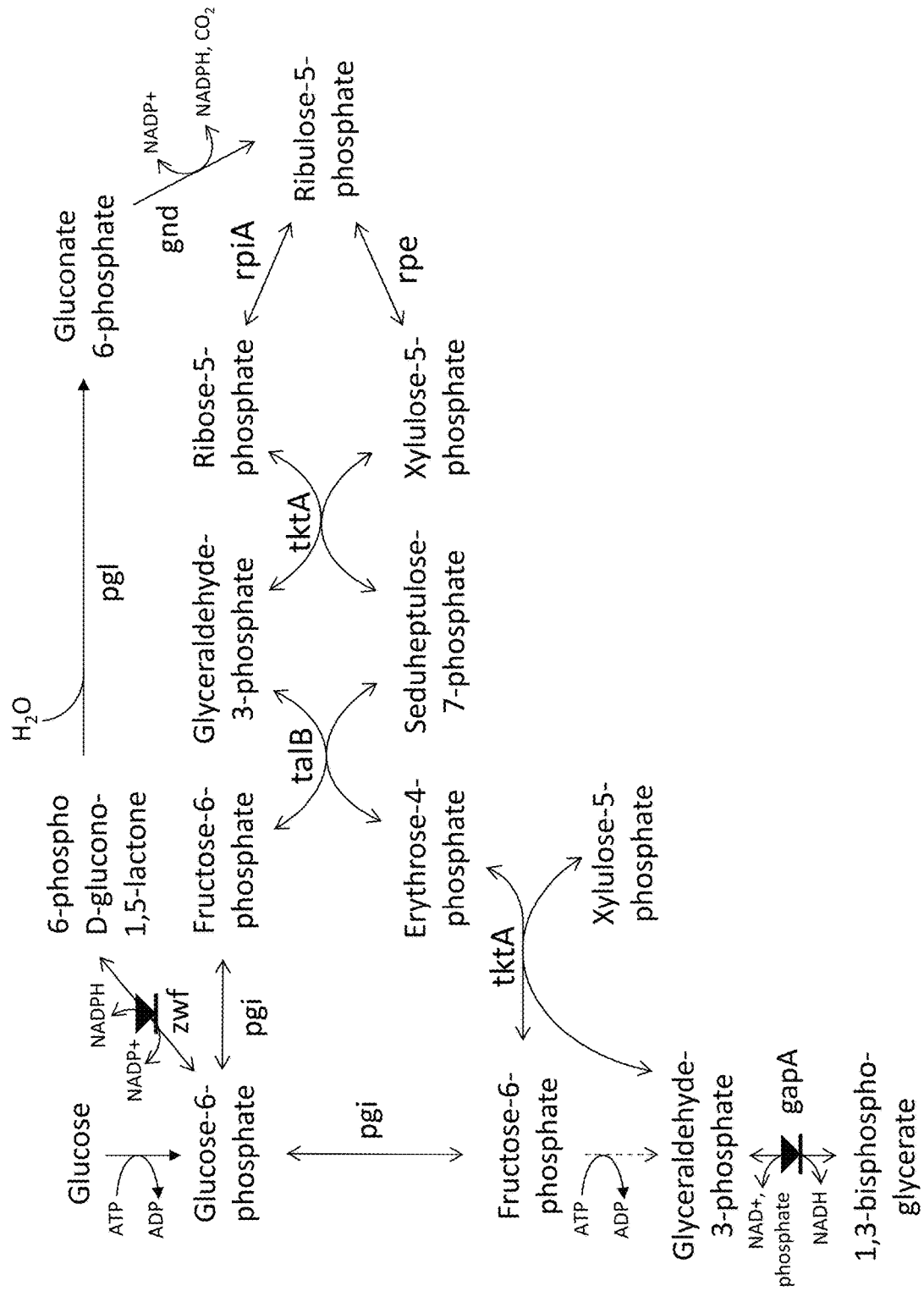
FIG. 1 illustrates lossless transformation of glucose to a pentose-phosphate. The symbol ▼ means enzymes to be potentially down regulated or inactivated/abolished, ie. respective gene potentially attenuated or deleted

The following definitions and abbreviations are to be used for the interpretation of the disclosure.

As used herein and in the appended claims, the singular forms "a," "an," and "the" include plural referents unless the context clearly dictates otherwise. Thus, for example, reference to "an enzyme" includes a plurality of such enzymes and reference to "the microorganism" includes reference to one or more microorganisms, and so forth.

As used herein, the terms "comprises," "comprising," "includes," "including," "has," "having, "contains," "containing," or any other variation thereof, are intended to cover a non-exclusive inclusion. A composition, mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive "or" and not to an exclusive "or."

The terms "about" and "around," as used herein to modify a numerical value, indicate a close range surrounding that explicit value. If "X" were the value, "about X" or "around X" would indicate a value from 0.9X to 1.1X, or, in some embodiments, a value from 0.95X to 1.05X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.98X."

As used herein, the terms "microbial," "microbial organism," and "microorganism" include any organism that exists as a microscopic cell that is included within the domains of archaea, bacteria or eukarya, the latter including yeast and filamentous fungi, protozoa, algae, or higher Protista. Therefore, the term is intended to encompass prokaryotic or eukaryotic cells or organisms having a microscopic size and includes bacteria, archaea, and eubacteria of all species as well as eukaryotic microorganisms such as yeast and fungi. Also included are cell cultures of any species that can be cultured for the production of a chemical.

As described herein, in some embodiments, the recombinant microorganisms are prokaryotic microorganism. In some embodiments, the prokaryotic microorganisms are bacteria. "Bacteria", or "eubacteria", refers to a domain of prokaryotic organisms. Bacteria include at least eleven distinct groups as follows: (1) Gram-positive (gram+) bacteria, of which there are two major subdivisions: (1) high G+C group (*Actinomycetes, Mycobacteria, Micrococcus*, others) (2) low G+C group (*Bacillus, Clostridia, Lactobacillus, Staphylococci, Streptococci, Mycoplasmas*); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; (11) *Thermotoga* and Thermosipho thermophiles.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*.

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*.

The term "recombinant microorganism" and "recombinant host cell" are used interchangeably herein and refer to microorganisms that have been genetically modified to express or to overexpress endogenous enzymes, to express heterologous enzymes, such as those included in a vector, in an integration construct, or which have an alteration in expression of an endogenous gene. By "alteration" it is meant that the expression of the gene, or level of a RNA molecule or equivalent RNA molecules encoding one or more polypeptides or polypeptide subunits, or activity of one or more polypeptides or polypeptide subunits is up regulated or down regulated, such that expression, level, or activity is greater than or less than that observed in the absence of the alteration. For example, the term "alter" can mean "inhibit," but the use of the word "alter" is not limited to this definition. It is understood that the terms "recombinant microorganism" and "recombinant host cell" refer not only to the particular recombinant microorganism but to the progeny or potential progeny of such a microorganism. Because certain modifications may occur in succeeding generations due to either mutation or environmental influences, such progeny may not, in fact, be identical to the parent cell, but are still included within the scope of the term as used herein.

The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence. The level of expression of a desired product in a host cell may be determined on the basis of either the amount of corresponding mRNA that is present in the cell, or the amount of the desired product encoded by the selected sequence. For example, mRNA transcribed from a selected sequence can be quantitated by qRT-PCR or by Northern hybridization (see Sambrook et al., Molecular Cloning: A Laboratory Manual, Cold Spring Harbor Laboratory Press (1989)). Protein encoded by a selected sequence can be quantitated by various methods, e.g., by ELISA, by assaying for the biological activity of the protein, or by employing assays that are independent of such activity, such as western blotting or radioimmunoassay, using antibodies that recognize and bind the protein. See Sambrook et al., 1989, supra.

The term "polynucleotide" is used herein interchangeably with the term "nucleic acid" and refers to an organic polymer composed of two or more monomers including nucleotides, nucleosides or analogs thereof, including but not limited to single stranded or double stranded, sense or antisense deoxyribonucleic acid (DNA) of any length and, where appropriate, single stranded or double stranded, sense or antisense ribonucleic acid (RNA) of any length, including siRNA. The term "nucleotide" refers to any of several compounds that consist of a ribose or deoxyribose sugar joined to a purine or a pyrimidine base and to a phosphate group, and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers, respectively, to a nucleotide or nucleoside in which one or more individual atoms have been replaced with a different atom or with a different functional group. Accordingly, the term polynucleotide includes nucleic acids of any length, DNA, RNA, analogs and fragments thereof. A polynucleotide of three or more nucleotides is also called nucleotidic oligomer or oligonucleotide.

It is understood that the polynucleotides described herein include "genes" and that the nucleic acid molecules described herein include "vectors" or "plasmids." Accordingly, the term "gene", also called a "structural gene" refers to a polynucleotide that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including introns, 5'-untranslated region (UTR), and 3'-UTR, as well as the coding sequence.

The term "enzyme" as used herein refers to any substance that catalyzes or promotes one or more chemical or biochemical reactions, which usually includes enzymes totally or partially composed of a polypeptide or polypeptides, but can include enzymes composed of a different molecule including polynucleotides.

As used herein, the term "non-naturally occurring," when used in reference to a microorganism organism or enzyme activity of the disclosure, is intended to mean that the microorganism organism or enzyme has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microorganism's genetic material. Such modifications include, for example, coding regions and functional fragments thereof, for heterologous, homologous, or both heterologous and homologous polypeptides for the referenced species. Additional modifications include, for example, non-coding regulatory regions in which the modifications alter expression of a gene or operon. Exemplary non-naturally occurring microorganism or enzyme activity includes the hydroxylation activity described above.

The term "exogenous" as used herein with reference to various molecules, e.g., polynucleotides, polypeptides, enzymes, etc., refers to molecules that are not normally or naturally found in and/or produced by a given yeast, bacterium, organism, microorganism, or cell in nature.

On the other hand, the term "endogenous" or "native" as used herein with reference to various molecules, e.g., polynucleotides, polypeptides, enzymes, etc., refers to molecules that are normally or naturally found in and/or produced by a given yeast, bacterium, organism, microorganism, or cell in nature.

The term "heterologous" as used herein in the context of a modified host cell refers to various molecules, e.g., polynucleotides, polypeptides, enzymes, etc., wherein at least one of the following is true: (a) the molecule(s) is/are foreign ("exogenous") to (i.e., not naturally found in) the host cell; (b) the molecule(s) is/are naturally found in (e.g., is "endogenous to") a given host microorganism or host cell but is either produced in an unnatural location or in an unnatural amount in the cell; and/or (c) the molecule(s) differ(s) in nucleotide or amino acid sequence from the endogenous nucleotide or amino acid sequence(s) such that the molecule differing in nucleotide or amino acid sequence from the endogenous nucleotide or amino acid as found endogenously is produced in an unnatural (e.g., greater than naturally found) amount in the cell.

The term "homolog," as used herein with respect to an original enzyme or gene of a first family or species, refers to distinct enzymes or genes of a second family or species which are determined by functional, structural, or genomic analyses to be an enzyme or gene of the second family or species which corresponds to the original enzyme or gene of the first family or species. Homologs most often have functional, structural, or genomic similarities. Techniques are known by which homologs of an enzyme or gene can readily be cloned using genetic probes and PCR. Identity of cloned sequences as homologs can be confirmed using functional assays and/or by genomic mapping of the genes.

A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. Thus, the term "homologous proteins" is intended to mean that the two proteins have similar amino acid sequences. In certain instances, the homology between two proteins is indicative of its shared ancestry, related by evolution. The terms "homologous sequences" or "homologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. The degree of sequence identity may vary, but in one embodiment, is at least 50% (when using standard sequence alignment programs known in the art), at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%. Homology can be determined using software programs readily available in the art, such as those discussed in *Current Protocols in Molecular Biology* (F. M. Ausubel et al., eds., 1987) Supplement 30, section 7.718, Table 7.71. Some alignment programs are MacVector (Oxford Molecular Ltd, Oxford, U.K.) and ALIGN Plus (Scientific and Educational Software, Pennsylvania). Other non-limiting alignment programs include Sequencher (Gene Codes, Ann Arbor, Michigan), AlignX, and Vector NTI (Invitrogen, Carlsbad, CA). A similar biological function may include, but is not limited to: catalyzing the same or similar enzymatic reaction; having the same or similar selectivity for a substrate or co-factor; having the same or similar stability; having the same or similar tolerance to various fermentation conditions (temperature, pH, etc.); and/or having the same or similar tolerance to various metabolic substrates, products, by-products, intermediates, etc. The degree of similarity in biological function may vary, but in one embodiment, is at least 1%, at least 2%, at least 3%, at least 4%, at least 5%, at least 6%, at least 7%, at least 8%, at least 9%, at least 10%, at least 20%, at least 30%, at least 40%, at least 50%, at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%, according to one or more assays known to one skilled in the art to determine a given biological function.

The term "variant" refers to any polypeptide or enzyme described herein. A variant also encompasses one or more components of a multimer, multimers comprising an individual component, multimers comprising multiples of an individual component (e.g., multimers of a reference molecule), a chemical breakdown product, and a biological breakdown product. In particular, non-limiting embodiments, an enzyme may be a "variant" relative to a reference enzyme by virtue of alteration(s) in any part of the polypeptide sequence encoding the reference enzyme. A variant of a reference enzyme can have enzyme activity of at least 10%, at least 30%, at least 50%, at least 80%, at least 90%, at least 100%, at least 105%, at least 110%, at least 120%, at least 130% or more in a standard assay used to measure enzyme activity of a preparation of the reference enzyme. In some embodiments, a variant may also refer to polypeptides having at least 50%, at least 60%, at least 70%, at least 80%, at least 90%, at least 91%, at least 92%, at least 93%, at least 94%, at least 95%, at least 96%, at least 97%, at least 98%, or at least 99% sequence identity to the full-length, or unprocessed enzymes of the present disclosure. In some embodiments, a variant may also refer to polypeptides having at least 50%, at least 60%, at least 70%, at least 80%, at least 90%, at least 91%, at least 92%, at least 93%, at least 94%, at least 95%, at least 96%, at least 97%, at least 98%, or at least 99% sequence identity to the mature, or processed enzymes of the present disclosure.

The term "signal sequence" as used herein refers to an amino acid sequence that targets peptides and polypeptides to cellular locations or to the extracellular environment. Signal sequences are typically at the N-terminal portion of a polypeptide and are typically removed enzymatically. Polypeptides that have their signal sequences are referred to as being full-length and/or unprocessed. Polypeptides that have had their signal sequences removed are referred to as being mature and/or processed.

The term "yield potential" as used herein refers to a yield of a product from a biosynthetic pathway. In one embodiment, the yield potential may be expressed as a percent by weight of end product per weight of starting compound.

The term "thermodynamic maximum yield" as used herein refers to the maximum yield of a product obtained from fermentation of a given feedstock, such as glucose, based on the energetic value of the product compared to the feedstock. In a normal fermentation, without use of additional energy sources such as light, hydrogen gas or methane or electricity, for instance, the product cannot contain more energy than the feedstock. The thermodynamic maximum yield signifies a product yield at which all energy and mass from the feedstock is converted to the product. This yield can be calculated and is independent of a specific pathway. If a specific pathway towards a product has a lower yield than the thermodynamic maximum yield, then it loses mass and can most likely be improved upon or substituted with a more efficient pathway towards the product.

The term "redox balanced" refers to a set of reactions, which taken together produce as much redox cofactors as they consume. Designing metabolic pathways and engineering an organism such that the redox cofactors are balanced or close to being balanced usually results in a more efficient, higher yield production of the desired compounds. Redox reactions always occur together as two half-reactions happening simultaneously, one being an oxidation reaction and the other a reduction reaction. In redox processes, the reductant transfers electrons to the oxidant. Thus, in the reaction, the reductant or reducing agent loses electrons and is oxidized, and the oxidant or oxidizing agent gains electrons and is reduced. In one embodiment, the redox reactions take place in a biological system. Biological energy is frequently stored and released by means of redox reactions. Photosynthesis involves the reduction of carbon dioxide into sugars and the oxidation of water into molecular oxygen. The reverse reaction, respiration, oxidizes sugars to produce carbon dioxide and water. As intermediate steps, the reduced carbon compounds are used to reduce nicotinamide adenine dinucleotide (NAD+), which then contributes to the creation of a proton gradient, which drives the synthesis of adenosine triphosphate (ATP) and is maintained by the reduction of oxygen. The term redox state is often used to describe the balance of GSH/GSSG, NAD+/NADH and NADP+/NADPH in a biological system such as a cell or organ. The redox state is reflected in the balance of several sets of metabolites (e.g., lactate and pyruvate, beta-hydroxybutyrate, and acetoacetate), whose interconversion is dependent on these ratios. An abnormal redox state can develop in a variety of deleterious situations, such as hypoxia, shock, and sepsis.

The terms "C2 pathway", "C2 branch pathway", "C2 biochemical pathway" or "C2 stream" as used herein refers to a biochemical pathway wherein MEG can be produced via glycolaldehyde.

The terms "C3 pathway", "C3 branch pathway", "C3 biochemical pathway" or "C3 stream" as used herein refers to a biochemical pathway wherein MEG and/or one or more co-product such as acetone, isopropanol, propene, isobutene and/or serine pathway compounds can be produced via pyruvate, acetyl-CoA or dihydroxyacetonephosphate (DHAP).

Introduction

This disclosure combines the advantages of xylose degradation biochemistry for high yielding MEG (or glycolic acid) or MEG (or glycolic acid) and co-product formation with the advantages of readily available pure hexose sugar feedstocks. It does so by providing a lossless conversion of the hexose glucose to the intermediate D-xylulose-5-phosphate, and further to the pentoses D-xylulose or D-ribulose, to be used as intermediates for the production of MEG (or glycolic acid) or MEG (or glycolic acid) and a co-product by any one of the previously described D-xylose based methods. Apart from glucose, other hexoses such as fructose or hexose oligosaccharides such as starch or sucrose or cellobiose can be used. In some embodiments, hexoses may be selected from D-allose, D-altrose, D-glucose, D-mannose, D-gulose, D-idose, D-galactose, D-talose, D-tagtose, D-sorbose, D-fructose, D-psicose, and other hexoses known in the art. In some embodiments, pentoses may be selected from D-xylose, D-ribose, D-arabinose, D-lyxose, D-xylulose, D-ribulose, and other pentoses known in the art. In some embodiments, the hexoses and pentoses may be selected from the levorotary or dextrorotary entatiomer of any of the hexoses and pentoses disclosed herein.

Compared to other glucose based MEG or glycolic acid production methods, the present methods solve the following problems: ATP shortage, if co-production is utilized; large NADH excess; low overall product yield potential.

Compared to other xylose based MEG or glycolic acid production methods, the present methods solve the following challenges and problems: a process depending on xylose (availability/market limitations, price, purity); glucose induced inhibition of xylose utilization.

Fermentative MEG production is described in WO2010/076324 (or US2011/0294178; Metabolic Explorer), which is herein incorporated in its entirety. This application suggested diol production via 2-ketoacid decarboxylation and reduction, including a serine biosynthesis based pathway to the intermediate hydroxypyruvate and further to ethyleneglycol. However, the disclosed pathway has a reduced total yield potential of 0.69 g_MEG/g_glucose, while the thermodynamic maximum yield for a glucose→MEG conversion is 0.82 g/g. This pathway is also not redox balanced and has a high excess of 2 mol NADH per mol of consumed glucose, all of which needs to be re-oxidized for the cell to be viable. In an aerobic fermentation, this NADH can be used to generate ATP, which however would be in high excess (2 NADH→6 ATP), leading to excess biomass formation during the production phase and therefore reduced product formation and yield.

Thus, the fermentative MEG production pathway disclosed in WO2010/076324 has an ATP shortage (−1ATP per MEG), excess NADH (+1 NADH per MEG), low yield potential (ymax=0.69 g_MEG/g_glucose) and is a challenging pathway that has not been demonstrated at high efficiency/productivity.

The disclosure of WO2011/130378A1 (or US2011/0312049; Genomatica) proposes an approach similar to WO2010/076324 to produce MEG from glucose via hydroxypyruvate, but also mentions pathway variations with alternative, but related key intermediates glycerate or ethanolamine.

The disclosure of WO2011/130378A1 has the same drawbacks as WO2010/076324, except for ATP shortage. ATP can be +0 or +1 per MEG, depending on utilized enzymes.

In the case of glycolic acid, the described pathways from glucose also go through 3-phosphoglycerate and serine pathway reactions, or via the glyoxylate shunt. In both cases, one $CO_2$ is lost per glycolic acid, leading to a maximum yield (0.84 g/g) much lower than the thermodynamic maximum yield potential (1.7 g/g).

A demonstrated fermentative production of MEG from xylose (WO2013/126721), via ribulose-1-phosphate, has a high yield potential (0.82 g_MEG/g_xylose) which equals the thermodynamic maximum yield. It produces MEG via two different pathways which are active in parallel, a 2-carbon stream (via glycolaldehyde) and a 3-carbon stream (via dihydroxyacetonephosphate). The C2 stream is easy to implement, but the C3 stream is difficult to implement at high efficiency via metabolic engineering. The C3 stream utilizes the pathways presented in WO2010/076324 or WO2011/130378.

Assuming a typically ATP driven xylose import, the overall process is at least ATP neutral. Thus, some xylose and therefore yield will be lost in order to obtain some surplus ATP required for cell growth and maintenance.

However, the uptake of xylose is not as efficient and fast as that of glucose, the preferred carbon source of most microorganisms. Also, presence of glucose in the media usually inhibits utilization of other sugars such as xylose. For a more efficient process, the organism's regulation leading to this preferential consumption needs to be disrupted and the strain adapted towards xylose preference or sugar co-consumption.

The key challenge, however, is obtaining xylose as affordable and clean feedstock. Xylose as pure chemical is expensive and not available in bulk quantities. Xylose in hemicellulose hydrolysates is available in larger quantities and at potentially lower cost than glucose, but is accompanied by many impurities and substances that inhibit fermentations.

Therefore, the fermentative production of MEG (or glycolic acid) from xylose (WO2013/126721) poses a challenge with respect to using xylose as feedstock (availability, price, purity, inhibition of xylose utilization by glucose) and to using a C3 pathway, which has not been demonstrated at high efficiency/productivity. Moreover, there is an ATP shortage, +0ATP (or −1ATP if not using glycerate kinase), which is not sufficient for cell maintenance.

A further demonstrated fermentative production of MEG from xylose (Alkim et al., Microb Cell Fact (2015) 14:127), via xylulose-1-phosphate, is very similar to the route described by WO2013/126721. It has the same high yield potential (0.82 g/g), difficult to implement C3 stream for MEG production via DHAP, ATP shortage and feedstock challenges.

Another demonstrated fermentative production of MEG from xylose (WO2013/119020), via xylonate, shares similarities to the route described by WO2013/126721. It produces glycolaldehyde and pyruvate as key intermediates, allowing MEG production from glycolaldehyde with a yield potential of 0.41 g/g. This represents a high relative yield since it is achieved with only half the flux. However, no pathway to convert the remaining pyruvate to MEG is presented in WO2013/119020 or elsewhere. Currently, no realistic and efficient pathway is known to convert pyruvate to MEG. While pyruvate as a co-product itself would enable a redox neutral overall process (+0 NADH), it is not an economically interesting product and the process would lack 1 ATP (probably ~2 ATP more for pyruvate export). Thus, ideally a pyruvate derived, economically interesting co-product at high yield is required that delivers surplus ATP. Therefore, the fermentative production of MEG from xylose (WO2013/119020), via xylonate, poses a challenge with respect to using xylose as feedstock (availability, price, purity, inhibition of xylose utilization by glucose), low absolute yield of MEG, ATP shortage (depending on co-product, it could be −1 to −3 ATP with pyruvate), and to requiring a pyruvate derived co-product with high yield potential and surplus ATP.

U.S. Application No. 62/305,814, U.S. Application No. 62/430,742 and U.S. Application No. 62/406,684, each of which is herein incorporated in its entirety, describe high yielding, easy to implement pathways for the co-production of MEG and compounds such as acetone, isopropanol (IPA), propene or isobutene and offer solutions to most of the challenges described for the above mentioned MEG production methods. They furthermore offer solutions for challenges encountered for previously described IPA or isobutene productions from glucose.

All currently known MEG (or glycolic acid) production methods using glucose as feedstock have low yield potential. This is an intrinsic drawback of the biochemistry of how glucose is degraded to MEG, with one decarboxylation occurring per produced MEG (or glycolic acid) molecule for all the proposed and known pathways. However, one decarboxylation per MEG is too much to achieve redox-neutral and therefore optimal yield.

All the presented MEG (or glycolic acid) production methods using xylose as feedstock have high or high relative yield potential, due to utilization of specific, beneficial xylose degradation biochemistry, leading to or close to an ideal 0.5 decarboxylation reactions per MEG molecule. However, all these methods share the challenges of using xylose as a feedstock, such as its market limitations and technical challenges from feedstock impurity.

The present disclosure combines the advantages of xylose degradation biochemistry for high yielding MEG (or glycolic acid), or optionally, MEG (or glycolic acid) and one or more co-product, formation with the advantages of readily available pure hexose sugar feedstocks. It does so by providing a lossless conversion of the hexose glucose to the intermediate D-xylulose-5-phosphate, and further to the pentoses D-xylulose or D-ribulose, to be used as intermediates for the production of MEG (or glycolic acid), or optionally, MEG (or glycolic acid) and one or more co-product, by any one of the previously described D-xylose based methods. Glycolic acid (GA) can be produced instead of MEG by oxidation of glycolaldehyde. Apart from glucose, other hexoses such as fructose or hexose oligosaccharides such as starch or sucrose can be used.

Compared to other glucose based MEG (or glycolic acid) production methods, the recombinant microorganisms and methods of the present disclosure solves: the problem of ATP shortage, if co-production is utilized; the problem of large NADH excess; the problem of low overall product yield potential.

Compared to other xylose based MEG (or glycolic acid) production methods, the recombinant microorganisms and methods of the present disclosure solves the challenges of a process depending on xylose (availability/market limitations, price, purity) and the problem of glucose induced inhibition of xylose utilization.

The present disclosure relates to the production of MEG, or optionally, MEG and one or more co-product, from a hexose, preferably in E. coli. Alternatively, glycolic acid (GA) can be produced instead of MEG by oxidation of glycolaldehyde.

If glucose is utilized by glycolysis, the standard degradation pathway of E. coli and most other organisms, it will be degraded via 3-phosphoglycerate, the common key intermediate for all glucose to MEG methods described so far. However, this 3-carbon compound is degraded to one 2-carbon compound (MEG), losing one $CO_2$ per MEG, which is true for all described pathway variations, where NADH is in excess and means significant loss of yield potential (only 0.69 g_MEG per gram of sugar, vs 0.82 g_MEG thermodynamic maximum yield potential).

Utilization of a Non-Oxidative Entry into Pentose Phosphate Pathway

In the present disclosure, glucose flux is funneled into the pentose phosphate pathway instead of the glycolysis pathway (FIG. 1). A transketolase, such as encoded by tktA or tktB from E. coli, is used as a non-oxidative entry into the pentose phosphate pathway to transform the glycolysis intermediates fructose-6-phosphate and glyceraldehyde-3-phosphate into D-xylulose-5-phosphate and D-erythrose-4-phosphate (FIG. 1). This produces the key intermediate D-xylulose-5-phosphate.

Figure 9:
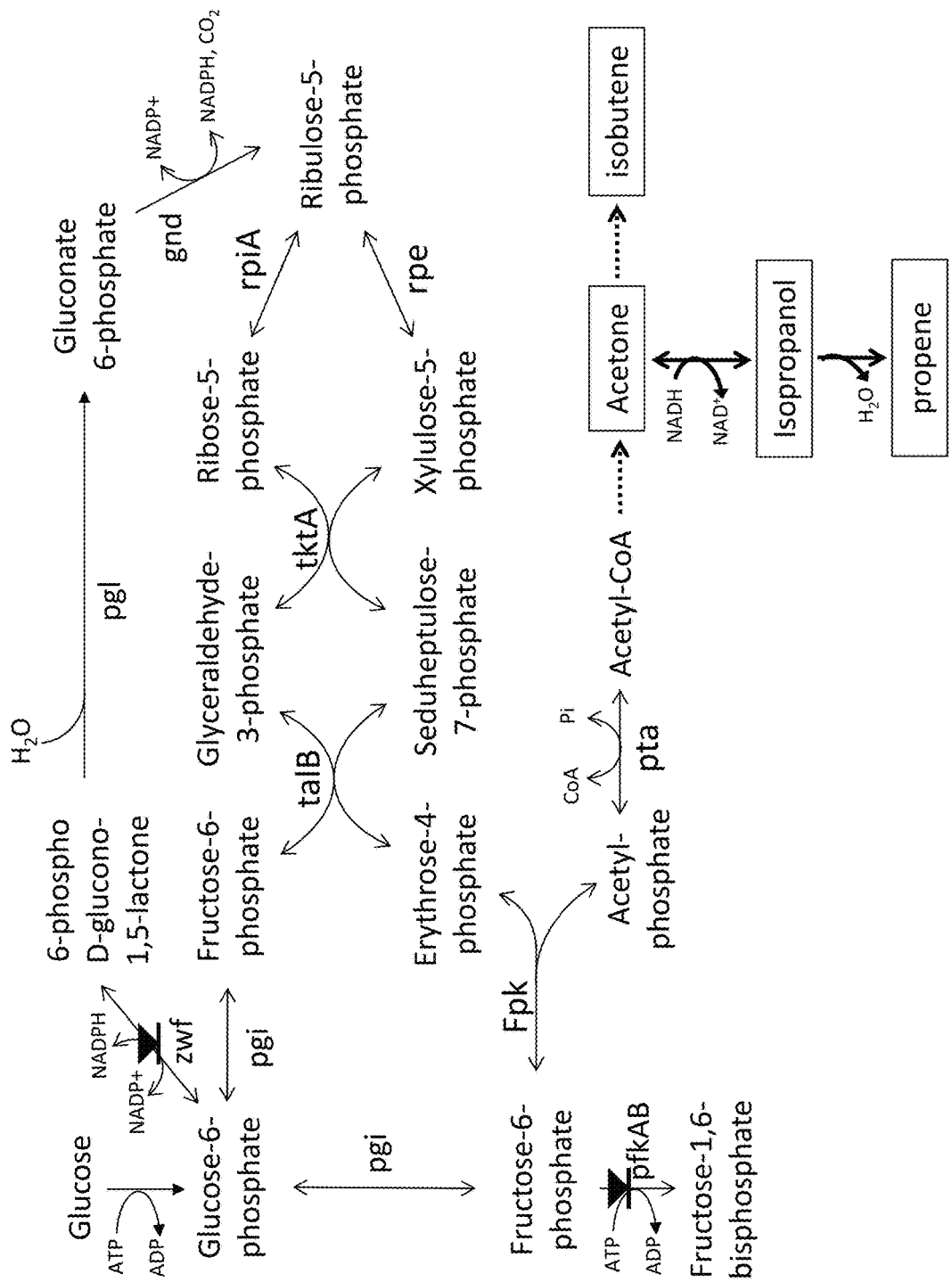
FIG. 9 illustrates lossless transformation of glucose to pentose phosphates and an acetyl-CoA. The symbol ▼ means enzymes to be potentially down regulated or inactivated/abolished, ie. respective gene potentially attenuated or deleted.

Alternatively, a fructose 6-phosphate phosphoketolase (Fpk) and a phosphate acetyltransferase (PTA) can be used as entry into the pentose phosphate pathway, making one erythrose-4-phosphate and one acetyl-CoA from fructose-6-phosphate (FIG. 9).

Utilization of Pentose Phosphate Pathway for Full Conversion into Pentose Intermediates For a lossless conversion of all hexose carbons into a pentose intermediate, D-erythrose-4-phosphate needs to be further processed. A transaldolase, such as encoded by talA or talB from E. coli, catalyzes the conversion of D-erythrose-4-phosphate and D-fructose-6-phosphate to generate D-seduheptulose-7-phosphate and D-glyceraldehyde-3-phosphate. These intermediates are further processed by a transketolase, such as encoded by tktA or tktB from E. coli, to generate D-ribose-5-phosphate and D-xylulose-5-phosphate. D-ribose-5-phosphate can be readily converted into D-ribulose-5-phosphate and further to D-xylulose-5-phosphate via ribose-5-phosphate isomerase (such as encoded by rpiA or rpiB in E. coli) and ribulose-5-phosphate 3-epimerase (such as encoded by rpe in E. coli), respectively. Thus, all glucose or fructose can be converted completely into D-xylulose-5-phosphate. The overall stoichiometry is:

2.5 Glucose+2.5 ATP+0.5 Phosphate→2 D-Xylulose-5-Phosphate+D-Ribose-5-Phosphate

The bidirectional isomerase and epimerase reactions can of course also transform the two produced D-xylulose-5-phosphates and one D-ribose-5-phosphate molecule into three D-ribulose-5-phosphates. The overall net transformation depends lastly on which intermediate, D-xylulose-5-phosphate or D-ribulose-5-phosphate, is actually consumed by the following pathway.

In case of the alternative entry into the pentose phosphate pathway via Fpk (FIG. 9), the stoichiometry is:

2 glucose+2 ATP+CoA→2 D-xylulose-5-phosphate+1 acetyl-CoA

Optimization of Flux Towards Non-Oxidative Entry into Pentose Phosphate Pathway

Deactivation of oxidative branch of pentose phosphate pathway

The common pathway in E. coli, the oxidative entry into the pentose phosphate pathway via 6-phospho D-glucono-1,5-lactone and oxidative decarboxylation to D-ribulose-5-phosphate, should not be utilized, since it transforms the hexose glucose into a pentose with loss of one carbon (FIG. 1). It is advantageous to inhibit at least one or more enzymes catalyzing one or more appropriate reactions in the oxidative branch of the pentose phosphate pathway, namely glucose 6-phosphate-1-dehydrogenase, 6-phosphogluconolactonase, and 6-phosphogluconate dehydrogenase, by deleting one or more of the genes responsible For example, in E. coli, the genes are zwf (glucose 6-phosphate-1-dehydrogenase), pgl (6-phosphogluconolactonase), and gnd (6-phosphogluconate dehydrogenase).

Downregulation of Glycolysis Downstream Reactions

The upper part of glycolysis is needed to transform 2.5 glucose or fructose into the key intermediates 2× fructose-6-phosphate and 1× glyceraldehyde-3-phosphate. To reduce or eliminate further flux through the lower part of glycolysis, i.e. the oxidative phosphorylation of glyceraldehyde-3-phosphate to 1,3-bisphospho D-glycerate an its subsequent conversion to 3-phospho-D-glycerate and 2-phospho-D-glycerate, activity of glyceraldehyde 3-phosphate dehydrogenase, phophoglycerate kinase and phosphoglycerate mutase, by gapA, pgk and gpmA/gpmM, respectively, in E. coli can be diminished.

However, if the alternative entry into the pentose phosphate pathway via fructose 6-phosphate phosphoketolase (Fpk) is utilized, then no glyceraldehyde 3-phosphate is needed and the appropriate 6-phosphofructokinase activity can be diminished or deleted (pfkA and/or pfkB genes in E. coli).

Connecting Pentose Phosphate Intermediates with MEG Production Routes

Figure 2:
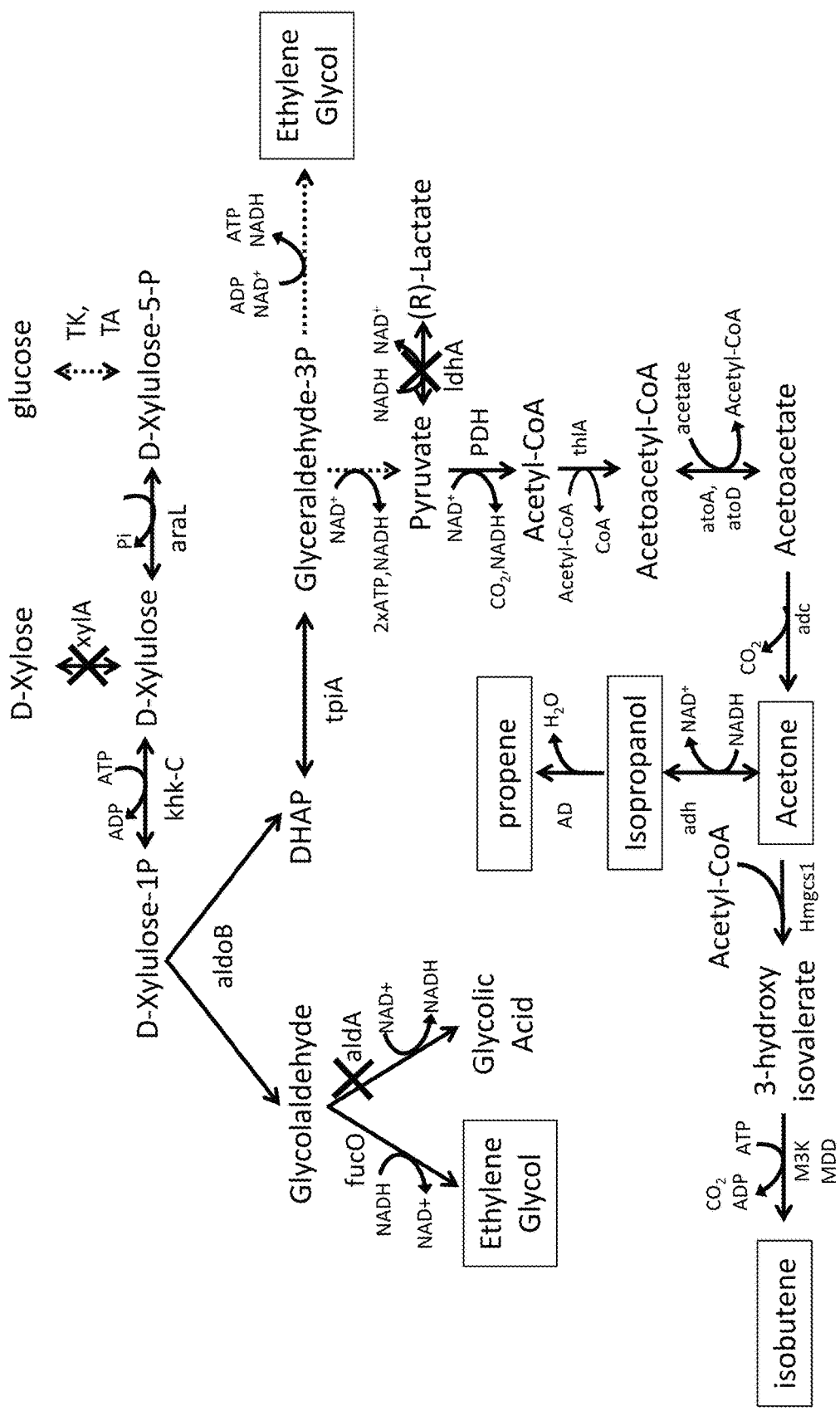
FIG. 2 illustrates MEG and possible co-production pathways via D-xylulose-1-phosphate.
Figure 4:
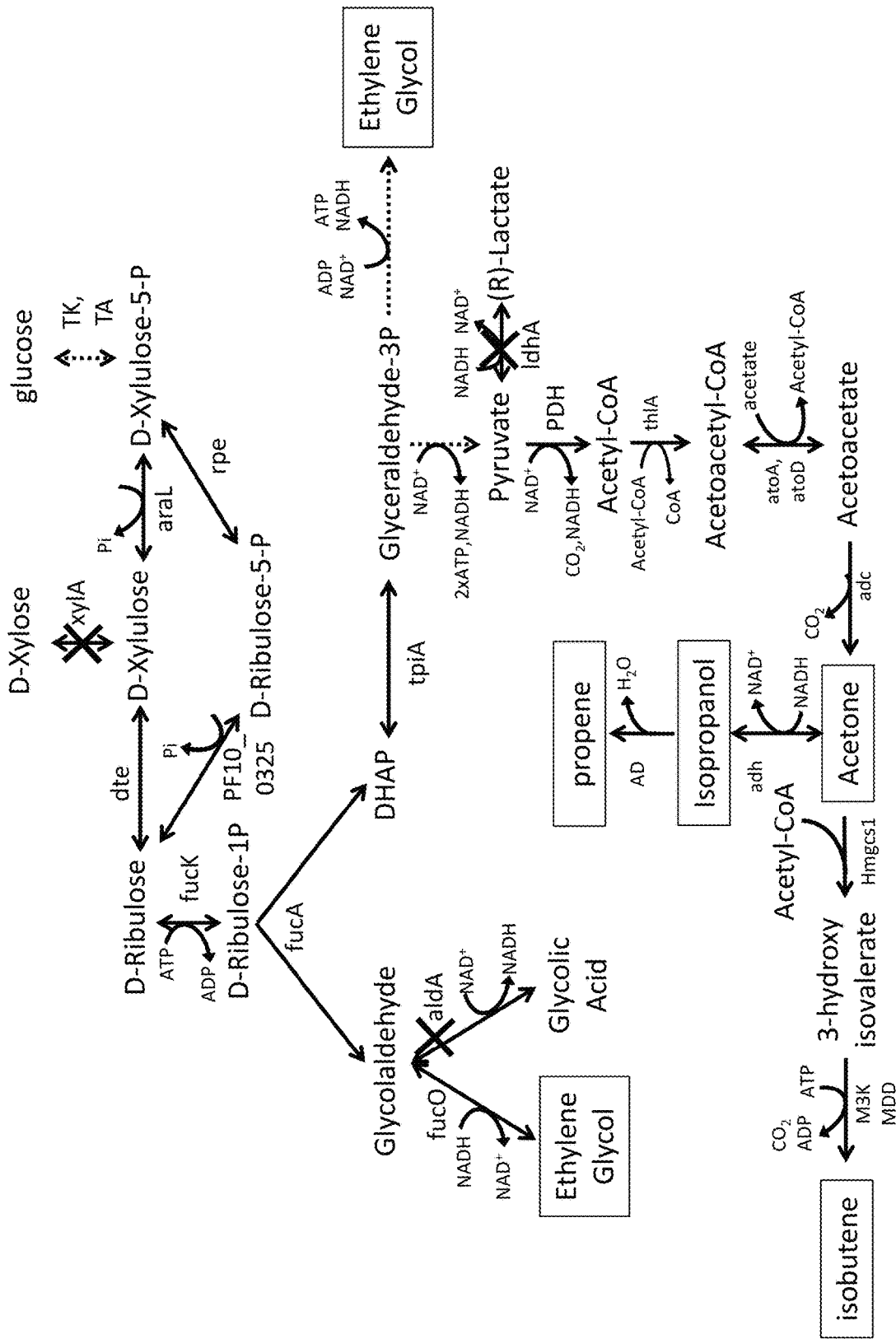
FIG. 4 illustrates MEG and possible co-production pathways via D-ribulose-1-phosphate.
Figure 5:
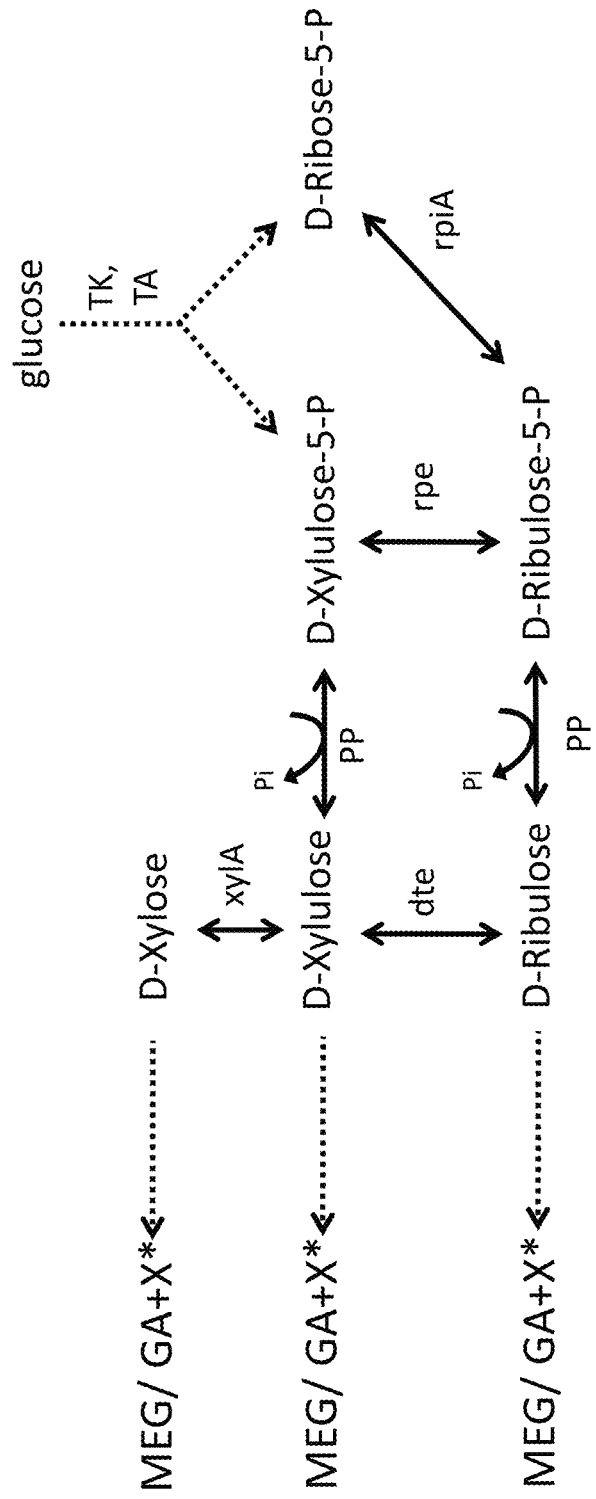
FIG. 5 illustrates a scheme of options for connecting pentose phosphate pathway and MEG production pathways via pentose phosphatases (PP).

To connect the pentose phosphate pathway intermediate D-xylulose-5-phosphate with any one of the known MEG or glycolic acid production pathways, the D-xylulose-5-phosphate intermediate needs to be dephosphorylated by a pentose 5-phosphatase to generate D-xylulose (FIG. 2 and FIG. 5). Similarly, the D-ribulose-5-phosphate intermediate may be connected to any one of the known MEG or glycolic acid production pathways through dephosphorylation by a pentose 5-phosphatase to generate D-ribulose (FIG. 4 and FIG. 5).

Figure 3:
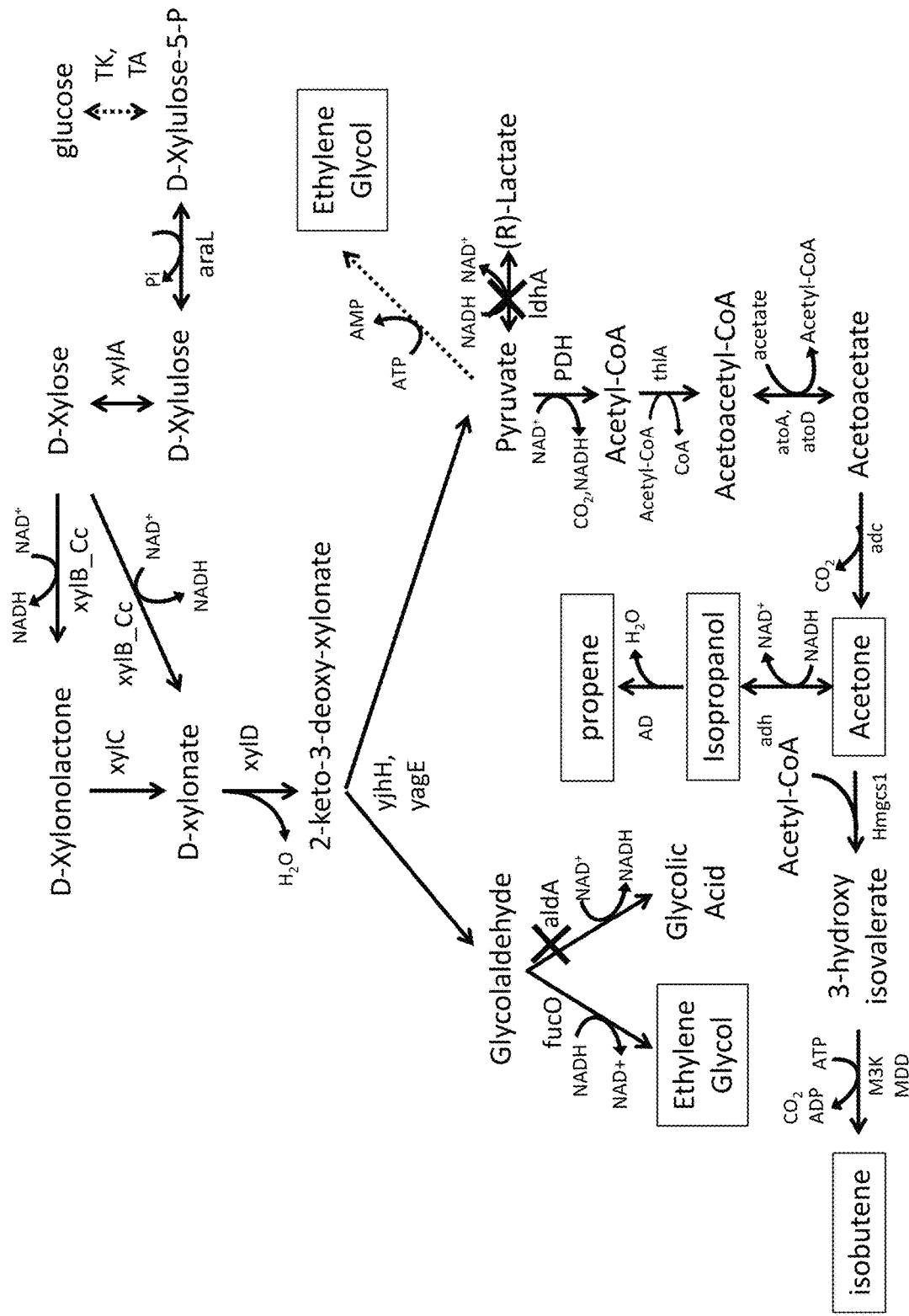
FIG. 3 illustrates MEG and possible co-production pathways via D-xylonate.

In the case of a xylonate based pathway to MEG, the xylose isomerase function, such as XylA from E. coli, is further required to transform the generated D-xylulose into D-xylose (FIG. 3).

Alternatives and Variations in Connecting Pentose-Phosphate Pathway with MEG Production Routes In the case of a D-ribulose-1-phosphate based pathway, the D-xylulose-5-phosphate intermediate can be connected to the pentose phosphate pathway as described via D-xylulose formation, following epimerization and phosphorylation (dte and fucK mediated) (FIG. 4). Alternatively, D-ribulose-5-phosphate can be used as an entry point and degraded to D-ribulose by utilizing a D-ribulose 5-phosphatase. This way, the necessary isomerization reaction is performed at the level of RPE rather than DTE (FIG. 4).

Figure 6:
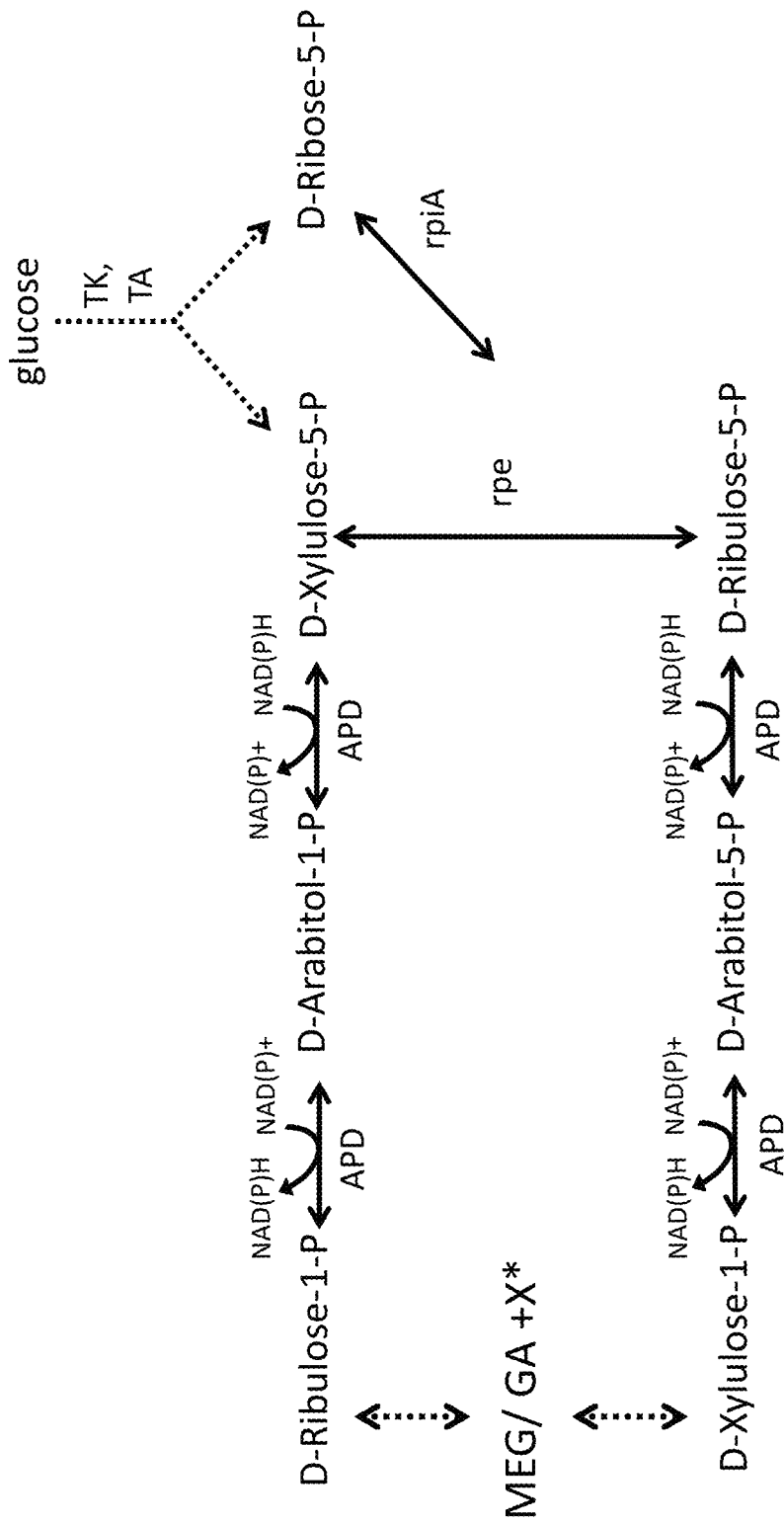
FIG. 6 illustrates a scheme for producing pentose-1-phosphates and derivatives from the pentose phosphate pathway via arabitol phosphate dehydrogenases (APD).
Figure 7:
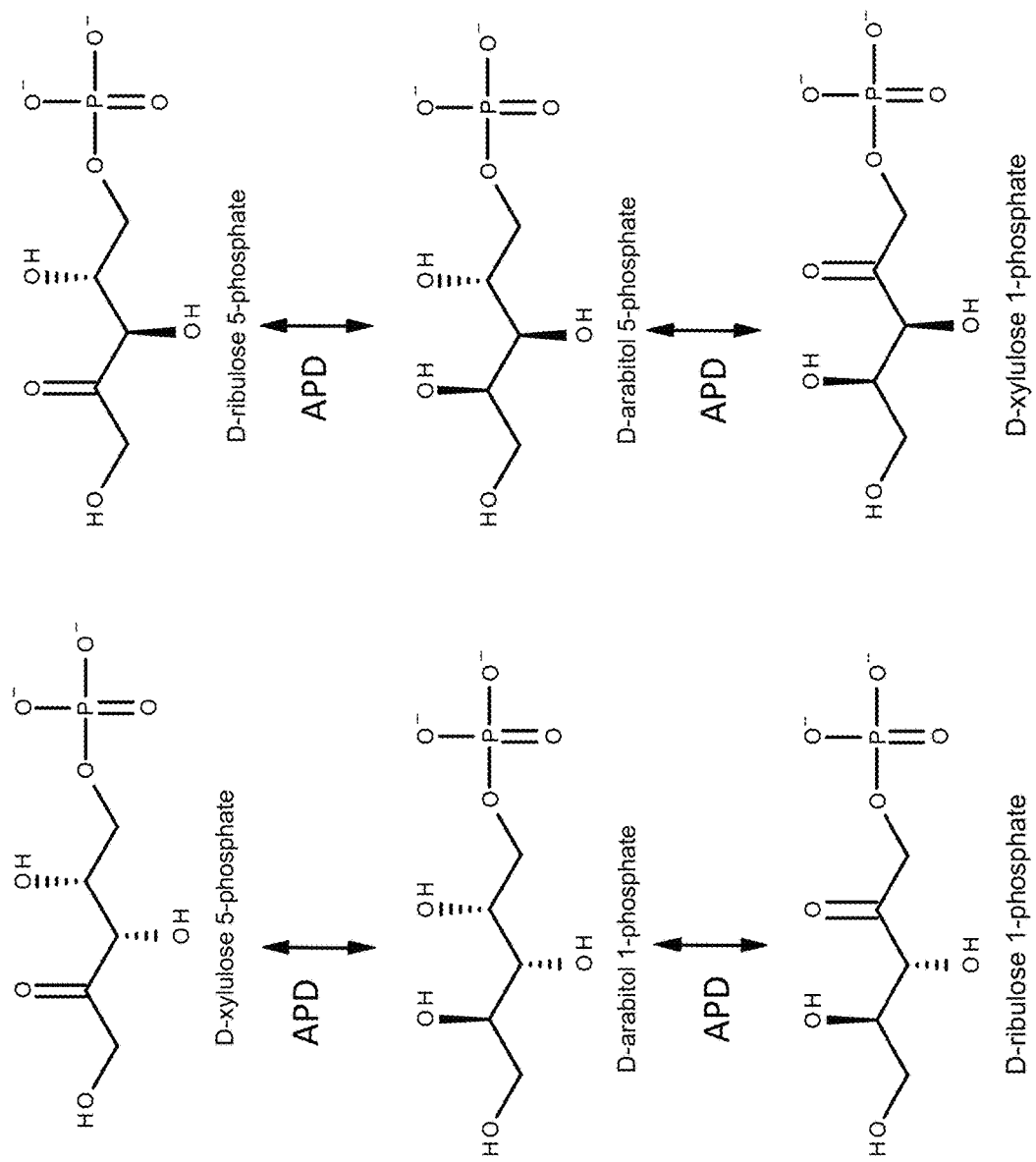
FIG. 7 illustrates the isomerization of pentose phosphates mediated by arabitol phosphate dehydrogenases (APD).
Figure 8:
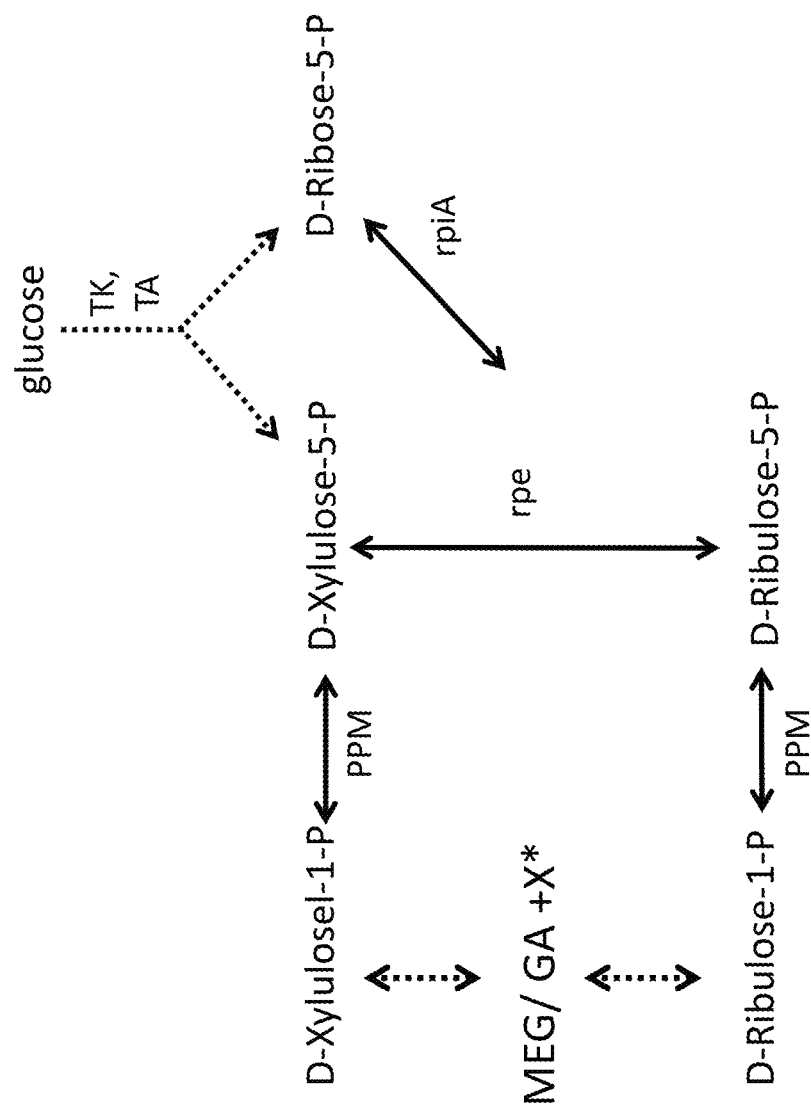
FIG. 8 illustrates a scheme for producing pentose-1-phosphates and derivatives from the pentose phosphate pathway via phosphopentomutases (PPM).

In some embodiments, pentose-5-phosphates can be transformed into pentose-1-phosphates using two arabitol dehydrogenase reactions in a row (FIG. 6). Here, the 2-keto position of D-xylulose-5-phosphate or D-ribulose-5-phosphate is reduced, then the 4-hydroxy position is oxidized to a keto group, turning the pentose-5-phosphates into pentose-1-phosphates (FIG. 7).

In further embodiments, pentose-5-phosphates can be transformed directly into pentose-1-phosphates through the action of a pentose phosphomutase (also known as phosphopentomutase or PPM). Similar to a phosphoglucomutase or phosphomannomutase, it transfers the phosphate residue from the last to the 1-position of the phospho sugar.

Hexose Utilization

The entry molecules of the pathway in the present disclosure are fructose-6-phosphate and glyceraldehyde-3-phosphate, both of which are obtained from normal glycolytic degradation of glucose or fructose in most organisms. If an organism has the ability to consume starch or sucrose or cellulose, for instance, via expression of a sucrose invertase, it will still generate glucose (and fructose), enabling it to utilize the methods of the present disclosure in the same way and to the same extent, yielding the same benefits.

Monoethylene Glycol (MEG)

Monoethylene glycol (MEG) is an important raw material for industrial applications. A primary use of MEG is in the manufacture of polyethylene terephthalate (PET) resins, films and fibers. In addition, MEG is important in the production of antifreezes, coolants, aircraft anti-icer and deicers and solvents. MEG is also known as ethane-1,2-diol.

Ethylene glycol is also used as a medium for convective heat transfer in, for example, automobiles and liquid cooled computers.

Because of its high boiling point and affinity for water, ethylene glycol is a useful desiccant. Ethylene glycol is widely used to inhibit the formation of natural gas clathrates (hydrates) in long multiphase pipelines that convey natural gas from remote gas fields to a gas processing facility. Ethylene glycol can be recovered from the natural gas and reused as an inhibitor after purification treatment that removes water and inorganic salts.

Minor uses of ethylene glycol include in the manufacture of capacitors, as a chemical intermediate in the manufacture of 1,4-dioxane, and as an additive to prevent corrosion in liquid cooling systems for personal computers. Ethylene glycol is also used in the manufacture of some vaccines; as a minor ingredient in shoe polish, inks and dyes; as a rot and fungal treatment for wood; and as a preservative for biological specimens.

Glycolic Acid

Glycolic acid is used in the textile industry as a dyeing and tanning agent, in food processing as a flavoring agent and as a preservative, and in the pharmaceutical industry as a skin care agent. It is also used in adhesives and plastics. Glycolic acid is often included into emulsion polymers, solvents and additives for ink and paint in order to improve flow properties and impart gloss. It is used in surface treatment products that increase the coefficient of friction on tile flooring.

Due to its excellent capability to penetrate skin, glycolic acid finds applications in skin care products to improve the skin's appearance and texture. It can be used as a chemical peel performed by a dermatologist in concentrations of 20 to 70% or at-home kits in lower concentrations between 10 and 20%. In addition to concentration, pH also plays a large part in determining the potency of glycolic acid in solution.

Glycolic acid can be synthesized in various ways. The predominant approach uses a catalyzed reaction of formaldehyde with synthesis gas (carbonylation of formaldehyde), for its low cost. It is also prepared by the reaction of chloroacetic acid with sodium hydroxide followed by re-acidification. Other methods, not noticeably in use, include hydrogenation of oxalic acid, and hydrolysis of the cyanohydrin derived from formaldehyde. Some of today's glycolic acids are formic acid-free. Glycolic acid can be isolated from natural sources, such as sugarcane, sugar beets, pineapple, cantaloupe and unripe grapes.

Glycolic acid is a useful intermediate for organic synthesis, in a range of reactions including: oxidation-reduction, esterification and long chain polymerization. It is used as a monomer in the preparation of polyglycolic acid and other biocompatible copolymers (e.g. PLGA). Commercially, important derivatives include the methyl (CAS #96-35-5) and ethyl (CAS #623-50-7) esters which are readily distillable. The butyl ester is a component of some varnishes, being desirable because it is nonvolatile and has good dissolving properties.

Acetone

Acetone (also known as propanone) is an organic compound with the formula $(CH3)_2CO$. It is a colorless, volatile, flammable liquid, and is the simplest ketone.

Acetone is miscible with water and serves as an important solvent, typically for cleaning purposes in the laboratory. Over 6.7 million tonnes are produced worldwide, mainly for use as a solvent and production of methyl methacrylate and bisphenol A. It is a common building block in organic chemistry. Familiar household uses of acetone are as the active ingredient in nail polish remover and as paint thinner.

Isopropanol

Isopropyl alcohol (IUPAC name 2-propanol), also called isopropanol, is a compound with the chemical formula $C_3H_8O$ or $C_3H_7OH$ or $CH_3CHOHCH_3$. It is a colorless, flammable chemical compound with a strong odor. It is the simplest example of a secondary alcohol, where the alcohol carbon atom is attached to two other carbon atoms sometimes shown as $(CH3)_2CHOH$. It is a structural isomer of propanol. It has a wide variety of industrial and household uses.

Propene, also known as propylene or methyl ethylene, is an unsaturated organic compound having the chemical formula $C_3H_6$. It has one double bond, and is the second simplest member of the alkene class of hydrocarbons.

Propene is produced from fossil fuels—petroleum, natural gas, and, to a much lesser extent, coal. Propene is a byproduct of oil refining and natural gas processing.

Isobutene

Isobutene (also known as isobutylene or 2-methylpropene) is a hydrocarbon of industrial significance. It is a four-carbon branched alkene (olefin), one of the four isomers of butylene (butene). At standard temperature and pressure it is a colorless flammable gas.

Isobutene is used as an intermediate in the production of a variety of products. It is reacted with methanol and ethanol in the manufacture of the gasoline oxygenates methyl tert-butyl ether (MTBE) and ethyl tert-butyl ether (ETBE), respectively. Alkylation with butane produces isooctane, another fuel additive. Isobutene is also used in the production of methacrolein. Polymerization of isobutene produces butyl rubber (polyisobutene). Antioxidants such as butylated hydroxytoluene (BHT) and butylated hydroxyanisole (BHA) are produced by Friedel-Crafts alkylation of phenols using isobutene.

Polymer and chemical grade isobutene is typically obtained by dehydrating tertiary butyl alcohol or catalytic dehydrogenation of isobutane. Gasoline oxygenates MTBE and ETBE are generally produced by reacting methanol or ethanol with isobutene contained in butene streams from olefin steam crackers or refineries. Isobutene is not isolated before the reaction as separating the ethers from the remaining butenes is simpler.

Serine Pathway Compounds

Compounds that may be co-produced with MEG (or glycolic acid) include serine pathway compounds, for example, serine, glycine, monoethanolamine (MEA) and ethylenediamine (EDA).

Serine is a non-essential amino acid that can be synthesized in the human body. Being highly water soluble, serine finds application as moisturizer in lotions of pharma and cosmetic industry. Further, there is a huge market for serine in the chemical industry because it can be converted into other chemicals such as plastics, detergents, dietary supplements and a variety of other products. In fact, serine has been mentioned as one of the 30 most promising biological substances to replace chemicals from the oil industry.

The α-decarboxylation of serine yields ethanolamine, an industrial product used as an intermediate in the herbicide, textile, metal, detergent, plastics, and personal care products industries with a production volume running into several hundreds of kilotonnes per annum (Scott, E. et al. (2007) Biomass in the manufacture of industrial products—the use of proteins and amino acids. Appl Microbiol Biotechnol. 75(4): 751-762).

Glycine, the simplest amino acid, is valuable for pharmaceutical and industrial applications. It is included as an additive in pet food and animal feed. For humans, glycine is sold as a sweetener/taste enhancer. Certain food supplements and protein drinks contain glycine. Certain drug formulations include glycine to improve gastric absorption of the drug. Glycine serves as a buffering agent in antacids, analgesics, antiperspirants, cosmetics, and toiletries. Many miscellaneous products use glycine or its derivatives, such as the production of rubber sponge products, fertilizers and metal complexants. Glycine is also valuable as an intermediate in the synthesis of a variety of chemical products. It is used in the manufacture of the herbicide glyphosate. Glycine can be converted to oxalic acid, which is used as a bleaching agent in the textile and pulp industries and wastewater treatment. Glycine is also extensively used in laboratory research, for example, in gel electrophoresis.

Ethylenediamine (EDA) (1,2-diaminoethane, $C_2H_4(NH_2)_2$) is used in large quantities for production of many industrial chemicals. It forms derivatives with carboxylic acids (including fatty acids), nitriles, alcohols (at elevated temperatures), alkylating agents, carbon disulfide, and aldehydes and ketones. Because of its bifunctional nature, having two amines, it readily forms heterocycles such as imidazolidines. A most prominent derivative of ethylenediamine is the chelating agent EDTA, which is derived from ethylenediamine via a Strecker synthesis involving cyanide and formaldehyde. Hydroxyethylethylenediamine is another commercially significant chelating agent. Numerous bio-active compounds and drugs contain the N—CH2-CH2-N linkage, including some antihistamines. Salts of ethylenebisdithiocarbamate are commercially significant fungicides under the brand names Maneb, Mancozeb, Zineb, and Metiram. Some imidazoline-containing fungicides are derived from ethylenediamine. Ethylenediamine is an ingredient in the common bronchodilator drug aminophylline, where it serves to solubilize the active ingredient theophylline. Ethylenediamine has also been used in dermatologic preparations. When used as a pharmaceutical excipient, after oral administration its bioavailability is about 0.34, due to a substantial first-pass effect. Less than 20% is eliminated by urinal excretion. Ethylenediamine, because it contains two amine groups, is a widely used precursor to various polymers. Condensates derived from formaldehyde are plasticizers. It is widely used in the production of polyurethane fibers. The PAMAM class of dendrimers are derived from ethylenediamine. The bleaching activator tetraacetylethylenediamine is generated from ethylenediamine. The derivative N,N-ethylenebis(stearamide) (EBS) is a commercially significant mold-release agent and a surfactant in gasoline and motor oil.

Ethylenediamine is also used as: a solvent to solubilize proteins such as albumins and casein; certain electroplating baths; corrosion inhibitor in paints and coolants; chemicals for color photography developing, binders, adhesives, fabric softeners, curing agents for epoxys, and dyes. Ethylenediamine dihydroiodide (EDDI) is added to animal feeds as a source of iodide.

Xylitol

Xylitol is a chemical compound, a sugar alcohol, of considerable value as a sweetener. It is detected by the human palatte as approximately as sweet as sucrose, and it is non-toxic and non-cariogenic.

One method of producing xylitol utilizes xylan, a hemicellulose, which is extracted from hardwoods and corncobs. Xylans can be hydrolyzed into xylose, which is then catalytically hydrogenated into xylitol. Catalytic routes to xylitol are cost- and energy-intensive due to the use of extensive separation and purification steps involved in the process and have low overall yield. Another method of producing xylitol includes utilizing fermentative and biocatalytic processes in bacteria, fungi, and/or yeast cells.

Enzymes

Exemplary enzymes that may be used in the MEG (or glycolic acid), or optionally, MEG (or glycolic acid) and one or more co-product, biosynthesis pathways disclosed herein are listed in Table 1.

TABLE 1

| Described Reaction | EC no. | Required enzyme activity | Gene candidate | Source Organism | Natural/ annotated function | Gene Identifier (nt) | SEQ ID NO (nt) | Uniprot ID | SEQ ID NO (AA) |
|---|---|---|---|---|---|---|---|---|---|
| *Isomerases that may be used in D-xylonate pathways of the present disclosure* | | | | | | | | | |
| D-xylose + NAD(P)H <=> Xylitol + NAD(P)+ | 1.1.1.307 | xylose reductase | xyl1 | *Scheffersomyces stipitis* | D-xylose reductase | GeneID: 4839234 | 82, 83 | P31867 | 84 |
| D-xylose + NAD(P)H <=> Xylitol + NAD(P)+ | 1.1.1.307 | xylose reductase | GRE3 | *Saccharomyces cerevisiae* | aldose reductase | GeneID: 856504 | 85, 86 | P38715 | 87 |
| Xylitol + NAD+ <=> D-xylulose + NADH | 1.1.1.9 | xylitol dehydrogenase | xyl2 | *Scheffersomyces stipitis* | D-xylulose reductase | GeneID: 4852013 | 88, 89 | P22144 | 90 |
| Xylitol + NAD+ <=> D-xylulose + NADH | 1.1.1.9 | xylitol dehydrogenase | xdh1 | *Trichoderma reesei* | Xylitol dehydrogenase | ENA Nr.: AF428150.1 | 91 | Q876R2 | 92 |
| D-xylopyranose <=> D-xylulose | 5.3.1.5 | xylose isomerase | xylA | *Pyromyces sp.* | xylose isomerase | ENA Nr.: CAB76571.1 | 93, 94 | Q9P8C9 | 95 |
| D-xylopyranose <=> D-xylulose | 5.3.1.5 | xylose isomerase | xylA | *Escherichia coli* | xylose isomerase | GeneID: 948141 | 143 | P00944 | 144 |
| *Glycolaldehyde reductases that may be used in all MEG pathways* | | | | | | | | | |
| glycolaldehyde + NAD(P)H <=> monoethylene glycol + NAD(P)+ | 1.1.1.- | glycolaldehyde reductase | gldA | *Escherichia coli* | glycerol dehydrogenase | GeneID: 12933659 | 12 | P0A9S5 | 13 |
| glycolaldehyde + NAD(P)H <=> monoethylene glycol + NAD(P)+ | 1.1.1.- | glycolaldehyde reductase | GRE2 | *Saccharomyces cerevisiae* | methylglyoxal reductase | GeneID: 854014 | 14 | Q12068 | 15 |
| glycolaldehyde + NAD(P)H <=> monoethylene glycol + NAD(P)+ | 1.1.1.- | glycolaldehyde reductase | GRE3 | *Saccharomyces cerevisiae* | aldose reductase | GeneID: 856504 | 16 | P38715 | 17 |
| glycolaldehyde + NAD(P)H <=> monoethylene glycol + NAD(P)+ | 1.1.1.- | glycolaldehyde reductase | yqhD* | *Escherichia coli* | Alcohol dehydrogenase | GeneID: 947493 | 18, 19 | Modified version of Q46856; G149E | 20 |
| glycolaldehyde + NAD(P)H <=> monoethylene glycol + NAD(P)+ | 1.1.1.- | glycolaldehyde reductase | yqhD | *Escherichia coli* | Alcohol dehydrogenase | GeneID: 947493 | 21, 22 | Q46856 | 23 |
| glycolaldehyde + NAD(P)H <=> monoethylene glycol + NAD(P)+ | 1.1.1.- | glycolaldehyde reductase | ydjg | *Escherichia coli* | methylglyoxal reductase | GeneID: 12930149 | 24 | P77256 | 25 |
| glycolaldehyde + NAD(P)H <=> monoethylene glycol + NAD(P)+ | 1.1.1.- | glycolaldehyde reductase | fucO | *Escherichia coli* | lactaldehyde reductase | GeneID: 947273 | 26, 27 | P0A9S1 | 28 |
| glycolaldehyde + NAD(P)H <=> monoethylene glycol + NAD(P)+ | 1.1.1.- | glycolaldehyde reductase | yafB (dkgB) | *Escherichia coli* | methylglyoxal reductase [multifunctional] | 545778205 | 29 | P30863 | 30 |
| glycolaldehyde + NAD(P)H <=> monoethylene glycol + NAD(P)+ | 1.1.1.- | glycolaldehyde reductase | yqhE (dkgA) | *Escherichia coli* | 2,5-diketo-D-gluconic acid reductase A | GeneID: 947495 | 31 | Q46857 | 32 |
| *Enzymes that may be used in D-ribulose-1-phosphate pathway to MEG* | | | | | | | | | |
| D-xylulose <=> D-ribulose | 5.1.3.- | D-ribulose-3-epimerase | DTE | *Pseudomonas cichorii* | D-tagatose 3-epimerase | ENA Nr.: BAA24429.1 | 1, 2 | O50580 | 3 |
| D-xylulose <=> D-ribulose | 5.1.3.- | D-ribulose-3-epimerase | C1KKR1 | *Rhodobacter sphaeroides* | D-tagatose 3-epimerase | ENA Nr.: FJ851309.1 | 4 | C1KKR1 | 5 |
| D-ribulose + ATP <=> D-ribulose-1-phosphate + ADP | 2.7.1.- | D-ribulose-1-kinase | fucK | *Escherichia coli* | L-fuculokinase | GeneID: 946022 | 6, 7, 257 | P11553 | 8 |
| D-ribulose-1-phosphate <=> glyceraldehyde + dihydroxyacetone-phosphate | 4.1.2.- | D-ribulose-1-phosphate aldolase | fucA | *Escherichia coli* | L-fuculose phosphate aldolase | GeneID: 947282 | 9, 10 | P0AB87 | 11 |
| *Enzymes that may be used in D-xylulose-1-phosphate pathway to MEG* | | | | | | | | | |
| D-xylulose + ATP <=> D-xylulose-1-phosphate + ADP | 2.7.1.- | D-xylulose 1-kinase | khk-C (cDNA) | *Homo sapiens* | ketohexokinase C | GenBank: CR456801.1 | 53, 54, 256 | P50053 | 55 |

TABLE 1-continued

| Described Reaction | EC no. | Required enzyme activity | Gene candidate | Source Organism | Natural/annotated function | Gene Identifier (nt) | SEQ ID NO (nt) | Uniprot ID | SEQ ID NO (AA) |
|---|---|---|---|---|---|---|---|---|---|
| D-xylulose-1-phosphate <=> glyceraldehyde + dihydroxy-acetonephosphate | 4.1.2.- | D-xylulose-1-phosphate aldolase | aldoB (cDNA) | *Homo sapiens* | Fructose-bisphosphate aldolase B | CCDS6756.1 | 56, 57 | P05062 | 58 |
| Enzymes that may be used in D-xylonate pathway to MEG ||||||||||
| D-xylose + NAD+ <=> D-xylonolactone + NADH, or D-xylose + NAD+ <=> D-xylonate + NADH | 1.1.1.175 | xylose dehydrogenase | xylB | *Caulobacter crescentus* | D-xylose 1-dehydrogenase | GeneID: 7329904 | 59, 60 | B8H1Z0 | 61 |
| D-xylose + NADP+ <=> D-xylonolactone + NADPH, or D-xylose + NADP+ <=> D-xylonate + NADPH | 1.1.1.179 | xylose dehydrogenase | xdh1, HVO_B0028 | *Haloferax volcanii* | D-xylose 1-dehydrogenase | GeneID: 8919161 | 62 | D4GP29 | 63 |
| D-xylose + NADP+ <=> D-xylonolactone + NADPH, or D-xylose + NADP+ <=> D-xylonate + NADPH | 1.1.1.179 | xylose dehydrogenase | xyd1 | *Trichoderma reesei* | D-xylose 1-dehydrogenase | ENA Nr.: EF136590.1 | 64 | A0A024SMV2 | 65 |
| D-xylonolactone + H2O <=> D-xylonate | 3.1.1.68 | xylonolactonase | xylC | *Caulobacter crescentus* | Xylonolactonase | GeneID: 7329903 | 66 | A0A0H3C6P8 | 67 |
| D-xylonate <=> 2-keto-3-deoxy-xylonate + H2O | 4.2.1.82 | xylonate dehydratase | xylD | *Caulobacter crescentus* | xylonate dehydratase | GeneID: 7329902 | 68 | A0A0H3C6H6 | 69 |
| D-xylonate <=> 2-keto-3-deoxy-xylonate + H2O | 4.2.1.82 | xylonate dehydratase | yjhG | *Escherichia coli* | xylonate dehydratase | GeneID: 946829 | 70, 71 | P39358 | 72 |
| D-xylonate <=> 2-keto-3-deoxy-xylonate + H2O | 4.2.1.82 | xylonate dehydratase | yagF | *Escherichia coli* | xylonate dehydratase | GeneID: 944928 | 73, 74 | P77596 | 75 |
| 2-keto-3-deoxy-xylonate <=> glycolaldehyde + pyruvate | 4.1.2.- | 2-keto-3-deoxy-D-pentonate aldolase | yjhH | *Escherichia coli* | Uncharacterized lyase | GeneID: 948825 | 76, 77 | P39359 | 78 |
| 2-keto-3-deoxy-xylonate <=> glycolaldehyde + pyruvate | 4.1.2.- | 2-keto-3-deoxy-D-pentonate aldolase | yagE | *Escherichia coli* | Probable 2-keto-3-deoxy-galactonate aldolase | GeneID: 944925 | 79, 80 | P75682 | 81 |
| Enzymes that may be used in 2-propanol (IPA) pathway via acetone or in acetone pathway to isobutene ||||||||||
| 2 acetyl-Coa → acetoacetyl-CoA + CoA | 2.3.1.9 | acetyl coenzyme A acetyltransferase | thlA | *Clostridium acetobutylicum* | acetyl coenzyme A acetyltransferase | 3309200 | 33, 34 | P45359 | 35 |
| 2 acetyl-Coa → acetoacetyl-CoA + CoA | 2.3.1.9 | acetyl coenzyme A acetyltransferase | atoB | *Escherichia coli* | acetyl coenzyme A acetyltransferase | GeneID: 946727 | 36 | P76461 | 37 |
| 2 acetyl-Coa → acetoacetyl-CoA + CoA | 2.3.1.9 | acetyl coenzyme A acetyltransferase | ERG10 | *Saccharomyces cerevisiae* | acetyl coenzyme A acetyltransferase | 856079 | 38 | P41338 | 39 |
| acetoacetyl-CoA + acetate → acetoacetate + acetyl-CoA | 2.8.3.8 | Acetyl-CoA:acetoacetate-CoA transferase subunit | atoA | *Escherichia coli* | Acetyl-CoA:acetoacetate-CoA transferase subunit | 48994873 | 41, 42 | P76459 | 43 |
| acetoacetyl-CoA + acetate → acetoacetate + acetyl-CoA | 2.8.3.8 | Acetyl-CoA:acetoacetate-CoA transferase subunit | atoD | *Escherichia coli* | Acetyl-CoA:acetoacetate-CoA transferase subunit | 48994873 | 44, 45 | P76458 | 46 |
| acetoacetate → acetone + CO2 | 4.1.1.4 | acetoacetate decarboxylase | adc | *Clostridium acetobutylicum* | acetoacetate decarboxylase | 6466901 | 47, 48 | P23670 | 49 |
| acetoacetate → acetone + CO2 | 4.1.1.4 | acetoacetate decarboxylase | adc | *Clostridium beijerinckii* | acetoacetate decarboxylase | 149901357 | 50, 51 | A6M020 | 52 |
| acetone + acetyl-CoA + H2O ↔ 3-hydroxy-isovalerate | 2.3.3.- | 3-hydroxy-isovalerate synthase | Hmgcs1 | *Mus musculus* | hydroxymethyl-glutaryl-CoA synthase | CCDS56901.1; GeneID: 208715 | 104 | Q3UWQ9 | 105 |
| acetone + acetyl-CoA + H2O ↔ 3-hydroxy-isovalerate | 2.3.3.- | 3-hydroxy-isovalerate synthase | ERG13 | *Saccharomyces cerevisiae* | hydroxymethyl-glutaryl-CoA synthase | GeneID: 854913 | 106 | P54839 | 107 |

TABLE 1-continued

| Described Reaction | EC no. | Required enzyme activity | Gene candidate | Source Organism | Natural/annotated function | Gene Identifier (nt) | SEQ ID NO (nt) | Uniprot ID | SEQ ID NO (AA) |
|---|---|---|---|---|---|---|---|---|---|
| acetone + acetyl-CoA + H2O ↔ 3-hydroxy-isovalerate | 2.3.3.- | 3-hydroxy-isovalerate synthase | PksG | Lactobacillus crispatus ST1 | hydroxymethyl-glutaryl-CoA synthase/polyketide intermediate transferase | GeneID: 9107446 | 108 | AEL95_01455 | 109 |
| acetone + acetyl-CoA + H2O ↔ 3-hydroxy-isovalerate | 2.3.3.- | 3-hydroxy-isovalerate synthase | Pnap_0477 | Polaromonas naphthalenivorans | hydroxymethyl-glutaryl-CoA lyase | ABM35799.1 | 110 | A1VJH1 | 111 |
| 3-hydroxy-isovalerate + ATP ↔ ADP + H(+) + 3-phosphonoxyisovalerate | 2.7.1.- | hydroxy-isovalerate kinase | TA1305 | Thermoplasma acidophilum | mevalonate-diphosphate decarboxylase/mevalonate-monophosphate decarboxylase | GeneID: 1456782 | 112 | Q9HIN1 | 113 |
| 3-hydroxy-isovalerate + ATP ↔ ADP + H(+) + 3-phosphonoxyisovalerate | 2.7.1.- | hydroxy-isovalerate kinase | TA1305* (L200E) | Thermoplasma acidophilum | mevalonate-diphosphate decarboxylase/mevalonate-monophosphate decarboxylase | GeneID: 1456782 | 114 | Modified version of Q9HIN1; L200E | 115 |
| 3-hydroxy-isovalerate + ATP ↔ ADP + H(+) + 3-phosphonoxyisovalerate | 2.7.1.- | hydroxy-isovalerate kinase | PTO1356 | Picrophilus torridus | mevalonate-diphosphate decarboxylase | GeneID: 2845209 | 116 | Q6KZB1 | 117 |
| 3-phosphonoxy-isovalerate → CO(2) + isobutene | 4.1.1.- | 3-phosphonoxy-isovalerate decarboxylase | smi_1746 | Streptococcus mitis | mevalonate-diphosphate decarboxylase | Genbank: CBJ22986.1 | 118 | D3HAT7 | 119 |
| 3-phosphonoxy-isovalerate → CO(2) + isobutene | 4.1.1.- | 3-phosphonoxy-isovalerate decarboxylase | mvaD | Streptococcus gordonii | mevalonate-diphosphate decarboxylase | GeneID: 25051665 | 120 | A8AUU9 | 121 |
| 3-phosphonoxy-isovalerate → | 4.1.1.- | hydroxy-isovalerate decarboxylase | TA1305 | Thermoplasma acidophilum | mevalonate-diphosphate decarboxylase | GeneID: 1456782 | 112 | Q9HIN1 | 113 |
| 3-hydroxy-isovalerate → CO(2) + isobutene | 4.1.1.- | hydroxy-isovalerate decarboxylase | PTO1356 | Picrophilus torridus | mevalonate-diphosphate decarboxylase | GeneID: 2845209 | 116 | Q6KZB1 | 117 |
| 3-hydroxy-isovalerate → CO(2) + isobutene | 4.1.1.- | hydroxy-isovalerate decarboxylase | mvaD | Streptococcus gordonii | mevalonate-diphosphate decarboxylase | GeneID: 25051665 | 120 | A8AUU9 | 121 |
| Hydrolases that may be used in improved acetone pathway to isobutene | | | | | | | | | |
| Acetoacetyl-CoA + H(2)O <=> CoA + acetoacetate | 3.1.2.11 | acetate:acetoacetyl-CoA hydrolase | ctfA | Clostridium acetobutylicum | butyrate-acetoacetate CoA-transferase, complex A | NCBI-GeneID: 1116168 | 96 | P33752 | 97 |
| Acetoacetyl-CoA + H(2)O <=> CoA + acetoacetate | 3.1.2.11 | acetate:acetoacetyl-CoA hydrolase | ctfB | Clostridium acetobutylicum | butyrate-acetoacetate CoA-transferase, subunit B | NCBI-GeneID: 1116169 | 98 | P23673 | 99 |
| Acetoacetyl-CoA + H(2)O <=> CoA + acetoacetate | 3.1.2.11 | acetate:acetoacetyl-CoA hydrolase | atoA | Escherichia coli (strain K12) | Acetyl-CoA:acetoacetate-CoA transferase subunit | GeneID: 946719 | 100 | P76459 | 101 |
| Acetoacetyl-CoA + H(2)O <=> CoA + acetoacetate | 3.1.2.11 | acetate:acetoacetyl-CoA hydrolase | atoD | Escherichia coli (strain K12) | Acetyl-CoA:acetoacetate-CoA transferase subunit | GeneID: 947525 | 102 | P76458 | 103 |
| Enzymes that may be used in HMG-CoA pathway to isobutene | | | | | | | | | |
| acetyl-CoA + H2O + acetoacetyl-CoA <=> (S)-3-hydroxy-3-methylglutaryl-CoA + CoA | 2.3.3.10 | HMG-CoA synthase | hmgS | Saccharomyces cerevisiae | HMG-CoA synthase | GeneID: 854913 | 122 | P54839 | 123 |
| (S)-3-hydroxy-3-methylglutaryl-CoA <=> trans-3-methylglutaconyl-CoA + H(2)O | 4.2.1.18 | methyl-glutaconyl-CoA hydratase | liuC | Pseudomonas putida | methyl-glutaconyl-CoA hydratase | GeneID: 1041856 | 124 | Q88FM3 | 125 |

TABLE 1-continued

| Described Reaction | EC no. | Required enzyme activity | Gene candidate | Source Organism | Natural/ annotated function | Gene Identifier | SEQ ID NO (nt) | Uniprot ID | SEQ ID NO (AA) |
|---|---|---|---|---|---|---|---|---|---|
| ADP + phosphate + 3-methylglutaconyl-CoA <=>ATP + 3-methylcrotonoyl-CoA + HCO(3)(-) | 6.4.1.4. | methyl-crotonyl-CoA carboxylase | liuB | Pseudomonas aeruginosa | methylcrotonyl-CoA carboxylase subunit beta | GeneID: 878244 | 126 | O91297 | 127 |
| ADP + phosphate + 3-methylglutaconyl-CoA <=>ATP + 3-methylcrotonoyl-CoA + HCO(3)(-) | 6.4.1.4. | methyl-crotonyl-CoA carboxylase | liuD | Pseudomonas aeruginosa | methylcrotonyl-CoA carboxylase subunit alpha | GeneID: 879012 | 128 | O91299 | 129 |
| trans-2(or 3)-enoyl-CoA + H(2)O <=> (3S)-3-hydroxyacyl-CoA | 4.2.1.17 | methyl-crotonyl-CoA hydratase | fadA | E. coli | fatty acid oxidation complex, 3-ketoacyl-CoA thiolase | GeneID: 948324 | 130 | P21151 | 131 |
| trans-2(or 3)-enoyl-CoA + H(2)O <=> (3S)-3-hydroxyacyl-CoA | 4.2.1.17 | methyl-crotonyl-CoA hydratase | fadB | E. coli | fatty acid oxidation complex, enoyl-CoA hydratase | GeneID: 948336 | 132 | P21177 | 133 |
| 3-hydroxy-isovaleryl-CoA + H2O <=> 3-hydroxy-isovalerate + CoA | 3.1.2.- | 3-hydroxy-isovaleryl-CoA thioesterase | tesB | E. coli | acyl-CoA thioesterase | GeneID: 945074 | 134 | P0AGG2 | 135 |
| Enzymes that may be used in 2-propanol (IPA) pathway via acetone | | | | | | | | | |
| acetone + NAD(P)H → 2-propanol + NAD(P)+ | 1.1.1.2 | secondary alcohol dehydrogenase | adh | Clostridium beijerinckii | secondary alcohol dehydrogenase | 60592972 | 136, 137 | P25984 | 138 |
| acetone + NAD(P)H → 2-propanol + NAD(P)+ | 1.1.1.2 | secondary alcohol dehydrogenase | adh | Clostridium carboxidivorans | alcohol dehydrogenase | 308066805 | 139 | C6PZV5 | 140 |
| ADH + NADP+ ↔ NAD+ + NADPH | 1.6.1.1. | Soluble pyridine nucleotide trans-hydrogenase | udhA | Escherichia coli | Soluble pyridine nucleotide trans-hydrogenase | GeneID: 948461 | 141 | P27306 | 142 |
| Enzymes that may be used in hexose to pentose-5-phosphate pathways | | | | | | | | | |
| ATP + D-xylulose = ADP + D-xylulose 5-phosphate | 2.7.1.17 | Xylulose 5-kinase | xylB | E. coli | Xylulose kinase | GeneID: 948133 | 145 | P09099 | 146 |
| D-erythrose 4-phosphate + D-xylulose 5-phosphate ↔ β-D-fructofuranose 6-phosphate + D-glyceraldehyde 3-phosphate | 2.2.1.1 | Transketolase | tktA | E. coli | Transketolase | GeneID: 947420 | 147 | P27302 | 148 |
| D-sedoheptulose 7-phosphate + D-glyceraldehyde 3-phosphate ↔ D-ribose 5-phosphate + D-xylulose 5-phosphate | 2.2.1.1 | Transketolase | tktA | E. coli | Transketolase | GeneID: 947420 | 147 | P27302 | 148 |
| D-erythrose 4-phosphate + D-xylulose 5-phosphate ↔ β-D-fructofuranose 6-phosphate + D-glyceraldehyde 3-phosphate | 2.2.1.1 | Transketolase | tktB | E. coli | Transketolase | GeneID: 945865 | 149 | P33570 | 150 |
| D-sedoheptulose 7-phosphate + D-glyceraldehyde 3-phosphate ↔ D-ribose 5-phosphate + D-xylulose 5-phosphate | 2.2.1.1 | Transketolase | tktB | E. coli | Transketolase | GeneID: 945865 | 149 | P33570 | 150 |
| D-sedoheptulose 7-phosphate + D-glyceraldehyde 3-phosphate ↔ β-D-fructofuranose 6-phosphate + D-erythrose 4-phosphate | 2.2.1.2 | Transaldolase | talA | E. coli | Transaldolase | GeneID: 947006 | 151 | P0A867 | 152 |

TABLE 1-continued

| Described Reaction | EC no. | Required enzyme activity | Gene candidate | Source Organism | Natural/annotated function | Gene Identifier (nt) | SEQ ID NO (nt) | Uniprot ID | SEQ ID NO (AA) |
|---|---|---|---|---|---|---|---|---|---|
| D-sedoheptulose 7-phosphate + D-glyceraldehyde 3-phosphate ↔ β-D-fructofuranose 6-phosphate + D-erythrose 4-phosphate | 2.2.1.2 | Transaldolase | talB | *E. coli* | Transaldolase | GeneID: 944748 | 153 | P0A870 | 154 |
| D-ribose 5-phosphate ↔ D-ribulose 5-phosphate | 5.3.1.6 | Ribose-5-phosphate isomerase | rpiA | *E. coli* | Ribose-5-phosphate isomerase | GeneID: 947407 | 155 | P0A7Z0 | 156 |
| D-ribose 5-phosphate ↔ D-ribulose 5-phosphate | 5.3.1.6 | Ribose-5-phosphate isomerase | rpiB | *E. coli* | Ribose-5-phosphate isomerase | GeneID: 948602 | 254 | P37351 | 253 |
| D-ribulose 5-phosphate ↔ D-xylulose 5-phosphate | 5.1.3.1 | Ribulose-5-phosphate 3-epimerase | rpe | *E. coli* | Ribulose-5-phosphate 3-epimerase | GeneID: 947896 | 157 | P0AG07 | 158 |
| D-pentose 5-phosphate + H2O → D-pentose + phosphate | 3.1.3.1 | D-pentose-5-phosphatase (PP) | phoA | *E. coli* | alkaline phosphatase | GeneID: 945041 | 159 | P00634 | 160 |
| D-ribose 5-phosphate + H2O → D-ribose + phosphate | 3.1.3.23 | D-ribose-5-phosphatase (PP) | SGPP | *Arabidopsis thaliana* | Haloacid dehalogenase-like hydrolase | GeneID: 818456 | 161 | Q9ZVJ5 | 162 |
| D-xylulose 5-phosphate + H2O → D-xylulose + phosphate | 3.1.3.23 | D-xylulose-5-phosphatase (PP) | araL | *Bacillus subtilis* | sugar phosphatase | GeneID: 937431 | 163 | P94526 | 164 |
| D-ribose 5-phosphate + H2O → D-ribose + phosphate | 3.1.3.23 | D-ribose-5-phosphatase (PP) | PFLU_2693 | *Pseudomonas fluorescens* | haloacid dehalogenase-likee nzyme | GeneID: 7821858 | 165 | C3K9U8 | 166 |
| D-pentose 5-phosphate + H2O → D-pentose + phosphate | 3.1.3.23 | D-pentose-5-phosphatase (PP) | yfbT | *E. coli* | sugar phosphatase | GeneID: 946777 | 167 | P77625 | 168 |
| D-ribose 5-phosphate + H2O → D-ribose + phosphate | 3.1.3.23 | D-ribose-5-phosphatase (PP) | ybiV | *E. coli* | sugar phosphatase | GeneID: 945432 | 169 | P75792 | 170 |
| D-pentose 5-phosphate + H2O → D-pentose + phosphate | 3.1.3.23 | D-pentose-5-phosphatase (PP) | yidA | *E. coli* | sugar phosphatase | GeneID: 948204 | 171 | P0A8Y5 | 172 |
| D-ribulose 5-phosphate + H2O → D-ribulose + phosphate | 3.1.3.23 | D-ribulose-5-phosphatase (PP) | PF10_0325 | *Plasmodium falciparum* | Haloacid dehalogenase-like hydrolase | GeneID: 810482 | 173 | Q8IJ74 | 174 |
| D-arabitol 1-phosphate + NAD+ ↔ D-xylulose 5-phosphate + NADH + H+ | 1.1.1.301 | D-arabitol 1-phosphate 4-dehydrogenase (APD) | APDH | *Enterococcus avium* | D-arabitol-phosphate dehydrogenase | GenBank: AY078980.1 | 175 | Q8KQL2 | 176 |
| D-arabitol 5-phosphate + NAD+ ↔ D-ribulose 5-phosphate + NADH + H+ | 1.1.1.- | D-arabitol 5-phosphate 2-dehydrogenase (APD) | APDH | *Enterococcus avium* | D-arabitol-phosphate dehydrogenase | GenBank: AY078980.1 | 175 | Q8KQL2 | 176 |
| D-arabitol 1-phosphate + NAD+ ↔ D-ribulose 1-phosphate + NADH + H+ | 1.1.1.- | D-arabitol 1-phosphate 2-dehydrogenase (APD) | ARD1 | *Candida albicans* (strain WO-1) | D-arabitol 2-dehydrogenase | EMBL Translation: AAC37430.1 | 177 | P43066 | 178 |
| D-arabitol 1-phosphate + NAD+ ↔ D-ribulose 1-phosphate+ NADH + H+ | 1.1.1.- | D-arabitol 1-phosphate 2-dehydrogenase (APD) | ARD1 | *Candida tropicalis* | D-arabitol 2-dehydrogenase | EMBL Translation: AAA66355.1 | 179 | P50166 | 180 |
| D-arabitol 1-phosphate + NAD+ ↔ D-ribulose 1-phosphate + NADH + H+ | 1.1.1.- | D-arabitol 1-phosphate 2-dehydrogenase (APD) | ARDH | *Scheffersomyces stipitis* (strain ATCC 58785) | D-arabitol 2-dehydrogenase | EMBL Translation: CAA86939.1 | 181 | P50167 | 182 |
| D-arabitol 5-phosphate + NAD+ ↔ D-xylulose 1-phosphate + NADH + H+ | 1.1.1.- | D-arabitol 5-phosphate 4-dehydrogenase (APD) | mtlD | *Pseudomonas fluorescens* | D-arabitol 4-dehydrogenase | GenBank: AF007800.1 | 183 | GenBank: AAC04472.1 | 184 |
| D-arabitol 5-phosphate + NAD+ ↔ D-xylulose 1-phosphate + NADH + H+ | 1.1.1.- | D-arabitol 5-phosphate 4-dehydrogenase (APD) | dalD | *Klebsiella pneumoniae* | D-arabitol 4-dehydrogenase | NCBI: NZ_FLCX01000003.1 | 185 | O52720 | 186 |

TABLE 1-continued

| Described Reaction | EC no. | Required enzyme activity | Gene candidate | Source Organism | Natural/ annotated function | Gene Identifier (nt) | SEQ ID NO (nt) | Uniprot ID | SEQ ID NO (AA) |
|---|---|---|---|---|---|---|---|---|---|
| D-arabitol 5-phosphate + NAD+ ↔ D-xylulose 1-phosphate + NADH + H+ | 1.1.1.- | D-arabitol 5-phosphate 4-dehydrogenase (APD) | dalD | Ralstonia solanacearum (strain GMI1000) | D-arabitol 4-dehydrogenase | GeneID: 1220971 | 187 | P58708 | 188 |
| D-arabitol 5-phosphate + NAD+ ↔ D-xylulose 1-phosphate + NADH + H+ | 1.1.1.- | D-arabitol 5-phosphate 4-dehydrogenase (APD) | egsA (araM) | Bacillus subtilis | Glycerol-1-phosphate dehydrogenase | GeneID: 938011 | 189 | P94527 | 190 |
| D-arabitol 1-phosphate + NAD+ ↔ D-ribulose 1-phosphate + NADH + H+ | 1.1.1.- | D-arabitol 1-phosphate 2-dehydrogenase (APD) | egsA (araM) | Bacillus subtilis | Glycerol-1-phosphate dehydrogenase | GeneID: 938011 | 189 | P94527 | 190 |
| D-arabitol 5-phosphate + NAD+ ↔ D-xylulose 1-phosphate + NADH + H+ | 1.1.1.- | D-arabitol 5-phosphate 4-dehydrogenase (APD) | egsA | Aeropyrum pernix (strain ATCC 700893) | Glycerol-1-phosphate dehydrogenase | EMBL: BAA79484.3 | 191 | Q9YER2 | 192 |
| D-arabitol 1-phosphate + NAD+ ↔ D-ribulose 1-phosphate + NADH + H+ | 1.1.1.- | D-arabitol 1-phosphate 2-dehydrogenase (APD) | egsA | Aeropyrum pernix (strain ATCC 700893) | Glycerol-1-phosphate dehydrogenase | EMBL: BAA79484.3 | 191 | Q9YER2 | 192 |
| D-arabitol 5-phosphate + NAD+ ↔ D-xylulose 1-phosphate + NADH + H+ | 1.1.1.- | D-arabitol 5-phosphate 4-dehydrogenase (APD) | gpsA | E. coli | glycerol-3-phosphate dehydrogenase | GeneID: 948125 | 193 | P0A6S7 | 194 |
| D-arabitol 1-phosphate + NAD+ ↔ D-ribulose 1-phosphate + NADH + H+ | 1.1.1.- | D-arabitol 1-phosphate 2-dehydrogenase (APD) | gpsA | E. coli | glycerol-3-phosphate dehydrogenase | GeneID: 948125 | 193 | P0A6S7 | 194 |
| D-arabitol 5-phosphate + NAD+ ↔ D-xylulose 1-phosphate + NADH + H+ | 1.1.1.- | D-arabitol 5-phosphate 4-dehydrogenase (APD) | GPD1 | Saccharomyces cerevisiae | glycerol-3-phosphate dehydrogenase | GeneID: 851539 | 195 | Q00055 | 196 |
| D-arabitol 1-phosphate + NAD+ ↔ D-ribulose 1-phosphate + NADH + H+ | 1.1.1.- | D-arabitol 1-phosphate 2-dehydrogenase (APD) | GPD1 | Saccharomyces cerevisiae | glycerol-3-phosphate dehydrogenase | GeneID: 851539 | 195 | Q00055 | 196 |
| D-xylulose 5-phosphate ↔ D-xylulose 1-phosphate | 5.4.2.- | phosphopentomutase (PPM) | deoB | E. coli | phosphopentomutase | GeneID: 948910 | 197 | P0A6K6 | 198 |
| D-ribulose 5-phosphate ↔ D-ribulose 1-phosphate | 5.4.2.- | phosphopentomutase (PPM) | deoB | E. coli | phosphopentomutase | GeneID: 948910 | 197 | P0A6K6 | 198 |
| D-xylulose 5-phosphate ↔ D-xylulose 1-phosphate | 5.4.2.- | phosphopentomutase (PPM) | pgm | E. coli | alpha-phosphoglucomutase | GeneID: 945271 | 199 | P36938 | 200 |
| D-ribulose 5-phosphate ↔ D-ribulose 1-phosphate | 5.4.2.- | phosphopentomutase (PPM) | pgm | E. coli | alpha-phosphoglucomutase | GeneID: 945271 | 199 | P36938 | 200 |
| D-xylulose 5-phosphate ↔ D-xylulose 1-phosphate | 5.4.2.- | phosphopentomutase (PPM) | pgcA | Bacillus subtilis | alpha-phosphoglucomutase | GeneID: 936247 | 201 | P18159 | 202 |
| D-ribulose 5-phosphate ↔ D-ribulose 1-phosphate | 5.4.2.- | phosphopentomutase (PPM) | pgcA | Bacillus subtilis | alpha-phosphoglucomutase | GeneID: 936247 | 201 | P18159 | 202 |
| D-xylulose 5-phosphate ↔ D-xylulose 1-phosphate | 5.4.2.- | phosphopentomutase (PPM) | pgmB | Lactococcus lactis | beta-phosphoglucomutas | GeneID: 1114041 | 203 | P71447 | 204 |
| D-ribulose 5-phosphate ↔ D-ribulose 1-phosphate | 5.4.2.- | phosphopentomutase (PPM) | pgmB | Lactococcus lactis | beta-phosphoglucomutas | GeneID: 1114041 | 203 | P71447 | 204 |
| D-xylulose 5-phosphate ↔ D-xylulose 1-phosphate | 5.4.2.- | phosphopentomutase (PPM) | ycjU | E. coli | beta-phosphoglucomutas | GeneID: 945891 | 205 | P77366 | 206 |
| D-ribulose 5-phosphate ↔ D-ribulose 1-phosphate | 5.4.2.- | phosphopentomutase (PPM) | ycjU | E. coli | beta-phosphoglucomutas | GeneID: 945891 | 205 | P77366 | 206 |
| D-ribulose 5-phosphate ↔ D-ribulose 1-phosphate | 5.4.2.7 | phosphopentomutase (PPM) | PGM3 (PRM15) | Saccharomyces cerevisiae | phosphoribomutase | GenBank: NM_001182 785.1 Gene ID: 855321 | 255 | Q03262 | 258 |
| D-xylulose 5-phosphate ↔ D-xylulose 1-phosphate | 5.4.2.- | phosphopentomutase (PPM) | algC | Pseudomonas aeruginosa | phosphomannomutase | GenBank: M60873.1 | 207 | P26276 | 208 |

TABLE 1-continued

| Described Reaction | EC no. | Required enzyme activity | Gene candidate | Source Organism | Natural/ annotated function | Gene Identifier (nt) | SEQ ID NO (nt) | Uniprot ID | SEQ ID NO (AA) |
|---|---|---|---|---|---|---|---|---|---|
| D-ribulose 5-phosphate ↔ D-ribulose 1-phosphate | 5.4.2.- | phospho-pentomutase (PPM) | algC | Pseudomonas aeruginosa | phospho-mannose mutase | GenBank: M60873.1 | 207 | P26276 | 208 |
| D-xylulose 5-phosphate ↔ D-xylulose 1-phosphate | 5.4.2.- | phospho-pentomutase (PPM) | cpsG | E. coli | phospho-mannose mutase | GeneID: 946574 | 209 | P24175 | 210 |
| D-ribulose 5-phosphate ↔ D-ribulose 1-phosphate | 5.4.2.- | phospho-pentomutase (PPM) | cpsG | E. coli | phospho-mannose mutase | GeneID: 946574 | 209 | P24175 | 210 |
| D-fructose 6-phosphate + phosphate ↔ acetylphosphate + D-erythrose 4-phosphate + H2O | 4.1.2.22 | fructose 6-phosphate phospho-ketolase (Fpk) | BDP_1006 | Bifidobacterium dentium | fructose 6-phosphate phospho-ketolase | EMBL: ADB09649.1 | 211 | D2QA13 | 212 |
| D-fructose 6-phosphate + phosphate ↔ acetyl phosphate + D-erythrose 4-phosphate + H2O | 4.1.2.22 | fructose 6-phosphate phospho-ketolase (Fpk) | xfp | Bifidobacterium lactis | Xylulose-5-phosphate/ fructose-6-phosphate phosphoketolase | GeneID: 29696432 | 213 | Q9AEM9 | 214 |
| D-fructose 6-phosphate + phosphate ↔ acetyl phosphate + D-erythrose 4-phosphate + H2O | 4.1.2.22 | fructose 6-phosphate phospho-ketolase (Fpk) | xpkA | Lactobacillus paraplantarum | phosphoketolase | EMBL: AAQ64626.2 | 215 | Q6UPD8 | 216 |
| D-fructose 6-phosphate + phosphate ↔ acetyl phosphate + D-erythrose 4-phosphate + H2O | 4.1.2.22 | fructose 6-phosphate phospho-ketolase (Fpk) | xfp | Bifidobacterium breve | phosphoketolase | EMBL: ADF97524.1 | 217 | D6PAH1 | 218 |
| Acetyl-CoA + phosphate ↔ CoA + acetyl phosphate. | 2.3.1.8 | Phosphate acetyl-transferase | pta | E. coli | Phosphate acetyltransferase | GeneID: 946778 | 219 | P0A9M8 | 220 |
| Acetyl-CoA + phosphate ↔ CoA + acetyl phosphate. | 2.3.1.8 | Phosphate acetyl-transferase | pta | Clostridium acetobutylicum | Phosphate acetyltransferase | GeneID: 1117925 | 221 | P71103 | 222 |
| hydroxypyruvate + H ↔ CO2 + glycolaldehyde | 4.1.1.- | Hydroxy-pyruvate decarboxylase | kivd | Lactococcus lactis | a-ketoisovalerate decarboxylase | GenBank: AJ746364.1 | 223 | Q684J7 | 224 |
| hydroxypyruvate + H ↔ CO2 + glycolaldehyde | 4.1.1.- | Hydroxy-pyruvate decarboxylase | sucA | E. coli | 2-oxoglutarate decarboxylase | GeneID: 945303 | 225 | P0AFG3 | 226 |
| 3-phospho-D-glycerate + NAD+ ↔ 3-phospho-hydroxypyruvate + NADH + H+ | 1.1.1.95 | D-3-phospho-glycerate dehydrogenase | serA | E. coli | D-3-phosphoglycerate dehydrogenase | GeneID: 945258 | 227 | P0A9T0 | 228 |
| 3-phospho-L-serine + 2-oxoglutarate ↔ L-glutamate + 3-phospho-hydroxypyruvate | 2.6.1.52 | Phosphoserine amino-transferase | serC | E. coli | Phosphoserine aminotransferase | GeneID: 945527 | 229 | P23721 | 230 |
| 3-phospho-hydroxypyruvate + H2O → hydroxy-pyruvate + phosphate | — | 3-phospho-hydroxy pyruvate phosphatase | yeaB (nudL) | E. coli | putative CoA pyrophos phohydrolase | GeneID: 946330 | 231 | P43337 | 232 |
| 3-phospho-L-serine + H2O → L-serine + phosphate | 3.1.3.3 | Phosphoserine phosphatase | serB | E. coli | Phosphoserine phosphatase | GeneID: 948913 | 233 | P0AGB0 | 234 |
| L-serine + H+ → ethanolamine + CO2 | 4.1.1.65 | serine decarboxylase | AtSDC (AT1G43710) | Arabidopsis thaliana | serine decarboxylase | GeneID: 840958 | 235 | Q9MA74 | 236 |
| ethanolamine + oxygen + H2O → ammonium + hydrogen peroxide + glycolaldehyde | 1.4.3.8 | Ethanolamine oxidase | tynA | E. coli | amine oxidase | GeneID: 945939 | 237 | P46883 | 238 |
| ethanolamine + 2-oxoglutarate → glycolaldehyde + L-glutamate | 2.6.1.- | Ethanolamine amino-transferase | alaA | E. coli | glutamate-pyruvate amino-transferase | GeneID: 946772 | 239 | P0A959 | 240 |
| D-glycerate + NAD(P)+ ↔ hydroxy-pyruvate + NAD(P)H + H+ | 1.1.1.- | Hydroxy-pyruvate reductase | ghrB | E. coli | glyoxylate reductase | GeneID: 948074 | 241 | P37666 | 242 |

TABLE 1-continued

| Described Reaction | EC no. | Required enzyme activity | Gene candidate | Source Organism | Natural/annotated function | Gene Identifier (nt) | SEQ ID NO (nt) | Uniprot ID | SEQ ID NO (AA) |
|---|---|---|---|---|---|---|---|---|---|
| pyruvate + L-serine ↔ L-alanine + hydroxypyruvate | 2.6.1.51 | serine-pyruvate amino-transferase | AGXT1 | *Homo sapiens* | serine-pyruvate amino-transferase | GeneID: 189, CCDS2543.1 | 243 | P21549 | 244 |
| 3-phospho-D-glycerate + H2O → D-glycerate + phosphate | 3.1.3.38 | 3-phospho-glycerate phosphatase | phoA | *E. coli* | phospho-glycerate phosphatase | GeneID: 945041 | 245 | P00634 | 246 |
| 2-phospho-D-glycerate + H2O → D-glycerate + phosphate | 3.1.3.20 | 2-phospho-glycerate phosphatase | phoA | *E. coli* | phospho-glycerate phosphatase | GeneID: 945041 | 245 | P00634 | 246 |
| D-glycerate + ATP ↔ 3-phospho-D-glycerate + ADP + H+ | 2.7.1.31 | Glycerate 3-kinase | GLYK | *Arabidopsis thaliana* | Glycerate 3-kinase | GeneID: 844378, mRNA NM_179581.2 | 247 | Q944I4 | 248 |
| D-glycerate + ATP ↔ 2-phospho-D-glycerate + ADP + H+ | 2.7.1.165 | Glycerate 2-kinase | glxK | *E. coli* | Glycerate 2-kinase | GeneID: 945129 | 249 | P77364 | 250 |
| D-glycerate + ATP ↔ 2-phospho-D-glycerate + ADP + H+ | 2.7.1.165 | Glycerate 2-kinase | garK | *E. coli* | Glycerate 2-kinase | GeneID: 947632 | 251 | P23524 | 252 |

D-Tagatose 3-Epimerase (EC 5.1.3.31)

The present disclosure describes enzymes that can catalyze the epimerization of various ketoses at the C-3 position, interconverting D-fructose and D-psicose, D-tagatose and D-sorbose, D-ribulose and D-xylulose, and L-ribulose and L-xylulose. The specificity depends on the species. The enzymes from *Pseudomonas cichorii* and *Rhodobacter sphaeroides* require $Mn^{2+}$. In one embodiment, the enzyme is D-tagatose 3-epimerase (dte). In another embodiment, the D-tagatose 3-epimerase catalyzes the conversion of D-xylulose to D-ribulose.

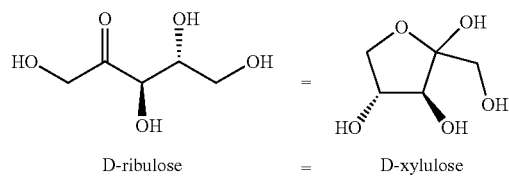 [SMILES: O=C(CO)[C@H](O)[C@H](O)CO ; OCC1(O)OC[C@@H](O)[C@@H]1O]

In one embodiment, the D-tagatose 3-epimerase is encoded by one or more nucleic acid molecules obtained from a microorganism selected from the group consisting of *Pseudomonas* sp., *Mesorhizobium* sp. and *Rhodobacter* sp. In some embodiments, the D-tagatose 3-epimerase is encoded by one or more nucleic acid molecules obtained from a microorganism selected from the group consisting of *Pseudomonas cichorii*, *Pseudomonas* sp. ST-24, *Mesorhizobium loti* and *Rhodobacter sphaeroides*. In some embodiments, the one or more nucleic acid molecules is dte and/or FJ851309.1, or homolog thereof. In a further embodiment, the D-tagatose 3-epimerase comprises an amino acid sequence selected from the group consisting of SEQ ID NOs: 3 and 5. In yet a further embodiment, the D-tagatose 3-epimerase is encoded by a nucleic acid sequence selected from the group consisting of SEQ ID NOs: 1, 2 and 4.

D-tagatose 3-epimerase may also be known as L-ribulose 3-epimerase or ketose 3-epimerase.

D-ribulokinase (EC 2.7.1.16)

The present disclosure describes enzymes that can catalyze the following reactions:

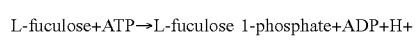

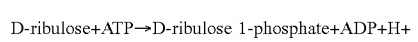

D-ribulokinase may also be known as L-fuculokinase, fuculokinase, ATP: L-fuculose 1-phosphotransferase or L-fuculose kinase.

Thus, in some embodiments, the disclosure provides for an enzyme that plays roles in the fucose degradation pathway, the super pathway of fucose and rhamnose degradation and/or the D-arabinose degradation I pathway.

In some embodiments, the enzyme can function as both an L-fucolokinase and a D-ribulokinase, the second enzyme of the L-fucose and D-arabinose degradation pathways, respectively.

In particular embodiments, the enzyme converts D-ribulose to D-ribulose-1-phosphate. In one embodiment, the D-ribulokinase is encoded by one or more nucleic acid molecules obtained from *E. coli*. In some embodiments, the one or more nucleic acid molecules is fucK, or homolog thereof. In a further embodiment, the D-ribulokinase comprises an amino acid sequence set forth in SEQ ID NO: 8. In yet a further embodiment, the D-ribulokinase is encoded by a nucleic acid sequence selected from the group consisting of SEQ ID NOs: 6 and 7.

D-Ribulose-1-Phosphate Aldolase (EC 4.1.2.17)

The present disclosure describes enzymes that can catalyze the following reversible reactions:

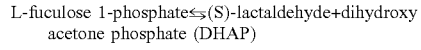

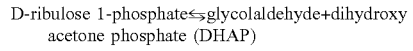

D-ribulose-1-phosphate aldolase may also be known as L-fuculose-phosphate aldolase, L-fuculose 1-phosphate aldolase or L-fuculose-1-phosphate (S)-lactaldehyde-lyase.

Thus, in some embodiments, the disclosure provides for an enzyme that plays roles in the fucose degradation pathway, the super pathway of fucose and rhamnose degradation and/or the D-arabinose degradation I pathway. In one embodiment, the enzyme may use $Zn^{2+}$ as a cofactor. In another embodiment, an inhibitor of this enzyme may be phosphoglycolohydroxamate.

In some embodiments, the enzyme can function as both an L-fuculose-phosphate aldolase and a D-ribulose-phosphate aldolase, the third enzyme of the L-fucose and D-arabinose degradation pathways, respectively.

The substrate specificity of the enzyme has been tested with a partially purified preparation from an *E. coli* strain.

Crystal structures of the enzyme and a number of point mutants have been solved. The combination of structural data and enzymatic activity of mutants allowed modelling and refinement of the catalytic mechanism of the enzyme. The enantiomeric selectivity of the enzyme has been studied.

In particular embodiments, the enzyme converts D-ribulose-1-phosphate to glycolaldehyde and DHAP. In one embodiment, the D-ribulose-1-phosphate aldolase is encoded by one or more nucleic acid molecules obtained from *E. coli*. In some embodiments, the one or more nucleic acid molecules is fucA, or homolog thereof. In a further embodiment, the D-ribulose-1-phosphate aldolase comprises an amino acid sequence set forth in SEQ ID NO: 11. In yet a further embodiment, the D-ribulose-1-phosphate aldolase is encoded by a nucleic acid sequence selected from the group consisting of SEQ ID NOs: 9 and 10.

Glycolaldehyde Reductase (EC 1.1.1.77)

The present disclosure describes enzymes that can catalyze the following reversible reactions:

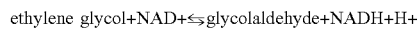

ethylene glycol+NAD+⇌glycolaldehyde+NADH+H+

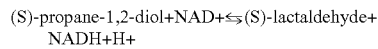

(S)-propane-1,2-diol+NAD+⇌(S)-lactaldehyde+ NADH+H+

Glycolaldehyde reductase may also be known as lactaldehyde reductase, propanediol oxidoreductase, (R) [or(S)]-propane-1,2-diol:NAD+ oxidoreductase or L-1,2-propanediol oxidoreductase.

Thus, in some embodiments, the disclosure provides for an enzyme that plays roles in the ethylene glycol degradation pathway, the super pathway of glycol metabolism and degradation, the anaerobic L-lactaldehyde degradation pathway and/or the super pathway of fucose and rhamnose degradation. In one embodiment, the enzyme may use $Fe^{2+}$ as a cofactor.

L-1,2-propanediol oxidoreductase is an iron-dependent group III dehydrogenase. It anaerobically reduces L-lactaldehyde, a product of both the L-fucose and L-rhamnose catabolic pathways, to L-1,2-propanediol, which is then excreted from the cell.

Crystal structures of the enzyme have been solved, showing a domain-swapped dimer in which the metal, cofactor and substrate binding sites could be located. An aspartate and three conserved histidine residues are required for $Fe^{2+}$ binding and enzymatic activity.

In vitro, the enzyme can be reactivated by high concentrations of NAD+ and efficiently inactivated by a mixture of $Fe^3$ and ascorbate or $Fe^{2+}$ and $H_2O_2$. Metal-catalyzed oxidation of the conserved His277 residue is proposed to be the cause of the inactivation.

Expression of FucO enables engineered one-turn reversal of the β-oxidation cycle. FucO activity contributes to the conversion of isobutyraldehyde to isobutanol in an engineered strain.

In particular embodiments, the enzyme converts glycolaldehyde to MEG. In some embodiments, the glycolaldehyde reductase is from *Escherichia coli*. In some embodiments, the glycolaldehyde reductase is encoded by the fucO gene.

In one embodiment, the glycolaldehyde reductase is encoded by one or more nucleic acid molecules obtained from a microorganism selected from *E. coli* and *S. cerevisiae*. In another embodiment, the one or more nucleic acid molecules is selected from gldA, GRE2, GRE3, yqhD, ydjG, fucO, yafB (dkgB), and/or yqhE (dkgA), or homolog thereof. In another embodiment, the one or more nucleic acid molecules is yqhD. In some embodiments, the yqhD comprises a G149E mutation. In a further embodiment, the glycolaldehyde reductase comprises an amino acid sequence selected from the group consisting of SEQ ID NOs: 13, 15, 17, 20, 23, 25, 28, 30 and 32. In yet a further embodiment, the glycolaldehyde reductase is encoded by a nucleic acid sequence selected from the group consisting of SEQ ID NOs: 12, 14, 16, 18, 19, 21, 22, 24, 26, 27, 29 and 31.

Aldehyde Reductases

A number of aldehyde reductases may be used to convert glycolaldehyde to MEG.

An NADPH-dependent aldehyde reductase (YqhD) can catalyze the following reactions:

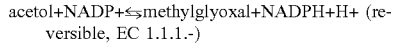

acetol+NADP+⇌methylglyoxal+NADPH+H+ (reversible, EC 1.1.1.-)

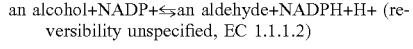

an alcohol+NADP+⇌an aldehyde+NADPH+H+ (reversibility unspecified, EC 1.1.1.2)

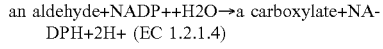

an aldehyde+NADP++H2O→a carboxylate+NADPH+2H+ (EC 1.2.1.4)

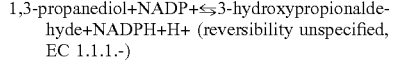

1,3-propanediol+NADP+⇌3-hydroxypropionaldehyde+NADPH+H+ (reversibility unspecified, EC 1.1.1.-)

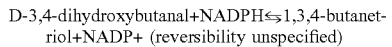

D-3,4-dihydroxybutanal+NADPH⇌1,3,4-butanetriol+NADP+ (reversibility unspecified)

YqhD is an NADPH-dependent aldehyde reductase that may be involved in glyoxal detoxification and/or be part of a glutathione-independent response to lipid peroxidation.

It has been reported that various alcohols, aldehydes, amino acids, sugars and α-hydroxy acids have been tested as substrates for YqhD. The purified protein only shows NADP-dependent alcohol dehydrogenase activity, with a preference for alcohols longer than C(3), but with Km values in the millimolar range, suggesting that they are not the physiological substrates. In contrast, YqhD does exhibit short-chain aldehyde reductase activity with substrates such as propanaldehyde, acetaldehyde, and butanaldehyde, as well as acrolein and malondialdehyde. In a metabolically engineered strain, phenylacetaldehyde and 4-hydroxyphenylacetaldehyde are reduced to 2-phenylethanol and 2-(4-hydroxyphenyl)ethanol by the endogenous aldehyde reductases YqhD, YjgB, and YahK.

Overexpression of YqhD increases 1,3-propanediol oxidoreductase activity of the cell. *E. coli* has been engineered to express YqhD for the industrial production of 1,3-propanediol. YqhD activity contributes to the production of isobutanol, 1,2-propanediol, 1,2,4-butanetriol and acetol as well. Mutation of yqhD enables production of butanol by an engineered one-turn reversal of the β-oxidation cycle.

YqhD has furfural reductase activity, which appears to cause growth inhibition due to depletion of NADPH in metabolically engineered strains that produce alcohol from lignocellulosic biomass.

The crystal structure of YqhD has been solved at 2 Å resolution. YqhD is an asymmetric dimer of dimers, and the active site contains a $Zn^{2+}$ ion. The NADPH cofactor is modified by hydroxyl groups at positions 5 and 6 in the nicotinamide ring.

Overexpression of yqhD leads to increased resistance to reactive oxygen-generating compounds such as hydrogen peroxide, paraquat, chromate and potassium tellurite. A yqhD deletion mutant shows increased sensitivity to these compounds and to glyoxal, and contains increased levels of reactive aldehydes that are generated during lipid peroxidation. Conversely, yqhD deletion leads to increased furfural tolerance.

In particular embodiments, an NADPH-dependent aldehyde reductase converts glycolaldehyde to MEG. In some embodiments, the NADPH-dependent aldehyde reductase is from *Escherichia coli*. In some embodiments, the NADPH-dependent aldehyde reductase is encoded by the yqhD gene.

A multi-functional methylglyoxal reductase (DkgA) can catalyze the following reactions:

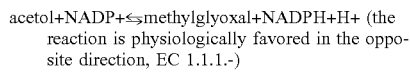
acetol+NADP+⇌methylglyoxal+NADPH+H+ (the reaction is physiologically favored in the opposite direction, EC 1.1.1.-)

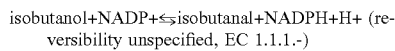
isobutanol+NADP+⇌isobutanal+NADPH+H+ (reversibility unspecified, EC 1.1.1.-)

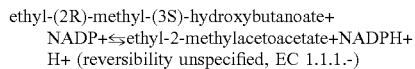
ethyl-(2R)-methyl-(3S)-hydroxybutanoate+ NADP+⇌ethyl-2-methylacetoacetate+NADPH+ H+ (reversibility unspecified, EC 1.1.1.-)

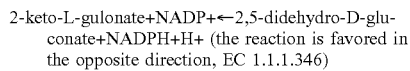
2-keto-L-gulonate+NADP+←2,5-didehydro-D-gluconate+NADPH+H+ (the reaction is favored in the opposite direction, EC 1.1.1.346)

DkgA (YqhE) belongs to the aldo-keto reductase (AKR) family and has been shown to have methylglyoxal reductase and beta-keto ester reductase activity.

dkgA is reported to encode a 2,5-diketo-D-gluconate reductase (25DKGR) A, one of two 25DKG reductases in *E. coli*. The enzyme uses NADPH as the preferred electron donor and is thought to be involved in ketogluconate metabolism. The specific activity of the enzyme towards 2,5-diketo-D-gluconate is reported to be almost 1000-fold lower than its activity towards methylglyoxal.

Due to its low Km for NADPH, reduction of furans by DkgA may deplete NADPH pools and thereby limit cellular biosynthesis. A broad survey of aldehyde reductases showed that DkgA was one of several endogenous aldehyde reductases that contribute to the degradation of desired aldehyde end products of metabolic engineering.

A crystal structure of DkgA has been solved at 2.16 Å resolution.

In particular embodiments, a multi-functional methylglyoxal reductase converts glycolaldehyde to MEG. In some embodiments, the multi-functional methylglyoxal reductase is from *Escherichia coli*. In some embodiments, the multi-functional methylglyoxal reductase is encoded by the dkgA gene.

A multi-functional methylglyoxal reductase (DkgB) can catalyze the following reactions:

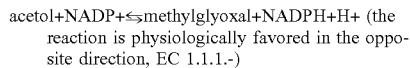
acetol+NADP+⇌methylglyoxal+NADPH+H+ (the reaction is physiologically favored in the opposite direction, EC 1.1.1.-)

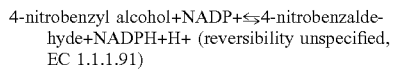
4-nitrobenzyl alcohol+NADP+⇌4-nitrobenzaldehyde+NADPH+H+ (reversibility unspecified, EC 1.1.1.91)

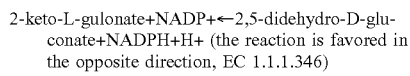
2-keto-L-gulonate+NADP+←2,5-didehydro-D-gluconate+NADPH+H+ (the reaction is favored in the opposite direction, EC 1.1.1.346)

DkgB (YafB) is a member of the aldo-keto reductase (AKR) subfamily 3F. DkgB was shown to have 2,5-diketo-D-gluconate reductase, methylglyoxal reductase and 4-nitrobenzaldehyde reductase activities.

dkgB is reported to encode 2,5-diketo-D-gluconate reductase (25DKGR) B, one of two 25DKG reductases in *E. coli*. The enzyme uses NADPH as the preferred electron donor and is thought to be involved in ketogluconate metabolism. However, the specific activity of the enzyme towards 2,5-diketo-D-gluconate is reported to be almost 1000-fold lower than its activity towards methylglyoxal.

In particular embodiments, a multi-functional methylglyoxal reductase converts glycolaldehyde to MEG. In some embodiments, the multi-functional methylglyoxal reductase is from *Escherichia coli*. In some embodiments, the multi-functional methylglyoxal reductase is encoded by the dkgB gene.

A methylglyoxal reductase (YeaE) can catalyze the following reaction:

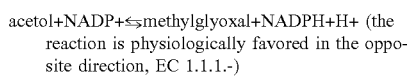
acetol+NADP+⇌methylglyoxal+NADPH+H+ (the reaction is physiologically favored in the opposite direction, EC 1.1.1.-)

YeaE has been shown to have methylglyoxal reductase activity.

The subunit structure of YeaE has not been determined, but its amino acid sequence similarity to the aldo-keto reductases DkgA (YqhE) and DkgB (YafB) suggests that it may be monomeric.

In particular embodiments, a methylglyoxal reductase converts glycolaldehyde to MEG. In some embodiments, the methylglyoxal reductase is from *Escherichia coli*. In some embodiments, the methylglyoxal reductase is encoded by the yeaE gene.

A L-glyceraldehyde 3-phosphate reductase (yghZ) can catalyze the following reactions:

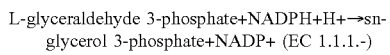
L-glyceraldehyde 3-phosphate+NADPH+H+→sn-glycerol 3-phosphate+NADP+ (EC 1.1.1.-)

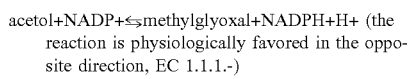
acetol+NADP+⇌methylglyoxal+NADPH+H+ (the reaction is physiologically favored in the opposite direction, EC 1.1.1.-)

YghZ is an L-glyceraldehyde 3-phosphate (L-GAP) reductase. The enzyme is also able to detoxify methylglyoxal at a low rate. YghZ defines the AKR14 (aldo-keto reductase 14) protein family.

L-GAP is not a natural metabolite and is toxic to *E. coli*. L-GAP is a substrate of both the glycerol-3-phosphate and hexose phosphate transport systems of *E. coli* K-12. It has been postulated that the physiological role of YghZ is the detoxification of L-GAP, which may be formed by non-enzymatic racemization of GAP or by an unknown cellular process.

The crystal structure of the *E. coli* enzyme has been determined and is suggested to be a tetramer. However, others have found that the protein forms an octamer based on gel filtration and electron microscopy studies.

In particular embodiments, a L-glyceraldehyde 3-phosphate reductase converts glycolaldehyde to MEG. In some embodiments, the L-glyceraldehyde 3-phosphate reductase is from *Escherichia coli*. In some embodiments, the L-glyceraldehyde 3-phosphate reductase is encoded by the yghZ gene.

An L-1,2-propanediol dehydrogenase/glycerol dehydrogenase (GldA) can catalyze the following reactions:

(S)-propane-1,2-diol+NAD+⇌acetol+NADH+H+ (reversible reaction)

aminoacetone+NADH+H+→(R)-1-aminopropan-2-ol+NAD+ (EC 1.1.1.75)

glycerol+NAD+⇌dihydroxyacetone+NADH+H+ (reversible reaction, EC 1.1.1.6)

The physiological function of the GldA enzyme has long been unclear. The enzyme was independently isolated as a glycerol dehydrogenase and a D-1-amino-2-propanol:NAD+ oxidoreductase. At that time, D-1-amino-2-propanol was thought to be an intermediate for the biosynthesis of vitamin B12, and although *E. coli* is unable to synthesize vitamin B12 de novo, enzymes catalyzing the synthesis of this compound were sought. It was later found that GldA was responsible for both activities.

The primary in vivo role of GldA was recently proposed to be the removal of dihydroxyacetone by converting it to glycerol. However, a dual role in the fermentation of glycerol has also recently been established. Glycerol dissimilation in *E. coli* can be accomplished by two different pathways. The glycerol and glycerophosphodiester degradation pathway requires the presence of a terminal electron acceptor and utilizes an ATP-dependent kinase of the Glp system, which phosphorylates glycerol to glycerol-3-phosphate. However, upon inactivation of the kinase and selection for growth on glycerol, it was found that an NAD+-linked dehydrogenase, GldA, was able to support glycerol fermentation. Recently, it was shown that GldA was involved in glycerol fermentation both as a glycerol dehydrogenase, producing dihydroxyacetone, and as a 1,2-propanediol dehydrogenase, regenerating NAD+ by producing 1,2-propanediol from acetol.

The enzyme is found in two catalytically active forms, a large form of eight subunits and a small form of two subunits. The large form appears to be the major species.

In particular embodiments, an L-1,2-propanediol dehydrogenase/glycerol dehydrogenase converts glycolaldehyde to MEG. In some embodiments, the L-1,2-propanediol dehydrogenase/glycerol dehydrogenase is from *Escherichia coli*. In some embodiments, the L-1,2-propanediol dehydrogenase/glycerol dehydrogenase is encoded by the gldA gene.

An NADPH-dependent methylglyoxal reductase (GRE2) from *Saccharomyces cerevisiae* can catalyze the following reactions:

(S)-lactaldehyde+NADP+⇌methylglyoxal+NADPH 3-methylbutanol+NAD(P)+⇌3-methylbutanal+NAD(P)H Gre2 is a versatile enzyme that catalyzes the stereoselective reduction of a broad range of substrates including aliphatic and aromatic ketones, diketones, as well as aldehydes, using NADPH as the cofactor.

The crystal structures of Gre2 from *S. cerevisiae* in an apo-form at 2.00 Å and NADPH-complexed form at 2.40 Å resolution have been solved. Gre2 forms a homodimer, each subunit of which contains an N-terminal Rossmann-fold domain and a variable C-terminal domain, which participates in substrate recognition. The induced fit upon binding to the cofactor NADPH makes the two domains shift toward each other, producing an interdomain cleft that better fits the substrate. Computational simulation combined with site-directed mutagenesis and enzymatic activity analysis enabled characterization of a potential substrate-binding pocket that determines the stringent substrate stereoselectivity for catalysis.

Gre2 catalyzes the irreversible reduction of the cytotoxic compound methylglyoxal (MG) to (S)-lactaldehyde as an alternative to detoxification of MG by glyoxalase I GLO1. MG is synthesized via a bypath of glycolysis from dihydroxyacetone phosphate and is believed to play a role in cell cycle regulation and stress adaptation. GRE2 also catalyzes the reduction of isovaleraldehyde to isoamylalcohol. The enzyme serves to suppress isoamylalcohol-induced filamentation by modulating the levels of isovaleraldehyde, the signal to which cells respond by filamentation. GRE2 is also involved in ergosterol metabolism.

In particular embodiments, an NADPH-dependent methylglyoxal reductase converts glycolaldehyde to MEG. In some embodiments, the NADPH-dependent methylglyoxal reductase is from *S. cerevisiae*. In some embodiments, the NADPH-dependent methylglyoxal reductase is encoded by the GRE2 gene.

Thiolase/Acetyl coenzyme A acetyltransferase (EC 2.3.1.9)

The present disclosure describes enzymes that can catalyze the following reaction:

2 acetyl-CoA⇌acetoacetyl-CoA+coenzyme A (reversible reaction)

Thiolase/Acetyl coenzyme A acetyltransferase may also be known as acetyl-CoA-C-acetyltransferase, acetoacetyl-CoA thiolase, acetyl-CoA:acetyl-CoA C-acetyltransferase or thiolase II.

Thus, in some embodiments, the disclosure provides for an enzyme that plays a role in acetoacetate degradation (to acetyl CoA). In one embodiment, an inhibitor of this enzyme may be acetoacetyl-CoA.

In particular embodiments, the enzyme converts acetyl-CoA to acetoacetyl-CoA. In one embodiment, the thiolase or acetyl coenzyme A acetyltransferase is encoded by one or more nucleic acid molecules obtained from a microorganism selected from the group consisting of *Clostridium* sp., *Bacillus* sp., *E. coli*, *Saccharomyces* sp. and *Marinobacter* sp. In some embodiments, the thiolase or acetyl coenzyme A acetyltransferase is encoded by one or more nucleic acid molecules obtained from a microorganism selected from the group consisting of *Clostridium acetobutylicum*, *Clostridium thermosaccharolyticum*, *Bacillus cereus*, *E. coli*, *Saccharomyces cerevisiae* and *Marinobacter hydrocarbonoclasticus*. In some embodiments, the one or more nucleic acid molecules is thlA, atoB and/or ERG10, or homolog thereof. In a further embodiment, the thiolase or acetyl coenzyme A acetyltransferase comprises an amino acid sequence selected from the group consisting of SEQ ID NOs: 35, 37 and 40. In yet a further embodiment, the thiolase or acetyl coenzyme A acetyltransferase is encoded by a nucleic acid sequence selected from the group consisting of SEQ ID NOs: 33, 34, 36, 38 and 39.

Acetyl-CoA:Acetoacetate-CoA Transferase (EC 2.8.3.-)

The present disclosure describes enzymes that can catalyze the following reaction:

acetoacetate+acetyl-CoA⇌acetoacetyl-CoA+acetate (reversible reaction, EC 2.8.3.-)

Acetyl-CoA:acetoacetate-CoA transferase may also be known as acetate:acetoacetyl-CoA transferase or acetoacetyl-CoA transferase.

Thus, in some embodiments, the disclosure provides for an enzyme that plays a role in acetoacetate degradation (to acetyl CoA). In one embodiment, inhibitors of this enzyme may include acetyl-CoA and coenzyme A.

The growth of *E. coli* on short-chain fatty acids (C3-C6) requires the activation of the acids to their respective thioesters. This activation is catalyzed by acetoacetyl-CoA transferase. The reaction takes place in two half-reactions which involves a covalent enzyme-CoA. The enzyme undergoes two detectable conformational changes during the reaction. It is thought likely that the reaction proceeds by a ping-pong mechanism. The enzyme can utilize a variety of short-chain acyl-CoA and carboxylic acid substrates but exhibits maximal activity with normal and 3-keto substrates.

In particular embodiments, the enzyme converts acetoacetyl-CoA to acetoacetate. In some embodiments, the acetyl-CoA:acetoacetate-CoA transferase is from *Clostridium* spp. In some embodiments, the acetyl-CoA:acetoacetate-CoA transferase is from *Clostridium acetobutylicum*. In some embodiments, the acetyl-CoA:acetoacetate-CoA transferase is from *Escherichia coli*. In some embodiments, the acetyl-CoA:acetoacetate-CoA transferase is encoded by the atoA and atoD genes. In another embodiment, the subunit composition of acetoacetyl-CoA transferase is [(AtoA)₂][(AtoD)₂], with (AtoA)₂ being the β complex and (AtoD)₂ being the α complex. In one embodiment, the acetyl-CoA:acetoacetate-CoA transferase is a fused acetyl-CoA:acetoacetate-CoA transferase: α subunit/β subunit. In another embodiment, the acetyl-CoA:acetoacetate-CoA transferase is encoded by the ydiF gene.

Acetate:Acetoacetyl-CoA Hydrolase (EC 3.1.2.11)

The present disclosure describes enzymes that can catalyze the following reaction:

acetoacetyl-CoA+H$_2$O⇌CoA+acetoacetate

Acetoacetyl-CoA hydrolase may also be known as acetoacetyl coenzyme A hydrolase, acetoacetyl CoA deacylase or acetoacetyl coenzyme A deacylase.

This enzyme belongs to the family of hydrolases, specifically those acting on thioester bonds.

In particular embodiments, the enzyme converts acetoacetyl-CoA to acetoacetate. In some embodiments, the acetate:acetoacetyl-CoA hydrolase is from *Clostridium* spp. In some embodiments, the acetate:acetoacetyl-CoA hydrolase is from *Clostridium acetobutylicum*. In another embodiment, the Acetoacetyl-CoA hydrolase is encoded by the ctfA (subunit A) and/or ctfB (subunit B) genes.

In a further embodiment, the acetyl-CoA:acetoacetate-CoA transferase or acetate:acetoacetyl-CoA hydrolase comprises an amino acid sequence selected from the group consisting of SEQ ID NOs: 43, 46, 97, 99, 101 and 103. In yet a further embodiment, the acetyl-CoA:acetoacetate-CoA transferase or acetate:acetoacetyl-CoA hydrolase is encoded by a nucleic acid sequence selected from the group consisting of SEQ ID NOs: 41, 42, 44, 45, 96, 98, 100 and 102.

Acetoacetate Decarboxylase (EC 4.1.1.4)

The present disclosure describes enzymes that can catalyze the following reaction:

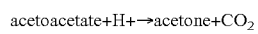

acetoacetate+H+→acetone+CO$_2$

Acetoacetate decarboxylase may also be known as ADC, AADC or acetoacetate carboxy-lyase.

Thus, in some embodiments, the disclosure provides for an enzyme that plays roles in isopropanol biosynthesis, pyruvate fermentation to acetone, the super pathway of *Clostridium acetobutylicum* acidogenic and solventogenic fermentation and/or the super pathway of *Clostridium acetobutylicum* solventogenic fermentation.

Acetoacetate decarboxylase (ADC) plays a key role in solvent production in *Clostridium acetobutylicum*. During the acidogenic phase of growth, acids accumulate causing a metabolic shift to solvent production. In this phase acids are re-assimilated and metabolized to produce acetone, butanol and ethanol.

Preliminary purification and crystallization of the enzyme has revealed that a lysine residue is implicated in the active site. The enzyme is a large complex composed of 12 copies of a single type of subunit.

The enzyme of *Clostridium acetobutylicum* ATCC 824 has been purified and the adc gene encoding it cloned. The enzyme has also been purified from the related strain *Clostridium acetobutylicum* DSM 792 and the gene cloned and sequenced. The decarboxylation reaction proceeds by the formation of a Schiff base intermediate.

ADC is a key enzyme in acid uptake, effectively pulling the CoA-transferase reaction in the direction of acetoacetate formation.

In particular embodiments, the enzyme converts acetoacetate to acetone. In one embodiment, the acetoacetate decarboxylase is encoded by one or more nucleic acid molecules obtained from a microorganism selected from the group consisting of *Clostridium* sp., *Bacillus* sp., *Chromobacterium* sp. and *Pseudomonas* sp. In another embodiment, the acetoacetate decarboxylase is encoded by one or more nucleic acid molecules obtained from a microorganism selected from the group consisting of *Clostridium acetobutylicum, Clostridium beijerinckii, Clostridium cellulolyticum, Bacillus polymyxa, Chromobacterium violaceum* and *Pseudomonas putida*. In some embodiments, the one or more nucleic acid molecules encoding the acetoacetate decarboxylase is adc, or homolog thereof. In a further embodiment, the acetoacetate decarboxylase comprises an amino acid sequence selected from the group consisting of SEQ ID NOs: 49 and 52. In yet another embodiment, the acetoacetate decarboxylase is encoded by a nucleic acid sequence selected from the group consisting of SEQ ID NOs: 47, 48, 50 and 51.

Alcohol Dehydrogenase (EC 1.1.1.-)

The present disclosure describes enzymes that can catalyze the reversible oxidation of primary or secondary alcohols to aldehydes or ketones, respectively. In one embodiment, the enzyme is a secondary alcohol dehydrogenase (S-ADH) and catalyzes the reduction of ketones such as acetone into secondary alcohols such as 2-propanol (isopropanol).

In some embodiments the S-ADH is from *Burkholderia* sp. In some embodiments, the S-ADH is from *Burkholderia* sp. AIU 652. In some embodiments, the S-ADH is from *Alcaligenes* sp. In some embodiments, the S-ADH is from *Alcaligenes eutrophus*. In some embodiments, the S-ADH is from *Clostridium* sp. In some embodiments, the S-ADH is from *Clostridium ragsdalei*. In some embodiments, the S-ADH is from *Clostridium beijerinckii*. In some embodiments, the S-ADH is from *Thermoanaerobacter* sp. In some embodiments, the S-ADH is from *Thermoanaerobacter brockii*. In some embodiments, the S-ADH is from *Thermoanaerobacter ethanolicus* (*Clostridium thermohydrosulfuricum*). In some embodiments, the S-ADH is encoded by the adhB gene. In some embodiments, the S-ADH is from the trypanosomatid *Phytomonas* sp. In some embodiments, the S-ADH is from *Rhodococcus* sp. In some embodiments, the S-ADH is from *Rhodococcus ruber*. In some embodiments, the S-ADH is from *Methanobacterium palustre*. In some embodiments, the S-ADH is from methanogenic archaea *Methanogenium liminatans*. In some embodiments, the S-ADH is from the parasitic protist *Entamoeba histolytica* (EhAdh1). In some embodiments, the S-ADH is from parasitic protozoan *Tritrichomonas foetus*. In some embodiments, the S-ADH is from human parasite *Trichomonas vaginalis*.

In some embodiments, the S-ADH is predicted from homology and can be from *Thermoanaerobacter mathranii*, *Micrococcus luteus*, *Nocardiopsis alba*, *Mycobacterium hassiacum*, *Helicobacter suis*, *Candida albicans*, *Candida parapsilosis*, *Candida orthopsilosis*, *Candida metapsilosis*, *Grosmannia clavigera* and *Scheffersomyces stipitis*.

In some embodiments, the alcohol dehydrogenase has at least 70% sequence identity, at least 80% sequence identity, or at least 90% sequence identity with an alcohol dehydrogenase from *Clostridium* sp. In other embodiments, the alcohol dehydrogenase is an alcohol dehydrogenase selected from *Clostridium beijerinckii* adh and *Clostridium carboxidivorans* adh. In a further embodiment, the alcohol dehydrogenase comprises an amino acid sequence selected from the group consisting of SEQ ID NOs: 138 and 140. In yet another embodiment, the alcohol dehydrogenase is encoded by a nucleic acid sequence selected from the group consisting of SEQ ID NOs: 136, 137, and 139.

Dehydratase (EC 4.2.1.-)

The present disclosure describes enzymes that can catalyze the following reactions:

D-Xylulose 1-Kinase (EC 2.7.1.-)

The present disclosure describes enzymes that can catalyze the conversion of D-xylulose to D-xylulose-1-phosphate. In some embodiments, the conversion can be catalyzed by a human ketohexokinase C (khk-C), also known as fructokinase.

Ketohexokinase, or fructokinase, phosphorylates fructose to fructose-1-phosphate. The enzyme is involved in fructose metabolism, which is part of carbohydrate metabolism. It is found in the liver, intestine and kidney cortex.

In human liver, purified fructokinase, when coupled with aldolase, has been discovered to contribute to an alternative mechanism to produce oxalate from xylitol. In coupled sequence, fructokinase and aldolase produce glycolaldehyde, a precursor to oxalate, from D-xylulose via D-xylulose 1-phosphate.

In particular embodiments, the enzyme converts D-xylulose to D-xylulose-1-phosphate. In one embodiment, the D-xylulose 1-kinase is encoded by one or more nucleic acid molecules obtained from *Homo sapiens*. In some embodiments, the one or more nucleic acid molecules encoding the D-xylulose 1-kinase is ketohexokinase C (khk-C), or homolog thereof. In another embodiment, the one or more nucleic acid molecules encoding the D-xylulose 1-kinase comprises an amino acid sequence set forth in SEQ ID NOs: 55 or 256. In a further embodiment, the one or more nucleic acid molecules encoding the D-xylulose 1-kinase is encoded by a nucleic acid sequence selected from the group consisting of SEQ ID NOs: 53 and 54.

D-Xylulose-1-Phosphate Aldolase (EC 4.1.2.-)

The present disclosure describes enzymes that can catalyze the conversion of D-xylulose-1-phosphate to glycolaldehyde and DHAP. In some embodiments, the conversion can be catalyzed by a human aldolase B, which is also known as fructose-bisphosphate aldolase B or liver-type aldolase.

Aldolase B is one of three isoenzymes (A, B, and C) of the class I fructose 1,6-bisphosphate aldolase enzyme (EC 4.1.2.13), and plays a key role in both glycolysis and gluconeogenesis. The generic fructose 1,6-bisphosphate aldolase enzyme catalyzes the reversible cleavage of fructose 1,6-bisphosphate (FBP) into glyceraldehyde 3-phosphate and dihydroxyacetone phosphate (DHAP) as well as the reversible cleavage of fructose 1-phosphate (F1P) into glyceraldehyde and dihydroxyacetone phosphate. In mammals, aldolase B is preferentially expressed in the liver, while aldolase A is expressed in muscle and erythrocytes and aldolase C is expressed in the brain. Slight differences in isozyme structure result in different activities for the two substrate molecules: FBP and fructose 1-phosphate. Aldolase B exhibits no preference and thus catalyzes both reactions, while aldolases A and C prefer FBP.

Aldolase B is a homotetrameric enzyme, composed of four subunits. Each subunit has a molecular weight of 36 kDa and contains an eight-stranded α/β barrel, which encloses lysine 229 (the Schiff-base forming amino acid that is key for catalysis).

In particular embodiments, the enzyme converts D-xylulose-1-phosphate to glycolaldehyde and DHAP. In one embodiment, the D-xylulose-1-phosphate aldolase is encoded by one or more nucleic acid molecules obtained from *Homo sapiens*. In another embodiment, the one or more nucleic acid molecules encoding the D-xylulose-1-phosphate aldolase is aldolase B (aldoB), or homolog thereof. In some embodiments, the one or more nucleic acid molecules encoding the D-xylulose-1-phosphate aldolase comprises an amino acid sequence set forth in SEQ ID NO: 58. In some embodiments, the one or more nucleic acid molecules encoding the D-xylulose-1-phosphate aldolase is encoded by a nucleic acid sequence selected from the group consisting of SEQ ID NOs: 56 and 57.

D-Xylose Isomerase (EC 5.3.1.5)

The present disclosure describes enzymes that can catalyze the following reversible reaction:

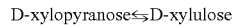

D-xylose isomerase may also be known as xylose isomerase or D-xylose ketol-isomerase.

Thus, in some embodiments, the disclosure provides for an enzyme that plays a role in xylose degradation.

Xylose isomerase catalyzes the first reaction in the catabolism of D-xylose.

Two conserved histidine residues, H101 and H271, were shown to be essential for catalytic activity. The fluorescence of two conserved tryptophan residues, W49 and W188, is quenched during binding of xylose, and W49 was shown to be essential for catalytic activity. The presence of $Mg^{2+}$, $Mn^{2+}$ or $Co^{2+}$ protects the enzyme from thermal denaturation.

The subunit composition has not been established experimentally.

In particular embodiments, the enzyme converts D-xylose to D-xylulose. In one embodiment, the recombinant microorganism further comprises an endogenous or exogenous xylose isomerase that catalyzes the conversion of D-xylose to D-xylulose. In one embodiment, the xylose isomerase is exogenous. In another embodiment, the xylose isomerase is encoded by one or more nucleic acid molecules obtained from *Pyromyces* sp or *E. coli*. In another embodiment, the one or more nucleic acid molecules encoding the xylose isomerase is xylA, or homolog thereof. In yet another embodiment, the one or more nucleic acid molecules encoding the xylose isomerase comprises an amino acid sequence selected from SEQ ID NOs: 95 and 144. In a further embodiment, the one or more nucleic acid molecules encoding the xylose isomerase is encoded by a nucleic acid sequence selected from the group consisting of SEQ ID NOs: 93, 94 and 143.

In some embodiments, a recombinant microorganism producing MEG or GA, or optionally, MEG or GA and one or more co-product, comprises a deletion, insertion, or loss of function mutation in a gene encoding a D-xylose isomerase to prevent conversion of D-xylose to D-xylulose and instead shunt the reaction toward the conversion of D-xylose to D-xylonate.

D-Xylulose 5-Kinase/Xylulokinase

The present disclosure describes enzymes that can catalyze the following reactions:

D-xylulose+ATP→D-xylulose 5-phosphate+ADP+H+ (EC 2.7.1.17)

ATP+1-deoxy-D-xylulose→1-deoxy-D-xylulose 5-phosphate+ADP+H+ (EC 2.7.1.-)

D-xylulose 5-kinase may also be known as xylulose kinase or xylulokinase.

Xylulokinase catalyzes the phosphorylation of D-xylulose, the second step in the xylose degradation pathway, producing D-xylulose-5-phosphate, an intermediate of the pentose phosphate pathway.

In the absence of substrate, xylulokinase has weak ATPase activity. Xylulokinase can also catalyze the phosphorylation of 1-deoxy-D-xylulose. This would allow a potential salvage pathway for generating 1-deoxy-D-xylulose 5-phosphate for use in the biosynthesis of terpenoids, thiamine and pyridoxal. The rate of phosphorylation of 1-deoxy-D-xylulose is 32-fold lower than the rate of phosphorylation of D-xylulose.

The kinetic mechanism of the bacterial enzyme has been studied, suggesting a predominantly ordered reaction mechanism. The enzyme undergoes significant conformational changes upon binding of the substrate and of ATP. Two conserved aspartate residues, D6 and D233, were found to be essential for catalytic activity, and a catalytic mechanism has been proposed.

Crystal structures of bacterial xylulokinase in the apo form and bound to D-xylulose have been determined at 2.7 and 2.1 Å resolution, respectively.

In particular embodiments, the enzyme converts D-xylulose to D-xylulose-5-phosphate. In some embodiments, the D-xylulose 5-kinase is from *Escherichia coli*. In some embodiments, the D-xylulose 5-kinase is encoded by the xylB gene. In some embodiments, the D-xylulose 5-kinase is from *Saccharomyces cerevisiae*. In some embodiments the D-xylulose 5-kinase is encoded by the XKS1 gene. In some embodiments, the D-xylulose 5-kinase is from *Pichia shpais*. In some embodiments the D-xylulose 5-kinase is encoded by the XYL3 gene.

In some embodiments, the D-xylulose 5-kinase is encoded by an amino acid sequence having at least 70% sequence identity to xylB from *E. coli*. In a further embodiment, the D-xylulose 5-kinase is encoded by an amino acid sequence having at least 80% sequence identity to xylB from *E. coli*. In yet a further embodiment, the D-xylulose 5-kinase is encoded by an amino acid sequence having at least 90% sequence identity to xylB from *E. coli*. In other embodiments, the D-xylulose 5-kinase is xylB from *E. coli*.

In one embodiment, the D-xylulose 5-kinase is encoded by one or more nucleic acid molecules obtained from *E. coli*. In some embodiments, the one or more nucleic acid molecules encoding the D-xylulose 5-kinase is xylB, or homolog thereof. In another embodiment, the one or more nucleic acid molecules encoding the D-xylulose 5-kinase comprises an amino acid sequence set forth in SEQ ID NO: 146. In a further embodiment, the one or more nucleic acid molecules encoding the D-xylulose 5-kinase is encoded by a nucleic acid sequence set forth in SEQ ID NO: 145.

Xylose Dehydrogenase (EC 1.1.1.175 or EC 1.1.1.179)

The present disclosure describes enzymes that can catalyze the following reactions:

aldehydo-D-xylose+NAD++H$_2$O→D-xylonate+ NADH+2H+

α-D-xylopyranose+NAD+⇌D-xylonolactone+ NADH+H+ (reversibility unspecified, EC 1.1.1.175)

Xylose dehydrogenase may also be known as D-xylose dehydrogenase, D-xylose 1-dehydrogenase, (NAD+)-linked D-xylose dehydrogenase, NAD+-D-xylose dehydrogenase, D-xylose:NAD+1-oxidoreductase D-xylose dehydrogenase catalyzes the NAD+-dependent oxidation of D-xylose to D-xylonolactone. This is the first reaction in the oxidative, non-phosphorylative pathway for the degradation of D-xylose in *Caulobacter crescentus*. This pathway is similar to the pathway for L-arabinose degradation in *Azospirillum brasilense*. The amino acid sequence of the *C. crescentus* enzyme is unrelated to that of xylose dehydrogenase from the archaeon *Haloarcula marismortui*, or the L-arabinose 1-dehydrogenase of *Azospirillum brasilense*.

D-xylose is the preferred substrate for recombinant D-xylose dehydrogenase from *Caulobacter crescentus*. The enzyme can use L-arabinose, but it is a poorer substrate. The Km for L-arabinose is 166 mM. Other substrates such as D-arabinose, L-xylose, D-ribose, D-galactose, D-glucose and D-glucose-6-phosphate showed little or no activity in the assay, as measured by NADH production. *C. crescentus* D-xylose dehydrogenase can convert D-xylose to D-xylonate directly.

Partially purified, native D-xylose dehydrogenase from *C. crescentus* had a Km of 70 μM for D-xylose. This value was lower than the Km of 760 μM for the recombinant, His-tagged enzyme.

In some embodiments, the D-xylose dehydrogenase is from the halophilic archaeon *Haloferax volcanii*. The *Haloferax volcanii* D-xylose dehydrogenase catalyzes the first reaction in the oxidative xylose degradation pathway of the halophilic archaeon *Haloferax volcanii*. The *H. volcanii* D-xylose dehydrogenase shows 59% amino acid sequence identity to a functionally characterized xylose dehydrogenase from *Haloarcula marismortui* and 56% identity to an ortholog in *Halorubrum lacusprofundi*, but is only 11% identical to the bacterial NAD+-dependent xylose dehydrogenase from *Caulobacter crescentus* CB15.

In particular embodiments, the enzyme converts D-xylose to D-xylonolactone. In one embodiment, the xylose dehydrogenase is encoded by one or more nucleic acid molecules obtained from a microorganism selected from the group consisting of *Caulobacter* sp., *Haloarcula* sp., *Haloferax* sp., *Halorubrum* sp. and *Trichoderma* sp. In another embodiment, the xylose dehydrogenase is encoded by one or more nucleic acid molecules obtained from a microorganism selected from the group consisting of *Caulobacter crescentus, Haloarcula marismortui, Haloferax volcanii, Halorubrum lacusprofundi* and *Trichoderma reesei*. In some embodiments, the one or more nucleic acid molecules encoding the xylose dehydrogenase is selected from xylB, xdh1 (HVO_B0028) and/or xyd1, or homolog thereof. In a further embodiment, the one or more nucleic acid molecules encoding the xylose dehydrogenase comprises an amino acid sequence selected from the group consisting of SEQ ID NOs: 61, 63 and 65. In yet another embodiment, the one or more nucleic acid molecules encoding the xylose dehydrogenase is encoded by a nucleic acid sequence selected from the group consisting of SEQ ID NOs: 59, 60, 62 and 64.

Xylonolactonase (3.1.1.68)

The present disclosure describes enzymes that can catalyze the following reaction:

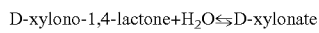

D-xylono-1,4-lactone+$H_2O$⇌D-xylonate

This enzyme belongs to the family of hydrolases, specifically those acting on carboxylic ester bonds. This enzyme participates in pentose and glucuronate interconversions.

Xylonolactonase may also be known as D-xylonolactonase, xylono-1,4-lactonase, xylono-gamma-lactonase or D-xylono-1,4-lactonelactonohydrolase.

In particular embodiments, the enzyme converts D-xylonolactone to D-xylonate. In one embodiment, the xylonolactonase is encoded by one or more nucleic acid molecules obtained from a microorganism selected from *Caulobacter* sp. and *Haloferax* sp. In another embodiment, the xylonolactonase is encoded by one or more nucleic acid molecules obtained from a microorganism selected from the group consisting of *Caulobacter crescentus, Haloferax volcanii* and *Haloferax gibbonsii*. In some embodiments, the one or more nucleic acid molecules encoding the xylonolactonase is xylC, or homolog thereof. In a further embodiment, the one or more nucleic acid molecules encoding the xylonolactonase comprises an amino acid sequence set forth in SEQ ID NO: 67. In yet another embodiment, the one or more nucleic acid molecules encoding the xylonolactonase is encoded by a nucleic acid sequence set forth in SEQ ID NO: 66.

Xylonate Dehydratase (EC 4.2.1.82)

The present disclosure describes enzymes that can catalyze the following reaction:

D-xylonate⇌2-keto-3-deoxy-D-xylonate+$H_2O$

This enzyme belongs to the family of lyases, specifically the hydro-lyases, which cleave carbon-oxygen bonds. This enzyme participates in pentose and glucuronate interconversions.

Xylonate dehydratase may also be known as D-xylonate hydro-lyase, D-xylo-aldonate dehydratase or D-xylonate dehydratase.

In particular embodiments, the enzyme converts D-xylonate to 2-keto-3-deoxy-D-xylonate. In one embodiment, the xylonate dehydratase is encoded by one or more nucleic acid molecules obtained from a microorganism selected from the group consisting of *Caulobacter* sp., *Sulfolobus* sp. and *E. coli*. In another embodiment, the xylonate dehydratase is encoded by one or more nucleic acid molecules obtained from a microorganism selected from the group consisting of *Caulobacter crescentus, Sulfolobus solfataricus* and *E. coli*. In some embodiments, the one or more nucleic acid molecules encoding the xylonate dehydratase is selected from xylD, yjhG and/or yagF, or homolog thereof. In a further embodiment, the one or more nucleic acid molecules encoding the xylonate dehydratase comprises an amino acid sequence selected from the group consisting of SEQ ID NOs: 69, 72 and 75. In yet another embodiment, the one or more nucleic acid molecules encoding the xylonate dehydratase is encoded by a nucleic acid sequence selected from the group consisting of SEQ ID NOs: 68, 70, 71, 73 and 74.

2-keto-3-deoxy-D-pentonate aldolase (4.1.2.28)

The present disclosure describes enzymes that can catalyze the following reaction:

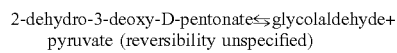

2-dehydro-3-deoxy-D-pentonate⇌glycolaldehyde+pyruvate (reversibility unspecified)

This enzyme belongs to the family of lyases, specifically the aldehyde-lyases, which cleave carbon-carbon bonds. This enzyme participates in pentose and glucuronate interconversions.

2-keto-3-deoxy-D-pentonate aldolase may also be known as 2-dehydro-3-deoxy-D-pentonate glycolaldehyde-lyase (pyruvate-forming), 2-dehydro-3-deoxy-D-pentonate aldolase, 3-deoxy-D-pentulosonic acid aldolase, and 2-dehydro-3-deoxy-D-pentonate glycolaldehyde-lyase.

YjhH appears to be a 2-dehydro-3-deoxy-D-pentonate aldolase. Genetic evidence suggests that YagE may also function as a 2-dehydro-3-deoxy-D-pentonate aldolase. yagE is part of the prophage CP4-6.

A yjhH yagE double mutant cannot use D-xylonate as the sole source of carbon, and crude cell extracts do not contain 2-dehydro-3-deoxy-D-pentonate aldolase activity. Both phenotypes are complemented by providing yjhH on a plasmid.

ArcA appears to activate yjhH gene expression under anaerobiosis. Two putative ArcA binding sites were identified 211 and 597 bp upstream of this gene, but no promoter upstream of it has been identified.

The crystal structure of YagE suggests that the protein is a homotetramer. Co-crystal structures of YagE in the presence of pyruvate and 2-keto-3-deoxygalactonate have been solved.

In particular embodiments, the enzyme converts 2-keto-3-deoxy-xylonate to glycolaldehyde and pyruvate. In one embodiment, the 2-keto-3-deoxy-D-pentonate aldolase is encoded by one or more nucleic acid molecules obtained from a microorganism selected from *Pseudomonas* sp. and *E. coli*. In another embodiment, the 2-keto-3-deoxy-D-pentonate aldolase is encoded by one or more nucleic acid molecules obtained from *E. coli*. In some embodiments, the one or more nucleic acid molecules encoding the 2-keto-3-deoxy-D-pentonate aldolase is selected from yjhH and/or yagE, or homolog thereof. In a further embodiment, the one or more nucleic acid molecules encoding the 2-keto-3-deoxy-D-pentonate aldolase comprises an amino acid sequence selected from the group consisting of SEQ ID NOs: 78 and 81. In yet another embodiment, the one or more nucleic acid molecules encoding the 2-keto-3-deoxy-D-pentonate aldolase is encoded by a nucleic acid sequence selected from the group consisting of SEQ ID NOs: 76, 77, 79 and 80.

Glycolaldehyde Dehydrogenase (1.2.1.21)

The present disclosure describes enzymes that can catalyze the following reaction:

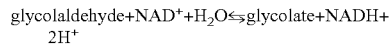

glycolaldehyde+$NAD^+$+$H_2O$⇌glycolate+NADH+$2H^+$

This enzyme belongs to the family of oxidoreductases, specifically those acting on the aldehyde or oxo group of donor with NAD+ or NADP+ as acceptor. This enzyme participates in glyoxylate and dicarboxylate metabolism.

Glycolaldehyde dehydrogenase may also be known as glycolaldehyde:NAD+ oxidoreductase or glycol aldehyde dehydrogenase.

In *E. coli* aldehyde dehydrogenase A (AldA) is an enzyme of relatively broad substrate specificity for small α-hydroxyaldehyde substrates. It is thus utilized in several metabolic pathways.

L-fucose and L-rhamnose are metabolized through parallel pathways which converge after their corresponding aldolase reactions yielding the same products: dihydoxyacetone phosphate and L-lactaldehyde. Aerobically, aldehyde dehydrogenase A oxidizes L-lactaldehyde to L-lactate.

In parallel pathways utilizing the same enzymes, D-arabinose and L-xylose can be metabolized to dihydoxy-acetone phosphate and glycolaldehyde, which is oxidized to glycolate by aldehyde dehydrogenase A.

Crystal structures of the enzyme alone and in ternary and binary complexes have been solved.

Aldehyde dehydrogenase A is only present under aerobic conditions and is most highly induced by the presence of fucose, rhamnose or glutamate. The enzyme is inhibited by NADH, which may act as a switch to shift from oxidation of lactaldehyde to its reduction by propanediol oxidoreductase. AldA is upregulated during short-term adaptation to glucose limitation.

Based on sequence similarity, AldA was predicted to be a succinate-semialdehyde dehydrogenase.

Regulation of aldA expression has been investigated. The gene is regulated by catabolite repression, repression under anaerobic conditions via ArcA, and induction by the carbon source.

In particular embodiments, the enzyme converts glycolaldehyde to glycolate. In some embodiments, the glycolaldehyde dehydrogenase is from *Escherichia coli*. In some embodiments, the glycolaldehyde dehydrogenase is encoded by the aldA gene.

In some embodiments, a recombinant microorganism producing MEG, or optionally, MEG and one or more co-product, comprises a deletion, insertion, or loss of function mutation in a gene encoding a glycolaldehyde dehydrogenase to prevent the production of glycolic acid from glycolaldehyde and instead shunt the reaction toward conversion of glycolaldehyde to MEG. In some embodiments, the deletion, disruption, mutation, and/or reduction in the activity of a glycolaldehyde dehydrogenase that catalyzes the conversion of glycolaldehyde to glycolic acid is partial, wherein an amount of glycolic acid is still produced.

In other embodiments, a recombinant microorganism producing glycolic acid comprises or expresses at least one nucleic acid molecule encoding a glycolaldehyde dehydrogenase.

Lactate Dehydrogenase (1.1.1.28)

The present disclosure describes enzymes that can catalyze the following reaction:

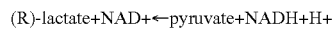

Lactate dehydrogenase (LDH) is an enzyme found in nearly all living cells such as in animals, plants and prokaryotes. LDH catalyzes the conversion of lactate to pyruvic acid and back, as it converts NADH to NAD+ and back. A dehydrogenase is an enzyme that transfers a hydride from one molecule to another.

LDH exist in four distinct enzyme classes. The most common one is NAD(P)-dependent L-lactate dehydrogenase. Other LDHs act on D-lactate and/or are dependent on cytochrome c: D-lactate dehydrogenase (cytochrome) and L-lactate dehydrogenase (cytochrome).

LDH has been of medical significance because it is found extensively in body tissues, such as blood cells and heart muscle. Because it is released during tissue damage, it is a marker of common injuries and disease such as heart failure.

Lactate dehydrogenase may also be known as lactic acid dehydrogenase, (R)-lactate:NAD+ oxidoreductase or D-lactate dehydrogenase—fermentative.

In *E. coli*, lactate dehydrogenase (LdhA) is a soluble NAD-linked lactate dehydrogenase (LDH) that is specific for the production of D-lactate. LdhA is a homotetramer and shows positive homotropic cooperativity under higher pH conditions.

*E. coli* contains two other lactate dehydrogenases: D-lactate dehydrogenase and L-lactate dehydrogenase. Both are membrane-associated flavoproteins required for aerobic growth on lactate.

LdhA is present under aerobic conditions but is induced when *E. coli* is grown on a variety of sugars under anaerobic conditions at acidic pH. Unlike most of the genes involved in anaerobic respiration, ldhA is not activated by Fnr; rather the ArcAB system and several genes involved in the control of carbohydrate metabolism (csrAB and mlc) appear to regulate expression. The expression of ldhA is negatively affected by the transcriptional regulator ArcA. ldhA belongs to the 632 regulon.

The ldhA gene is a frequent target for mutations in metabolic engineering, most often to eliminate production of undesirable fermentation side products, but also to specifically produce D-lactate.

In particular embodiments, the enzyme converts pyruvate to lactate. In some embodiments, the lactate dehydrogenase is from *Escherichia coli*. In some embodiments, the lactate dehydrogenase is encoded by the ldhA gene.

In some embodiments, a recombinant microorganism producing MEG or GA, or optionally, MEG or GA and one or more co-product, comprises a deletion, insertion, or loss of function mutation in a gene encoding a lactate dehydrogenase to prevent the production of lactate from pyruvate and instead shunt the reaction toward production of one or more co-products.

Xylose Reductase or Aldose Reductase (EC 1.1.1.21)

The present disclosure describes enzymes that can catalyze the following reactions:

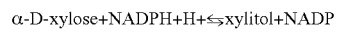

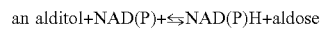

Aldose reductase may also be known as alditol:NAD(P)+ 1-oxidoreductase, polyol dehydrogenase or aldehyde reductase.

Aldose reductase is a cytosolic oxidoreductase that catalyzes the reduction of a variety of aldehydes and carbonyls, including monosaccharides.

Aldose reductase may be considered a prototypical enzyme of the aldo-keto reductase enzyme superfamily. The enzyme comprises 315 amino acid residues and folds into a β/α-barrel structural motif composed of eight parallel β strands. Adjacent strands are connected by eight peripheral α-helical segments running anti-parallel to the β sheet. The catalytic active site is situated in the barrel core. The NADPH cofactor is situated at the top of the β/α barrel, with the nicotinamide ring projecting down in the center of the barrel and pyrophosphate straddling the barrel lip.

The reaction mechanism of aldose reductase in the direction of aldehyde reduction follows a sequential ordered path where NADPH binds, followed by the substrate. Binding of NADPH induces a conformational change (Enzyme•NADPH→Enzyme*•NADPH) that involves hinge-like movement of a surface loop (residues 213-217) so as to cover a portion of the NADPH in a manner similar to that of a safety belt. The alcohol product is formed via a transfer of the pro-R hydride of NADPH to the face of the substrate's carbonyl carbon. Following release of the alcohol product, another conformational change occurs (E*•NAD(P)+→E•NAD(P)+) in order to release NADP+. Kinetic studies have shown that reorientation of this loop to permit release of NADP+ appears to represent the rate-limiting step in the direction of aldehyde reduction. As the rate of coenzyme release limits the catalytic rate, it can be seen that perturbation of interactions that stabilize coenzyme binding can have dramatic effects on the maximum velocity (Vmax).

D-xylose-fermenting *Pichia stipitis* and *Candida shehatae* were shown to produce one single aldose reductase (ALR) that is active both with NADPH and NADH. Other yeasts such as *Pachysolen tannophilus* and *C. tropicalis* synthesize multiple forms of ALR with different coenzyme specificities. The significant dual coenzyme specificity distinguishes the *P. stipitis* and the *C. shehatae* enzymes from most other ALRs so far isolated from mammalian or microbial sources. The yeast *Candida tenuis* CBS 4435 produces comparable NADH- and NADPH-linked aldehyde-reducing activities during growth on D-xylose.

In particular embodiments, the enzyme converts D-xylose to xylitol. In some embodiments, the xylose reductase or aldose reductase is encoded by one or more nucleic acid molecules obtained from a microorganism selected from the group consisting of *Hypocrea* sp., *Scheffersomyces* sp., *Saccharomyces* sp., *Pachysolen* sp., *Pichia* sp., *Candida* sp., *Aspergillus* sp., *Neurospora* sp., and *Cryptococcus* sp. In some embodiments, the xylose reductase or aldose reductase is encoded by one or more nucleic acid molecules obtained from a microorganism selected from the group consisting of *Hypocrea jecorina*, *Scheffersomyces stipitis*, *Saccharomyces cerevisiae*, *Pachysolen tannophilus*, *Pichia stipitis*, *Pichia quercuum*, *Candida shehatae*, *Candida tenuis*, *Candida tropicalis*, *Aspergillus niger*, *Neurospora crassa* and *Cryptococcus lactativorus*. In another embodiment, the one or more nucleic acid molecules encoding the xylose reductase or aldose reductase is xyl1 and/or GRE3 or homolog thereof. In some embodiments, the one or more nucleic acid molecules encoding the xylose reductase or aldose reductase comprises an amino acid sequence selected from the group consisting of SEQ ID NOs: 84 and 87. In some embodiments, the one or more nucleic acid molecules encoding the xylose reductase or aldose reductase is encoded by a nucleic acid sequence selected from the group consisting of SEQ ID NOs: 82, 83, 85 and 86.

Xylitol Dehydrogenase (1.1.1.9)

The present disclosure describes enzymes that can catalyze the following reaction:

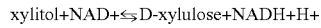

Xylitol dehydrogenase may also be known as D-xylulose reductase, NAD+-dependent xylitol dehydrogenase, erythritol dehydrogenase, 2,3-cis-polyol(DPN) dehydrogenase (C3-5), pentitol-DPN dehydrogenase, xylitol-2-dehydrogenase or xylitol:NAD+ 2-oxidoreductase (D-xylulose-forming).

Xylitol dehydrogenase (XDH) is one of several enzymes responsible for assimilating xylose into eukaryotic metabolism and is useful for fermentation of xylose contained in agricultural byproducts to produce ethanol. For efficient xylose utilization at high flux rates, cosubstrates should be recycled between the NAD+-specific XDH and the NADPH-preferring xylose reductase, another enzyme in the pathway.

In particular embodiments, the enzyme converts xylitol to D-xylulose. In one embodiment of any aspect disclosed above, the xylitol dehydrogenase is encoded by one or more nucleic acid molecules obtained from a microorganism selected from the group consisting of *Scheffersomyces* sp., *Trichoderma* sp., *Pichia* sp., *Saccharomyces* sp., *Gluconobacter* sp., *Galactocandida* sp., *Neurospora* sp., and *Serratia* sp. In another embodiment, the xylitol dehydrogenase is encoded by one or more nucleic acid molecules obtained from a microorganism selected from the group consisting of *Scheffersomyces stipitis*, *Trichoderma reesei*, *Pichia stipitis*, *Saccharomyces cerevisiae*, *Gluconobacter oxydans*, *Galactocandida mastotermitis*, *Neurospora crassa* and *Serratia marcescens*. In another embodiment, the one or more nucleic acid molecules encoding the xylitol dehydrogenase is xyl2 and/or xdh1, or homolog thereof. In some embodiments, the one or more nucleic acid molecules encoding the xylitol dehydrogenase comprises an amino acid sequence selected from the group consisting of SEQ ID NOs: 90 and 92. In some embodiments, the one or more nucleic acid molecule encoding the xylitol dehydrogenase is encoded by a nucleic acid sequence selected from the group consisting of SEQ ID NOs: 88, 89 and 91. In another embodiment, the enzyme converts D-xylulose to xylitol. In another embodiment, the enzyme has high activity for the conversion of D-xylulose to xylitol and preferably low activity or no activity for the reverse reaction, i.e. for the conversion of xylitol to D-xylulose. In another embodiment, this is achieved through enzyme engineering.

Soluble Pyridine Nucleotide Transhydrogenase (EC 1.6.1.1.)

The present disclosure describes enzymes that can catalyze the following reaction:

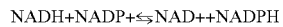

Soluble pyridine nucleotide transhydrogenase may also be known as NAD(P)+ transhydrogenase (B-specific), STH, pyridine nucleotide transhydrogenase, or transhydrogenase.

*E. coli* contains both a soluble and a membrane-bound pyridine nucleotide transhydrogenase. The soluble pyridine nucleotide transhydrogenase is the sthA or udhA gene product; its primary physiological role appears to be the reoxidation of NADPH. The membrane-bound proton-translocating transhydrogenase is the pntAB gene product; PntAB is a major source of NADPH.

UdhA contains noncovalently bound FAD and is present in a form consisting of seven or eight monomers.

Moderate overexpression of UdhA (SthA) allows an increased maximal growth rate of a phosphoglucose isomerase mutant, and a pgi sthA double mutant is not viable. These phenotypes may be due to the ability of UdhA to restore the cellular redox balance under conditions of excess NADPH formation. Mutations in sthA appear during adaptation of a pgi mutant strain to growth on glucose minimal medium.

Transcription of sthA is downregulated by growth on glycerol.

In some embodiments, expression of a transhydrogenase can increase activity of a NADPH-dependent alcohol dehydrogenase, leading to improved acetone to 2-propanol conversion. In one embodiment, the soluble pyridine nucleotide transhydrogenase is encoded by one or more nucleic acid molecules obtained from *E. coli*. In another embodiment, the one or more nucleic acid molecules encoding the soluble pyridine nucleotide transhydrogenase is udhA, or homolog thereof. In some embodiments, the one or more nucleic acid molecules encoding the soluble pyridine nucleotide transhydrogenase comprises an amino acid sequence set forth in SEQ ID NO: 142. In some embodiments, the one or more nucleic acid molecules encoding the soluble pyridine nucleotide transhydrogenase is encoded by a nucleic acid sequence set forth in SEQ ID NO: 141.

Hydroxymethylglutaryl-CoA Synthase (EC 2.3.3.-)

The present disclosure describes enzymes that can catalyze the following reaction:

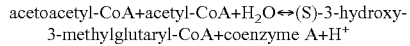
acetoacetyl-CoA+acetyl-CoA+H$_2$O↔(S)-3-hydroxy-3-methylglutaryl-CoA+coenzyme A+H$^+$ Hydroxymethylglutaryl-CoA synthase may also be known as (S)-3-hydroxy-3-methylglutaryl-CoA acetoacetyl-CoA-lyase (CoA-acetylating), 3-hydroxy-3-methylglutaryl CoA synthetase, 3-hydroxy-3-methylglutaryl coenzyme A synthase, 3-hydroxy-3-methylglutaryl coenzyme A synthetase, 3-hydroxy-3-methylglutaryl-CoA synthase, 3-hydroxy-3-methylglutaryl-coenzyme A synthase, β-hydroxy-β-methylglutaryl-CoA synthase, HMG-CoA synthase, acetoacetyl coenzyme A transacetase, hydroxymethylglutaryl coenzyme A synthase, and hydroxymethylglutaryl coenzyme A-condensing enzyme.

Hydroxymethylglutaryl-CoA synthase catalyzes the condensation of acetyl-CoA with acetoacetyl-CoA to form (S)-3-hydroxy-3-methylglutaryl-CoA, an early stage in the synthesis of (R)-mevalonate, a precursor of cholesterol.

The enzyme catalyzes a complex reaction that can be divided into four steps. The first step involves the formation of an enzyme acetyl-CoA binary complex, followed by the transfer of the acetyl group from the CoA thioester to a cysteine residue on the enzyme, forming a thioester acyl-enzyme intermediate. In the next step the now reduced CoA dissociates, and the second substrate, acetoacetyl-CoA, binds the enzyme. The third step involves the formation of a carbanion by removal of a proton from the methyl of the acetylcysteine. The activated acetylcysteine then undergoes a Claisen-like condensation with the γ-carbon of the acetoacetyl-CoA ligand, which forms the HMG-CoA while retaining the thioester bond to the enzyme. The last step comprises the hydrolysis of this bond, resulting in free HMG-CoA.

The HMGCS1 gene from *Homo sapiens* has been cloned and sequenced (Russ A P et al. (1992) Amplification and direct sequencing of a cDNA encoding human cytosolic 3-hydroxy-3-methylglutaryl-coenzyme A synthase. Biochim Biophys Acta 1132(3): 329-31). The gene was expressed in *Escherichia coli*, and the recombinant protein was purified and characterized (Rokosz L L et al. (1994) Human cytoplasmic 3-hydroxy-3-methylglutaryl coenzyme A synthase: expression, purification, and characterization of recombinant wild-type and Cys129 mutant enzymes. Arch Biochem Biophys 312(1): 1-13). The enzyme is a homodimer of 120 kDa. Catalysis proceeds by formation of a covalent acetyl-enzyme intermediate. Kinetic data suggest that the two substrates (acetyl-CoA and acetoacetyl-CoA) compete for binding to the same site.

In one embodiment, the hydroxymethylglutaryl-CoA synthase can have a 3-hydroxyisovalerate (3HIV) synthase activity and can catalyze the following reaction:

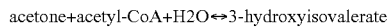
acetone+acetyl-CoA+H2O↔3-hydroxyisovalerate

In one embodiment, the 3HIV synthase is encoded by one or more nucleic acid molecules obtained from a microorganism selected from *Mus* sp., *Saccharomyces* sp., *Lactobacillus* sp. and *Polaromonas* sp. In another embodiment, the 3HIV synthase is encoded by one or more nucleic acid molecules obtained from a microorganism selected from *Mus musculus*, *Saccharomyces cerevisiae*, *Lactobacillus crispatus* and *Polaromonas naphthalenivorans*. In some embodiments, the one or more nucleic acid molecules encoding the 3HIV synthase is selected from Hmgcs1, ERG13, PksG and/or Pnap_0477, or homolog thereof. In a further embodiment, the one or more nucleic acid molecules encoding the 3HIV synthase comprises an amino acid sequence selected from the group consisting of SEQ ID NOs: 105, 107, 109 and 111. In yet another embodiment, the one or more nucleic acid molecules encoding the 3HIV synthase is encoded by a nucleic acid sequence selected from the group consisting of SEQ ID NOs: 104, 106, 108 and 110. In some embodiments, the one or more nucleic acid molecules encoding the hydroxymethylglutaryl-CoA synthase is hmgS, or homolog thereof. In a further embodiment, the one or more nucleic acid molecules encoding the hydroxymethylglutaryl-CoA synthase comprises an amino acid sequence set forth in SEQ ID NO: 123. In yet another embodiment, the one or more nucleic acid molecules encoding the hydroxymethylglutaryl-CoA synthase is encoded by a nucleic acid sequence set forth in SEQ ID NO: 122.

Methylglutaconyl-CoA Hydratase (EC 4.2.1.18)

The present disclosure describes enzymes that can catalyze the following reaction:

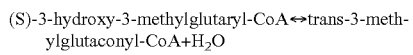
(S)-3-hydroxy-3-methylglutaryl-CoA↔trans-3-methylglutaconyl-CoA+H$_2$O This enzyme catalyzes the syn-hydration of 3-methylglutaconyl-CoA to (S)-3-hydroxy-3-methylglutaryl-CoA in the leucine degradation pathway. The bacterial enzyme has been characterized in *Pseudomonas putida*. It differs from the mammalian enzyme in having only one glutamyl residue in its active site rather than two, resulting in a different reaction mechanism. These enzymes are members of the crotonase superfamily (Wong B J and Gerlt J A (2004) Evolution of function in the crotonase superfamily: (3S)-methylglutaconyl-CoA hydratase from *Pseudomonas putida*. Biochemistry 43(16): 4646-4654) and reviewed in (Hamed R B et al. (2008) Mechanisms and structures of crotonase superfamily enzymes—how nature controls enolate and oxyanion reactivity. Cell Mol Life Sci 65(16): 2507-2527).

Recombinant enzyme was expressed in *Escherichia coli*, purified and characterized. The apparent molecular mass of the 10-His-tagged polypeptide was determined to be 32.251 kDa by ESI-MS. The 10-His-tag was subsequently removed before characterization of the enzyme (Wong and Gerlt 2004).

In one embodiment, the methylglutaconyl-CoA hydratase is encoded by one or more nucleic acid molecules obtained from *Pseudomonas* sp. In another embodiment, the methylglutaconyl-CoA hydratase is encoded by one or more nucleic acid molecules obtained from *Pseudomonas putida*. In some embodiments, the one or more nucleic acid molecules encoding the methylglutaconyl-CoA hydratase is liuC, or homolog thereof. In a further embodiment, the one or more nucleic acid molecules encoding the methylglutaconyl-CoA hydratase comprises an amino acid sequence set forth in SEQ ID NO: 125. In yet another embodiment, the one or more nucleic acid molecules encoding the methylglutaconyl-CoA hydratase is encoded by a nucleic acid sequence set forth in SEQ ID NO: 124.

Methylcrotonyl-CoA Carboxylase (EC 6.4.1.4)

The present disclosure describes enzymes that can catalyze the following reaction:

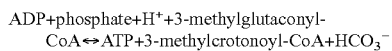
ADP+phosphate+H$^+$+3-methylglutaconyl-CoA↔ATP+3-methylcrotonoyl-CoA+HCO$_3^-$ The enzyme activity is associated with the 3-methylcrotonyl-CoA carboxylase complex. This enzyme is a biotin-containing, biotin-dependent carboxylase involved in the L-leucine (and isovalerate) degradation pathway of *Pseudomonas aeruginosa* PAO1. This pathway is also the last phase of the acyclic terpene utilization pathway (citronellol degradation and cis-genanyl-CoA degradation pathways). The enzyme is not expressed in citronellol or citronellate grown cells, but is expressed in isovalerate grown cells. Genes liuB and liuD encode the two subunits of 3-methylcrotonyl-CoA carboxylase. The subunits are encoded in the liuRABCDE gene cluster of this organism (Hoschle B et al. (2005) Methylcrotonyl-CoA and geranyl-CoA carboxylases are involved in leucine/isovalerate utilization (Liu) and acyclic terpene utilization (Atu), and are encoded by liuB/liuD and atuC/atuF, in *Pseudomonas aeruginosa*. Microbiology 151 (Pt 11): 3649-3656; Forster-Fromme K and Jendrossek D (2010). Catabolism of citronellol and related acyclic terpenoids in pseudomonads. Appl Microbiol Biotechnol 87(3): 859-869).

The enzyme was purified from cell extracts by avidin-affinity chromatography and the SDS-gel-isolated subunits were subjected to trypsin fingerprint analysis and ESI-MS which allowed identification of their corresponding genes (Hoschle et al. 2005).

The 3-methylcrotonyl-CoA carboxylase of *Pseudomonas citronellolis* was characterized in earlier work (Hector M L and Fall R R (1976) Multiple acyl-coenzyme A carboxylases in *Pseudomonas citronellolis*. Biochemistry 15(16): 3465-3472; Fall R R and Hector M L (1977) Acyl-coenzyme A carboxylases. Homologous 3-methylcrotonyl-CoA and geranyl-CoA carboxylases from *Pseudomonas citronellolis*. Biochemistry 16(18): 4000-4005; Fall R R (1981) 3-Methylcrotonyl-CoA and geranyl-CoA carboxylases from *Pseudomonas citronellolis*. Methods Enzymol 71 Pt C: 791-799).

In one embodiment, the methylcrotonyl-CoA carboxylase is encoded by one or more nucleic acid molecules obtained from *Pseudomonas* sp. In another embodiment, the methylcrotonyl-CoA carboxylase is encoded by one or more nucleic acid molecules obtained from *Pseudomonas aeruginosa*. In some embodiments, the one or more nucleic acid molecules encoding the methylcrotonyl-CoA carboxylase is selected from liuB and/or liuD, or homologs thereof. In a further embodiment, the one or more nucleic acid molecules encoding the methylcrotonyl-CoA carboxylase comprises an amino acid sequence selected from SEQ ID NOs: 127 and 129. In yet another embodiment, the one or more nucleic acid molecules encoding the methylcrotonyl-CoA carboxylase is encoded by a nucleic acid sequence selected from SEQ ID NOs: 126 and 128.

Methylcrotonyl-CoA Hydratase (EC 4.2.1.17)

The present disclosure describes enzymes that can catalyze the following reaction:

trans-2(or 3)-enoyl-CoA+H$_2$O↔(3S)-3-hydroxyacyl-CoA

An exemplary enzyme is a 3-ketoacyl-CoA thiolase. It is involved in the degradation of fatty acids via the β-oxidation cycle. It has broad chain-length specificity for substrates although it exhibits its highest activity with medium-chain substrates. It is part of a multienzyme complex and is coded for by the fadA gene (Yang S Y et al (1990) Nucleotide sequence of the fadA gene. Primary structure of 3-ketoacyl-coenzyme A thiolase from *Escherichia coli* and the structural organization of the fadAB operon. J Biol Chem 265 (18): 10424-10429;

3-ketoacyl-CoA thiolase may also be known as acetyl-CoA C-acyltransferase, β-ketothiolase, acetyl-CoA acyltransferase and acyl-CoA:acetyl-CoA C-acyltransferase.

Another exemplary enzyme is an enoyl-CoA hydratase. The alpha subunit has four enzymatic activities associated with it. It is part of a multienzyme complex. Two of the activities, enoyl-CoA hydratase (EC 4.2.1.17) and 3-OH acyl-CoA epimerase (EC 5.1.2.3) are carried out by the same N terminal active site (Yang S Y and Elzinga M (1993) Association of both enoyl coenzyme A hydratase and 3-hydroxyacyl coenzyme A epimerase with an active site in the amino-terminal domain of the multifunctional fatty acid oxidation protein from *Escherichia coli*. J Biol Chem 268 (9): 6588-6592).

In one embodiment, the methylcrotonyl-CoA hydratase is a 3-ketoacyl-CoA thiolase. In another embodiment, the methylcrotonyl-CoA hydratase is encoded by one or more nucleic acid molecules obtained from *Escherichia coli*. In some embodiments, the one or more nucleic acid molecules encoding the methylcrotonyl-CoA hydratase is fadA, or homolog thereof. In a further embodiment, the one or more nucleic acid molecules encoding the methylcrotonyl-CoA hydratase comprises an amino acid sequence set forth in SEQ ID NO: 131. In yet another embodiment, the one or more nucleic acid molecules encoding the methylcrotonyl-CoA hydratase is encoded by a nucleic acid sequence set forth in SEQ ID NO: 130.

In one embodiment, the methylcrotonyl-CoA hydratase is an enoyl-CoA hydratase. In another embodiment, the methylcrotonyl-CoA hydratase is encoded by one or more nucleic acid molecules obtained from *Escherichia coli*. In some embodiments, the one or more nucleic acid molecules encoding the methylcrotonyl-CoA hydratase is fadB, or homolog thereof. In a further embodiment, the one or more nucleic acid molecules encoding the methylcrotonyl-CoA hydratase comprises an amino acid sequence set forth in SEQ ID NO: 133. In yet another embodiment, the one or more nucleic acid molecules encoding the methylcrotonyl-CoA hydratase is encoded by a nucleic acid sequence set forth in SEQ ID NO: 132.

3-hydroxy-isovaleryl-CoA thioesterase (EC 3.1.2.-)

The present disclosure describes enzymes that can catalyze the following reactions:

3-hydroxyisovaleryl-CoA+H$_2$O↔3-hydroxyisovalerate+CoA an acyl-CoA+H$_2$O→a carboxylate+coenzyme A+H$^+$ An exemplary acyl-CoA thioesterase is TesB. Thioesterase II (TesB) is one of a number of thioesterases present in *E. coli*. The enzyme has relatively broad substrate specificity, cleaving medium- and long-chain acyl-CoA substrates; the best tested substrate was 3,5-tetradecadienoyl-CoA (Nie L et al. (2008) A novel paradigm of fatty acid beta-oxidation exemplified by the thioesterase-dependent partial degradation of conjugated linoleic acid that fully supports growth of *Escherichia coli*. Biochemistry 47(36): 9618-9626). Thioesterase II is one of the thioesterases supporting growth on oleate or conjugated linoleic acid as the sole source of carbon (Nie et al. 2008).

A crystal structure of the enzyme has been solved at 1.9 Å resolution. The D204 residue was predicted to be in the active site; its importance was confirmed by kinetic analysis of mutants (Li J et al. (2000) Crystal structure of the *Escherichia coli* thioesterase II, a homolog of the human Nef binding enzyme. Nat Struct Biol 7(7): 555-559).

Strains either lacking or overproducing tesB have no obvious defect (Narasimhan M L et al. (1986) Genetic and biochemical characterization of an *Escherichia coli* K-12 mutant deficient in acyl-coenzyme A thioesterase II. J Bacteriol 165(3): 911-917; Naggert J et al. (1991) Cloning, sequencing, and characterization of *Escherichia coli* thioesterase II. J Biol Chem 266(17): 11044-11050). Overproduction of TesB relieves inhibition of fatty acid synthesis by long-chain acyl-ACP molecules that accumulate upon glycerol starvation (Jiang P and Cronan J E (1994) Inhibition of fatty acid synthesis in *Escherichia coli* in the absence of phospholipid synthesis and release of inhibition by thioesterase action. J Bacteriol 176(10): 2814-2821).

In one embodiment, the 3-hydroxy-isovaleryl-CoA thioesterase is encoded by one or more nucleic acid molecules obtained from *E. coli*. In some embodiments, the one or more nucleic acid molecules encoding the 3-hydroxy-isovaleryl-CoA thioesterase is tesB, or homolog thereof. In a further embodiment, the one or more nucleic acid molecules encoding the 3-hydroxy-isovaleryl-CoA thioesterase comprises an amino acid sequence set forth in SEQ ID NO: 135. In yet another embodiment, the one or more nucleic acid molecules encoding the 3-hydroxy-isovaleryl-CoA thioesterase is encoded by a nucleic acid sequence set forth in SEQ ID NO: 134.

Mevalonate-3-Kinase (EC 2.7.1.-)

The present disclosure describes enzymes that can catalyze the following reaction:

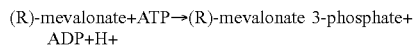

Mevalonate-3-kinase may also be known as (R)-MVA 3-phosphotransferase or 3-hydroxyisovalerate (3HIV) kinase.

The subunit structure of this enzyme from *Thermoplasma acidophilum* has not been reported.

The mevalonate-3-kinase from the thermophilic archaeon *Thermoplasma acidophilum* is thought to participate in a variant of the mevalonate pathway found in archaea Azami Y et al. (2014) (R)-Mevalonate 3-Phosphate Is an Intermediate of the Mevalonate Pathway in *Thermoplasma acidophilum*. J Biol Chem 289(23): 15957-15967; Vinokur J M et al. (2014) Evidence of a Novel Mevalonate Pathway in Archaea. Biochemistry 53(25): 4161-4168).

Recombinant His-tagged enzyme was expressed in *Escherichia coli*, purified and characterized. Despite its homology with diphosphomevalonate decarboxylase, it showed no decarboxylase activity (Azami et al. 2014; Vinokur et al. 2014). The enzyme showed weak phosphomevalonate kinase activity, producing small amounts of (R)-mevalonate diphosphate (Azami et al. 2014). It had no mevalonate-5-kinase activity (Vinokur et al. 2014).

In one embodiment, the 3HIV kinase is encoded by one or more nucleic acid molecules obtained from a microorganism selected from the group consisting of *Thermoplasma* sp. and *Picrophilus* sp. In another embodiment, the 3HIV kinase is encoded by one or more nucleic acid molecules obtained from a microorganism selected from the group consisting of *Thermoplasma acidophilum* and *Picrophilus torridus*. In some embodiments, the one or more nucleic acid molecules encoding the 3HIV kinase is TA1305 and/or PTO1356, or homolog thereof. In some embodiments, the TA1305 comprises a L200E mutation. In a further embodiment, the one or more nucleic acid molecules encoding the 3HIV-kinase comprises an amino acid sequence selected from the group consisting of SEQ ID NOs: 113, 115 and 117. In yet another embodiment, the one or more nucleic acid molecules encoding the 3HIV kinase is encoded by a nucleic acid sequence selected from the group consisting of SEQ ID NOs: 112, 114 and 116.

Mevalonate Diphosphate Decarboxylase (EC 4.1.1.-)

The present disclosure describes enzymes that can catalyze the following reactions:

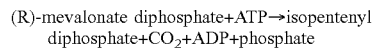

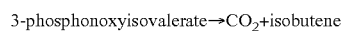

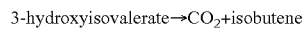

Mevalonate diphosphate decarboxylase may also be known as pyrophosphomevalonate decarboxylase, mevalonate-5-pyrophosphate decarboxylase, pyrophosphomevalonic acid decarboxylase, 5-pyrophosphomevalonate decarboxylase, mevalonate 5-diphosphate decarboxylase, and ATP:(R)-5-diphosphomevalonate carboxy-lyase (dehydrating), 3-phosphonoxyisovalerate decarboxylase, 3-hydroxyisovalerate-3-phosphate decarboxylase, 3HIV-3-phosphate decarboxylase, 3-hydroxyisovalerate decarboxylase and 3HIV decarboxylase.

This enzyme converts mevalonate 5-diphosphate (MVAPP) to isopentenyl diphosphate (IPP) through ATP dependent decarboxylation. The two substrates of this enzyme are ATP and mevalonate 5-diphosphate, whereas its four products are ADP, phosphate, isopentenyl diphosphate, and $CO_2$.

Mevalonate diphosphate decarboxylase catalyzes the final step in the mevalonate pathway. The mevalonate pathway is responsible for the biosynthesis of isoprenoids from acetate. This pathway plays a key role in multiple cellular processes by synthesizing sterol isoprenoids, such as cholesterol, and non-sterol isoprenoids, such as dolichol, heme A, tRNA isopentenyltransferase, and ubiquinone. This enzyme belongs to the family of lyases, specifically the carboxy-lyases, which cleave carbon-carbon bonds.

Mevalonate diphosphate decarboxylase recognizes and binds two substrates: ATP and mevalonate 5-diphosphate. After binding, the enzyme performs three types of reactions that can be separated into two main stages. First, phosphorylation occurs. This creates a reactive intermediate, which in the second stage undergoes concerted dephosphorylation and decarboxylation.

In one embodiment, the enzyme that catalyzes the reaction 3-phosphonoxyisovalerate→$CO_2$+isobutene is a 3HIV-3-phosphate decarboxylase. In another embodiment, the 3HIV-3-phosphate decarboxylase is encoded by one or more nucleic acid molecules obtained from *Streptococcus* sp. In some embodiments, the microorganism is selected from *Streptococcus mitis* and/or *Streptococcus gordonii*. In some embodiments, the one or more nucleic acid molecules encoding the 3HIV-3-phosphate decarboxylase comprises an amino acid sequence selected from SEQ ID NOs: 119 and 121. In further embodiments, the one or more nucleic acid molecule encoding the 3HIV-3-phosphate decarboxylase is encoded by a nucleic acid sequence selected from SEQ ID NOs: 118 and 120.

In one embodiment, the enzyme that catalyzes the reaction 3-hydroxyisovalerate→$CO_2$+isobutene is a 3HIVdecarboxylase. In another embodiment, the 3HIV decarboxylase is encoded by one or more nucleic acid molecules obtained from a microorganism selected from the group consisting of *Streptococcus* sp., *Thermoplasma* sp. and *Picrophilus* sp. In another embodiment, the 3HIV decarboxylase is encoded by one or more nucleic acid molecules obtained from a microorganism selected from the group consisting of *Streptococcus gordonii, Thermoplasma acidophilum* and *Picrophilus torridus*. In some embodiments, the one or more nucleic acid molecules encoding the 3HIV decarboxylase comprises mvaD, TA1305 and/or PTO1356, or homolog thereof. In a further embodiment, the one or more nucleic acid molecules encoding the 3HIV decarboxylase comprises an amino acid sequence selected from the group consisting of SEQ ID NOs: 113, 117 and 121. In yet another embodiment, the one or more nucleic acid molecules encoding the 3HIV decarboxylase is encoded by a nucleic acid sequence selected from the group consisting of SEQ ID NOs: 112, 116 and 120.

Transketolase (EC 2.2.1.1)

The present disclosure describes enzymes that can catalyze the following reactions:

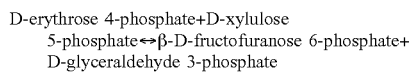

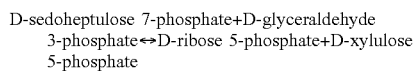

Transketolase may also be known as glycolaldehydetransferase.

Transketolase catalyzes the reversible transfer of a ketol group between several donor and acceptor substrates. This key enzyme is a reversible link between glycolysis and the pentose phosphate pathway. The enzyme is involved in the catabolism of pentose sugars, the formation of D-ribose 5-phosphate, and the provision of D-erythrose 4-phosphate, a precursor of aromatic amino acids and PLP. *E. coli* contains two transketolase isozymes, TktA and TktB. TktA is responsible for the major transketolase activity.

In addition to its function in central carbon metabolism, transketolase appears to also have an unexpected role in chromosome structure; a tktA mutant affects chromosome topology.

Crystal structures of TktA in complex with donor and acceptor substrates have been solved, elucidating the reaction mechanism and mode of action of transketolase. A computational model of transketolase activity using a quantum mechanical/molecular mechanical method has been proposed, defining a new route for thiamine diphosphate activation. Transketolase I (TktA) is homodimeric. The urea denaturation pathways of wild type and active site mutants of TktA have been investigated, and the effects of temperature and pH on the structure, stability, aggregation and activity of transketolase have been determined. The acceptor specificity of TktA has been investigated.

TktA abundance is affected by the SOS inducer and mutagen 7-methoxy-2-nitronaphtho[2,1-b]furan (R7000). tktA is negatively regulated during entry into stationary phase. The effect by RpoS is likely indirect and might be mediated by an intermediate regulator that itself is directly regulated by RpoS.

The subunit structure of transketolase II (TktB) has not been explicitly determined. Overproduction of TktB suppresses the tktA mutant phenotype. Expression of tktB is increased in a tyrR mutant in the presence of phenylalanine. tktB expression is increased in stationary phase and positively regulated by RpoS and ppGpp. Levels of TktB protein increase during osmotic stress under aerobic, but not anaerobic growth conditions. TktB appears to be associated with the degradosome and may connect carbon metabolism to replication.

Expression of tktA and tktB is complementary, resulting in approximately constant levels of transketolase expression throughout growth.

In some embodiments, the transketolase is encoded by an amino acid sequence having at least 70% sequence identity to tktA from *E. coli*. In a further embodiment, the transketolase is encoded by an amino acid sequence having at least 80% sequence identity to tktA from *E. coli*. In yet a further embodiment, the transketolase is encoded by an amino acid sequence having at least 90% sequence identity to tktA from *E. coli*. In other embodiments, the transketolase is tktA from *E. coli*. In some embodiments, the transketolase is encoded by an amino acid sequence having at least 70% sequence identity to tktB from *E. coli*. In a further embodiment, the transketolase is encoded by an amino acid sequence having at least 80% sequence identity to tktB from *E. coli*. In yet a further embodiment, the transketolase is encoded by an amino acid sequence having at least 90% sequence identity to tktB from *E. coli*. In other embodiments, the transketolase is tktB from *E. coli*.

In some embodiments, the one or more nucleic acid molecules encoding the transketolase is tktA, or homolog thereof. In some embodiments, the one or more nucleic acid molecules encoding the transketolase is tktB, or homolog thereof. In another embodiment, the one or more nucleic acid molecules encoding the transketolase comprises an amino acid sequence selected from the group consisting of SEQ ID NOs: 148 and 150. In a further embodiment, the one or more nucleic acid molecule encoding the transketolase is encoded by a nucleic acid sequence selected from the group consisting of SEQ ID NOs: 147 and 149.

Transaldolase (EC 2.2.1.2)

The present disclosure describes enzymes that can catalyze the following reaction:

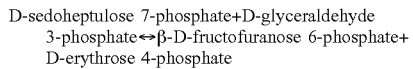

Transaldolase may also be known as dihydroxyacetonetransferase; dihydroxyacetone synthase; formaldehyde transketolase.

Transaldolase B is an enzyme of the non-oxidative branch of the pentose phosphate pathway. Along with transketolase, transaldolase creates a reversible link between the pentose phosphate pathway and glycolysis. It catalyzes the interconversion of glyceraldehyde-3-phosphate and sedoheptulose-7-phosphate to fructose-6-phosphate and erythrose-4-phosphate. The reversibility of this reaction and carbon flux through the pentose phosphate pathway has been addressed both experimentally and theoretically.

There are two closely related transaldolases in *E. coli*, encoded by talA and talB. Only transaldolase B has been biochemically characterized. TalB is a dimer in solution and in the crystal structure. Mutation of the R300 residue leads to the formation of catalytically active monomers. Catalytically important active site residues have been identified by site-directed mutagenesis.

Crystal structures of transaldolase B have been determined, confirming the presence of a Schiff-base intermediate at the active site and leading to a proposed reaction mechanism.

A talB null mutant has no growth defect on minimal media with glucose as the carbon source.

In some embodiments, the transaldolase is encoded by an amino acid sequence having at least 70% sequence identity to talA or talB from *E. coli*. In a further embodiment, the transaldolase is encoded by an amino acid sequence having at least 80% sequence identity to talA or talB from *E. coli*. In yet a further embodiment, the transaldolase is encoded by an amino acid sequence having at least 90% sequence identity to talA or talB from *E. coli*. In other embodiments, the transaldolase is talA from *E. coli*. In yet further embodiments, the transaldolase is talB from *E. coli*.

In some embodiments, the one or more nucleic acid molecules encoding the transaldolase is talA, or homolog thereof. In some embodiments, the one or more nucleic acid molecules encoding the transaldolase is talB, or homolog thereof. In another embodiment, the one or more nucleic acid molecules encoding the transaldolase comprises an amino acid sequence selected from the group consisting of SEQ ID NOs: 152 and 154. In a further embodiment, the one or more nucleic acid molecule encoding the transaldolase is encoded by a nucleic acid sequence selected from the group consisting of SEQ ID NOs: 151 and 153.

Ribose-5-Phosphate Isomerase (EC 5.3.1.6)

The present disclosure describes enzymes that can catalyze the following reaction:

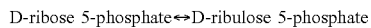

D-ribose 5-phosphate↔D-ribulose 5-phosphate

Ribose-5-phosphate isomerase may also be known as phosphopentosisomerase; phosphoriboisomerase; ribose phosphate isomerase; 5-phosphoribose isomerase; D-ribose 5-phosphate isomerase; D-ribose-5-phosphate ketol-isomerase.

There are two physically and genetically distinct ribose-5-phosphate isomerases present in *E. coli*. The constitutive ribose-5-phosphate isomerase A (rpiA) normally accounts for more than 99% of the ribose-5-phosphate isomerase activity in the cell and functions in the pentose phosphate pathway (non-oxidative branch). The inducible ribose-5-phosphate isomerase B (rpiB) can substitute for rpiA's function if its expression is induced. There is no sequence similarity between the two enzymes.

Crystal structures of rpiA have been solved and active site residues and an acid-base catalytic mechanism were predicted. An rpiA mutant requires ribose for growth.

In some embodiments, the ribose-5-phosphate isomerase is encoded by an amino acid sequence having at least 70% sequence identity to rpiA or rpiB from *E. coli*. In a further embodiment, the ribose-5-phosphate isomerase is encoded by an amino acid sequence having at least 80% sequence identity to rpiA or rpiB from *E. coli*. In yet a further embodiment, the ribose-5-phosphate isomerase is encoded by an amino acid sequence having at least 90% sequence identity to rpiA or rpiB from *E. coli*. In other embodiments, the ribose-5-phosphate isomerase is rpiA or rpiB from *E. coli*.

In some embodiments, the one or more nucleic acid molecules encoding the ribose-5-phosphate isomerase is rpiA, or homolog thereof. In another embodiment, the one or more nucleic acid molecules encoding the ribose-5-phosphate isomerase comprise an amino acid sequence set forth in SEQ ID NO: 156. In a further embodiment, the one or more nucleic acid molecules encoding the ribose-5-phosphate isomerase is encoded by a nucleic acid sequence set forth in SEQ ID NO: 155. In some embodiments, the one or more nucleic acid molecules encoding the ribose-5-phosphate isomerase is rpiB, or homolog thereof. In another embodiment, the one or more nucleic acid molecules encode the ribose-5-phosphate isomerase comprising an amino acid sequence set forth in SEQ ID NO: 253. In a further embodiment, the one or more nucleic acid molecules encoding the ribose-5-phosphate isomerase is encoded by a nucleic acid sequence set forth in SEQ ID NO: 254.

Ribulose-5-Phosphate 3-Epimerase (EC 5.1.3.1)

The present disclosure describes enzymes that can catalyze the following reaction:

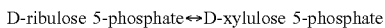

D-ribulose 5-phosphate↔D-xylulose 5-phosphate

Ribulose-5-phosphate 3-epimerase may also be known as ribulose-phosphate 3-epimerase; phosphoribulose epimerase; erythrose-4-phosphate isomerase; phosphoketopentose 3-epimerase; xylulose phosphate 3-epimerase; phosphoketopentose epimerase; D-ribulose phosphate-3-epimerase; D-ribulose 5-phosphate epimerase; D-ribulose-5-P 3-epimerase; D-xylulose-5-phosphate 3-epimerase; pentose-5-phosphate 3-epimerase.

Ribulose-5-phosphate 3-epimerase (Rpe) is an enzyme of the non-oxidative branch of the pentose phosphate pathway.

Rpe requires ferrous iron for activity and is vulnerable to damage by $H_2O_2$ due to Fenton chemistry. $Mn^{2+}$, $Co^{2+}$ and $Zn^{2+}$ can substitute for $Fe^{2+}$ to varying degrees, and Rpe containing these alternative cations is not vulnerable to $H_2O_2$. Induction of the manganese transporter can protect Rpe from $H_2O_2$ damage.

In some embodiments, the ribulose-5-phosphate 3-epimerase is encoded by an amino acid sequence having at least 70% sequence identity to rpe from *E. coli*. In a further embodiment, the ribulose-5-phosphate 3-epimerase is encoded by an amino acid sequence having at least 80% sequence identity to rpe from *E. coli*. In yet a further embodiment, the ribulose-5-phosphate 3-epimerase is encoded by an amino acid sequence having at least 90% sequence identity to rpe from *E. coli*. In other embodiments, the ribulose-5-phosphate 3-epimerase is rpe from *E. coli*.

In some embodiments, the one or more nucleic acid molecules encoding the ribulose-5-phosphate 3-epimerase is rpe, or homolog thereof. In another embodiment, the one or more nucleic acid molecules encoding the ribulose-5-phosphate 3-epimerase comprise an amino acid sequence set forth in SEQ ID NO: 158. In a further embodiment, the one or more nucleic acid molecule encoding the ribulose-5-phosphate 3-epimerase is encoded by a nucleic acid sequence set forth in SEQ ID NO: 157.

Fructose 6-Phosphate Phosphoketolase (Fpk, EC 4.1.2.22)

The present disclosure describes enzymes that can catalyze the following reaction:

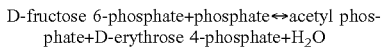

D-fructose 6-phosphate+phosphate↔acetyl phosphate+D-erythrose 4-phosphate+$H_2O$ The phosphoketolase reaction by which β-D-fructofuranose 6-phosphate is converted to D-erythrose 4-phosphate and acetyl phosphate is one of the key reactions in the *Bifidobacterium* shunt. There is evidence for the existence of two distinct F6P-phosphoketolase enzymes in bifidobacteria. One is specific solely for F6P while the other is able to utilize both F6P and D-xylulose 5-phosphate (EC: 4.1.2.9), a reaction that appears later in the *Bifidobacterium* shunt. The enzyme encoded by the xfp gene, originally discovered in *Bifidobacterium animalis* lactis, is the dual-specificity enzyme. A phosphoketolase has also been purified from *Leuconostoc nesenteroides* (LEUM_1961).

In some embodiments, an enzyme having fructose-6-phosphate phosphoketolase activity is encoded by an amino acid sequence having at least 70% sequence identity, at least 80% sequence identity, or at least 90% sequence identity to an enzyme having fructose-6-phosphate phosphoketolase activity selected from the group consisting of *Bifidobacterium dentium* BDP_1006, *Bifidobacterium lactis* xfp, *Lactobacillus paraplantarum* xpkA and *Bifidobacterium breve* xfp. In a preferred embodiment, an enzyme having fructose- 6-phosphate phosphoketolase activity is selected from the group consisting of *Bifidobacterium dentium* BDP 1006, *Bifidobacterium lactis* xfp, *Lactobacillus paraplantarum* xpkA and *Bifidobacterium breve* xfp. In another embodiment, the one or more nucleic acid molecules encoding the fructose-6-phosphate phosphoketolase comprise an amino acid sequence selected from the group consisting of SEQ ID NOs: 212, 214, 216 and 218. In a further embodiment, the one or more nucleic acid molecule encoding the fructose-6-phosphate phosphoketolase is encoded by a nucleic acid sequence selected from the group consisting of SEQ ID NOs: 211, 213, 215 and 217.

Phosphate Acetyltransferase (EC 2.3.1.8)

The present disclosure describes enzymes that can catalyze the following reaction:

Acetyl-CoA+phosphate↔CoA+acetyl phosphate

Phosphate acetyltransferase (Pta) catalyzes the reversible conversion between acetyl-CoA and acetylphosphate, a step in the metabolism of acetate. Both pyruvate and phosphoenolpyruvate activate the enzyme in the direction of acetylphosphate synthesis and inhibit the enzyme in the direction of acetyl-CoA synthesis. The acetate formation from acetyl-CoA I pathway has been the target of metabolic engineering to reduce the flux to acetate and increase the production of commercially desired end products. It has also been studied using systems biology approaches such as metabolic modeling and flux balance analysis.

Pta is composed of three domains; only the C-terminal domain is required for phosphate acetyltransferase activity. The N-terminal domain is involved in stabilization of the native quarternary structure and metabolic regulation.

Pta may be able to utilize both acetyl-CoA and propionyl-CoA. An ack pta double mutant has reduced levels of propionate from L-threonine, suggesting that the enzyme is part of the anaerobic pathway metabolizing L-threonine to propionate. A pta mutant does not grow on acetate as the sole source of carbon. Both pta and pta ackA mutants are impaired in their ability to survive glucose starvation. The growth defect of a pta mutant appears to be due to perturbation of acetyl-CoA flux. pta mutants produce large amounts of lactate when grown on glucose as the carbon source under microaerophilic conditions. The effect of a pta mutation on metabolism, enzyme activity and gene expression has been thoroughly studied recently. pta and recBC mutants are synthetically growth inhibited.

Levels of Pta are decreased by growth on acetate and under low pH conditions. pta belongs to the CreBC regulon. FNR has a slightly positive effect on pta expression. The growth-rate dependent expression pattern of pta-ackA was measured.

The pta gene that encodes the enzyme has been cloned from *Clostridium acetobutylicum*, sequenced and expressed in *Escherichia coli*. The gene is adjacent to the ackA gene, which encodes the enzyme that catalyzes the second step—acetate kinase. Enzyme activity assays performed on cell extracts from *Escherichia coli* and *Clostridium acetobutylicum* harboring the subclone showed elevated activity. The enzymes shows a decrease in specific activity when the organism reaches the solvent formation stage.

Enzymes having phosphate acetyltransferase activity or phosphate acetyltransferase genes have also been identified or measured from *E. coli* (eutD, pta), *Roseovarius nubinhibens* ISM, *Clostridium kluyveri*, *Chlamydomonas reinhardtii* (PAT2), *Dasytricha ruminantium*, *Pelobacter acetylenicus*, *Gottschalkia acidurici*, *Lactobacillus sanfranciscensis*, *Paracoccus denitrificans* NKNIS, *Eubacterium oxidoreducens* G41, *Mycoplasma pneumoniae* M129, *Thermotoga maritima*, *Moorella thermoacetica*, *Methanosarcina thermophile*, *Clostridium propionicum* and *Fusobacterium nucleatum*.

In some embodiments, an enzyme having phosphate acetyltransferase activity is encoded by an amino acid sequence having at least 70% sequence identity, at least 80% sequence identity, or at least 90% sequence identity to an enzyme having phosphate acetyltransferase activity selected from *E. coli* pta and *Clostridium acetobutylicum* pta. In a preferred embodiment, an enzyme having phosphate acetyltransferase activity is selected from *E. coli* pta and *Clostridium acetobutylicum* pta. In another embodiment, the one or more nucleic acid molecules encoding the phosphate acetyltransferase comprise an amino acid sequence selected from SEQ ID NOs: 220 and 222. In a further embodiment, the one or more nucleic acid molecule encoding the phosphate acetyltransferase is encoded by a nucleic acid sequence selected from SEQ ID NOs: 219 and 221.

Pentose Phosphatase (EC 3.1.3.23 and EC 3.1.3.1)

The present disclosure describes enzymes that can catalyze the following reactions:

D-pentose 5-phosphate+H₂O→D-pentose+phosphate

D-ribose 5-phosphate+H₂O→D-ribose+phosphate

D-xylulose 5-phosphate+H₂O→D-xylulose+phosphate

D-ribulose 5-phosphate+H₂O→D-ribulose+phosphate a sugar phosphate+H₂O→a sugar+phosphate

*E. coli* YbiV is a sugar phosphatase belonging to the family of type II haloacid dehalogenase (HAD)-like hydrolases. It shows a low level of discrimination between its preferred substrates. In addition, YbiV appears to have a low level of phosphotransferase activity using monophosphates as the phosphate donor. The phosphatase activity of YbiV was also discovered in a high-throughput screen of purified proteins. Crystal structures of YbiV have been solved, and a catalytic mechanism was suggested. YbiV may exist as a homodimer in solution.

*E. coli* YidA is a promiscuous sugar phosphatase belonging to the superfamily of haloacid dehalogenase (HAD)-like hydrolases. Its preferred substrate is erythrose-4-phosphate. YidA selectively hydrolyzes α-D-glucose-1-phosphate and has no activity with the β form. The reaction proceeds via the canonical phosphomonoester hydrolase mechanism, which involves breakage of the P—O bond, not the Cl—O bond. The phosphatase activity of YidA was first discovered in a high-throughput screen of purified proteins. Mutagenesis of the predicted catalytic Asp residue in YidA results in loss of phosphatase activity. YidA does not catalyze phosphoryl transfer to a sugar acceptor.

*E. coli* alkaline phosphatase (phoA) is a periplasmic, homodimeric enzyme that catalyses the hydrolysis and transphosphorylation of a wide variety of phosphate monoesters. The reaction proceeds through a phosphoseryl intermediate with the subsequent release of inorganic phosphate and alcohol. The transphosphorylation reaction results in the transfer of a phosphoryl group to the alcohol of acceptors such as Tris or ethanolamine. Alkaline phosphatase is a metalloenzyme, binding two zinc atoms and one magnesium ion per monomer. Alkaline phosphatase occurs in three major forms designated isozymes 1, 2 and 3 whose relative proportions are dependent on the growth conditions. The isozymes are differentiated by the presence or absence of an NH2-terminal arginine residue: present in both subunits of isozyme 1, absent in both subunits of isozyme 3 and heterogenous in isozyme 2. Removal of the N-terminal arginine is catalysed by the membrane-associated, proteolytic enzyme Tap. The precursor polypeptide is secreted across the inner membrane to the periplasmic space concommitant with removal of the signal sequence. Folding of PhoA in vivo is catalysed by the periplasmic protein, DsbA and is thought to occur as the polypeptide elongates from the ribosome. phoA is part of the phosphate regulon; its expression is positively regulated by the PhoB transcriptional regulator.

In some embodiments, the pentose phosphatase is an alkaline phosphatase. In some preferred embodiments, the alkaline phosphatase may be evolved to preferrably act on targeted pentose 5-phosphate. In some embodiments, the pentose phosphatase is a sugar phosphatase. In other embodiments, the sugar phosphatase may be evolved to preferrably act on targeted pentose 5-phosphate. In some embodiments, the pentose phosphatase is a haloacid dehalogenase-like hydrolase. In another embodiment, the haloacid dehalogenase-like hydrolase may be evolved to preferrably act on targeted pentose 5-phosphate.

In some embodiments, the pentose phosphatase is selected from one or more of a D-pentose-5-phosphatase, a D-xylulose-5-phosphatase, a D-ribose-5-phosphatase, and a D-ribulose-5-phosphatase. In some embodiments, the pentose phosphatase is encoded by an amino acid sequence having at least 70% sequence identity, at least 80% sequence identity, or at least 90% sequence identity to a D-pentose-5-phosphatase selected from the group consisting of *E. coli* phoA, *E. coli* yfbT and *E. coli* yidA. In some embodiments, the D-xylulose-5-phosphatase is encoded by an amino acid sequence having at least 70% sequence identity, at least 80% sequence identity, or at least 90% sequence identity to *Bacillus subtilis* araL. In some embodiments, the D-ribose-5-phosphatase is encoded by an amino acid sequence having at least 70% sequence identity, at least 80% sequence identity, or at least 90% sequence identity to a D-ribose-5-phosphatase selected from the group consisting of *Arabidopsis thaliana* SGPP, *Pseudomonas fluorescens* PFLU_2693, and *E. coli* ybiV. In some embodiments, the D-ribulose-5-phosphatase is encoded by an amino acid sequence having at least 70% sequence identity, at least 80% sequence identity, or at least 90% sequence identity to *Plasmodium falciparum* PF10_0325.

In some embodiments, the one or more nucleic acid molecules encoding the D-pentose-5-phosphatase is selected from the group consisting of SEQ ID NOs: 159, 161, 163, 165, 167, 169, 171 and 173. In another embodiment, the one or more nucleic acid molecules encoding the D-pentose-5-phosphatase comprise an amino acid sequence selected from the group consisting of SEQ ID NOs: 160, 162, 164, 166, 168, 170, 172 and 174.

Arabitol Phosphate Dehydrogenase (EC 1.1.1.-)

The present disclosure describes enzymes that can catalyze the following reactions:

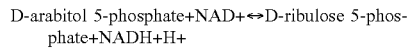

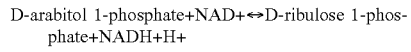

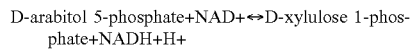

D-arabitol-phosphate dehydrogenase APDH from *Enterococcus avium* has been purified to homogeneity. The protein, which forms a homotetramer, catalyzes the dehydrogenation of both D-arabitol 1-phosphate and D-arabitol 5-phosphate, producing D-xylulose 5-phosphate and D-ribulose 5-phosphate, respectively. Maximal velocity with D-arabitol 1-phosphate was 10-fold than with D-arabitol 5-phosphate. The purified protein was partially sequenced, and the APDH gene encoding it was cloned. The enzyme requires Mn2+ and can not utilize Zn2+ for activity. Both NAD(+) and NADP(+) were accepted as cofactors, but reaction rates with NAD+/NADH were about 14 times higher than with NADP+/NADPH. The enzyme catalyzes a reversible reaction, but the rate of the reduction reaction is much higher that the oxidative reaction. Kinetic data suggests that the enzyme forms a ternary complex with its substrate and NADH. Both biochemical evidence and protein sequence homology comparisons indicate that similar enzymes are widespread among the Gram-positive bacteria and participate in arabitol catabolism.

In some embodiments, the pentol dehydrogenase activity may be evolved to apply to pentol phosphate.

In some embodiments, the arabitol phosphate dehydrogenase is selected from one or more of an enzyme having D-arabitol 1-phosphate 4-dehydrogenase activity, an enzyme having D-arabitol 5-phosphate 2-dehydrogenase activity, an enzyme having D-arabitol 1-phosphate 2-dehydrogenase activity and an enzyme having D-arabitol 5-phosphate 4-dehydrogenase activity.

In some embodiments, an enzyme having D-arabitol 1-phosphate 4-dehydrogenase activity is encoded by an amino acid sequence having at least 70% sequence identity, at least 80% sequence identity, or at least 90% sequence identity to APDH from *Enterococcus avium*. In a preferred embodiment, an enzyme having D-arabitol 1-phosphate 4-dehydrogenase activity is APDH from *Enterococcus avium*. In some embodiments, the one or more nucleic acid molecules encoding a D-arabitol 1-phosphate 4-dehydrogenase is set forth in SEQ ID NO: 175. In another embodiment, the one or more nucleic acid molecules encoding a D-arabitol 1-phosphate 4-dehydrogenase comprise an amino acid sequence set forth in SEQ ID NO: 176.

In some embodiments, an enzyme having D-arabitol 5-phosphate 2-dehydrogenase activity is encoded by an amino acid sequence having at least 70% sequence identity, at least 80% sequence identity, or at least 90% sequence identity to APDH from *Enterococcus avium*. In a preferred embodiment, an enzyme having D-arabitol 5-phosphate 2-dehydrogenase activity is APDH from *Enterococcus avium*. In some embodiments, the one or more nucleic acid molecules encoding a D-arabitol 5-phosphate 2-dehydrogenase is set forth in SEQ ID NO: 175. In another embodiment, the one or more nucleic acid molecules encoding a D-arabitol 5-phosphate 2-dehydrogenase comprise an amino acid sequence set forth in SEQ ID NO: 176.

In some embodiments, an enzyme having D-arabitol 1-phosphate 2-dehydrogenase activity is encoded by an amino acid sequence having at least 70% sequence identity, at least 80% sequence identity, or at least 90% sequence identity to an enzyme having D-arabitol 1-phosphate 2-dehydrogenase activity selected from the group consisting of *Candida albicans* ARD1, *Candida tropicalis* ARD1, *Scheffersomyces stipitis* ARDH, *Bacillus subtilis* egsA (araM), *Aeropyrum pernix* egsA, *E. coli* gpsA and *Saccharomyces cerevisiae* GPD1. In a preferred embodiment, an enzyme having D-arabitol 1-phosphate 2-dehydrogenase activity is selected from the group consisting of *Candida albicans*

ARD1, *Candida tropicalis* ARD1, *Scheffersomyces stipitis* ARDH, *Bacillus subtilis* egsA (araM), *Aeropyrum pernix* egsA, *E. coli* gpsA and *Saccharomyces cerevisiae* GPD1. In some embodiments, the one or more nucleic acid molecules encoding a D-arabitol 1-phosphate 2-dehydrogenase is selected from the group consisting of SEQ ID NOs: 177, 179, 181, 189, 191, 193 and 195. In another embodiment, the one or more nucleic acid molecules encoding a D-arabitol 1-phosphate 2-dehydrogenase comprise an amino acid sequence selected from the group consisting of SEQ ID NOs: 178, 180, 182, 190, 192, 194 and 196.

In some embodiments, an enzyme having D-arabitol 5-phosphate 4-dehydrogenase activity is encoded by an amino acid sequence having at least 70% sequence identity, at least 80% sequence identity, or at least 90% sequence identity to an enzyme having D-arabitol 5-phosphate 4-dehydrogenase activity selected from the group consisting of *Pseudomonas fluorescens* mtlD, *Klebsiella pneumoniae* dalD, *Ralstonia solanacearum* dalD, *Bacillus subtilis* egsA (araM), *Aeropyrum pernix* egsA, *E. coli* gpsA and *Saccharomyces cerevisiae* GPD1. In a preferred embodiment, an enzyme having D-arabitol 5-phosphate 4-dehydrogenase activity is selected from the group consisting of *Pseudomonas fluorescens* mtlD, *Klebsiella pneumoniae* dalD, *Ralstonia solanacearum* dalD, *Bacillus subtilis* egsA (araM), *Aeropyrum pernix* egsA, *E. coli* gpsA and *Saccharomyces cerevisiae* GPD1. In some embodiments, the one or more nucleic acid molecules encoding a D-arabitol 5-phosphate 4-dehydrogenase is selected from the group consisting of SEQ ID NOs: 183, 185, 187, 189, 191, 193 and 195. In another embodiment, the one or more nucleic acid molecules encoding a D-arabitol 5-phosphate 4-dehydrogenase comprise an amino acid sequence selected from the group consisting of SEQ ID NOs: 184, 186, 188, 190, 192, 194 and 196.

Phosphopentomutase (EC 5.4.2.-)

The present disclosure describes enzymes that can catalyze the following reactions:

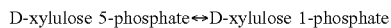

D-xylulose 5-phosphate↔D-xylulose 1-phosphate

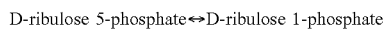

D-ribulose 5-phosphate↔D-ribulose 1-phosphate

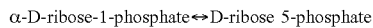

α-D-ribose-1-phosphate↔D-ribose 5-phosphate

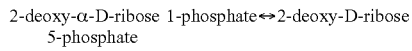

2-deoxy-α-D-ribose 1-phosphate↔2-deoxy-D-ribose 5-phosphate

*E. coli* phosphopentomutase deoB is a catabolic enzyme which catalyzes the transfer of a phosphate group between the C1 and the C5 carbon atoms of ribose and deoxyribose, respectively.

A mutation in deoB suppresses the high thymine requirement for growth of thy mutants and improves the survival of thyA mutants in stationary phase. Transposon insertion mutations in deoB suppress the growth defect of a tktA tktB mutant. Deletion of deoB increases glycerol consumption as well as hydrogen and ethanol production compared to wild type, and increases lycopene production in an engineered strain. The deo operon has a complex pattern of regulation. Expression of deoB is downregulated by nitrogen starvation. The *E. coli* phosphopentomutase appears to be biochemically and structurally distinct from mammalian phosphopentomutase, making it a potential target for antibiotic development.

In some embodiments, the phosphopentomutase (PPM), also named here as phosphosugarmutase (PSM) also has phosphoglucomutase activity, and is *Saccharomyces cerevisiae* phosphoribomutase PRM15 (also known as PGM3) (SEQ ID NO. 255 or SEQ ID NO: 258). In some embodiments, the phosphopentosemutase is encoded by an amino-acid sequence having at least 70% sequence identity, at least 80% sequence identity or at least 90% sequence identity to the Pgm3 from *Saccharomyces cerevisiae*.

In some embodiments, the phosphopentomutase is *Homo sapiens* phosphoglucomutase-2 (PGM2).

In some embodiments, a phosphopentomutase activity may be evolved to apply to D-xylulose 5-phosphate. In other embodiments, a phosphopentomutase activity may be evolved to apply to D-ribulose 5-phosphate. In some embodiments, an alpha-phosphoglucomutase activity may be evolved to apply to D-ribulose 5-phosphate or D-xylulose 5-phosphate. This enzyme from the class EC 5.4.2.2 is reported to require α-glucose 1,6-bisphosphate as co-factor. In further embodiments, a beta-phosphoglucomutase activity may be evolved to apply to D-ribulose 5-phosphate or D-xylulose 5-phosphate. Enzymes from the class EC 5.4.2.6 are reported to be able to autophosphorylate themselves, thus not requiring external glucose 1,6-bisphosphate as co-factor. In yet further embodiments, a phosphomannomutase activity may be evolved to apply to D-ribulose 5-phosphate or D-xylulose 5-phosphate. This enzyme from the class EC 5.4.2.8 is reported to require α-glucose 1,6-bisphosphate or α-D-Mannose 1,6-bisphosphate as co-factor.

In some embodiments, an enzyme having phosphopentomutase activity is encoded by an amino acid sequence having at least 70% sequence identity, at least 80% sequence identity, or at least 90% sequence identity to an enzyme having phosphopentomutase activity selected from the group consisting of *E. coli* deoB, *E. coli* pgm, *Bacillus subtilis* pgcA, *Lactococcus lactis* pgmB, *E. coli* ycjU, *Pseudomonas aeruginosa* algC, and *E. coli* cpsG. In a preferred embodiment, an enzyme having phosphopentomutase activity is selected from the group consisting of *E. coli* deoB, *E. coli* pgm, *Bacillus subtilis* pgcA, *Lactococcus lactis* pgmB, *E. coli* ycjU, *Pseudomonas aeruginosa* algC, *S. cerevisiae* PGM3, and *E. coli* cpsG. In some embodiments, the one or more nucleic acid molecules encoding a phosphopentomutase is selected from the group consisting of SEQ ID NOs: 197, 199, 201, 203, 205, 207 and 209. In another embodiment, the one or more nucleic acid molecules encoding a phosphopentomutase comprise an amino acid sequence selected from the group consisting of SEQ ID NOs: 198, 200, 202, 204, 206, 208 and 210.

Glucose-6-Phosphate 1-Dehydrogenase (EC 1.1.1.49)

The present disclosure describes enzymes that can catalyze the following reaction:

D-glucose 6-phosphate+NADP⁺↔6-phospho-D-glucono-1,5-lactone+NADPH

Glucose-6-phosphate 1-dehydrogenase may also be known as glucose-6-phosphate dehydrogenase (NADP+); NADP-glucose-6-phosphate dehydrogenase; Zwischenferment; D-glucose 6-phosphate dehydrogenase; glucose 6-phosphate dehydrogenase (NADP); NADP-dependent glucose 6-phosphate dehydrogenase; 6-phosphoglucose dehydrogenase; Entner-Doudoroff enzyme; G6PDH; GPD; glucose-6-phosphate dehydrogenase.

Glucose-6-phosphate dehydrogenase (G6PDH) is the first enzyme of the pentose phosphate pathway and provides a large fraction of the NADPH needed for anabolism.

The *E. coli* G6PDH shows a strong preference for NADP+ over NAD+. The structural basis for this preference was studied using molecular simulations, kinetic characterization of site-directed mutants and phylogenetic analyses.

Metabolic flux through the pathways of central carbon metabolism was measured using GC-MS and $^{13}C$ labeling and 2D NMR spectroscopy. Regulation of these pathways under different growth conditions was measured at the level of enzyme expression and activity.

Substitution of an NADH-producing glucose-6-phosphate dehydrogenase for the native NADPH-producing enzyme reduced the growth rate of otherwise wild-type cells, while increasing the growth rate of a Δpgi mutant. This suggests that whether production of NADH by G6PDH is beneficial or detrimental in vivo depends on the operation of the upper Embden-Meyerhof pathway.

In addition to its role in central carbon metabolism, G6PDH was found to be the source of a linear peptide with the amino acid sequence Asn-Asn-Trp-Asn-Asn (NNWNN) that acts as an "extracellular death factor" (EDF) for MazEF-mediated cell death. The peptide acts by increasing the endoribonuclease activity of the toxins MazF and ChpBK. EDF production under stress conditions is due to cleavage of the zwf mRNA at specific ACA sites by MazF, generating a leaderless truncated mRNA. The location of the EDF-coding region with respect to the MazF cleavage sites is important, and the trans-translation system is required.

zwf is one of the most consistently flux-coupled genes, which are genes whose expression transition patterns upon perturbations are correlated with their corresponding flux values. Expression of zwf is growth rate-regulated at the transcriptional level. G6PDH activity is greater in rapidly growing cells, and is greater under nitrogen-limited compared to carbon-limited growth conditions. zwf is a part of the SoxRS regulon which responds to superoxide stress. Additional regulators have been shown to activate transcription of zwf. Exposure to tellurite activates transcription of zwf and thereby increases the synthesis of NADPH.

A zwf null mutation does not affect the growth rate significantly. However, central carbon metabolism and metabolic flux is changed. A pgi zwf double mutant does not grow on glucose as the sole source of carbon. In the presence of glucose, it accumulates high levels of glucose-6-phosphate, which inhibits fructose-1,6-bisphosphatase I activity. Deletion of zwf reduces the organic solvent tolerance of E. coli JM109.

In some embodiments, a recombinant microorganism producing MEG (or glycolic acid), or optionally, MEG (or glycolic acid) and one or more co-product, comprises a deletion, insertion, or loss of function mutation in a gene encoding a glucose-6-phosphate dehydrogenase to prevent the flux of glucose-6-phosphate through the oxidative branch of the pentose phosphate pathway and instead shunt glucose-6-phosphate through the non-oxidative branch of the pentose phosphate pathway to produce one or more pentose-5-phosphate intermediate.

6-Phosphogluconolactonase (EC 3.1.1.31)

The present disclosure describes enzymes that can catalyze the following reaction:

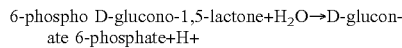
6-phospho D-glucono-1,5-lactone+$H_2O$→D-gluconate 6-phosphate+$H^+$ 6-phosphogluconolactonase may also be known as phosphogluconolactonase; 6-PGL.

6-phosphogluconolactonase is an enzyme of the oxidative pentose phosphate pathway.

A pgl mutant strain grows only slightly slower than wild type on glucose as the sole source of carbon. Growth on glucose may be due to non-enzymatic hydrolysis of 6-phospho D-glucono-1,5-lactone or a bypass pathway that involves dephosphorylation and export of gluconolactone, hydrolysis to gluconate, followed by gluconate re-import and phosphorylation. When grown on maltose medium, strains lacking Pgl activity turn blue after iodine treatment. The phenotype of a pgl deletion strain can be complemented by expression of the pgl gene from Pseudomonas putida, although there is no detectable similarity between the two genes.

A strategy for metabolic engineering of E. coli for the production of riboflavin included overexpression of pgl, leading to an increase in riboflavin titer.

pgl is part of a genomic region that is deleted in the E. coli B strain BL21, but is present in the K-12 strain MG1655.

In some embodiments, a recombinant microorganism producing MEG (or glycolic acid), or optionally, MEG (or glycolic acid) and one or more co-product, comprises a deletion, insertion, or loss of function mutation in a gene encoding a 6-phosphogluconolactonase to prevent the flux of glucose-6-phosphate through the oxidative branch of the pentose phosphate pathway and instead shunt glucose-6-phosphate through the non-oxidative branch of the pentose phosphate pathway to produce one or more pentose-5-phosphate intermediate.

6-Phosphogluconate Dehydrogenase, Decarboxylating (EC 1.1.1.44)

The present disclosure describes enzymes that can catalyze the following reaction:

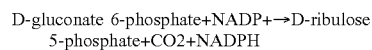
D-gluconate 6-phosphate+NADP+→D-ribulose 5-phosphate+CO2+NADPH 6-phosphogluconate dehydrogenase may also be known as phosphogluconate dehydrogenase (NADP+-dependent, decarboxylating); phosphogluconic acid dehydrogenase; 6-phosphogluconic dehydrogenase; 6-phosphogluconic carboxylase; 6-phospho-D-gluconate dehydrogenase; glyceraldehyde 3-phosphate dehydrogenase.

6-phosphogluconate dehydrogenase is an enzyme of the oxidative branch of the pentose phosphate pathway.

Three crystal structures of the enzyme in complex with substrate and cosubstrate compounds have been solved. Binding of NADP+ may induce a conformational change in the enzyme. A catalytic mechanism has been proposed.

gnd is a highly polymorphic gene within E. coli populations, likely due to interstrain transfer and recombination. This may be a result of its proximity to the rfb region, which determines O antigen structure.

Expression of 6-phosphogluconate dehydrogenase is growth rate-regulated. Most of the growth rate-dependent increase in Gnd levels is due to increased transcription, leading to higher mRNA levels. Posttranscriptional regulation involves a secondary structure element between codons 67 and 78 of the gnd mRNA. This region may function by sequestration of the translation initiation region into an mRNA secondary structure, thus reducing the efficiency of translation initiation. However, the effector of this regulatory mechanism has apparently not yet been identified. truA (hisT) mutants reduce the growth rate-dependent increase of Gnd expression by post-transcriptional regulation. Growth under acidic conditions upregulates expression of gnd. gnd is one of the most consistently flux-coupled genes (FCGs), which are genes whose expression transition patterns upon perturbations are correlated with their corresponding flux values.

Certain growth conditions selected for a deletion mutation in the promoter region that results in increased transcription of gnd and increased enzyme activity. An edd gnd double mutant is unable to grow on gluconate. A null mutation in gnd does not significantly alter the growth rate. However, cellular metabolism and metabolic flux is changed; succinate production is increased during growth on glucose or glycerol. A gnd deletion mutant shows enhanced ethanol and $H_2$ production compared to wild type during anaerobic growth on glycerol, whereas in a different, heavily engineered strain, overexpression of gnd increases ethanol and $H_2$ production.

In some embodiments, a recombinant microorganism producing MEG (or glycolic acid), or optionally, MEG (or glycolic acid) and one or more co-product, comprises a deletion, insertion, or loss of function mutation in a gene encoding a 6-phosphogluconate dehydrogenase to prevent the flux of glucose-6-phosphate through the oxidative branch of the pentose phosphate pathway and instead shunt glucose-6-phosphate through the non-oxidative branch of the pentose phosphate pathway to produce one or more pentose-5-phosphate intermediate.

Glyceraldehyde 3-Phosphate Dehydrogenase, Phosphorylating (EC 1.2.1.12)

The present disclosure describes enzymes that can catalyze the following reaction:

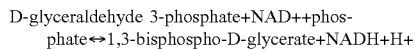

D-glyceraldehyde 3-phosphate+NAD++phosphate↔1,3-bisphospho-D-glycerate+NADH+H+

Glyceraldehyde 3-phosphate dehydrogenase may also be known as glyceraldehyde-3-phosphate dehydrogenase (phosphorylating); triosephosphate dehydrogenase; dehydrogenase, glyceraldehyde phosphate; phosphoglyceraldehyde dehydrogenase; 3-phosphoglyceraldehyde dehydrogenase; NAD+-dependent glyceraldehyde phosphate dehydrogenase; glyceraldehyde phosphate dehydrogenase (NAD+); glyceraldehyde-3-phosphate dehydrogenase (NAD+); NADH-glyceraldehyde phosphate dehydrogenase; glyceraldehyde-3-P-dehydrogenase.

Glyceraldehyde 3-phosphate dehydrogenase A catalyzes the reversible oxidative phosphorylation of D-glyceraldehyde-3-phosphate to 1,3-bisphospho-D-glycerate in the presence of NAD+ and phosphate during glycolysis and gluconeogenesis in E. coli. The enzyme is also found in many other organisms and its properties have been extensively studied.

E. coli is unusual in having two glyceraldehyde-3-phosphate dehydrogenase (GAPDH) activities encoded by gapA and epd (gapB). However, the gapA encoded enzyme has a highly efficient phosphorylating glyceraldehyde-3-phosphate dehydrogenase activity and a low phosphorylating erythrose-4-phosphate dehydrogenase activity, whereas the epd encoded enzyme has an efficient non-phosphorylating erythrose-4-phosphate dehydrogenase activity and a very low phosphorylating glyceraldehyde-3-phosphate dehydrogenase activity.

The GapA protein has a sequence that is more similar to eukaryotic sequences than to the thermophilic bacterial enzymes, and to prokaryotic enzymes in general. The gapA product is required for glycolysis, while the epd product is not. Both enzymes may be involved in production of pyridoxal 5'-phosphate (PLP).

Early studies of gapA mutants from E. coli K-10 implicated its role in glycolysis and demonstrated some of its catalytic properties. A gapA mutant exhibits a growth defect and also exhibits increased aggregation and lysis phenotypes that are rescued by high-salt media.

Regulation of gapA gene expression has been studied. The regulation of the fkpA, gapA, and hslT genes is affected by evolution under conditions of chronic heat stress.

The E. coli sequence contains several amino acids that are conserved in all GAPDHs and are postulated to be involved in NAD+ binding, or the catalytic mechanism.

The crystal structure of the wild-type enzyme in the presence of NAD+ has been determined at 1.80 Å resolution and was similar to those of other GAPDHs. The crystal structure of a N313T mutant was also determined at 2.17 Å resolution. Several other E. coli GAPDH crystal structures have been reported with and without bound NAD+, and in the hemiacetal intermediate state.

Molecular factors responsible for the NAD+ cofactor stereospecificity have been studied using site-directed mutagenesis. The enzyme is a B-specific dehydrogenase that catalyzes transfer of the pro-S hydrogen and binds NAD(H) in the syn nicotinamide orientation. Refolding of denatured E. coli GAPDH in the presence of chaperone protein Tig; trigger factor has been studied.

ADP-ribosylated GAPDH is a secreted virulence factor in some fungi and Gram-positive pathogens, as well as in pathogenic strains of E. coli. Non-pathogenic E. coli do not secrete GAPDH. Evidence suggests that E. coli GAPDH is also involved in DNA repair.

A series of vectors inducibly expressing paired-terminus antisense RNAs was constructed to silence central carbon metabolism in host E. coli K-12 MG1655. A vector that silenced gapA at 93% efficacy caused severe growth inhibition. Regulating the expression of an engineered E. coli gapA through changes in temperature has been demonstrated to control glycolysis.

In some embodiments, a recombinant microorganism producing MEG (or glycolic acid), or optionally, MEG (or glycolic acid) and one or more co-product, comprises a deletion, insertion, or loss of function mutation in a gene encoding a glyceraldehyde 3-phosphate dehydrogenase to prevent the conversion of glyceraldehyde 3-phosphate to 1,3-bisphospho-D-glycerate and instead allow D-glyceraldehyde 3-phosphate to be converted to D-xylulose-5-phosphate (with a concurrent conversion of fructose-6-phosphate to D-erythrose-4-phosphate) by a transketolase, and thus produce a pentose-5-phosphate intermediate needed for the production of MEG (or glycolic acid), or optionally, MEG (or glycolic acid) and one or more co-product and provide more D-erythrose-4-phosphate for the non-oxidative branch of the pentose phosphate pathway to further produce one or more pentose-5-phosphate intermediate.

6-Phosphofructokinase (EC 2.7.1.11)

Phosphofructokinase (Pfk) catalyzes the phosphorylation of fructose-6-phosphate on the C1 carbon during glycolysis. E. coli contains two Pfk isozymes, Pfk-1 (pfkA) and Pfk-2 (pfkB), which do not share sequence similarity. More than 90% of the phosphofructokinase activity present in wild type E. coli can be attributed to Pfk-1.

PfkA catalyzes the phosphorylation of fructose-6-phosphate and is a key enzyme regulating the glycolysis pathway. The enzyme cannot catalyze the reverse reaction in vivo. The enzyme shows cooperative kinetics with the substrate fructose-6-phosphate, but not with the other substrate, ATP. Recently, it was shown that PfkA also catalyzes phosphorylation of sedoheptulose-7-phosphate as part of the sedoheptulose bisphosphate bypass. Crystal structures of PfkA have been solved with and without activators and inhibitors. Based on sequence similarity, PfkA was predicted to be an NAD+ kinase.

PfkB is a member of the ribokinase family of sugar kinases. PfkB, unlike PfkA, does not show cooperative interaction with fructose-6-phosphate, inhibition by PEP or activation by ADP. $MgATP^{2-}$ is the true substrate of the enzyme. PfkB can also use tagatose-6-phosphate as a substrate. This reaction is part of the galactitol catabolism pathway. A crystal structure of PfkB in the tetrameric form inhibited by MgATP has been solved at 1.98 Å resolution. Comparison of this structure with a crystal structure of PfkB in complex with fructose-6-phosphate suggests negative interplay between fructose-6-phosphate binding and MgATP binding.

In some embodiments, a recombinant microorganism producing MEG (or glycolic acid), or optionally, MEG (or glycolic acid) and one or more co-product, comprises a deletion, insertion, or loss of function mutation in a gene encoding a 6-phosphofructokinase to prevent the conversion of fructose-6-phosphate to 1,6-bisphosphate and instead allow fructose-6-phosphate to be converted to erythrose-4-phosphate and acetyl-phosphate by a fructose-6-phosphate phosphoketolase, and provide more erythrose-4-phosphate for the non-oxidative branch of the pentose phosphate pathway to further produce one or more pentose-5-phosphate intermediate needed for the production of MEG (or GA), or optionally, MEG (or GA) and one or more co-product. In some embodiments, the 6-phosphofructokinase is pfkA and/or pfkB.

Hydroxypyruvate decarboxylase, 2-oxoglutarate decarboxylase, 2-keto acid decarboxylase (EC 4.1.1.-)

The present disclosure describes enzymes that can catalyze the following reactions:

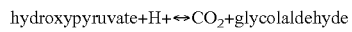
hydroxypyruvate+H+↔CO$_2$+glycolaldehyde

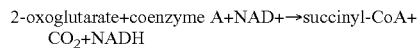
2-oxoglutarate+coenzyme A+NAD+→succinyl-CoA+
   CO$_2$+NADH

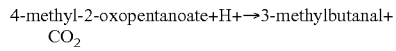
4-methyl-2-oxopentanoate+H+→3-methylbutanal+
   CO$_2$

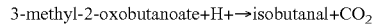
3-methyl-2-oxobutanoate+H+→isobutanal+CO$_2$

Hydroxypyruvate decarboxylase may also be known as hydroxypyruvate carboxy-lyase.

2-oxoglutarate decarboxylase may also be known as oxoglutarate decarboxylase; alpha-ketoglutarate decarboxylase; alpha-ketoglutaric decarboxylase; pre-2-oxoglutarate decarboxylase; 2-oxoglutarate carboxy-lyase.

*E. coli* SucA is responsible for the 2-oxoglutarate decarboxylase activity of the 2-oxoglutarate dehydrogenase multienzyme complex (OGDHC) that catalyzes the conversion of 2-oxoglutarate (2-ketoglutarate) to succinyl-CoA and CO$_2$, with the production of NADH.

The OGDHC is a member of the 2-oxo acid dehydrogenase family. Members of this family contain multiple copies of three enzymatic components: 2-oxoglutarate decarboxylase (E1), lipoamide acyltransferase (E2) and lipoamide dehydrogenase (E3). In most Gram-positive bacteria and in mitochondria the E1 component is a heterodimer composed of two subunits, while in most (but not all) Gram-negative bacteria it is made up of a single type of subunit. In both cases multiple copies of the E1 component along with multiple copies of the E3 component are assembled around an E2 core of 24 subunits with octahedral symmetry, or 60 subunits with eicosahedral symmetry (depending on which complex and species). In *E. coli* the E3 component is shared with the pyruvate dehydrogenase and glycine cleavage multi-enzyme complexes. E1 and E2 differ slightly for the 2-oxoglutarate and pyruvate dehydrogenase complexes, and are designated (o) and (p) to distinguish them.

The *E. coli* OGDHC contains 12 units of the E1(o) component 2-oxoglutarate decarboxylase, thiamine-requiring encoded by sucA, 24 units of the E2(o) comoponent dihydrolipoyltranssuccinylase encoded by sucB, and 2 units of the E3 component lipoamide dehydrogenase encoded by lpd. The 24 E2(o) units form the octahedral core of the complex. They contain lipoyllysine and binding sites for dimers of the E1(o) and E3 subunits. Electron cryotomography showed that they are flexibly tethered to the E2 core.

During the OGDHC reaction cycle, 2-oxoglutarate is bound and decarboxylated by SucA, a thiamin-diphosphate cofactor containing enzyme. The crystal structure of a truncated, apo form of SucA lacking the N-terminal 77 residues has been determined at 2.6 Å resolution. The structure of the holo form with thiamin diphosphate and Mg' was determined at 3.5 Å resolution. The truncated form retained decarboxylase activity but did not assemble with E2(o) into an OGDH complex. Data also suggested the presence of an AMP binding site. An oxygen-dependent thiamin free radical was demonstrated in the OGDHC, which was generated by a side reaction with O$_2$.

Studies of engineered SucA prepared by saturation mutagenesis of His260 and His298 suggested that His260 is required for substrate recognition, but His298 could be replaced by hydrophobic residues of similar size. Data also suggested that E2(o) has a role in specificity.

The sucA gene was cloned and sequenced in earlier work and regulation of sucABCD was studied. The sucAB and sucCD genes were shown to be mutually essential, with either pair sufficient to produce succinyl-CoA, but simultaneous deletion of sucAB and sucCD was not viable.

α-ketoisovalerate decarboxylase catalyzes the decarboxylation of 3-methyl-2-oxobutanoate to isobutanal. The enzyme is highly specific for 3-methyl-2-oxobutanoate, but also shows activity with other branched-chain 2-keto acids (4-methyl-2-oxopentanoate, 22.7% relative activity; (S)-3-methyl-2-oxopentanoate, 16.7%, 2-oxo-3-phenylpropanoate, 7.1% and 4-(methylthio)-2-oxobutanoate, 5.8%.

The enzyme is a homo-tetramer, encoded by the kivd gene, which has been sequenced and cloned. The deduced protein sequence shares 98.6% identity (over its first 438 amino acids) with an *L. lactis* strain IL1403 protein, encoded by the ipd gene (this gene is interrupted at position L439 by the insertion of an IS983 element). The kivd gene does not have any homology with any gene(s) in the sequenced genomes of *L. lactis* strains MG1363 and SK11.

A study of the Kivd activity testing 156 lactic acid bacteria strains (*Lactococcus, Lactobacillus, Leuconostoc*) indicated that only *L. lactis* strains possess the activity, and even within lactococcal strains, only 7 out of 45 strains had the activity.

A homologous protein has been described from *L. lactis* strain B1157 as branched-chain α-keto acid decarboxylase. That protein shows 89.8% identity with Kivd and also has a preference for 2-keto-isovalerate.

In some embodiments, an enzyme having 2-keto acid decarboxylase activity, an enzyme having hydroxypyruvate decarboxylase activity or an enzyme having 2-oxoglutarate decarboxylase activity converts hydroxypyruvate to glycolaldehyde. In some embodiments, the enzyme that converts hydroxypyruvate to glycolaldehyde is encoded by an amino acid sequence having at least 70% sequence identity, having at least 80% sequence identity, or having at least 90% sequence identity to Kivd or SucA. In some embodiments, the enzyme having 2-keto acid decarboxylase activity is Kivd. In some embodiments, the enzyme having 2-oxoglutarate decarboxylase activity is SucA.

In some embodiments, the one or more nucleic acid molecules encoding the enzyme having 2-oxoglutarate decarboxylase activity is sucA, or homolog thereof. In some embodiments, the one or more nucleic acid molecules encoding the enzyme having 2-keto acid decarboxylase activity is Kivd, or homolog thereof. In another embodiment, the one or more nucleic acid molecules encoding an enzyme having 2-keto acid decarboxylase activity, an enzyme having hydroxypyruvate decarboxylase activity or an enzyme having 2-oxoglutarate decarboxylase activity comprise an amino acid sequence selected from SEQ ID NOs: 224 and 226. In a further embodiment, the one or more nucleic acid molecule encoding an enzyme having 2-keto acid decarboxylase activity, an enzyme having hydroxypyruvate decarboxylase activity or an enzyme having 2-oxoglutarate decarboxylase activity is encoded by a nucleic acid sequence selected from SEQ ID NOs: 223 and 225.

2-Oxoglutarate Reductase, 3-Phospho-Hydroxypyruvate Reductase, 3-Phosphoglycerate Dehydrogenase (EC 1.1.1.-)

The present disclosure describes enzymes that can catalyze the following reactions:

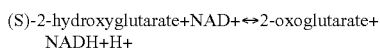
(S)-2-hydroxyglutarate+NAD+↔2-oxoglutarate+ NADH+H+

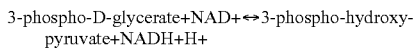
3-phospho-D-glycerate+NAD+↔3-phospho-hydroxypyruvate+NADH+H+

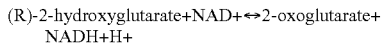
(R)-2-hydroxyglutarate+NAD+↔2-oxoglutarate+ NADH+H+

3-phosphoglycerate dehydrogenase may also be known as phosphoglycerate dehydrogenase; PHGDH (gene name); D-3-phosphoglycerate:NAD+ oxidoreductase; alpha-phosphoglycerate dehydrogenase; 3-phosphoglyceric acid dehydrogenase; D-3-phosphoglycerate dehydrogenase; glycerate 3-phosphate dehydrogenase; glycerate-1,3-phosphate dehydrogenase; phosphoglycerate oxidoreductase; phosphoglyceric acid dehydrogenase; SerA; 3-phosphoglycerate:NAD+ 2-oxidoreductase; SerA 3PG dehydrogenase; 3PHP reductase.

3-phosphoglycerate dehydrogenase catalyzes the first committed step in the biosynthesis of L-serine. The enzyme is regulated by allosteric end-product inhibition that shows cooperativity. Inhibition by serine acts primarily through reduction of catalytic velocity and has only a small effect on the Kms of the substrates; SerA is thus classified as a type V allosteric enzyme.

The basis for allosteric and cooperative inhibition by serine has been studied extensively. Occupation of two of the four serine binding sites in the homotetramer results in 85% inhibition of activity. Further binding of serine shows negative cooperativity. Phosphate is able to reduce the site-to-site cooperative effects on serine binding; the effect was mainly due to the presence of intrinsically bound NADH. A Trp139Gly mutation results in a homodimeric enzyme that has lost cooperativity in serine binding and allosteric inhibition. Site-directed mutagenesis of residues within the effector binding site, the regulatory interface between subunits, and a flexible hinge region support a model where movement of adjacent domains is involved in inhibition of the enzymatic activity. Transient kinetic analysis showed that the cooperativity of inhibition of catalytic activity results from a conformational change due to serine binding. An enzyme missing the regulatory domain is no longer inhibited by serine, but other kinetic parameters remain the same. Hybrid tetramers provided further insight into the mechanism of allosteric inhibition.

Site-directed mutagenesis has allowed the identification of residues within the active site that contribute to substrate binding and catalysis. Mutations in the hinge region between the substrate and nucleotide binding domains affect the kcat of the enzyme; certain mutations uncouple serine binding and catalytic inhibition.

Extensive site-directed mutagenesis and structural studies have contributed to a detailed view of the interactions between allosteric regulation, cooperativity and catalytic activity. Further insight into the catalytic pathway was provided by stopped-flow kinetic analysis, indicating that the rate-limiting step in both catalytic directions is a conformational change of the enzyme. Serine binding appears to lead to the formation of a dead-end quaternary complex between the enzyme, coenzyme, substrate, and effector that eliminates the conformational change subsequent to substrate binding.

The enzyme has been shown to also have an α-ketoglutarate reductase activity, producing 2-hydroxyglutarate. While the metabolic role of this reaction is not yet known, it is thought that it may play a role in regulating serine biosynthesis and in recycling NADH back to NAD+, especially during anaerobiosis.

Crystal structures of the wild type enzyme and various mutants have been solved. The structure showed that each subunit of the homotetramer consists of three distinct domains, a nucleotide binding domain, a substrate binding domain, and a regulatory/serine binding domain.

serA is essential for growth on glycerol minimal medium; the growth defect can be rescued by addition of serine.

In some embodiments, the enzyme having 3-phosphoglycerate dehydrogenase activity can be an enzyme having 3-phospho-hydroxypyruvate reductase activity or an enzyme having 2-oxoglutarate reductase activity. In some embodiments, an enzyme having 3-phosphoglycerate dehydrogenase activity, an enzyme having 3-phospho-hydroxypyruvate reductase activity, or an enzyme having 2-oxoglutarate reductase activity catalyzes the conversion of glycerate 3-phophate to 3-phosphohydroxypyruvate. In some embodiments, an enzyme having 3-phosphoglycerate dehydrogenase activity, an enzyme having 3-phospho-hydroxypyruvate reductase activity, or an enzyme having 2-oxoglutarate reductase activity is encoded by an amino acid sequence having at least 70% sequence identity, having at least 80% sequence identity, or having at least 90% sequence identity to serA. In some embodiments, the enzyme having 3-phosphoglycerate dehydrogenase activity, the enzyme having 3-phospho-hydroxypyruvate reductase activity, or the enzyme having 2-oxoglutarate reductase activity is serA.

In some embodiments, the one or more nucleic acid molecules encoding the enzyme having 3-phosphoglycerate dehydrogenase activity is serA, or homolog thereof. In another embodiment, the one or more nucleic acid molecules encoding an enzyme having 3-phosphoglycerate dehydrogenase activity, an enzyme having 3-phospho-hydroxypyruvate reductase activity, or an enzyme having 2-oxoglutarate reductase activity comprises an amino acid sequence set forth in SEQ ID NO: 228. In a further embodiment, the one or more nucleic acid molecule encoding an enzyme having 3-phosphoglycerate dehydrogenase activity, an enzyme having 3-phospho-hydroxypyruvate reductase activity, or an enzyme having 2-oxoglutarate reductase activity is encoded by a nucleic acid sequence set forth in SEQ ID NO: 227.

Phosphoserine Aminotransferase, Serine Aminotransferase, L-Serine Transaminase (EC 2.6.1.52)

The present disclosure describes enzymes that can catalyze the following reactions:

3-phospho-L-serine+2-oxoglutarate↔L-glutamate+3-phospho-hydroxypyruvate (3R)-3-hydroxy-2-oxo-4 phosphonooxybutanoate+L-glutamate↔4-phospho-hydroxy-L-threonine+2-oxoglutarate 2-oxoglutarate+N-succinyl-L,L-2,6-diaminopimelate↔L-glutamate+N-succinyl-2-amino-6-ketopimelate Phosphoserine aminotransferase may also be known as phosphoserine transaminase; PSAT; 3-phosphoserine aminotransferase; hydroxypyruvic phosphate-glutamic transaminase; L-phosphoserine aminotransferase; phosphohydroxypyruvate transaminase; phosphohydroxypyruvic-glutamic transaminase; 3-O-phospho-L-serine:2-oxoglutarate aminotransferase; SerC; PdxC; 3PHP transaminase The serC-encoded enzyme, phosphoserine/phosphohydroxythreonine aminotransferase, functions in the biosynthesis of both serine and pyridoxine, by using different substrates. Pyridoxal 5'-phosphate is a cofactor for both enzyme activities, suggesting that it can act in an autocatalytic fashion, stimulating its own biosynthesis.

The redundancy and promiscuity among aminotransferase enzymes has been investigated. No activity could be observed with non-phosphorylated substrates; however, 3-hydroxypyruvate was able to be used as the substrate for an assay of SerC enzymatic activity. In addition, genetic experiments showed that SerC is a minor alanine transaminase.

The normal activities of two enzymes, ArgD and SerC, are sufficient for succinyldiaminopimelate (SDAP) and lysine biosynthesis; a third enzyme, AstC, is sufficient for SDAP biosynthesis, but alone can not fulfill the cell's requirement for lysine. Additional enzymes, including GabT and PuuE, may be able to contribute to SDAP biosynthesis. Expression of argD, astC, serC, aspC, gabT, hisC, ilvE, patA, puuE, or tyrB from a plasmid allows growth of the triple ΔargD serC astC mutant on minimal medium.

Crystal structures of the enzyme in the unligated form and in complex with the substrate analog α-methyl-L-glutamate have been solved, and a molecular reaction mechanism was proposed.

serC is essential for growth on glycerol minimal medium; the growth defect can be rescued by addition of serine and pyridoxol/pyridoxine.

In some embodiments, the enzyme having phosphoserine aminotransferase activity can be an enzyme having L-serine transaminase activity or an enzyme having serine aminotransferase activity. In some embodiments, an enzyme having phosphoserine aminotransferase activity, an enzyme having L-serine transaminase activity or an enzyme having serine aminotransferase activity catalyzes the conversion of L-serine to hydroxypyruvate. In some embodiments, the enzyme having phosphoserine aminotransferase activity, the enzyme having L-serine transaminase activity or the enzyme having serine aminotransferase activity is encoded by an amino acid sequence having at least 70% sequence identity, having at least 80% sequence identity, or having at least 90% sequence identity to serC. In some embodiments, the enzyme having phosphoserine aminotransferase activity, the enzyme having L-serine transaminase activity or the enzyme having serine aminotransferase activity is serC.

In some embodiments, the one or more nucleic acid molecules encoding the enzyme having phosphoserine aminotransferase activity is serC, or homolog thereof. In another embodiment, the one or more nucleic acid molecules encoding an enzyme having phosphoserine aminotransferase activity, an enzyme having L-serine transaminase activity, or an enzyme having serine aminotransferase activity comprise an amino acid sequence set forth in SEQ ID NO: 230. In a further embodiment, the one or more nucleic acid molecule encoding an enzyme having phosphoserine aminotransferase activity, an enzyme having L-serine transaminase activity or an enzyme having serine aminotransferase activity is encoded by a nucleic acid sequence set forth in SEQ ID NO: 229.

3-phospho-hydroxypyruvate Phosphatase

The present disclosure describes enzymes that can catalyze the following reaction:

3-phospho-hydroxypyruvate+H₂O→hydroxypyruvate+phosphate

YeaB (NudL) belongs to the Nudix family of hydrolases and was predicted to have CoA pyrophosphohydrolase activity.

yeaB (nudL) was isolated as a multicopy suppressor of the repression of flhDC transcription in a pgsA mutant. The suppression may be due to the reduction of σ$^S$ expression in cells that overexpress nudL.

yeaB (nudL) was also isolated as a multicopy suppressor of the PLP auxotrophy of a pdxB deletion strain. NudL was found to be part of a serendipitous metabolic pathway that produces an intermediate of the pyridoxal 5'-phosphate biosynthesis I pathway, 4-phospho-hydroxy-L-threonine, that lies downstream of PdxB. The pathway diverts 3-phosphohydroxypyruvate from serine biosynthesis. With a K$_{cat}$ of $5.7×10^{-5}$, NudL is an inefficient catalyst of the conversion of 3-phosphohydroxypyruvate to hydroxypyruvate, but its activity appears to be sufficient for production of PLP.

In some embodiments, the enzyme having 3-phospho-hydroxypyruvate phosphatase activity is encoded by an amino acid sequence having at least 70% sequence identity, having at least 80% sequence identity, or having at least 90% sequence identity to yeaB. In some embodiments, the enzyme having 3-phospho-hydroxypyruvate phosphatase activity is yeaB.

In some embodiments, the one or more nucleic acid molecules encoding the enzyme having 3-phospho-hydroxypyruvate phosphatase activity is yeaB, or homolog thereof. In another embodiment, the one or more nucleic acid molecules encoding an enzyme having 3-phospho-hydroxypyruvate phosphatase activity comprise an amino acid sequence set forth in SEQ ID NO: 232. In a further embodiment, the one or more nucleic acid molecule encoding an enzyme having 3-phospho-hydroxypyruvate phosphatase activity is encoded by a nucleic acid sequence set forth in SEQ ID NO: 231.

Phosphoserine Phosphatase (EC 3.1.3.3)

The present disclosure describes enzymes that can catalyze the following reaction:

3-phospho-L-serine+H₂O→L-serine+phosphate

Phosphoserine phosphatase catalyzes the last step in serine biosynthesis. The enzyme belongs to the superfamily of haloacid dehalogenase (HAD)-like hydrolases. Enzymatic studies were originally performed using partially purified enzyme from E. coli strain W; assays of the purified enzyme were performed as part of an investigation of the HAD superfamily of enzymes.

serB is essential for growth on glycerol minimal medium; the growth defect can be rescued by addition of serine. Gph, HisB and YtjC were identified as multicopy suppressors of the conditional AserB phenotype. Directed evolution experiments identified mutations that increased fitness and enzymatic activity of these suppressors.

In some embodiments, the enzyme having phosphoserine phosphatase activity is encoded by an amino acid sequence having at least 70% sequence identity, having at least 80% sequence identity, or having at least 90% sequence identity to serB. In some embodiments, the enzyme having phosphoserine phosphatase activity is serB.

In some embodiments, the one or more nucleic acid molecules encoding the enzyme having phosphoserine phosphatase activity is serB, or homolog thereof. In another embodiment, the one or more nucleic acid molecules encoding an enzyme having phosphoserine phosphatase activity comprise an amino acid sequence set forth in SEQ ID NO: 234. In a further embodiment, the one or more nucleic acid molecule encoding an enzyme having phosphoserine phosphatase activity is encoded by a nucleic acid sequence set forth in SEQ ID NO: 233.

Serine-Pyruvate Aminotransferase (EC 2.6.1.51)

The present disclosure describes enzymes that can catalyze the following reactions:

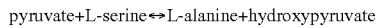

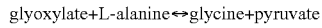

Serine-pyruvate aminotransferase may also be known as alanine-glyoxylate aminotransferase.

The peroxisomal serine-pyruvate aminotransferase (AGXT1) and mitochondrially localized alanine-glyoxylate aminotransferase 2 (AGXT2) both catalyze the conversion of glyoxylate to glycine using alanine as the amino donor. Unlike AGXT2, AGXT1 cannot utilize asymmetric dimethylarginine (ADMA) as an amino donor.

Peroxisomal serine-pyruvate aminotransferase is a pyridoxal phosphate dependent liver specific enzyme composed of a homodimer. Its location in the peroxisome is crucial for proper enzyme activity. A peroxisomal targeting sequence (PTS1) at the C-terminus is required for translocation into peroxisomes.

Dysfunction or mistargeting of serine-pyruvate aminotransferase leading to absence in hepatic peroxisomes, causes glyoxylate to escape into the cytosol where it is further metabolized to oxalate and glycolate. Oxalate cannot be further metabolized in humans and leads to the formation of insoluble calcium oxalate in the kidney and urinary tract. Mutations in the AGXT1 gene leads to improper peroxisomal targeting and causes the autosomal recessive metabolic disorder, primary hyperoxaluria type 1, which results in irreversible kidney damage. One-third of primary hyperoxaluria type 1 patients have a unique protein sorting defect in which the hepatic peroxisomal enzyme is mistargeted to the mitochondria.

In some embodiments, the enzyme having serine-pyruvate aminotransferase activity is encoded by an amino acid sequence having at least 70% sequence identity, having at least 80% sequence identity, or having at least 90% sequence identity to Homo sapiens AGXT1. In some embodiments, the enzyme having serine-pyruvate aminotransferase activity is Homo sapiens AGXT1.

In some embodiments, the one or more nucleic acid molecules encoding the enzyme having serine-pyruvate aminotransferase activity is AGXT1, or homolog thereof. In some embodiments, the one or more nucleic acid molecules encoding an enzyme having serine-pyruvate aminotransferase activity comprise an amino acid sequence set forth in SEQ ID NO: 244. In a further embodiment, the one or more nucleic acid molecule encoding an enzyme having serine-pyruvate aminotranserase activity is encoded by a nucleic acid sequence set forth in SEQ ID NO: 243.

Serine Decarboxylase (EC 4.1.1.65)

The present disclosure describes enzymes that can catalyze the following reaction:

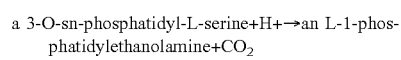

Serine decarboxylase may also be known as phosphatidylserine decarboxylase; PS decarboxylase; phosphatidyl-L-serine carboxy-lyase.

Phosphatidylserine decarboxylase is one of a small class of enzymes that use a covalently bound pyruvoyl prosthetic group. The pyruvoyl group is thought to act analogously to pyridoxal phosphate cofactor by forming a Schiff base with the amino group of the substrate and then serving as an electron sink to facilitate the decarboxylation.

Four of these enzymes, histidine decarboxylase (E.C. 4.1.1.22), phosphatidylserine decarboxylase, aspartate 1-decarboxylase, and S-adenosylmethionine decarboxylase are decarboxylases forming important biological amines. All of these enzymes are known to have the pyruvoyl prosthetic group attached via an amide linkage to the amino terminus of the α subunit. Two other enzymes in this group are D-proline reductase and glycine reductase (E.C. 1.21.4.2).

Pyruvoyl-containing enzymes are expressed as a zymogen which is processed post-translationally by a self-maturation cleavage called serinolysis. In this process the pyruvoul group is formed from a serine residue, splitting the presursor protein into two parts which become the α and β subunits. In some cases additional subunits may be involved.

This enzyme differs from other pyruvoyl-dependent decarboxylases composed of nonidentical subunits in that the pyruvate prosthetic group is associated with the smaller subunit. The enzyme is a multimer of unknown number of the heterodimer.

In some embodiments, an enzyme having serine decarboxylase activity catalyzes the conversion of L-serine to ethanolamine.

In some embodiments, the enzyme having serine decarboxylase activity is encoded by an amino acid sequence having at least 70% sequence identity, having at least 80% sequence identity, or having at least 90% sequence identity to Arabidopsis thaliana SDC. In some embodiments, the enzyme having serine decarboxylase activity is Arabidopsis thaliana SDC.

In some embodiments, the one or more nucleic acid molecules encoding the enzyme having serine decarboxylase activity is SDC, or homolog thereof. In some embodiments, the one or more nucleic acid molecules encoding an enzyme having serine decarboxylase activity comprise an amino acid sequence set forth in SEQ ID NO: 236. In a further embodiment, the one or more nucleic acid molecule encoding an enzyme having serine decarboxylase activity is encoded by a nucleic acid sequence set forth in SEQ ID NO: 235.

Ethanolamine Oxidoreductase (Deaminating) (EC 1.4.3.8), Ethanolamine Aminotransferase (EC 2.6.1.-)

The present disclosure describes enzymes that can catalyze the following reactions:

ethanolamine+oxygen+H$_2$O→ammonium+hydrogen peroxide+glycolaldehyde ethanolamine+2-oxoglutarate→glycolaldehyde+L-glutamate Ethanolamine oxidoreductase (deaminating) may also be known as ethanolamine oxidase. This enzyme belongs to the family of oxidoreductases, specifically those acting on the CH—NH$_2$ group of donors with oxygen as acceptor.

In some embodiments, an ethanolamine oxidase or an ethanolamine aminotransferase catalyzes the conversion of ethanolamine to gylcolaldehyde.

In some embodiments, the enzyme having ethanolamine oxidase activity is encoded by an amino acid sequence having at least 70% sequence identity, having at least 80% sequence identity, or having at least 90% sequence identity to *E. coli* tynA. In some embodiments, the enzyme having ethanolamine oxidase activity is *E. coli* tynA.

In some embodiments, the one or more nucleic acid molecules encoding the enzyme having ethanolamine oxidase activity is tynA, or homolog thereof. In some embodiments, the one or more nucleic acid molecules encoding an enzyme having ethanolamine oxidase activity comprise an amino acid sequence set forth in SEQ ID NO: 238. In a further embodiment, the one or more nucleic acid molecule encoding an enzyme having ethanolamine oxidase activity is encoded by a nucleic acid sequence set forth in SEQ ID NO: 237.

In some embodiments, the enzyme having ethanolamine aminotransferase activity is encoded by an amino acid sequence having at least 70% sequence identity, having at least 80% sequence identity, or having at least 90% sequence identity to *E. coli* alaA. In some embodiments, the enzyme having ethanolamine aminotransferase activity is *E. coli* alaA.

In some embodiments, the one or more nucleic acid molecules encoding the enzyme having ethanolamine aminotransferase activity is alaA, or homolog thereof. In some embodiments, the one or more nucleic acid molecules encoding an enzyme having ethanolamine aminotransferase activity comprise an amino acid sequence set forth in SEQ ID NO: 240. In a further embodiment, the one or more nucleic acid molecule encoding an enzyme having ethanolamine aminotransferase activity is encoded by a nucleic acid sequence set forth in SEQ ID NOs: 239.

Hydroxypyruvate Reductase (EC 1.1.1.-)

The present disclosure describes enzymes that can catalyze the following reactions:

D-glycerate+NAD(P)+⇌hydroxypyruvate+NAD(P)H+H+

Hydroxypyruvate reductase may also be known as beta-hydroxypyruvate reductase; NADH:hydroxypyruvate reductase; D-glycerate dehydrogenase.

Hydroxypyruvate reductase is an enzyme found in higher plants, algae, mammalian tissues and bacteria. In most cases it has been postulated to convert hydroxypyruvate to glycerate. However, most enzymes also carry the reduction of glyoxylate to glycolate.

In the serine cycle methylotrophs, hydroxypyruvate reductase plays a key role in the assimilation of carbon. It catalyzes the conversion of hydroxypyruvate to glycerate, a key step of the serine cycle, but it also plays an important role in the metabolism of C2 compounds, by interconverting glyoxylate and glycolate.

In some embodiments, hydroxypyruvate reductase catalyzes the conversion of glycerate to hydroxypyruvate.

In some embodiments, the enzyme having hydroxypyruvate reductase activity is encoded by an amino acid sequence having at least 70% sequence identity, having at least 80% sequence identity, or having at least 90% sequence identity to *E. coli* ghrB. In some embodiments, the enzyme having hydroxypyruvate reductase activity is *E. coli* ghrB.

In some embodiments, the one or more nucleic acid molecules encoding the hydroxypyruvate reductase is ghrB, or homolog thereof. In some embodiments, the one or more nucleic acid molecules encoding an enzyme having hydroxypyruvate reductase activity comprise an amino acid sequence set forth in SEQ ID NO: 242. In a further embodiment, the one or more nucleic acid molecule encoding an enzyme having hydroxypyruvate reductase activity is encoded by a nucleic acid sequence selected from the group consisting of SEQ ID NO: 241.

Glycerate Decarboxylase

The present disclosure describes enzymes that can catalyze the following reaction:

D-glycerate+H+→ethylene glycol+CO$_2$

In some embodiments, an enzyme having glycerate decarboxylase activity catalyzes the conversion of glycerate to ethylene glycol.

3-Phosphoglycerate Phosphatase (EC 3.1.3.38) or 2-Phosphoglycerate Phosphatase (EC 3.1.3.20)

The present disclosure describes enzymes that can catalyze the following reaction:

3-phospho-D-glycerate+H$_2$O→D-glycerate+phosphate 2-phospho-D-glycerate+H2O→D-glycerate+phosphate 3-phosphoglycerate phosphatase may also be known as D-3-phosphoglycerate phosphatase; 3-PGA phosphatase. 2-phosphoglycerate phosphatase may also be known as D-2-phosphoglycerate phosphatase; 2-PGA phosphatase. These enzymes belong to the family of hydrolases, specifically those acting on phosphoric monoester bonds.

In some embodiments, the enzyme having 3-phosphoglycerate phosphatase activity or the enzyme having 2-phosphoglycerate phosphatase activity is encoded by an amino acid sequence having at least 70% sequence identity, having at least 80% sequence identity, or having at least 90% sequence identity to *E. coli* phoA. In some embodiments, the enzyme having 3-phosphoglycerate phosphatase activity or enzyme having 2-phosphoglycerate phosphatase activity is *E. coli* phoA.

In some embodiments, the one or more nucleic acid molecules encoding the enzyme having 3-phosphoglycerate phosphatase activity or enzyme having 2-phosphoglycerate phosphatase activity is phoA, or homolog thereof. In some embodiments, the one or more nucleic acid molecules encoding an enzyme having 3-phosphoglycerate phosphatase activity or enzyme having 2-phosphoglycerate phosphatase activity comprise an amino acid sequence set forth in SEQ ID NO: 246. In a further embodiment, the one or more nucleic acid molecule encoding an enzyme having 3-phosphoglycerate phosphatase activity or enzyme having 2-phosphoglycerate phosphatase activity is encoded by a nucleic acid sequence set forth in SEQ ID NO: 245.

Glycerate Kinase (EC 2.7.1.31)

The present disclosure describes enzymes that can catalyze the following reaction:

D-glycerate+ATP↔3-phospho-D-glycerate+ADP+H+

D-glycerate+ATP↔2-phospho-D-glycerate+ADP+H+

Glycerate kinase may also be known as glycerate 3-kinase; glycerate kinase (phosphorylating) (ambiguous); D-glycerate 3-kinase; D-glycerate kinase (ambiguous); glycerate-kinase (ambiguous); GK (ambiguous); D-glyceric acid kinase (ambiguous); ATP: (R)-glycerate 3-phosphotransferase.

This enzyme belongs to the family of transferases, specifically those transferring phosphorus-containing groups (phosphotransferases) with an alcohol group as acceptor. This enzyme participates in 3 metabolic pathways: serine/glycine/threonine metabolism, glycerolipid metabolism, and glyoxylate-dicarboxylate metabolism.

In some embodiments, an enzyme having glycerate kinase activity catalyzes the conversion of 3-phosphoglycerate to glycerate. In other embodiments, an enzyme having glycerate kinase activity catalyzes the conversion of 2-phosphoglycerate to glycerate.

In some embodiments, the enzyme having glycerate kinase activity is a glycerate 3-kinase. In some embodiments, the enzyme having glycerate 3-kinase activity is encoded by an amino acid sequence having at least 70% sequence identity, having at least 80% sequence identity, or having at least 90% sequence identity to *Arabidopsis thaliana* GLYK. In some embodiments, the glycerate 3-kinase is *Arabidopsis thaliana* GLYK.

In some embodiments, the one or more nucleic acid molecules encoding the enzyme having glycerate 3-kinase activity is GLYK, or homolog thereof. In some embodiments, the one or more nucleic acid molecules encoding an enzyme having glycerate 3-kinase activity comprise an amino acid sequence set forth in SEQ ID NO: 248. In a further embodiment, the one or more nucleic acid molecule encoding an enzyme having glycerate 3-kinase activity is encoded by a nucleic acid sequence set forth in SEQ ID NO: 247.

In some embodiments, the enzyme having glycerate kinase activity is an enzyme having glycerate 2-kinase activity. In some embodiments, the enzyme having glycerate 2-kinase activity is encoded by an amino acid sequence having at least 70% sequence identity, having at least 80% sequence identity, or having at least 90% sequence identity to *E. coli* glxK. In some embodiments, the enzyme having glycerate 2-kinase activity is encoded by an amino acid sequence having at least 70% sequence identity, having at least 80% sequence identity, or having at least 90% sequence identity to *E. coli* garK. In other embodiments, the enzyme having glycerate 2-kinase activity is *E. coli* glxK. In some embodiments, the glycerate 2-kinase is *E. coli* garK.

In some embodiments, the one or more nucleic acid molecules encoding the enzyme having glycerate 2-kinase activity is glxK, or homolog thereof. In some embodiments, the one or more nucleic acid molecules encoding the enzyme having glycerate 2-kinase activity is garK, or homolog thereof. In some embodiments, the one or more nucleic acid molecules encoding an enzyme having glycerate 2-kinase activity comprise an amino acid sequence selected from SEQ ID NOs: 250 and 252. In a further embodiment, the one or more nucleic acid molecule encoding an enzyme having glycerate 2-kinase activity is encoded by a nucleic acid sequence selected from SEQ ID NOs: 249 and 251.

Transferase that Transfers One-Carbon Group (EC 2.1.2.-)

The present disclosure describes enzymes that can catalyze the following reaction:

M-THF+H2O↔THF+formaldehyde

Transferases such as the hydroxymethyl-, formyl- and related transferases may be used. Examples of hydroxymethyl-, formyl- and related transferases include glycine hydroxymethyltransferase, phosphoribosylglycinamide formyltransferase, phosphoribosylaminoimidazolecarboxamide formyltransferase, glycine formimidoyltransferase, glutamate formiminotransferase, D-alanine 2-hydroxymethyltransferase, deoxycytidylate 5-hydroxymethyltransferase, methionyl-tRNA formyltransferase, aminomethyltransferase, 3-methyl-2-oxobutanoate hydroxymethyltransferase and UDP-4-amino-4-deoxy-L-arabinose formyltransferase.

Serine Hydroxymethyltransferase (EC 2.1.2.1)

The present disclosure describes enzymes that can catalyze the following reaction:

L-serine+tetrahydrofolate (THF)↔Glycine+5,10-methylenetetrahydrofolate (M-THF)

Serine hydroxymethyltransferase (GlyA) converts serine to glycine, transferring a methyl group to tetrahydrofolate, thus forming 5,10-methylene-tetrahydrofolate (M-THF). M-THF is the major source of C1 units in the cell, making GlyA a key enzyme in the biosynthesis of purines, thymidine, methionine, choline and lipids.

The enzyme also catalyzes several side reactions including hydrolysis of 5,10-methenylTHF to 5-formylTHF and the reversible cleavage of 3-hydroxy amino acids (L-threonine, allothreonine, 3-phenylserine) to glycine and an aldehyde. D-alanine inactivates the enzyme by reacting with the pyridoxal phosphate prosthetic group to form pyridoxamine phosphate.

The Thr226 residue within a conserved region of the enzyme appears to be involved in substrate discrimination. The His228 residue plays a role in determining reaction specificity. Lys229 does not appear to play a catalytic role. Arg363 appears to be the binding site for the carboxyl group of the amino acid substrate. The hydroxyl group of Tyr65 may be involved in the conversion of the active site from a closed to an open conformation. Both Tyr55 and Arg235 are required for the transaldimination reaction.

Studies on refolding of the enzyme indicate that pyridoxal 5'-phosphate (PLP) only binds to the dimeric apoenzyme at the end of the folding pathway. The mechanism of PLP addition has been investigated further. At high concentrations of PLP, a second molecule of PLP can bind at Lys346. A conserved hydrophobic contact area is involved in stability of the PLP binding site. Tyr55 is required for correct positioning of the PLP cofactor.

Crystal structures of wild type and mutant serine hydroxymethyltransferase have been solved.

glyA mutants cannot use glycine as the sole source of nitrogen. A glyA mutant is auxotrophic for glycine; glyA was later shown to be essential for growth on glycerol minimal medium.

Sequences 3' to the structural gene within the glyA mRNA are required for mRNA stability.

In some embodiments, the enzyme having serine hydroxymethyltransferase activity is encoded by an amino acid sequence having at least 70% sequence identity, having at least 80% sequence identity, or having at least 90% sequence identity to *E. coli* glyA. In some embodiments, the one or more nucleic acid molecule encoding an enzyme having serine hydroxymethyltransferase comprises an amino acid sequence set forth in UniProt ID P0A825. In a further embodiment, the one or more nucleic acid molecule encoding an enzyme having serine hydroxymethyltransferase is encoded by a nucleic acid sequence set forth in Gene ID 947022.

Formaldehyde Dehydrogenase (EC 1.2.1.46 and EC 1.2.1.-)

The present disclosure describes enzymes that can catalyze the following reaction:

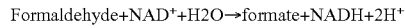

Formaldehyde+NAD⁺+H2O→formate+NADH+2H⁺

Formaldehyde dehydrogenase may also be known as NAD-linked formaldehyde dehydrogenase, NAD-dependent formaldehyde dehydrogenase or formaldehyde:NAD⁺ oxidoreductase.

Most of the formaldehyde dehydrogenases found in animals, plants and bacteria belong to a group called class III alcohol dehydrogenase group and require the addition of glutathione for activity. As a matter of fact, the true substrate for these enzymes was shown to be not formaldehyde, but S-hydroxymethylglutathione, which is formed nonenzymatically from formaldehyde and glutathione.

Unlike those enzymes, the enzyme isolated from *Pseudomonas putida* catalyzes the irreversible oxidation of formaldehyde to formate without the addition of glutathione. Since its substrate is formaldehyde, in an essence this is the "genuine" formaldehyde dehydrogenase. Like other formaldehyde dehydrogenases, the *P. putida* FDH is a zinc-containing metalloenzyme. It also requires NAD⁺ as the electron acceptor. However, unlike the enzymes that belong to the class III alcohol dehydrogenase group, it is sensitive to 4-methylpyrazole. In one embodiment, the formaldehyde dehydrogenase is from *Pseudomonas putida*. In some embodiments, the formaldehyde dehydrogenase is encoded by an amino acid sequence having at least 70% sequence identity, having at least 80% sequence identity, or having at least 90% sequence identity to *P. putida* fdhA. In some embodiments, the one or more nucleic acid molecule encoding a formaldehyde dehydrogenase comprises an amino acid sequence set forth in GenBank Accession BAA04743.1. In a further embodiment, the one or more nucleic acid molecule encoding a formaldehyde dehydrogenase is encoded by a nucleic acid sequence set forth in GenBank Accession D21201.1.

In the industrially important actinomycete *Corynebacterium glutamicum* ATCC 13032, evidence suggests that two enzymes contribute to the degradation of toxic formaldehyde, mycothiol-dependent formaldehyde dehydrogenase encoded by gene fadH, and to a lesser extent acetaldehyde dehydrogenase encoded by gene ald (acetaldehyde dehydrogenase). A mutant lacking both of these enzymes was unable to grow in formaldehyde-containing medium. It also did not grow in vanillate-containing medium because the oxidation of vanillate produces intracellular formaldehyde. Detoxification of formaldehyde is necessary when this soil bacterium encounters formaldehyde in its habitat, or when formaldehyde is generated during metabolism of environmental compounds such as vanillate. The formate produced by FadH can be further oxidized to CO2 by the formate dehydrogenase encoded by gene fdhF.

An ald mutant showed a reduction in formaldehyde degradation of about 30% as compared with wild-type. Inactivation of the chromosomal ald gene resulted in loss of acetaldehyde dehydrogenase activity and loss of the ability of this organism to grow on or utilize ethanol, suggesting a two step oxidation of ethanol to acetate. Expression of gene ald is dependent on the transcriptional regulator RamA, whereas RamB has a slightly negative effect on expression.

In one embodiment, the formaldehyde dehydrogenase is from *Corynebacterium glutamicum* ATCC 13032. In some embodiments, the formaldehyde dehydrogenase is encoded by an amino acid sequence having at least 70% sequence identity, having at least 80% sequence identity, or having at least 90% sequence identity to *Corynebacterium glutamicum* ATCC 13032 ald. In some embodiments, the one or more nucleic acid molecule encoding a formaldehyde dehydrogenase comprises an amino acid sequence set forth in UniProt ID Q8NLZ0. In a further embodiment, the one or more nucleic acid molecule encoding a formaldehyde dehydrogenase is encoded by a nucleic acid sequence set forth in Gene ID 1020739.

In some embodiments, the enzyme having formaldehyde dehydrogenase activity is encoded by an amino acid sequence having at least 70% sequence identity, having at least 80% sequence identity, or having at least 90% sequence identity to *Pseudomonas oleovorans* alkH.

In *Saccharomyces cerevisiae*, two tandem-repeated genes ALD2 and ALD3 encode two cytoplasmic stress-inducible isoforms of aldehyde dehydrogenase. The expression of these isoforms is dependent on the general-stress transcription factors Msn2 and Msn4 but is independent of the HOG MAP kinase pathway. Both forms can use the cofactor NAD+ much more efficiently that NADP+, and are not activated by any cations. While ALD3 is induced by a variety of stresses, including osmotic shock, heat shock, glucose exhaustion, oxidative stress and drugs, ALD2 is only induced by osmotic stress and glucose exhaustion.

In some embodiments, the enzyme having formaldehyde dehydrogenase activity is encoded by an amino acid sequence having at least 70% sequence identity, having at least 80% sequence identity, or having at least 90% sequence identity to *Saccharomyces cerevisiae* ALD2. In other embodiments, the enzyme having formaldehyde dehydrogenase activity is encoded by an amino acid sequence having at least 70% sequence identity, having at least 80% sequence identity, or having at least 90% sequence identity to *Saccharomyces cerevisiae* ALD3. In some embodiments, the one or more nucleic acid molecule encoding an enzyme having formaldehyde dehydrogenase activity comprises an amino acid sequence selected from UniProt ID P47771 and UniProt ID P54114. In a further embodiment, the one or more nucleic acid molecule encoding an enzyme having formaldehyde dehydrogenase activity is encoded by a nucleic acid sequence selected from Gene ID 855206 and Gene ID 855205.

In some embodiments, the enzyme having formaldehyde dehydrogenase activity is encoded by an amino acid sequence having at least 70% sequence identity, having at least 80% sequence identity, or having at least 90% sequence identity to *Homo sapiens* ALDH3A2. In other embodiments, the enzyme having formaldehyde dehydrogenase activity is encoded by an amino acid sequence having at least 70% sequence identity, having at least 80% sequence identity, or having at least 90% sequence identity to *Homo sapiens* ALDH9A1. In some embodiments, the one or more nucleic acid molecule encoding an enzyme having formaldehyde dehydrogenase activity comprises an amino acid sequence selected from UniProt ID P51648 and UniProt ID P49189. In a further embodiment, the one or more nucleic acid molecule encoding an enzyme having formaldehyde dehydrogenase activity is encoded by a nucleic acid sequence selected from Gene ID 224 and Gene ID 223.

Formate Dehydrogenase (EC 1.2.1.-)

The present disclosure describes enzymes that can catalyze the following reactions:

formate+an oxidized electron acceptor+H+→CO$_2$+a reduced electron acceptor formate+H+→CO$_2$+H$_2$ (catalyzed by complex)

formate+an oxidized hydrogenase 3→CO$_2$+a reduced hydrogenase 3

Formate dehydrogenase-H is one of three membrane-associated formate dehydrogenase isoenzymes in *E. coli*. All are functional in the anaerobic metabolism of the organism.

Formate dehydrogenase-H (FDH-H) is located in the cytoplasm and together with hydrogenase-3, FDH-H forms the formate-hydrogen lyase complex. The enzyme is oxygen sensitive and contains selenium as selenocysteine incorporated cotranslationally at the position of an in-frame UGA stop codon in the FdhF open reading frame. A crystal structure of FDH-H has been solved at 2.3 Å resolution, confirming the presence of a [4Fe-4S] cluster, coordination of the Mo cofactor by selenocysteine, and the position of the binding site for the inhibitor nitrate. Expression of fdhF is induced by formate and the absence of external electron acceptors, and is repressed by nitrate, nitrite, trimethylamine N-oxide, and oxygen. Formate can overcome repression by nitrate but not by oxygen. Inhibition of DNA gyrase enhances expression of fdhF.

fdnGHI encodes membrane bound formate dehydrogenase N (FDH-N)—a respiratory enzyme that catalyses the oxidation of formate to carbon dioxide, donating electrons to the quinone pool for the reduction of anaerobic respiratory substrates such as nitrate and trimethylamine N-oxide. FDH-N is a member of the complex iron sulfur molybdoenzyme (CISM) family. The oxidation of formate by FDH-N is electrogenic (H+/e-=1); oxidation of formate in the periplasm is accompanied by menaquinone reduction at the cytoplasmic face of the inner membrane. Expression of formate dehydrogenase-N is induced by nitrate and anaerobiosis, mediated by NarL and Fnr, respectively. Purified FDH-N contains three subunits, designated α (FdnG), β (FdnH) and γ (FdnI). A crystal structure, resolved at 1.6 Å, indicates that this subcomplex is further organised into physiologically relevant trimers with the α and β subunits located towards the periplasmic face of the inner membrane and the γ subunits located towards the cytoplasm. Electrons are transferred from the site of formate oxidation in the α subunit across the membrane to the site of menaquinone reduction in the γ subunit. Protons are taken up from the cytoplasm at the menaquinone reduction site.

fdoGHI encodes formate dehydrogenase O (FDH-O)—a respiratory molybdoenzyme that catalyses the oxidation of formate to carbon dioxide, donating electrons to the membrane soluble quinone pool for the reduction of nitrate. FDH-O and nitrate reductase Z participate in a formate to nitrate electron transport pathway that is active when cells are shifted from aerobic to anaerobic conditions. The pathway operates with either menaquinone or ubiquinone. FDH-O appears to be expressed constitutively; unlike formate dehydrogenase N (FDH-N), it is not regulated by Fnr or NarL. Expression of FDH-O is increased under aerobic conditions; under anaerobic conditions, nitrate stimulates expression slightly; the global regulators H-NS and CRP may play a role in regulation of FDH-O expression. FDH-O may contribute to the cells ability to rapidly adapt to anaerobiosis while levels of FDH-N are still insufficient. FDH-O is a heterotrimeric complex consisting of an α (FdoG), a β (FdoH) and a γ (FdoI) subunit—it shares extensive sequence similarity and immunological properties with the anaerobically expressed FDH-N.

*Candida boidinii* formate dehydrogenase FDH1 is an NAD-dependent enzyme that mediates the detoxification of formate and is strongly inhibited by Cu$^{2+}$, Hg, p-chloromercuribenzoate, cyanide, azide, thiocyanate and cyanate. The inhibition of cyanide is reversible and competes with formate. Protein expression is induced by methanol and repressed by glucose. Since the enzymatic reaction catalyzed by this formate dehydrogenase can regenerate NADH, it has been cloned into *E. coli* to optimize NADH requiring engineered pathways.

In the industrially important actinomycete *Corynebacterium glutamicum* ATCC 13032 evidence suggests that a formate dehydrogenase catalyzes the oxidation of formate to CO$_2$. Both formate and toxic formaldehyde are present in the environment and can be dissimilated by this soil bacterium via the oxidation of formaldehyde to formate. This can be accomplished via FadH and Ald. Formate is then converted to CO$_2$ by FdhF. FdhF is a molybdenum cofactor-dependent formate dehydrogenase that is active under oxic conditions, and was speculated to be involved in the stress response. The exact electron acceptor used by FdhF has not been defined. Gene fdhF is part of a gene cluster containing related genes fdhD and cg0617 that were shown by mutant analysis to be required for formate dehydrogenase activity. The growth of *Corynebacterium glutamicum* ATCC 13032 is inhibited to some extent in the presence of formate and strains lacking formate dehydrogenase activity show increased inhibition. Radiotracer experiments showed that when *Corynebacterium glutamicum* ATCC 13032 was grown with glucose and $^{13}$C-formate, it was metabolized to $^{13}$C-carbon dioxide. An fdhF deletion mutant could not metabolize formate. Growth studies also demonstrated the requirement for Mo$^{2+}$. Protein sequence analysis suggested that FdhF is not an integral membrane protein, but is likely either cytosolic or membrane-associated. Putative orthologs have been identified in a variety of other soil bacteria.

When *Cupriavidus oxalaticus* is grown on formate as the main carbon and energy source, NAD+-dependent formate dehydrogenase is the key enzyme that generates NADH and CO$_2$. The latter enters the ribulose diphosphate carboxylase reaction. The enzyme has been purified to homogeneity from cells grown with formate. The enzyme is a complex flavoprotein containing 2 FMN (flavin mononucleotide), 18-25 non-heme iron atoms and 15-20 acid-labile sulfides. The specific activity was 42 units/mg. The enzyme is specific toward its natural substrate formate, but can accept multiple nonphysiological electron acceptors, including methylviologen, phenazine methosulfate, methylene blue, nitro blue tetrazolium salt, FMN, FAD, riboflavin, and oxygen. It has been shown that the enzyme can also catalyze the reaction in the opposite direction. However, under the conditions employed the enzyme catalyzed the oxidation of formate about 30 times faster than CO$_2$ reduction.

NAD+-dependent formate dehydrogenase from *Gottschalkia acidurici* catalyzes a reversible reaction. While it catalyzes the oxidation of formate to CO$_2$, it also catalyzes the reduction of the latter to formate, which is then converted to acetate. The enzyme has been partially purified and found to be a large enzyme complex (molecular weight of at least 200 kDa) that is very sensitive to oxygen and light. The enzyme contains a L-selenocysteine. Crude preparations of the enzyme could be coupled to NAD reduction during formate oxidation through ferredoxin. When the artificial electron acceptor methyl viologen was used instead of NAD, ferredoxin was not required. Cyanide inhibited the enzyme 90%. Basal formate oxidation activity in cell extracts was 0.85 μmol/min/mg protein, but increased 12-fold upon the addition of tungstate and selenite. Interestingly, the enzyme from the related organism *Clostridium cylindrosporum*, while having a similar requirement for selenite, requires molybdate rather than tungstate, which has an antagonistic effect on it.

The tungsten-containing NAD+-dependent formate dehydrogenase from *Methylobacterium extorquens* is a heterodimer containing iron-sulfur clusters, FMN and tungsten. It is somewhat unusual to find a tungsten-containing enzyme in aerobic bacteria, although several other examples have been found. The smaller β subunit appears to be a fusion protein, with its N-terminal domain related to NueE-like subunits, and its C-terminal domain related to NuoF-like subunits of known NADH-ubiquinone oxidoreductases.

Two different forms of formate dehydrogenase FDH have been purified from *Methylosinus trichosporium* OB3b independently by two groups, and the two proteins were found to have different properties. This protein is composed of two types of subunits in an apparent α2β2 arrangement, with a total size of 315 kDa. It contains nonheme iron and sulfide, and no other metals, and appeared to require FMN.

The *Moraxella* sp. NAD+-dependent formate dehydrogenase fdh is a relatively simple dimeric protein, with no prosthetic groups.

In some embodiments, the enzyme having formate dehydrogenase activity is encoded by an amino acid sequence having at least 70% sequence identity, having at least 80% sequence identity, or having at least 90% sequence identity to a formate dehydrogenase selected from the group consisting of *E. coli* fdhF (chlF, FDH-H), *E. coli* FDH-N, *E. coli* FDH-O, *Candida boidinii* FDH1, *Corynebacterium glutamicum* fdhF, *Cupriavidus oxalaticus* NAD+-dependent formate dehydrogenase, *Gottschalkia acidurici* NAD+-dependent formate dehydrogenase, *Methylobacterium extorquens* Fdh1, *Methylosinus trichosporium* formate dehydrogenase, and *Moraxella* sp. NAD+-dependent formate dehydrogenase fdh. In some embodiments, the one or more nucleic acid molecule encoding a formate dehydrogenase or formate dehydrogenase subunit comprises an amino acid sequence selected from UniProt ID P07658, UniProt ID P0AEK7, UniProt ID P0AAJ3, UniProt ID P24183, UniProt ID P32176, UniProt ID P0AAJ5, UniProt ID P0AEL0, UniProt ID O13437, UniProt ID Q8NSY6, UniProt ID Q8KTI7, UniProt ID Q8KTI8, and UniProt ID O08375. In a further embodiment, the one or more nucleic acid molecule encoding a formate dehydrogenase or formate dehydrogenase subunit is encoded by a nucleic acid sequence selected from Gene ID 948584, Gene ID 946038, Gene ID 948794, Gene ID 946035, Gene ID 948394, Gene ID 948395, Gene ID 948383, GenBank accession AJ011046.2, Gene ID 1021531, GenBank accession AF489516, and GenBank accession Y13245.1.

Formate Hydrogenlyase Complex

The present disclosure describes enzymes that can catalyze the following reaction:

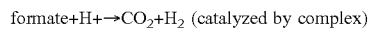

formate+H+→$CO_2$+$H_2$ (catalyzed by complex)

The component enzymes of formate hydrogenlyase complex are: 1) formate dehydrogenase H (also known as ChlF, FdhF, FDH-H), 2) hydrogenase 3, which has multiple subunits (hycBCDEFG gene: hycB, hycC, hycD, hycE, hycF, hycG).

Formate dehydrogenase-H (FDH-H) is described above.

Microbial hydrogenases catalyse the reversible reduction of protons to molecular hydrogen. *E. coli* hydrogenase 3, encoded by the hyc genes (hycD, hycC, hycF, hycG, hycB and hycE), is a multisubunit enzyme that forms part of the formate hydrogenlyase (FHL) complex responsible for the fermentative or anaerobic oxidation of formic acid to carbon dioxide and molecular hydrogen.

Hydrogenase 3 functions primarily in the production of H2 and is important for H2 production at acidic pH. Hydrogen uptake in a strain lacking hydrogenase 1 and hydrogenase 2 is further reduced by the incorporation of a hycE mutation, suggesting that hydrogenase 3 can also function in hydrogen uptake. Hydrogenase 3 shows a high tolerance to product ($H_2$) inhibition.

Hydrogenase 3 is a membrane associated H2 evolving respiratory [NiFe] hydrogenase. It contains the large (HycE) and small (HycG) subunits that are characteristic of 'standard' NiFe hydrogenases plus two additional hydrophilic subunits (HycB and HycF) and two inner membrane subunits (HycC and HycD). Fe—S prosthetic groups located in the hydrophilic part of the complex may form the electron transport pathway. Isolation of FHL using affinity chromatography indicates the presence of a core complex containing HycE, HycB HycF HycG and FdhF which has formate hydrogenlyase activity in vitro; a larger complex containing the membrane associated subunits HyC and HycD is isolated in the presence of detergent.

Formate oxidation in an anaerobically grown fermenting *E. coli* strain lacking hydrogenase 1 and hydrogenase 2 enzymes generates membrane potential.

Sequence similarity between the genes encoding hydrogenase 3 and those encoding subunits that form the core of energy conserving NADH: quinone oxidoreductase (complex I) has been reported and an evolutionary relationship between the two has been proposed.

Strains with insertion mutations of genes within the hyc operon are defective for hydrogenase activity.

Hydrogenase 3 is a nickel containing Fe—S protein.

The hyc operon is regulated coordinately with the structural gene for formate dehydrogenase H. Expression is repressed by oxygen and by nitrate and induced by formate under fermentative growth conditions. Formate is an obligate inducer of the formate hydrogenlyase complex genes.

*E. coli* K-12 contains three other hydrogenases: hydrogenase 1 and hydrogenase 2 (respiratory enzymes that function in H2 uptake) and hydrogenase 4 (less well characterised; possibly silent).

In some embodiments, the hydrogenase 3 is encoded by an amino acid sequence having at least 70% sequence identity, having at least 80% sequence identity, or having at least 90% sequence identity to a hydrogenase 3 selected from the group consisting of *E. coli* hycB, *E. coli* hycC, *E. coli* hycD, *E. coli* hycE, *E. coli* hycF, and *E. coli* hycG. In some embodiments, the one or more nucleic acid molecule encoding a hydrogenase 3 or formate hydrogenlyase complex comprises an amino acid sequence selected from UniProt ID P0AAK1, UniProt ID P16429, UniProt ID P16430, UniProt ID P16431, UniProt ID P16432, and UniProt ID 16433. In a further embodiment, the one or more nucleic acid molecule encoding a formate hydrogenlyase complex or formate hydrogenlyase subunit is encoded by a nucleic acid sequence selected from Gene ID 948002, Gene ID 945327, Gene ID 948994, Gene ID 947396, Gene ID 947048, and Gene ID 947191.

Glycine Cleavage System

The glycine cleavage system is composed of four proteins: three enzymes and a carrier protein. In animals, the system is loosely bound to the mitochondrial inner membrane. The enzymes are i) P-protein (a pyridoxal phosphate-containing protein) or glycine dehydrogenase (decarboxylating) (EC1.4.4.2), ii) T-protein or aminomethyl-transferase (EC2.1.2.10), and iii) L-protein or dihydrolipoamide dehydrogenase (EC1.8.1.4). The carrier protein is called H-protein (a lipoic acid-containing protein).

The glycine cleavage reaction catalyzes the following reversible reaction:

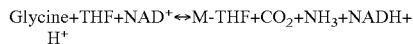

Glycine+THF+NAD$^+$↔M-THF+CO$_2$+NH$_3$+NADH+H$^+$

The system is partitioned into three partial reactions. The reaction is completely reversible, and in both glycine cleavage and glycine synthesis an aminomethyl moiety bound to the lipoic acid of H-protein represents an intermediate that is subsequently degraded to, or can be formed from, methylene-tetrahydrofolate (M-THF) and ammonia by the action of T-protein. Possibly the reaction may involve a ternary complex of P-protein, aminomethyl moiety of glycine and H-protein, as a crucial intermediary state.

Reaction Catalyzed by P-Protein

The first partial reaction of the glycine degradation is the decarboxylation catalyzed by P-protein (a glycine decarboxylase). H-protein serves as a co-substrate. One of the most characteristic properties of the glycine cleavage reaction is that, although P-protein should belong to a class of pyridoxal phosphate-dependent amino acid decarboxylases, P-protein requires H-protein to catalyze the decarboxylation of glycine significantly. The reaction proceeds via a sequential random mechanism where the carboxyl carbon of glycine is converted to carbon dioxide. The remnant of the glycine molecule is transferred to one of the sulfhydryl groups formed by the reductive cleavage of disulfide in lipoate attached to H-protein.

P-protein, a pyridoxal phosphate-containing protein of about 200 kDa, is either a homodimer or a dimer of heterodimers. The former has one molecule of pyridoxal phosphate per subunit, and the latter has one molecule of the cofactor per dimer on the β subunit. The pyridoxal cofactor is attached to a specific lysine residue. The pyridoxal cofactor interacts with the active-site pocket noncovalently. The active site of T. thermophilus P-protein is connected to the molecular surface by a channel with a broad entrance facing the solvent. The molecular surface around the channel is composed of several positively-charged amino acid residues, which are possibly involved in the complex formation with H-protein.

In some embodiments, the enzyme having glycine decarboxylase activity is encoded by an amino acid sequence having at least 70% sequence identity, having at least 80% sequence identity, or having at least 90% sequence identity to E. coli gcvP. In some embodiments, the one or more nucleic acid molecule encoding an enzyme having glycine decarboxylase activity comprises an amino acid sequence set forth in UniProt ID P33195. In a further embodiment, the one or more nucleic acid molecule encoding an enzyme having glycine decarboxylase activity is encoded by a nucleic acid sequence set forth in Gene ID 947394.

Reaction Catalyzed by T-Protein

The decarboxylated moiety of glycine attached to H-protein is subjected to further degradation catalyzed by T-protein (an aminomethyltransferase). The reaction requires THF and yields ammonia, M-THF, and H-protein with reduced lipoate. In the absence of THF, formaldehyde is produced instead of M-THF, but the reaction rate is less than 0.05% of that measured in the presence of THF. In the reverse reaction, T-protein catalyzes the formation of the H-protein-bound aminomethyl lipoate intermediate from M-THF, ammonia, and H-protein with reduced lipoate via an ordered Ter Bi mechanism, in which H-protein is the first substrate to bind followed by M-THF and ammonia. The order of the product release is THF and the methylamine-loaded H-protein.

T-protein is a monomer of about 40 kDa and forms a 1:1 complex with H-protein. A cross-linking study employing E. coli proteins revealed that the interaction of H-protein with T-protein causes a conformational change of T-protein. Intermolecular contact between Lys-288 of T-protein and Asp-43 of H-protein was found. The N-terminal region of T-protein is essential for the interaction with H-protein and for holding T-protein in a compact form. The crystal structure of human T-protein has been analyzed in a free form and that bound to N5-methyl-tetrahydrofolate, an analogue of M-THF. The overall structure consists of three cloverleaf-like structure with the central cavity where the THF cofactor is bound with the pteridin ring deeply buried into the hydrophobic pocket and the glutamyl group pointed to the C-terminal side surface. The structure resembles those of bacterial T-protein from Termotoga naritima, E. coli, and Pyrococcus horikoshii OT3. Structural and mutational analyses of human T-protein indicated that the invariant Asp-101 might play a key role in the initiation of the catalysis by increasing the nucleophilic character of the N10 atom of the folate substrate.

Residues involved in binding of folate have been identified by crosslinking and site-directed mutagenesis. The N-terminal region of GvcT is important for the proper conformation of GvcT, allowing interaction with the H-protein.

In some embodiments, the enzyme having aminomethyltransferase activity is encoded by an amino acid sequence having at least 70% sequence identity, having at least 80% sequence identity, or having at least 90% sequence identity to E. coli gcvT. In some embodiments, the one or more nucleic acid molecule encoding an enzyme having aminomethyltransferase activity comprises an amino acid sequence set forth in UniProt ID P27248. In a further embodiment, the one or more nucleic acid molecule encoding an enzyme having aminomethyltransferase activity is encoded by a nucleic acid sequence set forth in Gene ID 947390.

Reaction Catalyzed by L-Protein

The last step of the glycine cleavage reaction is the reoxidation of the reduced lipoate attached to H-protein catalyzed by L-protein. L-protein is well known as dihydrolipoamide dehydrogenase, lipoamide dehydrogenase, dihydrolipoyl dehydrogenase, or E3 protein component of 2-oxoacid (pyruvate, 2-oxoglutarate, and branched-chain 2-oxoacid) dehydrogenase multienzyme complexes. It catalyzes the transfer of electrons to the ultimate acceptor, NAD.

Experiments employing pea L-protein and H-protein showed that the oxidation of dihydrolipoyl H-protein was not affected by the presence of structurally related analogues such as apoH-protein or octanoylated H-protein. The structural interaction between L-protein and H-protein may not be essential for the oxidation reaction.

Kinetics of the reaction have been studied and suggest a modified ping-pong mechanism. Site-directed mutagenesis was used to identify and characterize the redox-active disulfide and a charged residue influencing the redox potential of the FAD cofactor. The insertion of the FAD cofactor is essential for dimerization and full activity.

An lpd null mutant produces more pyruvate and L-glutamate under aerobic conditions. Metabolic flux analysis shows that the Entner-Doudoroff pathway I and the glyoxylate shunt are activated. Another dihydrolipoate dehydrogenase activity has been detected in *E. coli* lpd mutants; thus, an isozyme may exist.

A mutation in the lpd gene in *E. coli* causes the pyruvate dehydrogenase complex to be less sensitive to NADH inhibition and active during anaerobic growth. Amino acid substitutions at Glu354 that lowered the sensitivity of the enzyme to NADH inhibition were proposed to act by restricting the movement of NADH.

Suppressor mutations in lpd have been shown to restore growth to a redox-defective mutant that lacks both the thioredoxin and glutathione/glutaredoxin reduction pathways. The suppressor mutations reduced Lpd activity resulting in dihydrolipoamide accumulation, which could then serve as an electron donor via reduction of glutaredoxins. The reoxidation of Lpd restored TCA cycle function.

lpd shows differential codon adaptation, resulting in differential translation efficiency signatures, in aerotolerant compared to obligate anaerobic microbes. It was therefore predicted to play a role in the oxidative stress response. An lpd deletion mutant was shown to be more sensitive than wild-type specifically to hydrogen peroxide exposure, but not other stresses.

In some embodiments, the enzyme having dihydrolipoamide dehydrogenase activity is encoded by an amino acid sequence having at least 70% sequence identity, having at least 80% sequence identity, or having at least 90% sequence identity to *E. coli* lpd (lpdA, E3 subunit). In some embodiments, the one or more nucleic acid molecule encoding an enzyme having dihydrolipoamide dehydrogenase activity comprises an amino acid sequence set forth in UniProt ID P0A9P0. In a further embodiment, the one or more nucleic acid molecule encoding an enzyme having dihydrolipoamide dehydrogenase activity is encoded by a nucleic acid sequence set forth in Gene ID 944854.

H-Protein

H-protein is a monomeric and heat-stable protein of about 14 kDa. Vertebrate H-protein is composed of 125 amino acid residues, and lipoic acid is covalently linked to Lys-59. The X-ray crystal structure of the lipoylated pea leaf H-protein (131 residues) revealed that the lipoyl-lysine was localized on the surface of the protein. As mentioned above, the lipoyllysine arm on H-protein shuttles the reaction intermediate and reducing equivalents between the active sites of the components of the glycine cleavage system. The mechanism is analogous to that found in 2-oxoacid dehydrogenase complexes.

Lipoylation of H-protein as well as acyltransferase (E2) components of 2-oxoacid dehydrogenase complexes is catalyzed by lipoate-protein ligase A (LplA) in *E. coli*. The enzyme catalyzes both the formation of lipoyl-AMP from lipoate and ATP and the transfer of the lipoyl-moiety of lipoyl-AMP to H-protein and E2 components. The X-ray crystallographic study showed that LplA consists of a large N-terminal domain and a small C-terminal domain with a substrate-binding pocket at the interface between the two domains.

In mammals, lipoylation is an intramitocondrial event. Lipoic acid is first activated to lipoyl-GMP by lipoate activating enzyme, employing GTP as a high-energy compound. Lipoate activating enzyme is the same protein already known as xenobiotic-metabolizing medium-chain fatty acid: CoA ligase-III. Lipoate is then transferred from lipoyl-GMP to apoproteins by the action of lipoyltransferase.

The H-protein, coded for by the gcvH gene in *E. coli*, is a lipoylprotein that is reduced as it shuttles the methylamine group of glycine from the P-protein to the T-protein and is reoxidized by the dihydrolipoamide dehydrogenase. GcvH functions as a substrate for the three enzymes of the gcv complex.

Residues 61-65 are predicted to contain the lipoyl modification (on lysine), based on conservation of these residues and their correspondence to the lipoate attachment site of the *Pisum sativum* protein.

The interaction between GcvH and GcvT has been examined. Interaction between the two proteins may be necessary to form the folate binding site, in which the folate polyglutamyl region binds, exposing the pteridine ring. The GcvT N terminus is important for interaction with GcvH, probably by mediating a conformational change, and residue D43 of GcvH is proximal to GcvT in the GcvH-GcvT complex.

In some embodiments, the H-protein is encoded by an amino acid sequence having at least 70% sequence identity, having at least 80% sequence identity, or having at least 90% sequence identity to *E. coli* gcvH. In some embodiments, the one or more nucleic acid molecule encoding an H-protein comprises an amino acid sequence set forth in UniProt ID P0A6T9. In a further embodiment, the one or more nucleic acid molecule encoding an H-protein is encoded by a nucleic acid sequence set forth in Gene ID 947393.

Glycolate Dehydrogenase or Glycolate Oxidase (EC 1.1.99.14)

The present disclosure describes enzymes that can catalyze the following reaction:

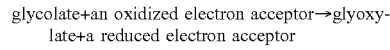

Glycolate dehydrogenase may also be known as glycolate oxidase, glycolate oxidoreductase and glycolate:(acceptor) 2-oxidoreductase.

Glycolate oxidase catalyzes the first step in the utilization of glycolate as the sole source of carbon. The enzyme may be membrane-associated. A cytoplasmic membrane-associated glycolate oxidoreductase activity from *E. coli* ATCC11775 (serovar O1:K1:H7) has been isolated, and the GlcF subunit itself could only be detected in the membrane fraction. The physiological electron acceptor is unknown. Crude extracts from an *E. coli* strain expressing glcDEF from a multicopy plasmid contain glycolate oxidase activity. Insertion mutants in either glcD, glcE, or glcF abolish this activity, suggesting that all three gene products are subunits of a glycolate oxidase complex. Expression of the glcDEFGB operon is induced by growth on glycolate.

A putative glycolate oxidase in *Arabidopsis thaliana* is a mitochondrial homodimeric protein that binds one FAD per monomer and is expressed in leaves, stems, flowers and roots. Enzyme activity is inhibited by cyanide ions. It catalyzes the oxidation of D-lactate to pyruvate stereospecifically, mediating the detoxification of methylglyoxal and D-lactate.

In some embodiments, the enzyme having glycolate dehydrogenase activity is encoded by an amino acid sequence having at least 70% sequence identity, having at least 80% sequence identity, or having at least 90% sequence identity to an enzyme having glycolate dehydrogenase activity selected from *E. coli* glycolate dehydrogenase GLC and *Arabidopsis thaliana* glycolate dehydrogenase. In some embodiments, the one or more nucleic acid molecule encoding a glycolate dehydrogenase or glycolate dehydrogenase subunit comprises an amino acid sequence selected from UniProt ID P0AEP9, UniProt ID P52073, UniProt ID P52074, and UniProt ID Q94AX4. In a further embodiment, the one or more nucleic acid molecule encoding a glycolate dehydrogenase or glycolate dehydrogenase subunit is encoded by a nucleic acid sequence selected from Gene ID 947353, Gene ID 2847718, Gene ID 2847717, and GenBank accession Y13245.1.

Alanine-Glyoxylate Aminotransferase (EC 2.6.1.44)

The present disclosure describes enzymes that can catalyze the following reaction:

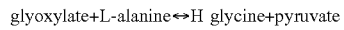

glyoxylate+L-alanine↔H glycine+pyruvate

In *Saccharomyces cerevisiae* alanine-glyoxylate aminotransferase subunit is one of three different enzymes used for glycine synthesis. The AGX1 gene, encoding this enzyme, was identified by comparing enzyme specific activities in knockout strains. When placed in a background defficient for the other enzymes responsible for glycine synthesis, the mutation in AGX1 produced complete glycine auxotrophy. The enzymes was subsequently purified and characterized. The enzyme, which contains pyridoxal 5'-phosphate as cofactor, is a homodimer of about 80 kDa, and is highly specific for L-alanine and glyoxylate.

The mitochondrially localized *Homo sapiens* alanine-glyoxylate aminotransferase 2 (AGXT2) and peroxisomal serine-pyruvate aminotransferase (AGXT1, see above) both catalyze the conversion of glyoxylate to glycine using alanine as the amino donor. However, AGXT2, but not AGXT1, can also utilize asymmetric dimethylarginine (ADMA) as an amino donor, leading to the formation of α-keto-δ-(NN-dimethylguanidino) valeric acid (DMGV). ADMA is a potent endogenous inhibitor of nitric-oxide (NO) synthase. ADMA levels are also controlled by cytosolic dimethylarginine dimethylaminohydrolases (DDAHs) that hydrolyze ADMA to citrulline and dimethylamine. Elevated levels of ADMA are associated with diabetes, hypertension, congestive heart failure, and atherosclerosis. AGXT2 is a pyridoxal phosphate dependent enzyme that is expressed primarily in the kidney, and its activity is one mechanism by which the kidney regulates blood pressure.

In *Arabidopsis thaliana*, alanine transaminases with four aminotransferase activities have been identified. AOAT1 (GGAT1) is peroxisomal located. Knock-out plants have reduced activity of AOAT, GPAT (glutamate:pyruvate aminotransferase), AGAT (alanine: glyoxylate aminotransferase) and GGAT (glutamate: glyoxylate aminotransferase). The GGAT and AGAT activities were reduced most drastically. These indicate AOAT1 is primarily involved in photorespiration. Similarly, AOAT2 (GGAT2), which is predicted to be located in the peroxisome, is likely involved in photorespiration. In vitro assay of the recombinant proteins indicated that GGAT1 and GGAT2 have four aminotransferase activities, namely GGAT, AGAT, GPAT and AOAT. The two recombinant proteins exhibited very similar Km values towards amino acid substrates glutamate and alanine, as well as the oxoacid substrates glyoxylate, pyruvate and 2-oxoglutarate.

In some embodiments, the enzyme having alanine-glyoxylate aminotransferase activity is encoded by an amino acid sequence having at least 70% sequence identity, having at least 80% sequence identity, or having at least 90% sequence identity to an enzyme having alanine-glyoxylate aminotransferase activity selected from *Saccharomyces cerevisiae* AGX1, *Homo sapiens* AGXT2, *Arabidopsis thaliana* AOAT1 and *Arabidopsis thaliana* AOAT2. In some embodiments, the one or more nucleic acid molecule encoding an enzyme having alanine-glyoxylate aminotransferase activity comprises an amino acid sequence selected from UniProt ID P43567, UniProt ID Q9BYV1, UniProt ID Q9LR30 and UniProt ID Q9S7E9. In a further embodiment, the one or more nucleic acid molecule encoding an enzyme having alanine-glyoxylate aminotransferase activity is encoded by a nucleic acid sequence selected from Gene ID 850514, Gene ID 64902, TAIR accession AT1G23310 and TAIR accession AT1G70580.

Alanine Transaminase (EC 2.6.1.2)

The present disclosure describes enzymes that can catalyze the following reaction:

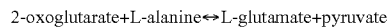

2-oxoglutarate+L-alanine↔L-glutamate+pyruvate

In some embodiments, the alanine transaminase is a glutamate-pyruvate aminotransferase. AlaA is one of three major alanine-synthesizing transaminases in *E. coli*. AlaA and AlaC together account for 90% of glutamic-pyruvic transaminase (GPT) activity in the cell. A crystal structure of AlaA has been solved at 2.11 Å resolution. The structure shows a symmetric α2 homodimer typical of fold type I aminotransferases. An alaA deletion strain has no growth defect, but an alaA avtA double mutant forms small colonies on agar plates. An alaA avtA alaC triple mutant has a slow growth phenotype in liquid medium. The defects of the double and triple mutants can be rescued by addition of alanine. Fitness and competitive growth experiments were performed under different growth conditions. Particularly under oxygen-limiting conditions, the doubling time of the AalaA strain in minimal media is increased compared to growth in rich media. Under competitive growth conditions, the ΔalaA mutation confers a disadvantage compared to wild type even in rich media. alaA was identified in a screen for genes that reduce the lethal effects of stress. An alaA insertion mutant is more sensitive than wild type to mitomycin C and other stresses and less sensitive to 10% SDS. The alaA gene was first identified as a mutant with a leaky requirement for alanine or valine.

AlaB is one of three major alanine-synthesizing transaminases in *E. coli*. AlaB catalyzes a glutamate-pyruvate aminotransferase reaction, generating alanine from pyruvate with glutamate as the amino donor. This activity has been assayed in crude cell extracts, and the gene encoding AlaB had been isolated on a plasmid. Expression of alaB from a multicopy plasmid partially suppresses the growth defect of an ilvE alaA mutant strain.

AlaC is one of three major alanine-synthesizing transaminases in *E. coli*. A homology model of the enzyme based on the crystal structure of AlaA has been generated. An alaC deletion strain has no growth defect, but an alaA avtA alaC triple mutant has a slow growth phenotype in liquid medium. The defect can be rescued by addition of alanine. Fitness and competitive growth experiments were performed under different growth conditions. Particularly under oxygen-limiting conditions, the doubling time of the ΔalaC strain in minimal media is increased compared to growth in rich media; unlike for the alaA and avtA mutants, addition of L-alanine returns the doubling time to that observed in DMEM medium. Under competitive growth conditions, the ΔalaC mutation confers a disadvantage compared to wild type even in rich media. Expression of alaC is activated by the transcriptional regulator SgrR. AlaC may thus play a role in glucose-phosphate stress. However, an alaC deletion mutant does not show altered sensitivity to α-methylglucoside, which induces sugar-phosphate stress.

In *Homo sapiens*, alanine aminotransferase is a cytoplasmic enzyme that catalyzes the reversible transamination between L-alanine and 2-oxoglutarate to form pyruvate and L-glutamate. The interconversion of these four major metabolic intermediates gives this enzyme both degradative and biosynthetic roles. It participates in the alanine-glucose cycle of skeletal muscle and liver, gluconeogenesis, and glutamate generation in the brain. Alanine aminotransferase is expressed in kidney, skeletal muscle, adipose tissue and heart. There are two isoforms of the enzyme: alanine aminotransferase 1 (GPT) and alanine aminotransferase 2 (GPT2). Human alanine aminotransferase 1 (GPT) was purified from liver. Recombinant human alanine aminotransferase 2 (GPT2) from adipose tissue was expressed in Escherichia coli and the molecular mass was determined by SDS-PAGE. The enzyme is expressed at high levels in adipose tissue, muscle, brain and kidney and at lower levels in breast and liver.

The subunit structure of an alanine transaminase from the marine polychaete annelid Arenicola marina (lugworm) has not been reported. It has a native apparent molecular mass of 91 kDa as determined by gel filtration chromatography. The gene encoding it in this organism has not been identified. In marine annelids and mollusks this reaction participates in an anaerobic energy generation pathway that operates during periods of hypoxia or anoxia. Alanine transaminase (glutamate pyruvate transaminase) from this organism has been partially purified from body wall muscle and characterized. High alanine transaminase activity was found in this tissue. Specific, reversible, L-glutamate-dependent L-alanine transaminase and L-aspartate transaminase activities have also been demonstrated in tissues of the mussel Mytilus edulis.

The Arabidopsis thaliana tryptophan aminotransferase TAA1 protein is involved in the formation of indole-3-pyruvate, a precursor to indole-3-acetate (IAA), a biologically important auxin that acts as a phytohormone in many plant species. In vitro assays reveal that this pyridoxal 5'-phosphate (PLP)-dependent aminotransferase can act on a number of different L-amino acids, including L-phenylalanine, L-tyrosine, L-leucine, L-alanine, L-methionine, and L-glutamine using either pyruvate or 2-oxoglutarate as a cosubstrate. However, enzymatic assays, in silico docking experiments, and mutant phenotypic analyses all suggest that L-tryptophan is the in vivo substrate for this enzyme. TAA1 has a Km of 0.29 mM and a Vmax of 12.9 µM/min when tested with L-tryptophan and pyruvate. It is unclear whether pyruvate or 2-oxoglutarate is the more biologically relevant cosubstrate for this enzyme.

The gene encoding this protein was identified in screens for shade avoidance mutants and mutants with a weak ethylene insensitivity suggesting that the auxin synthesized through a TAA1-mediated pathway is particularly important for the responses to specific environmental and hormonal stimuli. In addition, normal developmental processes, such as embryogenesis, that require proper auxin levels, are disrupted when TAA1 and one or more of its closely related family members (i.e. TAR1 and TAR2) are knocked-out in Arabidopsis plants. This enzyme activity appears to be widely distributed in the plant kingdom, based on the ability of enzymatic extracts from 30 different species distributed among 16 families, to catalyze the formation of IPA in a transaminase reaction. Three species of algae also have this activity.

In Arabidopsis thaliana, alanine transaminases with four aminotransferase activities have been identified. AOAT1 (GGAT1) is peroxisomal located. Knock-out plants have reduced activity of AOAT, GPAT (glutamate:pyruvate aminotransferase), AGAT (alanine: glyoxylate aminotransferase) and GGAT (glutamate: glyoxylate aminotransferase). The GGAT and AGAT activities were reduced most drastically. These indicate AOAT1 is primarily involved in photorespiration. Similarly, AOAT2 (GGAT2), which is predicted to be located in the peroxisome, is likely involved in photorespiration. In vitro assay of the recombinant proteins indicated that GGAT1 and GGAT2 have four aminotransferase activities, namely GGAT, AGAT, GPAT and AOAT. The two recombinant proteins exhibited very similar Km values towards amino acid substrates glutamate and alanine, as well as the oxoacid substrates glyoxylate, pyruvate and 2-oxoglutarate.

Alanine aminotransferase activities have also been described from Candida maltosa, Clostridium propionicum, Pyrococcus furiosus, Megathyrsus maximus and Panicum miliaceum. The Panicum miliaceum putative alanine aminotransferase was cloned from this NAD-ME type C4 plant and found to express in both mesophyll and bundle sheath cells, and the gene expression was light-inducible. The mRNA accumulation increased dramatically during greening in both cell types which is in agreement with its predicted role in C4 photosynthesis.

In some embodiments, the enzyme having alanine transaminase activity is encoded by an amino acid sequence having at least 70% sequence identity, having at least 80% sequence identity, or having at least 90% sequence identity to an enzyme having alanine transaminase activity selected from E. coli glutamate-pyruvate aminotransferase alaA, E. coli glutamate-pyruvate aminotransferase alaB, E. coli glutamate-pyruvate aminotransferase alaC, Homo sapiens alanine aminotransferase 1 (GPT), Homo sapiens alanine aminotransferase 2 (GPT2), Arenicola marina alanine transaminase, Arabidopsis thaliana tryptophan aminotransferase TAA1, Arabidopsis thaliana AOAT1, Arabidopsis thaliana AOAT2, Candida maltosa alanine aminotransferase, Clostridium propionicum alanine aminotransferase, Pyrococcus furiosus alanine aminotransferase aat, Megathyrsus maximus alanine transaminase, and Panicum miliaceum alanine transaminase AlaAT-2. In some embodiments, the one or more nucleic acid molecule encoding enzyme having alanine transaminase activity comprises an amino acid sequence selected from UniProt ID P0A959, UniProt ID P77434, UniProt ID P24298, UniProt ID Q8TD30, UniProt ID Q9S7N2, UniProt ID Q9LR30, UniProt ID Q9S7E9, UniProt ID Q9P9M8, and UniProt ID P34106. In a further embodiment, the one or more nucleic acid molecule encoding enzyme having alanine transaminase activity is encoded by a nucleic acid sequence selected from Gene ID 946772, Gene ID 946850, Gene ID 2875, Gene ID 84706, Gene ID 843393, TAIR accession AT1G23310, TAIR accession AT1G70580, GenBank accession AF163769.1 and GenBank accession X69421.1.

Glutamate Dehydrogenase (EC 1.4.1.2 and EC 1.4.1.3)

The present disclosure describes enzymes that can catalyze the following reactions:

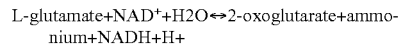
L-glutamate+NAD⁺+H2O↔2-oxoglutarate+ammonium+NADH+H+

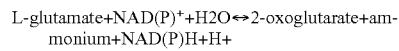
L-glutamate+NAD(P)⁺+H2O↔2-oxoglutarate+ammonium+NAD(P)H+H+

In some embodiments, the glutamate dehydrogenase is an NAD-dependent glutamate dehydrogenase from Saccharomyces cerevisiae (GDH2) that degrades glutamate to ammonia and alpha-ketoglutarate. Expression of GDH2 is sensitive to nitrogen catabolite repression and intracellular ammonia levels.

There are two NAD-dependent glutamate dehydrogenase (GDH) genes in Arabidopsis, GDH1 and GDH2, encoding the alpha- and beta-subunits, respectively. Seven hexameric isoforms of GDH have been detected which are composed of different ratios of the alpha and beta subunits. Different isoforms are distributed in different tissues under different environmental and physiological conditions. The enzyme activity of GDH is controlled in part at the transcriptional level.

Glutamate dehydrogenase from *Peptoniphilus asaccharolyticus* catalyzes the NAD-dependent, oxidative deamination of L-glutamate to 2-oxoglutarate. The reaction is highly substrate specific. No activity was observed in the presence of D-glutamate, D- or L-asparate, glutamine or when NADP replaced NAD. Using sucrose gradient density centrifugation, researchers estimated that the molecular weight of the native enzyme was between 300-340 kDa, suggesting that the enzyme may be a homohexamer. Other researchers, on the other hand, estimated that the molecular weight of the native enzyme was approximately 226 kDa, using gel filtration. The KM values for L-glutamate and NAD+ were 1.3 mM and 0.25 mM, respectively.

*Halobacterium salinarum* is one of the organisms reported to have more than one form of GDH, with different forms utilizing different cofactors (NAD and NADP). It was eventually shown that the organism has four genes encoding four different glutamate dehydrogenase enzymes. Two of these gene products have been purified and characterized biochemically. One of the genes, gdhAl, which was originally predicted to encode an NADP-specific form, was found to encode an NAD-specific enzyme.

*Homo sapiens* glutamate dehydrogenases (GDHs) are homohexameric mitochondrial matrix enzymes that catalyze the reversible oxidative deamination of L-glutamate to 2-oxoglutarate and ammonia. Mammalian GDHs are unusual enzymes, in that they are able to use either NAD or NADP as a co-factor. Humans express two GDH isoenzymes. Glutamate dehydrogenase 1 (GLUD1) is expressed at high levels in liver, brain, pancreas and kidney. Glutamate dehydrogenase 2 (GLUD2) is encoded by an X chromosome-linked intronless gene and is expressed in retina, testis, and brain. Mutations in GLUD1 that lead to enzyme overactivity, result in hyperinsulinemia. Allosteric control of mammalian GDH activity by positive effectors like ADP and L-leucine and negative effectors like GTP have been extensively studied.

*Bacillus subtilis* PCI 219 has a single glutamate dehydrogenase (GDH) with dual coenzyme specificity for NAD(H) and NADP(H). Its molecular weight was estimated to be 250,000+/−20,000 by gel filtration, and 270,000+/−30,000 by zone centrifugation in a sucrose density gradient. The subunit size was about 57,000, suggesting that it is a homotetramer.

A cDNA clone was isolated from *Solanum lycopersicum* tissues. The cDNA encoded a protein that shares identity with glutamate dehydrogenase (GDH) of plants. Expression analysis of this protein showed that it is expressed in stems, roots and leaves but is absent in fruit tissues. The study also showed that the two subunits of tomato GDH1 were encoded by a single gene. This enzyme converts 2-oxoglutarate to L-glutamate.

Glutamate dehydrogenase activities have also been described from *Clostridium propionicum* and *Thermotoga maritima*.

In some embodiments, the enzyme having glutamate dehydrogenase activity is encoded by an amino acid sequence having at least 70% sequence identity, having at least 80% sequence identity, or having at least 90% sequence identity to a glutamate dehydrogenase selected from *Saccharomyces cerevisiae* NAD-dependent glutamate dehydrogenase GDH2, *Arabidopsis thaliana* NAD-dependent glutamate dehydrogenase GDH2, *Arabidopsis thaliana* NAD-dependent glutamate dehydrogenase GDH1, *Peptoniphilus asaccharolyticus* NAD-dependent glutamate dehydrogenase gdhA, *Halobacterium salinarum* NAD-dependent glutamate dehydrogenase gdhA, *Thermotoga maritima* glutamate dehydrogenase, *Homo sapiens* glutamate dehydrogenase 1 (GLUD1), *Homo sapiens* glutamate dehydrogenase 2 (GLUD2), *Bacillus subtilis* glutamate dehydrogenase and *Solanum lycopersicum* glutamate dehydrogenase GDH1. In some embodiments, the one or more nucleic acid molecule encoding an enzyme having glutamate dehydrogenase activity comprises an amino acid sequence selected from UniProt ID P33327, UniProt ID Q38946, UniProt ID Q38946, UniProt ID P28997, UniProt ID P29051, UniProt ID P00367, UniProt ID P49448 and UniProt ID P93541. In a further embodiment, the one or more nucleic acid molecule encoding an enzyme having glutamate dehydrogenase activity is encoded by a nucleic acid sequence selected from Gene ID 461927, TAIR accession AT5G07440, TAIR accession AT5G18170, GenBank accession M76403.1, GenBank accession X63837.1, Gene ID 2746, Gene ID 2747 and GenBank accession U48695.1.

Acetaldehyde Dehydrogenase (EC 1.2.1.10)

The present disclosure describes enzymes that can catalyze the following reaction:

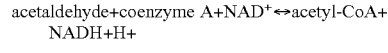

acetaldehyde+coenzyme A+NAD⁺↔acetyl-CoA+ NADH+H+

*E. coli* mhpF encodes an acylating acetaldehyde dehydrogenase. MhpF is active as a monomer; the rate-limiting step of the reaction appears to be transthioesterification. MhpF is involved in synthesis of n-butanol in an engineered reversal of the β-oxidation pathway. The expression of MhpE is translationally coupled to MhpF, and interaction between the two proteins appears to be required for solubility of MhpE.

*E. coli* AdhE is a homopolymeric protein with three Fe2+-dependent catalytic functions: alcohol dehydrogenase, coenzyme A-dependent acetaldehyde dehydrogenase, and pyruvate formate-lyase deactivase. However, the existence of the pyruvate formate-lyase deactivase activity of AdhE has been debated. The homopolymeric structure of AdhE is unusual in that 20-60 subunits are helically arranged to form rod-like ultrastructures. Under fermentative conditions AdhE catalyzes the reduction of acetyl-CoA to acetaldehyde and the latter compound to ethanol. Aerobically, in the reverse direction, AdhE can catalyze the oxidation of acetaldehyde to acetyl-CoA. Expression of adhE appears to be regulated at the transcriptional and translational levels, and possibly at the posttranslational level. Expression of adhE is approximately 10-fold higher during anaerobic growth than during aerobic growth. The AdhE from *E. coli* B was partially purified and characterized in early work. It was later purified to homogeneity from *E. coli* B and its coenzyme A-linked aldehyde dehydrogenase activity was subjected to detailed kinetic analysis. A bi-uni-uni-uni ping-pong mechanism was proposed. AdhE from *Salmonella enterica* subsp. *enterica* serovar *Typhimurium* showed 70% amino acid sequence identity to that of *E. coli*. It had a lower Km for alcohol substrates and some differences in substrate specificity as compared to the *E. coli* enzyme. In the metabolic engineering field, deletion of adhE is a determinant in the production of compounds such as succinate, D-lactate, and polyhydroxyalkanoates.

Chlamydomonas reinhardtii ADH1 encodes a dual function alcohol dehydrogenase/acetaldehyde dehydrogenase. It appears to be active under anoxic conditions and participates in two different anaerobic ethanol production pathways in Chlamydomonas.

DmpF is an acylating acetaldehyde dehydrogenase from Pseudomonas sp. The final two steps of the meta-cleavage pathway in Pseudomonas sp. CF600 involve the conversion of (S)-4-hydroxy-2-oxopentanoate to pyruvate and acetyl-CoA by the enzymes 4-hydroxy-2-oxovalerate aldolase and acetaldehyde dehydrogenase (acylating). Biochemical studies demonstrated that these two enzymes comprise a bifunctional aldolase-dehydrogenase heterodimer, and suggest that the product of the aldolase reaction, acetaldehyde, is transferred to the dehydrogenase active site via a channeling mechanism. This minimizes the risk to the cells posed by the toxic acetaldehyde.

The presence of the todI gene product in Pseudomonas putida F1 was suggested by the protein expression pattern of plasmid constructs. The predicted amino acid sequence of the todI gene product showed very high identity with other bacterial acylating aldehyde dehydrogenase gene products.

The adhE gene of Clostridium acetobutylicum ATCC 824 encodes a multifunctional enzyme that has both alcohol dehydrogenase and acetaldehyde dehydrogenase activities. Both activities are necessary for the formation of butan-1-ol and ethanol during solventogenesis. The adhE gene is part of the sol operon, which is located on the pSOL1 megaplasmid. Expression of the gene from a plasmid in Clostridium acetobutylicum ATCC 824 resulted in elevated activities of NADH-dependent butanol dehydrogenase, NAD-dependent acetaldehyde dehydrogenase and butyraldehyde dehydrogenase, and a small increase in NADH-dependent ethanol dehydrogenase. Complementation of a mutant deficient in butyraldehyde dehydrogenase, acetoacetate decarboxylase, and acetoacetyl-coenzyme A:acetate/butyrate:coenzyme A-transferase activities, which produces neither butanol nor acetone, by the adhE gene resulted in restored butanol formation without any acetone formation or any significant increase in ethanol production, suggesting that the primary role of the enzyme is in butanol formation, providing both a butanal dehydrogenase activity (converting butanoyl-CoA to butan-1-al) and butanol dehydrogenase activity. In addition, inactivation of the gene drastically reduced butanol production (by 85%), supporting this role. Another gene from the pSOL1 plasmid, adhE2, encodes a second multifunctional aldehyde/alcohol dehydrogenase involved in butanol production. However, that enzyme is produced only under alcohologenic conditions, and is not expressed under solventogenic conditions. The gene from strain ATCC 824 was originally called aad.

Acetaldehyde dehydrogenase activities have also been described from Leuconostoc mesenteroides, Pelobacter acetylenicus and Pseudomonas putida. The partially purified Leuconostoc mesenteroides CoA-dependent aldehyde dehydrogenase could not be separated from an NAD-linked alcohol dehydrogenase that co-purified with it. The enzyme was specific to NAD and could not use NADP. While acetaldehyde and 1-propanal were the best substrates, the enzyme could also use butan-1-al (31% of activity with acetaldehyde) and isobutanal (14%).

In some embodiments, the enzyme having acetaldehyde dehydrogenase activity is encoded by an amino acid sequence having at least 70% sequence identity, having at least 80% sequence identity, or having at least 90% sequence identity to an enzyme having acetaldehyde dehydrogenase activity selected from E. coli mhpF, E. coli AdhE, Chlamydomonas reinhardtii ADH1, Leuconostoc mesenteroides CoA-dependent acetaldehyde dehydrogenase, Pelobacter acetylenicus acetaldehyde dehydrogenase, Pseudomonas sp. dmpF, Pseudomonas putida acylating aldehyde dehydrogenase todI, Pseudomonas putida acetaldehyde dehydrogenase cmtH and Clostridium acetobutylicum alcohol/aldehyde dehydrogenase AdhE. In some embodiments, the one or more nucleic acid molecule encoding an enzyme having acetaldehyde dehydrogenase activity comprises an amino acid sequence selected from UniProt ID P77580, UniProt P0A9Q7, UniProt ID A8JI07, UniProt ID Q52060, UniProt ID Q51949 and UniProt ID P33744. In a further embodiment, the one or more nucleic acid molecule encoding an enzyme having acetaldehyde dehydrogenase activity is encoded by a nucleic acid sequence selected from Gene ID 945008, Gene ID 945837, Gene ID 5729132, GenBank accession X60835.1, GenBank accession U09250.1 and Gene ID 1116167.

Ethanolamine Ammonia Lyase (EC 4.3.1.7)

The present disclosure describes enzymes that can catalyze the following reaction:

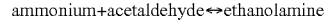

ammonium+acetaldehyde⇌ethanolamine

Ethanolamine ammonia-lyase (EAL) allows E. coli to utilize ethanolamine as the sole source of nitrogen and carbon in the presence of external vitamin B12. EAL is an adenosylcobalamin-dependent enzyme that is spontaneously inactivated by its substrate and can be reactivated by EutA. The enzyme was first studied in the non-K-12 strain NCIB 8114. Crystal structures of an N-terminally truncated, but active form of the enzyme both in binary and ternary complexes with the cofactor and substrate have been solved. The enzyme is composed of a hexamer of $(\alpha\beta)2$ dimers, with the $\alpha$ subunit holding the active site and the cobalamin cofactor bound at the interface between the $\alpha$ and $\beta$ subunits. The authors propose a reaction mechanism that is consistent with a previously described mechanism for adenosylcobalamin-dependent rearrangements. The stereochemical course of the reaction has been modeled on the basis of crystal structures, accounting for the apparent lack of stereospecificity of the enzyme. Production of EAL is catabolite repressed and is induced by the simultaneous presence of ethanolamine and the adenosylcobalamin cofactor. Ethanolamine ammonia-lyase comprises two subunits, $\alpha$ (EutB) and $\beta$ (EutC).

In some embodiments, the enzyme having ethanolamine ammonia lyase activity is encoded by an amino acid sequence having at least 70% sequence identity, having at least 80% sequence identity, or having at least 90% sequence identity to an E. coli enzyme having ethanolamine ammonia lyase activity. In some embodiments, the one or more nucleic acid molecule encoding an ethanolamine ammonia lyase subunit comprises an amino acid sequence selected from UniProt ID P0AEJ6 and UniProt ID P19636. In a further embodiment, the one or more nucleic acid molecule encoding an ethanolamine ammonia lyase subunit is encoded by a nucleic acid sequence selected from Gene ID 946924 and Gene ID 946925.

Serine Aminase (EC 2.6.1.-)

The present disclosure describes enzymes that can catalyze the following reaction:

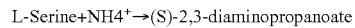

L-Serine+$NH_4^+$→(S)-2,3-diaminopropanoate

In some embodiments, an enzyme having serine aminase activity can be a serine-glyoxylate transaminase. In other embodiments, an enzyme having serine aminase activity can be a serine-pyruvate transaminase (see above).

Serine-glyoxylate aminotransferase catalyzes the transfer of the α-amino group of L-serine to glyoxylate, forming glycine and hydroxypyruvate. In the serine-cycle methylotrophs this enzyme plays two important roles: the formation of an acceptor (glycine) for a one-carbon unit, and the conversion of L-serine to hydroxypyruvate in the assimilatory pathway. This is the first microbial serine-glyoxylate aminotransferase to be purified, and a few years later the gene encoding it was identified as well.

Serine: glyoxylate aminotransferase encoded by *Arabidopsis thaliana* AGT1 is a. homodimer. The purified recombinant protein has the highest activity with the serine: glyoxylate transamination. It also catalyzed alanine: glyoxylate transamination and serine: pyruvate transamination with much lower specific activity.

sgaA is presumed to be the gene encoding serine-glyoxylate aminotransferase on the *Methylobacterium extorquens* chromosome. While the product of the cloned gene has not been expressed, mutation complementation was used to investigate its role. Mutations in this gene have abolished the ability to grow on C1 compounds, and complementation of the mutants by a cloned intact version of the gene fragment has restored activity. In addition, sgaA sequence is similar to a number of aminotransferases.

In further embodiments, an enzyme having serine aminase activity can be an enzyme having phosphoserine aminotransferase activity. In some embodiments, the one or more nucleic acid molecules encoding the phosphoserine aminotransferase is serC, or homolog thereof. In another embodiment, the one or more nucleic acid molecules encoding an enzyme having phosphoserine aminotransferase activity, an enzyme having L-serine transaminase activity, or an enzyme having serine aminotransferase activity comprise an amino acid sequence set forth in SEQ ID NO: 230. In a further embodiment, the one or more nucleic acid molecule encoding an enzyme having phosphoserine aminotransferase activity, an enzyme having L-serine transaminase activity, or an enzyme having serine aminotransferase activity is encoded by a nucleic acid sequence set forth in SEQ ID NO: 229. In some embodiments, the enzyme having phosphoserine aminotransferase activity is *Homo sapiens* PSAT1, or homolog thereof. In one embodiment, the one or more nucleic acid molecule encoding an enzyme having phosphoserine aminotransferase activity comprises an amino acid sequence set forth in UniProt ID Q9Y617. In another embodiment, the one or more nucleic acid molecule encoding an enzyme having phosphoserine aminotransferase activity is encoded by a nucleic acid sequence set forth in Gene ID 29968.

In some embodiments, the enzyme having serine aminase activity is encoded by an amino acid sequence having at least 70% sequence identity, having at least 80% sequence identity, or having at least 90% sequence identity to an *Arabidopsis thaliana* serine-glyoxylate aminotransferase AGT1, *Hyphomicrobium methylovorum* GM2 serine-glyoxylate aminotransferase sgaA and *Methylobacterium extorquens* sgaA. In some embodiments, the one or more nucleic acid molecule encoding an enzyme having serine-glyoxylate aminotransferase activity comprises an amino acid sequence selected from UniProt ID Q56YA5 and UniProt ID O08374. In a further embodiment, the one or more nucleic acid molecule encoding an enzyme having serine-glyoxylate aminotransferase activity is encoded by a nucleic acid sequence selected from TAIR accession AT2G13360, GenBank accession D86125.1 and GenBank accession L27235.1.

In some embodiments, an enzyme having serine aminase activity is an enzyme having serine-pyruvate aminotransferase activity. In some embodiments, the enzyme having serine-pyruvate aminotransferase activity is encoded by an amino acid sequence having at least 70% sequence identity, having at least 80% sequence identity, or having at least 90% sequence identity to *Homo sapiens* AGXT1. In some embodiments, the enzyme having serine-pyruvate aminotransferase activity is *Homo sapiens* AGXT1. In some embodiments, the one or more nucleic acid molecules encoding the enzyme having serine-pyruvate aminotransferase activity is AGXT1, or homolog thereof. In some embodiments, the one or more nucleic acid molecules encoding an enzyme having serine-pyruvate aminotransferase activity comprise an amino acid sequence set forth in SEQ ID NO: 244. In a further embodiment, the one or more nucleic acid molecule encoding an enzyme having serine-pyruvate aminotransferase activity is encoded by a nucleic acid sequence set forth in SEQ ID NO: 243.

In some embodiments, an enzyme having serine aminase activity is an enzyme having alanine-glyoxylate aminotransferase activity. In some embodiments, the enzyme having alanine-glyoxylate aminotransferase activity is encoded by an amino acid sequence having at least 70% sequence identity, having at least 80% sequence identity, or having at least 90% sequence identity to an enzyme having alanine-glyoxylate aminotransferase activity selected from *Saccharomyces cerevisiae* AGX1, *Homo sapiens* AGXT2, *Arabidopsis thaliana* AOAT1 and *Arabidopsis thaliana* AOAT2. In some embodiments, the one or more nucleic acid molecule encoding an enzyme having alanine-glyoxylate aminotransferase activity comprises an amino acid sequence selected from UniProt ID P43567, UniProt ID Q9BYV1, UniProt ID Q9LR30 and UniProt ID Q9S7E9. In a further embodiment, the one or more nucleic acid molecule encoding an enzyme having alanine-glyoxylate aminotransferase activity is encoded by a nucleic acid sequence selected from Gene ID 850514, Gene ID 64902, TAIR accession AT1G23310 and TAIR accession AT1G70580.

In some embodiments, an enzyme having serine aminase activity is an enzyme having alanine transaminase activity. In some embodiments, the enzyme having alanine transaminase activity is encoded by an amino acid sequence having at least 70% sequence identity, having at least 80% sequence identity, or having at least 90% sequence identity to an enzyme having alanine transaminase activity selected from *E. coli* glutamate-pyruvate aminotransferase alaA, *E. coli* glutamate-pyruvate aminotransferase alaB, *E. coli* glutamate-pyruvate aminotransferase alaC, *Homo sapiens* alanine aminotransferase 1 (GPT), *Homo sapiens* alanine aminotransferase 2 (GPT2), *Arenicola marina* alanine transaminase, *Arabidopsis thaliana* tryptophan aminotransferase TAA1, *Arabidopsis thaliana* AOAT1, *Arabidopsis thaliana* AOAT2, *Candida maltosa* alanine aminotransferase, *Clostridium propionicum* alanine aminotransferase, *Pyrococcus furiosus* alanine aminotransferase aat, *Megathyrsus maximus* alanine transaminase, and *Panicum miliaceum* alanine transaminase AlaAT-2. In some embodiments, the one or more nucleic acid molecule encoding an enzyme having alanine transaminase activity comprises an amino acid sequence selected from UniProt ID P0A959, UniProt ID P77434, UniProt ID P24298, UniProt ID Q8TD30, UniProt ID Q9S7N2, UniProt ID Q9LR30, UniProt ID Q9S7E9, UniProt ID Q9P9M8, and UniProt ID P34106. In a further embodiment, the one or more nucleic acid molecule encoding an enzyme having alanine transaminase activity is encoded by a nucleic acid sequence selected from Gene ID 946772, Gene ID 946850, Gene ID 2875, Gene ID 84706, Gene ID 843393, TAIR accession AT1G23310, TAIR accession AT1G70580, GenBank accession AF163769.1 and GenBank accession X69421.1.

Diaminobutyrate Decarboxylase (EC 4.1.1.86)

The present disclosure describes enzymes that can catalyze the following reaction:

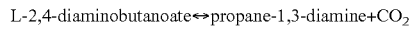

L-2,4-diaminobutanoate ↔ propane-1,3-diamine+$CO_2$

The systematic name of this enzyme class is L-2,4-diaminobutanoate carboxy-lyase (propane-1,3-diamine-forming). Diaminobutyrate decarboxylase may also be known as DABA DC, L-2,4-diaminobutyrate decarboxylase, L-2,4-diaminobutanoate carboxy-lyase.

This enzyme belongs to the family of transferases, specifically those transferring phosphorus-containing groups (phosphotransferases) with an alcohol group as acceptor. This enzyme participates in 3 metabolic pathways: serine/glycine/threonine metabolism, glycerolipid metabolism, and glyoxylate-dicarboxylate metabolism.

In some embodiments, a gene encoding a L-2,4-diaminobutyrate decarboxylase is the rhbB gene of Sinorhizobium meliloti Rm2011. The rhbB gene is homologous to the ddc gene of Acinetobacter baumannii, which are involved in the production of propane-1,3-diamine by that organism. Thus, it is proposed that these genes encode diaminobutyrate-2-oxoglutarate transaminase and L-2,4-diaminobutyrate decarboxylase, respectively.

In some embodiments, the diaminobutyrate decarboxylase is the L-2,4-diaminobutyrate decarboxylase. In some embodiments, the L-2,4-diaminobutyrate decarboxylase is encoded by an amino acid sequence having at least 70% sequence identity, having at least 80% sequence identity, or having at least 90% sequence identity to Sinorhizobium meliloti Rm2011 rhbB. In some embodiments, the L-2,4-diaminobutyrate decarboxylase is Sinorhizobium meliloti Rm2011 rhbB.

In some embodiments, the one or more nucleic acid molecules encoding the L-2,4-diaminobutyrate decarboxylase is rhbB, or homolog thereof. In some embodiments, the one or more nucleic acid molecule encoding L-2,4-diaminobutyrate decarboxylase comprises an amino acid sequence set forth in UniProt ID Q9Z3R2. In a further embodiment, the one or more nucleic acid molecule encoding L-2,4-diaminobutyrate decarboxylase is encoded by a nucleic acid sequence set forth in Gene ID 1236295.

Ornithine Decarboxylase (EC 4.1.1.17)

The present disclosure describes enzymes that can catalyze the following reaction:

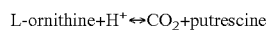

L-ornithine+$H^+$ ↔ $CO_2$+putrescine

The systematic name of this enzyme class is L-ornithine carboxy-lyase (putrescine-forming). Ornithine decarboxylase may also be known as SpeC and L-orinithine carboxy-lyase. E. coli encodes two ornithine decarboxylase enzymes, the biosynthetic (constitutive) SpeC and the degradative (inducible) SpeF. SpeF is activated by the guanosine nucleotides GTP, GDP, pppGpp and ppGpp. SpeF is overproduced from a speF-containing plasmid when cells are grown at pH 5.2, but not at pH 7. Overexpression of RNase III from a plasmid increases expression from the speF promoter, perhaps by processing of the 5' UTR.

When ornithine is available, E. coli is able to synthesize putrescine via two pathways. One pathway yields putrescine directly from ornithine by a reaction catalyzed by ornithine decarboxylase. The other pathway involves two reactions using arginine. In addition, E. coli possesses two forms of ornithine decarboxylase, a biosynthetic (or constitutive) form apparently present in all strains, and a biodegradative (or inducible) form which is present in some strains of E. coli. These two types of ornithine decarboxylases have been characterized in E. coli K-12. The biodegradative ornithine decarboxylase is induced by low pH and by the presence of ornithine in the growth medium. The activity of the biosynthetic ornithine decarboxylases is modulated by a number of positive and negative effectors. The positive effectors include nucleotides, GTP being more effective in activating ornithine decarboxylase, while ppGpp reacts as a negative effector of ornithine decarboxylase. The accumulation of ppGpp leads to the cessation of stable RNA synthesis and appears to be related to the fidelity of protein synthesis.

Ornithine decarboxylase regulation was reported to occur by a protein inhibitor named antizyme that binds to ornithine decarboxylase and non-competitively inhibits its activity. The antizyme is induced by polyamines. The gene encoding E. coli antizyme was cloned and identified as a bifunctional antizyme/transcriptional regulator. However another publication concluded that the E. coli antizyme is not a direct counterpart of mammalian antizyme genes. The product of E. coli gene atoC (see AtoC transcriptional activator; Az protein inhibitor of ODC) was later identified as the bifunctional protein that has both antizyme activity (posttranslational inhibition of polyamine biosynthetic enzymes) and activity as a transcriptional regulator of genes involved in short-chain fatty acid catabolism. Polyamines activated transcription of atoC. AtoC along with sensory histidine kinase AtoS is part of a two-component signal transduction system. Although AtoS-catalyzed phosphorylation of AtoC is essential for transcriptional activation of the atoDAEB operon for catabolism of short chain fatty acids, it is not yet known whether phosphorylation of antizyme plays a role in regulation of ornithine decarboxylase.

In some embodiments, genes encoding an ornithine decarboxylase are the speC and speF genes of Escherichia coli. In some embodiments, the ornithine decarboxylase is the L-ornithine decarboxylase. In some embodiments, the ornithine decarboxylase is encoded by an amino acid sequence having at least 70% sequence identity, having at least 80% sequence identity, or having at least 90% sequence identity to Escherichia coli speC or speF. In some embodiments, the ornithine decarboxylase is Escherichia coli speC or speF.

In some embodiments, the one or more nucleic acid molecules encoding the ornithine decarboxylase is speC, or homolog thereof. In some embodiments, the one or more nucleic acid molecules encoding the ornithine decarboxylase is speF, or homolog thereof. In some embodiments, the one or more nucleic acid molecules encoding ornithine decarboxylase comprise an amino acid sequence selected from UniProt ID P21169 and UniProt ID P24169. In a further embodiment, the one or more nucleic acid molecule encoding ornithine decarboxylase is encoded by a nucleic acid sequence selected from Gene ID 947457 and Gene ID 945297.

2,3-Diaminopropionate Ammonia-Lyase (EC 4.3.1.15)

The present disclosure describes enzymes that can catalyze the following reaction:

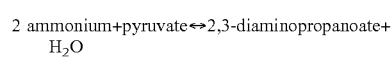

2 ammonium+pyruvate ↔ 2,3-diaminopropanoate+$H_2O$ 2,3-Diaminopropionate ammonia-lyase is not stereospecific and catalyzes the α,β-elimination of both the D and L stereoisomer of 2,3-diaminopropionate. The enzyme also exhibits weak activity toward D-serine, and does not exhibit activity toward L-serine, D-β-Cl-alanine, or L-β-Cl-alanine.

The enzyme is homodimeric and contains a pyridoxal 5′-phosphate prosthetic group, belonging to the fold-type II family of PLP-containing enzymes. Crystal structures of the apo- and holoenzyme and the enzyme in complex with a reaction intermediate and substrate have been solved. Kinetic properties of mutants in active site residues were analyzed, and a reaction mechanism was proposed.

In some embodiments, an enzyme having 2,3-diaminopropionate ammonia-lyase activity is encoded by an amino acid sequence having at least 70% sequence identity, having at least 80% sequence identity, or having at least 90% sequence identity to E. coli 2,3-diaminopropionate ammonia-lyase ygeX. In other embodiments, the enzyme having 2,3-diaminopropionate ammonia-lyase activity is E. coli ygeX. In some embodiments, the one or more nucleic acid molecule encoding an enzyme having 2,3-diaminopropionate ammonia-lyase activity comprises an amino acid sequence set forth in UniProt ID P66899. In further embodiments, the one or more nucleic acid molecule encoding an enzyme having 2,3-diaminopropionate ammonia-lyase activity is encoded by a nucleic acid sequence set forth in Gene ID 947012.

Glyoxylate Shunt

The glyoxylate cycle, a variation of the tricarboxylic acid cycle, is an anabolic pathway occurring in plants, bacteria, protists, and fungi. The glyoxylate cycle centers on the conversion of acetyl-CoA to succinate for the synthesis of carbohydrates. In microorganisms, the glyoxylate cycle allows cells to utilize simple carbon compounds as a carbon source when complex sources such as glucose are not available. The cycle is generally assumed to be absent in animals, with the exception of nematodes at the early stages of embryogenesis. In recent years, however, the detection of malate synthase and isocitrate lyase, key enzymes involved in the glyoxylate cycle, in some animal tissue has raised questions regarding the evolutionary relationship of enzymes in bacteria and animals and suggests that animals encode alternative enzymes of the cycle that differ in function from known malate synthase and isocitrate lyase in non-metazoan species.

The glyoxylate cycle utilizes five of the eight enzymes associated with the tricarboxylic acid cycle: citrate synthase, aconitase, succinate dehydrogenase, fumarase, and malate dehydrogenase. The two cycles differ in that in the glyoxylate cycle, isocitrate is converted into glyoxylate and succinate by isocitrate lyase instead of into α-ketoglutarate. This bypasses the decarboxylation steps that take place in the TCA cycle, allowing simple carbon compounds to be used in the later synthesis of macromolecules, including glucose. Glyoxylate is subsequently combined with acetyl-CoA to produce malate, catalyzed by malate synthase. Malate is also formed in parallel from succinate by the action of succinate dehydrogenase and fumarase.

Fatty acids from lipids are commonly used as an energy source by vertebrates as fatty acids are degraded through beta oxidation into acetate molecules. This acetate, bound to the active thiol group of coenzyme A, enters the citric acid cycle (TCA cycle) where it is fully oxidized to carbon dioxide. This pathway thus allows cells to obtain energy from fat. To utilize acetate from fat for biosynthesis of carbohydrates, the glyoxylate cycle, whose initial reactions are identical to the TCA cycle, is used.

Cell-wall containing organisms, such as plants, fungi, and bacteria, require very large amounts of carbohydrates during growth for the biosynthesis of complex structural polysaccharides, such as cellulose, glucans, and chitin. In these organisms, in the absence of available carbohydrates (for example, in certain microbial environments or during seed germination in plants), the glyoxylate cycle permits the synthesis of glucose from lipids via acetate generated in fatty acid β-oxidation.

The glyoxylate cycle bypasses the steps in the citric acid cycle where carbon is lost in the form of $CO_2$. The two initial steps of the glyoxylate cycle are identical to those in the citric acid cycle: acetate→citrate→isocitrate. In the next step, catalyzed by the first glyoxylate cycle enzyme, isocitrate lyase, isocitrate undergoes cleavage into succinate and glyoxylate (the latter gives the cycle its name). Glyoxylate condenses with acetyl-CoA (a step catalyzed by malate synthase), yielding malate. Both malate and oxaloacetate can be converted into phosphoenolpyruvate, which is the product of phosphoenolpyruvate carboxykinase, the first enzyme in gluconeogenesis. The net result of the glyoxylate cycle is therefore the production of glucose from fatty acids. Succinate generated in the first step can enter into the citric acid cycle to eventually form oxaloacetate.

Biosynthesis of MEG (or Glycolic Acid), or Optionally, MEG (or Glycolic Acid) and One or More Co-Product Using a Recombinant Microorganism As discussed above, in one aspect, the present disclosure provides a recombinant microorganism comprising one or more biochemical pathway that produces monoethylene glycol (MEG) (or glycolic acid) from one or more hexose feedstock via one or more pentose-5-phosphate intermediate. In one embodiment, one or more co-product is co-produced with MEG (or glycolic acid). In another embodiment, the one or more pentose-5-phosphate intermediate is one or more of D-xylulose-5-phosphate, D-ribulose-5-phosphate or D-ribose-5-phosphate.

Therefore, in one embodiment, the application relates to a recombinant microorganism comprising one or more biochemical pathway comprising at least one enzyme having an activity that converts one or more hexose feedstock in a lossless conversion to one or more pentose-5-phosphate intermediate.

In some embodiments, the recombinant microorganism comprises expression of at least one enzyme having transketolase activity. In some embodiments, the enzyme having transketolase activity is encoded by an amino acid sequence having at least 70% sequence identity, at least 80% sequence identity, or at least 90% sequence identity to tktA from E. coli. In other embodiments, the enzyme having transketolase activity is tktA from E. coli. In some embodiments, the enzyme having transketolase activity is encoded by an amino acid sequence having at least 70% sequence identity at least 80% sequence identity, or at least 90% sequence identity to tktB from E. coli. In other embodiments, the enzyme having transketolase activity is tktB from E. coli. In another embodiment, the one or more nucleic acid molecules encoding the enzyme having transketolase activity comprises an amino acid sequence selected from the group consisting of SEQ ID NOs: 148 and 150. In some embodiments, the one or more nucleic acid molecules encoding the enzyme having transketolase activity is tktA, or homolog thereof. In some embodiments, the one or more nucleic acid molecules encoding the enzyme having transketolase activity is tktB, or homolog thereof. In a further embodiment, the one or more nucleic acid molecule encoding the enzyme having transketolase activity is encoded by a nucleic acid sequence selected from the group consisting of SEQ ID NOs: 147 and 149.

In some embodiments, the recombinant microorganism comprises expression of at least one enzyme having transaldolase activity. In some embodiments, the enzyme having transaldolase activity is encoded by an amino acid sequence having at least 70% sequence identity, at least 80% sequence identity, or at least 90% sequence identity to talA or talB from *E. coli*. In some embodiments, the enzyme having transaldolase activity is talA from *E. coli*. In other embodiments, the enzyme having transaldolase activity is talB from *E. coli*. In another embodiment, the one or more nucleic acid molecules encoding the enzyme having transaldolase activity comprises an amino acid sequence selected from the group consisting of SEQ ID NOs: 152 and 154. In a further embodiment, the one or more nucleic acid molecule encoding the enzyme having transaldolase activity is encoded by a nucleic acid sequence selected from the group consisting of SEQ ID NOs: 151 and 153.

In some embodiments, the recombinant microorganism comprises expression of at least one enzyme having ribulose-5-phosphate 3-epimerase activity. In some embodiments, the enzyme having ribulose-5-phosphate 3-epimerase activity is encoded by an amino acid sequence having at least 70% sequence identity, at least 80% sequence identity, or at least 90% sequence identity to rpe from *E. coli*. In other embodiments, the enzyme having ribulose-5-phosphate 3-epimerase activity is rpe from *E. coli*. In another embodiment, the one or more nucleic acid molecules encoding the enzyme having ribulose-5-phosphate 3-epimerase activity comprise an amino acid sequence set forth in SEQ ID NO: 158. In a further embodiment, the one or more nucleic acid molecule encoding the enzyme having ribulose-5-phosphate 3-epimerase activity is encoded by a nucleic acid sequence set forth in SEQ ID NO: 157.

In some embodiments, the recombinant microorganism comprises expression of at least one enzyme having ribose-5-phosphate isomerase activity. In some embodiments, the enzyme having ribose-5-phosphate isomerase activity is encoded by an amino acid sequence having at least 70% sequence identity, at least 80% sequence identity, or at least 90% sequence identity to rpiA or rpiB from *E. coli*. In other embodiments, the enzyme having ribose-5-phosphate isomerase activity is rpiA or rpiB from *E. coli*. In another embodiment, the one or more nucleic acid molecules encoding the rpiA enzyme having ribose-5-phosphate isomerase activity comprise an amino acid sequence set forth in SEQ ID NO: 156. In a further embodiment, the one or more nucleic acid molecule encoding the rpiA enzyme having ribose-5-phosphate isomerase activity is encoded by a nucleic acid sequence set forth in SEQ ID NO: 155. In another embodiment, the one or more nucleic acid molecules encoding the rpiB enzyme having ribose-5-phosphate isomerase activity comprise an amino acid sequence set forth in SEQ ID NO: 253. In a further embodiment, the one or more nucleic acid molecule encoding the rpiB enzyme having ribose-5-phosphate isomerase activity is encoded by a nucleic acid sequence set forth in SEQ ID NO: 254.

In some embodiments, the recombinant microorganism comprises expression of at least one enzyme having a transketolase activity, a transaldolase activity, a ribulose-5-phosphate 3-epimerase activity, and a ribose-5-phosphate isomerase activity. In other embodiments, the recombinant microorganism further comprises a deleted or diminished activity in one or more endogenous enzymes selected from glyceraldehyde 3-phosphate dehydrogenase, phosphoglycerate kinase and phosphoglycerate mutase. In some embodiments, the endogenous glyceraldehyde 3-phosphate dehydrogenase enzyme is gapA, the phosphoglycerate kinase is pgk and the phosphoglycerate mutase is gpmA and/or gpmM.

In some embodiments, the recombinant microorganism comprises expression of at least one enzyme having fructose-6-phosphate phosphoketolase activity. In some embodiments, an enzyme having fructose-6-phosphate phosphoketolase activity is encoded by an amino acid sequence having at least 70% sequence identity, at least 80% sequence identity, or at least 90% sequence identity to an enzyme having fructose-6-phosphate phosphoketolase activity selected from the group consisting of *Bifidobacterium dentium* BDP_1006, *Bifidobacterium lactis* xfp, *Lactobacillus paraplantarum* xpkA and *Bifidobacterium breve* xfp. In a preferred embodiment, an enzyme having fructose-6-phosphate phosphoketolase activity is selected from the group consisting of *Bifidobacterium dentium* BDP_1006, *Bifidobacterium lactis* xfp, *Lactobacillus paraplantarum* xpkA and *Bifidobacterium breve* xfp. In another embodiment, the one or more nucleic acid molecules encoding the enzyme having fructose-6-phosphate phosphoketolase activity comprise an amino acid sequence selected from the group consisting of SEQ ID NOs: 212, 214, 216 and 218. In a further embodiment, the one or more nucleic acid molecule encoding the enzyme having fructose-6-phosphate phosphoketolase activity is encoded by a nucleic acid sequence selected from the group consisting of SEQ ID NOs: 211, 213, 215 and 217.

In some embodiments, the recombinant microorganism comprises expression of at least one enzyme having phosphate acetyltransferase activity. In some embodiments, an enzyme having phosphate acetyltransferase activity is encoded by an amino acid sequence having at least 70% sequence identity, at least 80% sequence identity, or at least 90% sequence identity to an enzyme having phosphate acetyltransferase activity selected from *E. coli* pta and *Clostridium acetobutylicum* pta. In a preferred embodiment, an enzyme having phosphate acetyltransferase activity is selected from *E. coli* pta and *Clostridium acetobutylicum* pta. In another embodiment, the one or more nucleic acid molecules encoding the enzyme having phosphate acetyltransferase activity comprise an amino acid sequence selected from SEQ ID NOs: 220 and 222. In a further embodiment, the one or more nucleic acid molecule encoding the enzyme having phosphate acetyltransferase activity is encoded by a nucleic acid sequence selected from SEQ ID NOs: 219 and 221.

In some embodiments, the recombinant microorganism comprises expression of at least one enzyme having a fructose-6-phosphate phosphoketolase activity, a phosphate acetyltransferase activity, a transketolase activity, a transaldolase activity, a ribulose-5-phosphate 3-epimerase activity, and a ribose-5-phosphate isomerase activity. In other embodiments, the recombinant microorganism further comprises a deleted or diminished activity in an endogenous 6-phosphofructokinase enzyme. In some embodiments, the endogenous 6-phosphofructokinase enzyme is pfkA and/or pfkB.

In another embodiment, the one or more pentose-5-phosphate intermediate produced in the lossless conversion of one or more hexose feedstock can be connected with any one of the known C2 MEG or glycolic acid production pathways by conversion of the one or more pentose-5-phosphate intermediate to one or more pentose and/or pentose-1-phosphate intermediate. In some embodiments, the recombinant microorganism comprises expression of at least one enzyme having a pentose phosphatase activity, an arabitol phosphate dehydrogenase activity, and/or a phosphopentomutase activity.

In some embodiments, the recombinant microorganism comprises expression of at least one enzyme having pentose phosphatase activity. In other embodiments, the at least one enzyme having pentose phosphatase activity is selected from one or more of an enzyme having D-pentose-5-phosphatase activity, an enzyme having D-xylulose-5-phosphatase activity, an enzyme having D-ribose-5-phosphatase activity, and an enzyme having D-ribulose-5-phosphatase activity. In some embodiments, the pentose phosphatase is encoded by an amino acid sequence having at least 70% sequence identity, at least 80% sequence identity, or at least 90% sequence identity to a D-pentose-5-phosphatase selected from the group consisting of *E. coli* phoA, *E. coli* yfbT and *E. coli* yidA. In some embodiments, the enzyme having D-xylulose-5-phosphatase activity is encoded by an amino acid sequence having at least 70% sequence identity, at least 80% sequence identity, or at least 90% sequence identity to *Bacillus subtilis* araL. In some embodiments, the enzyme having D-ribose-5-phosphatase activity is encoded by an amino acid sequence having at least 70% sequence identity, at least 80% sequence identity, or at least 90% sequence identity to an enzyme having D-ribose-5-phosphatase activity selected from the group consisting of *Arabidopsis thaliana* SGPP, *Pseudomonas fluorescens* PFLU 2693, and *E. coli* ybiV. In some embodiments, the enzyme having D-ribulose-5-phosphatase activity is encoded by an amino acid sequence having at least 70% sequence identity, at least 80% sequence identity, or at least 90% sequence identity to *Plasmodium falciparum* PF10_0325. In some embodiments, the one or more nucleic acid molecules encoding the enzyme having D-pentose-5-phosphatase activity is selected from the group consisting of SEQ ID NOs: 159, 161, 163, 165, 167, 169, 171 and 173. In another embodiment, the one or more nucleic acid molecules encoding the enzyme having D-pentose-5-phosphatase activity comprise an amino acid sequence selected from the group consisting of SEQ ID NOs: 160, 162, 164, 166, 168, 170, 172 and 174.

In some embodiments, the recombinant microorganism comprises expression of at least one enzyme having arabitol phosphate dehydrogenase activity. In some embodiments, the enzyme having arabitol phosphate dehydrogenase activity is selected from one or more of an enzyme having D-arabitol 1-phosphate 4-dehydrogenase activity, an enzyme having D-arabitol 5-phosphate 2-dehydrogenase activity, an enzyme having D-arabitol 1-phosphate 2-dehydrogenase activity and an enzyme having D-arabitol 5-phosphate 4-dehydrogenase activity.

In some embodiments, an enzyme having D-arabitol 1-phosphate 4-dehydrogenase activity is encoded by an amino acid sequence having at least 70% sequence identity, at least 80% sequence identity, or at least 90% sequence identity to APDH from *Enterococcus avium*. In a preferred embodiment, an enzyme having D-arabitol 1-phosphate 4-dehydrogenase activity is APDH from *Enterococcus avium*. In some embodiments, the one or more nucleic acid molecules encoding an enzyme having D-arabitol 1-phosphate 4-dehydrogenase activity is set forth in SEQ ID NO: 175. In another embodiment, the one or more nucleic acid molecules encoding an enzyme having D-arabitol 1-phosphate 4-dehydrogenase activity comprise an amino acid sequence set forth in SEQ ID NO: 176.

In some embodiments, an enzyme having D-arabitol 5-phosphate 2-dehydrogenase activity is encoded by an amino acid sequence having at least 70% sequence identity, at least 80% sequence identity, or at least 90% sequence identity to APDH from *Enterococcus avium*. In a preferred embodiment, an enzyme having D-arabitol 5-phosphate 2-dehydrogenase activity is APDH from *Enterococcus avium*. In some embodiments, the one or more nucleic acid molecules encoding an enzyme having D-arabitol 5-phosphate 2-dehydrogenase activity is set forth in SEQ ID NO: 175. In another embodiment, the one or more nucleic acid molecules encoding an enzyme having D-arabitol 5-phosphate 2-dehydrogenase activity comprise an amino acid sequence set forth in SEQ ID NO: 176.

In some embodiments, an enzyme having D-arabitol 1-phosphate 2-dehydrogenase activity is encoded by an amino acid sequence having at least 70% sequence identity, at least 80% sequence identity, or at least 90% sequence identity to an enzyme having D-arabitol 1-phosphate 2-dehydrogenase activity selected from the group consisting of *Candida albicans* ARD1, *Candida tropicalis* ARD1, *Scheffersomyces stipitis* ARDH, *Bacillus subtilis* egsA (araM), *Aeropyrum pernix* egsA, *E. coli* gpsA and *Saccharomyces cerevisiae* GPD1. In a preferred embodiment, an enzyme having D-arabitol 1-phosphate 2-dehydrogenase activity is selected from the group consisting of *Candida albicans* ARD1, *Candida tropicalis* ARD1, *Scheffersomyces stipitis* ARDH, *Bacillus subtilis* egsA (araM), *Aeropyrum pernix* egsA, *E. coli* gpsA and *Saccharomyces cerevisiae* GPD1. In some embodiments, the one or more nucleic acid molecules encoding an enzyme having D-arabitol 1-phosphate 2-dehydrogenase activity is selected from the group consisting of SEQ ID NOs: 177, 179, 181, 189, 191, 193 and 195. In another embodiment, the one or more nucleic acid molecules encoding an enzyme having D-arabitol 1-phosphate 2-dehydrogenase activity comprise an amino acid sequence selected from the group consisting of SEQ ID NOs: 178, 180, 182, 190, 192, 194 and 196.

In some embodiments, an enzyme having D-arabitol 5-phosphate 4-dehydrogenase activity is encoded by an amino acid sequence having at least 70% sequence identity, at least 80% sequence identity, or at least 90% sequence identity to an enzyme having D-arabitol 5-phosphate 4-dehydrogenase activity selected from the group consisting of *Pseudomonas fluorescens* mtlD, *Klebsiella pneumoniae* dalD, *Ralstonia solanacearum* dalD, *Bacillus subtilis* egsA (araM), *Aeropyrum pernix* egsA, *E. coli* gpsA and *Saccharomyces cerevisiae* GPD1. In a preferred embodiment, an enzyme having D-arabitol 5-phosphate 4-dehydrogenase activity is selected from the group consisting of *Pseudomonas fluorescens* mtlD, *Klebsiella pneumoniae* dalD, *Ralstonia solanacearum* dalD, *Bacillus subtilis* egsA (araM), *Aeropyrum pernix* egsA, *E. coli* gpsA and *Saccharomyces cerevisiae* GPD1. In some embodiments, the one or more nucleic acid molecules encoding an enzyme having D-arabitol 5-phosphate 4-dehydrogenase activity is selected from the group consisting of SEQ ID NOs: 183, 185, 187, 189, 191, 193 and 195. In another embodiment, the one or more nucleic acid molecules encoding an enzyme having D-arabitol 5-phosphate 4-dehydrogenase activity comprise an amino acid sequence selected from the group consisting of SEQ ID NOs: 184, 186, 188, 190, 192, 194 and 196.

In some embodiments, the recombinant microorganism comprises expression of at least one enzyme having phosphopentomutase activity. In some embodiments, an enzyme having phosphopentomutase activity is encoded by an amino acid sequence having at least 70% sequence identity, at least 80% sequence identity, or at least 90% sequence identity to an enzyme having phosphopentomutase activity selected from the group consisting of *E. coli* deoB, *E. coli* pgm, *Bacillus subtilis* pgcA, *Lactococcus lactis* pgmB, *E. coli* ycjU, *Pseudomonas aeruginosa* algC, and *E. coli* cpsG. In a preferred embodiment, an enzyme having phosphopentomutase activity is selected from the group consisting of *E. coli* deoB, *E. coli* pgm, *Bacillus subtilis* pgcA, *Lactococcus lactis* pgmB, *E. coli* ycjU, *Pseudomonas aeruginosa* algC, and *E. coli* cpsG. In some embodiments, the one or more nucleic acid molecules encoding an enzyme having phosphopentomutase activity is selected from the group consisting of SEQ ID NOs: 197, 199, 201, 203, 205, 207 and 209. In another embodiment, the one or more nucleic acid molecules encoding an enzyme having phosphopentomutase activity comprise an amino acid sequence selected from the group consisting of SEQ ID NOs: 198, 200, 202, 204, 206, 208 and 210.

In some embodiments of any of the recombinant microorganisms described above, the recombinant microorganism further comprises a diminished activity in one or more endogenous enzymes selected from glucose 6-phosphate-1-dehydrogenase, 6-phosphogluconolactonase, and 6-phosphogluconate dehydrogenase. In further embodiments, the glucose 6-phosphate-1-dehydrogenase is zwf, the 6-phosphogluconolactonase is pgl, and the 6-phosphogluconate dehydrogenase is gnd.

In some embodiments, the application provides for a recombinant microorganism that co-produces MEG (or glycolic acid) and one or more co-product selected from acetone, isopropanol, propene, isobutene and one or more serine pathway compounds. In some preferred embodiments, the one or more serine pathway compounds is selected from serine, glycine, monoethanolamine (MEA) and ethylenediamine (EDA).

In some embodiments, the one or more hexose feedstock is selected from glucose or oligomers of glucose thereof. In other embodiments, the oligomers of glucose are selected from fructose, sucrose, starch, cellobiose, maltose, lactose and cellulose.

In some embodiments, the expression of an enzyme having transketolase activity or an enzyme having fructose-6-phosphate phosphoketolase activity in the recombinant microorganism enables a lossless conversion of one or more hexose feedstock to one or more pentose-5-phosphate intermediate.

In some embodiments, the recombinant microorganism produces MEG or glycolic acid (GA) through the conversion of glycolaldehyde in a C2 pathway and through the conversion of dihydroxyacetone phosphate (DHAP) or pyruvate in a C3 pathway. In other embodiments, the glycolaldehyde is oxidized to glycolic acid by a glycolaldehyde dehydrogenase.

In some embodiments, the at least one enzyme for the production of MEG or GA through the conversion of DHAP or pyruvate in a C3 pathway are selected from at least one enzyme having an activity selected from a 3-phosphoglycerate dehydrogenase activity, a phosphoserine aminotransferase activity, a 3-phosphohydroxypyruvate phosphatase activity, a phosphoserine phosphatase activity, a serine transaminase activity, a hydroxypyruvate decarboxylase activity, a 3-phosphohydroxypyruvate reductase activity, a glycolaldehyde reductase activity, a glycolaldehyde dehydrogenase activity, a serine oxidoreductase (deaminating) or serine-pyruvate aminotransferase activity, a serine decarboxylase activity, an ethanolamine aminotransferase or ethanolamine oxidoreductase (deaminating) activity, a glycerate decarboxylase activity, a hydroxypyruvate reductase activity, a 3-phosphoglycerate phosphatase activity, a 2-phosphoglycerate phosphatase activity, a glycerate 3-kinase activity, and a glycerate 2-kinase activity.

In some embodiments, the recombinant microorganism produces MEG or glycolic acid (GA) through the conversion of glycolaldehyde in a C2 pathway and produces one or more co-product through the conversion of dihydroxyacetone phosphate (DHAP) or pyruvate in a C3 pathway. In other embodiments, the one or more co-product is selected from acetone, isopropanol, propene, isobutene and one or more serine pathway compounds. In some preferred embodiments, the one or more serine pathway compounds is selected from serine, glycine, monoethanolamine (MEA) and ethylenediamine (EDA).

In some embodiments, the at least one enzyme for the production of one or more co-product through the conversion of DHAP or pyruvate in a C3 pathway are selected from at least one enzyme having an activity selected from a thiolase or acetyl coenzyme A acetyltransferase activity, an acetyl-CoA:acetoacetate transferase or acetate:acetoacetyl-CoA hydrolase activity, and an acetoacetate decarboxylase activity, and the one or more co-product comprises acetone.

In some embodiments, the at least one enzyme for the production of one or more co-product through the conversion of DHAP or pyruvate in a C3 pathway are selected from at least one enzyme having an activity selected from a thiolase or acetyl coenzyme A acetyltransferase activity, an acetyl-CoA:acetoacetate transferase or acetate:acetoacetyl-CoA hydrolase activity, an acetoacetate decarboxylase activity, and a secondary alcohol dehydrogenase activity, and the one or more co-product comprises isopropanol.

In some embodiments, the at least one enzyme for the production of one or more co-product through the conversion of DHAP or pyruvate in a C3 pathway are selected from at least one enzyme having an activity selected from a thiolase or acetyl coenzyme A acetyltransferase activity, an acetyl-CoA:acetoacetate transferase or acetate:acetoacetyl-CoA hydrolase activity, an acetoacetate decarboxylase activity, a secondary alcohol dehydrogenase activity, and a dehydratase activity, and the one or more co-product comprises propene.

In some embodiments, the at least one enzyme for the production of one or more co-product through the conversion of DHAP or pyruvate in a C3 pathway are selected from at least one enzyme having an activity selected from a thiolase or acetyl coenzyme A acetyltransferase activity, an acetyl-CoA:acetoacetate transferase or acetate:acetoacetyl-CoA hydrolase activity, an acetoacetate decarboxylase activity, a 3-hydroxyisovalerate (3HIV) synthase activity, a hydroxymethylglutaryl-CoA synthase activity, a methylglutaconyl-CoA hydratase activity, a methylcrotonyl-CoA carboxylase activity, a methylcrotonyl-CoA hydratase activity, a 3-hydroxyisovaleryl-CoA thioesterase activity, a 3HIV kinase activity, a 3HIV-3-phosphate decarboxylase activity, and a 3HIV decarboxylase activity, and the one or more co-product comprises isobutene.

In some embodiments, the at least one enzyme for the production of one or more co-product through the conversion of DHAP or pyruvate in a C3 pathway are selected from at least one enzyme having an activity selected from a 3-phosphoglycerate dehydrogenase activity, a phosphoserine aminotransferase activity, a 3-phosphohydroxypyruvate phosphatase activity, a phosphoserine phosphatase activity, a serine oxidoreductase (deaminating) or serine-pyruvate aminotransferase activity, a hydroxypyruvate reductase activity, a 3-phosphoglycerate phosphatase activity, a 2-phosphoglycerate phosphatase activity, a glycerate 3-kinase activity, and a glycerate 2-kinase activity, and wherein the one or more co-product comprises L-serine.

In some embodiments, the at least one enzyme for the production of one or more co-product through the conversion of DHAP or pyruvate in a C3 pathway are selected from at least one enzyme having an activity selected from a serine hydroxymethyltransferase activity, a transferase activity, a formaldehyde dehydrogenase activity, a formate dehydrogenase activity, an activity associated with glycine cleavage system, a 3-phosphoglycerate dehydrogenase activity, a phosphoserine aminotransferase activity, a 3-phosphohydroxypyruvate phosphatase activity, a phosphoserine phosphatase activity, a serine transaminase activity, a hydroxypyruvate decarboxylase activity, a serine oxidoreductase (deaminating) activity, a serine decarboxylase activity, an ethanolamine aminotransferase or ethanolamine oxidoreductase (deaminating) activity, a hydroxypyruvate reductase activity, a 3-phosphoglycerate phosphatase activity, a 2-phosphoglycerate phosphatase activity, a glycerate 3-kinase activity, a glycerate 2-kinase activity, a glycolaldehyde dehydrogenase activity, a glycolate dehydrogenase activity, an alanine-glyoxylate aminotransferase activity, an alanine transaminase activity, an NAD(P)H dependent glutamate dehydrogenase activity, and wherein the one or more co-product comprises glycine. In another embodiment, the activity associated with glycine cleavage system comprise an enzyme or protein selected from a glycine decarboxylase (P protein), an aminomethyltransferase (T protein), a dihydrolipoamide dehydrogenase (L protein), and an H protein.

In some embodiments, the at least one enzyme for the production of one or more co-product through the conversion of DHAP or pyruvate in a C3 pathway are selected from at least one enzyme having an activity selected from a 3-phosphoglycerate dehydrogenase activity, a phosphoserine aminotransferase activity, a 3-phosphohydroxypyruvate phosphatase activity, a phosphoserine phosphatase activity, a transaminase activity, a hydroxypyruvate decarboxylase activity, a serine oxidoreductase (deaminating) or serine-pyruvate aminotransferase activity, a serine decarboxylase activity, a hydroxypyruvate reductase activity, a 3-phosphoglycerate phosphatase activity, a 2-phosphoglycerate phosphatase activity, a glycerate 3-kinase activity, a glycerate 2-kinase activity, an acetaldehyde dehydrogenase activity, and an ethanolamine ammonia lyase activity, and the one or more co-product comprises monoethanolamine (MEA).

In some embodiments, the at least one enzyme for the production of one or more co-product through the conversion of DHAP or pyruvate in a C3 pathway are selected from at least one enzyme having an activity selected from a serine dehydrogenase activity, a 2-aminomalonate semialdehyde decarboxylase activity, an aminoacetaldehyde transaminase activity, a 2-aminomalonate semialdehyde transaminase activity, a 2,3-diaminopropanoate decarboxylase activity, a serine decarboxylase activity, an ethanolamine dehydrogenase activity, a serine hydroxymethyltransferase activity, an aldehyde oxidase activity, an N-acetyl transferase or O-acetyl transferase activity, an N-acetylserine dehydrogenase activity, a transaminase activity, a deacetylase activity, a serine aminase activity, and a 2,3-diaminopropanoate ammonia lyase activity, and the one or more co-product comprises ethylenediamine (EDA).

In some embodiments, the at least one enzyme for the production of MEG or GA from glycolaldehyde in a C2 pathway are selected from at least one enzyme having an activity selected from a D-tagatose 3-epimerase activity, a D-ribulokinase activity, a D-ribulose-1-phosphate aldolase activity, a D-xylulose 1-kinase activity, a D-xylulose-1-phosphate aldolase activity, a xylose reductase or aldose reductase activity, a xylitol dehydrogenase activity, a xylose isomerase activity, a xylose dehydrogenase activity, a xylonolactonase activity, a xylonate dehydrogenase activity, a 2-keto-3-deoxy-D-pentonate aldolase activity, a glycolaldehyde reductase activity and a glycolaldehyde dehydrogenase activity.

In some embodiments of any of the recombinant microorganisms described above, the recombinant microorganism further comprises one or more modifications to diminish or delete activity in a glycolaldehyde dehydrogenase, a lactate dehydrogenase, a xylose isomerase, a xylulose kinase or combination thereof.

In one embodiment, at least a portion of the excess NADH produced in the C3 pathway is used as a source of reducing equivalents in the C2 pathway. In another embodiment, at least a portion of the excess NADH produced in the C3 pathway is used to produce ATP.

In one embodiment, excess biomass formation is minimized and production of MEG (or glycolic acid) or MEG (or glycolic acid) and one or more co-products is maximized.

Hexose to Pentose-5-Phosphate Intermediate

In the present disclosure, glucose flux is funneled into the pentose phosphate pathway instead of the glycolysis pathway by using a non-oxidative entry into the pentose phosphate pathway.

[A] Therefore, in one embodiment, the application relates to a recombinant microorganism capable of producing one or more pentose-5-phosphate intermediate from one or more hexose feedstock, wherein the recombinant microorganism expresses one or more of the following from (a) to (d):
  (a) at least one endogenous or exogenous nucleic acid molecule encoding an enzyme having transketolase activity that catalyzes a reversible conversion of fructose-6-phosphate and glyceraldehyde-3-phosphate to erythrose-4-phosphate and D-xylulose-5-phosphate, respectively, and/or that catalyzes a reversible conversion of glyceraldehyde-3-phosphate from (b) and seduheptulose-7-phosphate from (b) to D-ribose-5-phosphate and D-xylulose-5-phosphate, respectively;
  (b) at least one endogenous or exogenous nucleic acid molecule encoding an enzyme having transaldolase activity that catalyzes a reversible conversion of fructose-6-phosphate and erythrose-4-phosphate from (a) to glyceraldehyde-3-phosphate and seduheptulose-7-phosphate, respectively;
  (c) at least one endogenous or exogenous nucleic acid molecule encoding an enzyme having ribose-5-phosphate isomerase activity that catalyzes an interconversion of D-ribose-5-phosphate from (a) and D-ribulose-5-phosphate;
  (d) at least one endogenous or exogenous nucleic acid molecule encoding an enzyme having ribulose-5-phosphate 3-epimerase activity that catalyzes an interconversion of D-xylulose-5-phosphate from (a) and D-ribulose-5-phosphate from (c);
  wherein the recombinant microorganism optionally further comprises a deletion, insertion, or loss of function mutation in a gene encoding a glyceraldehyde 3-phosphate dehydrogenase;
  wherein the one or more hexose feedstock is converted to fructose-6-phosphate and glyceraldehyde-3-phosphate through an endogenous glycolysis pathway in the recombinant microorganism,
  and wherein the one or more pentose-5-phosphate intermediate produced is one or more of D-ribose-5-phosphate, D-xylulose-5-phosphate or D-ribulose-5-phosphate.

[B] In another embodiment, the application relates to a recombinant microorganism capable of producing one or more pentose-5-phosphate intermediate from one or more hexose feedstock, wherein the recombinant microorganism expresses one or more of the following from (a) to (f):

(a) at least one endogenous or exogenous nucleic acid molecule encoding an enzyme having fructose-6-phosphate phosphoketolase activity that catalyzes a reversible conversion of fructose-6-phosphate to erythrose-4-phosphate and acetyl-phosphate;

(b) at least one endogenous or exogenous nucleic acid molecule encoding an enzyme having phosphate acetyltransferase activity that catalyzes a reversible conversion of acetyl-phosphate from (a) to acetyl-CoA;

(c) at least one endogenous or exogenous nucleic acid molecule encoding an enzyme having transaldolase activity that catalyzes a reversible conversion of fructose-6-phosphate and erythrose-4-phosphate from (a) to glyceraldehyde-3-phosphate and seduheptulose-7-phosphate, respectively;

(d) at least one endogenous or exogenous nucleic acid molecule encoding an enzyme having transketolase activity that catalyzes a reversible conversion of glyceraldehyde-3-phosphate from (c) and seduheptulose-7-phosphate from (c) to D-ribose-5-phosphate and D-xylulose-5-phosphate, respectively;

(e) at least one endogenous or exogenous nucleic acid molecule encoding an enzyme having ribose-5-phosphate isomerase activity that catalyzes an interconversion of D-ribose-5-phosphate from (d) and D-ribulose-5-phosphate;

(f) at least one endogenous or exogenous nucleic acid molecule encoding an enzyme having ribulose-5-phosphate 3-epimerase activity that catalyzes an interconversion of D-xylulose-5-phosphate from (d) and D-ribulose-5-phosphate from (e);

wherein the recombinant microorganism optionally further comprises a deletion, insertion, or loss of function mutation in a gene encoding a 6-phosphofructokinase;

wherein the one or more hexose feedstock is converted to fructose-6-phosphate through an endogenous glycolysis pathway in the recombinant microorganism, wherein the acetyl-CoA produced in step (b) can be used to produce one or more co-products selected from acetone, isopropanol, propene, isobutene, and serine pathway compounds;

and wherein the one or more pentose-5-phosphate intermediate produced is one or more of D-ribose-5-phosphate, D-xylulose-5-phosphate or D-ribulose-5-phosphate.

In some embodiments, the oxidative branch of the pentose phosphate pathway is deleted or inactivated to optimize flux towards the non-oxidative entry into the pentose phosphate pathway.

[C] Therefore, in one embodiment, the recombinant microorganism of embodiment [A] or embodiment [B] optionally further comprises one or more modifications selected from the group consisting of:

(i) a deletion, insertion, or loss of function mutation in a gene encoding a glucose 6-phosphate-1-dehydrogenase that catalyzes the conversion of glucose-6-phosphate to 6-phospho-D-glucono-1,5-lactone;

(ii) a deletion, insertion, or loss of function mutation in a gene encoding a 6-phosphogluconolactonase that catalyzes the conversion of 6-phospho-D-glucono-1,5-lactone to gluconate-6-phosphate; and (iii) a deletion, insertion, or loss of function mutation in a gene encoding a 6-phosphogluconate dehydrogenase that catalyzes the conversion of gluconate-6-phosphate to D-ribulose-5-phosphate.

In some embodiments, the enzyme having transketolase activity is encoded by an amino acid sequence having at least 70% sequence identity, having at least 80% sequence identity, or having at least 90% sequence identity to *E. coli* tktA. In other embodiments, the transketolase is encoded by an amino acid sequence having at least 70% sequence identity, having at least 80% sequence identity, or having at least 90% sequence identity to *E. coli* tktB. In some embodiments, the transketolase is *E. coli* tktA. In other embodiments, the transketolase is *E. coli* tktB.

In some embodiments, the one or more nucleic acid molecules encoding the enzyme having transketolase activity is tktA, or homolog thereof. In some embodiments, the one or more nucleic acid molecules encoding the enzyme having transketolase activity is tktB, or homolog thereof. In another embodiment, the one or more nucleic acid molecules encoding the enzyme having transketolase activity comprises an amino acid sequence selected from the group consisting of SEQ ID NOs: 148 and 150. In a further embodiment, the one or more nucleic acid molecule encoding the enzyme having transketolase activity is encoded by a nucleic acid sequence selected from the group consisting of SEQ ID NOs: 147 and 149.

In some embodiments, the enzyme having transaldolase activity is encoded by an amino acid sequence having at least 70% sequence identity, at least 80% sequence identity, or at least 90% sequence identity to talA or talB from *E. coli*. In some embodiments, the enzyme having transaldolase activity is talA from *E. coli*. In other embodiments, the enzyme having transaldolase activity is talB from *E. coli*. In another embodiment, the one or more nucleic acid molecules encoding the enzyme having transaldolase activity comprises an amino acid sequence selected from the group consisting of SEQ ID NOs: 152 and 154. In a further embodiment, the one or more nucleic acid molecule encoding the enzyme having transaldolase activity is encoded by a nucleic acid sequence selected from the group consisting of SEQ ID NOs: 151 and 153.

In one embodiment, the enzyme having ribose-5-phosphate isomerase activity is encoded by an amino acid sequence having at least 70% sequence identity, having at least 80% sequence identity, or having at least 90% sequence identity to *E. coli* rpiA or rpiB. In some embodiments, the enzyme having ribose-5-phosphate isomerase activity is *E. coli* rpiA or rpiB.

In some embodiments, the one or more nucleic acid molecules encoding the enzyme having ribose-5-phosphate isomerase activity is rpiA, or homolog thereof. In another embodiment, the one or more nucleic acid molecules encoding an enzyme having ribose-5-phosphate isomerase activity comprise an amino acid sequence set forth in SEQ ID NO: 156. In a further embodiment, the one or more nucleic acid molecule encoding an enzyme having ribose-5-phosphate isomerase activity is encoded by a nucleic acid sequence set forth in SEQ ID NO: 155.

In one embodiment, the enzyme having ribulose-5-phosphate 3-epimerase activity is encoded by an amino acid sequence having at least 70% sequence identity, having at least 80% sequence identity, or having at least 90% sequence identity to *E. coli* rpe. In some embodiments, the enzyme having ribulose-5-phosphate 3-epimerase activity is *E. coli* rpe.

In some embodiments, the one or more nucleic acid molecules encoding the enzyme having ribulose-5-phosphate 3-epimerase activity is rpe, or homolog thereof. In another embodiment, the one or more nucleic acid molecules encoding the enzyme having ribulose-5-phosphate 3-epimerase activity comprise an amino acid sequence set forth in SEQ ID NO: 158. In a further embodiment, the one or more nucleic acid molecule encoding the enzyme having ribulose-5-phosphate 3-epimerase activity is encoded by a nucleic acid sequence set forth in SEQ ID NO: 157.

In one embodiment, the enzyme having fructose-6-phosphate phosphoketolase activity is encoded by an amino acid sequence having at least 70% sequence identity, at least 80% sequence identity, or at least 90% sequence identity to an enzyme having fructose-6-phosphate phosphoketolase activity selected from the group consisting of *Bifidobacterium dentium* BDP_1006, *Bifidobacterium lactis* xfp, *Lactobacillus paraplantarum* xpkA and *Bifidobacterium breve* xfp. In other embodiments, the enzyme having fructose-6-phosphate phosphoketolase activity is selected from the group consisting of *Bifidobacterium dentium* BDP_1006, *Bifidobacterium lactis* xfp, *Lactobacillus paraplantarum* xpkA and *Bifidobacterium breve* xfp.

In some embodiments, the one or more nucleic acid molecules encoding the enzyme having fructose-6-phosphate phosphoketolase activity is selected from BDP_1006, xfp, xpkA, or homolog thereof. In another embodiment, the one or more nucleic acid molecules encoding the enzyme having fructose-6-phosphate phosphoketolase activity comprise an amino acid sequence selected from the group consisting of SEQ ID NOs: 212, 214, 216 and 218. In a further embodiment, the one or more nucleic acid molecule encoding the enzyme having fructose-6-phosphate phosphoketolase activity is encoded by a nucleic acid sequence selected from the group consisting of SEQ ID NOs: 211, 213, 215 and 217.

In one embodiment, the enzyme having phosphate acetyltransferase activity is encoded by an amino acid sequence having at least 70% sequence identity, at least 80% sequence identity, or at least 90% sequence identity to an enzyme having phosphate acetyltransferase activity selected from *E. coli* pta and *Clostridium acetobutylicum* pta. In other embodiments, the enzyme having phosphate acetyltransferase activity is selected from *E. coli* pta and *Clostridium acetobutylicum* pta.

In some embodiments, the one or more nucleic acid molecules encoding the enzyme having phosphate acetyltransferase activity is pta, or homolog thereof. In another embodiment, the one or more nucleic acid molecules encoding the enzyme having phosphate acetyltransferase activity comprise an amino acid sequence selected from SEQ ID NOs: 220 and 222. In a further embodiment, the one or more nucleic acid molecule encoding the enzyme having phosphate acetyltransferase activity is encoded by a nucleic acid sequence selected from SEQ ID NOs: 219 and 221.

Connecting Pentose Phosphate Pathway and MEG (or Glycolic Acid) Production Pathways In another aspect, a pentose-5-phosphate intermediate produced in embodiment [A] or embodiment [B] (and optionally comprising embodiment [C]) can be connected with any one of the known MEG or glycolic acid production pathways by pentose phosphatases.

[D] Therefore, in one embodiment, the application relates to a recombinant microorganism capable of producing D-xylulose from D-xylulose-5-phosphate, wherein the recombinant microorganism expresses one or more enzyme having pentose-5-phosphatase activity, wherein the D-xylulose-5-phosphate is produced by non-oxidative branch of pentose phosphate pathway, and wherein the D-xylulose can be used to produce MEG (or glycolic acid) and optionally, one or more co-product.

In one embodiment, the enzyme having pentose-5-phosphatase activity is encoded by an amino acid sequence having at least 70% sequence identity, at least 80% sequence identity, or at least 90% sequence identity to an enzyme having pentose-5-phosphatase activity selected from the group consisting of *E. coli* phoA, *E. coli* yfbT and *E. coli* yidA. In further embodiments, the enzyme having pentose-5-phosphatase activity is selected from *E. coli* phoA, *E. coli* yfbT and *E. coli* yidA.

In some embodiments, the one or more nucleic acid molecules encoding the enzyme having pentose-5-phosphatase activity is phoA, yfbT, yidA or homolog thereof. In another embodiment, the one or more nucleic acid molecules encoding the enzyme having pentose-5-phosphatase activity comprises an amino acid sequence selected from the group consisting of SEQ ID NOs: 160, 168 and 172. In a further embodiment, the one or more nucleic acid molecules encoding the enzyme having pentose-5-phosphatase activity is encoded by a nucleic acid sequence selected from the group consisting of SEQ ID NOs: 159, 167 and 171.

In another embodiment, the pentose-5-phosphatase is a D-xylulose-5-phosphatase. In another embodiment, the D-xylulose-5-phosphatase is encoded by an amino acid sequence having at least 70% sequence identity, at least 80% sequence identity, or at least 90% sequence identity to *Bacillus subtilis* araL. In further embodiments, the D-xylulose-5-phosphatase is *Bacillus subtilis* araL.

In some embodiments, the one or more nucleic acid molecules encoding the enzyme having D-xylulose-5-phosphatase activity is araL, or homolog thereof. In another embodiment, the one or more nucleic acid molecules encoding the enzyme having D-xylulose-5-phosphatase activity comprises an amino acid sequence set forth in SEQ ID NO: 164. In a further embodiment, the one or more nucleic acid molecules encoding the enzyme having D-xylulose-5-phosphatase activity is encoded by a nucleic acid sequence set forth in SEQ ID NO: 163.

[E] In one embodiment, the application relates to a recombinant microorganism capable of producing D-ribulose from D-ribulose-5-phosphate or from D-ribose-5-phosphate, wherein the recombinant microorganism expresses one or more of the following from (a) to (c):

(a) at least one endogenous or exogenous nucleic acid molecule encoding an enzyme having D-ribulose-5-phosphatase activity and/or an enzyme having pentose-5-phosphatase activity that catalyzes a reversible conversion of D-ribulose-5-phosphate to D-ribulose;

(b) at least one endogenous or exogenous nucleic acid molecule encoding an enzyme having D-ribose-5-phosphatase activity and/or an enzyme having pentose-5-phosphatase activity that catalyzes a reversible conversion of D-ribose-5-phosphate to D-ribose;

(c) at least one endogenous or exogenous nucleic acid molecule encoding an enzyme having D-ribose isomerase activity that catalyzes a reversible conversion of D-ribose from (b) to D-ribulose;

wherein the D-ribulose-5-phosphate and/or D-ribose-5-phosphate is produced by non-oxidative branch of pentose phosphate pathway, and wherein the D-ribulose can be used to produce MEG (or glycolic acid) and optionally, one or more co-product.

In one embodiment, the enzyme having pentose-5-phosphatase activity is encoded by an amino acid sequence having at least 70% sequence identity, at least 80% sequence identity, or at least 90% sequence identity to an enzyme having pentose-5-phosphatase activity selected from the group consisting of *E. coli* phoA, *E. coli* yfbT and *E. coli* yidA. In further embodiments, the enzyme having pentose-5-phosphatase activity is selected from *E. coli* phoA, *E. coli* yfbT and *E. coli* yidA.

In some embodiments, the one or more nucleic acid molecules encoding the enzyme having pentose-5-phosphatase activity is phoA, yfbT, yidA or homolog thereof. In another embodiment, the one or more nucleic acid molecules encoding the enzyme having pentose-5-phosphatase activity comprises an amino acid sequence selected from the group consisting of SEQ ID NOs: 160, 168 and 172. In a further embodiment, the one or more nucleic acid molecules encoding the enzyme having pentose-5-phosphatase activity is encoded by a nucleic acid sequence selected from the group consisting of SEQ ID NOs: 159, 167 and 171.

In another embodiment, the enzyme having D-ribulose-5-phosphatase activity is encoded by an amino acid sequence having at least 70% sequence identity, at least 80% sequence identity, or at least 90% sequence identity to *Plasmodium falciparum* PF10_0325. In further embodiments, the enzyme having D-ribulose-5-phosphatase activity is *Plasmodium falciparum* PF10_0325.

In some embodiments, the one or more nucleic acid molecules encoding the enzyme having D-ribulose-5-phosphatase activity is PF10_0325, or homolog thereof. In another embodiment, the one or more nucleic acid molecules encoding the enzyme having D-ribulose-5-phosphatase activity comprises an amino acid sequence set forth in SEQ ID NO: 174. In a further embodiment, the one or more nucleic acid molecules encoding the enzyme having D-ribulose-5-phosphatase activity comprises a nucleic acid sequence set forth in SEQ ID NO: 173.

In one embodiment, the enzyme having D-ribose-5-phosphatase activity is encoded by an amino acid sequence having at least 70% sequence identity, at least 80% sequence identity, or at least 90% sequence identity to an enzyme having D-ribose-5-phosphatase activity selected from the group consisting of *Arabidopsis thaliana* SGPP, *Pseudomonas fluorescens* PFLU_2693, and *E. coli* ybiV. In some embodiments, the enzyme having D-ribose-5-phosphatase activity is selected from the group consisting of *Arabidopsis thaliana* SGPP, *Pseudomonas fluorescens* PFLU 2693, and *E. coli* ybiV.

In some embodiments, the one or more nucleic acid molecules encoding the enzyme having D-ribose-5-phosphatase activity is selected from SGPP, PFLU_2693, ybiV, or homolog thereof. In another embodiment, the one or more nucleic acid molecules encoding the enzyme having D-ribose-5-phosphatase activity comprises an amino acid sequence selected from the group consisting of SEQ ID NOs: 162, 166 and 170. In a further embodiment, the one or more nucleic acid molecules encoding the enzyme having D-ribose-5-phosphatase activity comprises a nucleic acid sequence selected from the group consisting of SEQ ID NOs: 161, 165 and 169.

In another aspect, a pentose-5-phosphate intermediate produced in embodiment [A] or embodiment [B] (and optionally comprising embodiment [C]) can be connected with any one of the known MEG or glycolic acid production pathways by arabitol phosphate dehydrogenases.

[F] In one embodiment, the application relates to a recombinant microorganism capable of producing D-ribulose-1-phosphate from D-xylulose-5-phosphate or producing D-xylulose-1-phosphate from D-ribulose-5-phosphate, wherein the recombinant microorganism expresses one or more arabitol phosphate dehydrogenase, wherein the one or more arabitol phosphate dehydrogenase catalyzes one or more of the following from (a) to (d):

(a) a reversible conversion of D-xylulose-5-phosphate to D-arabitol-1-phosphate;
(b) a reversible conversion of D-arabitol-1-phosphate from (a) to D-ribulose-1-phosphate;
(c) a reversible conversion of D-ribulose-5-phosphate to D-arabitol-5-phosphate;
(d) a reversible conversion of D-arabitol-5-phosphate from (c) to D-xylulose-1-phosphate,
wherein the D-xylulose-5-phosphate and/or D-ribulose-5-phosphate is produced by non-oxidative branch of pentose phosphate pathway, and wherein the D-ribulose-1-phosphate and/or D-xylulose-1-phosphate can be used to produce MEG (or glycolic acid) and optionally, one or more co-product.

In some embodiments, the enzyme having arabitol phosphate dehydrogenase activity is selected from one or more of an enzyme having D-arabitol 1-phosphate 4-dehydrogenase activity, an enzyme having D-arabitol 5-phosphate 2-dehydrogenase activity, an enzyme having D-arabitol 1-phosphate 2-dehydrogenase activity and an enzyme having D-arabitol 5-phosphate 4-dehydrogenase activity.

In some embodiments, an enzyme having D-arabitol 1-phosphate 4-dehydrogenase activity is encoded by an amino acid sequence having at least 70% sequence identity, at least 80% sequence identity, or at least 90% sequence identity to APDH from *Enterococcus avium*. In a preferred embodiment, an enzyme having D-arabitol 1-phosphate 4-dehydrogenase activity is APDH from *Enterococcus avium*. In some embodiments, the one or more nucleic acid molecules encoding an enzyme having D-arabitol 1-phosphate 4-dehydrogenase activity is set forth in SEQ ID NO: 175. In another embodiment, the one or more nucleic acid molecules encoding an enzyme having D-arabitol 1-phosphate 4-dehydrogenase activity comprise an amino acid sequence set forth in SEQ ID NO: 176.

In some embodiments, an enzyme having D-arabitol 5-phosphate 2-dehydrogenase activity is encoded by an amino acid sequence having at least 70% sequence identity, at least 80% sequence identity, or at least 90% sequence identity to APDH from *Enterococcus avium*. In a preferred embodiment, an enzyme having D-arabitol 5-phosphate 2-dehydrogenase activity is APDH from *Enterococcus avium*. In some embodiments, the one or more nucleic acid molecules encoding an enzyme having D-arabitol 5-phosphate 2-dehydrogenase activity is set forth in SEQ ID NO: 175. In another embodiment, the one or more nucleic acid molecules encoding an enzyme having D-arabitol 5-phosphate 2-dehydrogenase activity comprise an amino acid sequence set forth in SEQ ID NO: 176.

In some embodiments, an enzyme having D-arabitol 1-phosphate 2-dehydrogenase activity is encoded by an amino acid sequence having at least 70% sequence identity, at least 80% sequence identity, or at least 90% sequence identity to an enzyme having D-arabitol 1-phosphate 2-dehydrogenase activity selected from the group consisting of *Candida albicans* ARD1, *Candida tropicalis* ARD1, *Scheffersomyces stipitis* ARDH, *Bacillus subtilis* egsA (araM), *Aeropyrum pernix* egsA, *E. coli* gpsA and *Saccharomyces cerevisiae* GPD1. In a preferred embodiment, an enzyme having D-arabitol 1-phosphate 2-dehydrogenase activity is selected from the group consisting of *Candida albicans* ARD1, *Candida tropicalis* ARD1, *Scheffersomyces stipitis* ARDH, *Bacillus subtilis* egsA (araM), *Aeropyrum pernix* egsA, *E. coli* gpsA and *Saccharomyces cerevisiae* GPD1. In some embodiments, the one or more nucleic acid molecules encoding an enzyme having D-arabitol 1-phosphate 2-dehydrogenase activity is selected from the group consisting of SEQ ID NOs: 177, 179, 181, 189, 191, 193 and 195. In another embodiment, the one or more nucleic acid molecules encoding an enzyme having D-arabitol 1-phosphate 2-dehydrogenase activity comprise an amino acid sequence selected from the group consisting of SEQ ID NOs: 178, 180, 182, 190, 192, 194 and 196.

In some embodiments, an enzyme having D-arabitol 5-phosphate 4-dehydrogenase activity is encoded by an amino acid sequence having at least 70% sequence identity, at least 80% sequence identity, or at least 90% sequence identity to an enzyme having D-arabitol 5-phosphate 4-dehydrogenase activity selected from the group consisting of *Pseudomonas fluorescens* mtlD, *Klebsiella pneumoniae* dalD, *Ralstonia solanacearum* dalD, *Bacillus subtilis* egsA (araM), *Aeropyrum pernix* egsA, *E. coli* gpsA and *Saccharomyces cerevisiae* GPD1. In a preferred embodiment, an enzyme having D-arabitol 5-phosphate 4-dehydrogenase activity is selected from the group consisting of *Pseudomonas fluorescens* mtlD, *Klebsiella pneumoniae* dalD, *Ralstonia solanacearum* dalD, *Bacillus subtilis* egsA (araM), *Aeropyrum pernix* egsA, *E. coli* gpsA and *Saccharomyces cerevisiae* GPD1. In some embodiments, the one or more nucleic acid molecules encoding an enzyme having D-arabitol 5-phosphate 4-dehydrogenase activity is selected from the group consisting of SEQ ID NOs: 183, 185, 187, 189, 191, 193 and 195. In another embodiment, the one or more nucleic acid molecules encoding an enzyme having D-arabitol 5-phosphate 4-dehydrogenase activity comprise an amino acid sequence selected from the group consisting of SEQ ID NOs: 184, 186, 188, 190, 192, 194 and 196.

In another aspect, a pentose-5-phosphate intermediate produced in embodiment [A] or embodiment [B] (and optionally comprising [C]) can be connected with any one of the known MEG or glycolic acid production pathways by phosphopentomutases.

[G] In one embodiment, the application relates to a recombinant microorganism capable of producing D-xylulose-1-phosphate from D-xylulose-5-phosphate or producing D-ribulose-1-phosphate from D-ribulose-5-phosphate, wherein the recombinant microorganism expresses one or more phosphopentomutases, wherein the D-xylulose-5-phosphate and/or D-ribulose-5-phosphate is produced by non-oxidative branch of pentose phosphate pathway, and wherein the D-ribulose-1-phosphate and/or D-xylulose-1-phosphate can be used to produce MEG (or glycolic acid) and optionally, one or more co-product.

In some embodiments, an enzyme having phosphopentomutase activity is encoded by an amino acid sequence having at least 70% sequence identity, at least 80% sequence identity, or at least 90% sequence identity to an enzyme having phosphopentomutase activity selected from the group consisting of *E. coli* deoB, *E. coli* pgm, *Bacillus subtilis* pgcA, *Lactococcus lactis* pgmB, *E. coli* ycjU, *Pseudomonas aeruginosa* algC, and *E. coli* cpsG. In a preferred embodiment, an enzyme having phosphopentomutase activity is selected from the group consisting of *E. coli* deoB, *E. coli* pgm, *Bacillus subtilis* pgcA, *Lactococcus lactis* pgmB, *E. coli* ycjU, *Pseudomonas aeruginosa* algC, and *E. coli* cpsG. In some embodiments, the one or more nucleic acid molecules encoding an enzyme having phosphopentomutase activity is selected from the group consisting of SEQ ID NOs: 197, 199, 201, 203, 205, 207 and 209. In another embodiment, the one or more nucleic acid molecules encoding an enzyme having phosphopentomutase activity comprise an amino acid sequence selected from the group consisting of SEQ ID NOs: 198, 200, 202, 204, 206, 208 and 210.

MEG (or Glycolic Acid), or Optionally MEG (or Glycolic Acid) and Co Product Production Pathways In some embodiments, the pentose or pentose-1-phosphate intermediates produced in embodiments [D], [E], [F], and [G] are used in known MEG (or glycolic acid) C2 production pathways, which are coupled to C3 pathways, as described below, to co-produce additional MEG (or glycolic acid) and/or one or more co-products.

In some embodiments, MEG (or glycolic acid) is produced via a C2 pathway that uses D-xylulose-1-phosphate.

[H] In one embodiment, the application relates to a recombinant microorganism capable of producing monoethylene glycol (MEG) (or glycolic acid) from one or more hexose feedstock, wherein the recombinant microorganism from embodiment [A] or from embodiment [B] (and optionally comprising embodiment [C]), and comprising additionally one or more of embodiments [D], [F], and [G], further expresses one or more of the following from (a) to (d):

(a) at least one endogenous or exogenous nucleic acid molecule encoding an enzyme having D-xylulose 1-kinase activity that catalyzes the conversion of D-xylulose from embodiment [D] to D-xylulose-1-phosphate;

(b) at least one endogenous or exogenous nucleic acid molecule encoding an enzyme having D-xylulose-1-phosphate aldolase activity that catalyzes the conversion of D-xylulose-1-phosphate from (a), from embodiment [F] and/or from embodiment [G], to glycolaldehyde and dihydroxyacetonephosphate (DHAP);

(c) at least one endogenous or exogenous nucleic acid molecule encoding an enzyme having glycolaldehyde reductase activity or an enzyme having aldehyde reductase activity that catalyzes the conversion of glycolaldehyde from (b) to MEG;

(d) at least one endogenous or exogenous nucleic acid molecule encoding an enzyme having glycolaldehyde dehydrogenase activity that catalyzes the conversion of glycolaldehyde from (b) to glycolic acid;

wherein MEG (or glycolic acid) and DHAP are produced.

In one embodiment, the enzyme having D-xylulose 1-kinase activity is encoded by one or more nucleic acid molecules obtained from *Homo sapiens*. In some embodiments, the one or more nucleic acid molecules encoding the enzyme having D-xylulose 1-kinase activity is ketohexokinase C (khk-C), or homolog thereof. In another embodiment, the one or more nucleic acid molecules encoding the enzyme having D-xylulose 1-kinase activity comprises an amino acid sequence set forth in SEQ ID NO: 55. In a further embodiment, the one or more nucleic acid molecules encoding the enzyme having D-xylulose 1-kinase activity is encoded by a nucleic acid sequence selected from the group consisting of SEQ ID NOs: 53 and 54.

In one embodiment, the enzyme having D-xylulose-1-phosphate aldolase activity is encoded by one or more nucleic acid molecules obtained from *Homo sapiens*. In another embodiment, the one or more nucleic acid molecules encoding the enzyme having D-xylulose-1-phosphate aldolase activity is aldolase B (aldoB), or homolog thereof. In some embodiments, the one or more nucleic acid molecules encoding the enzyme having D-xylulose-1-phosphate aldolase activity comprises an amino acid sequence set forth in SEQ ID NO: 58. In some embodiments, the one or more nucleic acid molecule encoding the enzyme having D-xylulose-1-phosphate aldolase activity is encoded by a nucleic acid sequence selected from the group consisting of SEQ ID NOs: 56 and 57.

In some embodiments, MEG (or glycolic acid) is produced via a C2 pathway that uses D-ribulose-1-phosphate.

[I] In one embodiment, the application relates to a recombinant microorganism capable of producing monoethylene glycol (MEG) (or glycolic acid) from one or more hexose feedstock, wherein the recombinant microorganism from embodiment [A] or from embodiment [B] (and optionally comprising embodiment [C]), and comprising additionally one or more of embodiments [D], [E], [F], and [G], further expresses one or more of the following from (a) to (e):

(a) at least one endogenous or exogenous nucleic acid molecule encoding an enzyme having D-tagatose 3-epimerase activity that catalyzes the conversion of D-xylulose from embodiment [D] to D-ribulose;

(b) at least one endogenous or exogenous nucleic acid molecule encoding an enzyme having D-ribulokinase activity that catalyzes the conversion of D-ribulose from (a) and/or from embodiment [E] to D-ribulose-1-phosphate;

(c) at least one endogenous or exogenous nucleic acid molecule encoding an enzyme having D-ribulose-1-phosphate aldolase activity that catalyzes the conversion of D-ribulose-1-phosphate from (b), from embodiment [F] and/or from embodiment [G] to glycolaldehyde and dihydroxyacetonephosphate (DHAP);

(d) at least one endogenous or exogenous nucleic acid molecule encoding an enzyme having glycolaldehyde reductase activity that catalyzes the conversion of glycolaldehyde from (c) to MEG;

(e) at least one endogenous or exogenous nucleic acid molecule encoding an enzyme having glycolaldehyde dehydrogenase activity that catalyzes the conversion of glycolaldehyde from (c) to glycolic acid;

wherein MEG (or glycolic acid) and DHAP are produced.

In one embodiment, the enzyme having D-tagatose 3-epimerase activity is encoded by one or more nucleic acid molecules obtained from a microorganism selected from the group consisting of *Pseudomonas* sp., *Mesorhizobium* sp. and *Rhodobacter* sp. In some embodiments, the enzyme having D-tagatose 3-epimerase activity is encoded by one or more nucleic acid molecules obtained from a microorganism selected from the group consisting of *Pseudomonas cichorii*, *Pseudomonas* sp. ST-24, *Mesorhizobium loti* and *Rhodobacter sphaeroides*. In some embodiments, the one or more nucleic acid molecules is dte and/or FJ851309.1, or homolog thereof. In a further embodiment, the enzyme having D-tagatose 3-epimerase activity comprises an amino acid sequence selected from the group consisting of SEQ ID NOs: 3 and 5. In yet a further embodiment, the enzyme having D-tagatose 3-epimerase activity is encoded by a nucleic acid sequence selected from the group consisting of SEQ ID NOs: 1, 2 and 4.

In one embodiment, the enzyme having D-ribulokinase activity is encoded by one or more nucleic acid molecules obtained from *E. coli*. In some embodiments, the one or more nucleic acid molecules is fucK, or homolog thereof. In a further embodiment, the enzyme having D-ribulokinase activity comprises an amino acid sequence set forth in SEQ ID NO: 8. In yet a further embodiment, the enzyme having D-ribulokinase activity is encoded by a nucleic acid sequence selected from the group consisting of SEQ ID NOs: 6, 7, and 257.

In one embodiment, the enzyme having D-ribulose-1-phosphate aldolase activity is encoded by one or more nucleic acid molecules obtained from *E. coli*. In some embodiments, the one or more nucleic acid molecules is fucA, or homolog thereof. In a further embodiment, the enzyme having D-ribulose-1-phosphate aldolase activity comprises an amino acid sequence set forth in SEQ ID NO: 11. In yet a further embodiment, the enzyme having D-ribulose-1-phosphate aldolase activity is encoded by a nucleic acid sequence selected from the group consisting of SEQ ID NOs: 9 and 10.

In some embodiments, MEG (or glycolic acid) is produced via a C2 pathway that uses D-xylonate.

[J] In one embodiment, the application relates to a recombinant microorganism capable of producing monoethylene glycol (MEG) (or glycolic acid) from one or more hexose feedstock, wherein the recombinant microorganism from embodiment [A] or from embodiment [B] (and optionally comprising embodiment [C]), and comprising additionally embodiment [D], further expresses one or more of the following from (a) to (d):

(a) at least one endogenous or exogenous nucleic acid molecule encoding an enzyme having xylose isomerase activity that catalyzes the conversion of D-xylulose from embodiment [D] to D-xylose;

(b) at least one endogenous or exogenous nucleic acid molecule encoding an enzyme having xylose dehydrogenase activity that catalyzes the conversion of D-xylose from (a) to D-xylonolactone;

(c) at least one endogenous or exogenous nucleic acid molecule encoding an enzyme having xylonolactonase activity that catalyzes the conversion of D-xylonolactone from (b) to D-xylonate;

(d) at least one endogenous or exogenous nucleic acid molecule encoding an enzyme having xylose dehydrogenase activity that catalyzes the conversion of D-xylose from (a) to D-xylonate;

wherein the recombinant microorganism further expresses one or more of the following from (e) to (h):

(e) at least one endogenous or exogenous nucleic acid molecule encoding an enzyme having xylonate dehydratase activity that catalyzes the conversion of D-xylonate from (c) or (d) to 2-keto-3-deoxy-xylonate;

(f) at least one endogenous or exogenous nucleic acid molecule encoding an enzyme having 2-keto-3-deoxy-D-pentonate aldolase activity that catalyzes the conversion of 2-keto-3-deoxy-xylonate from (e) to glycolaldehyde and pyruvate;

(g) at least one endogenous or exogenous nucleic acid molecule encoding an enzyme having glycolaldehyde reductase activity that catalyzes the conversion of glycolaldehyde from (f) to MEG;

(h) at least one endogenous or exogenous nucleic acid molecule encoding an enzyme having glycolaldehyde dehydrogenase activity that catalyzes the conversion of glycolaldehyde from (f) to glycolic acid;

wherein MEG (or glycolic acid) and pyruvate are produced.

In some embodiments, the recombinant microorganism comprises an endogenous or exogenous enzyme having xylose isomerase activity that catalyzes the conversion of D-xylulose to D-xylose. In one embodiment, the enzyme having xylose isomerase activity is exogenous. In another embodiment, the enzyme having xylose isomerase activity is encoded by one or more nucleic acid molecules obtained from *Pyromyces* sp. In a further embodiment, the enzyme having xylose isomerase activity is encoded by one or more nucleic acid molecules obtained from *E. coli*. In another embodiment, the one or more nucleic acid molecules encoding the enzyme having xylose isomerase activity is xylA, or homolog thereof. In yet another embodiment, the one or more nucleic acid molecules encoding the enzyme having xylose isomerase activity comprises an amino acid sequence selected from SEQ ID NOs: 95 and 144. In a further embodiment, the one or more nucleic acid molecules encoding the enzyme having xylose isomerase activity comprises a nucleic acid sequence selected from the group consisting of SEQ ID NOs: 93, 94 and 143.

In one embodiment, the enzyme having xylose dehydrogenase activity is encoded by one or more nucleic acid molecules obtained from a microorganism selected from the group consisting of *Caulobacter* sp., Haloarcula sp., *Haloferax* sp., Halorubrum sp. and *Trichoderma* sp. In another embodiment, the enzyme having xylose dehydrogenase activity is encoded by one or more nucleic acid molecules obtained from a microorganism selected from the group consisting of *Caulobacter crescentus, Haloarcula marismortui, Haloferax volcanii, Halorubrum lacusprofundi* and *Trichoderma reesei*. In some embodiments, the one or more nucleic acid molecules encoding the enzyme having xylose dehydrogenase activity is selected from xylB, xdh1 (HVO_B0028) and/or xyd1, or homolog thereof. In a further embodiment, the one or more nucleic acid molecules encoding the enzyme having xylose dehydrogenase activity comprises an amino acid sequence selected from the group consisting of SEQ ID NOs: 61, 63 and 65. In yet another embodiment, the one or more nucleic acid molecules encoding the enzyme having xylose dehydrogenase activity comprises a nucleic acid sequence selected from the group consisting of SEQ ID NOs: 59, 60, 62 and 64.

In one embodiment, the enzyme having xylonolactonase activity is encoded by one or more nucleic acid molecules obtained from a microorganism selected from *Caulobacter* sp. and *Haloferax* sp. In another embodiment, the enzyme having xylonolactonase activity is encoded by one or more nucleic acid molecules obtained from a microorganism selected from the group consisting of *Caulobacter crescentus, Haloferax volcanii* and *Haloferax gibbonsii*. In some embodiments, the one or more nucleic acid molecules encoding the enzyme having xylonolactonase activity is xylC, or homolog thereof. In a further embodiment, the one or more nucleic acid molecules encoding the enzyme having xylonolactonase activity comprises an amino acid sequence set forth in SEQ ID NO: 67. In yet another embodiment, the one or more nucleic acid molecules encoding the enzyme having xylonolactonase activity comprises a nucleic acid sequence set forth in SEQ ID NO: 66.

In one embodiment, the enzyme having xylonate dehydratase activity is encoded by one or more nucleic acid molecules obtained from a microorganism selected from the group consisting of *Caulobacter* sp., *Sulfolobus* sp. and *E. coli*. In another embodiment, the enzyme having xylonate dehydratase activity is encoded by one or more nucleic acid molecules obtained from a microorganism selected from the group consisting of *Caulobacter crescentus, Sulfolobus solfataricus* and *E. coli*. In some embodiments, the one or more nucleic acid molecules encoding the enzyme having xylonate dehydratase activity is selected from xylD, yjhG and/or yagF, or homolog thereof. In a further embodiment, the one or more nucleic acid molecules encoding the enzyme having xylonate dehydratase activity comprises an amino acid sequence selected from the group consisting of SEQ ID NOs: 69, 72 and 75. In yet another embodiment, the one or more nucleic acid molecules encoding the enzyme having xylonate dehydratase activity comprises a nucleic acid sequence selected from the group consisting of SEQ ID NOs: 68, 70, 71, 73 and 74.

In one embodiment, the enzyme having 2-keto-3-deoxy-D-pentonate aldolase activity is encoded by one or more nucleic acid molecules obtained from a microorganism selected from *Pseudomonas* sp. and *E. coli*. In another embodiment, the enzyme having 2-keto-3-deoxy-D-pentonate aldolase activity is encoded by one or more nucleic acid molecules obtained from *E. coli*. In some embodiments, the one or more nucleic acid molecules encoding the enzyme having 2-keto-3-deoxy-D-pentonate aldolase activity is selected from yjhH and/or yagE, or homolog thereof. In a further embodiment, the one or more nucleic acid molecules encoding the enzyme having 2-keto-3-deoxy-D-pentonate aldolase activity comprises an amino acid sequence selected from the group consisting of SEQ ID NOs: 78 and 81. In yet another embodiment, the one or more nucleic acid molecules encoding the enzyme having 2-keto-3-deoxy-D-pentonate aldolase activity comprises a nucleic acid sequence selected from the group consisting of SEQ ID NOs: 76, 77, 79 and 80.

Co-Production of MEG (or Glycolic Acid) Via a C2 Pathway and MEG (or Glycolic Acid) Via a C3 Pathway In one aspect, MEG (or glycolic acid) is produced from one or more hexose feedstock by the lossless transformation of the one or more hexose feedstock to one or more pentose-5-phosphate intermediate, followed by a conversion of the one or more pentose-5-phosphate intermediate to one or more pentose and/or pentose-1-phosphate intermediate, followed by a conversion of the one or more pentose and/or pentose-1-phosphate intermediate to MEG (or glycolic acid) and DHAP or pyruvate via a C2 pathway, and a conversion of DHAP or pyruvate to MEG via a C3 pathway.

In some embodiments, the application relates to a recombinant microorganism capable of producing MEG (or glycolic acid) from one or more hexose feedstock, wherein the recombinant microorganism from embodiment [A] or from embodiment [B] (and optionally comprising embodiment [C]), and having additionally one or more of embodiments [D], [E], [F], and [G], further comprises one or more C2 biosynthesis pathway selected from embodiments [H], [I] and [J] for production of MEG (or glycolic acid) and one or more C3 biosynthesis pathway for the production of MEG (or glycolic acid). The C3 biosynthesis pathways for the production of MEG are, for example, as described in WO 2010/076324 (Metabolic Explorer), herein incorporated by reference in its entirety.

In some embodiments, the C3 biosynthesis pathway for the production of MEG comprises three enzymatic reactions starting with transformation of the 3-phosphohydroxypyruvate precursor (precursor for serine). First, a phosphatase activity allows conversion of phosphohydroxypyruvate into hydroxypyruvate. Hydroxypyruvate is then transformed into glycolaldehyde with a 2-keto acid decarboxylase activity. Finally, a hydroxy aldehyde reductase activity allows the conversion of glycolaldehyde into ethylene glycol. Another pathway for the production of ethylene glycol starts from L-serine as precursor. First a transaminase or an amino acid oxidase activity allows conversion of serine into hydroxypyruvate. The next two steps to convert hydroxypyruvate into glycolaldehyde and then to MEG are similar to the first pathway described above.

In a preferred embodiment, the disclosure provides for a recombinant microorganism comprising one or more C3 biosynthesis pathways for production of MEG. In some embodiments, the recombinant microorganism, particularly a bacterium, contains at least one gene encoding a polypeptide with 2-keto acid decarboxylase activity and one gene encoding a polypeptide with hydroxy aldehyde reductase activity. These genes can be exogenous or endogenous, and can be expressed chromosomally or extrachromosomally.

In a further embodiment of the disclosure, the recombinant microorganism, particularly a bacterium, comprises modifications in which the availability of the intermediate 3-phosphoglycerate is increased. Preferably, the increase is achieved by attenuating the level of expression of genes encoding phosphoglycerate mutases, in particular one or both genes gpmA and pgmM. This can be done by replacing the wild-type promoter of these genes by a weaker promoter, or by the use of an element destabilizing the corresponding messenger RNA or the protein. If needed, complete attenuation of the genes can also be achieved by the deletion of the corresponding DNA sequences.

In another embodiment, the recombinant microorganism, particularly a bacterium, comprises modifications in which flux into the serine biosynthesis pathway is stimulated. This can be achieved by increasing the level of expression of 3-phosphoglycerate dehydrogenase and/or phosphoserine aminotransferase, encoded by the serA and serC genes, respectively. Increasing the level of expression of the 3-phosphoglycerate dehydrogenase and/or phosphoserine aminotransferase can be accomplished by introducing artificial promoters that drive the expression of the serA and/or serC genes, by increasing the number of copies in the cell or by introducing mutations into the serA and/or serC genes that increase the activity of the corresponding proteins. The expression of the serA gene can also be increased by replacing the wild type lrp gene (encoding the leucine-responsive regulatory protein) by an lrp mutated allele (such as the lrp-1 allele corresponding to a GLU 114 ASP substitution in the lrp protein) leading to the constitutive activation of the transcription of the serA gene.

In a particular embodiment of the disclosure mutations can be introduced into the serA gene that reduce the sensitivity of the SerA protein to the feed-back inhibitor serine (feed-back desensitized alleles) and thus permit an increased activity in the presence of serine. Examples of desensitized alleles, i.e. feed-back insensitive alleles, have been described in EP 0 931 833 (Ajinomoto) or EP 0 620 853 (Wacker).

In another embodiment, the recombinant microorganism, particularly a bacterium, comprises modifications in which flux into the hydroxypyruvate biosynthesis pathway is stimulated. This result may be achieved by increasing the level of expression of serine transaminase or serine oxidase (for the pathway starting from serine as precursor), or by increasing the expression of 3-phosphohydroxypyruvate phosphatase. Increasing the level of expression of serine oxidase can be accomplished by introducing and overexpressing the gene coding for L-amino acid oxidase from *R. opacus*, or by introducing mutations into the gene that increase the activity of the corresponding protein. An increase in the expression of serine transaminase can be accomplished by introducing artificial promoters that drive the expression of the serC gene of *E. coli*, by increasing the number of copies in the cell or by introducing mutations into the serC gene that increase the activity of the corresponding protein. An increase of the expression of 3-phosphohydroxypyruvate phosphatase can be accomplished by introducing artificial promoters that drive the expression of the yeaB gene or serB gene of *E. coli*, by increasing the number of copies in the cell or by introducing mutations into the yeaB gene or the serB gene that increase the activity of the corresponding proteins. An increase of the expression of 3-phosphohydroxypyruvate phosphatase can also be accomplished by introducing and overexpressing the gene GPP2 from *S. cerevisiae*, or by introducing mutations into the GPP2 gene that increase the activity of the corresponding protein.

In a further embodiment of the disclosure, the recombinant microorganism, particularly a bacterium, comprises modifications to present an attenuated level of glycolaldehyde conversion to other compounds than ethylene glycol This may be achieved by attenuating the level of glycolaldehyde consuming enzymes like hydroxythreonine aldolase (encoded by UaE) or glycolaldehyde dehydrogenase (encoded by aldA, aldB). Attenuation of these genes can be done by replacing the natural promoter by a lower strength promoter or by elements destabilizing the corresponding messenger RNA or the protein. If needed, complete attenuation of the gene can also be achieved by a deletion of the corresponding DNA sequence.

In a further embodiment of the disclosure, the efficiency of sugar import is increased, either by using a sugar import system not relying on phosphoenolpyruvate (PEP) as phosphordonor like galP that is known to transport glucose, or by providing more phosphoenolpyruvate (PEP) to the sugar-phosphotransferase system. Various means exist that may be used to increase the availability of PEP in a microorganism. In particular, this can be accomplished by attenuating the reaction PEP→pyruvate. Preferentially, at least one gene selected among pykA and pykF, encoding pyruvate kinase, is attenuated in said strain in order to obtain this result. Another way to increase the availability of PEP is to favour the reaction pyruvate→PEP. This can be accomplished by increasing the activity of phosphoenolpyruvate synthase which catalyzes the above reaction. This enzyme is encoded by the ppsA gene. Therefore, in the microorganism, the expression of the ppsA gene is preferentially increased. Both modifications can be present in the microorganism simultaneously.

In a further embodiment of the disclosure, the recombinant microorganism, particularly a bacterium, comprises modifications to present an attenuated level of serine conversion to other compounds than ethylene glycol. This result may be achieved by attenuating the level of serine consuming enzymes like serine deaminases (encoded by sdaA, sdaB and/or tdcG), serine transacetylase (encoded by cysE), tryptophan synthase (encoded by trpAB) or serine hydroxymethyltransferase (encoded by glyA). These genes can be attenuated by replacing the natural promoter by a lower strength promoter or by elements destabilizing the corresponding messenger RNA or the protein. If needed, complete attenuation of the gene can also be achieved by a deletion of the corresponding DNA sequence.

In a further embodiment of the disclosure, the recombinant microorganism, particularly a bacterium, comprises modifications to present an attenuated level of hydroxypyruvate conversion to other compounds than glycolaldehyde. This result may be achieved by attenuating the level of hydroxypyruvate consuming enzymes like hydroxypyruvate reductase (encoded by ghrA) or hydroxypyruvate isomerase (encoded by hyi). These genes can be attenuated by replacing the natural promoter by a lower strength promoter or by elements destabilizing the corresponding messenger RNA or the protein. If needed, complete attenuation of the gene can also be achieved by a deletion of the corresponding DNA sequence.

In some embodiments, the application relates to a recombinant microorganism capable of producing MEG (or glycolic acid) from one or more hexose feedstock, wherein the recombinant microorganism from embodiment [A] or from embodiment [B] (and optionally comprising embodiment

[C]), and having additionally one or more of embodiments [D], [E], [F], and [G], further comprises one or more C3 biosynthesis pathway for the production of MEG (or glycolic acid). The C3 biosynthesis pathways for the production of MEG are, for example, as described in as described in WO 2011/130378 (Genomatica), herein incorporated by reference in its entirety.

In some embodiments, the disclosure provides a recombinant microorganism comprising an ethylene glycol pathway having at least one exogenous nucleic acid encoding an ethylene glycol pathway enzyme expressed in a sufficient amount to produce ethylene glycol, the ethylene glycol pathway including a serine aminotransferase, a serine oxidoreductase (deaminating), a hydroxypyruvate decarboxylase, a glycolaldehyde reductase, a serine decarboxylase, an ethanolamine aminotransferase, an ethanolamine oxidoreductase (deaminating), a hydroxypyruvate reductase or a glycerate decarboxylase.

In some embodiments, the recombinant microorganism comprises an ethylene glycol pathway having at least one exogenous nucleic acid encoding ethylene glycol pathway enzymes expressed in a sufficient amount to produce ethylene glycol, the ethylene glycol pathway including a serine aminotransferase or a serine oxidoreductase (deaminating); a hydroxypyruvate decarboxylase, and a glycolaldehyde reductase.

In some embodiments, the recombinant microorganism comprises an ethylene glycol pathway having at least one exogenous nucleic acid encoding ethylene glycol pathway enzymes expressed in a sufficient amount to produce ethylene glycol, the ethylene glycol pathway including a serine aminotransferase or a serine oxidoreductase (deaminating); a hydroxypyruvate reductase, and a glycerate decarboxylase.

In some embodiments, the recombinant microorganism comprises an ethylene glycol pathway having at least one exogenous nucleic acid encoding ethylene glycol pathway enzymes expressed in a sufficient amount to produce ethylene glycol, the ethylene glycol pathway including a serine decarboxylase; an ethanolamine aminotransferase or an ethanolamine oxidoreductase (deaminating), and a glycolaldehyde reductase.

In some embodiments, the disclosure provides a recombinant microorganism comprising an ethylene glycol pathway having at least one exogenous nucleic acid encoding an ethylene glycol pathway enzyme expressed in a sufficient amount to produce ethylene glycol, the ethylene glycol pathway including a hydroxypyruvate decarboxylase, glycolaldehyde reductase, a hydroxypyruvate reductase, a glycerate decarboxylase, a 3-phosphoglycerate phosphatase, and a glycerate kinase.

In some embodiments, the recombinant microorganism comprises an ethylene glycol pathway having at least one exogenous nucleic acid encoding ethylene glycol pathway enzymes expressed in a sufficient amount to produce ethylene glycol, the ethylene glycol pathway including a hydroxypyruvate reductase; a hydroxypyruvate decarboxylase, and a glycolaldehyde reductase.

In some embodiments, the recombinant microorganism comprises an ethylene glycol pathway having at least one exogenous nucleic acid encoding ethylene glycol pathway enzymes expressed in a sufficient amount to produce ethylene glycol, the ethylene glycol pathway including a 3-phosphoglycerate phosphatase or a glycerate kinase; a hydroxypyruvate reductase; a hydroxypyruvate decarboxylase, and a glycolaldehyde reductase.

In some embodiments, the recombinant microorganism comprises an ethylene glycol pathway having at least one exogenous nucleic acid encoding an ethylene glycol pathway enzyme expressed in a sufficient amount to produce ethylene glycol, the ethylene glycol pathway including a glycerate decarboxylase.

In some embodiments, the recombinant microorganism comprises an ethylene glycol pathway having at least one exogenous nucleic acid encoding ethylene glycol pathway enzymes expressed in a sufficient amount to produce ethylene glycol, the ethylene glycol pathway including a 3-phosphoglycerate phosphatase or a glycerate kinase and a glycerate decarboxylase.

In some embodiments, the disclosure provides a recombinant microorganism comprising an ethylene glycol pathway, wherein the recombinant microorganism comprises at least one exogenous nucleic acid encoding an enzyme or protein that converts a substrate to a product selected from the group consisting of serine to hydroxypyruvate, hydroxypyruvate to glycolaldehyde, glycolaldehyde to ethylene glycol, serine to ethanolamine, ethanolamine to glycolaldehyde, 3-phosphoglycerate to glycerate, glycerate to hydroxypyruvate, hydroxypyruvate to glycerate, and glycerate to ethylene glycol. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, the disclosure provides a recombinant microorganism containing at least one exogenous nucleic acid encoding an enzyme or protein, where the enzyme or protein converts the substrates and products of an ethylene glycol pathway.

While generally described herein as a recombinant microorganism that contains an ethylene glycol pathway, it is understood that the disclosure additionally provides a recombinant microorganism comprising at least one exogenous nucleic acid encoding an ethylene glycol pathway enzyme expressed in a sufficient amount to produce an intermediate of an ethylene glycol pathway. Therefore, in addition to a recombinant microorganism containing an ethylene glycol pathway that produces ethylene glycol, the disclosure additionally provides a recombinant microorganism comprising at least one exogenous nucleic acid encoding an ethylene glycol pathway enzyme, where the microbial organism produces an ethylene glycol pathway intermediate, for example, hydroxypyruvate, ethanolamine, glycolaldehyde, or glycerate.

In some embodiments, a serine aminotransferase or serine oxidoreductase (deaminating) catalyzes the conversion of serine to hydroxypyruvate. In some embodiments, a hydroxypyruvate decarboxylase catalyzes the conversion of hydroxypyruvate to glycolaldehyde. In some embodiments, a glycolaldehyde reductase catalyzes the conversion of glycolaldehyde to ethylene glycol. In some embodiments, a serine decarboxylase catalyzes the conversion of serine to ethanolamine. In some embodiments, an ethanolamine aminotransferase or ethanolamine oxidoreductase (deaminating) catalyzes the conversion of ethanolamine to glycolaldehyde. In some embodiments, a hydroxypyruvate reductase catalyzes the conversion of glycerate to hydroxypyruvate. In some embodiments, a glycerate decarboxylase catalyzes the conversion of glycerate to ethylene glycol. In some embodiments, a 3-phosphoglycerate phosphatase or glycerate kinase catalyzes the conversion of 3-phosphoglycerate to glycerate.

In some embodiments, MEG (or glycolic acid) is produced from the lossless transformation of one or more hexose feedstock to one or more pentose-5-phosphate intermediate, followed by a conversion of the one or more pentose-5-phosphate intermediate to one or more pentose and/or pentose-1-phosphate intermediate, followed by a conversion of the one or more pentose and/or pentose-1-phosphate intermediate to MEG (or glycolic acid) and DHAP or pyruvate via a C2 pathway, and a conversion of DHAP or pyruvate to MEG (or glycolic acid) via a C3 pathway.

In some embodiments, the C2 pathway for production of MEG (or glycolic acid) comprises embodiment [H] and the C3 pathway for production of MEG (or glycolic acid) comprises embodiment [K]. In other embodiments, the C2 pathway for production of MEG (or glycolic acid) comprises embodiment [H] and the C3 pathway for production of MEG (or glycolic acid) comprises embodiment [L]. In some embodiments, the C2 pathway for production of MEG (or glycolic acid) comprises embodiment [I] and the C3 pathway for production of MEG (or glycolic acid) comprises embodiment [K]. In further embodiments, the C2 pathway for production of MEG (or glycolic acid) comprises embodiment [I] and the C3 pathway for production of MEG (or glycolic acid) comprises embodiment [L]. In some embodiments, the C2 pathway for production of MEG (or glycolic acid) comprises embodiment [J] and the C3 pathway for production of MEG (or glycolic acid) comprises embodiment [K]. In some embodiments, the C2 pathway for production of MEG (or glycolic acid) comprises embodiment [J] and the C3 pathway for production of MEG (or glycolic acid) comprises embodiment [L].

[K] In one embodiment, the application relates to a recombinant microorganism capable of producing monoethylene glycol (MEG) (or glycolic acid) from one or more hexose feedstock, wherein the recombinant microorganism from embodiment [A] or from embodiment [B] (and optionally comprising embodiment [C]), and comprising additionally one or more of embodiments [D], [E], [F], and [G], further comprising one or more of embodiments [H], [I], and [J], further expresses one or more of the following from (a) to (h):
- (a) at least one endogenous or exogenous nucleic acid molecule encoding an enzyme having 3-phosphoglycerate dehydrogenase activity that catalyzes the conversion of 3-phosphoglycerate to 3-phosphohydroxypyruvate;
- (b) at least one endogenous or exogenous nucleic acid molecule encoding an enzyme having phosphoserine aminotransferase activity that catalyzes the conversion of 3-phosphohydroxypyruvate from (a) to phospho-L-serine;
- (c) at least one endogenous or exogenous nucleic acid molecule encoding an enzyme having 3-phosphohydroxypyruvate phosphatase activity that catalyzes the conversion of 3-phosphohydroxypyruvate from (a) to hydroxypyruvate;
- (d) at least one endogenous or exogenous nucleic acid molecule encoding an enzyme having phosphoserine phosphatase activity that catalyzes the conversion of phospho-L-serine from (b) to L-serine;
- (e) at least one endogenous or exogenous nucleic acid molecule encoding an enzyme having L-serine transaminase or serine oxidase activity that catalyzes the conversion of L-serine from (d) to hydroxypyruvate;
- (f) at least one endogenous or exogenous nucleic acid molecule encoding an enzyme having hydroxypyruvate decarboxylase activity that catalyzes the conversion of hydroxypyruvate from (c) or (e) to glycolaldehyde;
- (g) at least one endogenous or exogenous nucleic acid molecule encoding an enzyme having glycolaldehyde reductase activity that catalyzes the conversion of glycolaldehyde from (f) to MEG;
- (h) at least one endogenous or exogenous nucleic acid molecule encoding an enzyme having glycolaldehyde dehydrogenase activity that catalyzes the conversion of glycolaldehyde from (f) to glycolic acid;
wherein the produced intermediate DHAP from embodiments [H] and/or [I] and/or pyruvate from embodiment [J] is converted to 3-phosphoglycerate through endogenous glycolysis or gluconeogenesis, respectively, in the microorganism, and wherein MEG (or glycolic acid) is produced.

[L] In one embodiment, the application relates to a recombinant microorganism capable of producing monoethylene glycol (MEG) (or glycolic acid) from one or more hexose feedstock, wherein the recombinant microorganism from embodiment [A] or from embodiment [B] (and optionally comprising embodiment [C]), and comprising additionally one or more of embodiments [D], [E], [F], and [G], further comprising one or more of embodiments [H], [I], and [J], further expresses one or more of the following from (a) to (j):
- (a) at least one endogenous or exogenous nucleic acid molecule encoding an enzyme having 2-phosphoglycerate phosphatase activity and/or an enzyme having glycerate-2-kinase activity that catalyzes the conversion of 2-phosphoglycerate to glycerate;
- (b) at least one endogenous or exogenous nucleic acid molecule encoding an enzyme having 3-phosphoglycerate phosphatase activity or an enzyme having glycerate-3-kinase activity that catalyzes the conversion of 3-phosphoglycerate to glycerate;
- (c) at least one endogenous or exogenous nucleic acid molecule encoding an enzyme having hydroxypyruvate reductase activity that catalyzes the conversion of glycerate from (a) and/or (b) to hydroxypyruvate;
- (d) at least one endogenous or exogenous nucleic acid molecule encoding an enzyme having serine aminotransferase activity or an enzyme having serine oxidoreductase (deaminating) activity that catalyzes the conversion of L-serine to hydroxypyruvate;
- (e) at least one endogenous or exogenous nucleic acid molecule encoding an enzyme having L-serine decarboxylase activity that catalyzes the conversion of L-serine to ethanolamine;
- (f) at least one endogenous or exogenous nucleic acid molecule encoding an enzyme having hydroxypyruvate decarboxylase activity that catalyzes the conversion of hydroxypyruvate from (c) and/or (d) to glycolaldehyde;
- (g) at least one endogenous or exogenous nucleic acid molecule encoding an enzyme having ethanolamine aminotransferase or ethanolamine oxidoreductase (deaminating) activity that catalyzes the conversion of ethanolamine from (e) to glycolaldehyde;
- (h) at least one endogenous or exogenous nucleic acid molecule encoding an enzyme having glycerate decarboxylase activity that catalyzes the conversion of glycerate from (a) and/or (b) to MEG;
- (i) at least one endogenous or exogenous nucleic acid molecule encoding an enzyme having glycolaldehyde reductase activity that catalyzes the conversion of glycolaldehyde from (f) and/or (g) to MEG;

(j) at least one endogenous or exogenous nucleic acid molecule encoding an enzyme having glycolaldehyde dehydrogenase activity that catalyzes the conversion of glycolaldehyde from (f) and/or (g) to glycolic acid;

wherein the produced intermediate DHAP from embodiments [H] and/or [I] and/or pyruvate from embodiment [J] is converted to 3-phosphoglycerate and/or 2-phosphoglycerate through endogenous glycolysis or gluconeogenesis in the microorganism, and wherein MEG (or glycolic acid) is produced.

In some embodiments, a 2-keto acid decarboxylase, a hydroxypyruvate decarboxylase or a 2-oxoglutarate decarboxylase converts hydroxypyruvate to glycolaldehyde. In some embodiments, the enzyme that converts hydroxypyruvate to glycolaldehyde is encoded by an amino acid sequence having at least 70% sequence identity, having at least 80% sequence identity, or having at least 90% sequence identity to Kivd, dxs, or SucA. In some embodiments, the 2-keto acid decarboxylase is Kivd from *Lactococcus lactis*. In yet another embodiment, the one or more nucleic acid molecules encoding the 2-keto acid decarboxylase comprises an amino acid sequence set forth in SEQ ID NO: 224. In a further embodiment, the one or more nucleic acid molecules encoding the 2-keto acid decarboxylase comprises by a nucleic acid sequence set forth in SEQ ID NO: 223. In some embodiments, the 2-oxoglutarate decarboxylase is SucA from *E. coli*. In yet another embodiment, the one or more nucleic acid molecules encoding the 2-oxoglutarate decarboxylase comprises an amino acid sequence set forth in SEQ ID NO: 226. In a further embodiment, the one or more nucleic acid molecules encoding the 2-oxoglutarate decarboxylase comprises a nucleic acid sequence set forth in SEQ ID NO: 225.

In some embodiments, the hydroxy aldehyde reductase can be a glycolaldehyde reductase. In some embodiments, the enzyme having glycolaldehyde reductase activity is encoded by an amino acid sequence having at least 70% sequence identity, having at least 80% sequence identity, or having at least 90% sequence identity to yqhD or FucO. In some embodiments, the enzyme having glycolaldehyde reductase activity is encoded by one or more nucleic acid molecules obtained from a microorganism selected from *E. coli* and *S. cerevisiae*. In another embodiment, the one or more nucleic acid molecules is selected from gldA, GRE2, GRE3, yqhD, ydjG, fucO, yafB (dkgB), and/or yqhE (dkgA), or homolog thereof. In another embodiment, the one or more nucleic acid molecules is yqhD. In some embodiments, the yqhD comprises a G149E mutation. In a further embodiment, the enzyme having glycolaldehyde reductase activity comprises an amino acid sequence selected from the group consisting of SEQ ID NOs: 13, 15, 17, 20, 23, 25, 28, 30 and 32. In yet a further embodiment, the enzyme having glycolaldehyde reductase activity is encoded by a nucleic acid sequence selected from the group consisting of SEQ ID NOs: 12, 14, 16, 18, 19, 21, 22, 24, 26, 27, 29 and 31.

In some embodiments, the 3-phosphoglycerate dehydrogenase can be a 3-phospho-hydroxypyruvate reductase or a 2-oxoglutarate reductase. In some embodiments, the enzyme having 3-phospho-hydroxypyruvate reductase activity is encoded by an amino acid sequence having at least 70% sequence identity, having at least 80% sequence identity, or having at least 90% sequence identity to serA. In some embodiments, the enzyme having 3-phospho-hydroxypyruvate reductase activity is serA from *E. coli*. In yet another embodiment, the one or more nucleic acid molecules encoding the enzyme having 3-phospho-hydroxypyruvate reductase activity comprises an amino acid sequence set forth in SEQ ID NO: 228. In a further embodiment, the one or more nucleic acid molecules encoding the enzyme having 3-phospho-hydroxypyruvate reductase activity comprises a nucleic acid sequence set forth in SEQ ID NO: 227.

In some embodiments, the phosphoserine aminotransferase can be an L-serine transaminase, a serine aminotransferase or a serine-pyruvate aminotransferase. In some embodiments, the enzyme having phosphoserine aminotransferase activity is encoded by an amino acid sequence having at least 70% sequence identity, having at least 80% sequence identity, or having at least 90% sequence identity to serC. In some embodiments, the enzyme having phosphoserine aminotransferase activity is serC from *E. coli*. In yet another embodiment, the one or more nucleic acid molecules encoding the enzyme having phosphoserine aminotransferase activity comprises an amino acid sequence set forth in SEQ ID NO: 230. In a further embodiment, the one or more nucleic acid molecules encoding the enzyme having phosphoserine aminotransferase activity comprises a nucleic acid sequence set forth in SEQ ID NO: 229.

In some embodiments, the enzyme having serine-pyruvate aminotransferase activity is AGXT1 from *Homo sapiens*. In yet another embodiment, the one or more nucleic acid molecules encoding the enzyme having serine-pyruvate aminotransferase activity comprises an amino acid sequence set forth in SEQ ID NO: 244. In a further embodiment, the one or more nucleic acid molecules encoding the enzyme having serine-pyruvate aminotransferase activity comprises a nucleic acid sequence set forth in SEQ ID NO: 243.

In some embodiments, the enzyme having 3-phospho-hydroxypyruvate phosphatase activity is encoded by an amino acid sequence having at least 70% sequence identity, having at least 80% sequence identity, or having at least 90% sequence identity to yeaB (nudL). In some embodiments, the enzyme having 3-phospho-hydroxypyruvate phosphatase activity is yeaB (nudL) from *E. coli*. In yet another embodiment, the one or more nucleic acid molecules encoding the enzyme having 3-phospho-hydroxypyruvate phosphatase activity comprises an amino acid sequence set forth in SEQ ID NO: 232. In a further embodiment, the one or more nucleic acid molecules encoding the enzyme having 3-phospho-hydroxypyruvate phosphatase activity comprises a nucleic acid sequence set forth in SEQ ID NO: 231.

In some embodiments, the enzyme having phosphoserine phosphatase activity is encoded by an amino acid sequence having at least 70% sequence identity, having at least 80% sequence identity, or having at least 90% sequence identity to serB. In some embodiments, the enzyme having phosphoserine phosphatase activity is serB from *E. coli*. In yet another embodiment, the one or more nucleic acid molecules encoding the enzyme having phosphoserine phosphatase activity comprises an amino acid sequence set forth in SEQ ID NO: 234. In a further embodiment, the one or more nucleic acid molecules encoding the enzyme having phosphoserine phosphatase activity comprises a nucleic acid sequence set forth in SEQ ID NO: 233.

In some embodiments, an enzyme having 2-phosphoglycerate phosphatase activity or an enzyme having glycerate-2-kinase activity converts 2-phosphoglycerate to glycerate. In some embodiments, the enzyme that converts 2-phosphoglycerate to glycerate is encoded by an amino acid sequence having at least 70% sequence identity, having at least 80% sequence identity, or having at least 90% sequence identity to phoA, glxK or garK. In some embodiments, the enzyme having 2-phosphoglycerate phosphatase activity is phoA from *E. coli*. In yet another embodiment, the one or more nucleic acid molecules encoding the enzyme having 2-phosphoglycerate phosphatase activity comprises an amino acid sequence set forth in SEQ ID NO: 246. In a further embodiment, the one or more nucleic acid molecules encoding the enzyme having 2-phosphoglycerate phosphatase activity comprises a nucleic acid sequence set forth in SEQ ID NO: 245. In some embodiments, the enzyme having glycerate-2-kinase activity is glxK from *E. coli*. In yet another embodiment, the one or more nucleic acid molecules encoding the enzyme having glycerate-2-kinase activity comprises an amino acid sequence set forth in SEQ ID NO: 250. In a further embodiment, the one or more nucleic acid molecules encoding the enzyme having glycerate-2-kinase activity comprises a nucleic acid sequence set forth in SEQ ID NO: 249. In some embodiments, the enzyme having glycerate-2-kinase activity is garK from *E. coli*. In yet another embodiment, the one or more nucleic acid molecules encoding the enzyme having glycerate-2-kinase activity comprises an amino acid sequence set forth in SEQ ID NO: 252. In a further embodiment, the one or more nucleic acid molecules encoding the enzyme having glycerate-2-kinase activity comprises a nucleic acid sequence set forth in SEQ ID NO: 251.

In some embodiments, an enzyme having 3-phosphoglycerate phosphatase activity or an enzyme having glycerate-3-kinase activity converts 3-phosphoglycerate to glycerate. In some embodiments, the enzyme that converts 3-phosphoglycerate to glycerate is encoded by an amino acid sequence having at least 70% sequence identity, having at least 80% sequence identity, or having at least 90% sequence identity to phoA or GLYK. In some embodiments, the enzyme having 3-phosphoglycerate phosphatase activity is phoA from *E. coli*. In yet another embodiment, the one or more nucleic acid molecules encoding the enzyme having 3-phosphoglycerate phosphatase activity comprises an amino acid sequence set forth in SEQ ID NO: 246. In a further embodiment, the one or more nucleic acid molecules encoding the enzyme having 3-phosphoglycerate phosphatase activity comprises a nucleic acid sequence set forth in SEQ ID NO: 245. In some embodiments, the enzyme having glycerate-3-kinase activity is GLYK from *Arabidopsis thaliana*. In yet another embodiment, the one or more nucleic acid molecules encoding the enzyme having glycerate-3-kinase activity comprises an amino acid sequence set forth in SEQ ID NO: 248. In a further embodiment, the one or more nucleic acid molecules encoding the enzyme having glycerate-3-kinase activity comprises a nucleic acid sequence set forth in SEQ ID NO: 247.

In some embodiments, an enzyme having hydroxypyruvate reductase activity converts glycerate to hydroxypyruvate. In some embodiments, the enzyme that converts glycerate to hydroxypyruvate is encoded by an amino acid sequence having at least 70% sequence identity, having at least 80% sequence identity, or having at least 90% sequence identity to ghrB. In some embodiments, the enzyme having hydroxypyruvate reductase activity is ghrB from *E. coli*. In yet another embodiment, the one or more nucleic acid molecules encoding the enzyme hydroxypyruvate reductase activity comprises an amino acid sequence set forth in SEQ ID NO: 242. In a further embodiment, the one or more nucleic acid molecules encoding the enzyme hydroxypyruvate reductase activity comprises a nucleic acid sequence set forth in SEQ ID NO: 241.

In some embodiments, an enzyme having serine decarboxylase activity converts L-serine to ethanolamine. In some embodiments, the enzyme that converts L-serine to ethanolamine is encoded by an amino acid sequence having at least 70% sequence identity, having at least 80% sequence identity, or having at least 90% sequence identity to SDC. In some embodiments, the enzyme having serine decarboxylase activity is SDC from *Arabidopsis thaliana*. In yet another embodiment, the one or more nucleic acid molecules encoding the enzyme having serine decarboxylase activity comprises an amino acid sequence set forth in SEQ ID NO: 236. In a further embodiment, the one or more nucleic acid molecules encoding the enzyme having serine decarboxylase activity comprises a nucleic acid sequence set forth in SEQ ID NO: 235.

In some embodiments, an enzyme having ethanolamine aminotransferase activity or an enzyme having ethanolamine oxidoreductase (deaminating) activity converts ethanolamine to glycolaldehyde. In some embodiments, the enzyme that converts ethanolamine to glycolaldehyde is encoded by an amino acid sequence having at least 70% sequence identity, having at least 80% sequence identity, or having at least 90% sequence identity to alaA or tynA. In some embodiments, the enzyme having ethanolamine aminotransferase activity is alaA from *E. coli*. In yet another embodiment, the one or more nucleic acid molecules encoding the enzyme having ethanolamine aminotransferase activity comprises an amino acid sequence set forth in SEQ ID NO: 240. In a further embodiment, the one or more nucleic acid molecules encoding the enzyme having ethanolamine aminotransferase activity comprises a nucleic acid sequence set forth in SEQ ID NO: 239. In some embodiments, the enzyme having ethanolamine oxidoreductase (deaminating) activity is tynA from *E. coli*. In yet another embodiment, the one or more nucleic acid molecules encoding the enzyme having ethanolamine oxidoreductase (deaminating) activity comprises an amino acid sequence set forth in SEQ ID NO: 238. In a further embodiment, the one or more nucleic acid molecules encoding the enzyme having ethanolamine oxidoreductase (deaminating) activity comprises a nucleic acid sequence set forth in SEQ ID NO: 237.

In another aspect, MEG (or glycolic acid) is produced from the lossless transformation of one or more hexose feedstock to one or more pentose-5-phosphate intermediate, followed by a conversion of the one or more pentose-5-phosphate intermediate to one or more pentose and/or pentose-1-phosphate intermediate, followed by a conversion of the one or more pentose and/or pentose-1-phosphate intermediate to MEG (or glycolic acid) and DHAP or pyruvate via a C2 pathway, and a conversion of DHAP or pyruvate to one or more co-product via a C3 pathway. In some embodiments, the C2 pathway comprises embodiment [H]. In further embodiments, the C2 pathway comprises embodiment [I]. In yet further embodiments, the C2 pathway comprises embodiment [J].

Co-Production of MEG (or Glycolic Acid) Via a C2 Pathway and Acetone, Isopropanol, Propene and/or Isobutene Via a C3 Pathway In some embodiments, MEG (or glycolic acid) is produced from the lossless transformation of one or more hexose feedstock to one or more pentose-5-phosphate intermediate, followed by a conversion of the one or more pentose-5-phosphate intermediate to one or more pentose and/or pentose-1-phosphate intermediate, followed by a conversion of the one or more pentose and/or pentose-1-phosphate intermediate to MEG (or glycolic acid) and DHAP or pyruvate via a C2 pathway, and a conversion of DHAP or pyruvate to acetone via a C3 pathway. In some embodiments, the C2 pathway comprises embodiment [H].

In further embodiments, the C2 pathway comprises embodiment [I]. In yet further embodiments, the C2 pathway comprises embodiment [J].

In some embodiments, the C2 pathway for production of MEG (or glycolic acid) comprises embodiment [H] and the C3 pathway for production of acetone comprises embodiment [M]. In some embodiments, the C2 pathway for production of MEG (or glycolic acid) comprises embodiment [I] and the C3 pathway for production of acetone comprises embodiment [M]. In some embodiments, the C2 pathway for production of MEG (or glycolic acid) comprises embodiment [J] and the C3 pathway for production of acetone comprises embodiment [M].

[M] In one embodiment, the application relates to a recombinant microorganism capable of co-producing monoethylene glycol (MEG) (or glycolic acid) and acetone, from one or more hexose feedstock, wherein the recombinant microorganism from embodiment [A] or from embodiment [B] (and optionally comprising embodiment [C]), and comprising additionally one or more of embodiments [D], [E], [F] and [G], further comprising one or more of embodiments [H], [I], and [J], further expresses one or more of the following from (a) to (c):
  (a) at least one endogenous or exogenous nucleic acid molecule encoding an enzyme having thiolase or acetyl coenzyme A acetyltransferase activity that catalyzes the conversion of acetyl-CoA to acetoacetyl-CoA;
  (b) at least one endogenous or exogenous nucleic acid molecule encoding an enzyme having acetyl-CoA:acetoacetate-CoA transferase activity or an enzyme having acetate:acetoacetyl-CoA hydrolase activity that catalyzes the conversion of acetoacetyl-CoA from (a) to acetoacetate; and/or
  (c) at least one endogenous or exogenous nucleic acid molecule encoding an enzyme having acetoacetate decarboxylase activity that catalyzes the conversion of acetoacetate from (b) to acetone;
  wherein the produced intermediate DHAP from embodiments [H] and/or [I] and/or pyruvate from embodiment [J] is converted to acetyl-CoA through endogenous glycolysis in the microorganism, and wherein MEG (or glycolic acid) and acetone are co-produced.

In some embodiments, MEG (or glycolic acid) is produced from the lossless transformation of one or more hexose feedstock to one or more pentose-5-phosphate intermediate, followed by a conversion of the one or more pentose-5-phosphate intermediate to one or more pentose and/or pentose-1-phosphate intermediate, followed by a conversion of the one or more pentose and/or pentose-1-phosphate intermediate to MEG (or glycolic acid) and DHAP or pyruvate via a C2 pathway, and a conversion of DHAP or pyruvate to isobutene via a C3 pathway. In some embodiments, the C2 pathway comprises embodiment [H]. In further embodiments, the C2 pathway comprises embodiment [I]. In yet further embodiments, the C2 pathway comprises embodiment [J].

In some embodiments, the C2 pathway for production of MEG (or glycolic acid) comprises embodiment [H] and the C3 pathway for production of isobutene comprises embodiment [N]. In some embodiments, the C2 pathway for production of MEG (or glycolic acid) comprises embodiment [I] and the C3 pathway for production of isobutene comprises embodiment [N]. In some embodiments, the C2 pathway for production of MEG (or glycolic acid) comprises embodiment [J] and the C3 pathway for production of isobutene comprises embodiment [N].

[N] In some embodiments, the application relates to a recombinant microorganism capable of co-producing monoethylene glycol (MEG) (or glycolic acid) and isobutene via acetone or HMG-CoA, from one or more hexose feedstock, wherein the recombinant microorganism from embodiment [A] or from embodiment [B] (and optionally comprising embodiment [C]), and comprising additionally one or more of embodiments [D], [E], [F] and [G], further comprising one or more of embodiments [H], [I], and [J], further expresses one or more of the following from (a) to (d):
  (a) at least one endogenous or exogenous nucleic acid molecule encoding an enzyme having thiolase or acetyl coenzyme A acetyltransferase activity that catalyzes the conversion of acetyl-CoA to acetoacetyl-CoA;
  (b) at least one endogenous or exogenous nucleic acid molecule encoding an enzyme having acetyl-CoA:acetoacetate-CoA transferase activity or an enzyme having acetate:acetoacetyl-CoA hydrolase activity that catalyzes the conversion of acetoacetyl-CoA from (a) to acetoacetate;
  (c) at least one endogenous or exogenous nucleic acid molecule encoding an enzyme having acetoacetate decarboxylase activity that catalyzes the conversion of acetoacetate from (b) to acetone;
  (d) at least one endogenous or exogenous nucleic acid molecule encoding an enzyme having 3-hydroxyisovalerate synthase activity that catalyzes the conversion of acetone from (c) and acetyl-CoA to 3-hydroxyisovalerate (3HIV);
  or
  wherein the recombinant microorganism expresses one or more of the following from (e) to (j):
  (e) at least one endogenous or exogenous nucleic acid molecule encoding an enzyme having thiolase or acetyl coenzyme A acetyltransferase activity that catalyzes the conversion of acetyl-CoA to acetoacetyl-CoA;
  (f) at least one endogenous or exogenous nucleic acid molecule encoding an enzyme having hydroxymethylglutaryl-CoA synthase activity that catalyzes the conversion of acetoacetyl-CoA from (e) and acetyl-CoA to 3-hydroxy-3-methylglutaryl-CoA (HMG-CoA);
  (g) at least one endogenous or exogenous nucleic acid molecule encoding an enzyme having methylglutaconyl-CoA hydratase activity that catalyzes the conversion of HMG-CoA from (f) to 3-methylglutaconyl-CoA;
  (h) at least one endogenous or exogenous nucleic acid molecule encoding an enzyme having methylcrotonyl-CoA carboxylase activity that catalyzes the conversion of 3-methylglutaconyl-CoA from (g) to 3-methylcrotonyl-CoA;
  (i) at least one endogenous or exogenous nucleic acid molecule encoding an enzyme having methylcrotonyl-CoA hydratase activity that catalyzes the conversion of 3-methylcrotonyl-CoA from (h) to 3-hydroxyisovaleryl-CoA;
  (j) at least one endogenous or exogenous nucleic acid molecule encoding an enzyme having 3-hydroxyisovaleryl-CoA thioesterase activity that catalyzes the conversion of 3-hydroxyisovaleryl-CoA from (i) to 3HIV;
  wherein the recombinant microorganism further expresses (a1) and (a2), and/or (b1) selected from:
  (a1) at least one endogenous or exogenous nucleic acid molecule encoding an enzyme having 3HIV kinase activity that catalyzes the conversion of 3HIV from (d) or (j) to 3HIV-3-phosphate;

(a2) at least one endogenous or exogenous nucleic acid molecule encoding an enzyme having 3HIV-3-phosphate decarboxylase activity that catalyzes the conversion of 3HIV-3-phosphate from (a1) to isobutene;

(b1) at least one endogenous or exogenous nucleic acid molecule encoding a an enzyme having 3HIV decarboxylase activity that catalyzes the conversion of 3HIV from (d) or (j) to isobutene;

wherein the produced intermediate DHAP from embodiments [H] and/or [I] and/or pyruvate from embodiment [J] is converted to acetyl-CoA through endogenous glycolysis in the microorganism, and wherein MEG (or glycolic acid) and isobutene are co-produced.

In some embodiments, MEG (or glycolic acid) is produced from the lossless transformation of one or more hexose feedstock to one or more pentose-5-phosphate intermediate, followed by a conversion of the one or more pentose-5-phosphate intermediate to one or more pentose and/or pentose-1-phosphate intermediate, followed by a conversion of the one or more pentose and/or pentose-1-phosphate intermediate to MEG (or glycolic acid) and DHAP or pyruvate via a C2 pathway, and a conversion of DHAP or pyruvate to isopropanol via a C3 pathway. In some embodiments, the C2 pathway comprises embodiment [H]. In further embodiments, the C2 pathway comprises embodiment [I]. In yet further embodiments, the C2 pathway comprises embodiment [J].

[O] In one embodiment, the recombinant microorganisms from embodiment [M] and/or [N] (optionally comprising embodiment [EE]), optionally further express at least one endogenous or exogenous nucleic acid molecule encoding an enzyme having secondary alcohol dehydrogenase activity that catalyzes the conversion of acetone to isopropanol.

In some embodiments, the alcohol dehydrogenase has at least 70% sequence identity, at least 80% sequence identity, or at least 90% sequence identity with an alcohol dehydrogenase from *Clostridium* sp. In other embodiments, the alcohol dehydrogenase is an alcohol dehydrogenase selected from *Clostridium beijerinckii* adh and *Clostridium carboxidivorans* adh. In a further embodiment, the alcohol dehydrogenase comprises an amino acid sequence selected from the group consisting of SEQ ID NOs: 138 and 140. In yet another embodiment, the alcohol dehydrogenase is encoded by a nucleic acid sequence selected from the group consisting of SEQ ID NOs: 136, 137, and 139.

In some embodiments, MEG (or glycolic acid) is produced from the lossless transformation of one or more hexose feedstock to one or more pentose-5-phosphate intermediate, followed by a conversion of the one or more pentose-5-phosphate intermediate to one or more pentose and/or pentose-1-phosphate intermediate, followed by a conversion of the one or more pentose and/or pentose-1-phosphate intermediate to MEG (or glycolic acid) and DHAP or pyruvate via a C2 pathway, and a conversion of DHAP or pyruvate to propene via a C3 pathway. In some embodiments, the C2 pathway comprises embodiment [H]. In further embodiments, the C2 pathway comprises embodiment [I]. In yet further embodiments, the C2 pathway comprises embodiment [J].

[P] In another embodiment, the recombinant microorganisms from embodiment [O] (optionally comprising embodiment [EE]), optionally further expresses at least one endogenous or exogenous nucleic acid molecule encoding an enzyme having dehydratase activity that catalyzes the conversion of isopropanol to propene.

In one embodiment of any pathway disclosed above for isobutene co-production, the enzyme having 3-hydroxyisovalerate synthase activity is encoded by one or more nucleic acid molecules obtained from a microorganism selected from Mus sp., *Saccharomyces* sp., *Lactobacillus* sp. and *Polaromonas* sp. In another embodiment, the enzyme having 3-hydroxyisovalerate synthase activity is encoded by one or more nucleic acid molecules obtained from a microorganism selected from *Mus musculus, Saccharomyces cerevisiae, Lactobacillus* crispatus and *Polaromonas naphthalenivorans*. In some embodiments, the one or more nucleic acid molecules encoding the enzyme having 3-hydroxyisovalerate synthase activity is selected from Hmgcs1, ERG13, PksG and/or Pnap_0477, or homolog thereof. In a further embodiment, the one or more nucleic acid molecules encoding the enzyme having 3-hydroxyisovalerate synthase activity comprises an amino acid sequence selected from the group consisting of SEQ ID NOs: 105, 107, 109 and 111. In yet another embodiment, the one or more nucleic acid molecules encoding the enzyme having 3-hydroxyisovalerate synthase activity comprises a nucleic acid sequence selected from the group consisting of SEQ ID NOs: 104, 106, 108 and 110.

In one embodiment of any pathway disclosed above for isobutene co-production, the enzyme having hydroxymethylglutaryl-CoA synthase activity is encoded by one or more nucleic acid molecules obtained from *Saccharomyces* sp. In another embodiment, the enzyme having hydroxymethylglutaryl-CoA synthase activity is encoded by one or more nucleic acid molecules obtained from *Saccharomyces cerevisiae*. In some embodiments, the one or more nucleic acid molecules encoding the enzyme having hydroxymethylglutaryl-CoA synthase activity is HmgS, or homolog thereof. In a further embodiment, the one or more nucleic acid molecules encoding the enzyme having hydroxymethylglutaryl-CoA synthase activity comprises an amino acid sequence set forth in SEQ ID NO: 123. In yet another embodiment, the one or more nucleic acid molecules encoding the enzyme having hydroxymethylglutaryl-CoA synthase activity comprises a nucleic acid sequence set forth in SEQ ID NO: 122.

In one embodiment of any pathway disclosed above for isobutene co-production, the enzyme having methylglutaconyl-CoA hydratase activity is encoded by one or more nucleic acid molecules obtained from *Pseudomonas* sp. In another embodiment, the enzyme having methylglutaconyl-CoA hydratase activity is encoded by one or more nucleic acid molecules obtained from *Pseudomonas putida*. In some embodiments, the one or more nucleic acid molecules encoding the enzyme having methylglutaconyl-CoA hydratase activity is liuC, or homolog thereof. In a further embodiment, the one or more nucleic acid molecules encoding the enzyme having methylglutaconyl-CoA hydratase activity comprises an amino acid sequence set forth in SEQ ID NO: 125. In yet another embodiment, the one or more nucleic acid molecules encoding the enzyme having methylglutaconyl-CoA hydratase activity comprises a nucleic acid sequence set forth in SEQ ID NO: 124.

In one embodiment of any pathway disclosed above for isobutene co-production, the enzyme having methylcrotonyl-CoA carboxylase activity is encoded by one or more nucleic acid molecules obtained from *Pseudomonas* sp. In another embodiment, the enzyme having methylcrotonyl-CoA carboxylase activity is encoded by one or more nucleic acid molecules obtained from *Pseudomonas aeruginosa*. In some embodiments, the one or more nucleic acid molecules encoding the enzyme having methylcrotonyl-CoA carboxylase activity is liuB, and/or liuD, or homologs thereof. In a further embodiment, the one or more nucleic acid molecules encoding the enzyme having methylcrotonyl-CoA carboxylase activity comprises an amino acid sequence selected from SEQ ID NOs: 127 and 129. In yet another embodiment, the one or more nucleic acid molecules encoding the enzyme having methylcrotonyl-CoA carboxylase activity comprises a nucleic acid sequence selected from SEQ ID NOs: 126 and 128.

In one embodiment of any pathway disclosed above for isobutene co-production, the enzyme having methylcrotonyl-CoA hydratase activity is a 3-ketoacyl-CoA thiolase. In another embodiment, the enzyme having methylcrotonyl-CoA hydratase activity is an enoyl-CoA hydratase. In another embodiment, the enzyme having methylcrotonyl-CoA hydratase activity is encoded by one or more nucleic acid molecules obtained from E. coli. In some embodiments, the one or more nucleic acid molecules encoding the enzyme having methylcrotonyl-CoA hydratase activity is fadA, and/or fadB, or homologs thereof. In a further embodiment, the one or more nucleic acid molecules encoding the enzyme having methylcrotonyl-CoA hydratase activity comprises an amino acid sequence selected from SEQ ID NOs: 131 and 133. In yet another embodiment, the one or more nucleic acid molecules encoding the enzyme having methylcrotonyl-CoA hydratase activity comprises a nucleic acid sequence selected from SEQ ID NOs: 130 and 132.

In one embodiment of any pathway disclosed above for isobutene co-production, the enzyme having 3-hydroxyisovaleryl-CoA thioesterase activity is encoded by one or more nucleic acid molecules obtained from E. coli. In some embodiments, the one or more nucleic acid molecules encoding the enzyme having 3-hydroxyisovaleryl-CoA thioesterase activity is tesB, or homolog thereof. In a further embodiment, the one or more nucleic acid molecules encoding the enzyme having 3-hydroxyisovaleryl-CoA thioesterase activity comprises an amino acid sequence set forth in SEQ ID NO: 135. In yet another embodiment, the one or more nucleic acid molecules encoding the enzyme having 3-hydroxyisovaleryl-CoA thioesterase activity comprises a nucleic acid sequence set forth in SEQ ID NO: 134.

In one embodiment of any pathway disclosed above for isobutene co-production, the enzyme having 3HIV kinase activity is encoded by one or more nucleic acid molecules obtained from a microorganism selected from the group consisting of Thermoplasma sp. and Picrophilus sp. In another embodiment, the enzyme having 3HIV kinase activity is encoded by one or more nucleic acid molecules obtained from a microorganism selected from the group consisting of Thermoplasma acidophilum and Picrophilus torridus. In some embodiments, the one or more nucleic acid molecules encoding the enzyme having 3HIV kinase activity is TA1305 and/or PTO1356, or homolog thereof. In some embodiments, the TA1305 comprises a L200E mutation. In a further embodiment, the one or more nucleic acid molecules encoding the enzyme having 3HIV kinase activity comprises an amino acid sequence selected from the group consisting of SEQ ID NOs: 113, 115 and 117. In yet another embodiment, the one or more nucleic acid molecules encoding the enzyme having 3HIV kinase activity comprises a nucleic acid sequence selected from the group consisting of SEQ ID NOs: 112, 114 and 116.

In one embodiment of any pathway disclosed above for isobutene co-production, the enzyme having 3HIV-3-phosphate decarboxylase activity is encoded by one or more nucleic acid molecules obtained from Streptococcus sp. In another embodiment, the enzyme having 3HIV-3-phosphate decarboxylase activity is encoded by one or more nucleic acid molecules obtained from a microorganism selected from Streptococcus mitis and Streptococcus gordonii. In some embodiments, the one or more nucleic acid molecules encoding the enzyme having 3HIV-3-phosphate decarboxylase activity comprises smi_1746 and/or mvaD, or homolog thereof. In a further embodiment, the one or more nucleic acid molecules encoding the enzyme having 3HIV-3-phosphate decarboxylase activity comprises an amino acid sequence selected from SEQ ID NOs: 119 and 121. In yet another embodiment, the one or more nucleic acid molecules encoding the enzyme having 3HIV-3-phosphate decarboxylase activity comprises a nucleic acid sequence selected from SEQ ID NOs: 118 and 120.

In one embodiment of any pathway disclosed above for isobutene co-production, the enzyme having 3HIV decarboxylase activity is encoded by one or more nucleic acid molecules obtained from a microorganism selected from the group consisting of Streptococcus sp., Thermoplasma sp. and Picrophilus sp. In another embodiment, the enzyme having 3HIV decarboxylase activity is encoded by one or more nucleic acid molecules obtained from a microorganism selected from the group consisting of Streptococcus gordonii, Thermoplasma acidophilum and Picrophilus torridus. In some embodiments, the one or more nucleic acid molecules encoding the enzyme having 3HIV decarboxylase activity comprises mvaD, TA1305 and/or PTO1356, or homolog thereof. In a further embodiment, the one or more nucleic acid molecules encoding the enzyme having 3HIV decarboxylase activity comprises an amino acid sequence selected from the group consisting of SEQ ID NOs: 113, 117 and 121. In yet another embodiment, the one or more nucleic acid molecules encoding the enzyme having 3HIV decarboxylase activity comprises a nucleic acid sequence selected from the group consisting of SEQ ID NOs: 112, 116 and 120.

Figure 10:
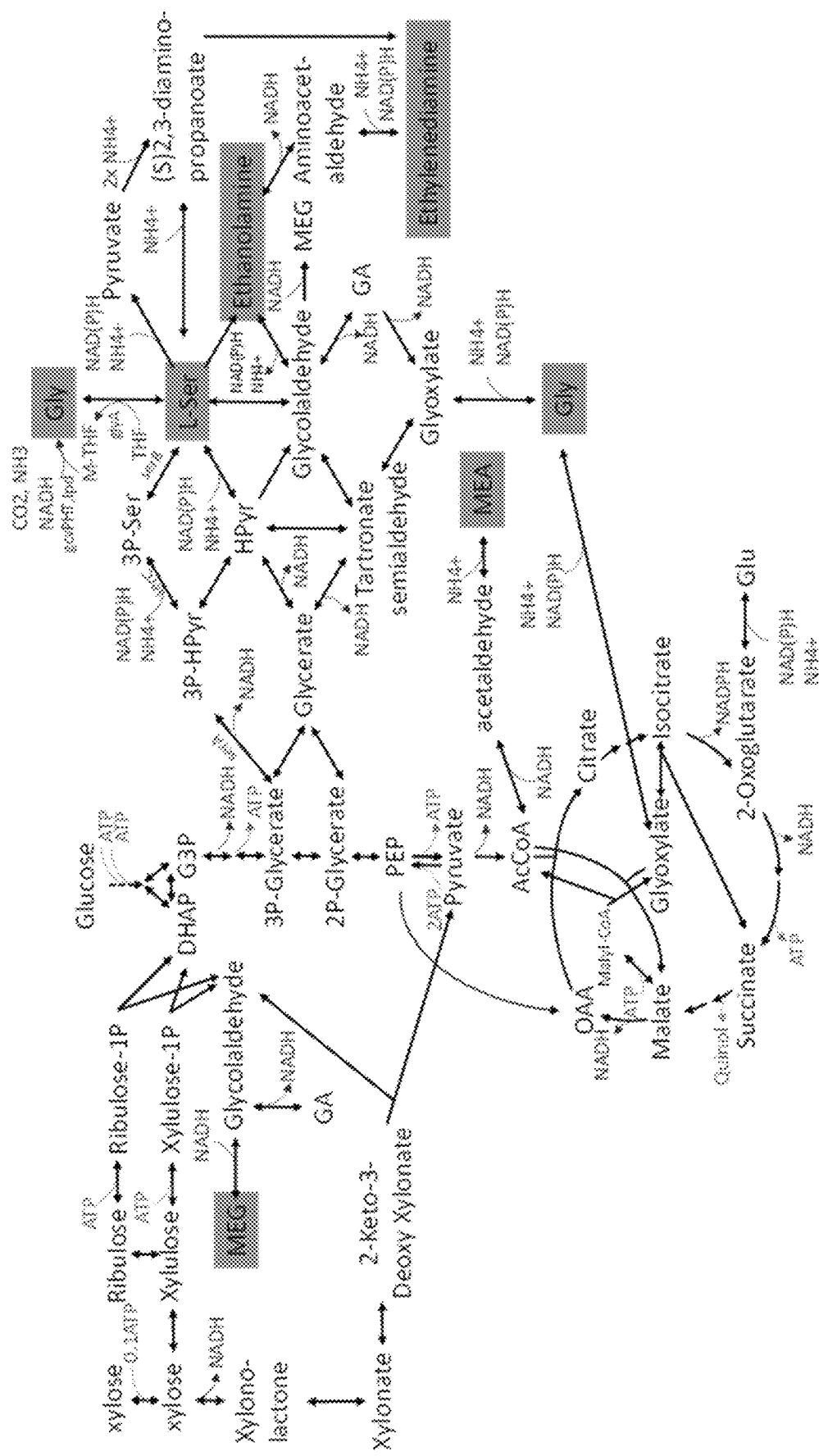
FIG. 10 illustrates an overview of the MEG and Ser, Gly, MEA, EDA co-production pathways.

Co-Production of MEG (or Glycolic Acid) Via a C2 Pathway and One or More Serine Pathway Compound Via a C3 Pathway In some embodiments, the production of MEG via a C2 pathway is coupled to the production of one or more serine pathway compound via a C3 pathway. In one embodiment, one or more serine pathway compound relates to the L-serine biosynthetic pathway. In another embodiment, the one or more serine pathway compound is L-serine (Ser), glycine (Gly), monoethanolamine (MEA), and/or ethylenediamine (EDA) (FIG. 10).

Production of Monoethylene Glycol (MEG) or Glycolic Acid Via One or More C2 Pathway To produce MEG, one or more hexose sugar or hexose feedstock is converted to one or more pentose-5-phosphate intermediates via a non-oxidative entry into the pentose phosphate pathway in a manner that preserves yield potential, as described above. The one or more pentose-5-phosphate intermediates are then converted to one or more pentose-1-phosphate or pentose intermediates by pentose-5-phosphatases, D-arabitol phosphate dehydrogenases and/or phosphopentomutases (as described above). The one or more pentose-1-phosphate or pentose intermediates are then degraded by known C2 pathways (D-xylulose-1-phosphate pathway (Alkim et al., Microb Cell Fact (2015) 14:127), D-ribulose-1-phosphate pathway (WO2013/126721), or D-xylonate pathway (WO2013/119020)) into the C2 carbon compound glycolaldehyde and the C3 carbon compound dihydroxy acetonephosphate (DHAP) or pyruvate by an aldolase. Glycolaldehyde is reduced to MEG, consuming an NADH. Alternatively, glycolaldehyde can be oxidized by a glycolaldehyde dehydrogenase to glycolic acid. The C3 compound DHAP is further oxidized to one or more of the L-serine pathway compounds Ser, Gly, MEA, or EDA, producing NADH.

Ammonia (NH$_3$)

Ammonia is a compound of nitrogen and hydrogen with the formula NH$_3$, which serves as a precursor to food and fertilizers as well as a building block for the synthesis of pharmaceutical products and commercial cleaning products. Ammonia is present as an ammonium cation when it is positively charged, whose chemical formula is NH$_4^+$.

The present disclosure teaches that ammonia or a similar compound is utilized as nitrogen source. When ammonia or a similar compound is used as a nitrogen source, it is fixed into organic matter, for example, glutamate. In one embodiment, when 2-oxoglutarate is usually formed into glutamate, the ammonia is fixed and this process consumes one NADH.

Production of L-serine (Ser)

Ser is produced by the natural pathway via phosphoserine or a variation thereof. In one embodiment, DHAP produced from the production of MEG (or glycolic acid) via a C2 pathway is converted by endogenous glycolysis in the microorganism to 3-phospho-D-glycerate (3-phosphoglycerate). 3-phosphoglycerate is converted to 3-phosphohydroxypyruvate by a D-3-phosphoglycerate dehydrogenase (EC 1.1.1.95). The 3-phosphohydroxypyruvate is then converted to 3-phosphoserine by a phosphoserine aminotransferase (EC 2.6.1.52). The 3-phosphoserine is then converted to L-serine by a phosphoserine phosphatase (EC 3.1.3.3).

In some embodiments the reaction from 3-phosphoglycerate to L-serine is the following:

3-phospho-D-glycerate+NAD$^+$+L-glutamate+ H2O→L-serine+NADH+2-oxoglutarate+phosphate Considering the production of two NADH from DHAP to 3-phosphohydroxypyruvate and one NADH required for fixation of NH$_3$, Ser production produces exactly one excess NADH, which is needed for the equimolar co-production of one MEG (or glycolic acid).

In some embodiments, the production of MEG (or glycolic acid) and L-serine is very close to the thermodynamic maximum yield potential using the lossless conversion of one or more hexose to one or more pentose-5-phosphate intermediates, followed by the conversion of the one or more pentose-5-phosphate intermediates to one or more pentose-1-phosphate and/or pentose intermediates, and then followed by the co-production of MEG (or glycolic acid) via a C2 pathway and L-serine via a C3 pathway from the one or more pentose-1-phosphate and/or pentose intermediates. In some embodiments, the thermodynamic yield potential is 14% better for co-production of MEG (or glycolic acid) and L-serine via the pathways disclosed in the present application compared to production of L-serine made from glucose by the natural, standard C3 pathway.

Co-production: hexose+NH$_3$→MEG (or glycolic acid)+Ser+0 ATP

Y(pathway)=(0.371+0.629) g/g=1.00 g (MEG (or glycolic acid)+Ser)/g(hexose+NH$_3$), 96% of Y(max)(heat of combustion)=1.044 g/g Standard pathway: glucose+2 NH$_3$→2 Ser+2 NADH+0 ATP Y(pathway)=0.981 g (Ser)/g(glucose+2NH$_3$), 84% of Y(max)(heat of combustion)=1.164 g/g In some embodiments, MEG (or glycolic acid) and serine are co-produced from the lossless transformation of one or more hexose feedstock to one or more pentose-5-phosphate intermediate, followed by a conversion of the one or more pentose-5-phosphate intermediate to one or more pentose and/or pentose-1-phosphate intermediate, followed by a conversion of the one or more pentose and/or pentose-1-phosphate intermediate to MEG (or glycolic acid) and DHAP or pyruvate via a C2 pathway, and a conversion of DHAP or pyruvate to serine via a C3 pathway. In some embodiments, the C2 pathway comprises embodiment [H]. In further embodiments, the C2 pathway comprises embodiment [I]. In yet further embodiments, the C2 pathway comprises embodiment [J].

In some embodiments, the C2 pathway for production of MEG (or glycolic acid) comprises embodiment [H] and the C3 pathway for production of serine comprises embodiment [Q]. In some embodiments, the C2 pathway for production of MEG (or glycolic acid) comprises embodiment [I] and the C3 pathway for production of serine comprises embodiment [Q]. In some embodiments, the C2 pathway for production of MEG (or glycolic acid) comprises embodiment [J] and the C3 pathway for production of serine comprises embodiment [Q].

[Q] In one embodiment, the application relates to a recombinant microorganism capable of co-producing monoethylene glycol (MEG) (or glycolic acid) and serine, from one or more hexose feedstock and a nitrogen source, wherein the recombinant microorganism from embodiment [A] or from embodiment [B] (and optionally comprising embodiment [C]), and comprising additionally one or more of embodiments [D], [E], [F] and [G], further comprising one or more of embodiments [H], [I], and [J], further expresses one or more of the following from (a) to (h):

(a) at least one endogenous or exogenous nucleic acid molecule encoding an enzyme having 3-phosphoglycerate dehydrogenase activity that catalyzes the conversion of 3-phosphoglycerate to 3-phosphohydroxypyruvate;

(b) at least one endogenous or exogenous nucleic acid molecule encoding an enzyme having 3-phosphoglycerate phosphatase activity and/or an enzyme having glycerate 3-kinase activity that catalyzes the conversion of 3-phosphoglycerate to glycerate;

(c) at least one endogenous or exogenous nucleic acid molecule encoding an enzyme having 2-phosphoglycerate phosphatase activity and/or an enzyme having glycerate 2-kinase activity that catalyzes the conversion of 2-phosphoglycerate to glycerate;

(d) at least one endogenous or exogenous nucleic acid molecule encoding an enzyme having phosphoserine aminotransferase activity that catalyzes the conversion of 3-phosphohydroxypyruvate from (a) to phospho-L-serine;

(e) at least one endogenous or exogenous nucleic acid molecule encoding an enzyme having 3-phosphohydroxypyruvate phosphatase activity that catalyzes the conversion of 3-phosphohydroxypyruvate from (a) to hydroxypyruvate;

(f) at least one endogenous or exogenous nucleic acid molecule encoding an enzyme having phosphoserine phosphatase activity that catalyzes the conversion of phospho-L-serine from (d) to L-serine;

(g) at least one endogenous or exogenous nucleic acid molecule encoding an enzyme having hydroxypyruvate reductase activity that catalyzes the conversion of glycerate from (b) and/or (c) to hydroxypyruvate;

(h) at least one endogenous or exogenous nucleic acid molecule encoding an enzyme having serine-pyruvate aminotransferase activity that catalyzes the conversion of hydroxypyruvate from (e) and/or (g) to L-serine; wherein the produced intermediate DHAP from embodiments [H] and/or [I] and/or pyruvate from embodiment [J] is converted to 3-phosphoglycerate and/or 2-phosphoglycerate through endogenous glycolysis or gluconeogenesis in the microorganism, and wherein MEG (or glycolic acid) and serine are produced.

Production of Glycine (Gly)

Gly is produced by natural pathways, for instance via Ser, or variations thereof.

In one embodiment, Gly is produced via a Ser based pathway. In the Ser based pathway, 5,10-methylene tetrahydrofolate (M-THF) is produced from THF and L-serine is converted to glycine by a serine hydroxymethyltransferase. M-THF is utilized in the biosynthesis of various cellular compounds, for instance in methylation reactions.

In a preferred embodiment, M-THF can also be used to produce two more NADH or one NADH and one H2:

M-THF+$H_2O$↔THF+formaldehyde (EC 2.1.2.-; transferases such as hydroxymethyl-, formyl- and related transferases that transfers one-carbon group), subsequent oxidation of formaldehyde (EC 1.2.1.46; formaldehyde dehydrogenase) to formate and NADH, and further oxidation of formate to $CO_2$ and NADH (formate dehydrogenase, FDH) or $CO_2$ and H2 (formate hydrogenlyase complex).

In some embodiments, this reconstitution of THF, if done partially, can be used to generate just enough NADH to perform another, distinct glycine biosynthesis route. In one embodiment, the route via the glycine cleavage system, which utilizes M-THF, $NH_3$, $CO_2$ and NADH to synthesize glycine directly, can be used together with the serine based glycine production to utilize the generated excess M-THF to generate more glycine.

The glycine-cleavage system (GCV) is a multienzyme complex that catalyzes the reversible oxidation of glycine, yielding carbon dioxide, ammonia, 5,10-methylenetetrahydrofolate (M-THF) and a reduced pyridine nucleotide:

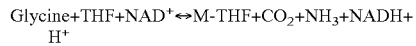

Tetrahydrofolate serves as a recipient for one-carbon units generated during glycine cleavage to form the methylene group. The GCV system consists of four protein components, the P protein, H protein, T protein, and L protein. P protein (EC 1.4.4.2, glycine dehydrogenase (decarboxylating)) catalyzes the pyridoxal phosphate-dependent liberation of $CO_2$ from glycine, leaving a methylamine moiety. The methylamine moiety is transferred to the lipoic acid group of the H protein, which is bound to the P protein prior to decarboxylation of glycine. The T protein (EC 2.1.2.10, aminomethyltransferase) catalyzes the release of $NH_3$ from the methylamine group and transfers the remaining C1 unit to THF, forming 5,10-mTHF. The L protein (EC 1.8.1.4, dihydrolipoyl dehydrogenase) then oxidizes the lipoic acid component of the H protein and transfers the electrons to NAD+, forming NADH.

The same set of enzymes is sometimes referred to as glycine synthase when it runs in the reverse direction to form glycine. In the anaerobic bacteria, *Clostridium acidiurici*, the glycine cleavage system runs mostly in the direction of glycine synthesis.

Alternatively, in another embodiment, glycine can also be produced via transamination of glyoxylate by alanine-glyoxylate aminotransferase (EC 2.6.1.44). Though in organisms like *Saccharomyces cerevisiae*, this pathway is only expressed during growth on non-fermentable carbon sources like ethanol or acetate, this pathway can be readily overexpressed in any microorganism. The amino group donor alanine gets reconstituted by transamination with glutamate (alanine transaminase, EC 2.6.1.2), which in turn gets reconstituted by fixation of ammonia by a NADH or NADPH dependent glutamate dehydrogenase (EC 1.4.1.2 or EC 1.4.1.3). In one embodiment, this glycine pathway avoids the intermediate L-serine and does not lead to the production of M-THF, but rather directly produces two reducing equivalents such as NADH.

In some embodiments, the production of MEG (or glycolic acid) and glycine is closer to the thermodynamic maximum yield potential using the lossless conversion of one or more hexose to one or more pentose-5-phosphate intermediates, followed by the conversion of the one or more pentose-5-phosphate intermediates to one or more pentose-1-phosphate and/or pentose intermediates, and then followed by the co-production of MEG (or glycolic acid) via a C2 pathway and glycine via a C3 pathway from the one or more pentose-1-phosphate and/or pentose intermediates. In some embodiments, the thermodynamic yield potential is 37% better for co-production of MEG (or glycolic acid) and glycine via the pathways disclosed in the present application compared to production of glycine made from glucose by the natural, standard C3 pathway.

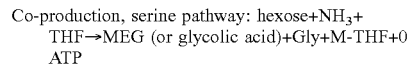

Co-production, serine pathway, assuming THF reconstitution via formate and using FDH:

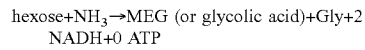

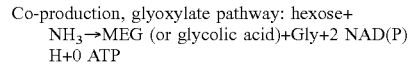

Co-production, serine pathway, assuming partial THF reconstitution via formate and FDH plus glycine synthesis via glycine cleavage system:

Partial THF reconstitution through NADH production: M-THF→2/3 M-THF+1/3 THF+2/3 NADH Utilization of remaining M-THF and generated NADH for glycine cleavage system:

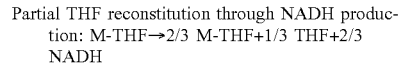

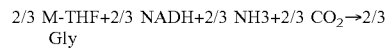

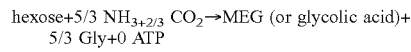

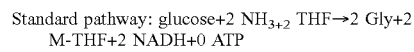

In some embodiments, MEG (or glycolic acid) and glycine are co-produced from the lossless transformation of one or more hexose feedstock to one or more pentose-5-phosphate intermediate, followed by a conversion of the one or more pentose-5-phosphate intermediate to one or more pentose and/or pentose-1-phosphate intermediate, followed by a conversion of the one or more pentose and/or pentose-1-phosphate intermediate to MEG (or glycolic acid) and DHAP or pyruvate via a C2 pathway, and a conversion of DHAP or pyruvate to glycine via a C3 pathway. In some embodiments, the C2 pathway comprises embodiment [H]. In further embodiments, the C2 pathway comprises embodiment [I]. In yet further embodiments, the C2 pathway comprises embodiment [J].

In some embodiments, the C2 pathway for production of MEG (or glycolic acid) comprises embodiment [H] and the C3 pathway for production of glycine comprises embodiment [R]. In other embodiments, the C2 pathway for production of MEG (or glycolic acid) comprises embodiment [H] and the C3 pathway for production of glycine comprises embodiment [S]. In further embodiments, the C2 pathway for production of MEG (or glycolic acid) comprises embodiment [H] and the C3 pathway for production of glycine comprises embodiment [T]. In some embodiments, the C2 pathway for production of MEG (or glycolic acid) comprises embodiment [I] and the C3 pathway for production of glycine comprises embodiment [R]. In other embodiments, the C2 pathway for production of MEG (or glycolic acid) comprises embodiment [I] and the C3 pathway for production of glycine comprises embodiment [S]. In further embodiments, the C2 pathway for production of MEG (or glycolic acid) comprises embodiment [I] and the C3 pathway for production of glycine comprises embodiment [T]. In some embodiments, the C2 pathway for production of MEG (or glycolic acid) comprises embodiment [J] and the C3 pathway for production of glycine comprises embodiment [R]. In other embodiments, the C2 pathway for production of MEG (or glycolic acid) comprises embodiment [J] and the C3 pathway for production of glycine comprises embodiment [S]. In further embodiments, the C2 pathway for production of MEG (or glycolic acid) comprises embodiment [J] and the C3 pathway for production of glycine comprises embodiment [T].

[R] In one embodiment, the application relates to a recombinant microorganism capable of producing monoethylene glycol (MEG) (or glycolic acid) and glycine, from one or more hexose feedstock and a nitrogen source, wherein the recombinant microorganism from embodiment [A] or from embodiment [B] (and optionally comprising embodiment [C]), and comprising additionally one or more of embodiments [D], [E], [F] and [G], further comprising one or more of embodiments [H], [I], and [J], further expresses one or more of the following from (a) to (e):
(a) at least one endogenous or exogenous nucleic acid molecule encoding an enzyme having serine hydroxymethyltransferase activity that catalyzes the conversion of L-serine and tetrahydrofolate (THF) to glycine and 5,10-methylene tetrahydrofolate (M-THF);
(b) at least one endogenous or exogenous nucleic acid molecule encoding an enzyme having transferase activity that catalyzes the conversion of M-THF from (a) to formaldehyde;
(c) at least one endogenous or exogenous nucleic acid molecule encoding an enzyme having formaldehyde dehydrogenase activity that catalyzes the conversion of formaldehyde from (b) to formate and NADH;
(d) at least one endogenous or exogenous nucleic acid molecule encoding an enzyme having formate dehydrogenase activity that catalyzes the conversion of formate from (c) to $CO_2$ and NADH;
(e) at least one endogenous or exogenous nucleic acid molecule encoding a protein of the glycine cleavage system that catalyze the conversion of M-THF from (a), $CO_2$, $NH_3$ and NADH from (c) or (d) to glycine and THF;
wherein THF is reconstituted from steps (b) through (e), wherein optionally formate from (c) is further oxidized to $CO_2$ and H2 by a formate hydrogenaselyase complex, and wherein MEG (or glycolic acid) and glycine are produced.

[S] In one embodiment, the application relates to a recombinant microorganism capable of co-producing monoethylene glycol (MEG) (or glycolic acid) and glycine, from one or more hexose feedstock and a nitrogen source, wherein the recombinant microorganism from embodiment [A] or from embodiment [B] (and optionally comprising embodiment [C]), and comprising additionally one or more of embodiments [D], [E], [F] and [G], further comprising one or more of embodiments [H], [I], and [J], further expresses one or more of the following from (a) to (k):
(a) at least one endogenous or exogenous nucleic acid molecule encoding an enzyme having 3-phosphoglycerate dehydrogenase activity that catalyzes the conversion of 3-phosphoglycerate to 3-phosphohydroxypyruvate;
(b) at least one endogenous or exogenous nucleic acid molecule encoding an enzyme having phosphoserine aminotransferase activity that catalyzes the conversion of 3-phosphohydroxypyruvate from (a) to phospho-L-serine;
(c) at least one endogenous or exogenous nucleic acid molecule encoding an enzyme having 3-phosphohydroxypyruvate phosphatase activity that catalyzes the conversion of 3-phosphohydroxypyruvate from (a) to hydroxypyruvate;
(d) at least one endogenous or exogenous nucleic acid molecule encoding an enzyme having phosphoserine phosphatase activity that catalyzes the conversion of phospho-L-serine from (b) to L-serine;
(e) at least one endogenous or exogenous nucleic acid molecule encoding an enzyme having L-serine transaminase or serine oxidase activity that catalyzes the conversion of L-serine from (d) to hydroxypyruvate;
(f) at least one endogenous or exogenous nucleic acid molecule encoding an enzyme having hydroxypyruvate decarboxylase activity that catalyzes the conversion of hydroxypyruvate from (c) or (e) to glycolaldehyde;
(g) at least one endogenous or exogenous nucleic acid molecule encoding an enzyme having glycolaldehyde dehydrogenase activity that catalyzes the conversion of glycolaldehyde from (f) to glycolic acid;
(h) at least one endogenous or exogenous nucleic acid molecule encoding an enzyme having glycolate dehydrogenase activity that catalyzes the conversion of glycolic acid from (g) to glyoxylate;
(i) at least one endogenous or exogenous nucleic acid molecule encoding an enzyme having alanine-glyoxylate aminotransferase activity that catalyzes the conversion of glyoxylate from (h) and alanine to glycine and pyruvate;
(j) at least one endogenous or exogenous nucleic acid molecule encoding an enzyme having alanine transaminase activity that catalyzes the conversion of pyruvate from (i) and glutamate to alanine and 2-oxoglutarate;
(k) at least one endogenous or exogenous nucleic acid molecule encoding an enzyme having NAD(P)H dependent glutamate dehydrogenase activity that catalyzes the conversion of 2-oxoglutarate from (j) and ammonia to glutamate;

wherein the produced intermediate DHAP from embodiments [H] and/or [I] and/or pyruvate from embodiment [J] is converted to 3-phosphoglycerate and/or 2-phosphoglycerate through endogenous glycolysis or gluconeogenesis in the microorganism, wherein the glyoxylate for step (i) optionally comes from glyoxylate shunt in the microorganism, wherein alanine and glutamate are reconstituted from steps (j) and (k), and wherein MEG (or glycolic acid) and glycine are co-produced.

[T] In one embodiment, the application relates to a recombinant microorganism capable of co-producing monoethylene glycol (MEG) (or glycolic acid) and glycine, from one or more hexose feedstock and a nitrogen source, wherein the recombinant microorganism from embodiment [A] or from embodiment [B] (and optionally comprising embodiment [C]), and comprising additionally one or more of embodiments [D], [E], [F] and [G], further comprising one or more of embodiments [H], [I], and [J], further expresses one or more of the following from (a) to (1):

(a) at least one endogenous or exogenous nucleic acid molecule encoding an enzyme having 2-phosphoglycerate phosphatase activity and/or an enzyme having glycerate-2-kinase activity that catalyzes the conversion of 2-phosphoglycerate to glycerate;

(b) at least one endogenous or exogenous nucleic acid molecule encoding an enzyme having 3-phosphoglycerate phosphatase activity and/or an enzyme having glycerate-3-kinase activity that catalyzes the conversion of 3-phosphoglycerate to glycerate;

(c) at least one endogenous or exogenous nucleic acid molecule encoding an enzyme having hydroxypyruvate reductase activity that catalyzes the conversion of glycerate from (a) and/or (b) to hydroxypyruvate;

(d) at least one endogenous or exogenous nucleic acid molecule encoding an enzyme having serine aminotransferase or serine oxidoreductase (deaminating) activity that catalyzes the conversion of L-serine to hydroxypyruvate;

(e) at least one endogenous or exogenous nucleic acid molecule encoding an enzyme having L-serine decarboxylase activity that catalyzes the conversion of L-serine to ethanolamine;

(f) at least one endogenous or exogenous nucleic acid molecule encoding an enzyme having hydroxypyruvate decarboxylase activity that catalyzes the conversion of hydroxypyruvate from (c) and/or (d) to glycolaldehyde;

(g) at least one endogenous or exogenous nucleic acid molecule encoding an enzyme having ethanolamine aminotransferase activity or an enzyme having ethanolamine oidoreductase (deaminating) activity that catalyzes the conversion of ethanolamine from (e) to glycolaldehyde;

(h) at least one endogenous or exogenous nucleic acid molecule encoding an enzyme having glycolaldehyde dehydrogenase activity that catalyzes the conversion of glycolaldehyde from (f) and/or (g) to glycolic acid;

(i) at least one endogenous or exogenous nucleic acid molecule encoding an enzyme having glycolate dehydrogenase activity that catalyzes the conversion of glycolic acid from (g) to glyoxylate;

(j) at least one endogenous or exogenous nucleic acid molecule encoding an enzyme having alanine-glyoxylate aminotransferase activity that catalyzes the conversion of glyoxylate from (i) and alanine to glycine and pyruvate;

(k) at least one endogenous or exogenous nucleic acid molecule encoding an enzyme having alanine transaminase activity that catalyzes the conversion of pyruvate from (j) and glutamate to alanine and 2-oxoglutarate;

(l) at least one endogenous or exogenous nucleic acid molecule encoding an enzyme having NAD(P)H dependent glutamate dehydrogenase activity that catalyzes the conversion of 2-oxoglutarate from (k) and ammonia to glutamate;

wherein the produced intermediate DHAP from embodiments [H] and/or [I] and/or pyruvate from embodiment [J] is converted to 3-phosphoglycerate and/or 2-phosphoglycerate through endogenous glycolysis or gluconeogenesis in the microorganism, wherein the glyoxylate for step (j) optionally comes from glyoxylate shunt in the microorganism, wherein alanine and glutamate are reconstituted from steps (k) and (l), and wherein MEG (or glycolic acid) and glycine are co-produced.

In some embodiments, an enzyme having serine hydroxymethyltransferase activity converts L-serine to glycine. In some embodiments, the enzyme that converts L-serine to glycine is encoded by an amino acid sequence having at least 70% sequence identity, having at least 80% sequence identity, or having at least 90% sequence identity to *E. coli* glyA. In some embodiments, the one or more nucleic acid molecule encoding an enzyme having serine hydroxymethyltransferase activity comprises an amino acid sequence set forth in UniProt ID P0A825. In a further embodiment, the one or more nucleic acid molecule encoding an enzyme having serine hydroxymethyltransferase activity is encoded by a nucleic acid sequence set forth in Gene ID 947022.

In some embodiments, an enzyme having transferase activity that transfers one-carbon groups is used to convert M-THF to formaldehyde. Transferases such as the hydroxymethyl-, formyl- and related transferases may be used. Examples of hydroxymethyl-, formyl- and related transferases include glycine hydroxymethyltransferase, phosphoribosylglycinamide formyltransferase, phosphoribosylaminoimidazolecarboxamide formyltransferase, glycine formimidoyltransferase, glutamate formiminotransferase, D-alanine 2-hydroxymethyltransferase, deoxycytidylate 5-hydroxymethyltransferase, methionyl-tRNA formyltransferase, aminomethyltransferase, 3-methyl-2-oxobutanoate hydroxymethyltransferase and UDP-4-amino-4-deoxy-L-arabinose formyltransferase.

In some embodiments, an enzyme having formaldehyde dehydrogenase activity is used to convert formaldehyde to formate and NADH. In some embodiments, the enzyme having formaldehyde dehydrogenase activity is encoded by an amino acid sequence having at least 70% sequence identity, having at least 80% sequence identity, or having at least 90% sequence identity to a formaldehyde dehydrogenase selected from *Saccharomyces cerevisiae* ALD2, *Saccharomyces cerevisiae* ALD3, *Homo sapiens* ALDH3A2, and *Homo sapiens* ALDH9A1. In some embodiments, the one or more nucleic acid molecule encoding an enzyme having formaldehyde dehydrogenase activity comprises an amino acid sequence selected from UniProt ID P47771, UniProt ID P54114, UniProt ID P51648 and UniProt ID P49189. In a further embodiment, the one or more nucleic acid molecule encoding an enzyme having formaldehyde dehydrogenase activity is encoded by a nucleic acid sequence selected from Gene ID 855206, Gene ID 855205, Gene ID 224 and Gene ID 223.

In some embodiments, an enzyme having formate dehydrogenase activity is used to convert formate to $CO_2$ and NADH. In some embodiments, the enzyme having formate dehydrogenase activity is encoded by an amino acid sequence having at least 70% sequence identity, having at least 80% sequence identity, or having at least 90% sequence identity to an enzyme having formate dehydrogenase activity selected from the group consisting of *E. coli* fdhF (chlF, FDH-H), *E. coli* FDH-N, *E. coli* FDH-O, *Candida boidinii* FDH1, *Corynebacterium glutamicum* fdhF, *Cupriavidus oxalaticus* NAD+-dependent formate dehydrogenase, Gottschalkia *acidurici* NAD+-dependent formate dehydrogenase, *Methylobacterium extorquens* Fdh1, *Methylosinus trichosporium* formate dehydrogenase, and *Moraxella* sp. NAD+-dependent formate dehydrogenase fdh. In some embodiments, the one or more nucleic acid molecule encoding an enzyme or subunit of an enzyme associated with formate dehydrogenase activity comprises an amino acid sequence selected from UniProt ID P07658, UniProt ID P0AEK7, UniProt ID P0AAJ3, UniProt ID P24183, UniProt ID P32176, UniProt ID P0AAJ5, UniProt ID P0AEL0, UniProt ID O13437, UniProt ID Q8NSY6, UniProt ID Q8KTI7, UniProt ID Q8KTI8, and UniProt ID O08375. In a further embodiment, the one or more nucleic acid molecule encoding an enzyme or subunit of an enzyme associated with formate dehydrogenase activity comprises a nucleic acid sequence selected from Gene ID 948584, Gene ID 946038, Gene ID 948794, Gene ID 946035, Gene ID 948394, Gene ID 948395, Gene ID 948383, GenBank accession AJ011046.2, Gene ID 1021531, GenBank accession AF489516, and GenBank accession Y13245.1.

In some embodiments, one or more proteins of the glycince cleavage system are used to produce glycine from M-THF, $CO_2$, $NH_3$ and NADH. In some embodiments, the proteins of the glycine cleavage system comprise: i) P-protein (a pyridoxal phosphate-containing protein) or glycine decarboxylase (EC 1.4.4.2), ii) T-protein or aminomethyltransferase (EC 2.1.2.10), iii) L-protein or dihydrolipoamide dehydrogenase (EC1.8.1.4), and iv) a carrier protein called H-protein (a lipoic acid-containing protein). In some embodiments, the enzyme having glycine decarboxylase activity is encoded by an amino acid sequence having at least 70% sequence identity, having at least 80% sequence identity, or having at least 90% sequence identity to *E. coli* gcvP. In some embodiments, the one or more nucleic acid molecule encoding an enzyme having glycine decarboxylase activity comprises an amino acid sequence set forth in UniProt ID P33195. In a further embodiment, the one or more nucleic acid molecule encoding an enzyme having glycine decarboxylase activity comprises a nucleic acid sequence set forth in Gene ID 947394. In some embodiments, the enzyme having aminomethyltransferase activity is encoded by an amino acid sequence having at least 70% sequence identity, having at least 80% sequence identity, or having at least 90% sequence identity to *E. coli* gcvT. In some embodiments, the one or more nucleic acid molecule encoding an enzyme having aminomethyltransferase activity comprises an amino acid sequence set forth in UniProt ID P27248. In a further embodiment, the one or more nucleic acid molecule encoding an enzyme having aminomethyltransferase activity comprises a nucleic acid sequence set forth in Gene ID 947390. In some embodiments, the enzyme having dihydrolipoamide dehydrogenase activity is encoded by an amino acid sequence having at least 70% sequence identity, having at least 80% sequence identity, or having at least 90% sequence identity to *E. coli* lpd (lpdA, E3 subunit). In some embodiments, the one or more nucleic acid molecule encoding an enzyme having dihydrolipoamide dehydrogenase activity comprises an amino acid sequence set forth in UniProt ID P0A9P0. In a further embodiment, the one or more nucleic acid molecule encoding an enzyme having dihydrolipoamide dehydrogenase activity comprises a nucleic acid sequence set forth in Gene ID 944854. In some embodiments, the H-protein is encoded by an amino acid sequence having at least 70% sequence identity, having at least 80% sequence identity, or having at least 90% sequence identity to *E. coli* gcvH. In some embodiments, the one or more nucleic acid molecule encoding an H-protein comprises an amino acid sequence set forth in UniProt ID P0A6T9. In a further embodiment, the one or more nucleic acid molecule encoding an H-protein is encoded by a nucleic acid sequence set forth in Gene ID 947393.

In some embodiments, an enzyme having glycolate dehydrogenase activity is used to convert glycolic acid to glyoxylate. In some embodiments, the enzyme having glycolate dehydrogenase activity is encoded by an amino acid sequence having at least 70% sequence identity, having at least 80% sequence identity, or having at least 90% sequence identity to an enzyme having glycolate dehydrogenase activity selected from *E. coli* glycolate dehydrogenase GLC and *Arabidopsis thaliana* glycolate dehydrogenase. In some embodiments, the one or more nucleic acid molecule encoding an enzyme or enzyme subunit associated with glycolate dehydrogenase activity comprises an amino acid sequence selected from UniProt ID P0AEP9, UniProt ID P52073, UniProt ID P52074, and UniProt ID Q94AX4. In a further embodiment, the one or more nucleic acid molecule encoding an enzyme or enzyme subunit associated with glycolate dehydrogenase activity comprises a nucleic acid sequence selected from Gene ID 947353, Gene ID 2847718, Gene ID 2847717, and GenBank accession Y13245.1.

In some embodiments, an enzyme having alanine-glyoxylate aminotransferase activity is used to convert glyoxylate to glycine. In some embodiments, the enzyme having alanine-glyoxylate aminotransferase activity is encoded by an amino acid sequence having at least 70% sequence identity, having at least 80% sequence identity, or having at least 90% sequence identity to an enzyme having alanine-glyoxylate aminotransferase activity selected from *Saccharomyces cerevisiae* AGX1, *Homo sapiens* AGXT2, *Arabidopsis thaliana* AOAT1 and *Arabidopsis thaliana* AOAT2. In some embodiments, the one or more nucleic acid molecule encoding an enzyme having alanine-glyoxylate aminotransferase activity comprises an amino acid sequence selected from UniProt ID P43567, UniProt ID Q9BYV1, UniProt ID Q9LR30 and UniProt ID Q9S7E9. In a further embodiment, the one or more nucleic acid molecule encoding an enzyme having alanine-glyoxylate aminotransferase activity comprises a nucleic acid sequence selected from Gene ID 850514, Gene ID 64902, TAIR accession AT1G23310 and TAIR accession AT1G70580.

In some embodiments, an enzyme having alanine transaminase activity is used to reconstitute alanine from pyruvate and glutamate. In some embodiments, the enzyme having alanine transaminase activity is encoded by an amino acid sequence having at least 70% sequence identity, having at least 80% sequence identity, or having at least 90% sequence identity to an enzyme having alanine transaminase activity selected from *E. coli* glutamate-pyruvate aminotransferase alaA, *E. coli* glutamate-pyruvate aminotransferase alaB, *E. coli* glutamate-pyruvate aminotransferase alaC, *Homo sapiens* alanine aminotransferase 1 (GPT), *Homo sapiens* alanine aminotransferase 2 (GPT2), *Arenicola marina* alanine transaminase, *Arabidopsis thaliana* tryptophan aminotransferase TAA1, *Arabidopsis thaliana* AOAT1, *Arabidopsis thaliana* AOAT2, *Candida maltosa* alanine aminotransferase, *Clostridium propionicum* alanine aminotransferase, *Pyrococcus furiosus* alanine aminotransferase aat, *Megathyrsus maximus* alanine transaminase, and *Panicum miliaceum* alanine transaminase AlaAT-2. In some embodiments, the one or more nucleic acid molecule encoding an enzyme having alanine transaminase activity comprises an amino acid sequence selected from UniProt ID P0A959, UniProt ID P77434, UniProt ID P24298, UniProt ID Q8TD30, UniProt ID Q9S7N2, UniProt ID Q9LR30, UniProt ID Q9S7E9, UniProt ID Q9P9M8, and UniProt ID P34106. In a further embodiment, the one or more nucleic acid molecule encoding an enzyme having alanine transaminase activity comprises a nucleic acid sequence selected from Gene ID 946772, Gene ID 946850, Gene ID 2875, Gene ID 84706, Gene ID 843393, TAIR accession AT1G23310, TAIR accession AT1G70580, GenBank accession AF163769.1 and GenBank accession X69421.1.

In some embodiments, an enzyme having glutamate dehydrogenase activity is used to reconstitute glutamate from ammonia and 2-oxoglutarate. In some embodiments, the enzyme having glutamate dehydrogenase activity is encoded by an amino acid sequence having at least 70% sequence identity, having at least 80% sequence identity, or having at least 90% sequence identity to an enzyme having glutamate dehydrogenase activity selected from *Saccharomyces cerevisiae* NAD-dependent glutamate dehydrogenase GDH2, *Arabidopsis thaliana* NAD-dependent glutamate dehydrogenase GDH2, *Arabidopsis thaliana* NAD-dependent glutamate dehydrogenase GDH1, *Peptoniphilus asaccharolyticus* NAD-dependent glutamate dehydrogenase gdhA, *Halobacterium salinarum* NAD-dependent glutamate dehydrogenase gdhA, *Thermotoga maritima* glutamate dehydrogenase, *Homo sapiens* glutamate dehydrogenase 1 (GLUD1), *Homo sapiens* glutamate dehydrogenase 2 (GLUD2), *Bacillus subtilis* glutamate dehydrogenase and *Solanum lycopersicum* glutamate dehydrogenase GDH1. In some embodiments, the one or more nucleic acid molecule encoding an enzyme having glutamate dehydrogenase activity comprises an amino acid sequence selected from UniProt ID P33327, UniProt ID Q38946, UniProt ID Q38946, UniProt ID P28997, UniProt ID P29051, UniProt ID P00367, UniProt ID P49448 and UniProt ID P93541. In a further embodiment, the one or more nucleic acid molecule encoding an enzyme having glutamate dehydrogenase activity is encoded by a nucleic acid sequence selected from Gene ID 461927, TAIR accession AT5G07440, TAIR accession AT5G18170, GenBank accession M76403.1, GenBank accession X63837.1, Gene ID 2746, Gene ID 2747 and GenBank accession U48695.1.

Production of Monoethanolamine (MEA)

MEA can be produced via decarboxylation of Ser or transamination of glycolaldehyde.

In some preferred embodiments, serine decarboxylases are utilized, since they are found naturally, i.e. in choline biosynthesis pathways in plants, and the transamination of a glycolaldehyde intermediate would create a cross talk between the MEG and MEA pathway.

Alternatively, in another embodiment, MEA may be formed by ethanolamine ammonia lyase (EC 4.3.1.7) from acetaldehyde and ammonia:

Acetaldehyde+NH$_3$↔ethanolamine

In this case, MEA is not formed via the Ser biosynthesis pathway, but rather from acetyl-CoA and its reduction to acetaldehyde by acetaldehyde dehydrogenase. While the redox situation does not change, this pathway yields +1 ATP versus the Ser based pathway. It also avoids the toxic intermediate Ser, but has the toxic and volatile intermediate acetaldehyde.

In some embodiments, the production of MEG (or glycolic acid) and MEA is very close to the thermodynamic maximum yield potential using the lossless conversion of one or more hexose to one or more pentose-5-phosphate intermediates, followed by the conversion of the one or more pentose-5-phosphate intermediates to one or more pentose-1-phosphate and/or pentose intermediates, and then followed by the co-production of MEG (or glycolic acid) via a C2 pathway and MEA via a C3 pathway from the one or more pentose-1-phosphate and/or pentose intermediates. In some embodiments, the thermodynamic yield potential is 15% better for co-production of MEG (or glycolic acid) and MEA via the pathways disclosed in the present application compared to production of MEA made from glucose by natural or published similar pathways.

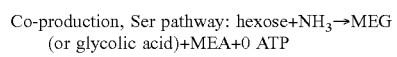

Co-production, Ser pathway: hexose+NH$_3$→MEG (or glycolic acid)+MEA+0 ATP

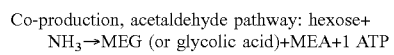

Co-production, acetaldehyde pathway: hexose+ NH$_3$→MEG (or glycolic acid)+MEA+1 ATP Y(pathway)=(0.371+0.365) g/g=0.736 g(MEG (or glycolic acid)+MEA)/g(hexose+NH$_3$), 98% of Y(max)(heat of combustion)=0.749 g/g Standard pathway: glucose+2 NH$_3$→2 MEA+2 NADH+0 ATP

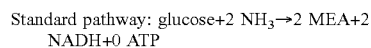

Y(pathway)=0.570 g(MEA)/g(glucose+2NH$_3$), 85% of Y(max)(heat of combustion)=0.669 g/g In some embodiments, MEG (or glycolic acid) and MEA are co-produced from one or more hexose feedstock by the lossless transformation of the one or more hexose feedstock to one or more pentose-5-phosphate intermediate, followed by a conversion of the one or more pentose-5-phosphate intermediate to one or more pentose and/or pentose-1-phosphate intermediate, followed by a conversion of the one or more pentose and/or pentose-1-phosphate intermediate to MEG (or glycolic acid) and DHAP or pyruvate via a C2 pathway, and a conversion of DHAP or pyruvate to MEA via a C3 pathway.

In some embodiments, the C2 pathway for production of MEG (or glycolic acid) comprises embodiment [H] and the C3 pathway for production of MEA comprises embodiment [U]. In other embodiments, the C2 pathway for production of MEG (or glycolic acid) comprises embodiment [H] and the C3 pathway for production of MEA comprises embodiment [V]. In further embodiments, the C2 pathway for production of MEG (or glycolic acid) comprises embodiment [H] and the C3 pathway for production of MEA comprises embodiment [W]. In some embodiments, the C2 pathway for production of MEG (or glycolic acid) comprises embodiment [I] and the C3 pathway for production of MEA comprises embodiment [U]. In other embodiments, the C2 pathway for production of MEG (or glycolic acid) comprises embodiment [I] and the C3 pathway for production of MEA comprises embodiment [V]. In further embodiments, the C2 pathway for production of MEG (or glycolic acid) comprises embodiment [I] and the C3 pathway for production of MEA comprises embodiment [W]. In some embodiments, the C2 pathway for production of MEG (or glycolic acid) comprises embodiment [J] and the C3 pathway for production of MEA comprises embodiment [U]. In other embodiments, the C2 pathway for production of MEG (or glycolic acid) comprises embodiment [J] and the C3 pathway for production of MEA comprises embodiment [V]. In other embodiments, the C2 pathway for production of MEG (or glycolic acid) comprises embodiment [J] and the C3 pathway for production of MEA comprises embodiment [W].

[U] In one embodiment, the application relates to a recombinant microorganism capable of co-producing monoethylene glycol (MEG) (or glycolic acid) and monoethanolamine (MEA), from one or more hexose feedstock and a nitrogen source, wherein the recombinant microorganism from embodiment [A] or from embodiment [B] (and optionally comprising embodiment [C]), and comprising additionally one or more of embodiments [D], [E], [F] and [G], further comprising one or more of embodiments [H], [I], and [J], further expresses one or more of the following from (a) to (i):
- (a) at least one endogenous or exogenous nucleic acid molecule encoding an enzyme having 3-phosphoglycerate dehydrogenase activity that catalyzes the conversion of 3-phosphoglycerate to 3-phosphohydroxypyruvate;
- (b) at least one endogenous or exogenous nucleic acid molecule encoding an enzyme having 3-phosphoglycerate phosphatase activity and/or an enzyme having glycerate 3-kinase activity that catalyzes the conversion of 3-phosphoglycerate to glycerate;
- (c) at least one endogenous or exogenous nucleic acid molecule encoding an enzyme having 2-phosphoglycerate phosphatase activity and/or an enzyme having glycerate 2-kinase activity that catalyzes the conversion of 2-phosphoglycerate to glycerate;
- (d) at least one endogenous or exogenous nucleic acid molecule encoding an enzyme having phosphoserine aminotransferase activity that catalyzes the conversion of 3-phosphohydroxypyruvate from (a) to phospho-L-serine;
- (e) at least one endogenous or exogenous nucleic acid molecule encoding an enzyme having 3-phosphohydroxypyruvate phosphatase activity that catalyzes the conversion of 3-phosphohydroxypyruvate from (a) to hydroxypyruvate;
- (f) at least one endogenous or exogenous nucleic acid molecule encoding an enzyme having phosphoserine phosphatase activity that catalyzes the conversion of phospho-L-serine from (d) to L-serine;
- (g) at least one endogenous or exogenous nucleic acid molecule encoding an enzyme having hydroxypyruvate reductase activity that catalyzes the conversion of glycerate from (b) and/or (c) to hydroxypyruvate;
- (h) at least one endogenous or exogenous nucleic acid molecule encoding an enzyme having serine-pyruvate aminotransferase activity that catalyzes the conversion of hydroxypyruvate from (e) and/or (g) to L-serine;
- (i) at least one endogenous or exogenous nucleic acid molecule encoding an enzyme having serine decarboxylase activity that catalyzes the conversion of L-serine from (f) and/or (h) to MEA;
- wherein the produced intermediate DHAP from embodiments [H] and/or [I] and/or pyruvate from embodiment [J] is converted to 3-phosphoglycerate and/or 2-phosphoglycerate through endogenous glycolysis or gluconeogenesis in the microorganism, and wherein MEG (or glycolic acid) and MEA are co-produced.

[V] In one embodiment, the application relates to a recombinant microorganism capable of co-producing monoethylene glycol (MEG) (or glycolic acid) and monoethanolamine (MEA) from one or more hexose feedstock and a nitrogen source, wherein the recombinant microorganism from embodiment [A] or from embodiment [B] (and optionally comprising embodiment [C]), and comprising additionally one or more of embodiments [D], [E], [F], and [G], further comprising one or more of embodiments [H], [I], and [J], further expresses one or more of the following from (a) to (f):
- (a) at least one endogenous or exogenous nucleic acid molecule encoding an enzyme having 2-phosphoglycerate phosphatase activity and/or an enzyme having glycerate-2-kinase activity that catalyzes the conversion of 2-phosphoglycerate to glycerate;
- (b) at least one endogenous or exogenous nucleic acid molecule encoding an enzyme having 3-phosphoglycerate phosphatase activity and/or an enzyme having glycerate-3-kinase activity that catalyzes the conversion of 3-phosphoglycerate to glycerate;
- (c) at least one endogenous or exogenous nucleic acid molecule encoding an enzyme having hydroxypyruvate reductase activity that catalyzes the conversion of glycerate from (a) and/or (b) to hydroxypyruvate;
- (d) at least one endogenous or exogenous nucleic acid molecule encoding an enzyme having serine-pyruvate aminotransferase or serine oxidoreductase (deaminating) activity that catalyzes the conversion of L-serine to hydroxypyruvate;
- (e) at least one endogenous or exogenous nucleic acid molecule encoding an enzyme having hydroxypyruvate decarboxylase activity that catalyzes the conversion of hydroxypyruvate from (c) and/or (d) to glycolaldehyde;
- (f) at least one endogenous or exogenous nucleic acid molecule encoding an enzyme having transaminase activity that catalyzes the conversion of glycolaldehyde from (e) to MEA;
- wherein the produced intermediate DHAP from embodiments [H] and/or [I] and/or pyruvate from embodiment [J] is converted to 3-phosphoglycerate and/or 2-phosphoglycerate through endogenous glycolysis or gluconeogenesis in the microorganism, and wherein MEG (or glycolic acid) and MEA are co-produced.

[W] In one embodiment, the application relates to a recombinant microorganism capable of co-producing monoethylene glycol (MEG) (or glycolic acid) and monoethanolamine (MEA) from one or more hexose feedstock and a nitrogen source, wherein the recombinant microorganism from embodiment [A] or from embodiment [B] (and optionally comprising embodiment [C]), and comprising additionally one or more of embodiments [D], [E], [F], and [G], further comprising one or more of embodiments [H], [I], and [J], further expresses one or more of the following from (a) to (b):
- (a) at least one endogenous or exogenous nucleic acid molecule encoding an enzyme having acetaldehyde dehydrogenase activity that catalyzes the conversion of acetyl-CoA to acetaldehyde;
- (b) at least one endogenous or exogenous nucleic acid molecule encoding an enzyme having ethanolamine ammonia lyase activity that catalyzes the conversion of acetaldehyde and ammonia to MEA;
- wherein the produced intermediate DHAP from embodiments [H] and/or [I] and/or pyruvate from embodiment [J] is converted to acetyl-CoA through endogenous glycolysis in the microorganism, and wherein MEG (or glycolic acid) and MEA are co-produced.

In some embodiments, an enzyme having acetaldehyde dehydrogenase activity is used to reduce acetyl-CoA to acetaldehyde. In some embodiments, the enzyme having acetaldehyde dehydrogenase activity is encoded by an amino acid sequence having at least 70% sequence identity, having at least 80% sequence identity, or having at least 90% sequence identity to an enzyme having acetaldehyde dehydrogenase activity selected from E. coli mhpF, E. coli AdhE, Chlamydomonas reinhardtii ADH1, Leuconostoc mesenteroides CoA-dependent acetaldehyde dehydrogenase, Pelobacter acetylenicus acetaldehyde dehydrogenase, Pseudomonas sp. dmpF, Pseudomonas putida acylating aldehyde dehydrogenase todl, Pseudomonas putida acetaldehyde dehydrogenase cmtH and Clostridium acetobutylicum alcohol/aldehyde dehydrogenase AdhE. In some embodiments, the one or more nucleic acid molecule encoding an enzyme having acetaldehyde dehydrogenase activity comprises an amino acid sequence selected from UniProt ID P77580, UniProt P0A9Q7, UniProt ID A8JI07, UniProt ID Q52060, UniProt ID Q51949 and UniProt ID P33744. In a further embodiment, the one or more nucleic acid molecule encoding an enzyme having acetaldehyde dehydrogenase activity comprises a nucleic acid sequence selected from Gene ID 945008, Gene ID 945837, Gene ID 5729132, GenBank accession X60835.1, GenBank accession U09250.1 and Gene ID 1116167.

In some embodiments, an enzyme having ethanolamine ammonia lyase activity is used to convert acetaldehyde and ammonia to MEA. In some embodiments, the enzyme having ethanolamine ammonia lyase activity is encoded by an amino acid sequence having at least 70% sequence identity, having at least 80% sequence identity, or having at least 90% sequence identity to an E. coli ethanolamine ammonia lyase. In some embodiments, the one or more nucleic acid molecule encoding an ethanolamine ammonia lyase subunit comprises an amino acid sequence selected from UniProt ID P0AEJ6 and UniProt ID P19636. In a further embodiment, the one or more nucleic acid molecule encoding an ethanolamine ammonia lyase subunit is encoded by a nucleic acid sequence selected from Gene ID 946924 and Gene ID 946925.

Production of Ethylenediamine (EDA)

Figure 11:
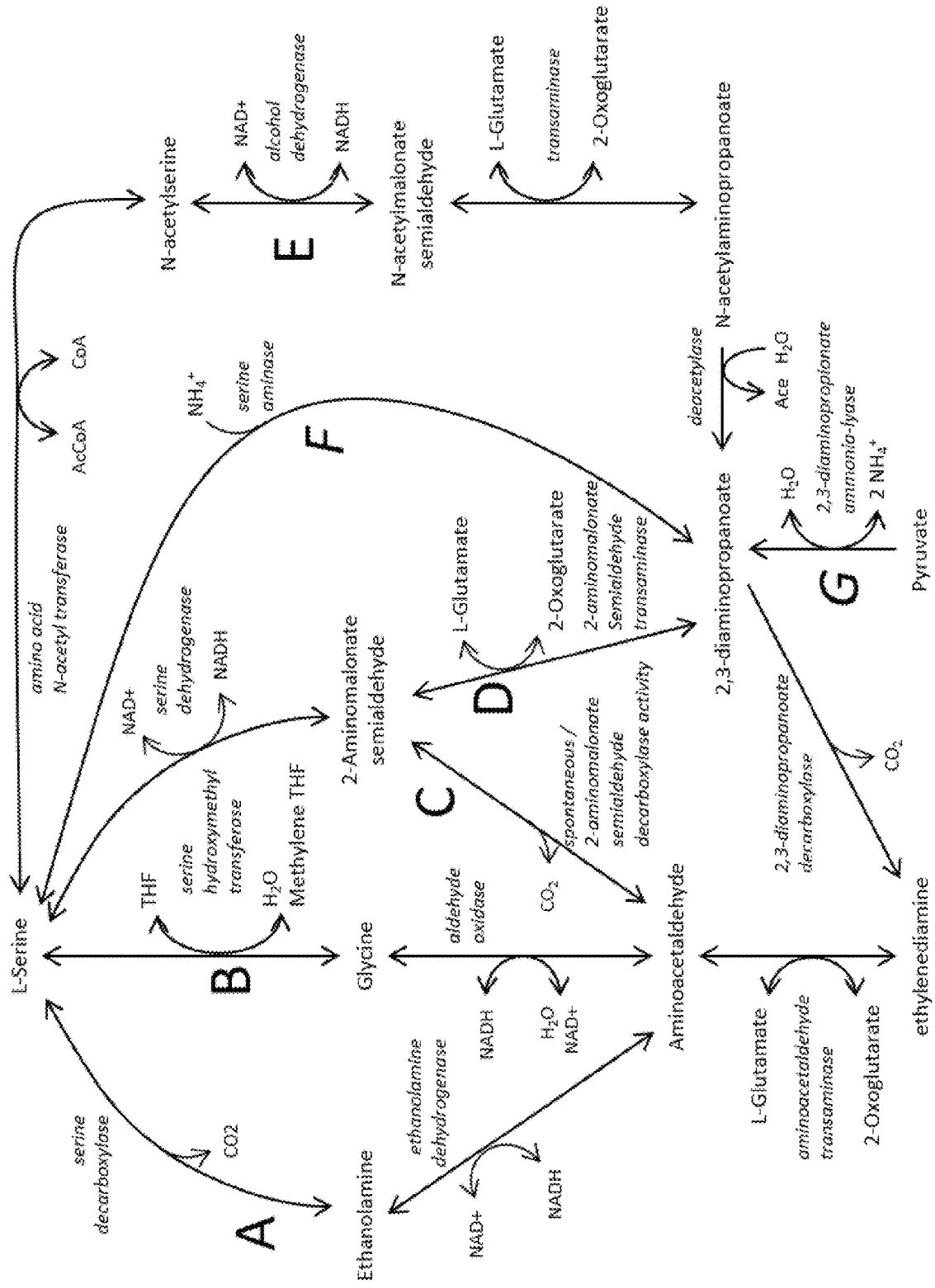
FIG. 11 illustrates published EDA production pathways. From WO 2014/049382. Reaction F: direct L-serine amination via L-serine aminase. Reaction G: direct pyruvate amination via 2,3-diaminopropionate ammonia lyase.

EDA can be produced by any of the pathways A through E described in WO 2014/049382, which is herein incorporated in its entirety (FIG. 11).

In some embodiments, MEG (or glycolic acid) and EDA are co-produced from one or more hexose feedstock by the lossless transformation of the one or more hexose feedstock to one or more pentose-5-phosphate intermediate, followed by a conversion of the one or more pentose-5-phosphate intermediate to one or more pentose and/or pentose-1-phosphate intermediate, followed by a conversion of the one or more pentose and/or pentose-1-phosphate intermediate to MEG (or glycolic acid) and DHAP or pyruvate via a C2 pathway, and a conversion of DHAP or pyruvate to EDA via a C3 pathway.

In some embodiments, the C2 pathway for production of MEG (or glycolic acid) comprises embodiment [H] and the C3 pathway for production of EDA comprises embodiment [X]. In other embodiments, the C2 pathway for production of MEG (or glycolic acid) comprises embodiment [H] and the C3 pathway for production of EDA comprises embodiment [Y]. In further embodiments, the C2 pathway for production of MEG (or glycolic acid) comprises embodiment [H] and the C3 pathway for production of EDA comprises embodiment [Z]. In yet further embodiments, the C2 pathway for production of MEG (or glycolic acid) comprises embodiment [H] and the C3 pathway for production of EDA comprises embodiment [AA]. In other embodiments, the C2 pathway for production of MEG (or glycolic acid) comprises embodiment [H] and the C3 pathway for production of EDA comprises embodiment [BB].

In some embodiments, the C2 pathway for production of MEG (or glycolic acid) comprises embodiment [I] and the C3 pathway for production of EDA comprises embodiment [X]. In other embodiments, the C2 pathway for production of MEG (or glycolic acid) comprises embodiment [I] and the C3 pathway for production of EDA comprises embodiment [Y]. In further embodiments, the C2 pathway for production of MEG (or glycolic acid) comprises embodiment [I] and the C3 pathway for production of EDA comprises embodiment [Z]. In yet further embodiments, the C2 pathway for production of MEG (or glycolic acid) comprises embodiment [I] and the C3 pathway for production of EDA comprises embodiment [AA]. In other embodiments, the C2 pathway for production of MEG (or glycolic acid) comprises embodiment [I] and the C3 pathway for production of EDA comprises embodiment [BB].

In some embodiments, the C2 pathway for production of MEG (or glycolic acid) comprises embodiment [J] and the C3 pathway for production of EDA comprises embodiment [X]. In other embodiments, the C2 pathway for production of MEG (or glycolic acid) comprises embodiment [J] and the C3 pathway for production of EDA comprises embodiment [Y]. In other embodiments, the C2 pathway for production of MEG (or glycolic acid) comprises embodiment [J] and the C3 pathway for production of EDA comprises embodiment [Z]. In other embodiments, the C2 pathway for production of MEG (or glycolic acid) comprises embodiment [J] and the C3 pathway for production of EDA comprises embodiment [AA]. In other embodiments, the C2 pathway for production of MEG (or glycolic acid) comprises embodiment [J] and the C3 pathway for production of EDA comprises embodiment [BB].

[X] In one embodiment, the application relates to a recombinant microorganism capable of co-producing monoethylene glycol (MEG) (or glycolic acid) and ethylenediamine (EDA), from one or more hexose feedstock and a nitrogen source, wherein the recombinant microorganism from embodiment [A] or from embodiment [B] (and optionally comprising embodiment [C]), and comprising additionally one or more of embodiments [D], [E], [F] and [G], further comprising one or more of embodiments [H], [I], and [J], further expresses one or more of the following from (a) to (c):

(a) at least one endogenous or exogenous nucleic acid molecule encoding an enzyme having serine dehydrogenase activity that catalyzes the conversion of L-serine to 2-aminomalonate semialdehyde;

(b) at least one endogenous or exogenous nucleic acid molecule encoding an enzyme having 2-aminomalonate semialdehyde decarboxylase activity that catalyzes the conversion of 2-aminomalonate semialdehyde from (a) to aminoacetaldehyde;

(c) at least one endogenous or exogenous nucleic acid molecule encoding an enzyme having aminoacetaldehyde transaminase activity that catalyzes the conversion of aminoacetaldehyde from (b) to EDA;

wherein 2-aminomalonate semialdehyde may optionally be converted to aminoacetaldehyde by a spontaneous reaction, and wherein MEG (or glycolic acid) and EDA are co-produced.

According to this aspect of the disclosure, the recombinant microorganism overexpresses at least one of the genes encoding enzymes exhibiting activity of serine dehydrogenase and aminoacetaldehyde transaminase. These genes may be endogenous genes or exogenous genes.

The first reaction of the conversion of L-serine into 2-aminomalonate semialdehyde is catalysed by a serine dehydrogenase enzyme. This enzyme belongs to the large enzyme family of alcohol dehydrogenases also called aldehyde reductases. Several enzymes are known to exhibit serine dehydrogenase activity. In one embodiment of the disclosure, these enzymes are encoded by genes chosen among a list of genes well known in the art (Chowdhury et al., 1996, Yao et al., 2010, Tchigvintsev et al., 2012, Fujisawa et al., 2003, Hawes et al., 1996 and Lokanath et al., 2005), including but not limited to the genes listed here: mmsB from *Pseudomonas putida*, from *Synechococcus* PCC6301 or from *Bacillus cereus*; hibdh from *Pseudomonas putida* E23; PA0743 from *Pseudomonas aeruginosa*; ydfG from *Escherichia coli* or from *Bacillus brevis* or from *Bacillus subtilis*; sdh from *Agrobacterium tumefaciens*; hibadh from *Rattus norvegicus* or from *Thermus thermophilus* HB8; yiaY from *Escherichia coli*.

In a preferred embodiment of the disclosure, the serine dehydrogenase is encoded by ydfG from *Escherichia coli* or mmsB from *Pseudomonas putida*, or yiaY from *Escherichia coli*. Preferably, these enzymes are optimized by mutating the encoding genes in order to improve their catalytic efficiency of L-serine into 2-aminomalonate semialdehyde.

In another embodiment of the disclosure the serine dehydrogenase enzyme is obtained by evolving enzymes in order to modify their substrate specificity and/or their catalytic efficiency to obtain an enzyme which exhibits specificity for serine and activity of serine dehydrogenase. These enzymes are selected among the group of enzymes having the same type of catalytic activity on substrates chemically similar to L-serine. Preferably these enzymes may be chosen among 3-hydroxyisobutyrate dehydrogenases and serine dehydrogenases. More preferably they are encoded by genes chosen among a list of genes well known in the art, including but not limited to the genes here: gldA from *Escherichia coli* or from *Leuconostoc citreum* or from *Symbiobacterium thermophilum*; yqhE from *Escherichia coli*; yafB from *Escherichia coli*; alr from *Leishmania donovani*; sakR1 from *Synechococcus* sp.; yhdN from *Bacillus subtilis*; ytbE from *Bacillus subtilis*; AKR4C9 from *Arabidopsis thaliana*; fucO from *Escherichia coli*. Any polypeptide having at least 90% sequence identity to any of the polypeptides encoded by these genes may be used.

Evolution of these enzymes is carried out by means and methods well known by one skilled in the art in order to obtain enzyme having improved specificity for the substrate L-serine and/or enabling to convert it into 2-aminomalonate semialdehyde with an improved activity. The selection of the evolved enzymes is performed by expressing the evolved enzymes in the microorganism of the disclosure or in vitro with L-serine as substrate and by detecting the product 2-aminomalonate semialdehyde.

The second reaction of the conversion of 2-aminomalonate semialdehyde into aminoacetaldehyde is performed spontaneously in the cell (Fujisawa et al., 2003). In another embodiment of the disclosure, the second reaction of conversion of 2-aminomalonate semialdehyde into aminoacetaldehyde is catalysed by an enzyme having 2-aminomalonate semialdehyde decarboxylase activity. This enzyme is not encountered naturally. Therefore it is obtained by evolution of known enzyme or by screening metagenomic libraries. The 2-aminomalonate semialdehyde decarboxylase activity is performed with an evolved amino acid decarboxylase or an evolved keto-acid decarboxylase which catalyses the decarboxylation of amino acids or keto acids. Preferably an evolved amino acid decarboxylase is chosen.

More preferably the evolved amino acid decarboxylase is chosen among histidine decarboxylase, serine decarboxylase, aspartate decarboxylase, diaminobutanoate decarboxylase, omithine decarboxylase. These enzymes are encoded by genes chosen among a list of genes well known in the art, including but not limited to the genes listed here: sdc from *Arabidopsis thaliana*; panD from *Aquifex aeolicus* or from *Bacillus subtilis*; GAD or GAD2 or GAD3 or GAD4 or GAD5 from *Arabidopsis thaliana*; GAD or GAD2 or OAZ1 or ODC1 from *Bos Taurus*; gadA or gadB or panD or speC or speF from *Escherichia coli*; SCC105.13 from *Streptomyces coelicolor*; gadB from *Mannheimia succiniciproducens*; bdb from *Haloferax volcanii*; odcl from *Lactobacillus* sp.; kivD from *Lactococcus lactis* subsp. *Lactis*; kdcA from *Lactococcus lactis*; OAZ1 or ODC1 from *Bos taurus*; speC or speF from *Escherichia coli*; SPE1 from *Saccharomyces cerevisiae*. Any polypeptide having at least 90% sequence identity to any of the polypeptides encoded by these genes may be used. Preferably, the sdc gene from *Arabidopsis thaliana* is used for obtaining the 2-aminomalonate semialdehyde decarboxylase activity.

Evolution of these enzymes is carried out by means and methods well known by one skilled in the art in order to obtain enzymes having specificity for the substrate 2-aminomalonate semialdehyde and enabling to convert it into aminoacetaldehyde. The selection of the evolved enzyme is performed by expressing the evolved enzyme in the microorganism of the invention or in vitro with 2-aminomalonate semialdehyde as substrate and by quantifying the product aminoacetaldehyde.

The last reaction of the conversion of aminoacetaldehyde into ethylenediamine is catalysed by an aminoacetaldehyde transaminase. This enzyme is not encountered naturally. Therefore it is obtained by evolution of a known enzyme or by screening metagenomic libraries. In one embodiment of the invention, the aminoacetaldehyde transaminase activity is performed with an evolved transaminase or aminotransferase which catalyses the exchange of an amino group of one molecule with an oxo group on another molecule. Preferably, the evolved aminotransferase is chosen among phosphoserine aminotransferase or aspartate aminotransferase or glutamate aminotransferase. More preferably, the evolved aminotransferase is chosen among aminotransferases using glutamate as amino group donor. These enzymes are encoded by genes chosen among a list of genes well known in the art, including but not limited to the genes listed here: serC from *Escherichia coli* or from *Bacillus subtilis* or from *Corynebacterium glutamicum*; GOT1 from *Sus scrofa*; patA from *Escherichia coli*; ygjG from *Brucella canis*; rocD from *Rhizobium* NGR 234 or from *Streptomyces avermitilis*; SCO1284 from *Streptomyces coelicolor*; AGT or AGT2 or AGT3 or GGT1 from *Arabidopsis thaliana*; AGXT from *Bos taurus*. Any polypeptide having at least 90% sequence identity to any of the polypeptides encoded by these genes may be used. Preferably, genes serC from *Escherichia coli* or GOT1 from *Sus scrofa* are used for obtaining the aminoacetaldehyde transaminase activity.

Evolution of these enzymes is carried out by means and methods well known by one skilled in the art in order to obtain enzymes having specificity for the substrate aminoacetaldehyde and enabling to convert it into ethylenediamine. The selection of the evolved enzyme is done by expressing the evolved enzyme in the microorganism of the invention or in vitro with aminoacetaldehyde as substrate and by detecting the product ethylenediamine.

In another embodiment of the disclosure, aminoacetaldehyde transaminase enzymes can be isolated from strains growing on ethylenediamine as sole carbon and nitrogen source. For this purpose enrichment cultures from environmental samples on ethylenediamine are cultivated on minimal medium with ethylenediamine as sole nitrogen and carbon source. Metagenomic libraries are generated from these cultures and screened for the presence of aminoacetaldehyde transaminase enzymes. This approach allows isolating the gene corresponding to the enzymatic activity and is well-known to the expert in the field.

According to a specific aspect of the disclosure, the microorganism from embodiment [X] is engineered to overexpress at least one of the following genes: ydfG gene or mmsB gene or yiaY gene, encoding for the serine dehydrogenase; and/or an evolved serC gene or GOT1 gene, encoding for the aminoacetaldehyde transaminase activity.

[Y] In one embodiment, the application relates to a recombinant microorganism capable of co-producing monoethylene glycol (MEG) (or glycolic acid) and ethylenediamine (EDA), from one or more hexose feedstock and a nitrogen source, wherein the recombinant microorganism from embodiment [A] or from embodiment [B] (and optionally comprising embodiment [C]), and comprising additionally one or more of embodiments [D], [E], [F] and [G], further comprising one or more of embodiments [H], [I], and [J], further expresses one or more of the following from (a) to (c):
  (a) at least one endogenous or exogenous nucleic acid molecule encoding an enzyme having serine dehydrogenase activity that catalyzes the conversion of L-serine to 2-aminomalonate semialdehyde;
  (b) at least one endogenous or exogenous nucleic acid molecule encoding an enzyme having 2-aminomalonate semialdehyde transaminase activity that catalyzes the conversion of 2-aminomalonate semialdehyde from (a) to 2,3-diaminopropanoate;
  (c) at least one endogenous or exogenous nucleic acid molecule encoding an enzyme having 2,3-diaminopropanoate decarboxylase activity that catalyzes the conversion of 2,3-diaminopropanoate from (b) to EDA;
  wherein MEG (or glycolic acid) and EDA are co-produced.

According to this aspect of the disclosure, the recombinant microorganism overexpresses at least one of the genes encoding enzymes exhibiting activity of serine dehydrogenase, 2-aminomalonate semialdehyde transaminase and 2,3-diaminopropanoate decarboxylase. These genes may be endogenous genes or exogenous genes.

The first reaction of conversion of L-serine into 2-aminomalonate semialdehyde is catalysed by a serine dehydrogenase enzyme. This enzyme belongs to the large enzyme family of alcohol dehydrogenases also called aldehyde reductases. Several enzymes are known to exhibit serine dehydrogenase activity. In one embodiment of the disclosure, the serine dehydrogenase is chosen among these known enzymes. These enzymes are encoded by genes chosen among a list of genes well known in the art (Chowdhury et al., 1996, Yao et al., 2010, Tchigvintsev et al., 2012, Fujisawa et al., 2003, Hawes et al., 1996 and Lokanath et al., 2005), including but not limited to the genes listed here: mmsB from *Pseudomonas putida*, from *Synechococcus* PCC6301 or from *Bacillus cereus*; hibdh from *Pseudomonas putida* E23; PA0743 from *Pseudomonas aeruginosa*; ydfG from *Escherichia coli* or from *Bacillus brevis* or from *Bacillus subtilis*; sdh from *Agrobacterium tumefaciens*; hibadh from *Rattus norvegicus* or from *Thermus thermophilus* HB8; yiaY from *Escherichia coli*.

In a preferred embodiment of the disclosure, the serine dehydrogenase is encoded by ydfG from *Escherichia coli* or mmsB from *Pseudomonas putida*, or yiaY from *Escherichia coli*. Preferably, these enzymes are optimized by mutating the encoding genes in order to improve their catalytic efficiency of L-serine into 2-aminomalonate semialdehyde.

In another embodiment of the disclosure the serine dehydrogenase enzyme is obtained by evolving enzymes in order to modify their substrate specificity and/or their catalytic efficiency to obtain an enzyme which exhibits specificity for serine and activity of serine dehydrogenase. These enzymes are selected among the group of enzymes having the same type of catalytic activity on substrates chemically similar to L-serine. Preferably these enzymes may be chosen among 3-hydroxyisobutyrate dehydrogenases and serine dehydrogenases. More preferably they are encoded by genes chosen among a list of genes well known in the art, including but not limited to the genes here: gldA from *Escherichia coli* or from *Leuconostoc* citreum or from Symbiobacterium *thermophilum*; yqhE from *Escherichia coli*; yafB from *Escherichia coli*; alr from *Leishmania donovani*; sakR1 from Synechococcus sp.; yhdN from *Bacillus subtilis*; ytbE from *Bacillus subtilis*; AKR4C9 from *Arabidopsis thaliana*; fucO from *Escherichia coli*. Any polypeptide having at least 90% sequence identity to any of the polypeptides encoded by these genes may be used.

Evolution of these enzymes is carried out by means and methods well known by one skilled in the art in order to obtain enzyme having improved specificity for the substrate L-serine and/or enabling to convert it into 2-aminomalonate semialdehyde with an improved activity. The selection of the evolved enzymes is performed by expressing the evolved enzymes in the microorganism of the disclosure or in vitro with L-serine as substrate and by detecting the product 2-aminomalonate semialdehyde.

The second reaction of conversion of 2-aminomalonate semialdehyde into 2,3-diaminopropanoate is catalysed by a 2-aminomalonate semialdehyde transaminase. This enzyme is not encountered naturally. Therefore it is obtained by evolution of a known enzyme or by screening metagenomic libraries. The 2-aminomalonate semialdehyde transaminase activity is performed with an evolved transaminase or aminotransferase which catalyses the exchange of an amino group of one molecule with an oxo group of another molecule. Preferably the evolved aminotransferase is chosen among phosphoserine aminotransferase or aspartate aminotransferase or glutamate aminotransferase. More preferably, the evolved aminotransferase is chosen among aminotransferase using glutamate as amino group donor. These enzymes are encoded by genes chosen among a list of genes well known in the art, including but not limited to the genes listed here: serC from *Escherichia coli* or from *Bacillus subtilis* or from *Corynebacterium glutamicum*; GOT1 from *Sus scrota*; patA from *Escherichia coli*; ygjG from *Brucella canis*; rocD from *Rhizobium* NGR 234 or from *Streptomyces avermitilis*; SCO1284 from *Streptomyces coelicolor*; AGT or AGT2 or AGT3 or GGT1 from *Arabidopsis thaliana*; AGXT from *Bos taurus*. Any polypeptide having at least 90% sequence identity to any of the polypeptides encoded by these genes may be used. Preferably, genes serC from *Escherichia coli* or GOT1 from *Sus scrofa* are used for obtaining the 2-aminomalonate semialdehyde transaminase activity.

Evolution of these enzymes is carried out by means and methods well known by the man skilled in the art in order to obtain enzymes having improved specificity for the substrate 2-aminomalonate semialdehyde and/or enabling to convert it into 2,3-diaminopropanoate with an improved activity. The selection of the evolved enzyme is done by expressing the evolved enzyme in the microorganism of the invention or in vitro with 2-aminomalonate semialdehyde as substrate and by quantifying the product 2,3-diaminopropanoate.

The third reaction of conversion of 2,3-diaminopropanoate into ethylenediamine is catalysed by an enzyme having 2,3-diaminopropanoate decarboxylase activity. This enzyme is not encountered naturally. Therefore it is obtained by evolution of known enzyme or by screening metagenomic libraries. The 2,3-diaminopropanoate decarboxylase activity is performed with an evolved amino acid decarboxylase or an evolved keto-acid decarboxylase which catalyses the decarboxylation of amino acids or keto-acids. Preferably an evolved amino acid decarboxylase is chosen. More preferably the evolved amino acid decarboxylase is chosen among histidine decarboxylase, serine decarboxylase, aspartate decarboxylase, diaminobutanoate decarboxylase, ornithine decarboxylase. These enzymes are encoded by genes chosen among a list of genes well known in the art, including but not limited to the genes listed here: sdc from *Arabidopsis thaliana*; padC or yclB from *Bacillus subtilis*; ubiD from *Campylobacter jejuni* or from *Escherichia coli*; PAD1 or GAD1 or SPE1 from *Saccharomyces cerevisiae*; panD from *Aquifex* aeolicus or from *Bacillus subtilis*; GAD or GAD2 or GAD3 or GAD4 or GAD5 from *Arabidopsis thaliana*; GAD or GAD2 or OAZ1 or ODC1 from *Bos Taurus*; gadA or gadB or panD or speC or speF from *Escherichia coli*; SCC105.13 from *Streptomyces coelicolor*; gadB from *Mannheimia succiniciproducens*; bdb from *Haloferax volcanii*; odcl from *Lactobacillus* sp.; kivD from *Lactococcus lactis* subsp. *Lactis*; kdcA from *Lactococcus lactis*; OAZ1 or ODC1 from *Bos Taurus*; speC or speF from *Escherichia coli*; SPE1 from *Saccharomyces cerevisiae*. Any polypeptide having at least 90% sequence identity to any of the polypeptides encoded by these genes may be used. Preferably, the sdc gene from *Arabidopsis thaliana* is used for obtaining the 2,3-diaminopropanoate decarboxylase activity.

Evolution of these enzymes is carried out by means and methods well known by the man skilled in the art in order to obtain enzymes having improved specificity for the substrate 2,3-diaminopropanoate and/or enabling to convert it into ethylenediamine with an improved activity. The selection of the evolved enzyme is performed by expressing the evolved enzyme in the microorganism of the invention or in vitro with 2,3-diaminopropanoate as substrate and by quantifying the product ethylenediamine. According to a specific aspect of the disclosure, the microorganism from embodiment [Y] is engineered to overexpress: ydfG gene, yiaY gene or mmsB gene, encoding for the serine dehydrogenase; and/or evolved serC gene or GOT1 gene, encoding for 2-aminomalonate semialdehyde transaminase activity; and/or evolved sdc gene from *Arabidopsis thaliana*, coding for the 2,3-diaminopropanoate decarboxylase.

[Z] In one embodiment, the application relates to a recombinant microorganism capable of co-producing monoethylene glycol (MEG) (or glycolic acid) and ethylenediamine (EDA), from one or more hexose feedstock and a nitrogen source, wherein the recombinant microorganism from embodiment [A] or from embodiment [B] (and optionally comprising embodiment [C]), and comprising additionally one or more of embodiments [D], [E], [F] and [G], further comprising one or more of embodiments [H], [I], and [J], further expresses one or more of the following from (a) to (c):

(a) at least one endogenous or exogenous nucleic acid molecule encoding an enzyme having serine decarboxylase activity that catalyzes the conversion of L-serine to ethanolamine;

(b) at least one endogenous or exogenous nucleic acid molecule encoding an enzyme having ethanolamine dehydrogenase activity that catalyzes the conversion of ethanolamine from (a) to aminoacetaldehyde;

(c) at least one endogenous or exogenous nucleic acid molecule encoding an enzyme having aminoacetaldehyde transaminase activity that catalyzes the conversion of aminoacetaldehyde from (b) to EDA;

wherein MEG (or glycolic acid) and EDA are co-produced.

According to this aspect of the disclosure, the recombinant microorganism overexpresses at least one of the genes encoding enzymes exhibiting activity of serine decarboxylase, ethanolamine dehydrogenase and aminoacetaldehyde transaminase. These genes may be endogenous genes or exogenous genes.

The first reaction of conversion of L-serine into ethanolamine is catalyzed by an enzyme having serine decarboxylase activity. This group of enzymes catalyses the decarboxylation of L-serine into ethanolamine. In a preferred embodiment of the invention, the serine decarboxylase is encoded by sdc from *Arabidopsis thaliana* (Rontein et al., 2001, WO2007/144346). The conversion of L-serine into ethanolamine by the serine decarboxylase, encoded by sdc from *Arabidopsis thaliana*, is disclosed in particular in patent application WO2007/144364, which is incorporated by reference herein. Preferably, these enzymes are optimized by mutating the encoding genes in order to improve their conversion efficiency of L-serine into ethanolamine.

In one embodiment of the disclosure, the serine decarboxylase activity is obtained by evolving enzymes in order to modify their substrate specificity and/or their catalytic efficiency to obtain an enzyme which exhibits specificity for serine and improved activity of serine decarboxylase. These enzymes are selected among the group of enzymes having the same type of catalytic activity on substrates chemically similar to ethanolamine. These enzymes are encoded by genes chosen among a list of genes well known in the art, including but not limited to the genes listed here: GAD1 or SPE1 from *Saccharomyces cerevisiae*; panD from *Aquifex* aeolicus or from *Bacillus subtilis*; GAD or GAD2 or GAD3 or GAD4 or GAD5 from *Arabidopsis thaliana*; GAD or GAD2 or OAZ1 or ODC1 from *Bos Taurus*; gadA or gadB or panD or speC or speF from *Escherichia coli*; SCC105.13 from *Streptomyces coelicolor*; gadB from *Mannheimia succiniciproducens*; bdb from *Haloferax volcanii*; odcl from *Lactobacillus* sp.; OAZ1 or ODC1 from *Bos Taurus*; speC or speF from *Escherichia coli*; SPE1 from *Saccharomyces cerevisiae*. Any polypeptide having at least 90% sequence identity to any of the polypeptides encoded by those genes may be used.

Evolution of these enzymes is carried out by means and methods well known by one skilled in the art in order to obtain enzymes having improved specificity for the substrate L-serine and enabling to convert it into ethanolamine with an improved activity. The selection of the evolved enzyme is performed by expressing the evolved enzyme in the microorganism of the invention or in vitro with L-serine as substrate and by quantifying the product ethanolamine.

The second reaction of conversion of ethanolamine into aminoacetaldehyde is catalysed by an ethanolamine dehydrogenase enzyme. Natural enzymes having this activity are not disclosed in prior art; however some enzymes have low catalytic activity. Therefore it is advantageous to evolve these enzymes with low catalytic activity towards evolved enzymes with improved activity. Useful enzymes can also be obtained by screening metagenomic libraries.

In one embodiment of the disclosure, the ethanolamine dehydrogenase activity is obtained by evolving enzymes in order to modify their substrate specificity and/or their catalytic efficiency to obtain an enzyme which exhibits specificity for ethanolamine and activity of ethanolamine dehydrogenase. These enzymes are selected among the group of enzymes having the same type of catalytic activity on substrates chemically similar to ethanolamine. These enzymes are encoded by genes chosen among a list of genes well known in the art, including but not limited to the genes listed here: mmsB from *Pseudomonas putida*, or from *Synechococcus* PCC6301, or from *Bacillus cereus*; hibdh from *Pseudomonas putida* E23; PA0743 from *Pseudomonas aeruginosa*; ydfG from *Escherichia coli* or from *Bacillus brevis* or from *Bacillus subtilis*; sdh from *Agrobacterium tumefaciens*; hibadh from *Rattus norvegicus* or from *Thermus thermophilus* HB8; gldA from *Escherichia coli* or from *Leuconostoc citreum* or from *Symbiobacterium thermophilum*; yqhE from *Escherichia coli*; yafB from *Escherichia coli*; aladh from *Enterobacter aerogenes*; alr from *Leishmania donovani*; sakR1 from *Synechococcus* sp.; yhdN from *Bacillus subtilis*; ytbE from *Bacillus subtilis*; yiaY from *Escherichia coli*; AKR4C9 from *Arabidopsis thaliana*; fucO from *Escherichia coli*. Any polypeptide having at least 90% sequence identity to any of the polypeptides encoded by these genes may be used. Preferably genes fucO from *Escherichia coli* or yiaY from *Escherichia coli* are used for obtaining the ethanolamine dehydrogenase activity.

Evolution of these enzymes is carried out by means and methods well known by one skilled in the art in order to obtain enzymes having improved specificity for the substrate ethanolamine and/or enabling to convert it into aminoacetaldehyde with an improved activity. The selection of evolved enzymes is done by expressing the evolved enzymes in the microorganism of the invention or in vitro with ethanolamine as substrate and by quantifying the product aminoacetaldehyde.

The last reaction of conversion of aminoacetaldehyde into ethylenediamine is catalysed by an aminoacetaldehyde transaminase. This enzyme is not encountered naturally. Therefore it is obtained by evolution of known enzyme or by screening metagenomic libraries. In one embodiment of the disclosure, the aminoacetaldehyde transaminase activity is performed with an evolved transaminase or aminotransferase which catalyses the exchange of an amino group of one molecule with an oxo group on another molecule. Preferably, the evolved aminotransferase is chosen among phosphoserine aminotransferase or aspartate aminotransferase or glutamate aminotransferase. More preferably the evolved aminotransferase is chosen among aminotransferase using glutamate as amino group donor. These enzymes are encoded by genes chosen among a list of genes well known in the art, including but not limited to the genes listed here: serC from *Escherichia coli* or from *Bacillus subtilis* or from *Corynebacterium glutamicum*; GOT1 from *Sus scrofa*; patA from *Escherichia coli*; ygjG from *Brucella canis*; rocD from *Rhizobium* NGR 234 or from *Streptomyces avermitilis*; SCO1284 from *Streptomyces coelicolor*; AGT or AGT2 or AGT3 or GGT1 from *Arabidopsis thaliana*; AGXT from *Bos taurus*. Any polypeptide having at least 90% sequence identity to any of the polypeptides encoded by these genes may be used. Preferably, genes serC from *Escherichia coli* or GOT1 from *Sus scrofa* are used.

Evolution of these enzymes is carried out by means and methods well known by one skilled in the art in order to obtain enzymes having improved specificity for the substrate aminoacetaldehyde and/or enabling to convert it into ethylenediamine with an improved activity. The selection of the evolved enzyme is done by expressing the evolved enzyme in the microorganism of the invention or in vitro with aminoacetaldehyde as substrate and by detecting the product ethylenediamine.

In another embodiment of the disclosure, aminoacetaldehyde transaminase enzymes can be isolated from strains growing on ethylenediamine as sole carbon and nitrogen source. For this purpose enrichment cultures from environmental samples on ethylenediamine are cultivated on minimal medium with ethylenediamine as sole nitrogen and carbon source. Metagenomic libraries are generated from these cultures and screened for the presence of aminoacetaldehyde transaminase enzymes. This approach allows isolating the gene corresponding to the enzymatic activity and is well-known to the expert in the field.

According to a specific aspect of the disclosure, the microorganism from embodiment [z] is engineered to overexpress: an sdc gene from *Arabidopsis thaliana*, encoding a serine decarboxylase; and/or fucO or yiaY genes from *Escherichia coli*, encoding for the ethanolamine dehydrogenase activity; and/or an evolved serC gene or GOT1 gene, encoding for aminoacetaldehyde transaminase activity.

[AA] In one embodiment, the application relates to a recombinant microorganism capable of co-producing monoethylene glycol (MEG) (or glycolic acid) and ethylenediamine (EDA), from one or more hexose feedstock and a nitrogen source, wherein the recombinant microorganism from embodiment [A] or from embodiment [B] (and optionally comprising embodiment [C]), and comprising additionally one or more of embodiments [D], [E], [F] and [G], further comprising one or more of embodiments [H], [I], and [J], further expresses one or more of the following from (a) to (c):
  (a) at least one endogenous or exogenous nucleic acid molecule encoding an enzyme having serine hydroxymethyltransferase activity that catalyzes the conversion of L-serine to glycine;
  (b) at least one endogenous or exogenous nucleic acid molecule encoding an enzyme having aldehyde oxidase activity that catalyzes the conversion of glycine from (a) to aminoacetaldehyde;
  (c) at least one endogenous or exogenous nucleic acid molecule encoding an enzyme having aminoacetaldehyde transaminase activity that catalyzes the conversion of aminoacetaldehyde from (b) to EDA;
  wherein MEG (or glycolic acid) and EDA are co-produced.

Preferably gene glyA from *Escherichia coli* is used for obtaining the serine hydroxymethyltransferase activity.

The aldehyde oxidase enzyme is obtained by evolving enzymes in order to modify their substrate specificity and/or their catalytic efficiency to obtain an enzyme which exhibits specificity for glycine and activity of aldehyde oxidase. These enzymes are selected among the group of enzymes having the same type of catalytic activity on substrates chemically similar to glycine. These enzymes are encoded by genes chosen among a list of genes well known in the art, including but not limited to the genes listed here: aldH1 from *Aquifex aeolicus*; dhaS from *Anoxybacillus flavithermus*; Aldh from *Apis mellifera*; aldX, aldY, dhaS, ycbD, yfmT or ywdH from *Bacillus subtilis*; prr from *Escherichia coli*; ALD2, ALD3, ALD4, ALD5, ALD6 from *Saccharomyces* cerevisiae; betB from *Roseobacter denitrificans*; AAur_0650 from *Arthrobacter aurescens*. Any polypeptide having at least 90% sequence identity to any of the polypeptides encoded by these genes may be used.

Conversion of aminoacetaldehyde into ethylenediamine by an enzyme having aminoacetaldehyde transaminase activity. This enzyme is obtained by evolving enzymes in order to modify their substrate specificity and/or their catalytic efficiency to obtain an enzyme which exhibits specificity for aminoacetaldehyde and activity of transaminase. These enzymes are selected among the group of enzymes having the same type of catalytic activity on substrates chemically similar to aminoacetaldehyde. These enzymes are encoded by genes chosen among a list of genes well known in the art, including but not limited to the genes listed here: serC from *Escherichia coli* or from *Bacillus subtilis* or from *Corynebacterium glutamicum*; GOT1 from *Sus scrota*; patA from *Escherichia coli*; ygjG from *Brucella canis*; rocD from *Rhizobium* NGR 234 or from *Streptomyces avermitilis*; SCO1284 from *Streptomyces coelicolor*; AGT or AGT2 or AGT3 or GGT1 from *Arabidopsis thaliana*; AGXT from *Bos taurus*. Any polypeptide having at least 90% sequence identity to any of the polypeptides encoded by these genes may be used.

According to a specific aspect of the disclosure, the microorganism from embodiment [AA] is engineered to overexpress an evolved serC gene or GOT1 gene, encoding for aminoacetaldehyde transaminase activity.

[BB] In one embodiment, the application relates to a recombinant microorganism capable of co-producing monoethylene glycol (MEG) (or glycolic acid) and ethylenediamine (EDA), from one or more hexose feedstock and a nitrogen source, wherein the recombinant microorganism from embodiment [A] or from embodiment [B] (and optionally comprising embodiment [C]), and comprising additionally one or more of embodiments [D], [E], [F] and [G], further comprising one or more of embodiments [H], [I], and [J], further expresses one or more of the following from (a) to (e):
  (a) at least one endogenous or exogenous nucleic acid molecule encoding an enzyme having an amino acid N-acetyl transferase activity or O-acetyl transferase activity that catalyzes the conversion of L-serine to N-acetylserine;
  (b) at least one endogenous or exogenous nucleic acid molecule encoding an enzyme having N-acetylserine dehydrogenase activity that catalyzes the conversion of N-acetylserine from (a) to N-acetylmalonate semialdehyde;
  (c) at least one endogenous or exogenous nucleic acid molecule encoding an enzyme having transaminase activity that catalyzes the conversion of N-acetylmalonate semialdehyde from (b) to acetylaminopropanoate;
  (d) at least one endogenous or exogenous nucleic acid molecule encoding an enzyme having deacetylase activity that catalyzes the conversion of acetylaminopropanoate from (c) to 2,3-diaminopropanoate;
  (e) at least one endogenous or exogenous nucleic acid molecule encoding an enzyme having 2,3-diaminopropanoate decarboxylase activity that catalyzes the conversion of 2,3-diaminopropanoate from (d) to EDA;
  wherein MEG (or glycolic acid) and EDA are co-produced.

The first conversion step of embodiment [BB] may be an amino acid N-acetyl transferase activity or O-acetyl transferase activity, since the transformation of O to N is spontaneous. Preferably gene argA from *Escherichia coli* is used for obtaining the amino acid N-acetyl transferase activity.

An enzyme having N-acetylserine dehydrogenase activity is obtained by evolving enzymes in order to modify their substrate specificity and/or their catalytic efficiency to obtain an enzyme which exhibits specificity for N-acetylserine and activity of N-acetylserine dehydrogenase. These enzymes are selected among the group of enzymes having the same type of catalytic activity on substrates chemically similar to N-acetylserine. These enzymes are encoded by genes chosen among a list of genes well known in the art, including but not limited to the genes listed here: mmsB from *Pseudomonas putida*, or from *Synechococcus* PCC6301, or from *Bacillus cereus*; hibdh from *Pseudomonas putida* E23; PA0743 from *Pseudomonas aeruginosa*; ydfG from *Escherichia coli* or from *Bacillus brevis* or from *Bacillus subtilis*; sdh from *Agrobacterium tumefaciens*; hibadh from *Rattus norvegicus* or from *Thermus thermophilus* HB8; gldA from *Escherichia coli* or from *Leuconostoc citreum* or from *Symbiobacterium thermophilum*; yqhE from *Escherichia coli*; yafB from *Escherichia coli*; aladh from *Enterobacter aerogenes*; alr from *Leishmania donovani*; sakR1 from Synechococcus sp.; yhdN from *Bacillus subtilis*; ytbE from *Bacillus subtilis*; yiaY from *Escherichia coli*; AKR4C9 from *Arabidopsis thaliana*; fucO from *Escherichia coli*. Any polypeptide having at least 90% sequence identity to any of the polypeptides encoded by these genes may be used.

An enzyme having a transaminase activity to convert N-acetylmalonate semialdehyde to acetylaminopropanoate may be obtained by evolving enzymes in order to modify their substrate specificity and/or their catalytic efficiency to obtain an enzyme which exhibits specificity for N-acetylmalonate semialdehyde and activity of N-acetylmalonate semialdehyde transaminase. These enzymes are selected among the group of enzymes having the same type of catalytic activity on substrates chemically similar to N-acetylmalonate semialdehyde. These enzymes are encoded by genes chosen among a list of genes well known in the art, including but not limited to the genes listed here: serC from *Escherichia coli* or from *Bacillus subtilis* or from *Corynebacterium glutamicum*; GOT1 from *Sus scrota*; patA from *Escherichia coli*; ygjG from *Brucella canis*; rocD from *Rhizobium* NGR 234 or from *Streptomyces avermitilis;* 2SCG18.31c from *Streptomyces coelicolor*; AGT or AGT2 or AGT3 or GGT1 from *Arabidopsis thaliana*; AGXT from *Bos taurus*. Any polypeptide having at least 90% sequence identity to any of the polypeptides encoded by these genes may be used.

Preferably gene argE from *Escherichia coli* is used for obtaining the deacetylase activity to convert acetylaminopropanoate into 2,3-diaminopropanoate.

An enzyme having amino-acid decarboxylase activity or keto acid decarboxylase activity to convert 2,3-diaminopropanoate into ethylenediamine may be obtained by evolving enzymes in order to modify their substrate specificity and/or their catalytic efficiency to obtain an enzyme which exhibits specificity for 2,3-diaminopropanoate and activity of amino acid decarboxylase or keto acid decarboxylase. These enzymes are selected among the group of enzymes having the same type of catalytic activity on substrates chemically similar to 2,3-diaminopropanoate. These enzymes are encoded by gene chosen among a list of genes well known in the art, including but not limited to the genes listed here: sdc from *Arabidopsis thaliana*; padC or yclB from *Bacillus subtilis*; ubiD from *Campylobacter jejuni* or from *Escherichia coli*; PAD1 or GAD1 or SPE1 from *Saccharomyces cerevisiae*; panD from *Aquifex aeolicus* or from *Bacillus*

*subtilis*; GAD or GAD2 or GAD3 or GAD4 or GAD5 from *Arabidopsis thaliana*; GAD or GAD2 or OAZ1 or ODC1 from *Bos Taurus*; gadA or gadB or panD or speC or speF from *Escherichia coli*; SCC105.13 from *Streptomyces coelicolor*; gadB from *Mannheimia succiniciproducens*; bdb from *Haloferax volcanii*; odcl from *Lactobacillus* sp.; kivD from *Lactococcus lactis* subsp. *Lactis*; kdcA from *Lactococcus lactis*; OAZ1 or ODC1 from *Bos Taurus*; speC or speF from *Escherichia coli*; SPE1 from *Saccharomyces cerevisiae*. Any polypeptide having at least 90% sequence identity to any of the polypeptides encoded by these genes may be used.

In a further embodiment of the disclosure, the method is performed with a microorganism wherein serine biosynthesis is optimized. This optimization is disclosed in particular in patent application WO 2007/144346, which is incorporated by reference herein.

Alternatively, in another embodiment, EDA can be produced by the following process: Ser can be directly aminated to (S)-2,3-diaminopropanoate by serine aminase (EC 2.6.1.-), then decarboxylated to EDA, for instance by an enzyme from the family of L-2,4-diaminobutyrate or ornithine decarboxylases (FIG. 11). However, if such an enzyme with (S)-2,3-diaminopropanoate decarboxylase activity is not specific, it may also act on other amino acids or serine itself In some embodiments, EDA can be produced by the following process: the intermediate (S)-2,3-diaminopropanoate may also be produced by direct amination of pyruvate using (S)-2,3-diaminopropanoate ammonia lyase (EC 4.3.1.15) (FIG. 11):

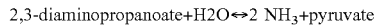

2,3-diaminopropanoate+H2O↔2 NH₃+pyruvate

In some embodiments, the production of MEG (or glycolic acid) and EDA is very close to the thermodynamic maximum yield potential using the lossless conversion of one or more hexose to one or more pentose-5-phosphate intermediates, followed by the conversion of the one or more pentose-5-phosphate intermediates to one or more pentose-1-phosphate and/or pentose intermediates, and then followed by the co-production of MEG (or glycolic acid) via a C2 pathway and EDA via a C3 pathway from the one or more pentose-1-phosphate and/or pentose intermediates. In some embodiments, the thermodynamic yield potential is 14% better for co-production of MEG (or glycolic acid) and EDA via the pathways disclosed in the present application compared to production of EDA made from glucose by natural or published similar pathways.

Co-production: hexose+2 NH₃→MEG (or glycolic acid)+EDA+0 ATP

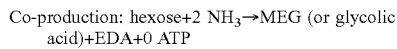

Y(pathway)=(0.337+0.326) g/g=0.663 g(MEG (or glycolic acid)+EDA)/g(hexose+2NH₃), 97% of Y(max)(heat of combustion)=0.687 g/g Standard pathway: glucose+4 NH₃→2 EDA+2 NADH+0 ATP

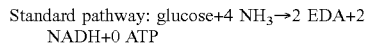

Y(pathway)=0.484 g(EDA)/g(glucose+4NH₃), 85% of Y(max)(heat of combustion)=0.571 g/g In some embodiments, the C2 pathway for production of MEG (or glycolic acid) comprises embodiment [H] and the C3 pathway for production of EDA comprises embodiment [CC]. In other embodiments, the C2 pathway for production of MEG (or glycolic acid) comprises embodiment [H] and the C3 pathway for production of EDA comprises embodiment [DD]. In some embodiments, the C2 pathway for production of MEG (or glycolic acid) comprises embodiment [I] and the C3 pathway for production of EDA comprises embodiment [CC]. In other embodiments, the C2 pathway for production of MEG (or glycolic acid) comprises embodiment [I] and the C3 pathway for production of EDA comprises embodiment [DD]. In some embodiments, the C2 pathway for production of MEG (or glycolic acid) comprises embodiment [J] and the C3 pathway for production of EDA comprises embodiment [CC]. In other embodiments, the C2 pathway for production of MEG (or glycolic acid) comprises embodiment [J] and the C3 pathway for production of EDA comprises embodiment [DD].

[CC] In one embodiment, the application relates to a recombinant microorganism capable of co-producing monoethylene glycol (MEG) (or glycolic acid) and ethylenediamine (EDA), from one or more hexose feedstock and a nitrogen source, wherein the recombinant microorganism from embodiment [A] or from embodiment [B] (and optionally comprising embodiment [C]), and comprising additionally one or more of embodiments [D], [E], [F] and [G], further comprising one or more of embodiments [H], [I], and [J], further expresses one or more of the following from (a) to (b):
   (a) at least one endogenous or exogenous nucleic acid molecule encoding an enzyme having a serine aminase activity that catalyzes the conversion of L-serine to (S)-2,3-diaminopropanoate;
   (b) at least one endogenous or exogenous nucleic acid molecule encoding an enzyme having an (S)-2,3-diaminopropanoate decarboxylase activity that catalyzes the conversion of (S)-2,3-diaminopropanoate from (a) to EDA;
   wherein MEG (or glycolic acid) and EDA are co-produced.

[DD] In one embodiment, the application relates to a recombinant microorganism capable of co-producing monoethylene glycol (MEG) (or glycolic acid) and ethylenediamine (EDA), from one or more hexose feedstock and a nitrogen source, wherein the recombinant microorganism from embodiment [A] or from embodiment [B] (and optionally comprising embodiment [C]), and comprising additionally one or more of embodiments [D], [E], [F] and [G], further comprising one or more of embodiments [H], [I], and [J], further expresses one or more of the following from (a) to (b):
   (a) at least one endogenous or exogenous nucleic acid molecule encoding an enzyme having an (S)-2,3-diaminopropanoate ammonia lyase activity that catalyzes the conversion of pyruvate and ammonium to (S)-2,3-diaminopropanoate;
   (b) at least one endogenous or exogenous nucleic acid molecule encoding an enzyme having (S)-2,3-diaminopropanoate decarboxylase activity that catalyzes the conversion of (S)-2,3-diaminopropanoate from (a) to EDA;
   wherein pyruvate is produced from endogenous glycolysis, and wherein MEG (or glycolic acid) and EDA are co-produced.

In some embodiments, an enzyme having 2,3-diaminopropionate ammonia-lyase activity is used to convert pyruvate and ammonium to (S)-2,3-diaminopropanoate. In some embodiments, an enzyme having 2,3-diaminopropionate ammonia-lyase activity is encoded by an amino acid sequence having at least 70% sequence identity, having at least 80% sequence identity, or having at least 90% sequence identity to *E. coli* 2,3-diaminopropionate ammonia-lyase ygeX. In other embodiments, the enzyme having 2,3-diaminopropionate ammonia-lyase activity is *E. coli* ygeX. In some embodiments, the one or more nucleic acid molecule encoding an enzyme having 2,3-diaminopropionate ammonia-lyase activity comprises an amino acid sequence set forth in UniProt ID P66899. In further embodiments, the one or more nucleic acid molecule encoding an enzyme having 2,3-diaminopropionate ammonia-lyase activity is encoded by a nucleic acid sequence set forth in Gene ID 947012.

In one embodiment of any aspect disclosed above, the enzyme having glycolaldehyde reductase activity is encoded by one or more nucleic acid molecules obtained from a microorganism selected from *E. coli* and *S. cerevisiae*. In another embodiment, the one or more nucleic acid molecules is selected from gldA, GRE2, GRE3, yqhD, ydjG, fucO, yafB (dkgB), and/or yqhE (dkgA), or homolog thereof. In another embodiment, the one or more nucleic acid molecules is yqhD. In some embodiments, the yqhD comprises a G149E mutation. In a further embodiment, the enzyme having glycolaldehyde reductase activity comprises an amino acid sequence selected from the group consisting of SEQ ID NOs: 13, 15, 17, 20, 23, 25, 28, 30 and 32. In yet a further embodiment, the enzyme having glycolaldehyde reductase activity is encoded by a nucleic acid sequence selected from the group consisting of SEQ ID NOs: 12, 14, 16, 18, 19, 21, 22, 24, 26, 27, 29 and 31.

In one embodiment of any aspect disclosed above, the enzyme having thiolase or acetyl coenzyme A acetyltransferase activity is encoded by one or more nucleic acid molecules obtained from a microorganism selected from the group consisting of *Clostridium* sp., *Bacillus* sp., *E. coli*, *Saccharomyces* sp. and *Marinobacter* sp. In some embodiments, the enzyme having thiolase or acetyl coenzyme A acetyltransferase activity is encoded by one or more nucleic acid molecules obtained from a microorganism selected from the group consisting of *Clostridium acetobutylicum*, *Clostridium thermosaccharolyticum*, *Bacillus cereus*, *E. coli*, *Saccharomyces cerevisiae* and *Marinobacter hydrocarbonoclasticus*. In some embodiments, the one or more nucleic acid molecules is thlA, atoB and/or ERG10, or homolog thereof. In a further embodiment, the enzyme having thiolase or acetyl coenzyme A acetyltransferase activity comprises an amino acid sequence selected from the group consisting of SEQ ID NOs: 35, 37 and 40. In yet a further embodiment, the enzyme having thiolase or acetyl coenzyme A acetyltransferase activity is encoded by a nucleic acid sequence selected from the group consisting of SEQ ID NOs: 33, 34, 36, 38 and 39.

In one embodiment of any aspect disclosed above, the enzyme having acetyl-CoA:acetoacetate-CoA transferase or acetate:acetoacetyl-CoA hydrolase activity is encoded by one or more nucleic acid molecules obtained from a microorganism selected from *Clostridium* sp. and *E. coli*. In another embodiment, the enzyme having acetyl-CoA:acetoacetate-CoA transferase or acetate:acetoacetyl-CoA hydrolase activity is encoded by one or more nucleic acid molecules obtained from *E. coli*. In some embodiments, the one or more nucleic acid molecules encoding the enzyme having acetyl-CoA:acetoacetate-CoA transferase activity is atoA and/or atoD, or homolog thereof. In another embodiment, the enzyme having acetyl-CoA:acetoacetate-CoA transferase or acetate:acetoacetyl-CoA hydrolase activity is encoded by one or more nucleic acid molecules obtained from *Clostridium acetobutylicum*. In some embodiments, the one or more nucleic acid molecules encoding the enzyme having acetate:acetoacetyl-CoA hydrolase activity is ctfA and/or ctfB, or homolog thereof. In a further embodiment, the enzyme having acetyl-CoA:acetoacetate-CoA transferase or acetate:acetoacetyl-CoA hydrolase activity comprises an amino acid sequence selected from the group consisting of SEQ ID NOs: 43, 46, 97, 99, 101 and 103. In yet a further embodiment, the enzyme having acetyl-CoA:acetoacetate-CoA transferase or acetate:acetoacetyl-CoA hydrolase activity is encoded by a nucleic acid sequence selected from the group consisting of SEQ ID NOs: 41, 42, 44, 45, 96, 98, 100 and 102.

In one embodiment of any aspect disclosed above, the enzyme having acetoacetate decarboxylase activity is encoded by one or more nucleic acid molecules obtained from a microorganism selected from the group consisting of *Clostridium* sp., *Bacillus* sp., *Chromobacterium* sp. and *Pseudomonas* sp. In another embodiment, the enzyme having acetoacetate decarboxylase activity is encoded by one or more nucleic acid molecules obtained from a microorganism selected from the group consisting of *Clostridium acetobutylicum*, *Clostridium beijerinckii*, *Clostridium cellulolyticum*, *Bacillus polymyxa*, *Chromobacterium violaceum* and *Pseudomonas putida*. In some embodiments, the one or more nucleic acid molecules encoding the enzyme having acetoacetate decarboxylase activity is adc, or homolog thereof. In a further embodiment, the enzyme having acetoacetate decarboxylase activity comprises an amino acid sequence selected from the group consisting of SEQ ID NOs: 49 and 52. In yet another embodiment, the enzyme having acetoacetate decarboxylase activity is encoded by a nucleic acid sequence selected from the group consisting of SEQ ID NOs: 47, 48, 50 and 51.

[EE] In another embodiment, the recombinant microorganism selected from embodiment [H], embodiment [I], and embodiment [J], optionally further comprises one or more modifications selected from the group consisting of:
  (i) a deletion, insertion, or loss of function mutation in a gene encoding a xylose isomerase that catalyzes the conversion of D-xylulose to D-xylose;
  (ii) a deletion, insertion, or loss of function mutation in a gene encoding a glycolaldehyde dehydrogenase that catalyzes the conversion of glycolaldehyde to glycolic acid; and
  (iii) a deletion, insertion, or loss of function mutation in a gene encoding a lactate dehydrogenase that catalyzes the conversion of pyruvate to lactate.

In some embodiments, a recombinant microorganism producing MEG (or glycolic acid) or, optionally, MEG (or glycolic acid) and one or more co-products, comprises a deletion, insertion, or loss of function mutation in a gene encoding a xylose isomerase to prevent the conversion of D-xylulose to D-xylose and instead shunt the reaction toward conversion of D-xylulose to D-xylulose-1-phosphate, D-xylulose-5-phosphate, or D-ribulose. In some embodiments, the xylose isomerase is from *Escherichia coli*. In some embodiments, the xylose isomerase is encoded by the xylA gene, or homolog thereof.

In some embodiments, a recombinant microorganism producing MEG (or glycolic acid) or, optionally, MEG (or glycolic acid) and one or more co-products, comprises a deletion, insertion, or loss of function mutation in a gene encoding a glycolaldehyde dehydrogenase to prevent the production of glycolic acid from glycolaldehyde and instead shunt the reaction toward conversion of glycolaldehyde to MEG. In some embodiments, the glycolaldehyde dehydrogenase is from *Escherichia coli*. In some embodiments, the glycolaldehyde dehydrogenase is encoded by the aldA gene, or homolog thereof. In some embodiments, the deletion, insertion, or loss of function mutation in a gene encoding a glycolaldehyde dehydrogenase is partial, wherein some glycolaldehyde dehydrogenase function is still present and an amount of glycolic acid is still produced.

In some embodiments, a recombinant microorganism producing MEG (or glycolic acid) or, optionally, MEG (or glycolic acid) and one or more co-products, comprises a deletion, insertion, or loss of function mutation in a gene encoding a lactate dehydrogenase to prevent the production of lactate from pyruvate and instead shunt the reaction toward production of one or more co-products. In some embodiments, the lactate dehydrogenase is from *Escherichia coli*. In some embodiments, the lactate dehydrogenase is encoded by the ldhA gene, or homolog thereof.

Non-limiting combinations of any of the recombinant microorganism and methods embodiments described herein are included as part of this disclosure.

Recombinant Microorganism

The disclosure provides microorganisms that can be engineered to express various endogenous or exogenous enzymes.

In various embodiments described herein, the recombinant microorganism is a eukaryotic microorganism. In some embodiments, the eukaryotic microorganism is a yeast. In exemplary embodiments, the yeast is a member of a genus selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Trichosporon, Rhodotorula*, and *Myxozyma*.

In some embodiments, the recombinant microorganism is a prokaryotic microorganism. In exemplary embodiments, the prokaryotic microorganism is a member of a genus selected from the group consisting of *Escherichia, Clostridium, Zymomonas, Salmonella, Rhodococcus, Pseudomonas, Bacillus, Lactobacillus, Enterococcus, Alcaligenes, Klebsiella, Paenibacillus, Arthrobacter, Corynebacterium*, and *Brevibacterium*.

In some embodiments, the recombinant microorganism is used to produce monoethylene glycol (MEG) or glycolic acid (GA), or optionally, MEG (or GA) and one or more co-product, disclosed herein.

Accordingly, in another aspect, the present inventions provide a method of producing MEG or GA, or optionally, MEG (or GA) and one or more co-product, using a recombinant microorganism described herein. In one embodiment, the method comprises cultivating the recombinant microorganism in a culture medium containing a feedstock providing a carbon source until MEG or GA, or optionally, MEG (or GA) and one or more co-product, is produced. In a further embodiment, the MEG (or GA), or optionally, MEG (or GA) and one or more co-product, is recovered. Recovery can be by methods known in the art, such as distillation, membrane-based separation gas stripping, solvent extraction, and expanded bed adsorption.

In some embodiments, the feedstock comprises a carbon source. In various embodiments described herein, the carbon source may be selected from sugars, glycerol, alcohols, organic acids, alkanes, fatty acids, lignocellulose, proteins, carbon dioxide, and carbon monoxide. In an exemplary embodiment, the carbon source is a sugar. In a further exemplary embodiment, the sugar is glucose or oligomers of glucose thereof. In other embodiments, the oligomers of glucose are selected from fructose, sucrose, starch, cellobiose, maltose, lactose and cellulose.

Biosynthesis of Xylitol, or Optionally, Xylitol and One or More Co-Product Using a Recombinant Microorganism In one aspect, the present disclosure provides a recombinant microorganism comprising one or more biochemical pathway that produces xylitol from one or more hexose feedstock. In one aspect, the present disclosure provides a recombinant microorganism comprising one or more biochemical pathway to produce xylitol from hexose, such as glucose, through the nonoxidative branch of the PPP (i.e., with the use of 1) transketolase, 2) transaldolase, 3) ribulose-5P epimerase and 4) ribose-5P isomerase. In another aspect, the present disclosure preferably provides a recombinant microorganism that has reduced or eliminated activity of at least one enzyme of the oxidative branch of the PPP (i.e., deletion or inactivation of the gene "zwf" in *E. coli* that codifies glucose-6-phosphate 1-dehydrogenase; and/or the gene "pgl" in *E. coli* that codifies the 6-phosphogluconolactonase; and/or gene "gnd" in *E. coli* that codifies the 6-phosphogluconate dehydrogenase, decarboxylating) in order to reduce carbon loss, resulting in an increased yield of xylitol. In one embodiment, one or more co-product is co-produced with xylitol.

Therefore, in one embodiment, the application relates to a recombinant microorganism comprising one or more biochemical pathway comprising at least one enzyme having an activity that converts one or more hexose feedstock in a lossless conversion to xylitol.

In one aspect, a microorganism of the present disclosure is capable of converting a hexose or an oligomer comprising a hexose into xylitol as a single end product. In one aspect, a microorganism of the present disclosure is capable of converting a hexose or an oligomer comprising a hexose into xylitol as a co-product.

In one aspect, a microorganism of the present disclosure is capable of (1) converting a hexose, such as glucose, to D-Ribose-5P and/or (2) D-xylulose-5P and/or D-ribulose-5P. In one aspect, a microorganism of the present disclosure is capable of converting D-Ribose-5P to D-Ribulose-5P via expression of rpiA. In one aspect, a microorganism of the present disclosure is capable of converting D-Ribulose-5P to D-Xylulose-5P via expression of rpe. In one aspect, a microorganism of the present disclosure is capable of converting D-Xylulose-5P to D-Ribulose-5P via expression of rpe. In one aspect, a microorganism of the present disclosure is capable of converting D-Xylulose-5P to D-Xylulose via expression of a phosphatase. In one aspect, the microorganism of the present disclosure comprises a phosphatase that has a high specificity and/or high activity on D-ribulose-5P and/or D-xylulose-5P.

Figure 12:
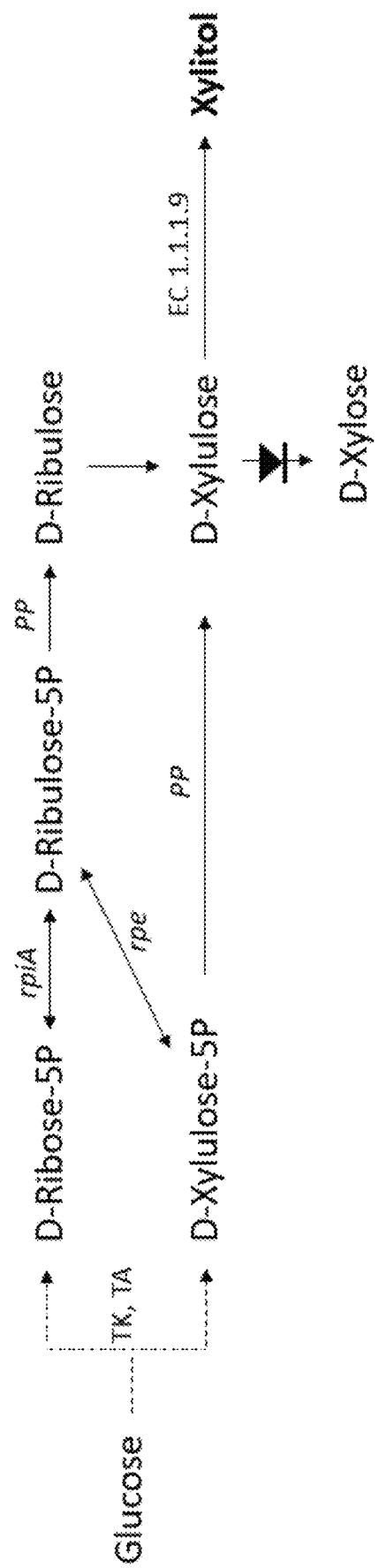
FIG. 12 illustrates the biosynthesis pathway of xylitol from glucose with the use of phosphatase. The symbol ▼ means enzymes to be potentially down regulated or inactivated/abolished, ie. respective gene potentially attenuated or deleted.

In one aspect, a microorganism of the present disclosure is capable of converting D-Ribulose-5P to D-Ribulose via expression of a phosphatase. In one aspect, a microorganism of the present disclosure is capable of converting D-Ribulose to D-Xylulose. In one aspect, a microorganism of the present disclosure is capable of converting D-Xylulose to Xylitol via expression of, but not limited to, EC 1.1.1.9. In some aspects, the microorganism of the present disclosure is capable of performing any one or more of the above reactions. In some aspects, the microorganism of the present disclosure is capable of performing any one or more of the reactions described in FIG. 12. In some aspects, the microorganism of the present disclosure does not have arabitol and/or xylitol-5P as an intermediate of the metabolic pathway.

Figure 13:
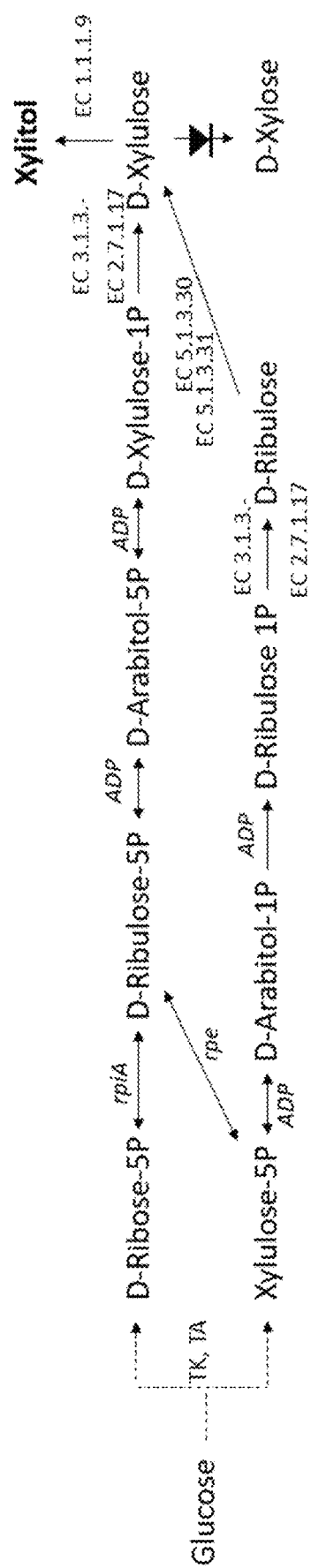
FIG. 13 illustrates the biosynthesis pathway of xylitol from glucose with the use of arabitol-P dehydrogenase (ADP). The symbol ▼ means enzymes to be potentially down regulated or inactivated/abolished, ie. respective gene potentially attenuated or deleted.

In one aspect, a microorganism of the present disclosure is capable of (1) converting a hexose, such as glucose, to D-Ribose-5P and/or (2) D-xylulose-5P and/or D-ribulose-5P. In one aspect, a microorganism of the present disclosure is capable of converting D-Ribose-5P to D-Ribulose-5P via expression of rpiA. In one aspect, a microorganism of the present disclosure is capable of converting D-Ribulose-5P to D-Xylulose-5P via expression of rpe. In one aspect, a microorganism of the present disclosure is capable of converting D-Xylulose-5P to D-Ribulose-5P via expression of rpe. In one aspect, a microorganism of the present disclosure is capable of converting (1) D-Ribulose-5P to D-Arabitol-5P via expression of ADP, (2) D-Arabitol-5P to D-Xylulose-1P via expression of ADP, (3) Xylulose-5P to D-Arabitol-1P via expression of ADP, and/or (4) D-Arabitol-1P to D-Ribulose-1P via expression of ADP. In one aspect, a microorganism of the present disclosure is capable of converting D-Ribulose-1P into D-Ribulose via expression of, but not limited to, EC 3.1.3.- and/or EC 2.7.1.17. In one aspect, a microorganism of the present disclosure is capable of converting D-Ribulose into D-Xylulose via expression of, but not limited to, EC 5.1.3.30 and/or EC 5.1.3.31. In one aspect, a microorganism of the present disclosure is capable of converting D-Xylulose-1P into D-Xylulose via expression of, but not limited to, EC 3.1.3.- and/or EC 2.7.1.17. In one aspect, a microorganism of the present disclosure is capable of converting D-Xylulose to Xylitol via expression of, but not limited to, EC 1.1.1.9. In some aspects, the microorganism of the present disclosure is capable of performing any one or more of the above reactions. In some aspects, the microorganism of the present disclosure is capable of performing any one or more of the reactions described in FIG. 13.

Figure 14:
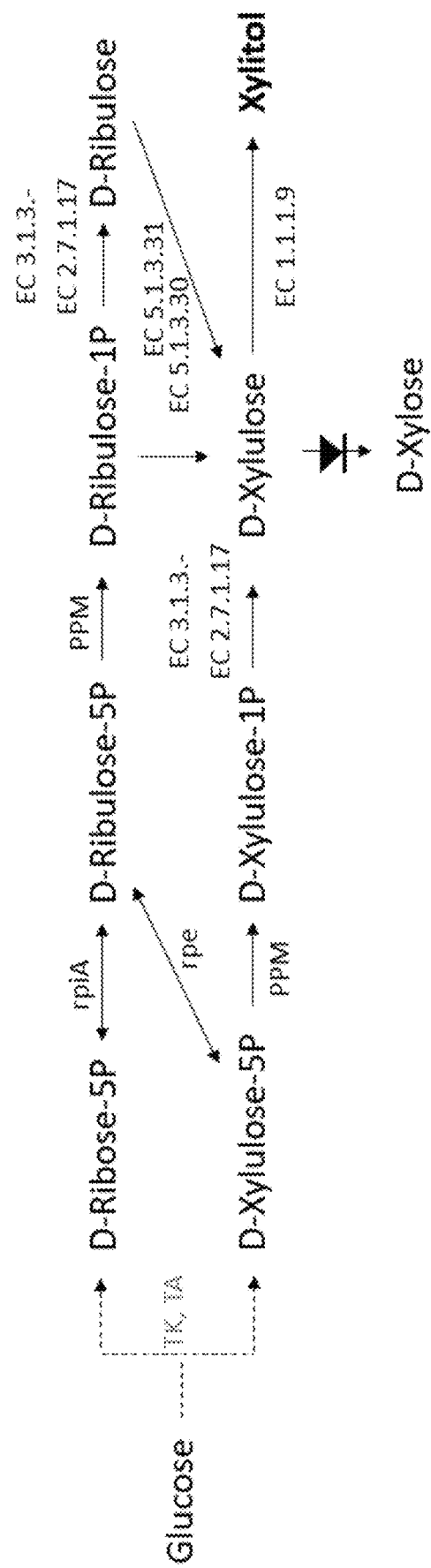
FIG. 14 illustrates the biosynthesis pathway of xylitol from glucose with the use of phosphopentomutase (PPM). The symbol ▼ means enzymes to be potentially down regulated or inactivated/abolished, ie. respective gene potentially attenuated or deleted.

In one aspect, a microorganism of the present disclosure is capable of (1) converting a hexose, such as glucose, to D-Ribose-5P and/or (2) D-xylulose-5P and/or D-ribulose-5P. In one aspect, a microorganism of the present disclosure is capable of converting D-Ribose-5P to D-Ribulose-5P via expression of rpiA. In one aspect, a microorganism of the present disclosure is capable of converting D-Ribulose-5P to D-Xylulose-5P via expression of rpe. In one aspect, a microorganism of the present disclosure is capable of converting D-Xylulose-5P to D-Ribulose-5P via expression of rpe. In one aspect, a microorganism of the present disclosure is capable of converting D-Ribulose-5P to D-Ribulose-1P via expression of PPM. In one aspect, a microorganism of the present disclosure is capable of converting D-Xylulose-5P to D-Xylulose-1P via expression of PPM. In one aspect, a microorganism of the present disclosure is capable of converting D-Ribulose-1P to D-Ribulose via expression of, but not limited to, EC 3.1.3.- and/or EC 2.7.1.17. In one aspect, a microorganism of the present disclosure is capable of converting D-Xylulose-1P to D-Xylulose via expression of, but not limited to, EC 3.1.3.- and/or EC 2.7.1.17. In one aspect, a microorganism of the present disclosure is capable of converting D-Ribulose to D-Xylulose via expression of, but not limited to, EC 5.1.3.31 and/or EC 5.1.3.30. In one aspect, a microorganism of the present disclosure is capable of converting D-Xylulose to Xylitol via expression of, but not limited to, EC 1.1.1.9. In some aspects, the microorganism of the present disclosure is capable of performing any one or more of the above reactions. In some aspects, the microorganism of the present disclosure is capable of performing any one or more of the reactions described in FIG. 14.

In some aspects, the enzymes indicated above include xylitol hydrogenase (EC 1.1.1.9) which is involved in the hydrogenation of D-xylulose to xylitol. In some aspects, the enzymes indicated above include sugar phosphatase (EC 3.1.3.-, or EC 3.1.3.23) or xylulokinase (EC 2.7.1.17) which are involved in the conversion of D-xylulose-1P to D-xylulose and/or of D-ribulose-1P to D-ribulose. In some aspects, the enzymes indicated above include D-psicose 3-epimerase (EC 5.1.3.30) or D-tagatose 3-epimerase (EC 5.1.3.31), which are involved in the conversion of D-ribulose to D-xylulose.

In some aspects, the one or more enzymes are heterologous to the microorganism. In some aspects, some of the enzymes are heterologous to the microorganism and other enzymes are native to the microorganism.

Methods of Producing a Recombinant Microorganism that Produces or Accumulates MEG (or Glycolic Acid), or Optionally, MEG (or Glycolic Acid) and One or More Co-Product As described above, in one aspect, the present application provides methods of producing a recombinant microorganism that produces or accumulates MEG (or glycolic acid) from one or more exogenous hexose feedstock via one or more pentose-5-phosphate intermediate, comprising: introducing into or expressing in the recombinant microorganism one or more enzyme for the conversion of the one or more hexose feedstock to the one or more pentose-5-phosphate intermediate; introducing into or expressing in the recombinant microorganism one or more enzyme for the conversion of the one or more pentose-5-phosphate intermediate to one or more pentose or pentose-1-phosphate intermediate; introducing into or expressing in the recombinant microorganism a C2 pathway comprising one or more enzyme for the production of MEG or GA from glycolaldehyde; and introducing into or expressing in the recombinant microorganism a C3 pathway comprising one or more enzyme for the production of MEG or GA derived from DHAP or pyruvate; and culturing the recombinant microorganism in a culture medium containing the one or more hexose feedstock to produce or accumulate MEG or GA, wherein glycolaldehyde and DHAP (or pyruvate) are intermediates produced in the C2 pathway, and wherein MEG or GA are produced in both the C2 and C3 pathways. In some embodiments, the glycolaldehyde is oxidized to glycolic acid by a glycolaldehyde dehydrogenase.

In another aspect, the present application provides methods of producing a recombinant microorganism that produces or accumulates MEG (or glycolic acid) and one or more co-product from one or more exogenous hexose feedstock via one or more pentose-5-phosphate intermediate, comprising: introducing into or expressing in the recombinant microorganism one or more enzyme for the conversion of the one or more hexose feedstock to the one or more pentose-5-phosphate intermediate; introducing into or expressing in the recombinant microorganism one or more enzyme for the conversion of the one or more pentose-5-phosphate intermediate to one or more pentose or pentose-1-phosphate intermediate; introducing into or expressing in the recombinant microorganism a C2 pathway comprising one or more enzyme for the production of MEG or GA from glycolaldehyde; and introducing into or expressing in the recombinant microorganism a C3 pathway comprising one or more enzyme for the production of one or more co-product derived from DHAP or pyruvate; and culturing the recombinant microorganism in a culture medium containing the one or more hexose feedstock to produce or accumulate MEG or GA and one or more co-product, wherein glycolaldehyde and DHAP (or pyruvate) are intermediates produced in the C2 pathway, and wherein MEG or GA is produced in the C2 pathway and the one or more co-product is produced in the C3 pathway. In some embodiments, the glycolaldehyde is oxidized to glycolic acid by a glycolaldehyde dehydrogenase.

In some embodiments, the enzymes for the conversion of the one or more hexose feedstock to the one or more pentose-5-phosphate intermediate are selected from one or more enzyme having a transketolase activity, a transaldolase activity, a ribulose-5-phosphate 3-epimerase activity, and a ribose-5-phosphate isomerase activity. In further embodiments, the method further comprises introducing into the recombinant microorganism one or more modifications to diminish or delete activity in one or more endogenous enzymes selected from glyceraldehyde 3-phosphate dehydrogenase (gapA), phosphoglycerate kinase (pgk) and phosphoglycerate mutase (gpmA and/or gpmM).

In some embodiments, the enzymes for the conversion of the one or more hexose feedstock to the one or more pentose-5-phosphate intermediate are selected from one or more enzyme having a fructose-6-phosphate phosphoketolase activity, a phosphate acetyltransferase activity, a transketolase activity, a transaldolase activity, a ribulose-5-phosphate 3-epimerase activity, and a ribose-5-phosphate isomerase activity. In further embodiments, the method further comprises introducing into the recombinant microorganism one or more modifications to diminish or delete activity in an endogenous 6-phosphofructokinase (pfkA and/or pfkB) enzyme.

In yet further embodiments, the method further comprises: introducing into the recombinant microorganism one or more modifications to delete or diminish activity in one or more endogenous enzymes selected from glucose 6-phosphate-1-dehydrogenase, 6-phosphogluconolactonase, and 6-phosphogluconate dehydrogenase. In some embodiments, the glucose 6-phosphate-1-dehydrogenase is zwf, the 6-phosphogluconolactonase is pgl, and the 6-phosphogluconate dehydrogenase is gnd.

In some embodiments, the one or more enzyme for the conversion of the one or more pentose-5-phosphate intermediate to one or more pentose or pentose-1-phosphate intermediate are selected from one or more enzyme having a pentose phosphatase activity, a D-ribulose-5-phosphatase activity, a D-ribose-5-phosphatase activity, a D-ribose isomerase activity, an arabitol phosphate dehydrogenase activity, and a phosphopentomutase activity.

In some embodiments, the one or more enzyme for the production of MEG or GA derived from DHAP or pyruvate in the C3 pathway are selected from one or more enzyme having an activity selected from a 3-phosphoglycerate dehydrogenase activity, a phosphoserine aminotransferase activity, a 3-phosphohydroxypyruvate phosphatase activity, a phosphoserine phosphatase activity, a serine transaminase activity, a hydroxypyruvate decarboxylase activity, a 3-phosphohydroxypyruvate reductase activity, a glycolaldehyde reductase activity, a glycolaldehyde dehydrogenase activity, a serine oxidoreductase (deaminating) or serine-pyruvate aminotransferase activity, a serine decarboxylase activity, an ethanolamine aminotransferase or ethanolamine oxidoreductase (deaminating) activity, a glycerate decarboxylase activity, a hydroxypyruvate reductase activity, a 3-phosphoglycerate phosphatase activity, a 2-phosphoglycerate phosphatase activity, a glycerate 3-kinase activity, and a glycerate 2-kinase activity.

In some embodiments, the one or more enzyme for the production of one or more co-product derived from DHAP or pyruvate in the C3 pathway are selected from one or more enzyme having an activity selected from a thiolase or acetyl coenzyme A acetyltransferase activity, an acetyl-CoA:acetoacetate transferase or acetate:acetoacetyl-CoA hydrolase activity, and an acetoacetate decarboxylase activity, and the one or more co-product comprises acetone.

In some embodiments, the one or more enzyme for the production of one or more co-product derived from DHAP or pyruvate in the C3 pathway are selected from one or more enzyme having an activity selected from a thiolase or acetyl coenzyme A acetyltransferase activity, an acetyl-CoA:acetoacetate transferase or acetate:acetoacetyl-CoA hydrolase activity, an acetoacetate decarboxylase activity, and a secondary alcohol dehydrogenase activity, and the one or more co-product comprises isopropanol.

In some embodiments, the one or more enzyme for the production of one or more co-product derived from DHAP or pyruvate in the C3 pathway are selected from one or more enzyme having an activity selected from a thiolase or acetyl coenzyme A acetyltransferase activity, an acetyl-CoA:acetoacetate transferase or acetate:acetoacetyl-CoA hydrolase activity, an acetoacetate decarboxylase activity, a secondary alcohol dehydrogenase activity, and a dehydratase activity, and the one or more co-product comprises propene.

In some embodiments, the one or more enzyme for the production of one or more co-product derived from DHAP or pyruvate in the C3 pathway are selected from one or more enzyme having an activity selected from a thiolase or acetyl coenzyme A acetyltransferase activity, an acetyl-CoA:acetoacetate transferase or acetate:acetoacetyl-CoA hydrolase activity, an acetoacetate decarboxylase activity, a 3-hydroxyisovalerate (3HIV) synthase activity, a hydroxymethylglutaryl-CoA synthase activity, a methylglutaconyl-CoA hydratase activity, a methylcrotonyl-CoA carboxylase activity, a methylcrotonyl-CoA hydratase activity, a 3-hydroxyisovaleryl-CoA thioesterase activity, a 3HIV kinase activity, a 3HIV-3-phosphate decarboxylase activity, and a 3HIV decarboxylase activity, and the one or more co-product comprises isobutene.

In some embodiments, the one or more enzyme for the production of one or more co-product derived from DHAP or pyruvate in the C3 pathway are selected from one or more enzyme having an activity selected from a 3-phosphoglycerate dehydrogenase activity, a phosphoserine aminotransferase activity, a 3-phosphohydroxypyruvate phosphatase activity, a phosphoserine phosphatase activity, a serine oxidoreductase (deaminating) or serine-pyruvate aminotransferase activity, a hydroxypyruvate reductase activity, a 3-phosphoglycerate phosphatase activity, a 2-phosphoglycerate phosphatase activity, a glycerate 3-kinase activity, and a glycerate 2-kinase activity, and the one or more co-product comprises L-serine.

In some embodiments, the one or more enzyme for the production of one or more co-product derived from DHAP or pyruvate in the C3 pathway are selected from one or more enzyme having an activity selected from a serine hydroxymethyltransferase activity, a transferase activity, a formaldehyde dehydrogenase activity, a formate dehydrogenase activity, an activity associated with glycine cleavage system, a 3-phosphoglycerate dehydrogenase activity, a phosphoserine aminotransferase activity, a 3-phosphohydroxypyruvate phosphatase activity, a phosphoserine phosphatase activity, a serine transaminase activity, a hydroxypyruvate decarboxylase activity, a serine oxidoreductase (deaminating) activity, a serine decarboxylase activity, an ethanolamine aminotransferase or ethanolamine oxidoreductase (deaminating) activity, a hydroxypyruvate reductase activity, a 3-phosphoglycerate phosphatase activity, a 2-phosphoglycerate phosphatase activity, a glycerate 3-kinase activity, a glycerate 2-kinase activity, a glycolaldehyde dehydrogenase activity, a glycolate dehydrogenase activity, an alanine-glyoxylate aminotransferase activity, an alanine transaminase activity, and an NAD(P)H dependent glutamate dehydrogenase activity, and the one or more co-product comprises glycine. In other embodiments, the activity associated with glycine cleavage system comprise an enzyme or protein selected from a glycine decarboxylase (P protein), an aminomethyltransferase (T protein), a dihydrolipoamide dehydrogenase (L protein), and an H protein.

In some embodiments, the one or more enzyme for the production of one or more co-product derived from DHAP or pyruvate in the C3 pathway are selected from one or more enzyme having an activity selected from 3-phosphoglycerate dehydrogenase activity, a phosphoserine aminotransferase activity, a 3-phosphohydroxypyruvate phosphatase activity, a phosphoserine phosphatase activity, a transaminase activity, a hydroxypyruvate decarboxylase activity, a serine oxidoreductase (deaminating) or serine-pyruvate aminotransferase activity, a serine decarboxylase activity, a hydroxypyruvate reductase activity, a 3-phosphoglycerate phosphatase activity, a 2-phosphoglycerate phosphatase activity, a glycerate 3-kinase activity, a glycerate 2-kinase activity, an acetaldehyde dehydrogenase activity, and an ethanolamine ammonia lyase activity, and the one or more co-product comprises monoethanolamine (MEA).

In some embodiments, the one or more enzyme for the production of one or more co-product derived from DHAP or pyruvate in the C3 pathway are selected from one or more enzyme having an activity selected from a serine dehydrogenase activity, a 2-aminomalonate semialdehyde decarboxylase activity, an aminoacetaldehyde transaminase activity, a 2-aminomalonate semialdehyde transaminase activity, a 2,3-diaminopropanoate decarboxylase activity, a serine decarboxylase activity, an ethanolamine dehydrogenase activity, a serine hydroxymethyltransferase activity, an aldehyde oxidase activity, an N-acetyl transferase or O-acetyl transferase activity, an N-acetylserine dehydrogenase activity, a transaminase activity, a deacetylase activity, a serine aminase activity, and a 2,3-diaminopropanoate ammonia lyase activity, and the one or more co-product comprises ethylenediamine (EDA).

In some embodiments, the one or more enzyme for the production of MEG or GA in the C2 pathway are selected from one or more enzyme having an activity selected from a D-tagatose 3-epimerase activity, a D-ribulokinase activity, a D-ribulose-1-phosphate aldolase activity, a D-xylulose 1-kinase activity, a D-xylulose-1-phosphate aldolase activity, a xylose reductase or aldose reductase activity, a xylitol dehydrogenase activity, a xylose isomerase activity, a xylose dehydrogenase activity, a xylonolactonase activity, a xylonate dehydrogenase activity, a 2-keto-3-deoxy-D-pentonate aldolase activity, a glycolaldehyde reductase activity and a glycolaldehyde dehydrogenase activity.

In some embodiments, any of the methods of producing a recombinant microorganism described above further comprises: introducing into the recombinant microorganism one or more modifications to diminish or delete activity in a glycolaldehyde dehydrogenase, a lactate dehydrogenase, a xylose isomerase, a xylulose kinase or combination thereof.

Hexose to Pentose-5-Phosphate Intermediate

In the present disclosure, glucose flux is funneled into the pentose phosphate pathway instead of the glycolysis pathway by using a non-oxidative entry into the pentose phosphate pathway.

[mA] In one embodiment, the application relates to a method of producing a recombinant microorganism capable of producing one or more pentose-5-phosphate intermediate from one or more hexose feedstock, comprising introducing into and/or overexpressing in the recombinant microorganism one or more of the following from (a) to (d):

(a) at least one endogenous or exogenous nucleic acid molecule encoding an enzyme having transketolase activity that catalyzes a reversible conversion of fructose-6-phosphate and glyceraldehyde-3-phosphate to erythrose-4-phosphate and D-xylulose-5-phosphate, respectively, and/or that catalyzes a reversible conversion of glyceraldehyde-3-phosphate from (b) and seduheptulose-7-phosphate from (b) to D-ribose-5-phosphate and D-xylulose-5-phosphate, respectively;

(b) at least one endogenous or exogenous nucleic acid molecule encoding an enzyme having transaldolase activity that catalyzes a reversible conversion of fructose-6-phosphate and erythrose-4-phosphate from (a) to glyceraldehyde-3-phosphate and seduheptulose-7-phosphate, respectively;

(c) at least one endogenous or exogenous nucleic acid molecule encoding an enzyme having ribose-5-phosphate isomerase activity that catalyzes an interconversion of D-ribose-5-phosphate from (a) and D-ribulose-5-phosphate;

(d) at least one endogenous or exogenous nucleic acid molecule encoding an enzyme having ribulose-5-phosphate 3-epimerase activity that catalyzes an interconversion of D-xylulose-5-phosphate from (a) and D-ribulose-5-phosphate from (c);

wherein the method optionally further comprises introducing a deletion, insertion, or loss of function mutation in a gene encoding a glyceraldehyde 3-phosphate dehydrogenase;

wherein the one more hexose feedstock is converted to fructose-6-phosphate and glyceraldehyde-3-phosphate through an endogenous glycolysis pathway in the recombinant microorganism, and wherein the one or more pentose-5-phosphate intermediate produced is one or more of D-ribose-5-phosphate, D-xylulose-5-phosphate or D-ribulose-5-phosphate.

[mB] In another embodiment, the application relates to a method of producing a recombinant microorganism capable of producing one or more pentose-5-phosphate intermediate from one or more hexose feedstock, comprising introducing into and/or overexpressing in the recombinant microorganism one or more of the following from (a) to (f):

(a) at least one endogenous or exogenous nucleic acid molecule encoding an enzyme having fructose-6-phosphate phosphoketolase activity that catalyzes a reversible conversion of fructose-6-phosphate to erythrose-4-phosphate and acetyl-phosphate;

(b) at least one endogenous or exogenous nucleic acid molecule encoding an enzyme having phosphate acetyltransferase activity that catalyzes a reversible conversion of acetyl-phosphate from (a) to acetyl-CoA;

(c) at least one endogenous or exogenous nucleic acid molecule encoding an enzyme having transaldolase activity that catalyzes a reversible conversion of fructose-6-phosphate and erythrose-4-phosphate from (a) to glyceraldehyde-3-phosphate and seduheptulose-7-phosphate, respectively;

(d) at least one endogenous or exogenous nucleic acid molecule encoding an enzyme having transketolase activity that catalyzes a reversible conversion of glyceraldehyde-3-phosphate from (c) and seduheptulose-7-phosphate from (c) to D-ribose-5-phosphate and D-xylulose-5-phosphate, respectively;

(e) at least one endogenous or exogenous nucleic acid molecule encoding an enzyme having ribose-5-phosphate isomerase activity that catalyzes an interconversion of D-ribose-5-phosphate from (d) and D-ribulose-5-phosphate;

(f) at least one endogenous or exogenous nucleic acid molecule encoding an enzyme having ribulose-5-phosphate 3-epimerase activity that catalyzes an interconversion of D-xylulose-5-phosphate from (d) and D-ribulose-5-phosphate from (e);

wherein the method optionally further comprises introducing a deletion, insertion, or loss of function mutation in a gene encoding a 6-phosphofructokinase;

wherein the one more hexose feedstock is converted to fructose-6-phosphate through an endogenous glycolysis pathway in the recombinant microorganism, wherein the acetyl-CoA produced in step (b) can be used to produce one or more co-products selected from acetone, isopropanol, propene, isobutene, and serine pathway compounds;

and wherein the one or more pentose-5-phosphate intermediate produced is one or more of D-ribose-5-phosphate, D-xylulose-5-phosphate or D-ribulose-5-phosphate.

In some embodiments, the oxidative branch of the pentose phosphate pathway is deleted or inactivated to optimize flux towards the non-oxidative entry into the pentose phosphate pathway.

[mC] Therefore, in one embodiment, the method of embodiment [mA] or embodiment [mB] optionally further comprises introducing into the recombinant microorganism one or more modifications selected from the group consisting of:

(i) a deletion, insertion, or loss of function mutation in a gene encoding a glucose 6-phosphate-1-dehydrogenase that catalyzes the conversion of glucose-6-phosphate to 6-phospho-D-glucono-1,5-lactone;

(ii) a deletion, insertion, or loss of function mutation in a gene encoding a 6-phosphogluconolactonase that catalyzes the conversion of 6-phospho-D-glucono-1,5-lactone to gluconate-6-phosphate; and (iii) a deletion, insertion, or loss of function mutation in a gene encoding a 6-phosphogluconate dehydrogenase that catalyzes the conversion of gluconate-6-phosphate to D-ribulose-5-phosphate.

Connecting Pentose Phosphate Pathway and MEG (or Glycolic Acid) Production Pathways In another aspect, a pentose-5-phosphate intermediate produced by the method of embodiment [mA] or embodiment [mB] (and optionally comprising embodiment [mC]) can be connected with any one of the known C2 MEG or glycolic acid production pathways by pentose phosphatases.

[mD] Therefore, in one embodiment, the application relates to a method of producing a recombinant microorganism capable of producing D-xylulose from D-xylulose-5-phosphate, wherein the method comprises introducing into or expressing in the recombinant microorganism one or more of a pentose-5-phosphatase, wherein the D-xylulose-5-phosphate is produced by non-oxidative branch of pentose phosphate pathway, and wherein the D-xylulose can be used to produce MEG (or glycolic acid) and optionally, one or more co-product.

[mE] In one embodiment, the application relates to a method of producing a recombinant microorganism capable of producing D-ribulose from D-ribulose-5-phosphate or from D-ribose-5-phosphate, wherein the method further comprises introducing into or expressing in the recombinant microorganism one or more of the following from (a) to (c):

(a) at least one endogenous or exogenous nucleic acid molecule encoding an enzyme having D-ribulose-5-phosphatase activity and/or an enzyme having pentose-5-phosphatase activity that catalyzes a reversible conversion of D-ribulose-5-phosphate to D-ribulose;

(b) at least one endogenous or exogenous nucleic acid molecule encoding an enzyme having D-ribose-5-phosphatase activity and/or an enzyme having pentose-5-phosphatase activity that catalyzes a reversible conversion of D-ribose-5-phosphate to D-ribose;

(c) at least one endogenous or exogenous nucleic acid molecule encoding an enzyme having D-ribose isomerase activity that catalyzes a reversible conversion of D-ribose from (b) to D-ribulose;

wherein the D-ribulose-5-phosphate and/or D-ribose-5-phosphate is produced by non-oxidative branch of pentose phosphate pathway, and wherein the D-ribulose can be used to produce MEG (or glycolic acid) and optionally, one or more co-product.

In another aspect, a pentose-5-phosphate intermediate produced by the method of embodiment [mA] or embodiment [mB] (and optionally comprising embodiment [mC]) can be connected with any one of the known C2 MEG or glycolic acid production pathways by arabitol phosphate dehydrogenases.

[mF] In one embodiment, the application relates to a method of producing a recombinant microorganism capable of producing D-ribulose-1-phosphate from D-xylulose-5-phosphate or producing D-xylulose-1-phosphate from D-ribulose-5-phosphate, wherein the method comprises introducing into or expressing in the recombinant microorganism one or more arabitol phosphate dehydrogenase, wherein the one or more arabitol phosphate dehydrogenase catalyzes one or more of the following from (a) to (d):

(a) a reversible conversion of D-xylulose-5-phosphate to D-arabitol-1-phosphate;

(b) a reversible conversion of D-arabitol-1-phosphate from (a) to D-ribulose-1-phosphate;

(c) a reversible conversion of D-ribulose-5-phosphate to D-arabitol-5-phosphate;

(d) a reversible conversion of D-arabitol-5-phosphate from (c) to D-xylulose-1-phosphate, wherein the D-xylulose-5-phosphate and/or D-ribulose-5-phosphate is produced by non-oxidative branch of pentose phosphate pathway, and wherein the D-ribulose-1-phosphate and/or D-xylulose-1-phosphate can be used to produce MEG (or glycolic acid) and optionally, one or more co-product.

In another aspect, a pentose-5-phosphate intermediate produced by the method of embodiment [mA] or embodiment [mB] (and optionally comprising embodiment [mC]) can be connected with any one of the known C2 MEG or glycolic acid production pathways by phosphopentomutases.

[mG] In one embodiment, the application relates to a method of producing a recombinant microorganism capable of producing D-xylulose-1-phosphate from D-xylulose-5-phosphate or producing D-ribulose-1-phosphate from D-ribulose-5-phosphate, wherein the method comprises introducing into or expressing in the recombinant microorganism one or more phosphopentomutases, wherein the D-xylulose-5-phosphate and/or D-ribulose-5-phosphate is produced by non-oxidative branch of pentose phosphate pathway, and wherein the D-ribulose-1-phosphate and/or D-xylulose-1-phosphate can be used to produce MEG (or glycolic acid) and optionally, one or more co-product.

MEG (or Glycolic Acid), or Optionally MEG (or Glycolic Acid) and One or More Co-Product Production Pathways In some embodiments, the pentose or pentose-1-phosphate intermediates produced in embodiments [mD], [mE],

[mF], and [mG] are used in known MEG (or glycolic acid) C2 production pathways, which are coupled to C3 pathways, as described below, to co-produce additional MEG (or glycolic acid) or one or more co-products.

In some embodiments, MEG (or glycolic acid) is produced via a C2 pathway that uses D-xylulose-1-phosphate.

[mH] In one embodiment, the application relates to a method of producing a recombinant microorganism capable of producing monoethylene glycol (MEG) (or glycolic acid) from one or more hexose feedstock, wherein the method of embodiment [mA] or embodiment [mB] (and optionally comprising embodiment [mC]), and comprising additionally one or more of embodiments [mD], [mF], and [mG], further comprises introducing into or rexpressing in the recombinant microorganism one or more of the following from (a) to (d):
- (a) at least one endogenous or exogenous nucleic acid molecule encoding an enzyme having D-xylulose 1-kinase activity that catalyzes the conversion of D-xylulose from embodiment [mD] to D-xylulose-1-phosphate;
- (b) at least one endogenous or exogenous nucleic acid molecule encoding an enzyme having D-xylulose-1-phosphate aldolase activity that catalyzes the conversion of D-xylulose-1-phosphate from (a), from embodiment [mF] and/or from embodiment [mG], to glycolaldehyde and dihydroxyacetonephosphate (DHAP);
- (c) at least one endogenous or exogenous nucleic acid molecule encoding an enzyme having glycolaldehyde reductase activity or an enzyme having aldehyde reductase activity that catalyzes the conversion of glycolaldehyde from (b) to MEG;
- (d) at least one endogenous or exogenous nucleic acid molecule encoding an enzyme having glycolaldehyde dehydrogenase activity that catalyzes the conversion of glycolaldehyde from (b) to glycolic acid;

wherein MEG (or glycolic acid) and DHAP are produced.

In some embodiments, MEG (or glycolic acid) is produced via a C2 pathway that uses D-ribulose-1-phosphate.

[mI] In one embodiment, the application relates to a method of producing a recombinant microorganism capable of producing monoethylene glycol (MEG) (or glycolic acid) from one or more hexose feedstock, wherein the method of embodiment [mA] or embodiment [mB] (and optionally comprising embodiment [mC]), and comprising additionally one or more of embodiments [mD], [mE], [mF], and [mG], further comprises introducing into or expressing in the recombinant microorganism one or more of the following from (a) to (e):
- (a) at least one endogenous or exogenous nucleic acid molecule encoding an enzyme having D-tagatose 3-epimerase activity that catalyzes the conversion of D-xylulose from embodiment [mD] to D-ribulose;
- (b) at least one endogenous or exogenous nucleic acid molecule encoding an enzyme having D-ribulokinase activity that catalyzes the conversion of D-ribulose from (a) and/or from embodiment [mE] to D-ribulose-1-phosphate;
- (c) at least one endogenous or exogenous nucleic acid molecule encoding an enzyme having D-ribulose-1-phosphate aldolase activity that catalyzes the conversion of D-ribulose-1-phosphate from (b), from embodiment [mF] and/or from embodiment [mG] to glycolaldehyde and dihydroxyacetonephosphate (DHAP);
- (d) at least one endogenous or exogenous nucleic acid molecule encoding an enzyme having glycolaldehyde reductase activity that catalyzes the conversion of glycolaldehyde from (c) to MEG;
- (e) at least one endogenous or exogenous nucleic acid molecule encoding an enzyme having glycolaldehyde dehydrogenase activity that catalyzes the conversion of glycolaldehyde from (c) to glycolic acid;

wherein MEG (or glycolic acid) and DHAP are produced.

In some embodiments, MEG (or glycolic acid) is produced via a C2 pathway that uses D-xylonate.

[mJ] In one embodiment, the application relates to a method of producing a recombinant microorganism capable of producing monoethylene glycol (MEG) (or glycolic acid) from one or more hexose feedstock, wherein the method of embodiment [mA] or embodiment [mB] (and optionally comprising embodiment [mC]), and comprising additionally embodiment [mD], further comprises introducing into and/or expressing in the recombinant microorganism one or more of the following from (a) to (d):
- (a) at least one endogenous or exogenous nucleic acid molecule encoding an enzyme having xylose isomerase activity that catalyzes the conversion of D-xylulose from embodiment [mD] to D-xylose;
- (b) at least one endogenous or exogenous nucleic acid molecule encoding an enzyme having xylose dehydrogenase activity that catalyzes the conversion of D-xylose from (a) to D-xylonolactone;
- (c) at least one endogenous or exogenous nucleic acid molecule encoding an enzyme having xylonolactonase activity that catalyzes the conversion of D-xylonolactone from (b) to D-xylonate;
- (d) at least one endogenous or exogenous nucleic acid molecule encoding an enzyme having xylose dehydrogenase activity that catalyzes the conversion of D-xylose from (a) to D-xylonate;

wherein the method further comprises introducing into or expressing in the recombinant microorganism one or more of the following from (e) to (h):
- (e) at least one endogenous or exogenous nucleic acid molecule encoding an enzyme having xylonate dehydratase activity that catalyzes the conversion of D-xylonate from (c) or (d) to 2-keto-3-deoxy-xylonate;
- (f) at least one endogenous or exogenous nucleic acid molecule encoding an enzyme having 2-keto-3-deoxy-D-pentonate aldolase activity that catalyzes the conversion of 2-keto-3-deoxy-xylonate from (e) to glycolaldehyde and pyruvate;
- (g) at least one endogenous or exogenous nucleic acid molecule encoding an enzyme having glycolaldehyde reductase activity that catalyzes the conversion of glycolaldehyde from (0 to MEG;
- (h) at least one endogenous or exogenous nucleic acid molecule encoding an enzyme having glycolaldehyde dehydrogenase activity that catalyzes the conversion of glycolaldehyde from (0 to glycolic acid;

wherein MEG (or glycolic acid) and pyruvate are produced.

In some embodiments, the C2 pathway for production of MEG (or glycolic acid) comprises embodiment [mH] and the C3 pathway for production of MEG (or glycolic acid) comprises embodiment [mK]. In other embodiments, the C2 pathway for production of MEG (or glycolic acid) comprises embodiment [mH] and the C3 pathway for production of MEG (or glycolic acid) comprises embodiment [mL]. In some embodiments, the C2 pathway for production of MEG (or glycolic acid) comprises embodiment [mI] and the C3 pathway for production of MEG (or glycolic acid) comprises embodiment [mK]. In further embodiments, the C2 pathway for production of MEG (or glycolic acid) comprises embodiment [mI] and the C3 pathway for production of MEG (or glycolic acid) comprises embodiment [mL]. In some embodiments, the C2 pathway for production of MEG (or glycolic acid) comprises embodiment [mJ] and the C3 pathway for production of MEG (or glycolic acid) comprises embodiment [mK]. In some embodiments, the C2 pathway for production of MEG (or glycolic acid) comprises embodiment [mJ] and the C3 pathway for production of MEG (or glycolic acid) comprises embodiment [mL].

[mK] In one embodiment, the application relates to a method of producing a recombinant microorganism capable of producing monoethylene glycol (MEG) (or glycolic acid) from one or more hexose feedstock, wherein the method of embodiment [mA] or embodiment [mB] (and optionally comprising embodiment [mC]), and comprising additionally one or more of embodiments [mD], [mE], [mF], and [mG], further comprising one or more of embodiments [mH], [mI], and [mJ], further comprises introducing into and/or expressing in the recombinant microorganism one or more of the following from (a) to (h):

(a) at least one endogenous or exogenous nucleic acid molecule encoding an enzyme having 3-phosphoglycerate dehydrogenase activity that catalyzes the conversion of 3-phosphoglycerate to 3-phosphohydroxypyruvate;

(b) at least one endogenous or exogenous nucleic acid molecule encoding an enzyme having phosphoserine aminotransferase activity that catalyzes the conversion of 3-phosphohydroxypyruvate from (a) to phospho-L-serine;

(c) at least one endogenous or exogenous nucleic acid molecule encoding an enzyme having 3-phosphohydroxypyruvate phosphatase activity that catalyzes the conversion of 3-phosphohydroxypyruvate from (a) to hydroxypyruvate;

(d) at least one endogenous or exogenous nucleic acid molecule encoding an enzyme having phosphoserine phosphatase activity that catalyzes the conversion of phospho-L-serine from (b) to L-serine;

(e) at least one endogenous or exogenous nucleic acid molecule encoding an enzyme having L-serine transaminase or serine oxidase activity that catalyzes the conversion of L-serine from (d) to hydroxypyruvate;

(f) at least one endogenous or exogenous nucleic acid molecule encoding an enzyme having hydroxypyruvate decarboxylase activity that catalyzes the conversion of hydroxypyruvate from (c) or (e) to glycolaldehyde;

(g) at least one endogenous or exogenous nucleic acid molecule encoding an enzyme having glycolaldehyde reductase activity that catalyzes the conversion of glycolaldehyde from (f) to MEG;

(h) at least one endogenous or exogenous nucleic acid molecule encoding an enzyme having glycolaldehyde dehydrogenase activity that catalyzes the conversion of glycolaldehyde from (f) to glycolic acid;

wherein the produced intermediate DHAP from embodiments [mH] and/or [mI] and/or pyruvate from embodiment [mJ] is converted to 3-phosphoglycerate through endogenous glycolysis or gluconeogenesis, respectively, in the microorganism, and wherein MEG (or glycolic acid) is produced.

[mL] In one embodiment, the application relates to a method of producing a recombinant microorganism capable of producing monoethylene glycol (MEG) (or glycolic acid) from one or more hexose feedstock, wherein the method of embodiment [mA] or embodiment [mB] (and optionally comprising embodiment [mC]), and comprising additionally one or more of embodiments [mD], [mE], [mF], and [mG], further comprising one or more of embodiments [mH], [mI], and [mJ], further comprises introducing into and/or expressing in the recombinant microorganism one or more of the following from (a) to (j):

(a) at least one endogenous or exogenous nucleic acid molecule encoding an enzyme having 2-phosphoglycerate phosphatase activity and/or an enzyme having glycerate-2-kinase activity that catalyzes the conversion of 2-phosphoglycerate to glycerate;

(b) at least one endogenous or exogenous nucleic acid molecule encoding an enzyme having 3-phosphoglycerate phosphatase activity or an enzyme having glycerate-3-kinase activity that catalyzes the conversion of 3-phosphoglycerate to glycerate;

(c) at least one endogenous or exogenous nucleic acid molecule encoding an enzyme having hydroxypyruvate reductase activity that catalyzes the conversion of glycerate from (a) and/or (b) to hydroxypyruvate;

(d) at least one endogenous or exogenous nucleic acid molecule encoding an enzyme having serine aminotransferase activity or an enzyme having serine oxidoreductase (deaminating) activity that catalyzes the conversion of L-serine to hydroxypyruvate;

(e) at least one endogenous or exogenous nucleic acid molecule encoding an enzyme having L-serine decarboxylase activity that catalyzes the conversion of L-serine to ethanolamine;

(f) at least one endogenous or exogenous nucleic acid molecule encoding an enzyme having hydroxypyruvate decarboxylase activity that catalyzes the conversion of hydroxypyruvate from (c) and/or (d) to glycolaldehyde;

(g) at least one endogenous or exogenous nucleic acid molecule encoding an enzyme having ethanolamine aminotransferase or ethanolamine oidoreductase (deaminating) activity that catalyzes the conversion of ethanolamine from (e) to glycolaldehyde;

(h) at least one endogenous or exogenous nucleic acid molecule encoding an enzyme having glycerate decarboxylase activity that catalyzes the conversion of glycerate from (a) and/or (b) to MEG;

(i) at least one endogenous or exogenous nucleic acid molecule encoding an enzyme having glycolaldehyde reductase activity that catalyzes the conversion of glycolaldehyde from (0 and/or (g) to MEG;

(j) at least one endogenous or exogenous nucleic acid molecule encoding an enzyme having glycolaldehyde dehydrogenase activity that catalyzes the conversion of glycolaldehyde from (0 and/or (g) to glycolic acid;

wherein the produced intermediate DHAP from embodiments [mH] and/or [mI] and/or pyruvate from embodiment [mJ] is converted to 3-phosphoglycerate and/or 2-phosphoglycerate through endogenous glycolysis or gluconeogenesis in the microorganism, and wherein MEG (or glycolic acid) is produced.

In some embodiments, the C2 pathway for production of MEG (or glycolic acid) comprises embodiment [mH] and the C3 pathway for production of acetone comprises embodiment [mM]. In some embodiments, the C2 pathway for production of MEG (or glycolic acid) comprises embodiment [mI] and the C3 pathway for production of acetone comprises embodiment [mM]. In some embodiments, the C2 pathway for production of MEG (or glycolic acid)

comprises embodiment [mJ] and the C3 pathway for production of acetone comprises embodiment [mM].

[mM] In one embodiment, the application relates to a method of producing a recombinant microorganism capable of co-producing monoethylene glycol (MEG) (or glycolic acid) and acetone, from one or more hexose feedstock, wherein the method of embodiment [mA] or embodiment [mB] (and optionally comprising embodiment [mC]), and comprising additionally one or more of embodiments [mD], [mE], [mF] and [mG], further comprising one or more of embodiments [mH], [mI], and [mJ], further comprises introducing into and/or expressing in the recombinant microorganism one or more of the following from (a) to (c):
- (a) at least one endogenous or exogenous nucleic acid molecule encoding an enzyme having thiolase or acetyl coenzyme A acetyltransferase activity that catalyzes the conversion of acetyl-CoA to acetoacetyl-CoA;
- (b) at least one endogenous or exogenous nucleic acid molecule encoding an enzyme having acetyl-CoA:acetoacetate-CoA transferase activity or an enzyme having acetate:acetoacetyl-CoA hydrolase activity that catalyzes the conversion of acetoacetyl-CoA from (a) to acetoacetate; and/or
- (c) at least one endogenous or exogenous nucleic acid molecule encoding an enzyme having acetoacetate decarboxylase activity that catalyzes the conversion of acetoacetate from (b) to acetone;

wherein the produced intermediate DHAP from embodiments [mH] and/or [mI] and/or pyruvate from embodiment [mJ] is converted to acetyl-CoA through endogenous glycolysis in the microorganism, and wherein MEG (or glycolic acid) and acetone are co-produced.

In some embodiments, the C2 pathway for production of MEG (or glycolic acid) comprises embodiment [mH] and the C3 pathway for production of isobutene comprises embodiment [mN]. In some embodiments, the C2 pathway for production of MEG (or glycolic acid) comprises embodiment [mI] and the C3 pathway for production of isobutene comprises embodiment [mN]. In some embodiments, the C2 pathway for production of MEG (or glycolic acid) comprises embodiment [mJ] and the C3 pathway for production of isobutene comprises embodiment [mN].

[mN] In some embodiments, the application relates to a method of producing a recombinant microorganism capable of co-producing monoethylene glycol (MEG) (or glycolic acid) and isobutene via acetone or HMG-CoA, from one or more hexose feedstock, wherein the method of embodiment [mA] or embodiment [mB] (and optionally comprising embodiment [mC]), and comprising additionally one or more of embodiments [mD], [mE], [mF] and [mG], further comprising one or more of embodiments [mH], [mI], and [mJ], further comprises introducing into and/or expressing in the recombinant microorganism one or more of the following from (a) to (d):
- (a) at least one endogenous or exogenous nucleic acid molecule encoding an enzyme having thiolase or acetyl coenzyme A acetyltransferase activity that catalyzes the conversion of acetyl-CoA to acetoacetyl-CoA;
- (b) at least one endogenous or exogenous nucleic acid molecule encoding an enzyme having acetyl-CoA:acetoacetate-CoA transferase activity or an enzyme having acetate:acetoacetyl-CoA hydrolase activity that catalyzes the conversion of acetoacetyl-CoA from (a) to acetoacetate;
- (c) at least one endogenous or exogenous nucleic acid molecule encoding an enzyme having acetoacetate decarboxylase activity that catalyzes the conversion of acetoacetate from (b) to acetone;
- (d) at least one endogenous or exogenous nucleic acid molecule encoding an enzyme having 3-hydroxyisovalerate synthase activity that catalyzes the conversion of acetone from (c) and acetyl-CoA to 3-hydroxyisovalerate (3HIV);

or
wherein the method comprises introducing into or expressing in the recombinant microorganism one or more of the following from (e) to (j):
- (e) at least one endogenous or exogenous nucleic acid molecule encoding an enzyme having thiolase or acetyl coenzyme A acetyltransferase activity that catalyzes the conversion of acetyl-CoA to acetoacetyl-CoA;
- (f) at least one endogenous or exogenous nucleic acid molecule encoding an enzyme having hydroxymethylglutaryl-CoA synthase activity that catalyzes the conversion of acetoacetyl-CoA from (e) and acetyl-CoA to 3-hydroxy-3-methylglutaryl-CoA (HMG-CoA);
- (g) at least one endogenous or exogenous nucleic acid molecule encoding an enzyme having methylglutaconyl-CoA hydratase activity that catalyzes the conversion of HMG-CoA from (f) to 3-methylglutaconyl-CoA;
- (h) at least one endogenous or exogenous nucleic acid molecule encoding an enzyme having methylcrotonyl-CoA carboxylase activity that catalyzes the conversion of 3-methylglutaconyl-CoA from (g) to 3-methylcrotonyl-CoA;
- (i) at least one endogenous or exogenous nucleic acid molecule encoding an enzyme having methylcrotonyl-CoA hydratase activity that catalyzes the conversion of 3-methylcrotonyl-CoA from (h) to 3-hydroxyisovaleryl-CoA;
- (j) at least one endogenous or exogenous nucleic acid molecule encoding an enzyme having 3-hydroxyisovaleryl-CoA thioesterase activity that catalyzes the conversion of 3-hydroxyisovaleryl-CoA from (i) to 3HIV;

wherein the method further introducing into or expressing in the recombinant microorganism (a1) and (a2), and/or (b1) selected from:
- (a1) at least one endogenous or exogenous nucleic acid molecule encoding an enzyme having 3HIV kinase activity that catalyzes the conversion of 3HIV from (d) or (j) to 3HIV-3-phosphate;
- (a2) at least one endogenous or exogenous nucleic acid molecule encoding an enzyme having 3HIV-3-phosphate decarboxylase activity that catalyzes the conversion of 3HIV-3-phosphate from (a1) to isobutene;
- (b1) at least one endogenous or exogenous nucleic acid molecule encoding a an enzyme having 3HIV decarboxylase activity that catalyzes the conversion of 3HIV from (d) or (j) to isobutene;

wherein the produced intermediate DHAP from embodiments [mH] and/or [mI] and/or pyruvate from embodiment [mJ] is converted to acetyl-CoA through endogenous glycolysis in the microorganism, and wherein MEG (or glycolic acid) and isobutene are co-produced.

[mO] In one embodiment, the method of embodiment [mM] and/or [mN] (optionally comprising embodiment [EE]), optionally further comprise introducing into and/or expressing in the recombinant microorganism at least one endogenous or exogenous nucleic acid molecule encoding an enzyme having secondary alcohol dehydrogenase activity that catalyzes the conversion of acetone to isopropanol.

[mP] In another embodiment, the method of embodiment [mO] (optionally comprising embodiment [EE]), optionally further comprises introducing into and/or expressing in the recombinant microorganism at least one endogenous or exogenous nucleic acid molecule encoding an enzyme having dehydratase activity that catalyzes the conversion of isopropanol to propene.

In some embodiments, the C2 pathway for production of MEG (or glycolic acid) comprises embodiment [mH] and the C3 pathway for production of serine comprises embodiment [mQ]. In some embodiments, the C2 pathway for production of MEG (or glycolic acid) comprises embodiment [mI] and the C3 pathway for production of serine comprises embodiment [mQ]. In some embodiments, the C2 pathway for production of MEG (or glycolic acid) comprises embodiment [mJ] and the C3 pathway for production of serine comprises embodiment [mQ].

[mQ] In one embodiment, the application relates to a method of producing a recombinant microorganism capable of co-producing monoethylene glycol (MEG) (or glycolic acid) and serine, from one or more hexose feedstock and a nitrogen source, wherein the method of embodiment [mA] or embodiment [mB] (and optionally comprising embodiment [mC]), and comprising additionally one or more of embodiments [mD], [mE], [mF] and [mG], further comprising one or more of embodiments [mH], [mI], and [mJ], further comprises introducing into and/or expressing in the recombinant microorganism one or more of the following from (a) to (h):
  (a) at least one endogenous or exogenous nucleic acid molecule encoding an enzyme having 3-phosphoglycerate dehydrogenase activity that catalyzes the conversion of 3-phosphoglycerate to 3-phosphohydroxypyruvate;
  (b) at least one endogenous or exogenous nucleic acid molecule encoding an enzyme having 3-phosphoglycerate phosphatase activity and/or an enzyme having glycerate 3-kinase activity that catalyzes the conversion of 3-phosphoglycerate to glycerate;
  (c) at least one endogenous or exogenous nucleic acid molecule encoding an enzyme having 2-phosphoglycerate phosphatase activity and/or an enzyme having glycerate 2-kinase activity that catalyzes the conversion of 2-phosphoglycerate to glycerate;
  (d) at least one endogenous or exogenous nucleic acid molecule encoding an enzyme having phosphoserine aminotransferase activity that catalyzes the conversion of 3-phosphohydroxypyruvate from (a) to phospho-L-serine;
  (e) at least one endogenous or exogenous nucleic acid molecule encoding an enzyme having 3-phosphohydroxypyruvate phosphatase activity that catalyzes the conversion of 3-phosphohydroxypyruvate from (a) to hydroxypyruvate;
  (f) at least one endogenous or exogenous nucleic acid molecule encoding an enzyme having phosphoserine phosphatase activity that catalyzes the conversion of phospho-L-serine from (d) to L-serine;
  (g) at least one endogenous or exogenous nucleic acid molecule encoding an enzyme having hydroxypyruvate reductase activity that catalyzes the conversion of glycerate from (b) and/or (c) to hydroxypyruvate;
  (h) at least one endogenous or exogenous nucleic acid molecule encoding an enzyme having serine-pyruvate aminotransferase activity that catalyzes the conversion of hydroxypyruvate from (e) and/or (g) to L-serine;

wherein the produced intermediate DHAP from embodiments [mH] and/or [mI] and/or pyruvate from embodiment [mJ] is converted to 3-phosphoglycerate and/or 2-phosphoglycerate through endogenous glycolysis or gluconeogenesis in the microorganism, and wherein MEG (or glycolic acid) and serine are produced.

In some embodiments, the C2 pathway for production of MEG (or glycolic acid) comprises embodiment [mH] and the C3 pathway for production of glycine comprises embodiment [mR]. In other embodiments, the C2 pathway for production of MEG (or glycolic acid) comprises embodiment [mH] and the C3 pathway for production of glycine comprises embodiment [mS]. In further embodiments, the C2 pathway for production of MEG (or glycolic acid) comprises embodiment [mH] and the C3 pathway for production of glycine comprises embodiment [mT]. In some embodiments, the C2 pathway for production of MEG (or glycolic acid) comprises embodiment [mI] and the C3 pathway for production of glycine comprises embodiment [mR]. In other embodiments, the C2 pathway for production of MEG (or glycolic acid) comprises embodiment [mI] and the C3 pathway for production of glycine comprises embodiment [mS]. In further embodiments, the C2 pathway for production of MEG (or glycolic acid) comprises embodiment [mI] and the C3 pathway for production of glycine comprises embodiment [mT]. In some embodiments, the C2 pathway for production of MEG (or glycolic acid) comprises embodiment [mJ] and the C3 pathway for production of glycine comprises embodiment [mR]. In other embodiments, the C2 pathway for production of MEG (or glycolic acid) comprises embodiment [mJ] and the C3 pathway for production of glycine comprises embodiment [mS]. In further embodiments, the C2 pathway for production of MEG (or glycolic acid) comprises embodiment [mJ] and the C3 pathway for production of glycine comprises embodiment [mT].

[mR] In one embodiment, the application relates to a method of producing a recombinant microorganism capable of producing monoethylene glycol (MEG) (or glycolic acid) and glycine, from one or more hexose feedstock and a nitrogen source, wherein the method of embodiment [mA] or embodiment [mB] (and optionally comprising embodiment [mC]), and comprising additionally one or more of embodiments [mD], [mE], [mF] and [mG], further comprising one or more of embodiments [mH], [mI], and [mJ], further comprises introducing into or expressing in the recombinant microorganism one or more of the following from (a) to (e):
  (a) at least one endogenous or exogenous nucleic acid molecule encoding an enzyme having serine hydroxymethyltransferase activity that catalyzes the conversion of L-serine and tetrahydrofolate (THF) to glycine and 5,10-methylene tetrahydrofolate (M-THF);
  (b) at least one endogenous or exogenous nucleic acid molecule encoding an enzyme having transferase activity that catalyzes the conversion of M-THF from (a) to formaldehyde;
  (c) at least one endogenous or exogenous nucleic acid molecule encoding an enzyme having formaldehyde dehydrogenase activity that catalyzes the conversion of formaldehyde from (b) to formate and NADH;
  (d) at least one endogenous or exogenous nucleic acid molecule encoding an enzyme having formate dehydrogenase activity that catalyzes the conversion of formate from (c) to $CO_2$ and NADH;
  (e) at least one endogenous or exogenous nucleic acid molecule encoding a protein of the glycine cleavage system that catalyze the conversion of M-THF from (a), $CO_2$, $NH_3$ and NADH from (c) or (d) to glycine and THF;

wherein THF is reconstituted from steps (b) through (e), wherein optionally formate from (c) is further oxidized to $CO_2$ and H2 by a formate hydrogenaselyase complex, and wherein MEG (or glycolic acid) and glycine are produced.

[mS] In one embodiment, the application relates to a method of producing a recombinant microorganism capable of co-producing monoethylene glycol (MEG) (or glycolic acid) and glycine, from one or more hexose feedstock and a nitrogen source, wherein the method of embodiment [mA] or embodiment [mB] (and optionally comprising embodiment [mC]), and comprising additionally one or more of embodiments [mD], [mE], [mF] and [mG], further comprising one or more of embodiments [mH], [mI], and [mJ], further comprises introducing into or expressing in the recombinant microorganism one or more of the following from (a) to (k):

(a) at least one endogenous or exogenous nucleic acid molecule encoding an enzyme having 3-phosphoglycerate dehydrogenase activity that catalyzes the conversion of 3-phosphoglycerate to 3-phosphohydroxypyruvate;

(b) at least one endogenous or exogenous nucleic acid molecule encoding an enzyme having phosphoserine aminotransferase activity that catalyzes the conversion of 3-phosphohydroxypyruvate from (a) to phospho-L-serine;

(c) at least one endogenous or exogenous nucleic acid molecule encoding an enzyme having 3-phosphohydroxypyruvate phosphatase activity that catalyzes the conversion of 3-phosphohydroxypyruvate from (a) to hydroxypyruvate;

(d) at least one endogenous or exogenous nucleic acid molecule encoding an enzyme having phosphoserine phosphatase activity that catalyzes the conversion of phospho-L-serine from (b) to L-serine;

(e) at least one endogenous or exogenous nucleic acid molecule encoding an enzyme having L-serine transaminase or serine oxidase activity that catalyzes the conversion of L-serine from (d) to hydroxypyruvate;

(f) at least one endogenous or exogenous nucleic acid molecule encoding an enzyme having hydroxypyruvate decarboxylase activity that catalyzes the conversion of hydroxypyruvate from (c) or (e) to glycolaldehyde;

(g) at least one endogenous or exogenous nucleic acid molecule encoding an enzyme having glycolaldehyde dehydrogenase activity that catalyzes the conversion of glycolaldehyde from (f) to glycolic acid;

(h) at least one endogenous or exogenous nucleic acid molecule encoding an enzyme having glycolate dehydrogenase activity that catalyzes the conversion of glycolic acid from (g) to glyoxylate;

(i) at least one endogenous or exogenous nucleic acid molecule encoding an enzyme having alanine-glyoxylate aminotransferase activity that catalyzes the conversion of glyoxylate from (h) and alanine to glycine and pyruvate;

(j) at least one endogenous or exogenous nucleic acid molecule encoding an enzyme having alanine transaminase activity that catalyzes the conversion of pyruvate from (i) and glutamate to alanine and 2-oxoglutarate;

(k) at least one endogenous or exogenous nucleic acid molecule encoding an enzyme having NAD(P)H dependent glutamate dehydrogenase activity that catalyzes the conversion of 2-oxoglutarate from (j) and ammonia to glutamate;

wherein the produced intermediate DHAP from embodiments [mH] and/or [mI] and/or pyruvate from embodiment [mJ] is converted to 3-phosphoglycerate and/or 2-phosphoglycerate through endogenous glycolysis or gluconeogenesis in the microorganism, wherein the glyoxylate for step (i) optionally comes from glyoxylate shunt in the microorganism, wherein alanine and glutamate are reconstituted from steps (j) and (k), and wherein MEG (or glycolic acid) and glycine are co-produced.

[mT] In one embodiment, the application relates to a method of producing a recombinant microorganism capable of co-producing monoethylene glycol (MEG) (or glycolic acid) and glycine, from one or more hexose feedstock and a nitrogen source, wherein the method of embodiment [A] or embodiment [B] (and optionally comprising embodiment [C]), and comprising additionally one or more of embodiments [D], [E], [F] and [G], further comprising one or more of embodiments [H], [I], and [J], further comprises introducing into or expressing in the recombinant microorganism one or more of the following from (a) to (l):

(a) at least one endogenous or exogenous nucleic acid molecule encoding an enzyme having 2-phosphoglycerate phosphatase activity and/or an enzyme having glycerate-2-kinase activity that catalyzes the conversion of 2-phosphoglycerate to glycerate;

(b) at least one endogenous or exogenous nucleic acid molecule encoding an enzyme having 3-phosphoglycerate phosphatase activity and/or an enzyme having glycerate-3-kinase activity that catalyzes the conversion of 3-phosphoglycerate to glycerate;

(c) at least one endogenous or exogenous nucleic acid molecule encoding an enzyme having hydroxypyruvate reductase activity that catalyzes the conversion of glycerate from (a) and/or (b) to hydroxypyruvate;

(d) at least one endogenous or exogenous nucleic acid molecule encoding an enzyme having serine aminotransferase or serine oxidoreductase (deaminating) activity that catalyzes the conversion of L-serine to hydroxypyruvate;

(e) at least one endogenous or exogenous nucleic acid molecule encoding an enzyme having L-serine decarboxylase activity that catalyzes the conversion of L-serine to ethanolamine;

(f) at least one endogenous or exogenous nucleic acid molecule encoding an enzyme having hydroxypyruvate decarboxylase activity that catalyzes the conversion of hydroxypyruvate from (c) and/or (d) to glycolaldehyde;

(g) at least one endogenous or exogenous nucleic acid molecule encoding an enzyme having ethanolamine aminotransferase activity or an enzyme having ethanolamine oidoreductase (deaminating) activity that catalyzes the conversion of ethanolamine from (e) to glycolaldehyde;

(h) at least one endogenous or exogenous nucleic acid molecule encoding an enzyme having glycolaldehyde dehydrogenase activity that catalyzes the conversion of glycolaldehyde from (f) and/or (g) to glycolic acid;

(i) at least one endogenous or exogenous nucleic acid molecule encoding an enzyme having glycolate dehydrogenase activity that catalyzes the conversion of glycolic acid from (g) to glyoxylate;

(j) at least one endogenous or exogenous nucleic acid molecule encoding an enzyme having alanine-glyoxylate aminotransferase activity that catalyzes the conversion of glyoxylate from (i) and alanine to glycine and pyruvate;
- (k) at least one endogenous or exogenous nucleic acid molecule encoding an enzyme having alanine transaminase activity that catalyzes the conversion of pyruvate from (j) and glutamate to alanine and 2-oxoglutarate;
- (l) at least one endogenous or exogenous nucleic acid molecule encoding an enzyme having NAD(P)H dependent glutamate dehydrogenase activity that catalyzes the conversion of 2-oxoglutarate from (k) and ammonia to glutamate;
- wherein the produced intermediate DHAP from embodiments [mH] and/or [mI] and/or pyruvate from embodiment [mJ] is converted to 3-phosphoglycerate and/or 2-phosphoglycerate through endogenous glycolysis or gluconeogenesis in the microorganism, wherein the glyoxylate for step (j) optionally comes from glyoxylate shunt in the microorganism, wherein alanine and glutamate are reconstituted from steps (k) and (l), and wherein MEG (or glycolic acid) and glycine are co-produced.

In some embodiments, the C2 pathway for production of MEG (or glycolic acid) comprises embodiment [mH] and the C3 pathway for production of MEA comprises embodiment [mI]. In other embodiments, the C2 pathway for production of MEG (or glycolic acid) comprises embodiment [mH] and the C3 pathway for production of MEA comprises embodiment [mV]. In further embodiments, the C2 pathway for production of MEG (or glycolic acid) comprises embodiment [mH] and the C3 pathway for production of MEA comprises embodiment [mW]. In some embodiments, the C2 pathway for production of MEG (or glycolic acid) comprises embodiment [mI] and the C3 pathway for production of MEA comprises embodiment [mI]. In other embodiments, the C2 pathway for production of MEG (or glycolic acid) comprises embodiment [mI] and the C3 pathway for production of MEA comprises embodiment [mV]. In further embodiments, the C2 pathway for production of MEG (or glycolic acid) comprises embodiment [mI] and the C3 pathway for production of MEA comprises embodiment [mW]. In some embodiments, the C2 pathway for production of MEG (or glycolic acid) comprises embodiment [mJ] and the C3 pathway for production of MEA comprises embodiment [mil]. In other embodiments, the C2 pathway for production of MEG (or glycolic acid) comprises embodiment [mJ] and the C3 pathway for production of MEA comprises embodiment [mV]. In other embodiments, the C2 pathway for production of MEG (or glycolic acid) comprises embodiment [mJ] and the C3 pathway for production of MEA comprises embodiment [mW].

[mU] In one embodiment, the application relates to a method of producing a recombinant microorganism capable of co-producing monoethylene glycol (MEG) (or glycolic acid) and monoethanolamine (MEA), from one or more hexose feedstock and a nitrogen source, wherein the method of embodiment [mA] or embodiment [mB] (and optionally comprising embodiment [mC]), and comprising additionally one or more of embodiments [mD], [mE], [mF] and [mG], further comprising one or more of embodiments [mH], [mI], and [mJ], further comprises introducing into or expressing in the recombinant microorganism one or more of the following from (a) to (i):
- (a) at least one endogenous or exogenous nucleic acid molecule encoding an enzyme having 3-phosphoglycerate dehydrogenase activity that catalyzes the conversion of 3-phosphoglycerate to 3-phosphohydroxypyruvate;
- (b) at least one endogenous or exogenous nucleic acid molecule encoding an enzyme having 3-phosphoglycerate phosphatase activity and/or an enzyme having glycerate 3-kinase activity that catalyzes the conversion of 3-phosphoglycerate to glycerate;
- (c) at least one endogenous or exogenous nucleic acid molecule encoding an enzyme having 2-phosphoglycerate phosphatase activity and/or an enzyme having glycerate 2-kinase activity that catalyzes the conversion of 2-phosphoglycerate to glycerate;
- (d) at least one endogenous or exogenous nucleic acid molecule encoding an enzyme having phosphoserine aminotransferase activity that catalyzes the conversion of 3-phosphohydroxypyruvate from (a) to phospho-L-serine;
- (e) at least one endogenous or exogenous nucleic acid molecule encoding an enzyme having 3-phosphohydroxypyruvate phosphatase activity that catalyzes the conversion of 3-phosphohydroxypyruvate from (a) to hydroxypyruvate;
- (f) at least one endogenous or exogenous nucleic acid molecule encoding an enzyme having phosphoserine phosphatase activity that catalyzes the conversion of phospho-L-serine from (d) to L-serine;
- (g) at least one endogenous or exogenous nucleic acid molecule encoding an enzyme having hydroxypyruvate reductase activity that catalyzes the conversion of glycerate from (b) and/or (c) to hydroxypyruvate;
- (h) at least one endogenous or exogenous nucleic acid molecule encoding an enzyme having serine-pyruvate aminotransferase activity that catalyzes the conversion of hydroxypyruvate from (e) and/or (g) to L-serine;
- (i) at least one endogenous or exogenous nucleic acid molecule encoding an enzyme having serine decarboxylase activity that catalyzes the conversion of L-serine from (f) and/or (h) to MEA;
- wherein the produced intermediate DHAP from embodiments [mH] and/or [mI] and/or pyruvate from embodiment [mJ] is converted to 3-phosphoglycerate and/or 2-phosphoglycerate through endogenous glycolysis or gluconeogenesis in the microorganism, and wherein MEG (or glycolic acid) and MEA are co-produced.

[mV] In one embodiment, the application relates to a method of producing a recombinant microorganism capable of co-producing monoethylene glycol (MEG) (or glycolic acid) and monoethanolamine (MEA) from one or more hexose feedstock and a nitrogen source, wherein the method of embodiment [mA] or embodiment [mB] (and optionally comprising embodiment [mC]), and comprising additionally one or more of embodiments [mD], [mE], [mF], and [mG], further comprising one or more of embodiments [mH], [mI], and [mJ], further comprises introducing into or expressing in the recombinant microorganism one or more of the following from (a) to (f):
- (a) at least one endogenous or exogenous nucleic acid molecule encoding an enzyme having 2-phosphoglycerate phosphatase activity and/or an enzyme having glycerate-2-kinase activity that catalyzes the conversion of 2-phosphoglycerate to glycerate;
- (b) at least one endogenous or exogenous nucleic acid molecule encoding an enzyme having 3-phosphoglycerate phosphatase activity and/or an enzyme having glycerate-3-kinase activity that catalyzes the conversion of 3-phosphoglycerate to glycerate;

(c) at least one endogenous or exogenous nucleic acid molecule encoding an enzyme having hydroxypyruvate reductase activity that catalyzes the conversion of glycerate from (a) and/or (b) to hydroxypyruvate;

(d) at least one endogenous or exogenous nucleic acid molecule encoding an enzyme having serine-pyruvate aminotransferase or serine oxidoreductase (deaminating) activity that catalyzes the conversion of L-serine to hydroxypyruvate;

(e) at least one endogenous or exogenous nucleic acid molecule encoding an enzyme having hydroxypyruvate decarboxylase activity that catalyzes the conversion of hydroxypyruvate from (c) and/or (d) to glycolaldehyde;

(f) at least one endogenous or exogenous nucleic acid molecule encoding an enzyme having transaminase activity that catalyzes the conversion of glycolaldehyde from (e) to MEA;

wherein the produced intermediate DHAP from embodiments [mH] and/or [mI] and/or pyruvate from embodiment [mJ] is converted to 3-phosphoglycerate and/or 2-phosphoglycerate through endogenous glycolysis or gluconeogenesis in the microorganism, and wherein MEG (or glycolic acid) and MEA are co-produced.

[mW] In one embodiment, the application relates to a method of producing a recombinant microorganism capable of co-producing monoethylene glycol (MEG) (or glycolic acid) and monoethanolamine (MEA) from one or more hexose feedstock and a nitrogen source, wherein the method of embodiment [mA] or embodiment [mB] (and optionally comprising embodiment [mC]), and comprising additionally one or more of embodiments [mD], [mE], [mF], and [mG], further comprising one or more of embodiments [mH], [mI], and [mJ], further comprises introducing into or expressing in the recombinant microorganism one or more of the following from (a) to (b):

(a) at least one endogenous or exogenous nucleic acid molecule encoding an enzyme having acetaldehyde dehydrogenase activity that catalyzes the conversion of acetyl-CoA to acetaldehyde;

(b) at least one endogenous or exogenous nucleic acid molecule encoding an enzyme having ethanolamine ammonia lyase activity that catalyzes the conversion of acetaldehyde and ammonia to MEA;

wherein the produced intermediate DHAP from embodiments [mH] and/or [mI] and/or pyruvate from embodiment [mJ] is converted to acetyl-CoA through endogenous glycolysis in the microorganism, and wherein MEG (or glycolic acid) and MEA are co-produced.

In some embodiments, the C2 pathway for production of MEG (or glycolic acid) comprises embodiment [mH] and the C3 pathway for production of EDA comprises embodiment [mX]. In other embodiments, the C2 pathway for production of MEG (or glycolic acid) comprises embodiment [mH] and the C3 pathway for production of EDA comprises embodiment [mY]. In further embodiments, the C2 pathway for production of MEG (or glycolic acid) comprises embodiment [mH] and the C3 pathway for production of EDA comprises embodiment [mZ]. In yet further embodiments, the C2 pathway for production of MEG (or glycolic acid) comprises embodiment [mH] and the C3 pathway for production of EDA comprises embodiment [mAA]. In other embodiments, the C2 pathway for production of MEG (or glycolic acid) comprises embodiment [mH] and the C3 pathway for production of EDA comprises embodiment [mBB].

In some embodiments, the C2 pathway for production of MEG (or glycolic acid) comprises embodiment [mI] and the C3 pathway for production of EDA comprises embodiment [mX]. In other embodiments, the C2 pathway for production of MEG (or glycolic acid) comprises embodiment [mI] and the C3 pathway for production of EDA comprises embodiment [mY]. In further embodiments, the C2 pathway for production of MEG (or glycolic acid) comprises embodiment [mI] and the C3 pathway for production of EDA comprises embodiment [mZ]. In yet further embodiments, the C2 pathway for production of MEG (or glycolic acid) comprises embodiment [mI] and the C3 pathway for production of EDA comprises embodiment [mAA]. In other embodiments, the C2 pathway for production of MEG (or glycolic acid) comprises embodiment [mI] and the C3 pathway for production of EDA comprises embodiment [mBB].

In some embodiments, the C2 pathway for production of MEG (or glycolic acid) comprises embodiment [mJ] and the C3 pathway for production of EDA comprises embodiment [mX]. In other embodiments, the C2 pathway for production of MEG (or glycolic acid) comprises embodiment [mJ] and the C3 pathway for production of EDA comprises embodiment [mY]. In other embodiments, the C2 pathway for production of MEG (or glycolic acid) comprises embodiment [mJ] and the C3 pathway for production of EDA comprises embodiment [mZ]. In other embodiments, the C2 pathway for production of MEG (or glycolic acid) comprises embodiment [mJ] and the C3 pathway for production of EDA comprises embodiment [mAA]. In other embodiments, the C2 pathway for production of MEG (or glycolic acid) comprises embodiment [mJ] and the C3 pathway for production of EDA comprises embodiment [mBB].

[mX] In one embodiment, the application relates to a method of producing a recombinant microorganism capable of co-producing monoethylene glycol (MEG) (or glycolic acid) and ethylenediamine (EDA), from one or more hexose feedstock and a nitrogen source, wherein the method of embodiment [mA] or embodiment [mB] (and optionally comprising embodiment [mC]), and comprising additionally one or more of embodiments [mD], [mE], [mF] and [mG], further comprising one or more of embodiments [mH], [mI], and [mJ], further comprises introducing into or expressing in the recombinant microorganism one or more of the following from (a) to (c):

(a) at least one endogenous or exogenous nucleic acid molecule encoding an enzyme having serine dehydrogenase activity that catalyzes the conversion of L-serine to 2-aminomalonate semialdehyde;

(b) at least one endogenous or exogenous nucleic acid molecule encoding an enzyme having 2-aminomalonate semialdehyde decarboxylase activity that catalyzes the conversion of 2-aminomalonate semialdehyde from (a) to aminoacetaldehyde;

(c) at least one endogenous or exogenous nucleic acid molecule encoding an enzyme having aminoacetaldehyde transaminase activity that catalyzes the conversion of aminoacetaldehyde from (b) to EDA;

wherein 2-aminomalonate semialdehyde may optionally be converted to aminoacetaldehyde by a spontaneous reaction, and wherein MEG (or glycolic acid) and EDA are co-produced.

[mY] In one embodiment, the application relates to a method of producing a recombinant microorganism capable of co-producing monoethylene glycol (MEG) (or glycolic acid) and ethylenediamine (EDA), from one or more hexose feedstock and a nitrogen source, wherein the method of embodiment [mA] or embodiment [mB] (and optionally comprising embodiment [mC]), and comprising additionally one or more of embodiments [mD], [mE], [mF] and [mG], further comprising one or more of embodiments [mH], [mI], and [mJ], further comprises introducing into or expressing in the recombinant microorganism one or more of the following from (a) to (c):
- (a) at least one endogenous or exogenous nucleic acid molecule encoding an enzyme having serine dehydrogenase activity that catalyzes the conversion of L-serine to 2-aminomalonate semialdehyde;
- (b) at least one endogenous or exogenous nucleic acid molecule encoding an enzyme having 2-aminomalonate semialdehyde transaminase activity that catalyzes the conversion of 2-aminomalonate semialdehyde from (a) to 2,3-diaminopropanoate;
- (c) at least one endogenous or exogenous nucleic acid molecule encoding an enzyme having 2,3-diaminopropanoate decarboxylase activity that catalyzes the conversion of 2,3-diaminopropanoate from (b) to EDA;
- wherein MEG (or glycolic acid) and EDA are co-produced.

[mZ] In one embodiment, the application relates to a method of producing a recombinant microorganism capable of co-producing monoethylene glycol (MEG) (or glycolic acid) and ethylenediamine (EDA), from one or more hexose feedstock and a nitrogen source, wherein the method of embodiment [mA] or embodiment [mB] (and optionally comprising embodiment [mC]), and comprising additionally one or more of embodiments [mD], [mE], [mF] and [mG], further comprising one or more of embodiments [mH], [mI], and [mJ], further comprises introducing into or expressing in the recombinant microorganism one or more of the following from (a) to (c):
- (a) at least one endogenous or exogenous nucleic acid molecule encoding an enzyme having serine decarboxylase activity that catalyzes the conversion of L-serine to ethanolamine;
- (b) at least one endogenous or exogenous nucleic acid molecule encoding an enzyme having ethanolamine dehydrogenase activity that catalyzes the conversion of ethanolamine from (a) to aminoacetaldehyde;
- (c) at least one endogenous or exogenous nucleic acid molecule encoding an enzyme having aminoacetaldehyde transaminase activity that catalyzes the conversion of aminoacetaldehyde from (b) to EDA;
- wherein MEG (or glycolic acid) and EDA are co-produced.

[mAA] In one embodiment, the application relates to a method of producing a recombinant microorganism capable of co-producing monoethylene glycol (MEG) (or glycolic acid) and ethylenediamine (EDA), from one or more hexose feedstock and a nitrogen source, wherein the method of embodiment [mA] or embodiment [mB] (and optionally comprising embodiment [mC]), and comprising additionally one or more of embodiments [mD], [mE], [mF] and [mG], further comprising one or more of embodiments [mH], [mI], and [mJ], further comprises introducing into or expressing in the recombinant microorganism one or more of the following from (a) to (c):
- (a) at least one endogenous or exogenous nucleic acid molecule encoding an enzyme having serine hydroxymethyltransferase activity that catalyzes the conversion of L-serine to glycine;
- (b) at least one endogenous or exogenous nucleic acid molecule encoding an enzyme having aldehyde oxidase activity that catalyzes the conversion of glycine from (a) to aminoacetaldehyde;
- (c) at least one endogenous or exogenous nucleic acid molecule encoding an enzyme having aminoacetaldehyde transaminase activity that catalyzes the conversion of aminoacetaldehyde from (b) to EDA;
- wherein MEG (or glycolic acid) and EDA are co-produced.

[mBB] In one embodiment, the application relates to a method of producing a recombinant microorganism capable of co-producing monoethylene glycol (MEG) (or glycolic acid) and ethylenediamine (EDA), from one or more hexose feedstock and a nitrogen source, wherein the method of embodiment [mA] or embodiment [mB] (and optionally comprising embodiment [mC]), and comprising additionally one or more of embodiments [mD], [mE], [mF] and [mG], further comprising one or more of embodiments [mH], [mI], and [mJ], further comprises introducing into or expressing in the recombinant microorganism one or more of the following from (a) to (e):
- (a) at least one endogenous or exogenous nucleic acid molecule encoding an enzyme having an amino acid N-acetyl transferase activity or O-acetyl transferase activity that catalyzes the conversion of L-serine to N-acetylserine;
- (b) at least one endogenous or exogenous nucleic acid molecule encoding an enzyme having N-acetylserine dehydrogenase activity that catalyzes the conversion of N-acetylserine from (a) to N-acetylmalonate semialdehyde;
- (c) at least one endogenous or exogenous nucleic acid molecule encoding an enzyme having transaminase activity that catalyzes the conversion of N-acetylmalonate semialdehyde from (b) to acetylaminopropanoate;
- (d) at least one endogenous or exogenous nucleic acid molecule encoding an enzyme having deacetylase activity that catalyzes the conversion of acetylaminopropanoate from (c) to 2,3-diaminopropanoate;
- (e) at least one endogenous or exogenous nucleic acid molecule encoding an enzyme having 2,3-diaminopropanoate decarboxylase activity that catalyzes the conversion of 2,3-diaminopropanoate from (d) to EDA;
- wherein MEG (or glycolic acid) and EDA are co-produced.

In some embodiments, the C2 pathway for production of MEG (or glycolic acid) comprises embodiment [mH] and the C3 pathway for production of EDA comprises embodiment [mCC]. In other embodiments, the C2 pathway for production of MEG (or glycolic acid) comprises embodiment [mH] and the C3 pathway for production of EDA comprises embodiment [mDD]. In some embodiments, the C2 pathway for production of MEG (or glycolic acid) comprises embodiment [mI] and the C3 pathway for production of EDA comprises embodiment [mCC]. In other embodiments, the C2 pathway for production of MEG (or glycolic acid) comprises embodiment [mI] and the C3 pathway for production of EDA comprises embodiment [mDD]. In some embodiments, the C2 pathway for production of MEG (or glycolic acid) comprises embodiment [mJ] and the C3 pathway for production of EDA comprises embodiment [mCC]. In other embodiments, the C2 pathway for production of MEG (or glycolic acid) comprises embodiment [mJ] and the C3 pathway for production of EDA comprises embodiment [mDD].

[mCC] In one embodiment, the application relates to a method of producing a recombinant microorganism capable of co-producing monoethylene glycol (MEG) (or glycolic acid) and ethylenediamine (EDA), from one or more hexose feedstock and a nitrogen source, wherein the method of embodiment [mA] or embodiment [mB] (and optionally comprising embodiment [mC]), and comprising additionally one or more of embodiments [mD], [mE], [mF] and [mG], further comprising one or more of embodiments [mH], [mI], and [mJ], further comprises introducing into or expressing in the recombinant microorganism one or more of the following from (a) to (b):
  (a) at least one endogenous or exogenous nucleic acid molecule encoding an enzyme having a serine aminase activity that catalyzes the conversion of L-serine to (S)-2,3-diaminopropanoate;
  (b) at least one endogenous or exogenous nucleic acid molecule encoding an enzyme having an (S)-2,3-diaminopropanoate decarboxylase activity that catalyzes the conversion of (S)-2,3-diaminopropanoate from (a) to EDA;
  wherein MEG (or glycolic acid) and EDA are co-produced.

[mDD] In one embodiment, the application relates to a method of producing a recombinant microorganism capable of co-producing monoethylene glycol (MEG) (or glycolic acid) and ethylenediamine (EDA), from one or more hexose feedstock and a nitrogen source, wherein the method of embodiment [mA] or embodiment [mB] (and optionally comprising embodiment [mC]), and comprising additionally one or more of embodiments [mD], [mE], [mF] and [mG], further comprising one or more of embodiments [mH], [mI], and [mJ], further comprises introducing into or expressing in the recombinant microorganism one or more of the following from (a) to (b):
  (a) at least one endogenous or exogenous nucleic acid molecule encoding an enzyme having an (S)-2,3-diaminopropanoate ammonia lyase activity that catalyzes the conversion of pyruvate and ammonium to (S)-2,3-diaminopropanoate;
  (b) at least one endogenous or exogenous nucleic acid molecule encoding an enzyme having (S)-2,3-diaminopropanoate decarboxylase activity that catalyzes the conversion of (S)-2,3-diaminopropanoate from (a) to EDA;
  wherein pyruvate is produced from endogenous glycolysis, and wherein MEG (or glycolic acid) and EDA are co-produced.

[mEE] In another embodiment, the method selected from embodiment [mH], embodiment [mI], and embodiment [mJ], optionally further comprises introducing into the recombinant microorganism one or more modifications selected from the group consisting of:
  (i) a deletion, insertion, or loss of function mutation in a gene encoding a xylose isomerase that catalyzes the conversion of D-xylulose to D-xylose;
  (ii) a deletion, insertion, or loss of function mutation in a gene encoding a glycolaldehyde dehydrogenase that catalyzes the conversion of glycolaldehyde to glycolic acid; and
  (iii) a deletion, insertion, or loss of function mutation in a gene encoding a lactate dehydrogenase that catalyzes the conversion of pyruvate to lactate.

Enzyme Engineering

The enzymes in the recombinant microorganism can be engineered to improve one or more aspects of the substrate to product conversion. Non-limiting examples of enzymes that can be further engineered for use in methods of the disclosure include a transketolase, a transaldolase, a pentose-5-phosphatase, an arabitol phosphate dehydrogenase, a phosphopentomutase, an aldehyde reductase, an acetoacetyl coenzyme A hydrolase, a xylose isomerase, a 3-phosphoglycerate dehydrogenase, a phosphoserine aminotransferase, a 3-phosphohydroxypyruvate phosphatase, a phosphoserine phosphatase, a serine transaminase, a hydroxypyruvate decarboxylase, a 3-phosphohydroxypyruvate reductase, a glycolaldehyde dehydrogenase, a serine oxidoreductase (deaminating) or serine-pyruvate aminotransferase, a serine decarboxylase, an ethanolamine aminotransferase or ethanolamine oxidoreductase (deaminating), a glycerate decarboxylase, a hydroxypyruvate reductase, a 3-phosphoglycerate phosphatase, a 2-phosphoglycerate phosphatase, a glycerate 3-kinase, a glycerate 2-kinase, a mevalonate diphosphate decarboxylase, and combinations thereof. These enzymes can be engineered for improved catalytic activity, improved selectivity, improved stability, improved tolerance to various fermentation conditions (temperature, pH, etc.), or improved tolerance to various metabolic substrates, products, by-products, intermediates, etc. The term "improved catalytic activity" as used herein with respect to a particular enzymatic activity refers to a higher level of enzymatic activity than that measured relative to a comparable non-engineered enzyme.

Directed evolution is a term used to describe the entire range of molecular biology techniques that allow natural evolutionary processes to be mimicked in the laboratory. For enzymes, this generally involves the random mutagenesis of one or more starting genes, followed by a screening or selection step to isolate or enrich for enzyme variants with improvements in one or more desirable properties. The process can be iterated until the desired level of change is reached, or until no further change is elicited. A wide range of tools and techniques have been developed over more than two decades to shorten the process from the millions of years taken by nature, to just weeks or months in the laboratory. The most common strategies mimic the mechanisms of evolution that occur in nature, such as error-prone PCR (epPCR), which introduces random point mutations in a population of DNA products, and DNA shuffling techniques, which allow random recombination typically between parent genes with >70% homology. Later techniques accessed a wider range of amino acids through saturation or cassette mutagenesis targeted to pre-chosen sites or at randomly distributed sites, and enabled the random recombination of non-homologous genes. Further techniques can create random insertions and deletions of codons, shuffle domains or exons, or loop regions, and produce a library of random truncations.

For example, engineering methods have been used to alter the stability, substrate specificity and stereospecificity of aldolases to produce excellent enzymes for biocatalytic processes. The thermostability and solvent tolerance of fructose-1,6-bisphosphate aldolase (FBP-aldolase) was increased using family DNA shuffling of the fda genes from *Escherichia coli* and *Edwardsiella ictaluri*. A fourth generation variant was identified which displayed an average 280-fold higher half-life at 53° C. than either parent. The same variant also displayed enhanced activity in various polar and non-polar organic solvents (Hao and Berry 2004 Protein Eng Des Sel 17:689-697).

As another example, acetoacetyl coenzyme A hydrolase can convert acetoacetyl-CoA to acetoacetate. However, the hydrolase is unspecific in that it also reacts with the same magnitude of order with acetyl-CoA, which is the substrate required for acetoacetyl-CoA formation by the enzyme thiolase. Thus, to create more efficient acetoacetyl-CoA hydrolases, these enzymes have been engineered to have at least 10× higher activity for the acetoacetyl-CoA substrate than for acetyl-CoA substrate by replacing several glutamic acid residues in the enzyme beta subunit that is important for catalysis (WO 2015/042588).

As another example, the *E. coli* YqhD enzyme is a broad substrate aldehyde reductase with NADPH-dependent reductase activity for more than 10 aldehyde substrates and is a useful enzyme to produce biorenewable fuels and chemicals (Jarboe 2010 *Applied Microbiology and Biotechnology* 89:249). Though YqhD enzyme activity is beneficial through its scavenging of toxic aldehydes, the enzyme is also NADPH-dependent and contributes to NADPH depletion and growth inhibition of organisms. Error-prone PCR of YqhD was performed in order to improve 1,3-propanediol production from 3-hydroxypropionaldehyde (3-HPA). This directed engineering yielded two mutants, D99QN147H and Q202A, with decreased Km and increased kcat for certain aldehydes, particularly 3-HPA (Li et al. 2008 Prog. Nat. Sci. 18 (12):1519-1524). The improved catalytic activity of the D99QN147H mutant is consistent with what is known about the structure of YqhD (Sulzenbacher et al. 2004 J. Mol. Biol. 342 (2):489-502), as residues Asp99 and Asn147 both interact with NADPH. Use of the D99QN147H mutant increased 1,3-propanediol production from 3-HPA 2-fold. Mutant YqhD enzymes with increased catalytic efficiency (increased Kcat/Km) toward NADPH have also been described in WO 2011012697 A2, which is herein incorporated in its entirety.

As another example, xylose isomerase is a metal-dependent enzyme that catalyzes the interconversion of aldose and ketose sugars, primarily between xylose to xylulose and glucose to fructose. It has lower affinity for lyxose, arabinose and mannose sugars. The hydroxyl groups of sugars may define the substrate preference of sugar isomerases. The aspartate at residue 256 of *Thermus thermophilus* xylose isomerase was replaced with arginine (Patel et al. 2012 Protein Engineering, Design & Selection vol. 25 no. 7 pp. 331-336). This mutant xylose isomerase exhibited an increase in specificity for D-lyxose, L-arabinose and D-mannose. The catalytic efficiency of the D256R xylose isomerase mutant was also higher for these 3 substrates compared to the wild type enzyme. It was hypothesized that the arginine at residue 256 in the mutant enzyme may play a role in the catalytic reaction or influence changes in substrate orientation.

As another example, the enzyme xylitol dehydrogenase plays a role in the utilization of xylose along with xylose reductase. Xylose reductase (XR) reduces xylose to xylitol and then xylitol dehydrogenase (XDH) reoxidizes xylitol to form xylulose. However, since XR prefers NADPH as cosubstrate, while XDH exclusively uses NAD+ as cosubstrate, a cosubstrate recycling problem is encountered. One solution is to engineer XDH such that its cosubstrate specificity is altered from NAD+ to NADP+ (Ehrensberger et al. 2006 Structure 14: 567-575). A crystal structure of the *Gluconobacter oxydans* holoenzyme revealed that Asp38 is largely responsible for the NAD+ specificity of XDH. Asp38 interacts with the hydroxyls of the adenosine ribose, and Met39 stacks under the purine ring and is also located near the 2' hydroxyl. A double mutant (D38S/M39R) XDH was constructed that exclusively used NADP+ without loss of enzyme activity.

As another example, the enzyme mevalonate diphosphate decarboxylase (MVD) is an ATP-dependent enzyme which catalyzes the phosphorylation/decarboxylation of (R)-mevalonate-5-diphosphate to isopentenyl pyrophosphate (IPP) in the mevalonate (MVA) pathway. In the classical MVA pathway, MVD catalyzes the final step, where it produces IPP from (R)-mevalonate-5-diphosphate (MVAPP) in an irreversible reaction dependent upon ATP. MVAPP is phosphorylated first, and consequent decarboxylation occurs with the concomitant release of inorganic phosphate. With the same mechanism, classical MVDs also catalyze the conversion of the nonphosphorylated 3-hydroxyisovalerate (3-HIV) to isobutene. Mevalonate diphosphate (MDP) decarboxylase variants having improved activity in converting 3-phosphonoxyisovalerate into isobutene are disclosed in, for example, WO 2012052427 and WO 2015004211, each of which is herein incorporated in its entirety.

Metabolic Engineering—Enzyme Overexpression or Enzyme Downregulation/Deletion for Increased Pathway Flux In various embodiments described herein, the exogenous and endogenous enzymes in the recombinant microorganism participating in the biosynthesis pathways described herein may be overexpressed.

The terms "overexpressed" or "overexpression" refers to an elevated level (e.g., aberrant level) of mRNAs encoding for a protein(s), and/or to elevated levels of protein(s) in cells as compared to similar corresponding unmodified cells expressing basal levels of mRNAs or having basal levels of proteins. In particular embodiments, mRNA(s) or protein(s) may be overexpressed by at least 2-fold, 3-fold, 4-fold, 5-fold, 6-fold, 8-fold, 10-fold, 12-fold, 15-fold or more in microorganisms engineered to exhibit increased gene mRNA, protein, and/or activity.

In some embodiments, a recombinant microorganism of the disclosure is generated from a host that contains the enzymatic capability to synthesize substrates such as D-xylulose, D-ribulose, D-ribulose-1-phosphate, D-xylulose-1-phosphate, D-ribulose-5-phosphate, D-xylulose-5-phosphate, D-xylonolactone, D-xylonate, 2-keto-3-deoxy-xylonate, glycolaldehyde, DHAP, pyruvate, acetoacetyl-CoA, acetoacetate or 3-hydroxyisovalerate. In some embodiments, it can be useful to increase the synthesis or accumulation of, for example, D-xylulose, D-ribulose, D-ribulose-1-phosphate, D-xylulose-1-phosphate, D-ribulose-5-phosphate, D-xylulose-5-phosphate, D-ribose-5-phosphate, D-xylonolactone, D-xylonate, 2-keto-3-deoxy-xylonate, glycolaldehyde, DHAP, pyruvate, acetoacetyl-CoA, acetoacetate or 3-hydroxyisovalerate, to increase the production of MEG (or GA), or optionally, MEG (or GA) and one or more co-product.

In some embodiments, it may be useful to increase the expression of endogenous or exogenous enzymes involved in the MEG (or GA), or optionally, MEG (or GA) and one or more co-product, biosynthesis pathways to increase flux from, for example, D-xylulose, D-ribulose, D-ribulose-1-phosphate, D-xylulose-1-phosphate, D-ribulose-5-phosphate, D-xylulose-5-phosphate, D-ribose-5-phosphate, D-xylonolactone, D-xylonate, 2-keto-3-deoxy-xylonate, glycolaldehyde, DHAP, pyruvate, acetoacetyl-CoA, acetoacetate or 3-hydroxyisovalerate, thereby resulting in increased synthesis or accumulation of MEG (or GA), or optionally, MEG (or GA) and one or more co-product.

Increased synthesis or accumulation can be accomplished by, for example, overexpression of nucleic acids encoding one or more of the above-described MEG (or GA), or optionally, MEG (or GA) and one or more co-product, biosynthesis pathway enzymes. Overexpression of a MEG (or GA), or optionally, MEG (or GA) and one or more co-product biosynthesis pathway enzyme or enzymes can occur, for example, through increased expression of an endogenous gene or genes, or through the expression, or increased expression, of an exogenous gene or genes. Therefore, naturally occurring organisms can be readily modified to generate non-natural, MEG (or GA), or optionally, MEG (or GA) and one or more co-product, producing microorganisms through overexpression of one or more nucleic acid molecules encoding a MEG (or GA), or optionally, MEG (or GA) and one or more co-product, biosynthesis pathway enzyme. In addition, a non-naturally occurring organism can be generated by mutagenesis of an endogenous gene that results in an increase in activity of an enzyme in the MEG (or GA), or optionally, MEG (or GA) and one or more co-product, biosynthesis pathways.

Equipped with the present disclosure, the skilled artisan will be able to readily construct the recombinant microorganisms described herein, as the recombinant microorganisms of the disclosure can be constructed using methods well known in the art as exemplified above to exogenously express at least one nucleic acid encoding a MEG (or GA), or optionally, MEG (or GA) and one or more co-product, biosynthesis pathway enzyme in sufficient amounts to produce MEG (or GA), or optionally, MEG (or GA) and one or more co-product.

Methods for constructing and testing the expression levels of a non-naturally occurring MEG (or GA)-producing, or optionally, MEG (or GA) and one or more co-product producing, host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); Ausubo et al., *Current Protocols in Molecular Biology*, John Wiley and Sons, Baltimore, Md. (1999).

A variety of mechanisms known in the art can be used to express, or overexpress, exogenous or endogenous genes. For example, an expression vector or vectors can be constructed to harbor one or more MEG (or GA), or optionally, MEG (or GA) and one or more co-product, biosynthesis pathway enzymes encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al. (1996) Nucl. Acids Res. 24: 216-218).

Those of skill in the art will recognize that, due to the degenerate nature of the genetic code, a variety of nucleic acid sequences can be used to encode a given enzyme of the disclosure. The nucleic acid sequences encoding the biosynthetic enzymes are referenced herein merely to illustrate an embodiment of the disclosure, and the disclosure includes any nucleic acid sequences that encode the amino acid sequences of the polypeptides and proteins of the enzymes of the present disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as the modified or variant polypeptides have the enzymatic anabolic or catabolic activity of the reference polypeptide. Furthermore, the amino acid sequences encoded by the nucleic acid sequences shown herein merely illustrate embodiments of the disclosure.

Expression control sequences are known in the art and include, for example, promoters, enhancers, polyadenylation signals, transcription terminators, internal ribosome entry sites (IRES), and the like, that provide for the expression of the polynucleotide sequence in a host cell. Expression control sequences interact specifically with cellular proteins involved in transcription (Maniatis et al., *Science*, 236: 1237-1245 (1987)). Exemplary expression control sequences are described in, for example, Goeddel, *Gene Expression Technology: Methods in Enzymology*, Vol. 185, Academic Press, San Diego, Calif. (1990).

In various embodiments, an expression control sequence may be operably linked to a polynucleotide sequence. By "operably linked" is meant that a polynucleotide sequence and an expression control sequence(s) are connected in such a way as to permit gene expression when the appropriate molecules (e.g., transcriptional activator proteins) are bound to the expression control sequence(s). Operably linked promoters are located upstream of the selected polynucleotide sequence in terms of the direction of transcription and translation. Operably linked enhancers can be located upstream, within, or downstream of the selected polynucleotide.

In some embodiments, the recombinant microorganism is manipulated to delete, disrupt, mutate, and/or reduce the activity of one or more endogenous enzymes that catalyzes a reaction in a pathway that competes with the biosynthesis pathway for the production of MEG (or GA), or optionally, MEG (or GA) and one or more co-product.

In some embodiments, the recombinant microorganism is manipulated to delete, disrupt, mutate, and/or reduce the activity of one or more endogenous enzymes in the oxidative branch of the pentose phosphate pathway. In some embodiments, the manipulation prevents the conversion of glucose-6-phosphate through the oxidative branch of the pentose phosphate pathway and instead shunts glucose-6-phosphate through the non-oxidative branch of the pentose phosphate pathway to produce one or more pentose-5-phosphate intermediate needed for the production of MEG (or GA), or optionally, MEG (or GA) and one or more co-product. In some such embodiments, the one or more endogenous enzyme is selected from glucose 6-phosphate-1-dehydrogenase, 6-phosphogluconolactonase, and 6-phosphogluconate dehydrogenase. In further embodiments, the glucose 6-phosphate-1-dehydrogenase is zwf, the 6-phosphogluconolactonase is pgl, and the 6-phosphogluconate dehydrogenase is gnd.

In some embodiments, the recombinant microorganism is manipulated to delete, disrupt, mutate, and/or reduce the activity of glyceraldehyde 3-phosphate dehydrogenase and/or phosphoglycerate kinase and/or phosphoglycerate mutase. In some embodiments, the manipulation prevents the conversion of glyceraldehyde 3-phosphate to 1,3-bisphospho-D-glycerate and subsequent intermediates and instead allow glyceraldehyde 3-phosphate to be converted to xylulose-5-phosphate (with a concurrent conversion of fructose-6-phosphate to erythrose-4-phosphate) by a transketolase, and thus produce a pentose-5-phosphate intermediate needed for the production of MEG, or optionally, MEG and one or more co-product, and provide more erythrose-4-phosphate for the non-oxidative branch of the pentose phosphate pathway to further produce one or more pentose-5-phosphate intermediate. In some embodiments, the glyceraldehyde 3-phosphate dehydrogenase is gapA, the phosphoglycerate kinase is pgk and the phosphoglycerate mutase is gpmA and/or gpmM.

In some embodiments, the recombinant microorganism is manipulated to delete, disrupt, mutate, and/or reduce the activity of 6-phosphofructokinase. In some embodiments, the manipulation prevents the conversion of fructose-6-phosphate to 1,6-bisphosphate and instead allow fructose-6-phosphate to be converted to erythrose-4-phosphate and acetyl-phosphate by a fructose-6-phosphate phosphoketolase, and provide more erythrose-4-phosphate for the non-oxidative branch of the pentose phosphate pathway to further produce one or more pentose-5-phosphate intermediate needed for the production of MEG (or GA), or optionally, MEG (or GA) and one or more co-product. In some embodiments, the 6-phosphofructokinase is pfkA and/or pfkB.

In some embodiments, the recombinant microorganism is manipulated to delete, disrupt, mutate, and/or reduce the activity of one or more endogenous enzymes that catalyzes the conversion of glycolaldehyde to glycolic acid. In some such embodiments, the enzyme that catalyzes the conversion of glycolaldehyde to glycolic acid is a glycolaldehyde dehydrogenase. In some embodiments, the glycolaldehyde dehydrogenase is from *Escherichia coli*. In some embodiments, the glycolaldehyde dehydrogenase is encoded by the aldA gene or homologs thereof. In some embodiments, the manipulation prevents the production of glycolic acid from glycolaldehyde and instead shunts the reaction toward conversion of glycolaldehyde to MEG. In some embodiments, the deletion, disruption, mutation, and/or reduction in the activity of one or more endogenous enzymes that catalyzes the conversion of glycolaldehyde to glycolic acid is partial, wherein some glycolaldehyde dehydrogenase function is still present and an amount of glycolic acid is still produced.

In some embodiments, the recombinant microorganism is manipulated to delete, disrupt, mutate, and/or reduce the activity of one or more endogenous enzymes that catalyzes the conversion of pyruvate to lactate. In some such embodiments, the enzyme that catalyzes the conversion of pyruvate to lactate is a lactate dehydrogenase. In some embodiments, the lactate dehydrogenase is from *Escherichia coli*. In some embodiments, the lactate dehydrogenase is encoded by the ldhA gene or homologs thereof. In some embodiments, the manipulation prevents the production of lactate from pyruvate and instead shunts the reaction toward production of isobutene.

In some embodiments, the recombinant microorganism is manipulated to delete, disrupt, mutate, and/or reduce the activity of one or more endogenous enzymes that catalyzes the conversion of D-xylulose to D-xylose. In some such embodiments, the enzyme that catalyzes the conversion of D-xylulose to D-xylose is a D-xylose isomerase. In some embodiments, the D-xylose isomerase is from *E. coli*. In some embodiments, the D-xylose isomerase is encoded by the xylA gene or homologs thereof. In some embodiments, the manipulation prevents conversion of D-xylulose to D-xylose and instead shunts the reaction toward the conversion of D-xylulose to D-xylulose-1-phosphate, D-xylulose-5-phosphate, or D-ribulose.

EXAMPLES

Example 1

In Vitro Enzymatic Assay for PGM3 Protein

Figure 15:
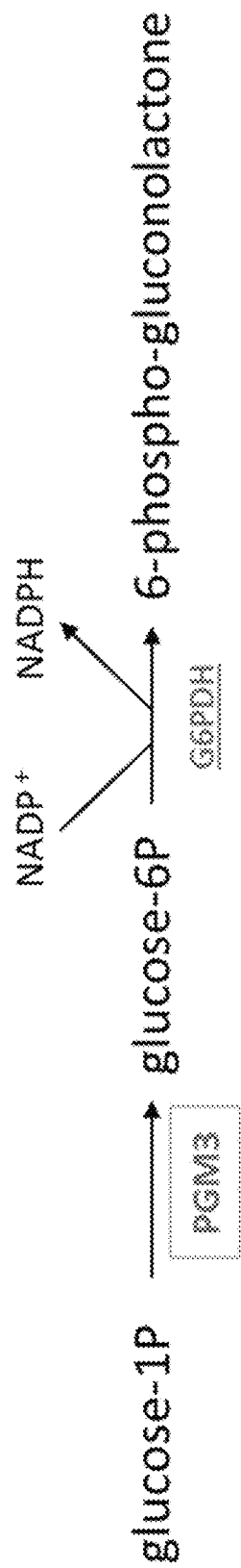
FIG. 15 is a scheme for an in vitro phosphoglucomutase assay on its natural substrate, glucose-1P.

The enzymatic assay of a phosphoglucomutase, which is a phosphopentomutase, encoded by ScPGM3 (SEQ ID NO: 255 or SEQ ID NO: 258)(PGM3 from *Saccharomyces cerevisiae*) was measured on its natural substrate, ribose-1-phosphate and glucose-1-phosphate in the presence of glucose-1,6-biphosphate, by monitoring the reduction of NADP+ into NADPH at OD 340 nm for 10 minutes (FIG. 15). Both glucose molecules were purchased from Merck. The reaction mixture contained HEPES 60 mM, pH 7.5, KCl 60 mM, $MgCl_2$ 3 mM, purified PGM3 protein, $NADP^+$ 0.5 mM, glucose-1,6-bisphosphate 5 µM, glucose-1-phosphate 8 mM, and commercially available Glucose-6-Phosphate dehydrogenase at 3 U/mL (from Merck).

Figure 16:
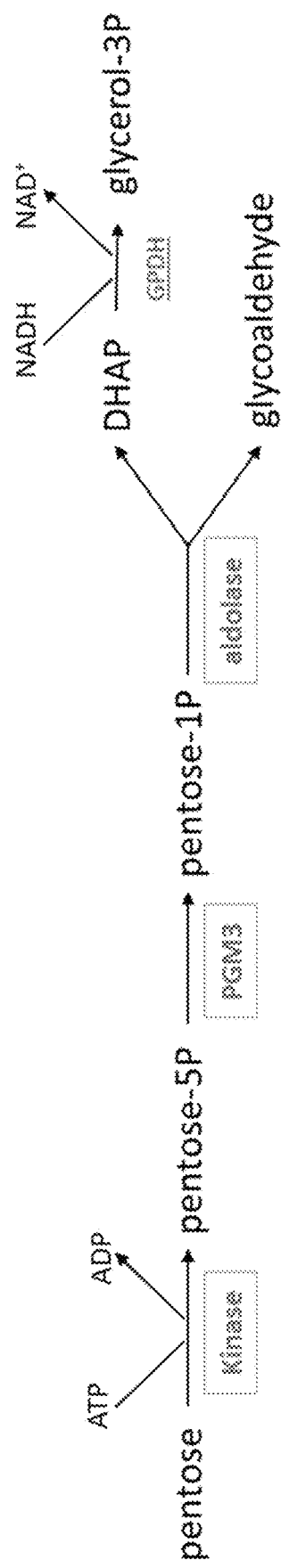
FIG. 16 is a scheme for in vitro conversion of pentose to glycolic acid precursors through key pentose-5P intermediates acted on by phosphoglucomutase enzymes.

The activity on pentose-5P substrates (ribulose-5P and xylulose-5) was determined according to the scheme in FIG. 16. The reaction mixture contained HEPES 60 mM, pH 7.5, KCl 60 mM, $MgCl_2$ 3 mM, NADH 0.25 mM, glucose-1,6-biphosphate 5 µM, pentose (ribulose or xylulose) 5 mM, ATP 4 mM, purified PGM3 protein, purified ribokinase or ribulokinase, and aldoB obtained as previously described (Cam Y. et al. (2015) Engineering of a Synthetic Metabolic Pathway for the Assimilation of (d)-Xylose into Value-Added Chemicals. ACS Synth Biol), glycerol-3-phosphate dehydrogenase (GPDH) at 2 U/mL (Merck). Results showed xylulose-5P PGM3 specific activity was about 0.015 µmol min−1 mg−1, and ribulose-5P PGM3 specifity was about 0.016±0.002 µmol min−1 mg−1.

Example 2

In Vivo Enzymatic Assay for PGM3 Protein

To assess the feasibility of using PGM3 for glycolic acid (GA) production in vivo, an assay was developed based on the use of a screening strain with the genotype MG1655 ΔtktA-ΔtktB. As described in FIG. 17, such a strain cannot grow on xylose by itself, because of the deletion of transketolase genes tktA (GenBank Gene ID: 947420) and tktB (GenBank Gene ID: 945865). However, a strain expressing an active PGM3 protein could use pentoses phosphorylated on carbon 5 to produce pentose phosphorylated on carbon 1, and subsequently convert pentose-1P to glycolaldehyde and DHAP by aldolase activity. Glycolaldehyde and glyceraldehyde-3-phosphate can enter the glyoxylate shunt and glycolysis and support strain growth. Consequently, in vivo PGM3 activity in the screening strain is directly correlated with cell growth.

Figure 17:
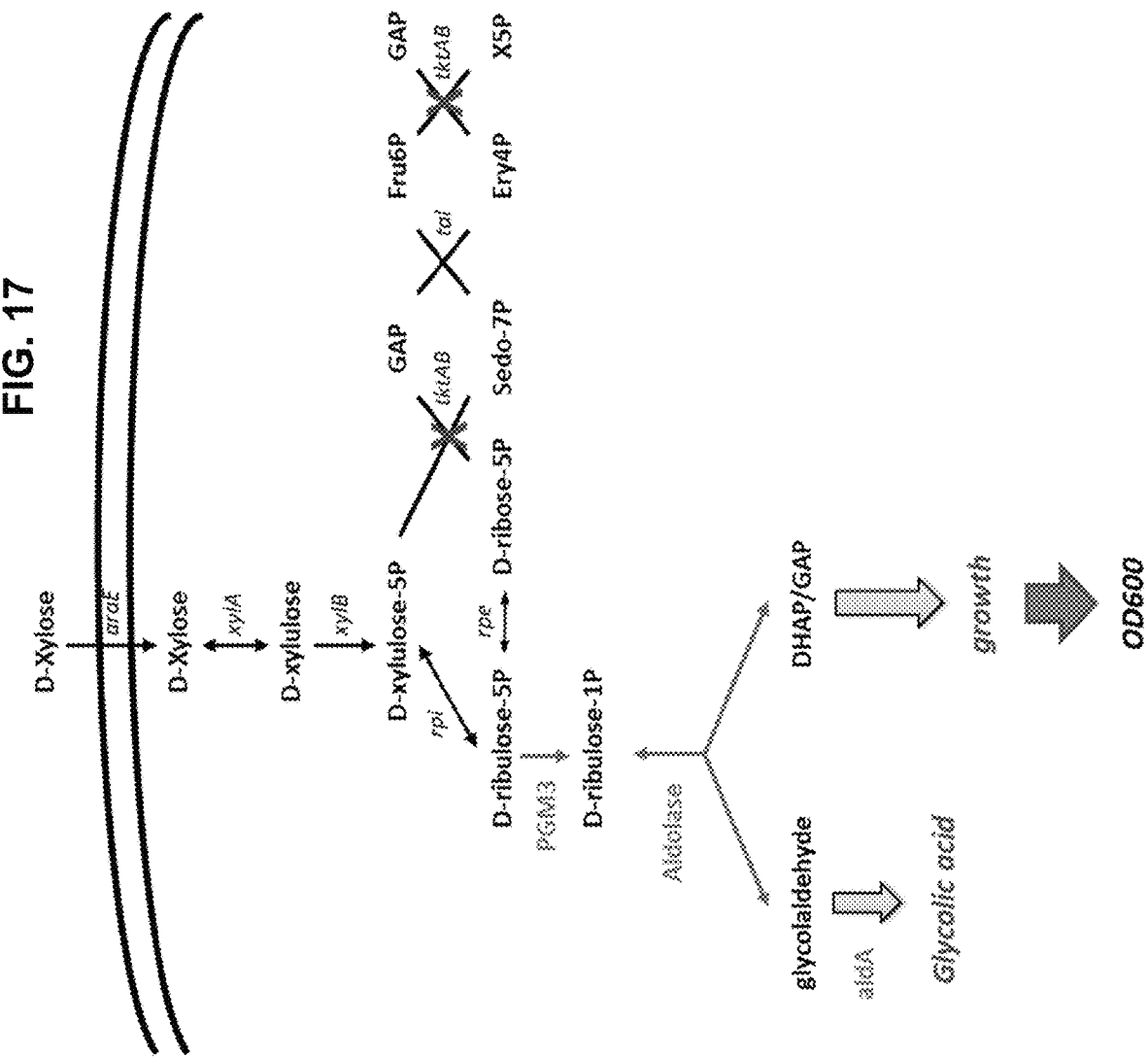
FIG. 17 is a scheme for in vivo screening of key enzyme candidates for facilitating conversion of pentose sugars to glycolic acid.

Screening strain PGM3 (MG1655 ΔtktA-ΔtktB) was transformed by electroporation with plasmid carrying both S. cerevisiae PGM3 and proper aldolase (aldoB or fucA) using standard procedure (Woodall C. A. E. coli Plasmid Vectors. Methods in Molecular Biology™. 2003. vol 235). Resulting strains were grown in M9 xylose medium (20 g/L xylose) for 50 hours. Kanamycin was added with a final concentration of 100 μg/mL. Growth was monitored by OD600 (FIG. 17).

Because pentose intermediates phosphorylated on carbon 5, such as ribulose-5P and xylulose-5P, can be naturally obtained from glucose via PPP pathways, active PGM3 from S. cerevisiae is also suitable to demonstrate in-vivo production of glycolic acid from glucose, in a similar approach. No E. coli MG1655 ΔtktA-ΔtktB cell growth is observed without PGM3.Sc overexpression plasmid. On the other hand, E. coli MG1655 ΔtktA-ΔtktB restored its ability to growth on xylose when the active PGM3 from S. cerevisiae was able to convert D-xylulose-5P and D-ribulose-5P into D-xylulose-1P and D-ribulose-1P, respectively, and so the pentose-1P intermediates converted into glycoaldehyde and G3P by aldolase activity (aldoB on D-xylulose-1P and fucA on D-ribulose-1P).

Example 3

Figure 18:
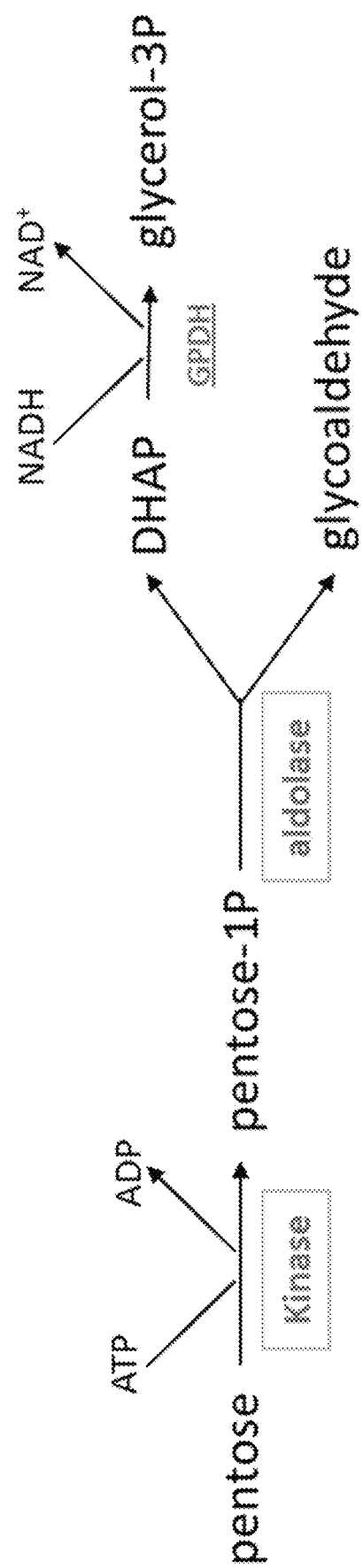
FIG. 18 is a scheme for in vitro conversion of pentose to glycolic acid precursors through key pentose-1P intermediates acted on by aldolase enzymes.

Enzymatic assay of D-xylulose-1-phosphate aldolase (aldoB) (Maylay A D, et al. (2002) Arch Biochem Biophys, 408:295-304) and D-ribulose-1-phosphate aldolase (FucA) (Elsinghorst E A, et al. (1994) J Bacteriol, 176:7223-7232) activities were tested according to the scheme in FIG. 18 on their natural substrates, xylulose-1P and ribulose-1P, respectively. The reaction mixture contained HEPES 60 mM, pH 7.5, KCl 60 mM, $MgCl_2$ 3 mM, NADH 0.25 mM, ATP 4 mM, purified kinase, and aldolase, GPDH at 2 U/mL. Furthermore, the kinases used to produce pentose-1P were fucK (SEQ ID NO: 257)(LeBlanc D J, et al. (1971) Metabolism of D-arabinose: origin of a D-ribulokinase activity in Escherichia coli. J Bacteriol, 106:82-89) for ribulose-1P, and khk-C(SEQ ID NO: 256) (Asipu A, et al. (2003) Properties of normal and mutant recombinant human ketohexokinases and implications for the pathogenesis of essential fructosuria. Diabetes, 52:2426-2432) for xyluolse-1P. Both proteins were tested as previously described for kinases producing pentose-5P.

HPLC Analysis.

Pentose, glycolate and glycerol quantifications were determined by high-performance liquid chromatography using Thermo Fisher Scientific system (Courtaboeuf, France) equipped with a RI detector, with a UV detector at 205 nm and a Phenomenex column (Rezex H+) at 50° C. using 2.5 mM $H_2SO_4$ as mobile phase at 0.5 mL/min.

Numbered Embodiments of the Disclosure

1. A recombinant microorganism comprising one or more biochemical pathways that produces monoethylene glycol (MEG) or glycolic acid (GA) from one or more hexose feedstock via one or more pentose-5-phosphate intermediate.

2. The recombinant microorganism of any one of the preceding embodiments, wherein one or more co-product is co-produced with MEG or GA.

3. The recombinant microorganism of any one of the preceding embodiments, wherein the one or more pentose-5-phosphate intermediate is one or more of D-ribose-5-phosphate, D-xylulose-5-phosphate or D-ribulose-5-phosphate.

4. The recombinant microorganism of any one of the preceding embodiments, wherein the one or more biochemical pathway comprises at least one enzyme having transketolase activity.

5. The recombinant microorganism of any one of the preceding embodiments, wherein the at least one enzyme having transketolase activity is encoded by an amino acid sequence having at least 70% sequence identity, at least 80% sequence identity, or at least 90% sequence identity to tktA or tktB from E. coli.

6. The recombinant microorganism of any one of the preceding embodiments, wherein the at least enzyme having transketolase activity comprises tktA or tktB from E. coli.

7. The recombinant microorganism of any one of the preceding embodiments, wherein the one or more biochemical pathway comprises at least one enzyme having transaldolase activity.

8. The recombinant microorganism of any one of the preceding embodiments, wherein the at least one enzyme having transaldolase activity is encoded by an amino acid sequence having at least 70% sequence identity, at least 80% sequence identity, or at least 90% sequence identity to talA or talB from E. coli. 9. The recombinant microorganism of any one of the preceding embodiments, wherein the at least one enzyme having transaldolase activity is selected from E. coli talA and E. coli talB.

10. The recombinant microorganism of any one of the preceding embodiments, wherein the one or more biochemical pathway comprises at least one enzyme having ribulose-5-phosphate 3-epimerase activity.

11. The recombinant microorganism of any one of the preceding embodiments, wherein the at least one enzyme having ribulose-5-phosphate 3-epimerase activity is encoded by an amino acid sequence having at least 70% sequence identity, at least 80% sequence identity, or at least 90% sequence identity to rpe from E. coli.

12. The recombinant microorganism of any one of the preceding embodiments, wherein the at least one enzyme having ribulose-5-phosphate 3-epimerase activity comprises rpe from E. coli.

13. The recombinant microorganism of any one of embodiments 1-12, wherein the one or more biochemical pathway comprises at least one enzyme having ribose-5-phosphate isomerase activity.

14. The recombinant microorganism of any one of the preceding embodiments, wherein the at least one enzyme having ribose-5-phosphate isomerase activity is encoded by an amino acid sequence having at least 70% sequence identity, at least 80% sequence identity, or at least 90% sequence identity to rpiA or rpiB from E. coli.

15. The recombinant microorganism of any one of the preceding embodiments, wherein the at least one enzyme having ribose-5-phosphate isomerase activity comprises rpiA or rpiB from E. coli.

16. The recombinant microorganism of any one of the preceding embodiments, wherein the recombinant microorganism further comprises a deleted or diminished activity in one or more endogenous enzymes selected from glyceraldehyde 3-phosphate dehydrogenase, phosphoglycerate kinase and phosphoglycerate mutase.

17. The recombinant microorganism of any one of the preceding embodiments, wherein the glyceraldehyde 3-phosphate dehydrogenase is gapA, the phosphoglycerate kinase is pgk and the phosphoglycerate mutase is gpmA and/or gpmM. 18. The recombinant microorganism of any one of the preceding embodiments, wherein the one or more biochemical pathway comprises at least one enzyme having fructose-6-phosphate phosphoketolase activity.

19. The recombinant microorganism of any one of the preceding embodiments, wherein the at least one enzyme having fructose-6-phosphate phosphoketolase activity is encoded by an amino acid sequence having at least 70% sequence identity, at least 80% sequence identity, or at least 90% sequence identity to an enzyme having fructose-6-phosphate phosphoketolase activity selected from the group consisting of *Bifidobacterium dentium* BDP_1006, *Bifidobacterium lactis* xfp, *Lactobacillus paraplantarum* xpkA and *Bifidobacterium breve* xfp.

20. The recombinant microorganism of any one of the preceding embodiments, wherein the at least one enzyme having fructose-6-phosphate phosphoketolase activity is selected from the group consisting of *Bifidobacterium dentium* BDP_1006, *Bifidobacterium lactis* xfp, *Lactobacillus paraplantarum* xpkA and *Bifidobacterium breve* xfp.

21. The recombinant microorganism of any one of the preceding embodiments, wherein the one or more biochemical pathway comprises at least one enzyme having phosphate acetyltransferase activity.

22. The recombinant microorganism of any one of the preceding embodiments, wherein the at least one enzyme having phosphate acetyltransferase activity is encoded by an amino acid sequence having at least 70% sequence identity, at least 80% sequence identity, or at least 90% sequence identity to an enzyme having phosphate acetyltransferase activity selected from *E. coli* pta and *Clostridium acetobutylicum* pta.

23. The recombinant microorganism of any one of the preceding embodiments, wherein the at least one enzyme having phosphate acetyltransferase activity is selected from *E. coli* pta and *Clostridium acetobutylicum* pta.

24. The recombinant microorganism of any one of the preceding embodiments or 18-23, wherein the recombinant microorganism further comprises a deleted or diminished activity in an endogenous 6-phosphofructokinase enzyme.

25. The recombinant microorganism of any one of the preceding embodiments, wherein the 6-phosphofructokinase is pfkAB.

26. The recombinant microorganism of any one of the preceding embodiments, wherein the one or more biochemical pathway comprises at least one enzyme having pentose phosphatase activity.

27. The recombinant microorganism of any one of the preceding embodiments, wherein the at least one enzyme having pentose phosphatase activity is selected from one or more of an enzyme having D-pentose-5-phosphatase activity, an enzyme having D-xylulose-5-phosphatase activity, an enzyme having D-ribose-5-phosphatase activity, and an enzyme having D-ribulose-5-phosphatase activity.

28. The recombinant microorganism of any one of the preceding embodiments, wherein the at least one enzyme having D-pentose-5-phosphatase activity is encoded by an amino acid sequence having at least 70% sequence identity, at least 80% sequence identity, or at least 90% sequence identity to an enzyme having D-pentose-5-phosphatase activity selected from the group consisting of *E. coli* phoA, *E. coli* yfbT and *E. coli* yidA.

29. The recombinant microorganism of any one of the preceding embodiments, wherein the at least one enzyme having D-pentose-5-phosphatase activity is selected from the group consisting of *E. coli* phoA, *E. coli* yfbT and *E. coli* yidA.

30. The recombinant microorganism of any one of the preceding embodiments, wherein the at least one enzyme having D-xylulose-5-phosphatase activity is encoded by an amino acid sequence having at least 70% sequence identity, at least 80% sequence identity, or at least 90% sequence identity to *Bacillus subtilis* araL.

31. The recombinant microorganism of any one of the preceding embodiments, wherein the at least one enzyme having D-xylulose-5-phosphatase activity is *Bacillus subtilis* araL.

32. The recombinant microorganism of any one of the preceding embodiments, wherein the at least one enzyme having D-ribose-5-phosphatase activity is encoded by an amino acid sequence having at least 70% sequence identity, at least 80% sequence identity, or at least 90% sequence identity to an enzyme having D-ribose-5-phosphatase activity selected from the group consisting of *Arabidopsis thaliana* SGPP, *Pseudomonas fluorescens* PFLU 2693, and *E. coli* ybiV.

33. The recombinant microorganism of any one of the preceding embodiments, wherein the at least one enzyme having D-ribose-5-phosphatase activity is selected from the group consisting of *Arabidopsis thaliana* SGPP, *Pseudomonas fluorescens* PFLU 2693, and *E. coli* ybiV.

34. The recombinant microorganism of any one of the preceding embodiments, wherein the at least one enzyme having D-ribulose-5-phosphatase activity is encoded by an amino acid sequence having at least 70% sequence identity, at least 80% sequence identity, or at least 90% sequence identity to *Plasmodium falciparum* PF10_0325.

35. The recombinant microorganism of any one of the preceding embodiments, wherein the at least one enzyme having D-ribulose-5-phosphatase activity is *Plasmodium falciparum* PF10_0325.

36. The recombinant microorganism of any one of any one of the preceding embodiments, wherein the one or more biochemical pathway comprises at least one enzyme having arabitol phosphate dehydrogenase activity.

37. The recombinant microorganism of any one of the preceding embodiments, wherein the at least one enzyme having arabitol phosphate dehydrogenase activity is selected from one or more of an enzyme having D-arabitol 1-phosphate 4-dehydrogenase activity, an enzyme having D-arabitol 5-phosphate 2-dehydrogenase activity, an enzyme having D-arabitol 1-phosphate 2-dehydrogenase activity and an enzyme having D-arabitol 5-phosphate 4-dehydrogenase activity.

38. The recombinant microorganism of any one of the preceding embodiments, wherein the at least one enzyme having D-arabitol 1-phosphate 4-dehydrogenase activity is encoded by an amino acid sequence having at least 70% sequence identity, at least 80% sequence identity, or at least 90% sequence identity to APDH from *Enterococcus avium*.

39. The recombinant microorganism of any one of the preceding embodiments, wherein the at least one enzyme having D-arabitol 1-phosphate 4-dehydrogenase activity is APDH from *Enterococcus avium*.

40. The recombinant microorganism of any one of the preceding embodiments, wherein the at least one enzyme having D-arabitol 5-phosphate 2-dehydrogenase activity is encoded by an amino acid sequence having at least 70% sequence identity, at least 80% sequence identity, or at least 90% sequence identity to APDH from *Enterococcus avium*.

41. The recombinant microorganism of any one of the preceding embodiments, wherein the at least one enzyme having D-arabitol 5-phosphate 2-dehydrogenase activity is APDH from *Enterococcus avium*.

42. The recombinant microorganism of any one of the preceding embodiments, wherein the at least one enzyme having D-arabitol 1-phosphate 2-dehydrogenase activity is encoded by an amino acid sequence having at least 70% sequence identity, at least 80% sequence identity, or at least 90% sequence identity to an enzyme having D-arabitol 1-phosphate 2-dehydrogenase activity selected from the group consisting of *Candida albicans* ARD1, *Candida tropicalis* ARD1, *Scheffersomyces stipitis* ARDH, *Bacillus subtilis* egsA (araM), *Aeropyrum pernix* egsA, *E. coli* gpsA and *Saccharomyces cerevisiae* GPD1.

43. The recombinant microorganism of any one of the preceding embodiments, wherein the at least one enzyme having D-arabitol 1-phosphate 2-dehydrogenase activity is selected from the group consisting of *Candida albicans* ARD1, *Candida tropicalis* ARD1, *Scheffersomyces stipitis* ARDH, *Bacillus subtilis* egsA (araM), *Aeropyrum pernix* egsA, *E. coli* gpsA and *Saccharomyces cerevisiae* GPD1.

44. The recombinant microorganism of any one of the preceding embodiments, wherein the at least one enzyme having D-arabitol 5-phosphate 4-dehydrogenase activity is encoded by an amino acid sequence having at least 70% sequence identity, at least 80% sequence identity, or at least 90% sequence identity to an enzyme having D-arabitol 5-phosphate 4-dehydrogenase activity selected from the group consisting of *Pseudomonas fluorescens* mtlD, *Klebsiella pneumoniae* dalD, *Ralstonia solanacearum* dalD, *Bacillus subtilis* egsA (araM), *Aeropyrum pernix* egsA, *E. coli* gpsA and *Saccharomyces cerevisiae* GPD1.

45. The recombinant microorganism of any one of the preceding embodiments, wherein the at least one enzyme having D-arabitol 5-phosphate 4-dehydrogenase activity is selected from the group consisting of *Pseudomonas fluorescens* mtlD, *Klebsiella pneumoniae* dalD, *Ralstonia solanacearum* dalD, *Bacillus subtilis* egsA (araM), *Aeropyrum pernix* egsA, *E. coli* gpsA and *Saccharomyces cerevisiae* GPD1.

46. The recombinant microorganism of any one of the preceding embodiments, wherein the one or more biochemical pathway comprises at least one enzyme having phosphopentomutase activity.

47. The recombinant microorganism of any one of the preceding embodiments, wherein the at least one enzyme having phosphopentomutase activity is encoded by an amino acid sequence having at least 70% sequence identity, at least 80% sequence identity, or at least 90% sequence identity to an enzyme having phosphopentomutase activity selected from the group consisting of *E. coli* deoB, *E. coli* pgm, *Bacillus subtilis* pgcA, *Lactococcus lactis* pgmB, *E. coli* ycjU, *Pseudomonas aeruginosa* algC, and *E. coli* cpsG.

48. The recombinant microorganism of any one of the preceding embodiments, wherein the at least one enzyme having phosphopentomutase activity is selected from the group consisting of *E. coli* deoB, *E. coli* pgm, *Bacillus subtilis* pgcA, *Lactococcus lactis* pgmB, *E. coli* ycjU, *Pseudomonas aeruginosa* algC, and *E. coli* cpsG.

49. The recombinant microorganism of any one of any one of the preceding embodiments, wherein the recombinant microorganism further comprises a deleted or diminished activity in one or more endogenous enzymes selected from glucose 6-phosphate-1-dehydrogenase, 6-phosphogluconolactonase and 6-phosphogluconate dehydrogenase.

50. The recombinant microorganism of any one of the preceding embodiments, wherein the glucose 6-phosphate-1-dehydrogenase is zwf, the 6-phosphogluconolactonase is pgl and the 6-phosphogluconate dehydrogenase is gnd.

51. The recombinant microorganism of any one of the preceding embodiments, wherein the one or more co-product is selected from acetone, isopropanol, propene, isobutene and one or more serine pathway compounds.

52. The recombinant microorganism of any one of the preceding embodiments, wherein the one or more serine pathway compounds is selected from serine, glycine, monoethanolamine (MEA) and ethylenediamine (EDA).

53. The recombinant microorganism of any one of the preceding embodiments, wherein the one or more hexose feedstock is selected from glucose or oligomers of glucose thereof.

54. The recombinant microorganism of any one of the preceding embodiments, wherein the oligomers of glucose are selected from fructose, sucrose, starch, cellobiose, maltose, lactose and cellulose.

55. The recombinant microorganism of any one of the preceding embodiments, wherein the expression of an enzyme having transketolase activity or an enzyme having fructose-6-phosphate phosphoketolase activity enables a lossless conversion of one or more hexose feedstock to the one or more pentose-5-phosphate intermediate.

56. The recombinant microorganism of any one of the preceding embodiments, wherein MEG or GA is produced through the conversion of glycolaldehyde in a C2 pathway and through the conversion of dihydroxyacetone phosphate (DHAP) or pyruvate in a C3 pathway.

57. The recombinant microorganism of any one of the preceding embodiments, wherein GA is produced by the oxidation of glycolaldehyde by a glycolaldehyde dehydrogenase.

58. The recombinant microorganism of any one of the preceding embodiments, wherein one or more enzyme for the production of MEG or GA through the conversion of DHAP or pyruvate in a C3 pathway are selected from one or more enzyme having an activity selected from a 3-phosphoglycerate dehydrogenase activity, a phosphoserine aminotransferase activity, a 3-phosphohydroxypyruvate phosphatase activity, a phosphoserine phosphatase activity, a serine transaminase activity, a hydroxypyruvate decarboxylase activity, a 3-phosphohydroxypyruvate reductase activity, a glycolaldehyde reductase activity, a glycolaldehyde dehydrogenase activity, a serine oxidoreductase (deaminating) or serine-pyruvate aminotransferase activity, a serine decarboxylase activity, an ethanolamine aminotransferase or ethanolamine oxidoreductase (deaminating) activity, a glycerate decarboxylase activity, a hydroxypyruvate reductase activity, a 3-phosphoglycerate phosphatase activity, a 2-phosphoglycerate phosphatase activity, a glycerate 3-kinase activity, and a glycerate 2-kinase activity.

59. The recombinant microorganism of any one of the preceding embodiments, wherein MEG or GA is produced through the conversion of glycolaldehyde in a C2 pathway and one or more co-product is produced through the conversion of dihydroxyacetone phosphate (DHAP) or pyruvate in a C3 pathway.

60. The recombinant microorganism of any one of the preceding embodiments, wherein one or more enzyme for the production of one or more co-product through the conversion of DHAP or pyruvate in a C3 pathway are selected from one or more enzyme having an activity selected from a thiolase or acetyl coenzyme A acetyltransferase activity, an acetyl-CoA:acetoacetate transferase or acetate:acetoacetyl-CoA hydrolase activity, and an acetoacetate decarboxylase activity, and wherein the one or more co-product comprises acetone.

61. The recombinant microorganism of any one of the preceding embodiments, wherein one or more enzyme for the production of one or more co-product through the conversion of DHAP or pyruvate in a C3 pathway are selected from one or more enzyme having an activity selected from a thiolase or acetyl coenzyme A acetyltransferase activity, an acetyl-CoA:acetoacetate transferase or acetate:acetoacetyl-CoA hydrolase activity, an acetoacetate decarboxylase activity, and a secondary alcohol dehydrogenase activity, and wherein the one or more co-product comprises isopropanol.

62. The recombinant microorganism of any one of the preceding embodiments, wherein one or more enzyme for the production of one or more co-product through the conversion of DHAP or pyruvate in a C3 pathway are selected from one or more enzyme having an activity selected from a thiolase or acetyl coenzyme A acetyltransferase activity, an acetyl-CoA:acetoacetate transferase or acetate:acetoacetyl-CoA hydrolase activity, an acetoacetate decarboxylase activity, a secondary alcohol dehydrogenase activity, and a dehydratase activity, and wherein the one or more co-product comprises propene.

63. The method of any one of the preceding embodiments, wherein one or more enzyme for the production of one or more co-product through the conversion of DHAP or pyruvate in a C3 pathway are selected from one or more enzyme having an activity selected from a thiolase or acetyl coenzyme A acetyltransferase activity, an acetyl-CoA:acetoacetate transferase or acetate:acetoacetyl-CoA hydrolase activity, an acetoacetate decarboxylase activity, a 3-hydroxyisovalerate (3HIV) synthase activity, a hydroxymethylglutaryl-CoA synthase activity, a methylglutaconyl-CoA hydratase activity, a methylcrotonyl-CoA carboxylase activity, a methylcrotonyl-CoA hydratase activity, a 3-hydroxyisovaleryl-CoA thioesterase activity, a 3HIV kinase activity, a 3HIV-3-phosphate decarboxylase activity, and a 3HIV decarboxylase activity, and wherein the one or more co-product comprises isobutene.

64. The method of any one of the preceding embodiments, wherein one or more enzyme for the production of one or more co-product through the conversion of DHAP or pyruvate in a C3 pathway are selected from one or more enzyme having an activity selected from a 3-phosphoglycerate dehydrogenase activity, a phosphoserine aminotransferase activity, a 3-phosphohydroxypyruvate phosphatase activity, a phosphoserine phosphatase activity, a serine oxidoreductase (deaminating) or serine-pyruvate aminotransferase activity, a hydroxypyruvate reductase activity, a 3-phosphoglycerate phosphatase activity, a 2-phosphoglycerate phosphatase activity, a glycerate 3-kinase activity, and a glycerate 2-kinase activity, and wherein the one or more co-product comprises L-serine.

65. The method of any one of the preceding embodiments, wherein one or more enzyme for the production of one or more co-product through the conversion of DHAP or pyruvate in a C3 pathway are selected from one or more enzyme having an activity selected from a serine hydroxymethyltransferase activity, a transferase activity, a formaldehyde dehydrogenase activity, a formate dehydrogenase activity, an activity associated with glycine cleavage system, a 3-phosphoglycerate dehydrogenase activity, a phosphoserine aminotransferase activity, a 3-phosphohydroxypyruvate phosphatase activity, a phosphoserine phosphatase activity, a serine transaminase activity, a hydroxypyruvate decarboxylase activity, a serine oxidoreductase (deaminating) activity, a serine decarboxylase activity, an ethanolamine aminotransferase or ethanolamine oxidoreductase (deaminating) activity, a hydroxypyruvate reductase activity, a 3-phosphoglycerate phosphatase activity, a 2-phosphoglycerate phosphatase activity, a glycerate 3-kinase activity, a glycerate 2-kinase activity, a glycolaldehyde dehydrogenase activity, a glycolate dehydrogenase activity, an alanine-glyoxylate aminotransferase activity, an alanine transaminase activity, an NAD(P)H dependent glutamate dehydrogenase activity, and wherein the one or more co-product comprises glycine.

66. The method of any one of the preceding embodiments, wherein the activity associated with glycine cleavage system comprise an enzyme or protein selected from a glycine decarboxylase (P protein), an aminomethyltransferase (T protein), a dihydrolipoamide dehydrogenase (L protein), and an H protein.

67. The method of any one of the preceding embodiments, wherein one or more enzyme for the production of one or more co-product through the conversion of DHAP or pyruvate in a C3 pathway are selected from one or more enzyme having an activity selected from a 3-phosphoglycerate dehydrogenase activity, a phosphoserine aminotransferase activity, a 3-phosphohydroxypyruvate phosphatase activity, a phosphoserine phosphatase activity, a transaminase activity, a hydroxypyruvate decarboxylase activity, a serine oxidoreductase (deaminating) or serine-pyruvate aminotransferase activity, a serine decarboxylase activity, a hydroxypyruvate reductase activity, a 3-phosphoglycerate phosphatase activity, a 2-phosphoglycerate phosphatase activity, a glycerate 3-kinase activity, a glycerate 2-kinase activity, an acetaldehyde dehydrogenase activity, and an ethanolamine ammonia lyase activity, and wherein the one or more co-product comprises monoethanolamine (MEA).

68. The method of any one of the preceding embodiments, wherein one or more enzyme for the production of one or more co-product through the conversion of DHAP or pyruvate in a C3 pathway are selected from one or more enzyme having an activity selected from a serine dehydrogenase activity, a 2-aminomalonate semialdehyde decarboxylase activity, an aminoacetaldehyde transaminase activity, a 2-aminomalonate semialdehyde transaminase activity, a 2,3-diaminopropanoate decarboxylase activity, a serine decarboxylase activity, an ethanolamine dehydrogenase activity, a serine hydroxymethyltransferase activity, an aldehyde oxidase activity, an N-acetyl transferase or O-acetyl transferase activity, an N-acetylserine dehydrogenase activity, a transaminase activity, a deacetylase activity, a serine aminase activity, and a 2,3-diaminopropanoate ammonia lyase activity, and wherein the one or more co-product comprises ethylenediamine (EDA).

69. The recombinant microorganism of any one of the preceding embodiments, wherein one or more enzyme for the production of MEG or GA from glycolaldehyde in a C2 pathway are selected from one or more enzyme having an activity selected from a D-tagatose 3-epimerase activity, a D-ribulokinase activity, a D-ribulose-1-phosphate aldolase activity, a D-xylulose 1-kinase activity, a D-xylulose-1-phosphate aldolase activity, a xylose reductase or aldose reductase activity, a xylitol dehydrogenase activity, a xylose isomerase activity, a xylose dehydrogenase activity, a xylonolactonase activity, a xylonate dehydrogenase activity, a 2-keto-3-deoxy-D-pentonate aldolase activity, a glycolaldehyde reductase activity and a glycolaldehyde dehydrogenase activity.

70. The recombinant microorganism of any one of the preceding embodiments, wherein the recombinant microorganism further comprises one or more modifications to diminish or delete activity in a glycolaldehyde dehydrogenase, a lactate dehydrogenase, a xylose isomerase, a xylulose kinase or combination thereof.

71. The recombinant microorganism of any one of the preceding embodiments, wherein at least a portion of the excess NADH produced in the C3 pathway is used as a source of reducing equivalents in the C2 pathway.

72. The recombinant microorganism of any one of the preceding embodiments, wherein at least a portion of the excess NADH produced in the C3 pathway is used to produce ATP.

73. The recombinant microorganism of any one of the preceding embodiments, wherein excess biomass formation is minimized and production of MEG (or GA) or MEG (or GA) and one or more co-product is maximized.

74. A method of producing MEG or glycolic acid (GA) using a recombinant microorganism of any of the preceding claims, wherein the method comprises cultivating the recombinant microorganism in a culture medium containing one or more hexose feedstock providing a carbon source until the MEG or GA is produced.

75. The method of any one of the preceding embodiments, wherein one or more co-product is co-produced with MEG or GA.

76. The method of any one of the preceding embodiments, wherein the one or more co-product is selected from acetone, isopropanol, propene, isobutene and one or more serine pathway compound.

77. The method of any one of the preceding embodiments, wherein the one or more serine pathway compound is selected from serine, glycine, monoethanolamine (MEA) and ethylenediamine (EDA).

78. A method of producing a recombinant microorganism that produces or accumulates MEG or glycolic acid (GA) from one or more exogenous hexose feedstock via one or more pentose-5-phosphate intermediate, comprising:
    introducing into the recombinant microorganism one or more enzyme for the conversion of the one or more hexose feedstock to the one or more pentose-5-phosphate intermediate;
    introducing into the recombinant microorganism one or more enzyme for the conversion of the one or more pentose-5-phosphate intermediate to one or more pentose or pentose-1-phosphate intermediate;
    introducing into the recombinant microorganism a C2 pathway comprising one or more enzyme for the production of MEG or GA from glycolaldehyde; and
    introducing into the recombinant microorganism a C3 pathway comprising one or more enzyme for the production of MEG or GA derived from DHAP or pyruvate; and
    culturing the recombinant microorganism in a culture medium containing the one or more hexose feedstock to produce or accumulate MEG or GA,
    wherein glycolaldehyde and DHAP (or pyruvate) are intermediates produced in the C2 pathway, and wherein MEG or GA are produced in both the C2 and C3 pathways.

79. A method of producing a recombinant microorganism that produces or accumulates MEG or glycolic acid (GA) and one or more co-product from one or more exogenous hexose feedstock via one or more pentose-5-phosphate intermediate, comprising:
    introducing into the recombinant microorganism one or more enzyme for the conversion of the one or more hexose feedstock to the one or more pentose-5-phosphate intermediate;
    introducing into the recombinant microorganism one or more enzyme for the conversion of the one or more pentose-5-phosphate intermediate to one or more pentose or pentose-1-phosphate intermediate;
    introducing into the recombinant microorganism a C2 pathway comprising one or more enzyme for the production of MEG or GA from glycolaldehyde; and
    introducing into the recombinant microorganism a C3 pathway comprising one or more enzyme for the production of one or more co-product derived from DHAP or pyruvate; and
    culturing the recombinant microorganism in a culture medium containing the one or more hexose feedstock to produce or accumulate MEG or GA and one or more co-product, wherein glycolaldehyde and DHAP (or pyruvate) are intermediates produced in the C2 pathway, and wherein MEG or GA is produced in the C2 pathway and the one or more co-product is produced in the C3 pathway.

80. The method of any one of the preceding embodiments, wherein the glycolaldehyde is oxidized to glycolic acid by a glycoladehyde dehydrogenase.

81. The method of any one of the preceding embodiments, wherein the one or more enzyme for the conversion of the one or more hexose feedstock to the one or more pentose-5-phosphate intermediate are selected from one or more enzyme having a transketolase activity, a transaldolase activity, a ribulose-5-phosphate 3-epimerase activity, and a ribose-5-phosphate isomerase activity.

82. The method of any one of the preceding embodiments, wherein the method further comprises introducing into the recombinant microorganism one or more modifications to diminish or delete activity in one or more endogenous enzymes selected from glyceraldehyde 3-phosphate dehydrogenase (gapA), phosphoglycerate kinase (pgk) and phosphoglycerate mutase (gpmA and/or gpmM).

83. The method of any one of the preceding embodiments, wherein the one or more enzyme for the conversion of the one or more hexose feedstock to the one or more pentose-5-phosphate intermediate are selected from one or more enzyme having a fructose-6-phosphate phosphoketolase activity, a phosphate acetyltransferase activity, a transketolase activity, a transaldolase activity, a ribulose-5-phosphate 3-epimerase activity, and a ribose-5-phosphate isomerase activity.

84. The method of any one of the preceding embodiments, wherein the method further comprises introducing into the recombinant microorganism one or more modifications to diminish or delete activity in an endogenous 6-phosphofructokinase (pfkAB) enzyme.

85. The method of any one of the preceding embodiments, wherein the method further comprises: introducing into the recombinant microorganism one or more modifications to diminish or delete activity in one or more endogenous enzymes selected from glucose 6-phosphate-1-dehydrogenase, 6-phosphogluconolactonase, and 6-phosphogluconate dehydrogenase.

86. The method of any one of the preceding embodiments, wherein the glucose 6-phosphate-1-dehydrogenase is zwf, the 6-phosphogluconolactonase is pgl, and the 6-phosphogluconate dehydrogenase is gnd.

87. The method of any one of the preceding embodiments, wherein the one or more enzyme for the conversion of the one or more pentose-5-phosphate intermediate to one or more pentose or pentose-1-phosphate intermediate are selected from one or more enzyme having a pentose phosphatase activity, a D-ribulose-5-phosphatase activity, a D-ribose-5-phosphatase activity, a D-ribose isomerase activity, an arabitol phosphate dehydrogenase activity, and a phosphopentomutase activity.

88. The method of any one of the preceding embodiments, wherein one or more enzyme for the production of MEG or GA derived from DHAP or pyruvate in the C3 pathway are selected from one or more enzyme having an activity selected from a 3-phosphoglycerate dehydrogenase activity, a phosphoserine aminotransferase activity, a 3-phosphohydroxypyruvate phosphatase activity, a phosphoserine phosphatase activity, a serine transaminase activity, a hydroxypyruvate decarboxylase activity, a 3-phosphohydroxypyruvate reductase activity, a glycolaldehyde reductase activity, a glycolaldehyde dehydrogenase activity, a serine oxidoreductase (deaminating) or serine-pyruvate aminotransferase activity, a serine decarboxylase activity, an ethanolamine aminotransferase or ethanolamine oxidoreductase (deaminating) activity, a glycerate decarboxylase activity, a hydroxypyruvate reductase activity, a 3-phosphoglycerate phosphatase activity, a 2-phosphoglycerate phosphatase activity, a glycerate 3-kinase activity, and a glycerate 2-kinase activity.

89. The method of any one of the preceding embodiments, wherein one or more enzyme for the production of one or more co-product derived from DHAP or pyruvate in the C3 pathway are selected from one or more enzyme having an activity selected from a thiolase or acetyl coenzyme A acetyltransferase activity, an acetyl-CoA:acetoacetate transferase or acetate:acetoacetyl-CoA hydrolase activity, and an acetoacetate decarboxylase activity, and wherein the one or more co-product comprises acetone.

90. The method of any one of the preceding embodiments, wherein one or more enzyme for the production of one or more co-product derived from DHAP or pyruvate in the C3 pathway are selected from one or more enzyme having an activity selected from a thiolase or acetyl coenzyme A acetyltransferase activity, an acetyl-CoA:acetoacetate transferase or acetate:acetoacetyl-CoA hydrolase activity, an acetoacetate decarboxylase activity, and a secondary alcohol dehydrogenase activity, and wherein the one or more co-product comprises isopropanol.

91. The method of any one of the preceding embodiments, wherein one or more enzyme for the production of one or more co-product derived from DHAP or pyruvate in the C3 pathway are selected from one or more enzyme having an activity selected from a thiolase or acetyl coenzyme A acetyltransferase activity, an acetyl-CoA:acetoacetate transferase or acetate:acetoacetyl-CoA hydrolase activity, an acetoacetate decarboxylase activity, a secondary alcohol dehydrogenase activity, and a dehydratase activity, and wherein the one or more co-product comprises propene.

92. The method of any one of the preceding embodiments, wherein one or more enzyme for the production of one or more co-product derived from DHAP or pyruvate in the C3 pathway are selected from one or more enzyme having an activity selected from a thiolase or acetyl coenzyme A acetyltransferase activity, an acetyl-CoA:acetoacetate transferase or acetate:acetoacetyl-CoA hydrolase activity, an acetoacetate decarboxylase activity, a 3-hydroxyisovalerate (3HIV) synthase activity, a hydroxymethylglutaryl-CoA synthase activity, a methylglutaconyl-CoA hydratase activity, a methylcrotonyl-CoA carboxylase activity, a methylcrotonyl-CoA hydratase activity, a 3-hydroxyisovaleryl-CoA thioesterase activity, a 3HIV kinase activity, a 3HIV-3-phosphate decarboxylase activity, and a 3HIV decarboxylase activity, and wherein the one or more co-product comprises isobutene.

93. The method of any one of the preceding embodiments, wherein one or more enzyme for the production of one or more co-product derived from DHAP or pyruvate in the C3 pathway are selected from one or more enzyme having an activity selected from a 3-phosphoglycerate dehydrogenase activity, a phosphoserine aminotransferase activity, a 3-phosphohydroxypyruvate phosphatase activity, a phosphoserine phosphatase activity, a serine oxidoreductase (deaminating) or serine-pyruvate aminotransferase activity, a hydroxypyruvate reductase activity, a 3-phosphoglycerate phosphatase activity, a 2-phosphoglycerate phosphatase activity, a glycerate 3-kinase activity, and a glycerate 2-kinase activity, and wherein the one or more co-product comprises L-serine.

94. The method of any one of the preceding embodiments, wherein one or more enzyme for the production of one or more co-product derived from DHAP or pyruvate in the C3 pathway are selected from one or more enzyme having an activity selected from a serine hydroxymethyltransferase activity, a transferase activity, a formaldehyde dehydrogenase activity, a formate dehydrogenase activity, an activity associated with glycine cleavage system, a 3-phosphoglycerate dehydrogenase activity, a phosphoserine aminotransferase activity, a 3-phosphohydroxypyruvate phosphatase activity, a phosphoserine phosphatase activity, a serine transaminase activity, a hydroxypyruvate decarboxylase activity, a serine oxidoreductase (deaminating) activity, a serine decarboxylase activity, an ethanolamine aminotransferase or ethanolamine oxidoreductase (deaminating) activity, a hydroxypyruvate reductase activity, a 3-phosphoglycerate phosphatase activity, a 2-phosphoglycerate phosphatase activity, a glycerate 3-kinase activity, a glycerate 2-kinase activity, a glycolaldehyde dehydrogenase activity, a glycolate dehydrogenase activity, an alanine-glyoxylate aminotransferase activity, an alanine transaminase activity, and an NAD(P)H dependent glutamate dehydrogenase activity, and wherein the one or more co-product comprises glycine.

95. The method of any one of the preceding embodiments, wherein the activity associated with glycine cleavage system comprise an enzyme or protein selected from a glycine decarboxylase (P protein), an aminomethyltransferase (T protein), a dihydrolipoamide dehydrogenase (L protein), and an H protein.

96. The method of any one of the preceding embodiments, wherein one or more enzyme for the production of one or more co-product derived from DHAP or pyruvate in the C3 pathway are selected from one or more enzyme having an activity selected from 3-phosphoglycerate dehydrogenase activity, a phosphoserine aminotransferase activity, a 3-phosphohydroxypyruvate phosphatase activity, a phosphoserine phosphatase activity, a transaminase activity, a hydroxypyruvate decarboxylase activity, a serine oxidoreductase (deaminating) or serine-pyruvate aminotransferase activity, a serine decarboxylase activity, a hydroxypyruvate reductase activity, a 3-phosphoglycerate phosphatase activity, a 2-phosphoglycerate phosphatase activity, a glycerate 3-kinase activity, a glycerate 2-kinase activity, an acetaldehyde dehydrogenase activity, and an ethanolamine ammonia lyase activity, and wherein the one or more co-product comprises monoethanolamine (MEA).

97. The method of any one of the preceding embodiments, wherein one or more enzyme for the production of one or more co-product derived from DHAP or pyruvate in the C3 pathway are selected from one or more enzyme having an activity selected from a serine dehydrogenase activity, a 2-aminomalonate semialdehyde decarboxylase activity, an aminoacetaldehyde transaminase activity, a 2-aminomalonate semialdehyde transaminase activity, a 2,3-diaminopropanoate decarboxylase activity, a serine decarboxylase activity, an ethanolamine dehydrogenase activity, a serine hydroxymethyltransferase activity, an aldehyde oxidase activity, an N-acetyl transferase or O-acetyl transferase activity, an N-acetylserine dehydrogenase activity, a transaminase activity, a deacetylase activity, a serine aminase activity, and a 2,3-diaminopropanoate ammonia lyase activity, and wherein the one or more co-product comprises ethylenediamine (EDA).

98. The method of any one of the preceding embodiments, wherein one or more enzyme for the production of MEG or GA in the C2 pathway are selected from one or more enzyme having an activity selected from a D-tagatose 3-epimerase activity, a D-ribulokinase activity, a D-ribulose-1-phosphate aldolase activity, a D-xylulose 1-kinase activity, a D-xylulose-1-phosphate aldolase activity, a xylose reductase or aldose reductase activity, a xylitol dehydrogenase activity, a xylose isomerase activity, a xylose dehydrogenase activity, a xylonolactonase activity, a xylonate dehydrogenase activity, a 2-keto-3-deoxy-D-pentonate aldolase activity, a glycolaldehyde reductase activity and a glycolaldehyde dehydrogenase activity.

99. The method of any one of the preceding embodiments, wherein the method further comprises: introducing into the recombinant microorganism one or more modifications to diminish or delete activity in a glycolaldehyde dehydrogenase, a lactate dehydrogenase, a xylose isomerase, xylulose kinase or combination thereof.

100. A recombinant microorganism comprising one or more biochemical pathway that produces monoethylene glycol (MEG) or glycolic acid (GA) from one or more hexose feedstock via one or more pentose-5-phosphate intermediate.

101. The recombinant microorganism of any one of the preceding embodiments, wherein one or more co-product is co-produced with MEG or GA.

102. The recombinant microorganism of any one of the preceding embodiments, wherein the one or more pentose-5-phosphate intermediate is one or more of D-ribose-5-phosphate, D-xylulose-5-phosphate or D-ribulose-5-phosphate.

103. The recombinant microorganism of any one of the preceding embodiments, wherein the one or more biochemical pathway comprises expression of at least one enzyme having transketolase activity.

104. The recombinant microorganism of any one of the preceding embodiments, wherein the at least one enzyme having transketolase activity is encoded by an amino acid sequence having at least 70% sequence identity, at least 80% sequence identity, or at least 90% sequence identity to tktA tktB from E. coli.

105. The recombinant microorganism of any one of the preceding embodiments, wherein the one or more biochemical pathway comprises expression of at least one enzyme having transaldolase activity.

106. The recombinant microorganism of any one of the preceding embodiments, wherein the at least one enzyme having transaldolase activity is encoded by an amino acid sequence having at least 70% sequence identity, at least 80% sequence identity, or at least 90% sequence identity to talB or talB from E. coli.

107. The recombinant microorganism of any one of the preceding embodiments, wherein the one or more biochemical pathway comprises expression of at least one enzyme having ribulose-5-phosphate 3-epimerase activity.

108. The recombinant microorganism of any one of the preceding embodiments, wherein the at least one enzyme having ribulose-5-phosphate 3-epimerase activity is encoded by an amino acid sequence having at least 70% sequence identity, at least 80% sequence identity, or at least 90% sequence identity to rpe from E. coli.

109. The recombinant microorganism of any one of the preceding embodiments, wherein the one or more biochemical pathway comprises expression of at least one enzyme having ribose-5-phosphate isomerase activity.

110. The recombinant microorganism of any one of the preceding embodiments, wherein the at least one enzyme having ribose-5-phosphate isomerase activity is encoded by an amino acid sequence having at least 70% sequence identity, at least 80% sequence identity, or at least 90% sequence identity to rpiA or rpiB from E. coli.

111. The recombinant microorganism of any one of the preceding embodiments, wherein the recombinant microorganism further comprises a deleted or diminished activity in at least one endogenous enzyme selected from glyceraldehyde 3-phosphate dehydrogenase, phosphoglycerate kinase and/or phosphoglycerate mutase.

112. The recombinant microorganism of any one of the preceding embodiments, wherein the one or more biochemical pathway comprises expression of at least one enzyme having fructose-6-phosphate phosphoketolase activity.

113. The recombinant microorganism of any one of the preceding embodiments, wherein the at least one enzyme having fructose-6-phosphate phosphoketolase activity is encoded by an amino acid sequence having at least 70% sequence identity, at least 80% sequence identity, or at least 90% sequence identity to an enzyme having fructose-6-phosphate phosphoketolase activity selected from the group consisting of Bifidobacterium dentium BDP_1006, Bifidobacterium lactis xfp, Lactobacillus paraplantarum xpkA and Bifidobacterium breve xfp.

114. The recombinant microorganism of any one of the preceding embodiments, wherein the one or more biochemical pathway comprises expression of at least one enzyme having phosphate acetyltransferase activity.

115. The recombinant microorganism of any one of the preceding embodiments, wherein the at least one enzyme having phosphate acetyltransferase activity is encoded by an amino acid sequence having at least 70% sequence identity, at least 80% sequence identity, or at least 90% sequence identity to an enzyme having phosphate acetyltransferase activity selected from E. coli pta and Clostridium acetobutylicum pta.

116. The recombinant microorganism of any one of the preceding embodiments, wherein the recombinant microorganism further comprises a deleted or diminished activity in an endogenous 6-phosphofructokinase enzyme.

117. The recombinant microorganism of any one of the preceding embodiments, wherein the one or more biochemical pathway comprises at least one enzyme having pentose phosphatase activity.

118. The recombinant microorganism of any one of the preceding embodiments, wherein the at least one enzyme having pentose phosphatase activity is selected from one or more of an enzyme having D-pentose-5-phosphatase activity, an enzyme having D-xylulose-5-phosphatase activity, an enzyme having D-ribose-5-phosphatase activity, and an enzyme having D-ribulose-5-phosphatase activity.

119. The recombinant microorganism of any one of the preceding embodiments, wherein the one or more biochemical pathway comprises at least one enzyme having arabitol phosphate dehydrogenase activity.

120. The recombinant microorganism of any one of the preceding embodiments, wherein the at least one enzyme having arabitol phosphate dehydrogenase activity is selected from one or more of an enzyme having D-arabitol 1-phosphate 4-dehydrogenase activity, an enzyme having D-arabitol 5-phosphate 2-dehydrogenase activity, an enzyme having D-arabitol 1-phosphate 2-dehydrogenase activity and an enzyme having D-arabitol 5-phosphate 4-dehydrogenase activity.

121. The recombinant microorganism of any one of the preceding embodiments, wherein the one or more biochemical pathway comprises at least one enzyme having phosphopentomutase activity.

122. The recombinant microorganism of any one of the preceding embodiments, wherein the recombinant microorganism further comprises a deleted or diminished activity in one or more endogenous enzymes selected from glucose 6-phosphate-1-dehydrogenase, 6-phosphogluconolactonase and 6-phosphogluconate dehydrogenase.

123. The recombinant microorganism of any one of the preceding embodiments, wherein the one or more co-product is selected from acetone, isopropanol, propene, isobutene and one or more serine pathway compounds.

124. The recombinant microorganism of any one of the preceding embodiments, wherein the one or more serine pathway compounds is selected from serine, glycine, monoethanolamine (MEA) and ethylenediamine (EDA).

125. The recombinant microorganism of any one of the preceding embodiments, wherein the one or more hexose feedstock is selected from glucose or oligomers of glucose thereof.

126. The recombinant microorganism of any one of the preceding embodiments, wherein the oligomers of glucose are selected from fructose, sucrose, starch, cellobiose, maltose, lactose and cellulose.

127. The recombinant microorganism of any one of the preceding embodiments, wherein the expression of an enzyme having transketolase activity or an enzyme having fructose-6-phosphate phosphoketolase activity enables a lossless conversion of one or more hexose feedstock to the one or more pentose-5-phosphate intermediate.

128. The recombinant microorganism of any one of the preceding embodiments, wherein MEG or GA is produced through the conversion of glycolaldehyde in a C2 pathway and through the conversion of dihydroxyacetone phosphate (DHAP) or pyruvate in a C3 pathway.

129. The recombinant microorganism of any one of the preceding embodiments, wherein GA is produced by the oxidation of glycolaldehyde by a glycolaldehyde dehydrogenase.

130. The recombinant microorganism of any one of the preceding embodiments, wherein one or more enzyme for the production of MEG or GA through the conversion of DHAP or pyruvate in a C3 pathway are selected from one or more enzyme having an activity selected from a 3-phosphoglycerate dehydrogenase activity, a phosphoserine aminotransferase activity, a 3-phosphohydroxypyruvate phosphatase activity, a phosphoserine phosphatase activity, a serine transaminase activity, a hydroxypyruvate decarboxylase activity, a 3-phosphohydroxypyruvate reductase activity, a glycolaldehyde reductase activity, a glycolaldehyde dehydrogenase activity, a serine oxidoreductase (deaminating) or serine-pyruvate aminotransferase activity, a serine decarboxylase activity, an ethanolamine aminotransferase or ethanolamine oxidoreductase (deaminating) activity, a glycerate decarboxylase activity, a hydroxypyruvate reductase activity, a 3-phosphoglycerate phosphatase activity, a 2-phosphoglycerate phosphatase activity, a glycerate 3-kinase activity, and a glycerate 2-kinase activity.

131. The recombinant microorganism of any one of the preceding embodiments, wherein MEG or GA is produced through the conversion of glycolaldehyde in a C2 pathway and one or more co-product is produced through the conversion of dihydroxyacetone phosphate (DHAP) or pyruvate in a C3 pathway.

132. The recombinant microorganism of any one of the preceding embodiments, wherein one or more enzyme for the production of one or more co-product through the conversion of DHAP or pyruvate in a C3 pathway are selected from one or more enzyme having an activity selected from a thiolase or acetyl coenzyme A acetyltransferase activity, an acetyl-CoA:acetoacetate transferase or acetate:acetoacetyl-CoA hydrolase activity, and an acetoacetate decarboxylase activity, and wherein the one or more co-product comprises acetone.

133. The recombinant microorganism of any one of the preceding embodiments, wherein one or more enzyme for the production of one or more co-product through the conversion of DHAP or pyruvate in a C3 pathway are selected from one or more enzyme having an activity selected from a thiolase or acetyl coenzyme A acetyltransferase activity, an acetyl-CoA:acetoacetate transferase or acetate:acetoacetyl-CoA hydrolase activity, an acetoacetate decarboxylase activity, and a secondary alcohol dehydrogenase activity, and wherein the one or more co-product comprises isopropanol.

134. The recombinant microorganism of any one of the preceding embodiments, wherein one or more enzyme for the production of one or more co-product through the conversion of DHAP or pyruvate in a C3 pathway are selected from one or more enzyme having an activity selected from a thiolase or acetyl coenzyme A acetyltransferase activity, an acetyl-CoA:acetoacetate transferase or acetate:acetoacetyl-CoA hydrolase activity, an acetoacetate decarboxylase activity, a secondary alcohol dehydrogenase activity, and a dehydratase-isomerase activity, and wherein the one or more co-product comprises propene.

135. The method of any one of the preceding embodiments, wherein one or more enzyme for the production of one or more co-product through the conversion of DHAP or pyruvate in a C3 pathway are selected from one or more enzyme having an activity selected from a thiolase or acetyl coenzyme A acetyltransferase activity, an acetyl-CoA:acetoacetate transferase or acetate:acetoacetyl-CoA hydrolase activity, an acetoacetate decarboxylase activity, a 3-hydroxyisovalerate (3HIV) synthase activity, a hydroxymethylglutaryl-CoA synthase activity, a methylglutaconyl-CoA hydratase activity, a methylcrotonyl-CoA carboxylase activity, a methylcrotonyl-CoA hydratase activity, a 3-hydroxyisovaleryl-CoA thioesterase activity, a 3HIV kinase activity, a 3HIV-3-phosphate decarboxylase activity, and a 3HIV decarboxylase activity, and wherein the one or more co-product comprises isobutene.

136. The method of any one of the preceding embodiments, wherein one or more enzyme for the production of one or more co-product through the conversion of DHAP or pyruvate in a C3 pathway are selected from one or more enzyme having an activity selected from a 3-phosphoglycerate dehydrogenase activity, a phosphoserine aminotransferase activity, a 3-phosphohydroxypyruvate phosphatase activity, a phosphoserine phosphatase activity, a serine oxidoreductase (deaminating) or serine-pyruvate aminotransferase activity, a hydroxypyruvate reductase activity, a 3-phosphoglycerate phosphatase activity, a 2-phosphoglycerate phosphatase activity, a glycerate 3-kinase activity, and a glycerate 2-kinase activity, and wherein the one or more co-product comprises L-serine.

137. The method of any one of the preceding embodiments, wherein one or more enzyme for the production of one or more co-product through the conversion of DHAP or pyruvate in a C3 pathway are selected from one or more enzyme having an activity selected from a serine hydroxymethyltransferase activity, a transferase activity, a formaldehyde dehydrogenase activity, a formate dehydrogenase activity, an activity associated with glycine cleavage system, a 3-phosphoglycerate dehydrogenase activity, a phosphoserine aminotransferase activity, a 3-phosphohydroxypyruvate phosphatase activity, a phosphoserine phosphatase activity, a serine transaminase activity, a hydroxypyruvate decarboxylase activity, a serine oxidoreductase (deaminating) activity, a serine decarboxylase activity, an ethanolamine aminotransferase or ethanolamine oxidoreductase (deaminating) activity, a hydroxypyruvate reductase activity, a 3-phosphoglycerate phosphatase activity, a 2-phosphoglycerate phosphatase activity, a glycerate 3-kinase activity, a glycerate 2-kinase activity, a glycolaldehyde dehydrogenase activity, a glycolate dehydrogenase activity, an alanine-glyoxylate aminotransferase activity, an alanine transaminase activity, an NAD(P)H dependent glutamate dehydrogenase activity, and wherein the one or more co-product comprises glycine.

138. The method of any one of the preceding embodiments, wherein the activity associated with glycine cleavage system comprise an enzyme or protein selected from a glycine decarboxylase (P protein), an aminomethyltransferase (T protein), a dihydrolipoamide dehydrogenase (L protein), and an H protein.

139. The method of any one of the preceding embodiments, wherein one or more enzyme for the production of one or more co-product through the conversion of DHAP or pyruvate in a C3 pathway are selected from one or more enzyme having an activity selected from a 3-phosphoglycerate dehydrogenase activity, a phosphoserine aminotransferase activity, a 3-phosphohydroxypyruvate phosphatase activity, a phosphoserine phosphatase activity, a transaminase activity, a hydroxypyruvate decarboxylase activity, a serine oxidoreductase (deaminating) or serine-pyruvate aminotransferase activity, a serine decarboxylase activity, a hydroxypyruvate reductase activity, a 3-phosphoglycerate phosphatase activity, a 2-phosphoglycerate phosphatase activity, a glycerate 3-kinase activity, a glycerate 2-kinase activity, an acetaldehyde dehydrogenase activity, and an ethanolamine ammonia lyase activity, and wherein the one or more co-product comprises monoethanolamine (MEA).

140. The method of any one of the preceding embodiments, wherein one or more enzyme for the production of one or more co-product through the conversion of DHAP or pyruvate in a C3 pathway are selected from one or more enzyme having an activity selected from a serine dehydrogenase activity, a 2-aminomalonate semialdehyde decarboxylase activity, an aminoacetaldehyde transaminase activity, a 2-aminomalonate semialdehyde transaminase activity, a 2,3-diaminopropanoate decarboxylase activity, a serine decarboxylase activity, an ethanolamine dehydrogenase activity, a serine hydroxymethyltransferase activity, an aldehyde oxidase activity, an N-acetyl transferase or O-acetyl transferase activity, an N-acetylserine dehydrogenase activity, a transaminase activity, a deacetylase activity, a serine aminase activity, and a 2,3-diaminopropanoate ammonia lyase activity, and wherein the one or more co-product comprises ethylenediamine (EDA).

141. The recombinant microorganism of any one of the preceding embodiments, wherein one or more enzyme for the production of MEG or GA from glycolaldehyde in a C2 pathway are selected from one or more enzyme having an activity selected from a D-tagatose 3-epimerase activity, a D-ribulokinase activity, a D-ribulose-1-phosphate aldolase activity, a D-xylulose 1-kinase activity, a D-xylulose-1-phosphate aldolase activity, a xylose reductase or aldose reductase activity, a xylitol dehydrogenase activity, a xylose isomerase activity, a xylose dehydrogenase activity, a xylonolactonase activity, a xylonate dehydrogenase activity, a 2-keto-3-deoxy-D-pentonate aldolase activity, a glycolaldehyde reductase activity and a glycolaldehyde dehydrogenase activity.

142. The recombinant microorganism of any one of the preceding embodiments, wherein the recombinant microorganism further comprises one or more modifications to diminish or delete activity in a glycolaldehyde dehydrogenase, a lactate dehydrogenase, a xylose isomerase, a xylulose kinase or combination thereof.

143. The recombinant microorganism of any one of the preceding embodiments, wherein at least a portion of the excess NADH produced in the C3 pathway is used as a source of reducing equivalents in the C2 pathway.

144. The recombinant microorganism of any one of the preceding embodiments, wherein at least a portion of the excess NADH produced in the C3 pathway is used to produce ATP.

145. The recombinant microorganism of any one of the preceding embodiments, wherein excess biomass formation is minimized and production of MEG (or GA) or MEG (or GA) and one or more co-product is maximized.

146. A method of producing MEG or glycolic acid (GA) using a recombinant microorganism of any of the preceding Embodiments, wherein the method comprises cultivating the recombinant microorganism in a culture medium containing one or more hexose feedstock providing a carbon source until the MEG or GA is produced.

147. The method of any one of the preceding embodiments, wherein one or more co-product is co-produced with MEG or GA.

148. The method of any one of the preceding embodiments, wherein the one or more co-product is selected from acetone, isopropanol, propene, isobutene and one or more serine pathway compound.

149. The method of any one of the preceding embodiments, wherein the one or more serine pathway compound is selected from serine, glycine, monoethanolamine (MEA) and ethylenediamine (EDA).

150. A method of producing a recombinant microorganism that produces or accumulates MEG or glycolic acid (GA) from one or more exogenous hexose feedstock via one or more pentose-5-phosphate intermediate, comprising:
    introducing into or expressing in the recombinant microorganism one or more enzyme for the conversion of the one or more hexose feedstock to the one or more pentose-5-phosphate intermediate;
    introducing into or expressing in the recombinant microorganism one or more enzyme for the conversion of the one or more pentose-5-phosphate intermediate to one or more pentose or pentose-1-phosphate intermediate;

introducing into or expressing in the recombinant microorganism a C2 pathway comprising one or more enzyme for the production of MEG or GA from glycolaldehyde; and introducing into or expressing in the recombinant microorganism a C3 pathway comprising one or more enzyme for the production of MEG or GA derived from DHAP or pyruvate; and culturing the recombinant microorganism in a culture medium containing the one or more hexose feedstock to produce or accumulate MEG or GA, wherein glycolaldehyde and DHAP (or pyruvate) are intermediates produced in the C2 pathway, and wherein MEG or GA are produced in both the C2 and C3 pathways.

151. A method of producing a recombinant microorganism that produces or accumulates MEG or glycolic acid (GA) and one or more co-product from one or more exogenous hexose feedstock via one or more pentose-5-phosphate intermediate, comprising:

introducing into or expressing in the recombinant microorganism one or more enzyme for the conversion of the one or more hexose feedstock to the one or more pentose-5-phosphate intermediate;

introducing into or expressing in the recombinant microorganism one or more enzyme for the conversion of the one or more pentose-5-phosphate intermediate to one or more pentose or pentose-1-phosphate intermediate;

introducing into or expressing in the recombinant microorganism a C2 pathway comprising one or more enzyme for the production of MEG or GA from glycolaldehyde; and introducing into or expressing in the recombinant microorganism a C3 pathway comprising one or more enzyme for the production of one or more co-product derived from DHAP or pyruvate; and culturing the recombinant microorganism in a culture medium containing the one or more hexose feedstock to produce or accumulate MEG or GA and one or more co-product, wherein glycolaldehyde and DHAP (or pyruvate) are intermediates produced in the C2 pathway, and wherein MEG or GA is produced in the C2 pathway and the one or more co-product is produced in the C3 pathway.

152. The method of any one of the preceding embodiments, wherein the glycolaldehyde is oxidized to glycolic acid by a glycoladehyde dehydrogenase.

153. The method of any one of the preceding embodiments, wherein the one or more enzyme for the conversion of the one or more hexose feedstock to the one or more pentose-5-phosphate intermediate are selected from one or more enzyme having a transketolase activity, a transaldolase activity, a ribulose-5-phosphate 3-epimerase activity, and a ribose-5-phosphate isomerase activity.

154. The method of any one of the preceding embodiments, wherein the method further comprises introducing into the recombinant microorganism one or more modifications to diminish or delete activity in one or more endogenous enzymes selected from glyceraldehyde 3-phosphate dehydrogenase (gapA), phosphoglycerate kinase (pgk) and phosphoglycerate mutase (gpmA and/or gpmM).

155. The method of any one of the preceding embodiments, wherein the one or more enzyme for the conversion of the one or more hexose feedstock to the one or more pentose-5-phosphate intermediate are selected from one or more enzyme having a fructose-6-phosphate phosphoketolase activity, a phosphate acetyltransferase activity, a transketolase activity, a transaldolase activity, a ribulose-5-phosphate 3-epimerase activity, and a ribose-5-phosphate isomerase activity.

156. The method of any one of the preceding embodiments, wherein the method further comprises introducing into the recombinant microorganism one or more modifications to diminish or delete activity in an endogenous 6-phosphofructokinase (pfkA and/or pfkB) enzyme.

157. The method of any one of the preceding embodiments, wherein the method further comprises: introducing into the recombinant microorganism one or more modifications to diminish or delete activity in one or more endogenous enzymes selected from glucose 6-phosphate-1-dehydrogenase, 6-phosphogluconolactonase, and 6-phosphogluconate dehydrogenase.

158. The method of any one of the preceding embodiments, wherein the one or more enzyme for the conversion of the one or more pentose-5-phosphate intermediate to one or more pentose or pentose-1-phosphate intermediate are selected from one or more enzyme having a pentose phosphatase activity, a D-ribulose-5-phosphatase activity, a D-ribose-5-phosphatase activity, a D-ribose isomerase activity, an arabitol phosphate dehydrogenase activity, and a phosphopentomutase activity.

159. The method of any one of the preceding embodiments, wherein one or more enzyme for the production of MEG or GA derived from DHAP or pyruvate in the C3 pathway are selected from one or more enzyme having an activity selected from a 3-phosphoglycerate dehydrogenase activity, a phosphoserine aminotransferase activity, a 3-phosphohydroxypyruvate phosphatase activity, a phosphoserine phosphatase activity, a serine transaminase activity, a hydroxypyruvate decarboxylase activity, a 3-phosphohydroxypyruvate reductase activity, a glycolaldehyde reductase activity, a glycolaldehyde dehydrogenase activity, a serine oxidoreductase (deaminating) or serine-pyruvate aminotransferase activity, a serine decarboxylase activity, an ethanolamine aminotransferase or ethanolamine oxidoreductase (deaminating) activity, a glycerate decarboxylase activity, a hydroxypyruvate reductase activity, a 3-phosphoglycerate phosphatase activity, a 2-phosphoglycerate phosphatase activity, a glycerate 3-kinase activity, and a glycerate 2-kinase activity.

160. The method of any one of the preceding embodiments, wherein one or more enzyme for the production of one or more co-product derived from DHAP or pyruvate in the C3 pathway are selected from one or more enzyme having an activity selected from a thiolase or acetyl coenzyme A acetyltransferase activity, an acetyl-CoA:acetoacetate transferase or acetate:acetoacetyl-CoA hydrolase activity, and an acetoacetate decarboxylase activity, and wherein the one or more co-product comprises acetone.

161. The method of any one of the preceding embodiments, wherein one or more enzyme for the production of one or more co-product derived from DHAP or pyruvate in the C3 pathway are selected from one or more enzyme having an activity selected from a thiolase or acetyl coenzyme A acetyltransferase activity, an acetyl-CoA:acetoacetate transferase or acetate:acetoacetyl-CoA hydrolase activity, an acetoacetate decarboxylase activity, and a secondary alcohol dehydrogenase activity, and wherein the one or more co-product comprises isopropanol.

162. The method of any one of the preceding embodiments, wherein one or more enzyme for the production of one or more co-product derived from DHAP or pyruvate in the C3 pathway are selected from one or more enzyme having an activity selected from a thiolase or acetyl coenzyme A acetyltransferase activity, an acetyl-CoA:acetoacetate transferase or acetate:acetoacetyl-CoA hydrolase activity, an acetoacetate decarboxylase activity, a secondary alcohol dehydrogenase activity, and a dehydratase activity, and wherein the one or more co-product comprises propene.

163. The method of any one of the preceding embodiments, wherein one or more enzyme for the production of one or more co-product derived from DHAP or pyruvate in the C3 pathway are selected from one or more enzyme having an activity selected from a thiolase or acetyl coenzyme A acetyltransferase activity, an acetyl-CoA:acetoacetate transferase or acetate:acetoacetyl-CoA hydrolase activity, an acetoacetate decarboxylase activity, a 3-hydroxyisovalerate (3HIV) synthase activity, a hydroxymethylglutaryl-CoA synthase activity, a methylglutaconyl-CoA hydratase activity, a methylcrotonyl-CoA carboxylase activity, a methylcrotonyl-CoA hydratase activity, a 3-hydroxyisovaleryl-CoA thioesterase activity, a 3HIV kinase activity, a 3HIV-3-phosphate decarboxylase activity, and a 3HIV decarboxylase activity, and wherein the one or more co-product comprises isobutene.

164. The method of any one of the preceding embodiments, wherein one or more enzyme for the production of one or more co-product derived from DHAP or pyruvate in the C3 pathway are selected from one or more enzyme having an activity selected from a 3-phosphoglycerate dehydrogenase activity, a phosphoserine aminotransferase activity, a 3-phosphohydroxypyruvate phosphatase activity, a phosphoserine phosphatase activity, a serine oxidoreductase (deaminating) or serine-pyruvate aminotransferase activity, a hydroxypyruvate reductase activity, a 3-phosphoglycerate phosphatase activity, a 2-phosphoglycerate phosphatase activity, a glycerate 3-kinase activity, and a glycerate 2-kinase activity, and wherein the one or more co-product comprises L-serine.

165. The method of any one of the preceding embodiments, wherein one or more enzyme for the production of one or more co-product derived from DHAP or pyruvate in the C3 pathway are selected from one or more enzyme having an activity selected from a serine hydroxymethyltransferase activity, a transferase activity, a formaldehyde dehydrogenase activity, a formate dehydrogenase activity, an activity associated with glycine cleavage system, a 3-phosphoglycerate dehydrogenase activity, a phosphoserine aminotransferase activity, a 3-phosphohydroxypyruvate phosphatase activity, a phosphoserine phosphatase activity, a serine transaminase activity, a hydroxypyruvate decarboxylase activity, a serine oxidoreductase (deaminating) activity, a serine decarboxylase activity, an ethanolamine aminotransferase or ethanolamine oxidoreductase (deaminating) activity, a hydroxypyruvate reductase activity, a 3-phosphoglycerate phosphatase activity, a 2-phosphoglycerate phosphatase activity, a glycerate 3-kinase activity, a glycerate 2-kinase activity, a glycolaldehyde dehydrogenase activity, a glycolate dehydrogenase activity, an alanine-glyoxylate aminotransferase activity, an alanine transaminase activity, and an NAD(P)H dependent glutamate dehydrogenase activity, and wherein the one or more co-product comprises glycine.

166. The method of any one of the preceding embodiments, wherein the activity associated with glycine cleavage system comprise an enzyme or protein selected from a glycine decarboxylase (P protein), an aminomethyltransferase (T protein), a dihydrolipoamide dehydrogenase (L protein), and an H protein.

167. The method of any one of the preceding embodiments, wherein one or more enzyme for the production of one or more co-product derived from DHAP or pyruvate in the C3 pathway are selected from one or more enzyme having an activity selected from 3-phosphoglycerate dehydrogenase activity, a phosphoserine aminotransferase activity, a 3-phosphohydroxypyruvate phosphatase activity, a phosphoserine phosphatase activity, a transaminase activity, a hydroxypyruvate decarboxylase activity, a serine oxidoreductase (deaminating) or serine-pyruvate aminotransferase activity, a serine decarboxylase activity, a hydroxypyruvate reductase activity, a 3-phosphoglycerate phosphatase activity, a 2-phosphoglycerate phosphatase activity, a glycerate 3-kinase activity, a glycerate 2-kinase activity, an acetaldehyde dehydrogenase activity, and an ethanolamine ammonia lyase activity, and wherein the one or more co-product comprises monoethanolamine (MEA).

168. The method of any one of the preceding embodiments, wherein one or more enzyme for the production of one or more co-product derived from DHAP or pyruvate in the C3 pathway are selected from one or more enzyme having an activity selected from a serine dehydrogenase activity, a 2-aminomalonate semialdehyde decarboxylase activity, an aminoacetaldehyde transaminase activity, a 2-aminomalonate semialdehyde transaminase activity, a 2,3-diaminopropanoate decarboxylase activity, a serine decarboxylase activity, an ethanolamine dehydrogenase activity, a serine hydroxymethyltransferase activity, an aldehyde oxidase activity, an N-acetyl transferase or O-acetyl transferase activity, an N-acetylserine dehydrogenase activity, a transaminase activity, a deacetylase activity, a serine aminase activity, and a 2,3-diaminopropanoate ammonia lyase activity, and wherein the one or more co-product comprises ethylenediamine (EDA).

169. The method of any one of the preceding embodiments, wherein one or more enzyme for the production of MEG or GA in the C2 pathway are selected from one or more enzyme having an activity selected from a D-tagatose 3-epimerase activity, a D-ribulokinase activity, a D-ribulose-1-phosphate aldolase activity, a D-xylulose 1-kinase activity, a D-xylulose-1-phosphate aldolase activity, a xylose reductase or aldose reductase activity, a xylitol dehydrogenase activity, a xylose isomerase activity, a xylose dehydrogenase activity, a xylonolactonase activity, a xylonate dehydrogenase activity, a 2-keto-3-deoxy-D-pentonate aldolase activity, a glycolaldehyde reductase activity and a glycolaldehyde dehydrogenase activity.

170. The method of any one of the preceding embodiments, wherein the method further comprises: introducing into the recombinant microorganism one or more modifications to diminish or delete activity in a glycolaldehyde dehydrogenase, a lactate dehydrogenase, a xylose isomerase, a xylulose kinase or combination thereof.

The foregoing detailed description has been given for clearness of understanding only and no unnecessary limitations should be understood there from as modifications will be obvious to those skilled in the art.

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure as come within known or customary practice within the art to which the disclosure pertains and as may be applied to the essential features hereinbefore set forth and as follows in the scope of the appended claims.

The disclosures, including the claims, figures and/or drawings, of each and every patent, patent application, and publication cited herein are hereby incorporated herein by reference in their entireties

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world. Further, the following references are hereby incorporated by reference. See PCT publication WO2001053306; U.S. Pat. No. 7,226,761B2; and EPO Publication No. EP2957640.

What is claimed is:

1. A recombinant microorganism that produces glycolic acid (GA) from one or more hexose feedstocks via
D-xylulose-5-phosphate and/or D-ribulose-5-phosphate;
wherein the recombinant microorganism comprises one or more overexpressed enzymes for the conversion of D-xylulose-5-phosphate and/or D-ribulose-5-phosphate to D-xylulose-1-phosphate or D-ribulose-1-phosphate,
wherein the one or more overexpressed enzymes is one or more enzymes having phosphopentomutase activity;
wherein the recombinant microorganism further comprises at least one overexpressed enzyme having transketolase activity or at least one overexpressed enzyme having fructose-6-phosphate phosphoketolase activity;
wherein the recombinant microorganism further comprises a deleted or diminished activity in one or more endogenous enzymes selected from glucose 6-phosphate-1-dehydrogenase (zwf), 6-phosphogluconolactonase (pgl), or 6-phosphogluconate dehydrogenase (gnd); and
wherein the recombinant microorganism is a recombinant E. coli.

2. The recombinant microorganism of claim 1, wherein one or more co-products is co-produced with GA, wherein the one or more co-products is selected from the group consisting of acetone, isopropanol, propene, and isobutene.

3. The recombinant microorganism of claim 1, wherein the recombinant microorganism comprises at least one overexpressed enzyme having transketolase activity, wherein the at least one overexpressed enzyme having transketolase activity comprises an amino acid sequence having at least 90% sequence identity to SEQ ID NO: 148 or SEQ ID NO: 150.

4. The recombinant microorganism of claim 1, wherein the recombinant microorganism further comprises at least one overexpressed enzyme having transaldolase activity, wherein the at least one overexpressed enzyme having transaldolase activity comprises an amino acid sequence having at least 90% sequence identity to SEQ ID NO: 152 or SEQ ID NO: 154.

5. The recombinant microorganism of claim 1, wherein the recombinant microorganism further comprises at least one overexpressed enzyme having ribulose-5-phosphate 3-epimerase activity, wherein the at least one overexpressed enzyme having ribulose-5-phosphate 3-epimerase activity comprises an amino acid sequence having at least 90% sequence identity to SEQ ID NO: 158.

6. The recombinant microorganism of claim 1, wherein the recombinant microorganism further comprises at least one overexpressed enzyme having ribose-5-phosphate isomerase activity, wherein the at least one overexpressed enzyme having ribose-5-phosphate isomerase activity comprises an amino acid sequence having at least 90% sequence identity to SEQ ID NO: 156 or SEQ ID NO: 253.

7. The recombinant microorganism of claim 1, wherein the recombinant microorganism further comprises a deleted or diminished activity in at least one endogenous enzyme selected from glyceraldehyde 3-phosphate dehydrogenase (gapA), phosphoglycerate kinase (pgk) and/or phosphoglycerate mutase (gpmA/gpmM).

8. The recombinant microorganism of claim 1, wherein the recombinant microorganism comprises at least one overexpressed enzyme having fructose-6-phosphate phosphoketolase activity, wherein the at least one overexpressed enzyme having fructose-6-phosphate phosphoketolase activity comprises an amino acid sequence having at least 90% sequence identity to SEQ ID NO: 212, SEQ ID NO: 214, SEQ ID NO: 216, or SEQ ID NO: 218.

9. The recombinant microorganism of claim 8, wherein the recombinant microorganism further comprises at least one overexpressed enzyme having phosphate acetyltransferase activity, wherein the at least one enzyme having phosphate acetyltransferase activity comprises an amino acid sequence having at least 90% sequence identity to SEQ ID NO: 220 or SEQ ID NO: 222.

10. The recombinant microorganism of claim 1, wherein the recombinant microorganism further comprises a deleted or diminished activity in an endogenous 6-phosphofructokinase enzyme (pfkA/pfkB).

11. The recombinant microorganism of claim 1, wherein the one or more enzymes having phosphopentomutase activity is Pgm3.

12. The recombinant microorganism of claim 1, wherein the overexpressed enzyme having transketolase activity or the overexpressed enzyme having fructose-6-phosphate phosphoketolase activity enables a conversion of one or more hexose feedstocks to D-xylulose-5-phosphate and/or D-ribulose-5-phosphate without loss of carbon.

13. The recombinant microorganism of claim 1, wherein GA is produced through the conversion of glycolaldehyde in a C2 pathway and through the conversion of dihydroxyacetone phosphate (DHAP) or pyruvate in a C3 pathway.

14. The recombinant microorganism of claim 1, wherein GA is produced through the conversion of glycolaldehyde in a C2 pathway and one or more co-products is produced through the conversion of dihydroxyacetone phosphate (DHAP) or pyruvate in a C3 pathway.

15. A method of producing glycolic acid (GA) using a recombinant microorganism of claim 1, wherein the method comprises cultivating the recombinant microorganism in a culture medium containing one or more hexose feedstocks providing a carbon source until the GA is produced.

16. A method of producing a recombinant microorganism that produces or accumulates glycolic acid (GA) from one or more exogenous hexose feedstocks via one or more pentose-5-phosphate intermediates, comprising:
expressing in the recombinant microorganism one or more enzymes for the conversion of the one or more hexose feedstocks to the one or more pentose-5-phosphate intermediates, wherein the one or more pentose- 5-phosphate intermediates is D-xylulose-5-phosphate and/or D-ribulose-5-phosphate;

overexpressing in the recombinant microorganism one or more enzymes for the conversion of D-xylulose-5-phosphate and/or D-ribulose-5-phosphate to D-xylulose-1-phosphate or D-ribulose-1-phosphate, wherein the one or more overexpressed enzymes is one or more enzyme having phosphopentomutase activity;

overexpressing in the recombinant microorganism at least one enzyme having transketolase activity or at least one enzyme having fructose-6-phosphate phosphoketolase activity;

deleting or diminishing activity in the recombinant microorganism of one or more endogenous enzymes selected from glucose 6-phosphate-1-dehydrogenase (zwf), 6-phosphogluconolactonase (pgl), or 6-phosphogluconate dehydrogenase (gnd);

expressing in the recombinant microorganism a C2 pathway comprising one or more enzymes for the production of GA from glycolaldehyde; and expressing in the recombinant microorganism a C3 pathway comprising one or more enzymes for the production of GA derived from DHAP or pyruvate; and culturing the recombinant microorganism in a culture medium containing the one or more hexose feedstocks to produce or accumulate GA, wherein glycolaldehyde and DHAP (or pyruvate) are intermediates produced in the C2 pathway, and wherein GA is produced in both the C2 and C3 pathways.

17. A method of producing a recombinant microorganism that produces or accumulates glycolic acid (GA) and one or more co-products from one or more exogenous hexose feedstocks via one or more pentose-5-phosphate intermediates, comprising:

expressing in the recombinant microorganism one or more enzymes for the conversion of the one or more hexose feedstocks to the one or more pentose-5-phosphate intermediates, wherein the one or more pentose-5-phosphate intermediates is D-xylulose-5-phosphate and/or D-ribulose-5-phosphate;

overexpressing in the recombinant microorganism one or more enzymes for the conversion of D-xylulose-5-phosphate and/or D-ribulose-5-phosphate to D-xylulose-1-phosphate or D-ribulose-1-phosphate, wherein the one or more overexpressed enzymes is one or more enzyme having or phosphopentomutase activity;

overexpressing in the recombinant microorganism at least one enzyme having transketolase activity or at least one enzyme having fructose-6-phosphate phosphoketolase activity;

deleting or diminishing activity in the recombinant microorganism of one or more endogenous enzymes selected from glucose 6-phosphate-1-dehydrogenase (zwf), 6-phosphogluconolactonase (pgl), or 6-phosphogluconate dehydrogenase (gnd);

expressing in the recombinant microorganism a C2 pathway comprising one or more enzymes for the production of GA from glycolaldehyde; and expressing in the recombinant microorganism a C3 pathway comprising one or more enzymes for the production of one or more co-product derived from DHAP or pyruvate; and culturing the recombinant microorganism in a culture medium containing the one or more hexose feedstocks to produce or accumulate GA and one or more co-products, wherein glycolaldehyde and DHAP (or pyruvate) are intermediates produced in the C2 pathway, and wherein GA is produced in the C2 pathway and the one or more co-products is produced in the C3 pathway.

* * * * *